United States Patent
Kawahara et al.

(10) Patent No.: US 7,410,971 B2
(45) Date of Patent: Aug. 12, 2008

(54) 1,2-DI(CYCLIC)SUBSTITUTED BENZENE COMPOUNDS

(75) Inventors: Tetsuya Kawahara, Tsukuba (JP); Makoto Kotake, Tsukuba (JP); Naoki Yoneda, Tsukuba (JP); Shinsuke Hirota, Tsukuba (JP); Masayoshi Ohkuro, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 10/581,591

(22) PCT Filed: Dec. 24, 2004

(86) PCT No.: PCT/JP2004/019795

§ 371 (c)(1),
(2), (4) Date: Jun. 5, 2006

(87) PCT Pub. No.: WO2005/063705

PCT Pub. Date: Jul. 14, 2005

(65) Prior Publication Data

US 2007/0112002 A1    May 17, 2007

(30) Foreign Application Priority Data

Dec. 26, 2003    (JP) .............................. 2003-434312
Dec. 26, 2003    (JP) .............................. 2003-435050

(51) Int. Cl.
| | |
|---|---|
| A61K 31/4965 | (2006.01) |
| A61K 31/445 | (2006.01) |
| A01N 43/40 | (2006.01) |
| C07D 241/04 | (2006.01) |
| C07D 295/00 | (2006.01) |
| C07D 211/60 | (2006.01) |
| C07D 211/06 | (2006.01) |
| C07D 211/30 | (2006.01) |
| C07D 211/32 | (2006.01) |
| C07D 211/22 | (2006.01) |

(52) U.S. Cl. .................. 514/255.03; 514/317; 544/392; 544/395; 546/221; 546/225; 546/226; 546/228

(58) Field of Classification Search ............ 514/255.03; 544/392, 395; 546/221, 225, 226, 228
See application file for complete search history.

(56) References Cited

U.S. PATENT DOCUMENTS

| | | | |
|---|---|---|---|
| 5,244,901 | A | 9/1993 | George et al. |
| 6,929,928 | B2 | 8/2005 | Cheng et al. |
| 2002/0119973 | A1 | 8/2002 | Luly et al. |
| 2002/0169155 | A1 | 11/2002 | Luly et al. |
| 2003/0045516 | A1 | 3/2003 | Luly et al. |
| 2004/0092507 | A1 | 5/2004 | Biggers et al. |

(Continued)

FOREIGN PATENT DOCUMENTS

| | | | |
|---|---|---|---|
| JP | 5-186434 | A | 7/1993 |
| JP | 2003-506377 | A | 2/2003 |
| JP | 2003-192673 | A | 7/2003 |
| JP | 2004-523529 | A | 8/2004 |
| JP | 2005-505621 | A | 2/2005 |
| WO | WO-01/09138 | A2 | 2/2001 |
| WO | WO-02/18320 | A2 | 3/2002 |
| WO | WO-02/059108 | A1 | 8/2002 |
| WO | WO-03/033466 | A1 | 4/2003 |
| WO | WO-03/089410 | A1 | 10/2003 |
| WO | 2005/005382 | * | 1/2005 |
| WO | WO-2005/005382 | A2 | 1/2005 |
| WO | WO-2005-005382 | A2 | 1/2005 |
| WO | WO-2005/063705 | A1 | 7/2005 |
| WO | WO-2006/068058 | A1 | 6/2006 |
| WO | WO-2006/126635 | A1 | 11/2006 |

OTHER PUBLICATIONS

Daniel K. Podolsky, N Engl J Med, vol. 347, No. 6, Aug. 8, 2002, pp. 417-429.

(Continued)

*Primary Examiner*—James O. Wilson
*Assistant Examiner*—Erich A Leeser
(74) *Attorney, Agent, or Firm*—Birch, Stewart, Kolasch & Birch, LLP

(57) ABSTRACT

A compound represented by the following general formula (1) or (100), a salt thereof or a hydrate of the foregoing has excellent cell adhesion inhibitory action or cell infiltration inhibitory action, and is useful as a therapeutic or prophylactic agent for various inflammatory diseases and autoimmune diseases associated with adhesion and infiltration of leukocytes, such as inflammatory bowel disease (particularly ulcerative colitis or Crohn's disease), irritable bowel syndrome, rheumatoid arthritis, psoriasis, multiple sclerosis, asthma and atopic dermatitis.

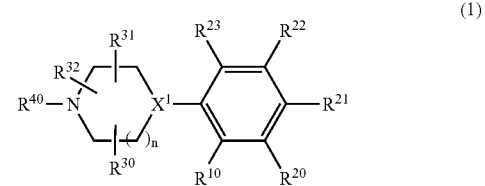

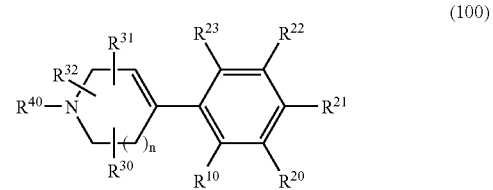

wherein R10 represents optionally substituted cycloalkyl, etc., R20-23 represent hydrogen, alkyl, alkoxy, etc., R30-32 represent hydrogen, alkyl, oxo, etc., and R40 represents optionally substituted alkyl, etc.

25 Claims, No Drawings

U.S. PATENT DOCUMENTS

| | | |
|---|---|---|
| 2004/0224383 A1 | 11/2004 | Cheng et al. |
| 2004/0268439 A1 | 12/2004 | Cheng et al. |
| 2005/0014219 A1 | 1/2005 | Cheng et al. |
| 2005/0014795 A1 | 1/2005 | Baroni et al. |
| 2005/0261291 A1 | 11/2005 | Kawahara et al. |
| 2006/0276465 A1 | 12/2006 | Kawahara et al. |
| 2006/0281747 A1 | 12/2006 | Kawahara et al. |

OTHER PUBLICATIONS

Subrata Ghosh et al., N Engl J Med, vol. 348;1 Jan. 2, 2003, pp. 24-32.
Takashi Shimoyama et al., Japanese Journal of Apheresis, vol. 18, No. 1 (1999), pp. 117-131.
G Barbara et al., Gut, 51 (Suppl 1), 2002, pp. i41-i44.
Susan E. Sweeney et al., The International Journal of Biochemistry & Cell Biology 36 (2004) pp. 372-378.
Mark Lebwohl, Lancet, vol. 361, Apr. 5, 2003, pp. 1197-1204.
Chris H Polman et al., The Lancet Neurology, vol. 2, Sep. 2003, pp. 563-566.
Mark Larché et al., J Allergy Clin Immunol, vol. 111, No. 3, 2003, pp. 450-463.
Michael P. Schön et al., The Journal of Investigative Dermatology, vol. 121, No. 5, Nov. 2003, pp. 951-962.
Marlon Cowart et al., J. Med. Chem. 2004, 47, pp. 3853-3864.
English language abstract of JP 5-186434 (Jul. 27, 1993).
English translation of IPER issued Aug. 22, 2006 in PCT/JP2004/019795.
Vippagunta et al., Advanced Drug Delivery Reviews, vol. 48, pp. 3-26, (2001).
"Merck Manual of Medical Information—Second Home Edition : Multiple Sclerosis" (online printout pp. 1-4). Last full review/revision Feb. 2003.
"Merck Manual of Medical Information—Second Home Edition: Atopic Dermatitis" (online printout pp. 1-8). Last full review/revision Dec. 2006.
"Merck Manual of Medical Information—Second Home Edition: Psoriasis" (online printout pp. 1-3). Last full review/revision Dec. 2006.

* cited by examiner

1,2-DI(CYCLIC)SUBSTITUTED BENZENE COMPOUNDS

TECHNICAL FIELD

The present invention relates to 1,2-di(cyclic)substituted benzene compounds which are useful as cell adhesion inhibitors or cell infiltration inhibitors, as well as to their salts and to hydrates of the foregoing.

The present invention relates to 1,2-di(cyclic)substituted benzene compounds which are useful as therapeutic or prophylactic agents for inflammatory diseases and autoimmune diseases, as well as to their salts and to hydrates of the foregoing.

The invention further relates to 1,2-di(cyclic)substituted benzene compounds which are useful as therapeutic or prophylactic agents for various diseases associated with adhesion and infiltration of leukocyte, such as inflammatory bowel disease (particularly ulcerative colitis or Crohn's disease), irritable bowel syndrome, rheumatoid arthritis, psoriasis, multiple sclerosis, asthma and atopic dermatitis, as well as to their salts and to hydrates of the foregoing.

BACKGROUND ART

Inflammatory reaction is accompanied by infiltration of leukocytes, typically neutrophils and lymphocytes, into inflammatory sites.

Infiltration of leukocytes is defined as migration of leukocytes such as neutrophils and lymphocytes out of vessels and into the surrounding tissues as a consequence of initiation and activation by cytokines, chemokines, lipids and complement to interact called "rolling" or "tethering" with vascular endothelial cells activated by cytokines such as IL-1 or TNFα, followed by adhesion to the vascular endothelial cells.

As explained below, relationship between leukocyte adhesion or infiltration and various inflammatory diseases and autoimmune diseases was reported. Such reports have raised the possibility that compounds having cell adhesion inhibitory action or cell infiltration inhibitory action may serve as therapeutic or prophylactic agents for such diseases.
(1) Therapeutic or prophylactic agents for inflammatory bowel disease (ulcerative colitis, Crohn's disease and the like) (see Non-patent documents 1, 2 and 3)
(2) Therapeutic or prophylactic agents for irritable bowel syndrome (see Non-patent document 4)
(3) Therapeutic or prophylactic agents for rheumatoid arthritis (see Non-patent document 5)
(4) Therapeutic or prophylactic agents for psoriasis (see Non-patent document 6)
(5) Therapeutic or prophylactic agents for multiple sclerosis (see Non-patent document 7)
(6) Therapeutic or prophylactic agents for asthma (see Non-patent document 8)
(7) Therapeutic or prophylactic agents for atopic dermatitis (see Non-patent document 9)

Thus, substances which inhibit cell adhesion or cell infiltration are expected to be useful as therapeutic or prophylactic agents for inflammatory diseases and autoimmune diseases and as therapeutic or prophylactic agents for various diseases associated with adhesion and infiltration of leukocytes, such as inflammatory bowel disease (particularly ulcerative colitis or Crohn's disease), irritable bowel syndrome, rheumatoid arthritis, psoriasis, multiple sclerosis, asthma and atopic dermatitis.

Compounds are also known which have anti-inflammatory action based on inhibition of adhesion of leukocyte and vascular endothelial cell, or anti-inflammatory action based on inhibition of leukocyte infiltration (these will hereinafter be referred to as cell adhesion inhibitors and cell infiltration inhibitors, respectively), such as the following compound:

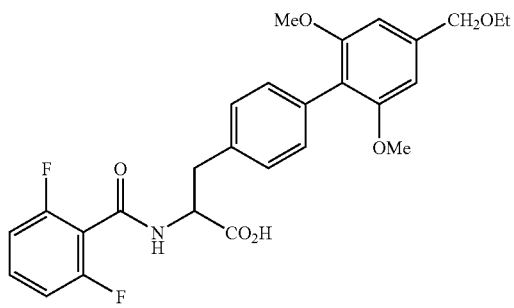

(see Patent document 1).

However, the compounds represented by general formula (1) according to the present invention are characterized by including a partial chemical structure having piperazine or piperidine at the ortho position of a benzene ring bonded to an aliphatic carbocyclic group such as cyclohexyl, therefore differ in their structures from the aforementioned cell adhesion inhibitors or cell infiltration inhibitors.

The known compound comprising a partial chemical structure having piperazine or piperidine at the ortho position of a benzene ring bonded to an aliphatic carbocyclic group such as cyclohexyl, as a chemical structural feature of the compounds represented by general formula (1) according to the present invention, is the compound represented by the following formula:

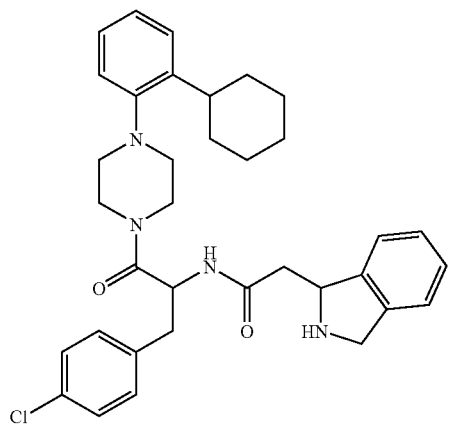

(see Patent document 2).

However, the patent application discloses only its use as an anti-obesity agent and diabetes treatment based on the melanocortin receptor agonistic activity of the compound, while it neither discloses nor suggests its use as an anti-inflammatory agent based on inhibitory action of leukocyte adhesion or infiltration.

Other than the above compound, the compound represented by the following formula:

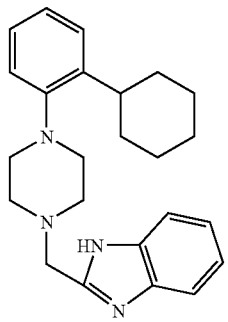

is known (see Non-patent document 10, compound number 45).

[Patent document 1] WO 2002/018320
[Patent document 2] WO 2002/059108
[Non-patent document 1] Inflammatory Bowel Disease (N. Engl. J. Med., 347:417-429 (2002))
[Non-patent document 2] Natalizumab for active Crohn's disease (N. Engl. J. Med., 348:24-32 (2003))
[Non-patent document 3] Granulocyte adsorption therapy in active period of ulcerative colitis (Japanese Journal of Apheresis 18:117-131 (1999))
[Non-patent document 4] A role for inflammation in irritable bowel syndrome (Gut., 51: i41-i44 (2002))
[Non-patent document 5] Rheumatoid arthritis (Int. J. Biochem. Cell Biol., 36:372-378 (2004))
[Non-patent document 6] Psoriasis (Lancet, 361:1197-1204 (2003))
[Non-patent document 7] New and emerging treatment options for multiple sclerosis (Lancet Neurology, 2:563-566 (2003))
[Non-patent document 8] The role of T lymphocytes in the pathogenesis of asthma (J. Allergy Clin. Immunol., 111: 450-463 (2003)
[Non-patent document 9] The molecular basis of lymphocyte recruitment to the skin (J. Invest. Dermatol., 121:951-962 (2003))
[Non-patent document 10] Discovery of 2-(4-pyridin-2-ylpiperazin-1-ylmethyl)-1H-benzimidazole (ABT-724), a dopaminergic agent with a novel mode of action for the potential treatment of erectile dysfunction (J. Med. Chem., 47: 3853-3864 (2004))

DISCLOSURE OF INVENTION

It is an object of the present invention to provide novel compounds having excellent cell adhesion inhibitory action and cell infiltration inhibitory action, which are useful as therapeutic or prophylactic agents for various inflammatory diseases and autoimmune diseases associated with adhesion and infiltration of leukocytes, such as inflammatory bowel disease (particularly ulcerative colitis or Crohn's disease), irritable bowel syndrome, rheumatoid arthritis, psoriasis, multiple sclerosis, asthma and atopic dermatitis.

As a result of intensive research, the present inventors have discovered that 1,2-di(cyclic)substituted benzene compounds having the novel chemical structure described herein have excellent cell adhesion inhibitory action and cell infiltration inhibitory action, and are useful as therapeutic or prophylactic agents for various inflammatory diseases and autoimmune diseases associated with adhesion and infiltration of leukocytes, such as inflammatory bowel disease (particularly ulcerative colitis or Crohn's disease), irritable bowel syndrome, rheumatoid arthritis, psoriasis, multiple sclerosis, asthma and atopic dermatitis, and the present invention was completed on the basis of this discovery.

Specifically, the invention is a compound having the following general formula (1) or (100), a salt thereof or a hydrate of the foregoing:

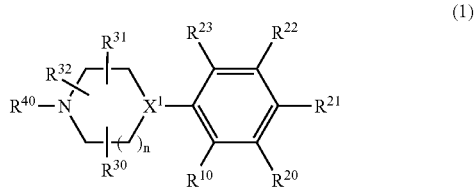

(1)

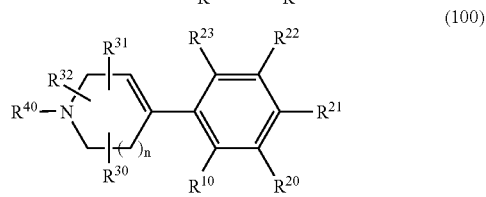

(100)

Also, the invention is a medicament comprising the compound having the aforementioned general formula (1) or (100), the salt thereof or the hydrate of the foregoing.

Further, the invention is a cell adhesion inhibitor and a cell infiltration inhibitor comprising the compounds having the aforementioned general formula (1) or (100), the salt thereof or the hydrate of the foregoing.

Still further, the invention is a therapeutic or prophylactic agent for inflammatory diseases or autoimmune diseases, comprising the compound having the aforementioned general formula (1) or (100), the salt thereof or the hydrate of the foregoing.

Particularly, the invention is a therapeutic or prophylactic agent for inflammatory bowel disease (particularly ulcerative colitis or Crohn's disease), irritable bowel syndrome, rheumatoid arthritis, psoriasis, multiple sclerosis, asthma, atopic dermatitis and the like, comprising the compound having the aforementioned general formula (1) or (100), the salt thereof or the hydrate of the foregoing.

Still particularly, the invention is use of the compound having the aforementioned general formula (1) or (100), the salt thereof or the hydrate of the foregoing for the manufacture of a medicament.

In formulas (1) and (100) above,

R10 represents 5- to 10-membered cycloalkyl optionally substituted with a substituent selected from Group A1 or 5- to 10-membered cycloalkenyl optionally substituted with a substituent selected from Group A1, R20, R21, R22 and R23 may be the same or different and each represents hydrogen, hydroxyl, halogen, cyano, C2-7 alkylcarbonyl, nitro, amino, mono(C1-6 alkyl)amino, di(C1-6 alkyl)amino, C1-6 alkyl optionally substituted with a substituent selected from Group B1, C1-6 alkoxy optionally substituted with a substituent selected from Group B1, a 4- to 8-membered heterocyclic group optionally substituted with a substituent selected from Group C1, or a 5- to 10-membered heteroaryl ring group optionally substituted with a substituent selected from Group C1, R30, R31 and R32 may be the same or different and each represents hydrogen, hydroxyl, halogen, cyano, carboxyl, C1-6 alkyl, C1-6 alkoxy or C2-7 alkoxycarbonyl, or two of R30, R31 and R32 bond together to form oxo (=O) or methylene (—CH$_2$—) and the other represents hydrogen, hydroxyl, halogen, cyano, carboxyl, C1-6 alkyl, C1-6 alkoxy or C2-7 alkoxycarbonyl, R40 represents C1-10 alkyl optionally substituted with a substituent selected from Group D1,3- to 8-membered cycloalkyl optionally substituted with a substituent selected from Group E1, a 4- to 8-membered heterocyclic group optionally substituted with a substituent selected from Group E1, C2-7 alkenyl optionally substituted with a substituent selected from Group F1, C2-7 alkynyl optionally substituted with a substituent selected from Group F1, C2-7 alkylcarbonyl optionally substituted with a substituent selected from Group G1, mono(C1-6 alkyl)aminocarbonyl, 4- to 8-membered heterocyclic carbonyl, C2-7 alkoxycarbonyl or C1-6 alkylsulfonyl, n represents an integer of 0, 1 or 2, X1 represents CH or nitrogen, Group A1 represents a group consisting of hydroxyl, halogen, cyano, C1-6 alkoxy, phenyl optionally substituted with a substituent selected from Group C1, C1-6 alkyl, C1-6 haloalkyl and C2-7 alkylene, where C2-7 alkylene is permissible only in the case that a spiro union is formed together with the substituted 5- to 10-membered cycloalkyl or the substituted 5- to 10-membered cycloalkenyl, Group B1 represents a group consisting of halogen, C2-7 alkoxycarbonyl and carboxyl, Group C1 represents a group consisting of cyano, halogen, C1-6 alkyl and C1-6 alkoxy, Group D1 represents a group consisting of hydroxyl, halogen, cyano, C1-6 alkoxy, C1-6 alkylthio, C1-6 alkylsulfonyl, C1-6 alkylsulfinyl, mono(C1-6 alkyl)amino, di(C1-6 alkyl)amino, C2-7 alkylcarbonylamino, 3- to 8-membered cycloalkyl optionally substituted with a substituent selected from Group H1, C2-7 alkoxycarbonyl, carboxyl, a 4- to 8-membered heterocyclic group, a 5- to 10-membered heteroaryl ring group, a 6- to 10-membered aryl ring group, C2-7 alkylcarbonyl, a 6- to 10-membered aryl ring carbonyl group, aminocarbonyl, mono(C1-6 alkyl)aminocarbonyl optionally substituted with halogen, mono(3- to 8-membered cycloalkyl)aminocarbonyl, mono(C2-7 alkoxyalkyl)aminocarbonyl, di(C1-6 alkyl)aminocarbonyl, mono(5- to 10-membered heteroaryl ring)aminocarbonyl, 4- to 8-membered heterocyclic carbonyl optionally substituted with C 1-6 alkyl, and 5- to 10-membered heteroaryl ring carbonyl, Group E1 represents a group consisting of halogen, C1-6 alkoxy, oxo (=O) and C1-6 alkyl, Group F1 represents a group consisting of halogen and C1-6 alkoxy, Group G1 represents a group consisting of 3- to 8-membered cycloalkyl, and Group H1 represents a group consisting of hydroxyl, C1-6 haloalkyl, C1-6 alkyl, C2-7 alkoxyalkyl, mono(C1-6 alkyl)aminocarbonyl, di(C1-6 alkyl)aminocarbonyl, C2-7 alkoxycarbonyl, carboxyl and C2-7 cyanoalkyl.

A compound represented by the formula

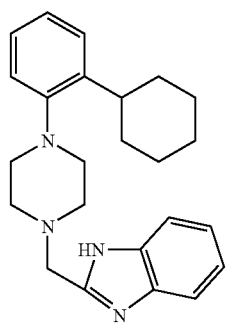

is excepted from the compound represented by the formula (1).

As examples of the "cycloalkyl" of the "cycloalkyl optionally substituted with a substituent selected from Group A1" for R10 above, there may be mentioned cyclopentyl, cyclohexyl, cycloheptyl, cyclooctyl, cyclononyl or cyclodecyl, among which cyclopentyl, cyclohexyl, cycloheptyl or cyclooctyl is preferred, and cyclohexyl is particularly preferred.

The "cycloalkenyl" of the "cycloalkenyl optionally substituted with a substituent selected from Group A1" for R10 above may have multiple double bonds, and as examples there may be mentioned cyclopentenyl (1-cyclopentenyl, 2-cyclopentenyl or 3-cyclopentenyl), cyclohexenyl (1-cyclohexenyl, 2-cyclohexenyl or 3-cyclohexenyl), cycloheptenyl (1-cycloheptenyl, 2-cycloheptenyl, 3-cycloheptenyl or 4-cycloheptenyl), cyclooctenyl (1-cyclooctenyl, 2-cyclooctenyl, 3-cyclooctenyl or 4-cyclooctenyl), cyclononenyl (1-cyclononenyl, 2-cyclononenyl, 3-cyclononenyl, 4-cyclononenyl or 5-cyclononenyl) or cyclodecenyl (1-cyclodecenyl, 2-cyclodecenyl, 3-cyclodecenyl, 4-cyclodecenyl or 5-cyclodecenyl), among which cyclopentenyl, cyclohexenyl, cycloheptenyl or cyclooctenyl is preferred, cyclohexenyl is more preferred, and 1-cyclohexenyl is most preferred.

As examples of the "halogen" for R20, R21, R22 and R23 above, there may be mentioned fluorine, chlorine, bromine or iodine, among which bromine, fluorine or chlorine is preferred.

The "C2-7 alkylcarbonyl" for R20, R21, R22 and R23 above is a carbonyl group having the "C1-6 alkyl" described below bonded thereto, and as examples there may be mentioned straight-chain or branched-chain groups such as acetyl, ethylcarbonyl, n-propylcarbonyl, isopropylcarbonyl, n-butylcarbonyl, isobutylcarbonyl, s-butylcarbonyl, t-butylcarbonyl, pentylcarbonyl, isopentylcarbonyl, 2-methylbutylcarbonyl, neopentylcarbonyl, 1-ethylpropylcarbonyl, hexylcarbonyl, isohexylcarbonyl, 4-methylpentylcarbonyl, 3-methylpentylcarbonyl, 2-methylpentylcarbonyl, 1-methylpentylcarbonyl, 3,3-dimethylbutylcarbonyl, 2,2-dimethylbutylcarbonyl, 1,1-dimethylbutylcarbonyl, 1,2-dimethylbutylcarbonyl, 1,3-dimethylbutylcarbonyl, 2,3-dimethylbutylcarbonyl, 1-ethylbutylcarbonyl or 2-ethylbutylcarbonyl, among which C2-5 groups are preferred, and acetyl or ethylcarbonyl is particularly preferred.

As examples of the "mono(C1-6 alkyl)amino" for R20, R21, R22 and R23 above, there may be mentioned straight-chain or branched-chain groups such as methylamino, ethylamino, propylamino, isopropylamino, butylamino, isobutylamino, s-butylamino, t-butylamino, pentylamino, isopentylamino, 2-methylbutylamino, neopentylamino, 1-ethylpropylamino, hexylamino, isohexylamino, 4-methylpentylamino, 3-methylpentylamino, 2-methylpentylamino, 1-methylpentylamino, 3,3-dimethylbutylamino, 2,2-dimethylbutylamino, 1,1-dimethylbutylamino, 1,2-dimethylbutylamino, 1,3-dimethylbutylamino, 2,3-dimethylbutylamino, 1-ethylbutylamino or 2-ethylbutylamino, among which methylamino or ethylamino is preferred, and methylamino is particularly preferred.

The "di(C1-6 alkyl)amino" for R20, R21, R22 and R23 above may be either symmetric or asymmetric, and as examples there may be mentioned straight-chain or branched-chain groups such as dimethylamino, methylethylamino, diethylamino, methylpropylamino, ethylpropylamino, dipropylamino, diisopropylamino, dibutylamino, diisobutylamino, di(s-butyl)amino, di(t-butyl)amino, methylpentylamino, dipentylamino, diisopentylamino, di(2-methylbutyl)amino, di(neopentyl)amino, di(1-ethylpropyl)amino, dihexylamino, methylisohexylamino, diisohexylamino, di(4-methylpentyl)amino, di(3-methylpentyl)amino, di(2-methylpentyl)amino, di(1-methylpentyl)amino, di(3,3-dimethylbutyl)amino, di(2,2-dimethylbutyl)amino, di(1,1-dimethylbutyl)amino, di(1,2-dimethylbutyl)amino, di(1,3-dimethylbutyl)amino, di(2,3-dimethylbutyl)amino, di(1-ethylbutyl)amino or di(2-ethylbutyl)amino, among which dimethylamino, methylethylamino or diethylamino is preferred, and dimethylamino is particularly preferred.

As examples of the "C1-6 alkyl" of the "C1-6 alkyl optionally substituted with a substituent selected from Group B1" for R20, R21, R22 and R23 above, there may be mentioned straight-chain or branched-chain groups such as methyl, ethyl, n-propyl, isopropyl, n-butyl, isobutyl, s-butyl, t-butyl, n-pentyl, isopentyl, s-pentyl, t-pentyl, 2-methylbutyl, 1-methylbutyl, 2-methylbutyl, neopentyl, 1,1-dimethylpropyl, 1,2-dimethylpropyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, among which C1-4 groups are preferred, methyl, ethyl or t-butyl is more preferred, and methyl is most preferred.

As examples of the "C1-6 alkoxy" of the "C1-6 alkoxy optionally substituted with a substituent selected from Group B1" for R20, R21, R22 and R23 above, there may be mentioned straight-chain or branched-chain groups such as methoxy, ethoxy, propoxy, isopropoxy, butoxy, isobutoxy, s-butoxy, t-butoxy, pentoxy, isopentoxy, 2-methylbutoxy, neopentoxy, hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy or 2,3-dimethylbutoxy, among which methoxy, ethoxy, propoxy or isopropoxy is preferred, methoxy or ethoxy is more preferred, and methoxy is most preferred.

The "4- to 8-membered heterocyclic group" of the "4- to 8-membered heterocyclic group optionally substituted with a substituent selected from Group C1" for R20, R21, R22 and R23 above is a monovalent group obtained by removing one hydrogen from any desired position of a "4- to 8-membered heterocycle" as described below.

The "4- to 8-membered heterocycle" is a non-aromatic ring (either completely saturated or partially unsaturated) having 4-8 atoms forming the ring and containing one or more heteroatoms among the atoms forming the ring, and as examples there may be mentioned an azetidine ring, a pyrrolidine ring, a piperidine ring, an azepane ring, an azocane ring, a tetrahydrofuran ring, a tetrahydropyran ring, a tetrahydrothiopyran ring, a morpholine ring, a thiomorpholine ring, a piperazine ring, a diazepane ring, a thiazolidine ring, an isoxazolidine ring, an imidazolidine ring, a pyrazolidine ring, a dioxane ring, a 1,3-dioxolane ring, an oxathiane ring, a dithiane ring, a pyran ring, a dihydropyran ring, a pyrroline ring, a pyrazoline ring, an oxazoline ring, an imidazoline ring or a thiazoline ring.

Preferable "4- to 8-membered heterocyclic groups" are completely saturated 4- to 8-membered heterocyclic groups, completely saturated 4- to 8-membered heterocyclic groups derived by eliminating hydrogen linked to nitrogen constituting the ring are more preferred, pyrrolidin-1-yl, azetidin-1-yl, thiomorpholin-4-yl, piperidin-1-yl or morpholin-4-yl is further preferred, and pyrrolidin-1-yl, piperidin-1-yl or morpholin-4-yl is most preferred.

The "5- to 10-membered heteroaryl ring group" of the "5- to 10-membered heteroaryl ring group optionally substituted with a substituent selected from Group C1" for R20, R21, R22 and R23 above is a monovalent group obtained by removing one hydrogen from any desired position of a "5- to 10-membered heteroaryl ring" as described below.

The "5- to 10-membered heteroaryl ring" is an aromatic ring having 5-10 atoms forming the ring and containing one or more heteroatoms among the atoms forming the ring (with regard to fused rings, at least one of the rings are aromatic), and as examples there may be mentioned a pyridine ring, a thiophene ring, a furan ring, a pyrrole ring, a oxazole ring, a isoxazole ring, a thiazole ring, a thiadiazole ring, an isothiazole ring, an imidazole ring, a triazole ring, a tetrazole ring, a pyrazole ring, a furazan ring, a thiadiazole ring, an oxadiazole ring, a pyridazine ring, a pyrimidine ring, a pyrazine ring, a triazine ring, an indole ring, an isoindole ring, an indazole ring, a quinoline ring, an isoquinoline ring, a cinnoline ring, a quinazoline ring, a quinoxaline ring, a naphthylidine ring, a phthalazine ring, a purine ring, a pteridine ring, a thienofuran ring, an imidazothiazole ring, a benzofuran ring, a benzothiophene ring, a benzoxazole ring, a benzothiazole ring, a benzothiadiazole ring, a benzimidazole ring, an imidazopyridine ring, a pyrrolopyridine ring, a pyrrolopyrimidine ring, a pyridopyrimidine ring, a coumarane ring, a chromene ring, a chroman ring, a isochroman ring, a indoline ring or a isoindoline ring. Preferable "5- to 10-membered heteroaryl ring groups" are 5- to 6-membered groups, an isoxazole ring group, an oxadiazole ring group, a tetrazole ring group, a pyridine ring group, a thiazole ring group or a thiophen ring group is more preferred, and a pyridine ring group, a thiazole ring group, a thiophen ring group or a tetrazole ring group is particularly preferred.

As the "halogen" for R30, R31 and R32 above there may be mentioned the same ones listed above, among which fluorine or chlorine is preferred.

As examples of the "C1-6 alkyl" for R30, R31 and R32 above there may be mentioned the same ones listed above, among which C1-4 groups are preferred, and methyl is particularly preferred.

As examples of the "C1-6 alkoxy" for R30, R31 and R32 above there may be mentioned the same ones listed above, among which C1-4 groups are preferred, and methoxy is particularly preferred.

The "C2-7 alkoxycarbonyl" for R30, R31 and R32 above is a carbonyl group having the aforementioned "C1-6 alkoxy" bonded thereto, and as examples there may be mentioned straight-chain or branched-chain groups such as methoxycarbonyl, ethoxycarbonyl, propoxycarbonyl, isopropoxycarbonyl, butoxycarbonyl, isobutoxycarbonyl, s-butoxycarbonyl, t-butoxycarbonyl, pentoxycarbonyl, isopentoxycarbonyl, 2-methylbutoxycarbonyl, neopentoxycarbonyl, hexyloxycarbonyl, 4-methylpentoxycarbonyl, 3-methylpentoxycarbonyl, 2-methylpentoxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl or 2,3-dimethylbutoxycarbonyl, among which methoxycarbonyl or ethoxycarbonyl is preferred.

As examples of the "C1-10 alkyl" of the "C1-10 alkyl optionally substituted with a substituent selected from Group D1" for R40 above there may be mentioned, in addition to the aforementioned C1-6 alkyl, straight-chain or branched-chain C7-C10 alkyl groups such as heptyl, 3-methylhexyl, octyl, nonyl or decyl, among which C1-6 alkyl groups are preferred, and methyl, ethyl, propyl, isopropyl, isobutyl, butyl or pentyl is particularly preferred.

As examples of the "3- to 8-membered cycloalkyl" of the "3- to 8-membered cycloalkyl optionally substituted with a substituent selected from Group E1" for R40 above, there may be mentioned cyclopropyl, cyclobutyl, cyclopentyl, cyclohexyl, cycloheptyl or cyclooctyl, among which cyclopropyl, cyclobutyl, cyclopentyl, cyclohexyl or cycloheptyl is preferred, and cyclobutyl, cyclopentyl or cyclohexyl is particularly preferred.

As examples of the "4- to 8-membered heterocyclic group" of the "4- to 8-membered heterocyclic group optionally substituted with a substituent selected from Group E1" for R40 above, there may be mentioned the same ones listed above, among which a pyrrolidine ring group, a piperidine ring group, a tetrahydrothiopyran ring group or a tetrahydropyran ring group is preferred.

The "C2-7 alkenyl" of the "C2-7 alkenyl optionally substituted with a substituent selected from Group F1" for R40 above is straight-chain or branched-chain alkenyl groups of 2 to 7 carbon which may contain 1 or 2 double bonds, and as examples there may be mentioned ethenyl, 1-propenyl, 2-propenyl, 1-butenyl, 2-butenyl, 3-butenyl, 2-methyl-1-propenyl, 2-methyl-2-propenyl, 1-pentenyl, 1-hexenyl, 1,6-hexadienyl or 1-heptenyl, among which C2-5 groups are preferred, and 2-propenyl or 2-methyl-2-propenyl is particularly preferred.

The "C2-7 alknyl" of the "C2-7 alkynyl optionally substituted with a substituent selected from Group F1" for R40 above is straight-chain or branched-chain alkynyl groups of 2 to 7 carbon which may contain 1 or 2 triple bonds, and as examples there may be mentioned ethynyl, 1-propynyl, 2-propynyl, 1-butynyl, 2-butynyl, 3-butenyl, 1-pentynyl, 1-hexynyl, 1,6-hexadienyl or 1-heptynyl, among which C2-5 groups are preferred, and 2-butynyl or 2-propynyl is particularly preferred.

As examples of the "C2-7 alkylcarbonyl" of "C2-7 alkylcarbonyl optionally substituted with a substituent selected from Group G1" for R40 above, there may be mentioned the same ones listed above, among which C2-5 groups are preferred, and acetyl or propylcarbonyl is particularly preferred.

The "mono(C1-6 alkyl)aminocarbonyl" for R40 above is a carbonyl group having the aforementioned "mono(C1-6 alkyl)amino" bonded thereto, and as examples there may be mentioned straight-chain or branched-chain groups such as methylaminocarbonyl, ethylaminocarbonyl, propylaminocarbonyl, isopropylaminocarbonyl, butylaminocarbonyl, isobutylaminocarbonyl, s-butylaminocarbonyl, t-butylaminocarbonyl, pentylaminocarbonyl, isopentylaminocarbonyl, 2-methylbutylaminocarbonyl, neopentylaminocarbonyl, 1-ethylpropylaminocarbonyl, hexylaminocarbonyl, isohexylaminocarbonyl, 4-methylpentylaminocarbonyl, 3-methylpentylaminocarbonyl, 2-methylpentylaminocarbonyl, 1-methylpentylaminocarbonyl, 3,3-dimethylbutylaminocarbonyl, 2,2-dimethylbutylaminocarbonyl, 1,1-dimethylbutylaminocarbonyl, 1,2-dimethylbutylaminocarbonyl, 1,3-dimethylbutylaminocarbonyl, 2,3-dimethylbutylaminocarbonyl, 1-ethylbutylaminocarbonyl or 2-ethylbutylaminocarbonyl, among which C2-5 groups (total number of carbon) are preferred and ethylaminocarbonyl is particularly preferred.

The "4- to 8-membered heterocyclic carbonyl" for R40 above is a carbonyl group having the aforementioned "4- to 8-membered heterocyclic group" bonded thereto, among which piperidin-1-ylcarbonyl or morpholin-4-ylcarbonyl is preferred.

As examples of "C2-7 alkoxycarbonyl" for R40 above there may be mentioned the same one listed above, among which methoxycarbonyl or ethoxycarbonyl is preferred.

The "C1-6 alkylsulfonyl" for R40 above is a sulfonyl group having the aforementioned "C1-6 alkyl" bonded thereto, as examples there may be mentioned straight-chain or branched-chain groups such as methylsulfonyl, ethylsulfonyl, propylsulfonyl, isopropylsulfonyl, butylsulfonyl, isobutylsulfonyl, s-butylsulfonyl, t-butylsulfonyl, pentylsulfonyl, isopentylsulfonyl, 2-methylbutylsulfonyl, neopentylsulfonyl, 1-ethylpropylsulfonyl, hexylsulfonyl, isohexylsulfonyl, 4-methylpentylsulfonyl, 3-methylpentylsulfonyl, 2-methylpentylsulfonyl, 1-methylpentylsulfonyl, 3,3-dimethylbutylsulfonyl, 2,2-dimethylbutylsulfonyl, 1,1-dimethylbutylsulfonyl, 1,2-dimethylbutylsulfonyl, 1,3-dimethylbutylsulfonyl, 2,3-dimethylbutylsulfonyl, 1-ethylbutylsulfonyl or 2-ethylbutylsulfonyl, among which propylsulfonyl is preferred.

As examples of the "halogen" of Group A1, there may be mentioned the same ones listed above, among which bromine, fluorine or chlorine is preferred.

As examples of the "C1-6 alkoxy" of Group A1, there may be mentioned the same ones listed above, among which C1-4 groups are preferred, and methoxy is particularly preferred.

As examples of the "C1-6 alkyl" of Group A1 and Group A2, there may be mentioned the same ones listed above, among which C1-4 groups are preferred, and methyl, ethyl, n-butyl or t-butyl is particularly preferred.

The "C1-6 haloalkyl" of Group A1 and Group A2 is aforementioned "C1-6 alkyl" having 1 to 6 aforementioned "halogen" bonded thereto, as examples there may be mentioned straight-chain or branched-chain alkyl groups such as methyl, ethyl, n-propyl, isopropyl, n-butyl, isobutyl, s-butyl, t-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl or 2-ethylbutyl, having fluorine or chlorine bonded thereto, among which C1-4 alkyl having 1 to 3 fluorine or chlorine bonded thereto is preferred, and trifluoromethyl is particularly preferred.

As examples of the "C2-7 alkylene", where C2-7 alkylene is permissible only in the case that a spiro union is formed together with the substituted 5- to 10-membered cycloalkyl or the substituted 5- to 10-membered cycloalkenyl, of Group A1 and Group A2, there may be mentioned straight-chain or branched-chain groups such as 1,2-ethylene, trimethylene, propylene, ethylethylene, tetramethylene, pentamethylene, hexamethylene or heptamethylene, among which 1,2-ethylene, tetramethylene or pentamethylene is preferred.

As examples of the "halogen" of Group B1, there may be mentioned the same ones listed above, among which fluorine or chlorine is preferred.

As examples of the "C2-7 alkoxycarbonyl" of Group B1, there may be mentioned the same ones listed above, among which methoxycarbonyl or ethoxycarbonyl is preferred.

As examples of the "halogen" of Group C1, there may be mentioned the same ones listed above, among which bromine, fluorine or chlorine is preferred.

As examples of the "C1-6 alkyl" of Group C1 and Group C2, there may be mentioned the same ones listed above, among which C1-4 groups are preferred, and methyl is particularly preferred.

As examples of the "C1-6 alkoxy" of Group C1 and Group C2, there may be mentioned the same ones listed above, among which C1-4 groups are preferred, and methoxy, ethoxy or isopropoxy is particularly preferred.

As examples of the "halogen" of Group D1 and Group D2, there may be mentioned the same ones listed above, among which fluorine or chlorine is preferred.

As examples of the "C1-6 alkoxy" of Group D1 and Group D2, there may be mentioned the same ones listed above, among which C1-4 groups are preferred, and methoxy or ethoxy is particularly preferred.

The "C1-6 alkylthio" of Group D1 is a thio group having the aforementioned "C1-6 alkyl" bonded thereto, and as examples there may be mentioned straight-chain or branched-chain groups such as methylthio, ethylthio, propylthio, isopropylthio, butylthio, isobutylthio, s-butylthio, t-butylthio, pentylthio, isopentylthio, 2-methylbutylthio, neopentylthio, 1-ethylpropylthio, hexylthio, isohexylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio, 1-ethylbutylthio or 2-ethylbutylthio, among which C1-4 groups are preferred and methylthio or ethylthio is particularly preferred.

As examples of the "C1-6 alkylsulfonyl" of Group D1 there may be mentioned the same ones listed above, among which C1-4 groups are preferred, and methylsulfonyl or ethylsulfonyl is particularly preferred.

The "C1-6 alkyl sulfinyl" of Group D1 is a sulfinyl group having the aforementioned "C1-6 alkyl" bonded thereto, as examples there may be mentioned straight-chain or branched-chain groups such as methylsulfinyl, ethylsulfinyl, propylsulfinyl, isopropylsulfinyl, butylsulfinyl, isobutylsulfinyl, s-butylsulfinyl, t-butylsulfinyl, pentylsulfinyl, isopentylsulfinyl, 2-methylbutylsulfinyl, neopentylsulfinyl, 1-ethylpropylsulfinyl, hexylsulfinyl, isohexylsulfinyl, 4-methylpentylsulfinyl, 3-methylpentylsulfinyl, 2-methylpentylsulfinyl, 1-methylpentylsulfinyl, 3,3-dimethylbutylsulfinyl, 2,2-dimethylbutylsulfinyl, 1,1-dimethylbutylsulfinyl, 1,2-dimethylbutylsulfinyl, 1,3-dimethylbutylsulfinyl, 2,3-dimethylbutylsulfinyl, 1-ethylbutylsulfinyl or 2-ethylbutylsulfinyl, among which C1-4 groups are preferred, and methylsulfinyl or ethylsulfinyl is particularly preferred.

As examples of the "mono(C1-6 alkyl)amino" of Group D1 there may be mentioned the same ones listed above, among which methylamino or ethylamino is preferred, and methylamino is particularly preferred.

As examples of the "di(C1-6 alkyl)amino" of Group D1 there may be mentioned the same ones listed above, among which dimethylamino, methylethylamino or diethylamino is preferred, and dimethylamino is particularly preferred.

The "C2-7 alkylcarbonylamino" of Group D1 is an amino group having the aforementioned "C2-7 alkylcarbonyl" bonded thereto, and as examples there may be mentioned straight-chain or branched-chain groups such as acetylamino, ethylcarbonylamino, n-propylcarbonyl amino, isopropylcarbonylamino, n-butylcarbonylamino, isobutylcarbonylamino, s-butylcarbonylamino, t-butylcarbonylamino, pentylcarbonylamino, isopentylcarbonylamino, 2-methylbutylcarbonylamino, neopentylcarbonylamino, 1-ethylpropylcarbonylamino, hexylcarbonylamino, isohexylcarbonylamino, 4-methylpentylcarbonylamino, 3-methylpentylcarbonylamino, 2-methylpentylcarbonylamino, 1-methylpentylcarbonylamino, 3,3-dimethylbutylcarbonylamino, 2,2-dimethylbutylcarbonylamino, 1,1-dimethylbutylcarbonylamino, 1,2-dimethylbutylcarbonylamino, 1,3-dimethylbutylcarbonylamino, 2,3-dimethylbutylcarbonylamino, 1-ethylbutylcarbonylamino or 2-ethylbutylcarbonylamino, among which amino groups having C2-5 alkylcarbonyl bonded thereto are preferred, and acetylamino or ethylcarbonylamino is particularly preferred.

As examples of the "3- to 8-membered cycloalkyl" of "3- to 8-membered cycloalkyl optionally substituted with a substituent selected from Group H1" of Group D1 and the "3- to 8-membered cycloalkyl" of Group D2, there may be mentioned the same ones listed above, among which cyclopropyl, cyclobutyl, cyclopentyl or cyclohexyl is preferred, cyclopropyl or cyclobutyl is more preferred, and cyclopropyl is most preferred.

As examples of the "C2-7 alkoxycarbonyl" of Group D1 there may be mentioned the same ones listed above, among which methoxycarbonyl or ethoxycarbonyl is preferred.

As examples of the "4- to 8-membered heterocyclic group" of Group D1 and Group D2, there may be mentioned the same ones listed above, among which a tetrahydropyran ring group or a tetrahydrofuran ring group is preferred, and tetrahydropyran-4-yl is particularly preferred.

As examples of the "5- to 10-membered heteroaryl ring group" of Group D1, there may be mentioned the same ones listed above, among which furyl, thienyl, pyridyl, pyrazyl, pyrimidinyl or pyridazinyl is preferred, and furyl, thienyl or pyridyl is particularly preferred.

The "6- to 10-membered aryl ring group" of Group D1 is aromatic hydrocarbon ring group of 6 to 10 carbon (with regard to fused rings, at least one of the rings are aromatic), as examples there may be mentioned phenyl, 1-naphthyl, 2-naphthyl, indenyl, indanyl, azulenyl or heptalenyl, among which phenyl, 1-naphthyl or 2-naphthyl is preferred, and phenyl is particularly preferred.

As examples of the "C2-7 alkylcarbonyl" of Group D1 and Group D2, there may be mentioned the same ones listed above, among which C2-5 groups are preferred, and acetyl or ethylcarbonyl is particularly preferred.

The "6- to 10-membered aryl ring carbonyl group" of Group D1 is a carbonyl group having the aforementioned "6- to 10-membered aryl ring group" bonded thereto, and as examples there may be mentioned benzoyl, 1-naphthoyl, 2-naphthoyl, indenylcarbonyl, indanylcarbonyl, azulenylcarbonyl or heptalenylcarbonyl, among which benzoyl, 1-naphthoyl or 2-naphthoyl is preferred, and benzoyl is particularly preferred.

As examples of the "mono(C1-6 alkyl)aminocarbonyl" of "mono(C1-6 alkyl)aminocarbonyl optionally substituted with halogen" for Group D1 and the "mono(C1-6 alkyl)aminocarbonyl" of Group D2, there may be mentioned the same ones listed above, among which C2-5 groups are preferred, methylaminocarbonyl, ethylaminocarbonyl, propylaminocarbonyl, isopropylaminocarbonyl or butylaminocarbonyl is more preferred, and methylaminocarbonyl, ethylaminocarbonyl, propylaminocarbonyl or isopropylaminocarbonyl is most preferred.

As examples of the "mono(3- to 8-membered cycloalkyl)aminocarbonyl" of Group D1, there may be mentioned cyclopropylaminocarbonyl, cyclobutylaminocarbonyl, cyclopentylaminocarbonyl, cyclohexylaminocarbonyl, cycloheptylaminocarbonyl or cyclooctylaminocarbonyl, among which cyclopropylaminocarbonyl, cyclobutylaminocarbonyl, cyclopentylaminocarbonyl or cyclohexylaminocarbonyl is preferred, and cyclopropylaminocarbonyl is particularly preferred.

The "mono(C2-7 alkoxyalkyl)aminocarbonyl" of Group D1 is an aminocarbonyl group having "C2-7 alkoxyalkyl" bonded thereto, where "C2-7 alkoxyalkyl" is aforementioned "C1-6 alkyl" having the aforementioned "C1-6 alkoxy" bonded thereto in the range of C2-7. As examples of "mono(C2-7 alkoxyalkyl)aminocarbonyl" there may be mentioned methoxymethylaminocarbonyl, methoxyethylaminocarbonyl, ethoxyethylaminocarbonyl, methoxypropylaminocarbonyl or propoxyethylaminocarbonyl, among which methoxyethylaminocarbonyl is preferred.

The "di(C1-6 alkyl)aminocarbonyl" of Group D1 and Group D2 is a carbonyl group having the aforementioned "di(C1-6 alkyl)amino" bonded thereto, and as examples there may be mentioned straight-chain or branched-chain groups such as dimethylaminocarbonyl, methylethylaminocarbonyl, diethylaminocarbonyl, methylpropylaminocarbonyl, ethylpropylaminocarbonyl, dipropylaminocarbonyl, diisopropylaminocarbonyl, dibutylaminocarbonyl, diisobutylaminocarbonyl, di(s-butyl)aminocarbonyl, di(t-butyl)aminocarbonyl, methylpentylaminocarbonyl, dipentylaminocarbonyl, diisopentylaminocarbonyl, di(2-methylbutyl)aminocarbonyl, di(neopentyl)aminocarbonyl, di(1-ethylpropyl)aminocarbonyl, dihexylaminocarbonyl, methylisohexylaminocarbonyl, diisohexylaminocarbonyl, di(4-methylpentyl)aminocarbonyl, di(3-methylpentyl)aminocarbonyl, di(2-methylpentyl) aminocarbonyl, di(1-methylpentyl)aminocarbonyl, di(3,3-dimethylbutyl)aminocarbonyl, di(2,2-dimethylbutyl) aminocarbonyl, di(1,1-dimethylbutyl)aminocarbonyl, di(1, 2-dimethylbutyl)aminocarbonyl, di(1,3-dimethylbutyl) aminocarbonyl, di(2,3-dimethylbutyl)aminocarbonyl, di(1-ethylbutyl)aminocarbonyl or di(2-ethylbutyl) aminocarbonyl, among which dimethylaminocarbonyl, methylethylaminocarbonyl or diethylaminocarbonyl is preferred, and dimethylaminocarbonyl is particularly preferred.

The "mono(5- to 10-membered heteroaryl ring)aminocarbonyl" of Group D1 is a group obtained by substituting one hydrogen of aminocarbonyl (carbamoyl) with the aforementioned "5- to 10-membered heteroaryl ring" group, where as examples of the "5- to 10-membered heteroaryl ring" there may be mentioned a pyridine ring, a thiophene ring, a furan ring, a pyrrole ring, a oxazole ring, a isoxazole ring, a thiazole ring, a thiadiazole ring, an isothiazole ring, an imidazole ring, a triazole ring, a tetrazole ring, a pyrazole ring, a furazan ring, a thiadiazole ring, an oxadiazole ring, a pyridazine ring, a pyrimidine ring, a pyrazine ring, a triazine ring, an indole ring, an isoindole ring, an indazole ring, a quinoline ring, an isoquinoline ring, a cinnoline ring, a quinazoline ring, a quinoxaline ring, a naphthylidine ring, a phthalazine ring, a purine ring, a pteridine ring, a thienofuran ring, an imidazothiazole ring, a benzofuran ring, a benzothiophene ring, a benzoxazole ring, a benzothiazole ring, a benzothiadiazole ring, a benzimidazole ring, an imidazopyridine ring, a pyrrolopyridine ring, a pyrrolopyrimidine ring, a pyridopyrimidine ring, a coumarane ring, a chromene ring, a chroman ring, a isochroman ring, a indoline ring or a isoindoline ring. Preferable mono(5- to 10-membered heteroaryl ring)aminocarbonyl is pyridine-2-ylaminocarbonyl.

As examples of the "4- to 8-membered heterocyclic carbonyl" of "4- to 8-membered heterocyclic carbonyl optionally substituted with C1-6 alkyl" for Group D1 and "4- to 8-membered heterocyclic carbonyl" of Group D2, there may be mentioned the same ones listed above, among which pyrrolidin-1-ylcarbonyl, azepan-1-ylcarbonyl, azocan-1-ylcarbonyl, piperidin-1-ylcarbonyl or morpholin-4-ylcarbonyl is preferred, and pyrrolidin-1-ylcarbonyl, piperidin-1-ylcarbonyl or morpholin-4-ylcarbonyl is particularly preferred.

The "5- to 10-membered heteroaryl ring carbonyl" of Group D1 is a carbonyl group having the aforementioned "5- to 10-membered heteroaryl ring group" bonded thereto.

The "5-membered heteroaryl ring group" of Group D2 is a group, the number of atoms constituting the ring is 5 in the aforementioned "5- to 10-membered heteroaryl ring group", as examples there may be mentioned thienyl, furyl, pyrrolyl, oxazolyl, isoxazolyl, thiazolyl, thiadiazolyl, isothiazolyl, imidazolyl, triazolyl, pyrazolyl, furazanyl or oxadiazolyl, among which thienyl or furyl is preferred.

As examples of the "halogen" of Group E1 there may be mentioned the same ones listed above, among which bromine, fluorine or chlorine is preferred.

As examples of the "C1-6 alkoxy" of Group E1 there may be mentioned the same ones listed above, among which C1-4 groups are preferred, and methoxy is particularly preferred.

As examples of the "C1-6 alkyl" of Group E1 there may be mentioned the same ones listed above, among which C1-4 groups are preferred, and methyl is particularly preferred.

As examples of the "halogen" of Group F1 there may be mentioned the same ones listed above, among which fluorine or chlorine is preferred.

As examples of the "C1-6 alkoxy" of Group F1 there may be mentioned the same ones listed above, among which C1-4 groups are preferred, and methoxy is particularly preferred.

As examples of the "3- to 8-membered cycloalkyl" of Group G1 there may be mentioned the same ones listed above, among which cyclohexyl or cyclopropyl is preferred.

As examples of the "C1-6 haloalkyl" of Group H1 there may be mentioned the same ones listed above, among which chloromethyl or fluoromethyl is particularly preferred.

As examples of the "C1-6 alkyl" of Group H1 there may be mentioned the same ones listed above, among which C1-4 groups are preferred, and methyl is particularly preferred.

As examples of the "C2-7 alkoxyalkyl" of Group H1 there may be mentioned the same ones listed above, among which methoxymethyl is preferred.

As examples of the "mono(C1-6 alkyl)aminocarbonyl" of Group H1 there may be mentioned the same ones listed above, among which methylaminocarbonyl is preferred.

As examples of the "di(C1-6 alkyl)aminocarbonyl" of Group H1 there may be mentioned the same ones listed above, among which dimethylaminocarbonyl or diethylaminocarbonyl is preferred, and dimethylaminocarbonyl is particularly preferred.

As examples of the "C2-7 alkoxycarbonyl" of Group H1 there may be mentioned the same ones listed above, among which methoxycarbonyl or ethoxycarbonyl is preferred.

The "C2-7 cyanoalkyl" of H1 is an aforementioned "C1-6 alkyl" having cyano group bonded thereto, as examples there may be mentioned straight-chain or branched-chain alkyl groups such as methyl, ethyl, n-propyl, isopropyl, n-butyl, isobutyl, s-butyl, t-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl or 2-ethylbutyl having cyano group bonded thereto, among which C1-4 alkyl having cyano group bonded thereto is preferred, and cyanomethyl is particularly preferred.

The term "optionally substituted with a substituent" as used herein has the same meaning as "optionally substituted with 1-6 substituents of 1 or 2 or more kinds at any desired combination at substitutable positions", so long as the number and kind of substituents is not particularly restricted.

Several of the structural formulas for the compounds throughout the present specification represent only one isomeric form for convenience, but the invention encompasses any and all of the geometric isomers as well as optical isomers based on asymmetric carbons, stereoisomers and tautomers, and mixtures of those isomers, which are implied by the structures of the compounds, without being limited to any of the formulas shown for convenience. The compounds of the invention therefore include all those having asymmetric carbons therein and existing in optically active or racemic form, with no particular restrictions on the invention. There are also no restrictions when polymorphic crystalline forms thereof exist, and the compounds may be in one crystalline form or a mixture of different crystalline forms, while anhydrides and hydrates of the compounds of the invention are also included. Also encompassed within the scope of the invention are metabolites of the compounds (1) and (100) of the invention, produced by decomposition of the compounds in vivo. In addition, the invention further encompasses compounds which are metabolized in vivo by oxidation, reduction, hydrolysis, conjugation or the like to produce the compounds (1) and (100) of the invention (i.e., "prodrugs").

The term "salt" as used herein is not particularly restricted so long as a salt is formed with a compound of the invention, and the salt is pharmacologically acceptable, and as examples there may be mentioned inorganic acid salts, organic acid salts, inorganic base salts, organic base salts, and acidic or basic amino acid salts.

As preferred examples of inorganic acid salts there may be mentioned hydrochloride, hydrobromide, sulfate, nitrate and phosphate, and as preferred examples of organic acid salts there may be mentioned acetate, succinate, fumarate, maleate, tartarate, citrate, lactate, stearate, benzoate, methanesulfonate, ethanesulfonate, benzenesulfonate and p-toluenesulfonate.

As preferred examples of inorganic base salts there may be mentioned alkali metal salts such as sodium salts and potassium salts, alkaline earth metal salts such as calcium salts and magnesium salts, and aluminum or ammonium salts, and as preferred examples of organic base salts there may be mentioned diethylamine salts, diethanolamine salts, meglumine salts and N,N'-dibenzylethylenediamine salts.

As preferred examples of acidic amino acid salts there may be mentioned aspartate and glutamate, and as preferred examples of basic amino acid salts there may be mentioned arginine salts, lysine salts and ornithine salts.

Preferred compounds according to the invention include the following compounds.

(2) the compound, the salt thereof or the hydrate of the foregoing, wherein R10 represents 5- to 10-membered cycloalkyl optionally substituted with a substituent selected from Group A2, or 5- to 10-membered cycloalkenyl optionally substituted with a substituent selected from Group A2, wherein Group A2 consists of hydroxyl, phenyl, C1-6 alkyl, C1-6 haloalkyl and C2-7 alkylene, where C2-7 alkylene is permissible only in the case that a spiro union is formed together with the substituted 5- to 10-membered cycloalkyl or the substituted 5- to 10-membered cycloalkenyl.

(3) the compound, the salt thereof or the hydrate of the foregoing, wherein R10 represents 5- to 10-membered cycloalkyl optionally substituted with hydroxyl, phenyl, C1-6 alkyl, C1-6 haloalkyl, 1,2-ethylene, trimethylene, tetramethylene or pentamethylene, or 5- to 10-membered cycloalkenyl optionally substituted with hydroxyl, phenyl, C1-6 alkyl, C1-6 haloalkyl, 1,2-ethylene, trimethylene, tetramethylene or pentamethylene, where 1,2-ethylene, trimethylene, tetramethylene or pentamethylene is permissible only in the case that a spiro union is formed together with the substituted 5- to 10-membered cycloalkyl or the substituted 5- to 10-membered cycloalkenyl.

(4) the compound, the salt thereof or the hydrate of the foregoing, wherein R10 represents cyclohexyl, 4-t-butylcyclohexyl, 4,4-dimethylcyclohexyl, 4,4-dimethylcyclohexyl, 3,3,5,5-tetramethylcyclohexyl, 3,5-dimethylcyclohexyl, 4-phenylcyclohexyl, 4-trifluoromethylcyclohexyl, 4-n-butylcyclohexyl, cyclopentyl, 3,3,4,4-tetramethylcyclopentyl, cycloheptyl, cyclooctyl or a group represented by the formula:

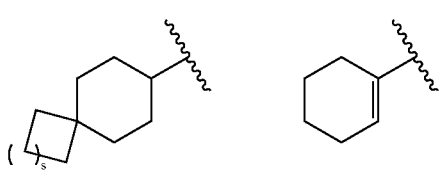

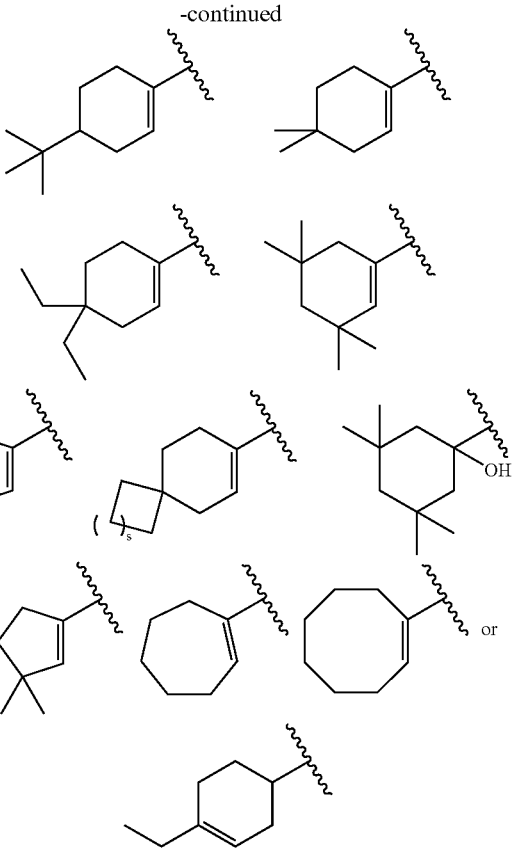

wherein s represents an integer of 0, 1, 2 or 3.

(4-1) the compound, the salt thereof or the hydrate of the foregoing, wherein R10 represents cyclohexyl.

(4-2) the compound, the salt thereof or the hydrate of the foregoing, wherein R10 represents 4-t-butylcyclohexyl.

(4-3) the compound, the salt thereof or the hydrate of the foregoing, wherein R10 represents 4,4-dimethylcyclohexyl.

(4-4) the compound, the salt thereof, or the hydrate of the foregoing, wherein R10 represents 4,4-dimethylcyclohexyl.

(4-5) the compound, the salt thereof, or the hydrate of the foregoing, wherein R10 represents 3,3,5,5-tetramethylcyclohexyl.

(4-6) the compound, the salt thereof, or the hydrate of the foregoing, wherein R10 represents 3,5-dimethylcyclohexyl.

(4-7) the compound, the salt thereof, or the hydrate of the foregoing, wherein R10 represents 4-phenylcyclohexyl.

(4-8) the compound, the salt thereof, or the hydrate of the foregoing, wherein R10 represents 4-trifluoromethylcyclohexyl.

(4-9) the compound, the salt thereof, or the hydrate of the foregoing, wherein R10 represents 4-n-butylcyclohexyl.

(4-10) the compound, the salt thereof, or the hydrate of the foregoing, wherein R10 represents cyclopentyl.

(4-11) the compound, the salt thereof, or the hydrate of the foregoing, wherein R10 represents 3,3,4,4-tetramethylcyclopentyl.

(4-12) the compound, the salt thereof, or the hydrate of the foregoing, wherein R10 represents cycloheptyl.

(4-13) the compound, the salt thereof, or the hydrate of the foregoing, wherein R10 represents cyclooctyl.

(4-14) the compound, the salt thereof, or the hydrate of the foregoing, wherein R10 represents a group represented by the following formula:

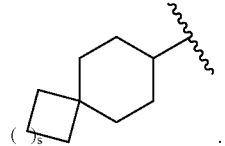

wherein s represents an integer of 0, 1, 2 or 3;

(4-15) the compound, the salt thereof or the hydrate of the foregoing, wherein R10 represents a group represented by the following formula:

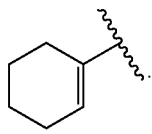

(4-16) the compound, the salt thereof or the hydrate of the foregoing, wherein R10 represents a group represented by the following formula:

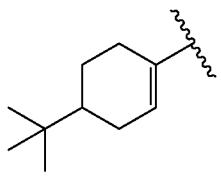

(4-17) the compound, the salt thereof or the hydrate of the foregoing, wherein R10 represents a group represented by the following formula:

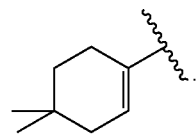

(4-18) the compound, the salt thereof or the hydrate of the foregoing, wherein R10 represents a group represented by the following formula:

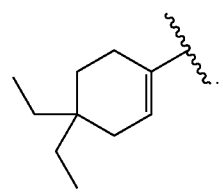

(4-19) the compound, the salt thereof or the hydrate of the foregoing, wherein R10 represents a group represented by the following formula:

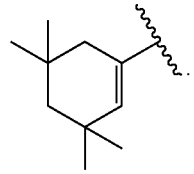

(4-20) the compound, the salt thereof or the hydrate of the foregoing, wherein R10 represents a group represented by the following formula:

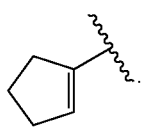

(4-21) the compound, the salt thereof or the hydrate of the foregoing, wherein R10 represents a group represented by the following formula:

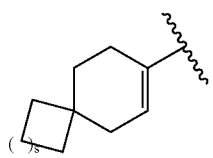

wherein s represents an integer of 0, 1, 2 or 3.

(4-22) the compound, the salt thereof or the hydrate of the foregoing, wherein R10 represents a group represented by the following formula:

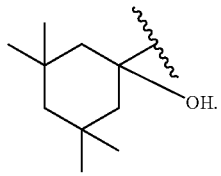

(4-23) the compound, the salt thereof or the hydrate of the foregoing, wherein R10 represents a group represented by the following formula:

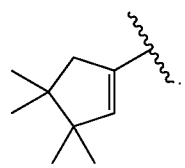

(4-24) the compound, the salt thereof or the hydrate of the foregoing, wherein R10 represents a group represented by the following formula:

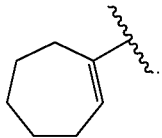

(4-25) the compound, the salt thereof or the hydrate of the foregoing, wherein R10 represents a group represented by the following formula:

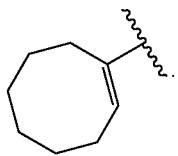

(4-26) the compound, the salt thereof or the hydrate of the foregoing, wherein R10 represents a group represented by the following formula:

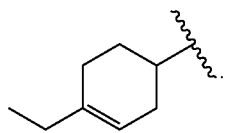

(5) the compound, the salt thereof or the hydrate of the foregoing, wherein R20, R21, R22 and R23 may be the same or different, and each represents hydrogen, hydroxyl, halogen, cyano, C2-7 alkylcarbonyl, nitro, amino, mono(C1-6 alkyl)amino, di(C1-6 alkyl)amino, C1-6 alkyl optionally substituted with a substituent selected from Group B1, C1-6 alkoxy optionally substituted with a substituent selected from Group B1, a 4- to 8-membered heterocyclic group optionally substituted with a substituent selected from Group C1 or a 5- to 6-membered heteroaryl ring group optionally substituted with a substituent selected from Group C1.

(6) the compound, the salt thereof or the hydrate of the foregoing, wherein R20, R21, R22 and R23 may be the same or different, and each represents hydrogen, hydroxyl, halogen, cyano, acetyl, nitro, amino, monomethylamine, monoethylamine, dimethylamino, C1-6 alkyl optionally substituted with a substituent selected from Group B1, C1-6 alkoxy optionally substituted with a substituent selected from Group B1, a 4- to 8-membered heterocyclic group optionally substituted with a substituent selected from Group C1, where the 4- to 8-membered heterocyclic group is derived by eliminating hydrogen linked to nitrogen of a 4- to 8-membered heterocycle, or a 5- to 6-membered heteroaryl ring group optionally substituted with a substituent selected from Group C2, wherein Group C2 consists of C1-6 alkoxy and C1-6 alkyl.

(7) the compound, the salt thereof or the hydrate of the foregoing, wherein R20, R21, R22 and R23 may be the same or different and each represents hydrogen, halogen, cyano, acetyl, monomethylamine, monoethylamine, dimethylamino, methyl, methoxy, ethoxy, morpholin-4-yl optionally substituted with a substituent selected from Group C2, piperidin-1-yl optionally substituted with a substituent selected from Group C2, pyrrolidin-1-yl optionally substituted with a substituent selected from Group C2, azetidin-1-yl, pyridin-2-yl or pyridin-3-yl.

(8) the compound, the salt thereof or the hydrate of the foregoing, wherein at least two of R20, R21, R22 and R23 are hydrogen, and the remaining groups, which may be the same or different, are hydrogen, halogen, cyano, acetyl, monomethylamine, monoethylamine, dimethylamino, methyl, methoxy, ethoxy, morpholin-4-yl optionally substituted with a substituent selected from Group C2, piperidin-1-yl optionally substituted with a substituent selected from Group C2, pyrrolidin-1-yl optionally substituted with a substituent selected from Group C2, azetidin-1-yl, pyridin-2-yl or pyridin-3-yl.

(9) the compound, the salt thereof or the hydrate of the foregoing, wherein three of R20, R21, R22 and R23 are hydrogen, and the remaining group is hydrogen, fluorine, cyano, dimethylamino, methyl, methoxy, morpholin-4-yl optionally substituted with a substituent selected from Group C3, piperidin-1-yl optionally substituted with a substituent selected from Group C3 or pyrrolidin-1-yl optionally substituted with a substituent selected from Group C3, wherein Group C3 consists of methoxy, ethoxy and methyl.

(9-1) the compound, the salt thereof or the hydrate of the foregoing, wherein at least three of R20, R21, R22 and R23 represent hydrogen, and the remaining group represents fluorine.

(9-2) the compound, the salt thereof or the hydrate of the foregoing, wherein at least three of R20, R21, R22 and R23 represent hydrogen, and the remaining group represents cyano.

(9-3) the compound, the salt thereof or the hydrate of the foregoing, wherein at least three of R20, R21, R22 and R23 represent hydrogen, and the remaining group represents dimethylamino.

(9-4) the compound, the salt thereof or the hydrate of the foregoing, wherein at least three of R20, R21, R22 and R23 represent hydrogen, and the remaining group represents methyl.

(9-5) the compound, the salt thereof or the hydrate of the foregoing, wherein at least three of R20, R21, R22 and R23 represent hydrogen, and the remaining group represents methoxy.

(9-6) the compound, the salt thereof or the hydrate of the foregoing, wherein at least three of R20, R21, R22 and R23 represent hydrogen, and the remaining group represents morpholin-4-yl optionally substituted with a substituent selected from Group C2.

(9-7) the compound, the salt thereof or the hydrate of the foregoing, wherein at least three of R20, R21, R22 and R23 represent hydrogen, and the remaining group represents piperidin-1-yl optionally substituted with a substituent selected from Group C2.

(9-8) the compound, the salt thereof or the hydrate of the foregoing, wherein at least three of R20, R21, R22 and R23 represent hydrogen, and the remaining group represents pyrrolidin-1-yl optionally substituted with a substituent selected from Group C2.

(9-9) the compound, the salt thereof or the hydrate of the foregoing, wherein all of R20, R21, R22 and R23 represent hydrogen.

(10) the compound, the salt thereof or the hydrate of the foregoing, wherein R30, R31 and R32 may be the same or different, and each represents hydrogen or C1-6 alkyl, or R30 and R31 bond together to form oxo (═O) and R32 represents hydrogen or C1-6 alkyl.

(11) the compound, the salt thereof or the hydrate of the foregoing, wherein R30, R31 and R32 may be the same or different, and each represents hydrogen or methyl, or R30 and R31 bond together to form oxo (=O) and R32 represents hydrogen or methyl.

(12) the compound, the salt thereof or the hydrate of the foregoing, wherein all of R30, R31 and R32 represent hydrogen.

(13) the compound, the salt thereof or the hydrate of the foregoing, wherein R40 represents C1-6 alkyl optionally substituted with a substituent selected from Group D1,3- to 8-membered cycloalkyl optionally substituted with a substituent selected from Group E1, C2-7 alkenyl, C2-7 alkynyl or C2-7 alkylcarbonyl.

(14) the compound, the salt thereof or the hydrate of the foregoing, wherein R40 represents C1-6 alkyl optionally substituted with a substituent selected from Group D2, wherein Group D2 consists of hydroxyl, halogen, cyano, C1-6 alkoxy, 3- to 8-membered cycloalkyl, a 4- to 8-membered heterocyclic group, mono(C1-6 alkyl)aminocarbonyl, di(C1-6 alkyl)aminocarbonyl, C2-7 alkylcarbonyl, a 5-membered heteroaryl ring group, 4- to 8-membered heterocyclic carbonyl or phenyl.

(15) the compound, the salt thereof or the hydrate of the foregoing, wherein R40 represents n-propyl, n-butyl, n-pentyl, isobutyl, ethylcarbonylmethyl, methoxyethyl, ethoxyethyl, cyclopropylmethyl or tetrahydropyran-4-ylmethyl.

(15-1) the compound, the salt thereof or the hydrate of the foregoing, wherein R40 represents n-propyl.

(15-2) the compound, the salt thereof or the hydrate of the foregoing, wherein R40 represents n-butyl.

(15-3) the compound, the salt thereof or the hydrate of the foregoing, wherein R40 represents n-pentyl.

(15-4) the compound, the salt thereof or the hydrate of the foregoing, wherein R40 represents isobutyl.

(15-5) the compound, the salt thereof or the hydrate of the foregoing, wherein R40 represents ethylcarbonylmethyl.

(15-6) the compound, the salt thereof or the hydrate of the foregoing, wherein R40 represents methoxyethyl.

(15-7) the compound, the salt thereof or the hydrate of the foregoing, wherein R40 represents ethoxyethyl.

(15-8) the compound, the salt thereof or the hydrate of the foregoing, wherein R40 represents cyclopropylmethyl.

(15-9) the compound, the salt thereof or the hydrate of the foregoing, wherein R40 represents tetrahydropyran-4-ylmethyl;

(16) the compound, the salt thereof or the hydrate of the foregoing, wherein n represents an integer of 1.

(17) the compound, the salt thereof or the hydrate of the foregoing, wherein X1 represents nitrogen (only in the case of the compound represented by the formula (1)).

Also preferable is a compound, a salt thereof or a hydrate of the foregoing, which are obtained by any combination of:
R10 selected from (2) to (4) and (4-1) to (4-26) above,
R20, R21, R22 and R23 selected from (5) to (9) and (9-1) to (9-9) above,
R30, R31 and R32 selected from (10) to (12) above,
R40 selected from (14) to (15) and (15-1) to (15-9) above,
n selected from (16) above, and
X1 selected from (17) above.

As preferred compounds of the invention there may be mentioned
1-[2-(4,4-dimethylcyclohexyl)-5-methoxyphenyl]-4-pentylpiperazine,
1-butyl-4-[2-(4-t-butylcyclohex-1-enyl)-4-(4-methoxypiperidin-1-yl)phenyl]piperazine,
1-butyl-4-[2-(3,3,5,5-tetramethylcyclohexyl)phenyl]piperazine,
1-cyclopropylmethyl-4-[2-(3,3,5,5-tetramethylcyclohexyl) phenyl]piperazine,
2-{4-[2-(4-t-butylcyclohexyl)phenyl]piperazin-1-yl}-N-ethylacetamide,
cis-4-(4-t-butylcyclohexyl)-3-(4-butylpiperazine-1-yl)benzonitrile,
trans-4-(4-t-butylcyclohexyl)-3-(4-butylpiperazine-1-yl) benzonitrile,
1-butyl-4-(2-cyclohexylphenyl)piperazine,
1-butyl-4-[2-(4-t-butylcyclohexyl)phenyl]piperazine,
1-{4-[2-(4,4-dimethylcyclohexyl)phenyl]piperazin-1-yl}butan-2-one,
4-[3-(4-t-butylcyclohex-1-enyl)-4-(4-butylpiperazine-1-yl) phenyl]morpholine,
1-[2-(4-t-butylcyclohexyl)phenyl]-4-(2-methoxyethyl)piperazine,
1-[2-(4-t-butylcyclohex-1-enyl)-4-(4-methoxypiperidin-1-yl)phenyl]-4-cyclopropylmethylpiperazine,
1-(tetrahydropyran-4-ylmethyl)-4-[2-(3,3,5,5-tetramethylcyclohex-1-enyl)phenyl]piperazine,
4-[4-(4-propylpiperazin-1-yl)-3-(3,3,5,5-tetramethylcyclohex-1-enyl)phenyl]morpholine,
1-{4-[2-(4,4-diethylcyclohex-1-enyl)-4-morpholin-4-ylphenyl]piperazin-1-yl}butan-2-one,
1-propyl-4-[2-(3,3,5,5-tetramethylcyclohexyl)phenyl]piperazine,
1-butyl-4-[4-(4-methoxypiperidin-1-yl)-2-(3,3,5,5-tetramethylcyclohexyl)phenyl]piperazine,
1-butyl-4-[2-(3,5-dimethylcyclohexyl)phenyl]piperazine,
1-[2-(4,4-dimethylcyclohexyl)phenyl]-4-(tetrahydropyran-4-ylmethyl)piperazine,
4-[4-(4-butylpiperazine-1-yl)-3-(3,3,5,5-tetramethylcyclohex-1-enyl)phenyl]morpholine,
4-[4-(4-butylpiperazine-1-yl)-3-(3,3,5,5-tetramethylcyclohexyl)phenyl]morpholine,
1-[4-(4-ethoxypiperidin-1-yl)-2-(3,3,5,5-tetramethylcyclohexyl)phenyl]-4-propylpiperazine,
cis-4-[4-(4-butylpiperazine-1-yl)-3-(4,4-dimethylcyclohexyl)phenyl]-2,6-dimethylmorpholine,
4-{4-(4-pentylpiperazin-1-yl)-3-spiro[2.5]oct-6-ylphenyl}morpholine,
1-[3-fluoro-2-(3,3,5,5-tetramethylcyclohex-1-enyl)phenyl]-4-propylpiperazine,
1-cyclopropylmethyl-4-[2-(3,3,5,5-tetramethylcyclohexyl) phenyl]-1,2,3,6-tetrahydropyridine,
1-butyl-4-{2-(3,3,4,4-tetramethylcyclopentyl) phenyl}piperazine,
1-butyl-4-[2-(4,4-dimethylcyclohexyl)-4-(4-ethoxypiperidin-1-yl)phenyl]piperazine,
1-butyl-4-[2-(3,3,5,5-tetramethylcyclohex-1-enyl)phenyl] piperazine,
1-cyclopropylmethyl-4-[2-(3,3,5,5-tetramethylcyclohex-1-enyl)phenyl]piperazine,
1-{4-[2-(3,3,5,5-tetramethylcyclohex-1-enyl)phenyl]piperazin-1-yl}butan-2-one,
1-(2-methoxyethyl)-4-[2-(3,3,5,5-tetramethylcyclohex-1-enyl)phenyl]piperazine,
1-{4-[2-(3,3,5,5-tetramethylcyclohexyl)phenyl]piperazin-1-yl}butan-2-one,
1-(2-methoxyethyl)-4-[2-(3,3,5,5-tetramethylcyclohexyl) phenyl]piperazine,
4-[4-(4-butylpiperazine-1-yl)-5-(4,4-dimethylcyclohexyl)-2-methoxyphenyl]-morpholine,
1-butyl-4-(2-spiro[4.5]dec-8-ylphenyl)piperazine, 1-[2-(4,4-dimethylcyclohex-1-enyl)phenyl]-4-isobutylpiperazine,
1-cyclopropylmethyl-4-[2-(4,4-dimethylcyclohexyl)-4-(4-methoxypiperidin-1-yl)phenyl]piperazine,
4-[3-(4,4-dimethylcyclohexyl)-4-(4-isobutylpiperazine-1-yl)phenyl]morpholine,
{4-[2-(3,3,5,5-tetramethylcyclohexyl)phenyl]piperazin-1-yl}acetonitrile,
1-(2-ethoxyethyl)-4-[2-(3,3,5,5-tetramethylcyclohexyl)phenyl]piperazine,
(R)-1-butyl-4-[2-(4,4-dimethylcyclohexyl)-4-(3-methoxypyrrolidin-1-yl)phenyl]piperazine,
1-[4-methyl-2-(3,3,5,5-tetramethylcyclohexyl)phenyl]-4-propylpiperazine,
1-[4-methoxy-2-(3,3,5,5-tetramethylcyclohexyl)phenyl]-4-(tetrahydropyran-4-ylmethyl)piperazine,
1-butyl-4-[2-(3,3,5,5-tetramethylcyclohexyl)phenyl]piperidine,
1-isobutyl-4-[2-(3,3,4,4-tetramethylcyclopent-1-enyl)phenyl]piperazine, and
1-[2-(4-cyclopropylmethylpiperazin-1-yl)phenyl]-3,3,5,5-tetramethylcyclohexanol.

In addition to the compounds above, the following compounds are also preferable compounds. The definitions of the terms in the following compounds are similar to those defined above.

<101> A compound represented by the following general formula, a salt thereof or a hydrate of the foregoing.

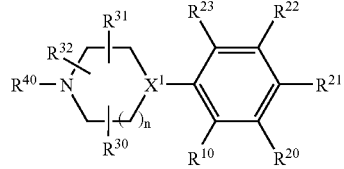

wherein R10 represents cyclohexyl optionally substituted with a substituent selected from Group A1' or cyclohexenyl optionally substituted with a substituent selected from Group A1', R20, R21, R22 and R23 may be the same or different and each represents hydrogen, hydroxyl, halogen, cyano, nitro, amino, mono(C1-6 alkyl)amino, di(C1-6 alkyl)amino, C1-6 alkyl optionally substituted with a substituent selected from Group B1', C1-6 alkoxy optionally substituted with a substituent selected from Group B1', a 4- to 8-membered heterocyclic group optionally substituted with a substituent selected from Group C1' or a 5- to 10-membered heteroaryl ring group optionally substituted with a substituent selected from Group C1', R30, R31 and R32 may be the same or different and each represents hydrogen, hydroxyl, halogen, cyano, carboxyl, C1-6 alkyl, C1-6 alkoxy or C2-7 alkoxycarbonyl, or two of R30, R31 and R32 bond together to form oxo (=O), R40 represents C1-10 alkyl optionally substituted with a substituent selected from Group D1' or 3- to 8-membered cycloalkyl, n represents an integer of 1 or 2, and X1 represents CH or nitrogen, wherein Group A1' consists of halogen, C1-6 alkyl and C2-7 alkylene, where C2-7 alkylene is permissible only in the case that a spiro union is formed together with cyclohexyl or cyclohexenyl, Group B1' consists of halogen, Group C1' consists of cyano, halogen, C1-6 alkyl and C1-6 alkoxy, and Group D1' consists of hydroxyl, halogen, cyano, C1-6 alkoxy, 3- to 8-membered cycloalkyl, a 4- to 8-membered heterocyclic group, a 5- to 10-membered heteroaryl ring group, C2-7 alkylcarbonyl, mono(C1-6 alkyl)aminocarbonyl, di(C1-6 alkyl)aminocarbonyl, 4- to 8-membered heterocyclic carbonyl and 5- to 10-membered heteroaryl ring carbonyl.

<102> The compound according to <101>, the salt thereof or the hydrate of the foregoing, wherein R10 represents cyclohexyl optionally substituted with a substituent selected from Group A2', or cyclohexenyl optionally substituted with a substituent selected from Group A2', wherein Group A2' consists of C1-6 alkyl and C2-7 alkylene, where C2-7 alkylene is permissible only in the case that a spiro union is formed together with cyclohexyl or cyclohexenyl.

<103> The compound according to <101>, the salt thereof or the hydrate of the foregoing, wherein R10 represents cyclohexyl optionally substituted with C1-6 alkyl, 1,2-ethylene, trimethylene, tetramethylene or pentamethylene, or cyclohexenyl optionally substituted with C1-6 alkyl, 1,2-ethylene, trimethylene, tetramethylene or pentamethylene, where 1,2-ethylene, trimethylene, tetramethylene or pentamethylene is permissible only in the case that a spiro union is formed together with cyclohexyl or cyclohexenyl.

<104> The compound according to <101>, the salt thereof or the hydrate of the foregoing, wherein R10 represents cyclohexyl, 4-(t-butyl)cyclohexyl, 4,4-dimethylcyclohexyl, 4,4-dimethylcyclohexyl, 3,3,5,5-tetramethylcyclohexyl, or a group represented by the formula:

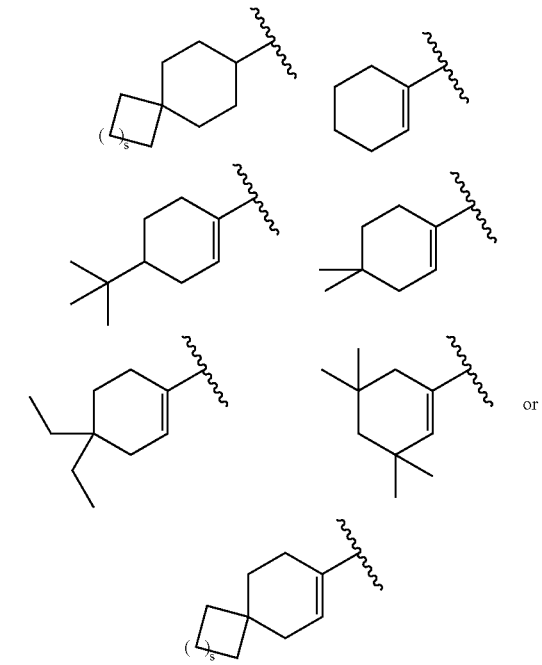

wherein s represents an integer of 0-3.

<105> The compound according to any one of <101> to <104>, the salt thereof or the hydrate of the foregoing, wherein R20, R21, R22 and R23 may be the same or different, and each represents hydrogen, halogen, cyano, amino, mono(C1-6 alkyl)amino, di(C1-6 alkyl)amino, C1-6 alkyl optionally substituted with fluorine, C1-6 alkoxy optionally substituted with fluorine, or a 4- to 8-membered heterocyclic group optionally substituted with a substituent selected from Group C2', wherein Group C2' consists of C1-6 alkoxy and C1-6 alkyl.

<106> The compound according to any one of <101> to <104>, the salt thereof or the hydrate of the foregoing, wherein R20, R21, R22 and R23 may be the same or different, and each represents hydrogen, halogen, cyano, amino, monomethylamino, dimethylamino, methyl, methoxy, morpholino optionally substituted with a substituent selected from Group C2' or piperidino optionally substituted with a substituent selected from Group C2', wherein Group C2' consists of C1-6 alkoxy and C1-6 alkyl.

<107> The compound according to any one of <101> to <104>, the salt thereof or the hydrate of the foregoing, wherein at least three of R20, R21, R22 and R23 are hydrogen, and the remaining group is hydrogen, halogen, methoxy or cyano.

<108> The compound according to any one of <101> to <107>, the salt thereof or the hydrate of the foregoing, wherein R30, R31 and R32 may be the same or different, and each represents hydrogen or C1-6 alkyl, or R30 and R31 bond together to form oxo (═O) and R32 represents hydrogen or C1-6 alkyl.

<109> The compound according to any one of <101> to <107>, the salt thereof or the hydrate of the foregoing, wherein R30, R31 and R32 may be the same or different, and each represents hydrogen or methyl, or R30 and R31 bond together to form oxo (═O) and R32 represents hydrogen or methyl.

<110> The compound according to any one of <101> to <107>, the salt thereof or the hydrate of the foregoing, wherein all of R30, R31 and R32 represent hydrogen.

<111> The compound according to any one of <101> to <110>, the salt thereof or the hydrate of the foregoing, wherein R40 represents C1-6 alkyl optionally substituted with a substituent selected from Group D2', wherein Group D2' consists of C1-6 alkoxy, 3- to 8-membered cycloalkyl, a 4- to 8-membered heterocyclic group, cyano, mono(C1-6 alkyl)aminocarbonyl, C2-7 alkylcarbonyl and 4- to 8-membered heterocyclic carbonyl.

<112> The compound according to any one of <101> to <110>, the salt thereof or the hydrate of the foregoing, wherein R40 represents C1-6 alkyl optionally substituted with a substituent selected from Group D3', wherein Group D3' consists of methoxy, ethoxy, cyclopropyl, cyano, ethylaminocarbonyl, n-propylaminocarbonyl, ethylcarbonyl, piperidinocarbonyl and 4-tetrahydropyranyl.

<113> The compound according to any one of <101> to <110>, the salt thereof or the hydrate of the foregoing, wherein R40 represents n-propyl, n-butyl, n-pentyl, ethylcarbonylmethyl, methoxyethyl, ethoxyethyl, cyclopropylmethyl or 4-tetrahydropyranylmethyl.

<114> The compound according to any one of <101> to <113>, the salt thereof or the hydrate of the foregoing, wherein n represents an integer of 1.

<115> The compound according to any one of <101> to <114>, the salt thereof or the hydrate of the foregoing, wherein X1 represents nitrogen.

<117> A medicament comprising the compound according to <101>, the salt thereof or the hydrate of the foregoing.

<118> A cell adhesion inhibitor or cell infiltration inhibitor comprising the compound according to <101>, the salt thereof or the hydrate of the foregoing.

<119> A therapeutic or prophylactic agent for inflammatory bowel disease, rheumatoid arthritis, psoriasis, multiple sclerosis, asthma or atopic dermatitis, comprising the compound according to <101>, the salt thereof or the hydrate of the foregoing.

<120> A therapeutic or prophylactic agent for an inflammatory bowel disease, comprising the compound according to <101>, the salt thereof or the hydrate of the foregoing.

<121> A therapeutic or prophylactic agent for ulcerative colitis or Crohn's disease, comprising the compound according to <101>, the salt thereof or the hydrate of the foregoing.

The compounds of the invention have excellent cell adhesion inhibitory action or cell infiltration inhibitory action, and are therefore useful as therapeutic or prophylactic agents for inflammatory diseases and autoimmune diseases, particularly as therapeutic or prophylactic agents for various diseases associated with adhesion and infiltration of leukocytes, such as inflammatory bowel disease (particularly ulcerative colitis or Crohn's disease), irritable bowel syndrome, rheumatoid arthritis, psoriasis, multiple sclerosis, asthma and atopic dermatitis.

BEST MODE FOR CARRYING OUT THE INVENTION

The compounds (1) and (100) of the invention may be produced by the methods described below. However, it is to be understood that the production methods for the compounds of the invention are not limited to those described below.

Compound (1) according to the invention may be produced by the following Method A, Method B, Method C, Method D, Method E, Method N, Method P or Method V.

Compound (1A), the compound (1) according to the invention wherein X1 is nitrogen may be produced by the following Method F, Method G Method H, Method K, Method M, Method Q or Method R.

Compound (1B), the compound (1) according to the invention wherein X1 is a group of the formula CH, and Compound (100) of the invention may be produced by the following Method A, Method B, Method C, Method D, Method E, Method K, Method M, Method S, Method T or Method U.

Each of these methods will now be explained in detail.

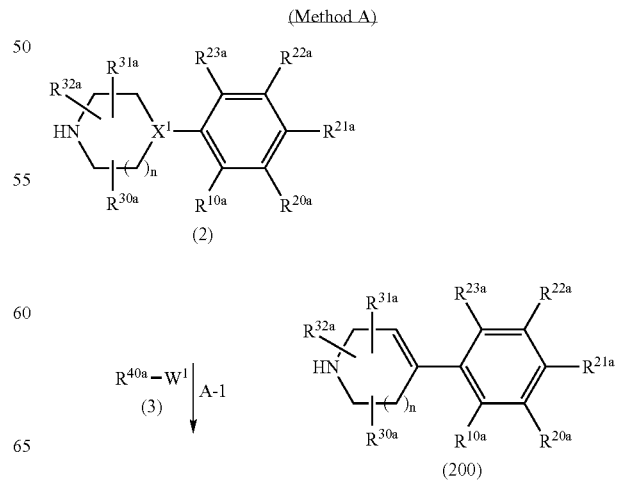

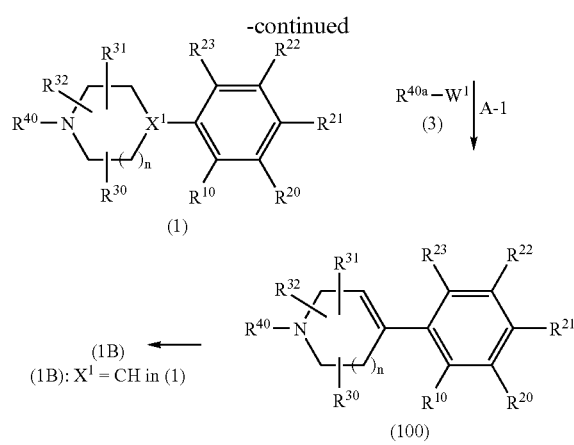

(1B): X¹ = CH in (1)

Method A is a method of producing compound (1) of the invention by reacting compound (2) with an alkylating agent (3), carbonylating agent (3) or sulfonylating agent (3) in an inert solvent, in the presence or in the absence of a base, in the presence or in the absence of an additive, and optionally removing any protecting groups on the resultant compound, or a method of producing compound (100) of the invention by reacting compound (200) in a similar manner.

In this scheme, R10, R20, R21, R22, R23, R30, R31, R32, R40, X1 and n have the same definitions as above, R10a, R20a, R21a, R22a, R23a, R30a, R31a, R32a and R40a have the same definitions as the corresponding groups R10, R20, R21, R22, R23, R30, R31, R32 and R40, or are the corresponding groups R10, R20, R21, R22, R23, R30, R31, R32 and R40 with the respective substituents on the groups protected, and W1 represents a leaving group which is chlorine, bromine or iodine, alkylsulfonyloxy such as methanesulfonyloxy or ethanesulfonyloxy, haloalkanesulfonyloxy such as trifluoromethanesulfonyloxy or nonafluorobutanesulfonyloxy, or arylsulfonyloxy such as benzenesulfonyloxy or p-toluenesulfonyloxy, among which chlorine, bromine, iodine, methanesulfonyloxy, p-toluenesulfonyloxy, nonafluorobutanesulfonyloxy or trifluoromethanesulfonyloxy is preferred.

(Alkylation)

There are no particular restrictions on the solvent used so long as it dissolves the starting compound to some extent and does not inhibit the reaction of this step, and specifically there may be mentioned amides such as formamide, dimethylformamide, dimethylacetamide, hexamethylphosphoric triamide and N-methylpyrrolidone, nitriles such as acetonitrile and isobutyronitrile, aromatic hydrocarbons such as toluene, benzene and xylene, ethers such as diethyl ether, diisopropyl ether, tetrahydrofuran, dioxane, dimethoxyethane and diethyleneglycol dimethyl ether or sulfoxides such as dimethyl sulfoxide, as well as mixtures of these solvents, among which dimethylformamide, acetonitrile, toluene or tetrahydrofuran is preferred.

There are no particular restrictions on the base used so long as it can yield the target compound and does not produce any unseparable by-products, and specifically there may be mentioned organic bases such as triethylamine and pyridine or inorganic bases such as potassium carbonate, sodium carbonate, potassium hydrogencarbonate, sodium hydrogencarbonate and cesium carbonate, among which potassium carbonate or triethylamine is preferred.

Sodium iodide or potassium iodide is used as an additive to accelerate the reaction if necessary.

The reaction temperature will differ depending on the starting materials, solvent and reagents, but will usually be between −30° C. and 180° C., and is preferably between 0° C. and 120° C.

The reaction time will differ depending on the starting materials, solvent, reagents and reaction temperature, but will usually be 0.5 to 100 hours, and is preferably 0.5 to 24 hours.

(Carbonylation or Sulfonylation)

There are no particular restrictions on the solvent used so long as it dissolves the starting compound to some extent and does not inhibit the reaction of this step, and specifically there may be mentioned halogenated hydrocarbons such as chloroform, dichloromethane, 1,2-dichloroethane and carbon tetrachloride, ethers such as diethyl ether, diisopropyl ether, tetrahydrofuran, dioxane, dimethoxyethane and diethyleneglycol dimethyl ether, amides such as formamide, dimethylformamide, dimethylacetamide, hexamethylphosphoric triamide and N-methylpyrrolidone, organic bases such as pyridine, or water, as well as mixtures of these solvents, among which dichloromethane, tetrahydrofuran, dioxane, dimethylformamide, pyridine or water, or mixtures thereof, are preferred.

There are no particular restrictions on the base used so long as it can yield the target compound and does not produce any unseparable by-products, and specifically there may be mentioned organic bases such as triethylamine and pyridine or inorganic bases such as potassium carbonate, sodium carbonate, potassium hydrogencarbonate, sodium hydrogencarbonate, cesium carbonate and sodium hydroxide, among which potassium carbonate or triethylamine is preferred.

4-Dimethylaminopyridine is used as an additive to accelerate the reaction if necessary.

The reaction temperature will differ depending on the starting materials, solvent and reagents, but will usually be between −70° C. and 120° C., and is preferably between −70° C. and 60° C.

The reaction time will differ depending on the starting materials, solvent, reagents and reaction temperature, but will usually be 0.5 to 48 hours, and is preferably 0.5 to 12 hours.

Compounds (1) and (100) of the invention may be isolated or purified from the reaction mixture obtained above, by the method described below.

When R10 of the resultant compounds (1) and (100) is optionally substituted 5- to 10-membered cycloalkenyl, it may be subjected to hydrogenation to yield compounds (1) or (1B) (the compound (1) wherein X1 is CH) of the invention wherein R10 is 5- to 10-membered cycloalkyl optionally substituted with the corresponding substituent.

When R10 of the resultant compound (100) is optionally substituted 5- to 10-membered cycloalkyl, it may be subjected to hydrogenation to yield compound (1B) (the compound (1) wherein X1 is CH) of the invention.

The hydrogenation may be carried out as follows.

Specifically, hydrogenation reaction may be carried out using a metal catalyst in an inert solvent, under a hydrogen atmosphere or in the presence of hydrogen-donating reagent, in the presence or in the absence of an acid.

There are no particular restrictions on the solvent used so long as it dissolves the starting compound to some extent and does not inhibit the reaction of this step, and specifically there may be mentioned water, alcohols such as methanol and ethanol, ethers such as diethyl ether, diisopropyl ether, tetrahydrofuran, dioxane, dimethoxyethane and diethyleneglycol dimethyl ether, esters such as methyl acetate, ethyl acetate, propyl acetate, butyl acetate and diethyl carbonate, amides such as formamide, dimethylformamide, dimethylacetamide, hexamethylphosphoric triamide and N-methylpyrrolidone, aliphatic hydrocarbons such as hexane, heptane, ligroin and petroleum ether or organic acids such as acetic acid, or mixtures of these solvents, among which methanol, ethanol, ethyl acetate, tetrahydrofuran, a mixed solvent of methanol and tetrahydrofuran, or a mixed solvent of ethanol and tetrahydrofuran is preferred.

There are no particular restrictions on the metal catalyst used so long as it can yield the target compound and does not produce any unseparable by-products, and specifically there may be mentioned heterogeneous rare metal catalysts such as palladium, palladium hydroxide, platinum, platinum oxide, rhodium, ruthenium and nickel (preferably supported on a carrier such as activated carbon, alumina, silica or zeolite) and homogeneous metal complex catalysts such as chlorotris (triphenylphosphine)rhodium(I) (Wilkinson's complex), among which heterogeneous rare metal catalysts (especially 5 to 10% palladium-activated carbon or platinum oxide, optionally wetted with water) are preferred.

The number of equivalents of the metal catalyst used (including the carrier) will differ depending on the starting materials, solvent and reagents, but will usually be a proportion of 0.05 to 10 and preferably 0.05 to 3, in terms of the weight ratio with respect to the starting material.

There are no particular restrictions on the acid used so long as it can yield the target compound and does not produce any unseparable by-products, and specifically there may be mentioned organic acids such as methanesulfonic acid, trifluoromethanesulfonic acid, acetic acid and trifluoroacetic acid, or inorganic acids such as hydrochloric acid and hydrobromic acid.

The reaction temperature will differ depending on the starting materials, solvent and reagents, but will usually be between −10° C. and 80° C., and is preferably between 0° C. and 50° C.

The reaction pressure of the hydrogen will also differ depending on the starting materials, solvent and reagents, but will usually be between 1 and 100 atmospheres, and preferably between 1 and 5 atmospheres.

The reaction time will differ depending on the starting materials, solvent, reagents and reaction temperature, but will usually be 0.5 to 200 hours, and is preferably 0.5 to 100 hours.

When the resultant compound is to be converted to an acid salt, this may be accomplished by a conventional method. The step of producing the salt and the step of hydrogenation may be carried out in a different order where appropriate.

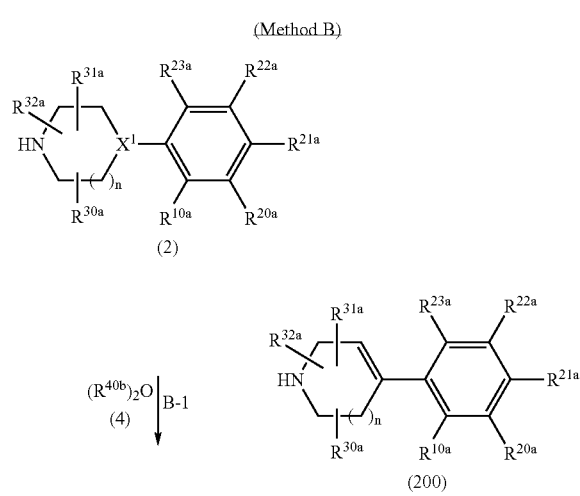

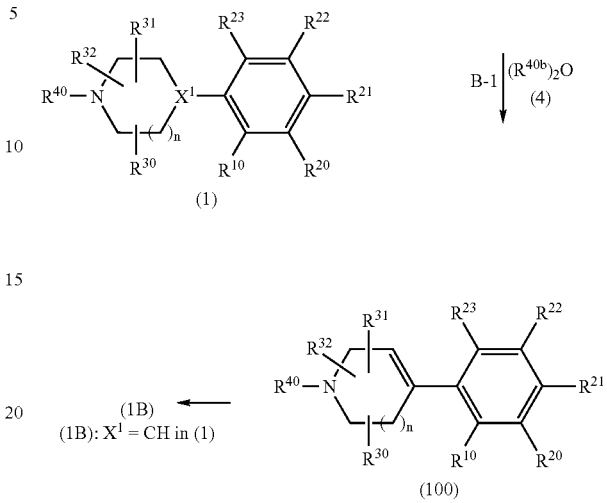

Method B is a method of producing compound (1) of the invention by reacting compound (2) with an acid anhydride (4) in an inert solvent, in the presence or in the absence of a base, and optionally removing any protecting groups on the resultant compound, or a method of producing compound (100) of the invention by reacting compound (200) in a similar manner.

In this scheme, R10, R20, R21, R22, R23, R30, R31, R32, R40, X1, n, R10a, R20a, R21a, R22a, R23a, R30a, R31a and R32a have the same definitions as above. Also, R40b is a group comprising carbonyl or sulfonyl, which is suitable for obtaining R40 and can form an acid anhydride. Substituents on R40b may also be protected.

This method may also be carried out in a manner similar to the carbonylation or sulfonylation step of Method A described above.

Compounds (1) and (100) of the invention may be isolated or purified from the reaction mixture obtained above, by the method described below.

When R10 of the resultant compounds (1) and (100) is optionally substituted 5- to 10-membered cycloalkenyl, it may be subjected to the hydrogenation described above in Method A to yield compound (1) of the invention or compound (1B) of the invention (the compound (1) wherein X1 is CH) wherein R10 is 5- to 10-membered cycloalkyl optionally substituted with the corresponding substituent.

When R10 of the resultant compound (100) is optionally substituted 5- to 10-membered cycloalkyl, it may be subjected to hydrogenation to yield compound (1B) (the compound (1) wherein X1 is CH) of the invention.

When the resultant compound is to be converted to an acid salt, this may be carried out by a conventional method. The step of producing the salt and the step of hydrogenation may be carried out in a different order where appropriate.

(Method C)

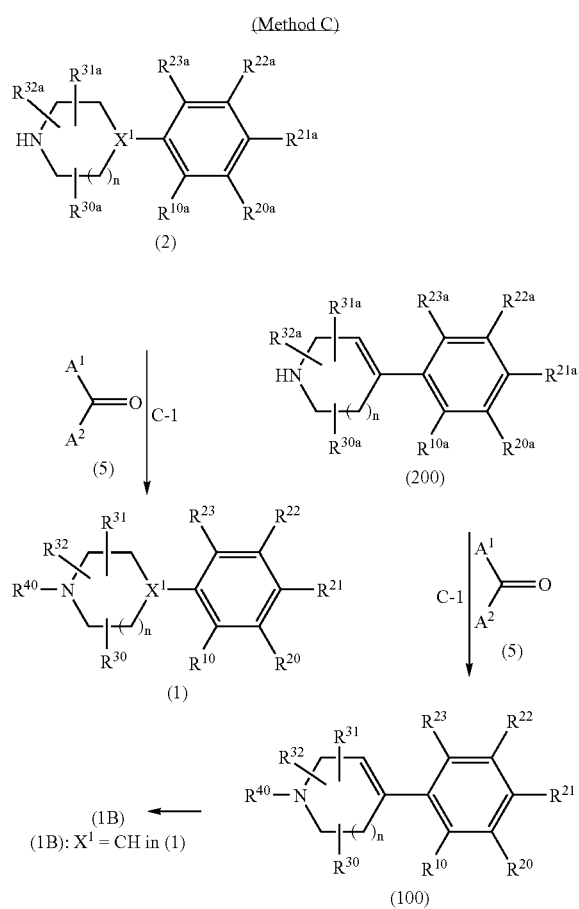

Method C is a method of producing compound (1) of the invention by reacting compound (2) with an aldehyde (5) or ketone (5) in an inert solvent, in the presence of a reducing agent, in the presence or in the absence of an acid, in the presence or in the absence of an additive, and optionally removing any protecting groups on the resultant compound, or a method of producing compound (100) of the invention by reacting compound (200) in a similar manner.

In this scheme, R10, R20, R21, R22, R23, R30, R31, R32, R40, X1, n, R10a, R20a, R21a, R22a, R23a, R30a, R31a and R32a have the same definitions as above. Also, A1 and A2 are groups suitable for obtaining R40. Substituents on A1 or A2 may also be protected.

There are no particular restrictions on the solvent used so long as it dissolves the starting compound to some extent and does not inhibit the reaction of this step, and specifically there may be mentioned ethers such as diethyl ether, diisopropyl ether, tetrahydrofuran, dioxane, dimethoxyethane and diethyleneglycol dimethyl ether, halogenated hydrocarbons such as chloroform, dichloromethane, 1,2-dichloroethane and carbon tetrachloride, nitriles such as acetonitrile and isobutyronitrile, aromatic hydrocarbons such as toluene, benzene and chlorobenzene or alcohols such as methanol and ethanol, among which ethers (particularly tetrahydrofuran) and halogenated hydrocarbons (particularly dichloroethane) are preferred.

There are no particular restrictions on the reducing agent used so long as it can yield the target compound and does not produce any unseparable by-products, and specifically there may be mentioned boron reducing agents such as sodium triacetoxyborohydride, sodium cyanoborohydride and borane-pyridine, and metal catalyst-hydrogen gas, among which sodium triacetoxyborohydride is preferred.

There are no particular restrictions on the acid used so long as it can yield the target compound and does not produce any unseparable by-products, and specifically there may be mentioned organic acids such as acetic acid and trifluoroacetic acid or Lewis acids such as titanium tetraisopropoxide and zinc chloride, among which organic acids (particularly acetic acid) are preferred.

There are no particular restrictions on the use of an additive so long as it can yield the target compound and does not produce any unseparable by-products, and specifically there may be mentioned molecular sieve or magnesium sulfate, among which Molecular Sieve 4 Å is preferred.

The reaction temperature will differ depending on the starting materials, solvent and reagents, but will usually be between −70° C. and 120° C., and is preferably between 0° C. and 50° C.

The reaction time will differ depending on the starting materials, solvent, reagents and reaction temperature, but will usually be 0.1 to 200 hours, and is preferably 0.1 to 24 hours.

As supplementary literature to be used as reference for carrying out this method, there may be mentioned, but not limited to, Ahmed F. Abdel-Magid et al., J. Org. Chem. (1996), 61, 3849.

Compounds (1) and (100) of the invention may be isolated or purified from the reaction mixture obtained above, by the method described below.

When R10 of the resultant compounds (1) and (100) is optionally substituted 5- to 10-membered cycloalkenyl, it may be subjected to the hydrogenation described above in Method A to yield compound (1) of the invention or compound (1B) (the compound (1) wherein X1 is CH) wherein R10 is 5- to 10-membered cycloalkyl optionally substituted with the corresponding substituent.

When R10 of the resultant compound (100) is optionally substituted 5- to 10-membered cycloalkyl, it may be subjected to hydrogenation to yield compound (1B) (the compound (1) wherein X1 is CH) of the invention.

When the resultant compound is to be converted to an acid salt, this may be carried out by a conventional method. The step of producing the salt and the step of hydrogenation may be carried out in a different order where appropriate.

(Method D)

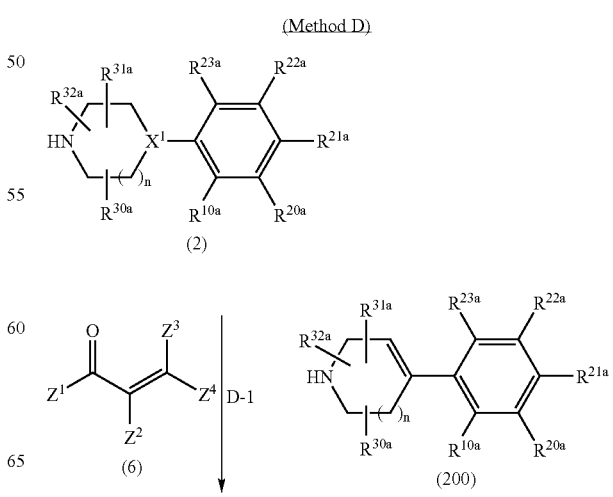

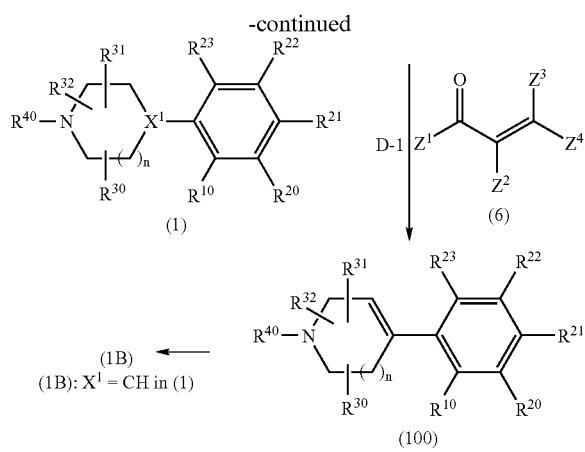

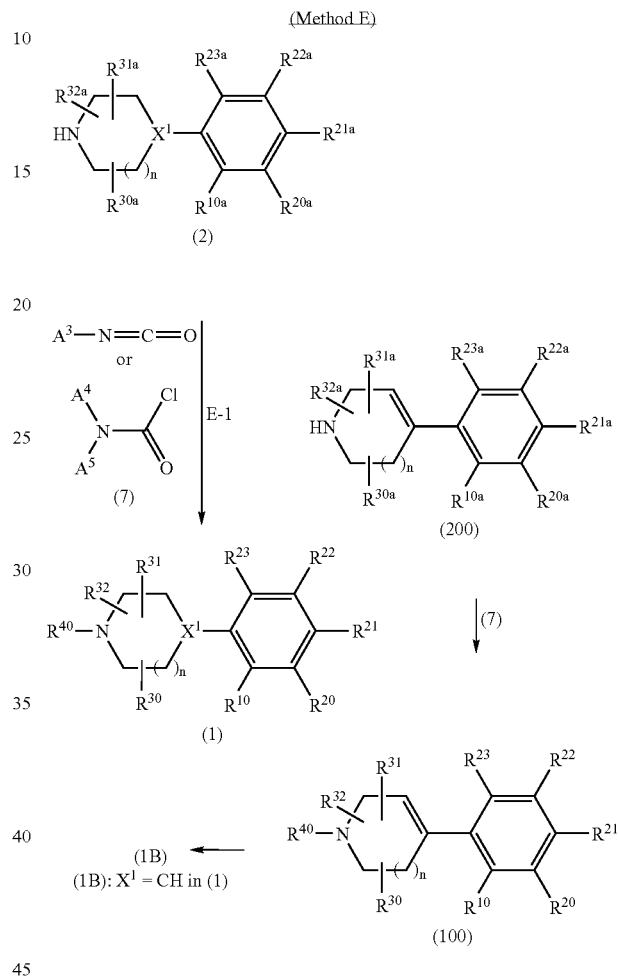

Method D is a method of producing compound (1) of the invention by reacting compound (2) with a conjugated carbonyl compound (6) by Michael addition reaction in an inert solvent, and optionally removing protecting groups on the resultant compound, or a method of producing compound (100) of the invention by reacting compound (200) in a similar manner.

In this scheme, R10, R20, R21, R22, R23, R30, R31, R32, R40, X1, n, R10a, R20a, R21a, R22a, R23a, R30a, R31a and R32a have the same definitions as above. Also, Z1, Z2, Z3 and Z4 are groups suitable for obtaining R40. Substituents on Z1, Z2, Z3 and Z4 may also be protected.

There are no particular restrictions on the solvent used so long as it dissolves the starting compound to some extent and does not inhibit the reaction of this step, and specifically there may be mentioned alcohols such as methanol, ethanol, n-propanol, isopropanol, n-butanol, isobutanol, t-butanol, isoamyl alcohol, diethylene glycol and glycerin, halogenated hydrocarbons such as chloroform, dichloromethane, 1,2-dichloroethane and carbon tetrachloride, ethers such as diethyl ether, diisopropyl ether, tetrahydrofuran, dioxane, dimethoxyethane and diethyleneglycol dimethyl ether, amides such as formamide, dimethylformamide, dimethylacetamide, hexamethylphosphoric triamide and N-methylpyrrolidone, and aromatic hydrocarbons such as benzene, toluene and xylene, among which halogenated hydrocarbons (particularly chloroform) or ethers (particularly tetrahydrofuran) are preferred.

The reaction temperature will differ depending on the starting materials, solvent and reagents, but will usually be between −30° C. and 150° C., and is preferably between 0° C. and 120° C.

The reaction time will differ depending on the starting materials, solvent, reagents and reaction temperature, but will usually be 0.5 to 48 hours, and is preferably 0.5 to 24 hours.

Compounds (1) and (100) of the invention may be isolated or purified from the reaction mixture obtained above, by the method described below.

When R10 of the resultant compounds (1) and (100) is optionally substituted 5- to 10-membered cycloalkenyl, it may be subjected to the hydrogenation described above in Method A to yield compound (1) of the invention or compound (1B) of the invention (the compound (1) wherein X1 is CH) wherein R10 is 5- to 10-membered cycloalkyl optionally substituted with the corresponding substituent.

When R10 of the resultant compound (100) is optionally substituted 5- to 10-membered cycloalkyl, it may be subjected to hydrogenation to yield compound (1B) (the compound (1) wherein X1 is CH) of the invention.

When the resultant compound is to be converted to an acid salt, this may be carried out by a conventional method. The step of producing the salt and the step of hydrogenation may be carried out in a different order where appropriate.

(Method E)

Method E is a method of producing compound (1) of the invention by reacting compound (2) with an isocyanate compound (7) or a substituted aminocarbonylchloride compound (7) in an inert solvent, in the presence or in the absence of a base, and optionally removing protecting groups on the resultant compound, or a method of producing compound (100) of the invention by reacting compound (200) in a similar manner.

In this scheme, R10, R20, R21, R22, R23, R30, R31, R32, R40, X1, n, R10a, R20a, R21a, R22a, R23a, R30a, R31a and R32a have the same definitions as above. Also, A3, A4 and A5 are groups suitable for obtaining R40. Substituents on A3, A4 and A5 may also be protected.

There are no particular restrictions on the solvent used so long as it dissolves the starting compound to some extent and does not inhibit the reaction of this step, and specifically there may be mentioned halogenated hydrocarbons such as chloroform, dichloromethane, 1,2-dichloroethane and carbon tetrachloride, aromatic hydrocarbons such as benzene, toluene and chlorobenzene, and ethers such as diethyl ether, diisopropyl ether, tetrahydrofuran, dioxane, dimethoxyethane and diethyleneglycol dimethyl ether, among which dichloromethane or tetrahydrofuran is preferred.

There are no particular restrictions on the base used so long as it can yield the target compound and does not produce any unseparable by-products, and specifically there may be mentioned organic bases such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU), among which triethylamine or pyridine is preferred.

The reaction temperature will differ depending on the starting materials, solvent and reagents, but will usually be between −70° C. and 100° C.

The reaction time will differ depending on the starting materials, solvent, reagents and reaction temperature, but will usually be 1 to 24 hours.

Compound (1) of the invention may be isolated or purified from the reaction mixture obtained above, by the method described below.

When R10 of the resultant compounds (1) and (100) is optionally substituted 5- to 10-membered cycloalkenyl, it may be subjected to the hydrogenation described above in Method A to yield compound (1) of the invention or compound (1B) of the invention (the compound (1) wherein X1 is CH) wherein R10 is 5- to 10-membered cycloalkyl optionally substituted with the corresponding substituent.

When R10 of the resultant compound (100) is optionally substituted 5- to 10-membered cycloalkyl, it may be subjected to hydrogenation to yield compound (1B) (the compound (1) wherein X1 is CH) of the invention.

When the resultant compound is to be converted to an acid salt, this may be carried out by a conventional method. The step of producing the salt and the step of hydrogenation may be carried out in a different order where appropriate.

(Method F)

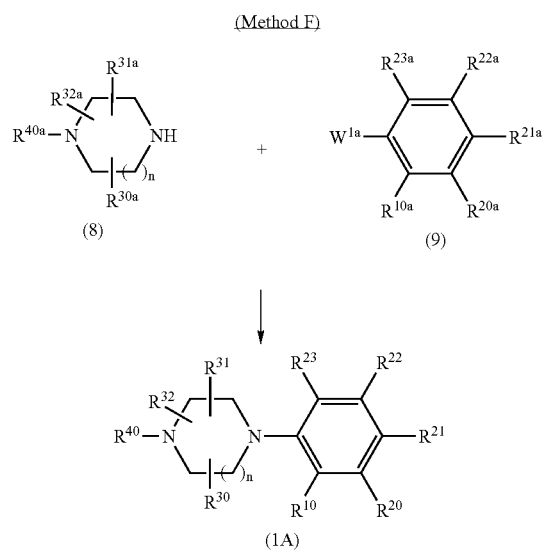

Method F is a method of producing compound (1A) of the invention (the compound according to the formula (1) above wherein X1 is nitrogen) by reacting compound (8) with compound (9) (amination or amidation) in an inert solvent, in the presence of a palladium(0) catalyst or copper catalyst, in the presence or in the absence of a base, in the presence or in the absence of an additive, under or not under an inert gas atmosphere, and optionally removing protecting groups on the resultant compound.

In this scheme, R10, R20, R21, R22, R23, R30, R31, R32, R40, n, R10a, R20a, R21a, R22a, R23a, R30a, R31a and R32a have the same definitions as above. Also, W1a represents chlorine, bromine or iodine, or a trifluoromethanesulfonyloxy group.

(Reaction in the Presence of Palladium(0) Catalyst)

There are no particular restrictions on the solvent used so long as it dissolves the starting compound to some extent and does not inhibit the reaction of this step, and specifically there may be mentioned amides such as dimethylformamide, dimethylacetamide, hexamethylphosphoric triamide and N-methylpyrrolidone, aromatic hydrocarbons such as toluene, benzene, xylene and mesitylene, ethers such as diethyl ether, diisopropyl ether, tetrahydrofuran, dioxane, dimethoxyethane and diethyleneglycol dimethyl ether, alcohols such as methanol, ethanol, n-propanol, isopropanol, n-butanol, isobutanol, t-butanol, isoamyl alcohol, diethylene glycol, glycerin, octanol and cyclohexanol, nitriles such as acetonitrile and isobutyronitrile, or mixtures of these solvents, among which dimethylformamide, toluene, xylene, tetrahydrofuran, dioxane or dimethoxyethane is preferred.

There are no particular restrictions on the palladium(0) catalyst used so long as it can yield the target compound and does not produce any unseparable by-products, and specifically there may be mentioned tetrakis(triphenylphosphine) palladium, tris(dibenzylideneacetone)dipalladium, bis (dibenzylideneacetone)palladium, bis(tri-t-butylphosphine) palladium and palladium black, or palladium(0) catalysts produced in the reaction system by combination of the palladium complexes which can be palladium(0) precursors mentioned below and various ligands mentioned below.

There are no particular restrictions on various palladium complexes which can be used as palladium(0) precursors, so long as they can yield the target compound without producing any unseparable by-products, and specifically there may be mentioned palladium acetate, 1,1'-bis(diphenylphosphino) ferrocene dichloropalladium, dichlorobis(tri-o-tolylphosphine)palladium, dichlorobis(triscyclohexylphosphine)palladium, and the like.

There are no particular restrictions on ligands used so long as they can yield the target compound without producing any unseparable by-products, and specifically there may be mentioned 2,2'-bis(diphenylphosphino)-1,1'-binaphthyl (BINAP), 9,9-dimethyl-4,5-bis(diphenylphosphino)xanthene (Xantphos), tri-t-butylphosphine, tri(4-methylphenyl)phosphine, tri-2-furylphosphine, 2-(di-t-butylphosphino)biphenyl, 2-(dicyclohexylphosphino)biphenyl, tricyclohexylphosphine, 2-dicyclohexylphosphino-2'-(N,N-dimethylamino) biphenyl, 1,1'-bis(diphenylphosphino)ferrocene, di-t-butylphosphonium tetrafluoroborate and 1,3-bis(2,4,6-trimethylphenyl)imidazol-2-ylidene.

There are no particular restrictions on the base used so long as it can yield the target compound and does not produce any unseparable by-products, and specifically there may be mentioned inorganic bases such as sodium t-butoxide, potassium t-butoxide, tripotassium phosphate, trisodium phosphate, cesium carbonate, potassium carbonate, sodium carbonate, cesium bicarbonate, potassium hydrogencarbonate, sodium hydrogencarbonate, sodium acetate, potassium acetate, cesium acetate, potassium fluoride, cesium fluoride, sodium hydroxide and potassium hydroxide, or organic bases such as triethylamine, 1,8-bis(dimethylamino)naphthalene, 1,4-diazabicyclo[2.2.2]octane (DABCO) and 1,8-diazabicyclo[5.4.0]undec-7-ene (DBU).

There are no particular restrictions on the additive used so long as it can yield the target compound and does not produce any unseparable by-products, and specifically there may be mentioned lithium fluoride, sodium fluoride, lithium chloride, sodium chloride, lithium bromide, sodium bromide, 1,4,7,10,13,16-hexaoxacyclooctadecane (18-Crown-6), 1,4,7,10,13-pentaoxacyclopentadecane (15-Crown-5), tetrabutylammonium fluoride and tetrabutylammonium bromide.

The reaction temperature will differ depending on the starting materials, solvent and reagents, but will usually be between 0° C. and 150° C., and is preferably between 20° C. and 110° C.

The reaction time will differ depending on the starting materials, solvent, reagents and reaction temperature, but will usually be 0.1 to 100 hours, and is preferably 0.5 to 48 hours.

When the reaction is carried out in an inert gas atmosphere, the inert gas is not particularly restricted so long as it does not inhibit the reaction of this step, and specifically it may be argon or nitrogen gas.

As supplementary literature to be used as reference for carrying out this method, there may be mentioned, but not limited to, D. Prim et al., Tetrahedron (2002), 58, 2041 and L. Buchwald et al., J. Organomet. Chem. (1999), 576, 125.

(Reaction in the Presence of Copper Catalyst)

There are no particular restrictions on the solvent used so long as it dissolves the starting compound to some extent and does not inhibit the reaction of this step, and specifically there may be mentioned amides such as formamide, dimethylformamide, dimethylacetamide, hexamethylphosphoric triamide and N-methylpyrrolidone, aromatic hydrocarbons such as toluene, benzene, xylene, mesitylene and nitrobenzene, ethers such as diethyl ether, diisopropyl ether, tetrahydrofuran, dioxane, dimethoxyethane and diethyleneglycol dimethyl ether, alcohols such as methanol, ethanol, n-propanol, isopropanol, n-butanol, isobutanol, t-butanol, isoamyl alcohol, diethylene glycol, glycerin, octanol, cyclohexanol and methylcellosolve, or mixtures of these solvents, among which isopropanol, N-methylpyrrolidone, toluene and dimethylformamide are preferred.

There are no particular restrictions on the copper catalyst used so long as it can yield the target compound and does not produce any unseparable by-products, and specifically there may be mentioned copper (powder), copper(I) chloride, copper(II) chloride, copper(I) iodide, copper(I) oxide, copper(II) oxide, copper(II) acetate, copper(II) sulfate pentahydrate, copper(II) acetylacetonate, copper(I) thiocyanate and the like, among which copper (powder) and copper(I) chloride are preferred.

There are no particular restrictions on the ligand used so long as it can yield the target compound and does not produce any unseparable by-products, and specifically there may be mentioned ethylene glycol, diethylene glycol, cresol, 2,6-dimethylphenol, 1-naphthol, 2-naphthol, ethylenediamine, N,N'-dimethylethylenediamine and diisopropylamine, among which ethylene glycol and ethylenediamine are preferred.

There are no particular restrictions on the base used so long as it can yield the target compound and does not produce any unseparable by-products, and specifically there may be mentioned inorganic bases such as sodium t-butoxide, potassium t-butoxide, tripotassium phosphate, trisodium phosphate, cesium carbonate, potassium carbonate, sodium carbonate and sodium hydride, or organic bases such as potassium bis(trimethylsilyl)amide, among which potassium carbonate and tripotassium phosphate are preferred.

The reaction temperature will differ depending on the starting materials, solvent and reagents, but will usually be between 0° C. and 250° C., and is preferably between 80° C. and 150° C.

The reaction time will differ depending on the starting materials, solvent, reagents and reaction temperature, but will usually be 0.1 to 100 hours, and is preferably 0.5 to 48 hours.

When the reaction is carried out in an inert gas atmosphere, the inert gas is not particularly restricted so long as it does not inhibit the reaction of this step, and specifically it may be argon or nitrogen gas.

As supplementary literature to be used as reference for carrying out this method, there may be mentioned, but not limited to, L. Buchwald et al., Org. Lett. (2002), 4, 581.

Compound (1A) of the invention may be isolated or purified from the reaction mixture obtained above, by the method described below.

When R10 of the resultant compound (1A) is optionally substituted 5- to 10-membered cycloalkenyl, it may be subjected to the hydrogenation described above in Method A to yield compound (1A) of the invention wherein R10 is 5- to 10-membered cycloalkyl optionally substituted with the corresponding substituent.

When the resultant compound is to be converted to an acid salt, this may be carried out by a conventional method. The step of producing the salt and the step of hydrogenation may be carried out in a different order where appropriate.

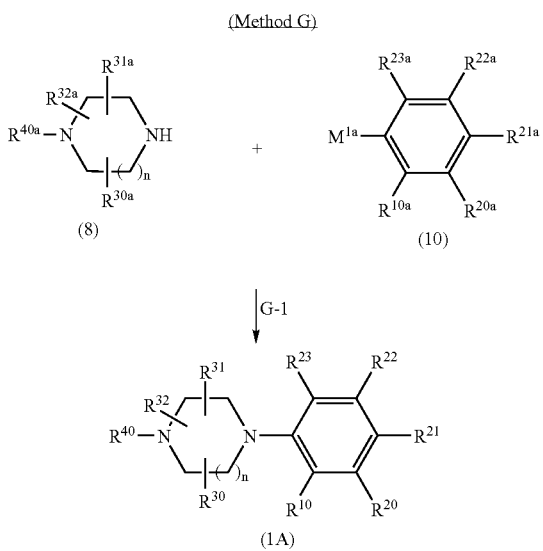

Method G is a method of producing compound (1A) of the invention (the compound according to the formula (1) above wherein X1 is nitrogen) by reacting compound (8) with compound (10) in an inert solvent, in the presence of a copper catalyst, in the presence of a base, in the presence or in the absence of oxygen, and optionally removing protecting groups on the resultant compound.

In this scheme, R10, R20, R21, R22, R23, R30, R31, R32, R40, n, R10a, R20a, R21a, R22a, R23a, R30a, R31a, R32a and R40a have the same definitions as above. M1a is a group represented by the formula —B(OH)$_2$.

There are no particular restrictions on the solvent used so long as it dissolves the starting compound to some extent and does not inhibit the reaction of this step, and specifically there may be mentioned amides such as formamide, dimethylformamide, dimethylacetamide, hexamethylphosphoric triamide and N-methylpyrrolidone, halogenated hydrocarbons such as chloroform, dichloromethane, 1,2-dichloroethane and carbon tetrachloride, aromatic hydrocarbons such as toluene, benzene and xylene or ethers such as diethyl ether, diisopropyl ether, tetrahydrofuran, dioxane, dimethoxyethane and diethyleneglycol dimethyl ether, or mixtures of these solvents, among which halogenated hydrocarbons (particularly dichloromethane) are preferred.

There are no particular restrictions on the copper catalyst used so long as it can yield the target compound and does not produce any unseparable by-products, and specifically there may be mentioned copper(II) acetate, copper(I) acetate, copper(II) trifluoromethanesulfonate and copper(II) isobutyrate, among which copper(II) acetate is preferred.

There are no particular restrictions on the base used so long as it can yield the target compound and does not produce any unseparable by-products, and specifically there may be mentioned organic bases such as triethylamine, pyridine, 2,6-lutidine, N-methylmorpholine and 1,8-diazabicyclo[5.4.0]undec-7-ene, among which triethylamine or pyridine is preferred.

There are no particular restrictions on the additive used to accelerate the reaction so long as it can yield the target compound and does not produce any unseparable by-products, and specifically there may be mentioned molecular sieve, pyridine-N-oxide and 2,2,6,6-tetramethylpiperidinooxy, among which molecular sieve (particularly 4 Å) is preferred.

The reaction temperature will differ depending on the starting materials, solvent and reagents, but will usually be between 0° C. and 80° C., and is preferably between 10° C. and 50° C.

The reaction time will differ depending on the starting materials, solvent, reagents and reaction temperature, but will usually be 1 to 100 hours, and is preferably 24 to 48 hours.

Compound (1A) of the invention may be isolated or purified from the reaction mixture obtained in the manner described above, by the following method.

When R10 of the resultant compound (1A) is optionally substituted 5- to 10-membered cycloalkenyl, it may be subjected to the hydrogenation described above in Method A to yield compound (1A) of the invention wherein R10 is 5- to 10-membered cycloalkyl optionally substituted with the corresponding substituent.

When the resultant compound is to be converted to an acid salt, this may be carried out by a conventional method. The step of producing the salt and the step of hydrogenation may be carried out in a different order where appropriate.

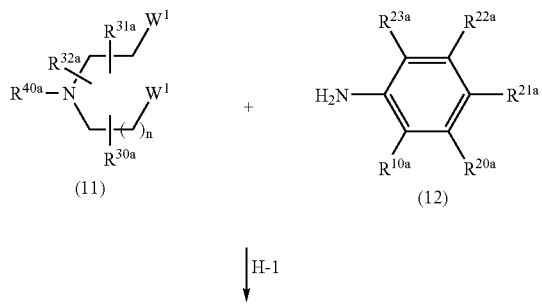

(Method H)

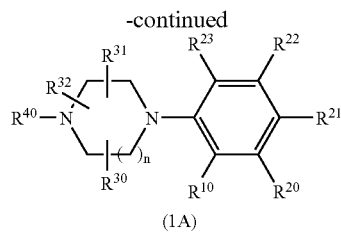

Method H is a method of producing compound (1A) of the invention (the compound according to the formula (1) above wherein X1 is nitrogen) by reacting compound (11) with compound (12) in an inert solvent or in the absence of a solvent, under or not under an inert gas atmosphere, in the presence or in the absence of a base, in the presence or in the absence of an additive, and optionally removing protecting groups on the resultant compound.

In this scheme, R10, R20, R21, R22, R23, R30, R31, R32, R40, n, W1, R10a, R20a, R21a, R22a, R23a, R30a, R31a, R32a and R40a have the same definitions as above.

There are no particular restrictions on the solvent used so long as it dissolves the starting compound to some extent and does not inhibit the reaction of this step, and specifically there may be mentioned alcohols such as methanol, ethanol, n-propanol, isopropanol, n-butanol, isobutanol, t-butanol, isoamyl alcohol, diethylene glycol, glycerin, octanol, cyclohexanol and methylcellosolve, aromatic hydrocarbons such as benzene, chlorobenzene, 1,2-dichlorobenzene, toluene and xylene, ethers such as diethyl ether, diisopropyl ether, tetrahydrofuran, dioxane, dimethoxyethane and diethyleneglycol dimethyl ether, and amides such as dimethylformamide, dimethylacetamide, hexamethylphosphoric triamide and N-methylpyrrolidone, among which butanol, 1,2-dichlorobenzene, toluene, xylene, tetrahydrofuran, dioxane, dimethylformamide or hexamethylphosphoric triamide is preferred.

When no solvent is used, the reaction may be carried out using a microwave reactor or with alumina or silica gel as a carrier.

When the reaction is carried out under an atmosphere of an inert gas, there are no particular restrictions on the inert gas so long as it does not inhibit the reaction of this step, and specifically there may be mentioned argon or nitrogen gas.

There are no particular restrictions on the base used so long as it can yield the target compound and does not produce any unseparable by-products, and specifically there may be mentioned organic bases such as triethylamine, pyridine, diisopropylethylamine, 4-dimethylaminopyridine, DBU and DABCO, or inorganic bases such as potassium carbonate, sodium carbonate and sodium hydrogencarbonate.

There are no particular restrictions on the additive used to accelerate the reaction so long as it can yield the target compound and does not produce any unseparable by-products, and specifically there may be mentioned alkali metal iodides such as sodium iodide and potassium iodide.

The reaction temperature will differ depending on the starting materials, solvent and reagents, but will usually be between 0° C. and 270° C.

The reaction time will differ depending on the starting materials, solvent, reagents and reaction temperature, but will usually be 0.5 to 100 hours.

Compound (1A) of the invention may be isolated or purified from the reaction mixture obtained above, by the method described below.

When R10 of the resultant compound (1A) is optionally substituted 5- to 10-membered cycloalkenyl, it may be subjected to the hydrogenation described above in Method A to yield compound (1A) of the invention wherein R10 is 5- to 10-membered cycloalkyl optionally substituted with the corresponding substituent.

When the resultant compound is to be converted to an acid salt, this may be carried out by a conventional method. The step of producing the salt and the step of hydrogenation may be carried out in a different order where appropriate.

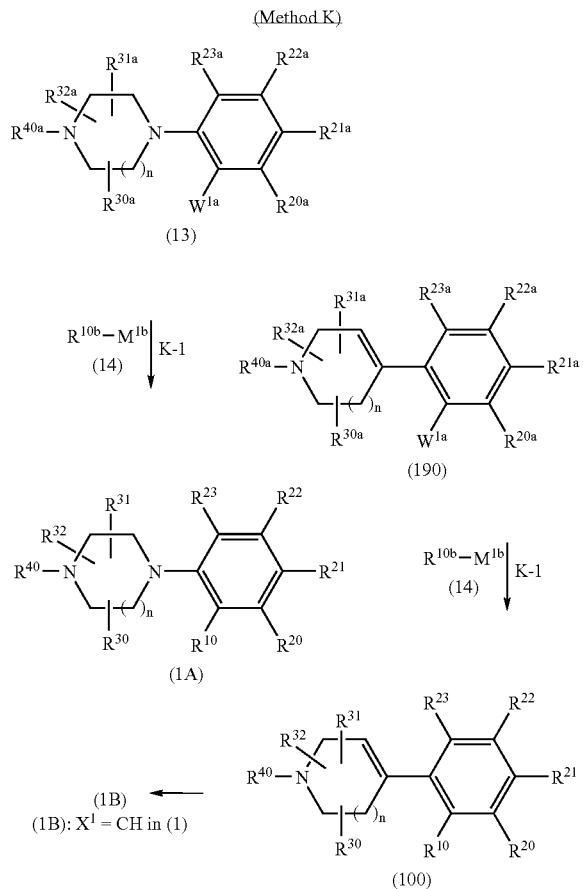

Method K is a method of producing compound (1A) of the invention (the compound according to the formula (1) wherein X1 is nitrogen) by reacting compound (113) with a boron metal reagent (14) or a tin metal reagent (14) (Suzuki reaction or Stille reaction) in an inert solvent, in the presence of a palladium(0) catalyst, under or not under an inert gas atmosphere, in the presence or in the absence of a base, in the presence or in the absence of an additive, and optionally removing protecting groups on the resultant compound, or a method of producing compound (100) of the invention by reacting compound (190) in a similar manner.

In this scheme, R10, R20, R21, R22, R23, R30, R31, R32, R40, n, W1a, R20a, R21a, R22a, R23a, R30a, R31a, R32a and R40a have the same definitions as above. R10b represents optionally substituted 5- to 10-membered cycloalkenyl, where the substituent may be protected and has the same definition as the substituent of the "optionally substituted 5- to 10-membered cycloalkenyl" for R10.

Also, M1b represents the group $B(OE^{10c})_2$ or $Sn(E^{10b})_3$, wherein $E^{10c}$ represents C1-6 alkyl or the two of $E^{10c}$ bond together to form C2-3 alkylene optionally substituted with methyl, and E1b represents C1-6 alkyl.

This method will differ depending on the nature of M1b.

(Suzuki Coupling Reaction)

This method is a method of producing compound (1A) of the invention (the compound according to the formula (1) wherein X1 is nitrogen) by reacting compound (13) with compound (14) in an inert solvent, in the presence of a palladium(0) catalyst, in the presence of a base, in the presence or in the absence of an additive, under or not under an inert gas atmosphere, and optionally removing protecting groups on the resultant compound, or a method of producing compound (100) of the invention by reacting compound (190) in a similar manner.

There are no particular restrictions on the solvent used so long as it dissolves the starting compound to some extent and does not inhibit the reaction of this step, and specifically there may be mentioned amides such as formamide, dimethylformamide, dimethylacetamide, hexamethylphosphoric triamide and N-methylpyrrolidone, aromatic hydrocarbons such as toluene, benzene, xylene and mesitylene, ethers such as diethyl ether, diisopropyl ether, tetrahydrofuran, dioxane, dimethoxyethane and diethyleneglycol dimethyl ether, alcohols such as methanol, ethanol, n-propanol, isopropanol, n-butanol, isobutanol, t-butanol, isoamyl alcohol, diethylene glycol, glycerin, octanol, cyclohexanol and methylcellosolve, nitriles such as acetonitrile and isobutyronitrile, sulfoxides such as dimethylsulfoxide and sulfolane, or water, or mixtures of these solvents, among which dimethylformamide, toluene, xylene, tetrahydrofuran, dioxane, dimethoxyethane or water, or mixtures of these solvents, are preferred.

There are no particular restrictions on the palladium(0) catalyst used so long as it can yield the target compound and does not produce any unseparable by-products, and specifically there may be mentioned tetrakis(triphenylphosphine) palladium, tris(dibenzylideneacetone)dipalladium, bis(dibenzylideneacetone)palladium, bis(tri-t-butylphosphine) palladium, palladium black and the like, or palladium(0) catalysts produced in the reaction system by combination of the palladium complexes which can be palladium(0) precursors mentioned below and various ligands mentioned below.

There are no particular restrictions on various palladium complexes which can be used as palladium(0) precursor, so long as they can yield the target compound without producing any unseparable by-products, and specifically there may be mentioned palladium acetate, 1,1'-bis(diphenylphosphino) ferrocene dichloropalladium, dichlorobis(tri-o-tolylphosphine)palladium, dichlorobis(triscyclohexylphosphine)palladium, and the like.

There are no particular restrictions on ligands used so long as they can yield the target compound without producing any unseparable by-products, and specifically there may be mentioned triphenylphosphine, tri-t-butylphosphine, tri(4-methylphenyl)phosphine, 2-(di-t-butylphosphino)biphenyl, 2-(dicyclohexylphosphino)biphenyl, tricyclohexylphosphine, 1,1'-bis(diphenylphosphino)ferrocene and di-t-butylphosphonium tetrafluoroborate.

There are no particular restrictions on the base used so long as it can yield the target compound and does not produce any unseparable by-products, and specifically there may be mentioned inorganic bases such as tripotassium phosphate, trisodium phosphate, cesium carbonate, potassium carbonate, sodium carbonate, cesium bicarbonate, potassium hydrogencarbonate, sodium hydrogencarbonate, sodium acetate, barium hydroxide, potassium hydroxide, potassium fluoride and cesium fluoride, metal alkoxides such as sodium ethoxide and sodium-t-butoxide, alkali metal acetate such as sodium acetate or potassium acetate, or organic bases such as triethylamine.

There are no particular restrictions on the additive used so long as it can yield the target compound and does not produce any unseparable by-products, and specifically there may be mentioned lithium chloride, sodium chloride, lithium bromide, sodium bromide and tetrabutylammonium bromide.

The reaction temperature will differ depending on the starting materials, solvent and reagents, but will usually be between 0° C. and 150° C., and is preferably between 20° C. and 120° C.

The reaction time will differ depending on the starting materials, solvent, reagents and reaction temperature, but will usually be 0.5 to 100 hours, and is preferably 0.5 to 48 hours. When the reaction is carried out in an inert gas atmosphere, the inert gas is not particularly restricted so long as it does not inhibit the reaction of this step, and specifically it may be argon or nitrogen gas.

As supplementary literature to be used as reference for carrying out this method, there may be mentioned, but not limited to, S. P. Stanforth, Tetrahedron (1998), 54, 263. and N. Miyaura, A. Suzuki, Chem. Rev. (1995), 95, 2457.

(Stille Coupling Reaction)

This method is a method of producing compound (1A) of the invention (the compound according to the formula (1) wherein X1 is nitrogen) by reacting compound (13) with compound (14) in an inert solvent, in the presence of a palladium(0) catalyst, in the presence or in the absence of an additive, under or not under an inert gas atmosphere, and optionally removing protecting groups on the resultant compound, or a method of producing compound (100) of the invention by reacting compound (190) in a similar manner.

There are no particular restrictions on the solvent used so long as it dissolves the starting compound to some extent and does not inhibit the reaction of this step, and specifically there may be mentioned amides such as dimethylformamide, dimethylacetamide, hexamethylphosphoric triamide and N-methylpyrrolidone, aromatic hydrocarbons such as toluene, benzene, xylene and mesitylene, ethers such as diethyl ether, diisopropyl ether, tetrahydrofuran, dioxane, dimethoxyethane and diethyleneglycol dimethyl ether, or mixtures of these solvents, among which dimethylformamide, toluene, xylene, tetrahydro furan, dioxane and dimethoxyethane are preferred.

There are no particular restrictions on the palladium(0) catalyst used so long as it can yield the target compound and does not produce any unseparable by-products, and specifically there may be mentioned tetrakis(triphenylphosphine) palladium, tris(dibenzylideneacetone)dipalladium, bis(dibenzylideneacetone)palladium, bis(tri-t-butylphosphine) palladium, palladium black and the like, or palladium(0) catalysts produced in the reaction system by combination of the palladium complexes which can be palladium(0) precursors mentioned below and various ligands mentioned below.

There are no particular restrictions on various palladium complexes which can be used as palladium(0) precursors, so long as they can yield the target compound without producing any unseparable by-products, and specifically there may be mentioned palladium acetate, 1,1'-bis(diphenylphosphino) ferrocene dichloropalladium, dichlorobis(tri-o-tolylphosphine)palladium, dichlorobis(acetonitrile)palladium and dichlorobis(triscyclohexylphosphine)palladium.

There are no particular restrictions on ligands used so long as they can yield the target compound without producing any unseparable by-products, and specifically there may be mentioned triphenylphosphine, tri-t-butylphosphine, tri(4-methylphenyl)phosphine, 2-(di-t-butylphosphino)biphenyl, 2-(dicyclohexylphosphino)biphenyl, tricyclohexylphosphine, tri-2-furylphosphine, 1,1'-bis(diphenylphosphino)ferrocene, di-t-butylphosphonium tetrafluoroborate and triphenylarsine.

There are no particular restrictions on the additive used so long as it can yield the target compound and does not produce any unseparable by-products, and specifically there may be mentioned cesium fluoride, potassium fluoride, lithium chloride, lithium bromide, sodium bromide, tetrabutylammonium fluoride, copper iodide, copper oxide and zinc chloride.

The reaction temperature will differ depending on the starting materials, solvent and reagents, but will usually be between 0° C. and 150° C., and is preferably between 20° C. and 110° C.

The reaction time will differ depending on the starting materials, solvent, reagents and reaction temperature, but will usually be 0.1 to 100 hours, and is preferably 0.5 to 48 hours.

When the reaction is carried out in an inert gas atmosphere, the inert gas is not particularly restricted so long as it does not inhibit the reaction of this step, and specifically it may be argon or nitrogen gas.

As supplementary literature to be used as reference for carrying out this method, there may be mentioned, but not limited to, S. P. Stanforth, Tetrahedron (1998), 54, 263 and J. K. Stille, Angew. Chem. Int. Ed. Engl. (1986), 25, 508.

Compounds (1A) and (100) of the invention may be isolated or purified from the reaction mixture obtained above, by the method described below.

When R10 of the resultant compounds (1A) and (100) is optionally substituted 5- to 10-membered cycloalkenyl, it may be subjected to the hydrogenation described above in Method A to yield compound (1A) of the invention or compound (1B) of the invention (the compound (1) wherein X1 is CH) wherein R10 is 5- to 10-membered cycloalkyl optionally substituted with the corresponding substituent.

When R10 of the resultant compound (100) is optionally substituted 5- to 10-membered cycloalkyl, it may be subjected to hydrogenation to yield compound (1B) (the compound (1) wherein X1 is CH) of the invention.

When the resultant compound is to be converted to an acid salt, this may be carried out by a conventional method. The step of producing the salt and the step of hydrogenation may be carried out in a different order where appropriate.

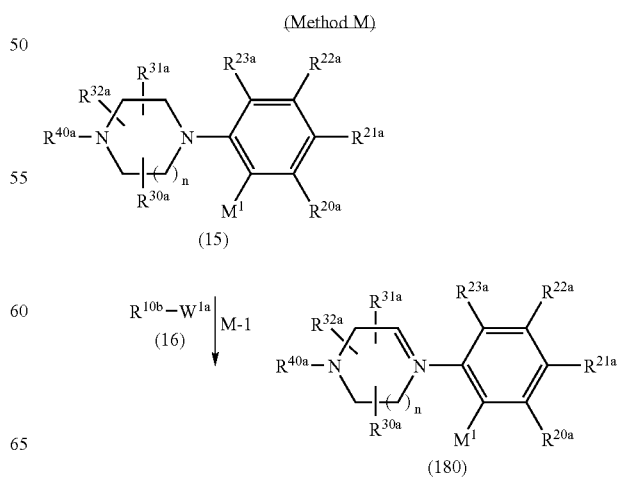

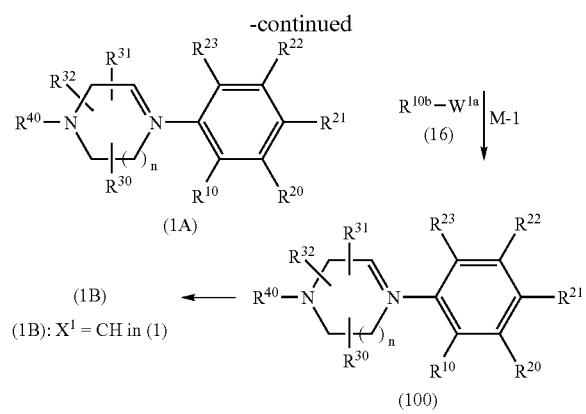

(1A)

(1B)

(1B): $X^1$ = CH in (1)

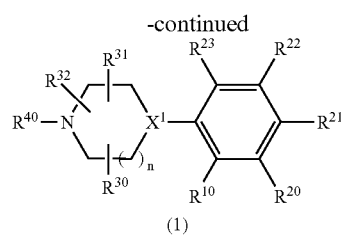

(100)

Method M is a method of producing compound (1A) of the invention (the compound according to the formula (1) wherein X1 is nitrogen) by reacting compound (16) with a boron metal reagent (15) or tin metal reagent (15) (Suzuki reaction or Stille reaction) in an inert solvent, in the presence of a palladium(0) catalyst, under or not under an inert gas atmosphere, in the presence or in the absence of a base, in the presence or in the absence of an additive, and optionally removing protecting groups on the resultant compound, or a method of producing compound (100) of the invention by reacting compound (180) in a similar manner.

In this scheme, R10, R20, R21, R22, R23, R30, R31, R32, R40, n, W1a, R20a, R21a, R22a, R23a, R30a, R31a, R32a and R40a have the same definitions as above. R10b also has the same definition as above.

M1 represents the group $B(OE^{10a})_2$ or $Sn(E^{10b})_3$, wherein $E^{10a}$ represents hydrogen, C1-6 alkyl or the two of $E^{10a}$ bond together to form C2-3 alkylene optionally substituted with methyl, and $E^{10b}$ represents C1-6 alkyl.

This method may be carried out in a manner similar to Method K described above.

Compounds (1A) and (100) of the invention may be isolated or purified from the reaction mixture obtained above, by the method described below.

When R10 of the resultant compounds (1A) and (100) is optionally substituted 5- to 10-membered cycloalkenyl, it may be subjected to the hydrogenation described above in Method A to yield compound (1A) of the invention or compound (1B) of the invention (the compound (1) wherein X1 is CH) wherein R10 is 5- to 10-membered cycloalkyl optionally substituted with the corresponding substituent.

When R10 of the resultant compound (100) is optionally substituted 5- to 10-membered cycloalkyl, it may be subjected to hydrogenation to yield compound (1B) (the compound (1) wherein X1 is CH) of the invention.

When the resultant compound is to be converted to an acid salt, this may be carried out by a conventional method. The step of producing the salt and the step of hydrogenation may be carried out in a different order where appropriate.

(Method N)

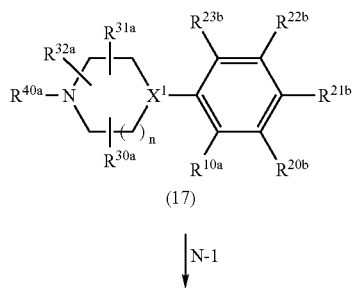

(17)

↓ N-1

-continued (1)

Method N is a method of producing compound (1) of the invention by reacting compound (17) with a halogenating reagent in an inert solvent, in the presence or in the absence of an additive, in the presence or in the absence of an inert gas, to yield a compound halogenated on the benzene ring to which R10a is bonded (Step N-1-1), and optionally removing protecting groups on the resultant compound.

Alternatively, (Step N-1-1) may be followed by reaction of the halogenated compound with a compound which can introduce a desired substituent, or a reactive derivative thereof, in the presence of a transition metal catalyst, in an inert solvent, in the presence or in the absence of an additive, in the presence or in the absence of an inert gas (Step N-1-2), and optionally removing any protecting groups on the resultant compound, to produce compound (1) of the invention.

In this scheme, R10, R20, R21, R22, R23, R30, R31, R32, R40, n, X1, R10a, R30a, R31a, R32a and R40a have the same definitions as above. Also, at least one of R20b, R21b, R22b and R23b is hydrogen, and the remaining groups are groups corresponding to R20a, R21a, R22a and R23a, respectively.

(Step N-1-1)

This is a halogenating step.

There are no particular restrictions on the solvent used so long as it dissolves the starting compound to some extent and does not inhibit the reaction of this step, and specifically there may be mentioned alcohols such as methanol, ethanol, n-propanol, isopropanol, n-butanol, isobutanol, t-butanol, isoamyl alcohol, diethylene glycol, glycerin, octanol, cyclohexanol and methylcellosolve, aliphatic hydrocarbons such as hexane, heptane, ligroin and petroleum ether, ethers such as dioxane, dimethoxyethane and diethyleneglycol dimethyl ether, halogenated hydrocarbons such as chloroform, dichloromethane, 1,2-dichloroethane and carbon tetrachloride, ethers such as diethyl ether, diisopropyl ether, tetrahydrofuran, dioxane, dimethoxyethane and diethyleneglycol dimethyl ether, amides such as formamide, dimethylformamide, dimethylacetamide and hexamethylphosphoric triamide, and organic acids such as acetic acid, among which alcohols (particularly methanol) are preferred.

There are no particular restrictions on the halogenating agent used so long as it can yield the target compound and does not produce any unseparable by-products, and specifically there may be mentioned chlorine ($Cl_2$), bromine ($Br_2$), iodine ($I_2$), N-chlorosuccinimide, N-bromosuccinimide, N-iodosuccinimide, iodine monochloride and thionyl chloride, among which chlorine, bromine and iodine are preferred.

As additives to be used there may be mentioned alkali metal acetate such as sodium acetate and potassium acetate, among which sodium acetate is preferred.

The reaction temperature will differ depending on the starting materials, solvent and reagents, but will usually be between −20° C. and 100° C., and is preferably between 20° C. and 50° C.

The reaction time will differ depending on the starting materials, solvent, reagents and reaction temperature, but will usually be 0.25 to 48 hours, and is preferably 12 to 24 hours.

Compound (1) of the invention may be isolated or purified from the reaction mixture obtained above, by the method described below.

When R10 of the resultant compound (1) is optionally substituted 5- to 10-membered cycloalkenyl, the hydrogenation described above in Method A may be carried out by selecting the reaction conditions so as to avoid reducing the introduced halogen, to yield compound (1) of the invention wherein R10 is 5- to 10-membered cycloalkyl optionally substituted with the corresponding substituent.

When the resultant compound is to be converted to an acid salt, this may be carried out by a conventional method. The step of producing the salt and the step of hydrogenation may be carried out in a different order where appropriate.

(Step N-1-2)

In this step, the halogenated compound obtained in Step N-1-1 is converted to a compound having a desired substituent in the presence of a transition metal catalyst, and protecting groups on the resultant compound are optionally removed by the method described below, to produce compound (1) of the invention.

The aryl halide compound obtained in Step N-1-1 may then be subjected to cross coupling reaction with a compound which can introduce a desired substituent or a reactive derivative thereof, in the presence of a transition metal such as palladium, copper, nickel, zinc or zirconium, or a catalyst comprising a combination of any of these metals with a ligand. The bond formation reaction type may be carbon-carbon bond formation, carbon-nitrogen bond formation or carbon-oxygen bond formation. Method F and Method K are examples of these reactions, and as supplementary literature to be used as reference for carrying out this step there may be mentioned, but not limited to, John F. Hartwig; Angew. Chem. Int. Ed.; (1998), 37, 2046., Steven P. Nolan, et al.; Org. Lett. (2001), 3, 10, 1511., Stephen L. Buchwald and Gregory C. Fu, et al.; Org. Lett. (2000), 2, 12, 1729., Stephen P. Stanforth; Tetrahedron (1998), 54, 263., Karen, E. et. al.; J.A.C.S. (2001), 123, 10770., Stephen L. Buchwald, et. al.; J.A.C.S. (1999), 121, 4369., D. M. Tschaen and R. Desmond, et al.; Synth. Comm. (1994), 24, 6, 887., John F. Hartwig, et. al.; J.A.C.S. (2001), 123, 8410., Gregory C. Fu, et al.; Org. Lett. (2001), 3, 26, 4295., Damien Prim, et al.; and Tetrahedron (2002), 58, 2041.

For example, introduction of morpholine as a substituent in a carbon-nitrogen bond formation reaction may be carried out in the following manner.

There are no particular restrictions on the solvent used so long as it dissolves the starting compound to some extent and does not inhibit the reaction of this step, and specifically there may be mentioned aromatic hydrocarbons such as benzene, toluene and xylene, ethers such as dioxane, dimethoxyethane and tetrahydrofuran, and amides such as dimethylformamide, among which xylene is preferred.

There are no particular restrictions on the additive used so long as it can yield the target compound and does not produce any unseparable by-products, and it may be appropriately selected from among palladium catalysts such as palladium (II) acetate, bases such as potassium t-butoxide, sodium t-butoxide and cesium carbonate, and phosphines such as 2,2'-bis(diphenylphosphino)-1,1'-binaphthyl and tri-t-butylphosphonium tetrafluoroborate, among which a combination of palladium(II) acetate, sodium t-butoxide and tri-t-butylphosphonium tetrafluoroborate is preferred.

The reaction temperature will differ depending on the starting materials, solvent and reagents, but will usually be between 50° C. and 200° C., and is preferably between 70° C. and 150° C.

The reaction time will differ depending on the starting materials, solvent, reagents and reaction temperature, but will usually be 0.5 to 72 hours, and is preferably 2 to 24 hours.

Compound (1) of the invention may be isolated or purified from the reaction mixture obtained above, by the following method.

When R10 of the resultant compound (1) is optionally substituted 5- to 10-membered cycloalkenyl, it may be subjected to the hydrogenation described above in Method A to yield compound (1) of the invention wherein R10 is 5- to 10-membered cycloalkyl optionally substituted with the corresponding substituent.

When the resultant compound is to be converted to an acid salt, this may be carried out by a conventional method. The step of producing the salt and the step of hydrogenation may be carried out in a different order where appropriate.

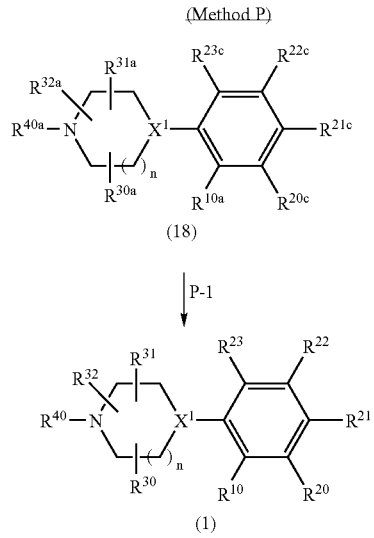

Method P is a method of producing compound (1) of the invention by reacting compound (18) with a trifluoromethanesulfonylating agent in an inert solvent, to yield a compound wherein the phenolic hydroxyl has been trifluoromethanesulfonylated (Step P-1-1), and optionally removing protecting groups on the resultant compound, or alternatively, (Step P-1-1) may be followed by reaction with a compound which can introduce a desired substituent into the phenyltriflate compound, or a reactive derivative thereof (Step P-1-2), and optionally removal of protecting groups on the resultant compound, to produce compound (1) of the invention.

This method may be carried out when a phenolic hydroxyl group is present on the benzene ring to which R10a is bonded.

In this scheme, R10, R20, R21, R22, R23, R30, R31, R32, R40, n, X1, R10a, R30a, R31a, R32a and R40a have the same definitions as above. Also, one of R20c, R21c, R22c and R23c is a phenolic hydroxyl group, while the remaining groups correspond to R20a, R21a, R22a and R23a, respectively.

(Step P-1-1)

This step may be carried out in a manner similar to the sulfonylation described in Method A or Method B above.

Trifluoromethanesulfonylation may be replaced by nonafluorobutanesulfonylation or toluenesulfonylation.

Compound (1) of the invention may be isolated or purified from the reaction mixture obtained above, by the method described below.

When R10 of the resultant compound (1) is optionally substituted 5- to 10-membered cycloalkenyl, it may be subjected to the hydrogenation described above in Method A to yield compound (1) of the invention wherein R10 is 5- to 10-membered cycloalkyl optionally substituted with the corresponding substituent.

When the resultant compound is to be converted to an acid salt, this may be carried out by a conventional method. The step of producing the salt and the step of hydrogenation may be carried out in a different order where appropriate.

(Step P-1-2)

This is a step of converting the trifluoromethanesulfonyloxy group of the compound obtained in Step P-1-1 to a desired substituent.

This step may be carried out in a manner similar to Method N-1-2 described above. As supplementary literature to be used as reference for carrying out this method, there may be mentioned, but not limited to, Kurt Ritter; Synthesis, (1993), 735.

Compound (1) of the invention may be isolated or purified from the reaction mixture obtained above, by the method described below.

When R10 of the resultant compound (1) is optionally substituted 5- to 10-membered cycloalkenyl, it may be subjected to the hydrogenation described above in Method A to yield compound (1) of the invention wherein R10 is 5- to 10-membered cycloalkyl optionally substituted with the corresponding substituent.

When the resultant compound is to be converted to an acid salt, this may be carried out by a conventional method. The step of producing the salt and the step of hydrogenation may be carried out in a different order where appropriate.

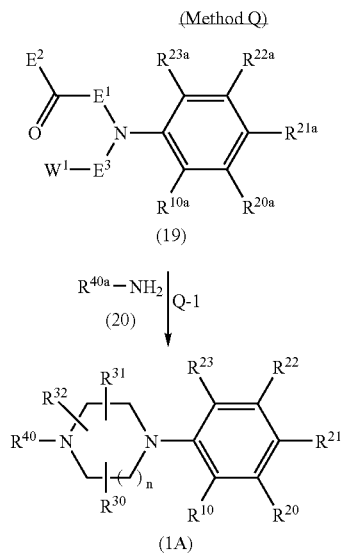

presence of an additive, and optionally removing protecting groups on the resultant compound.

In this scheme, R10, R20, R21, R22, R23, R30, R31, R32, R40, n, W1, R10a, R20a, R21a, R22a, R23a and R40a have the same definitions as above. Also, E1, E2 and E3 are groups suitable for obtaining the desired group of the formula:

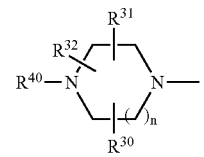

Substituents on E1, E2 or E3 may optionally be protected.

This method may be carried out in a manner similar to Method C described above.

Compound (1A) of the invention may be isolated or purified from the reaction mixture obtained above, by the method described below.

When R10 of the resultant compound (1A) is optionally substituted 5- to 10-membered cycloalkenyl, it may be subjected to the hydrogenation described above in Method A to yield compound (1A) of the invention wherein R10 is 5- to 10-membered cycloalkyl optionally substituted with the corresponding substituent.

When the resultant compound is to be converted to an acid salt, this may be carried out by a conventional method. The step of producing the salt and the step of hydrogenation may be carried out in a different order where appropriate.

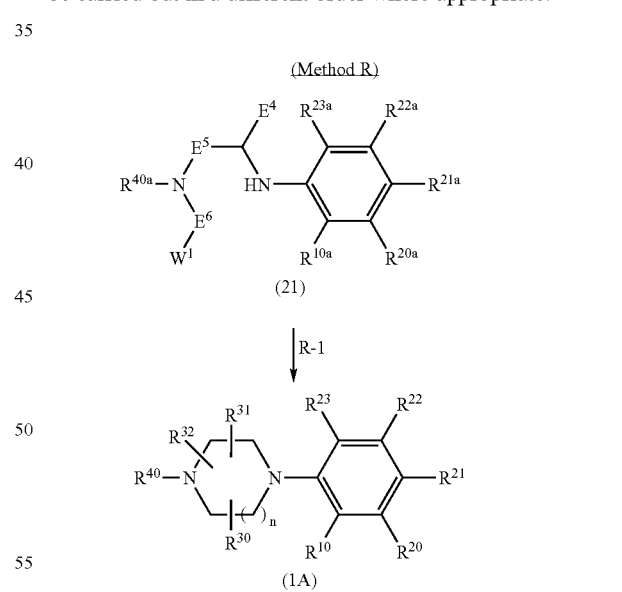

Method R is a method of producing compound (1A) of the invention (the compound according to the formula (1) wherein X1 is nitrogen) by reacting compound (21) with a base in an inert solvent, and optionally removing protecting groups on the resultant compound.

In this scheme, R10, R20, R21, R22, R23, R30, R31, R32, R40, n, W1, R10a, R20a, R21a, R22a, R23a and R40a have the same definitions as above. Also, E4, E5 and E6 are groups suitable for obtaining the desired group of the formula:

Method Q is a method of producing compound (1A) of the invention (the compound according to the formula (1) wherein X1 is nitrogen) by reacting compound (19) and compound (20) in an inert solvent, in the presence of a reducing agent, in the presence or in the absence of an acid, in the

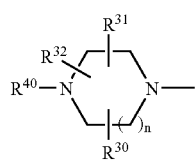

Substituents on E4, E5 or E6 may optionally be protected.

This method may be carried out in a manner similar to Method A described above.

Compound (1A) of the invention may be isolated or purified from the reaction mixture obtained above, by the method described below.

When R10 of the resultant compound (1A) is optionally substituted 5- to 10-membered cycloalkenyl, it may be subjected to the hydrogenation described above in Method A to yield compound (1A) of the invention wherein R10 is 5- to 10-membered cycloalkyl optionally substituted with the corresponding substituent.

When the resultant compound is to be converted to an acid salt, this may be carried out by a conventional method. The step of producing the salt and the step of hydrogenation may be carried out in a different order where appropriate.

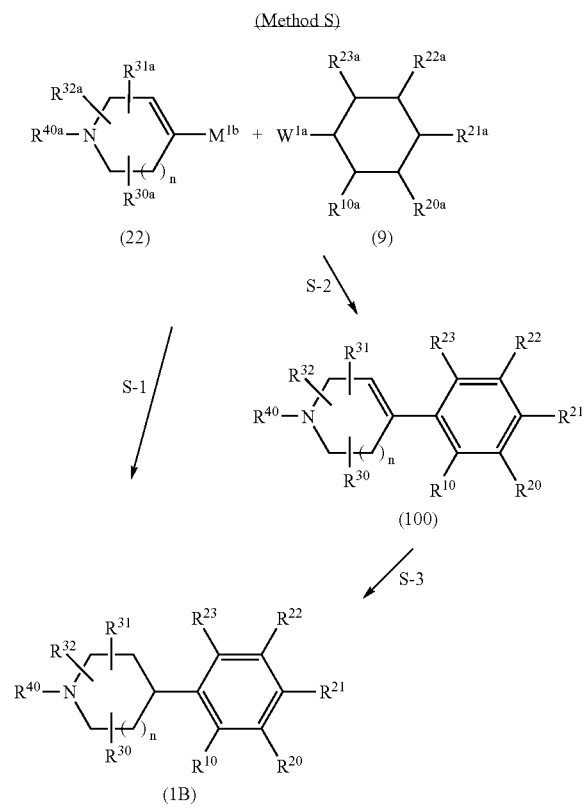

Method S is a method of producing compound (1B) of the invention (the compound according to the formula (1) wherein X1 is CH) by reacting a palladium(0) catalyst, compound (22) and compound (9) in an inert solvent, and then hydrogenating the product and optionally removing protecting groups on the compound (Method S-1) or a method of producing compound (100) of the invention by reacting compounds (22) and (9) in the same manner and optionally removing protecting groups on the resultant compound (Method S-2), and a method of leading to compound (1B) of the invention further by hydrogenation if necessary (Method S-3).

In this scheme, R10, R20, R21, R22, R23, R30, R31, R32, R40, n, W1a, M1b, R10a, R20a, R21a, R22a, R23a, R30a, R31a, R32a and R40a have the same definitions as above.

This method may be carried out in a manner similar to Method K described above, followed by hydrogenation reaction in a manner similar to Method A above.

Compound (1B) and (100) of the invention may be isolated or purified from the reaction mixture obtained above, by the method described below.

When the resultant compound is to be converted to an acid salt, this may be carried out by a conventional method. The step of producing the salt and the step of hydrogenation after reaction between compound (22) and compound (9) may be carried out in a different order where appropriate.

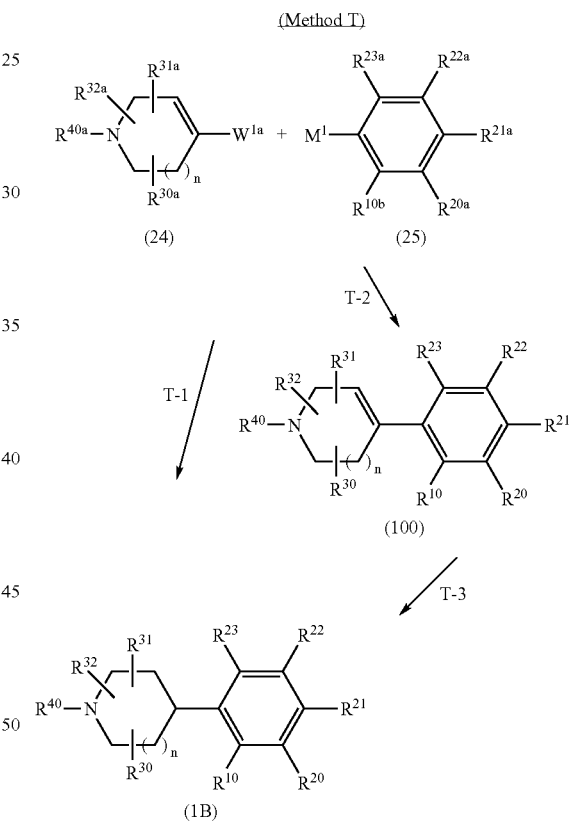

Method T is a method of producing compound (1B) of the invention (the compound according to the formula (1) wherein X1 is CH) by reacting compound (24) and compound (25) in an inert solvent, in the presence of a palladium(0) catalyst, and then hydrogenating the product and optionally removing protecting groups on the resultant compound (Method T-1), or a method of producing compound (100) of the invention by reacting compounds (24) and (25) in the same manner and optionally removing protecting groups on the resultant compound (Method T-2), and a method of leading to compound (1B) of the invention further by hydrogenation if necessary (Method T-3).

In this scheme, R10, R20, R21, R22, R23, R30, R31, R32, R40, n, W1a, M1, R10b, R20a, R21a, R22a, R23a, R30a, R31a, R32a and R40a have the same definitions as above.

This method may be carried out in a manner similar to Method K described above, followed by hydrogenation reaction in a manner similar to Method A above.

Compounds (1B) and (100) of the invention may be isolated or purified from the reaction mixture obtained above, by the method described below.

When the resultant compound is to be converted to an acid salt, this may be carried out by a conventional method. The step of producing the salt and the step of hydrogenation after reaction between compound (24) and compound (25) may be carried out in a different order where appropriate.

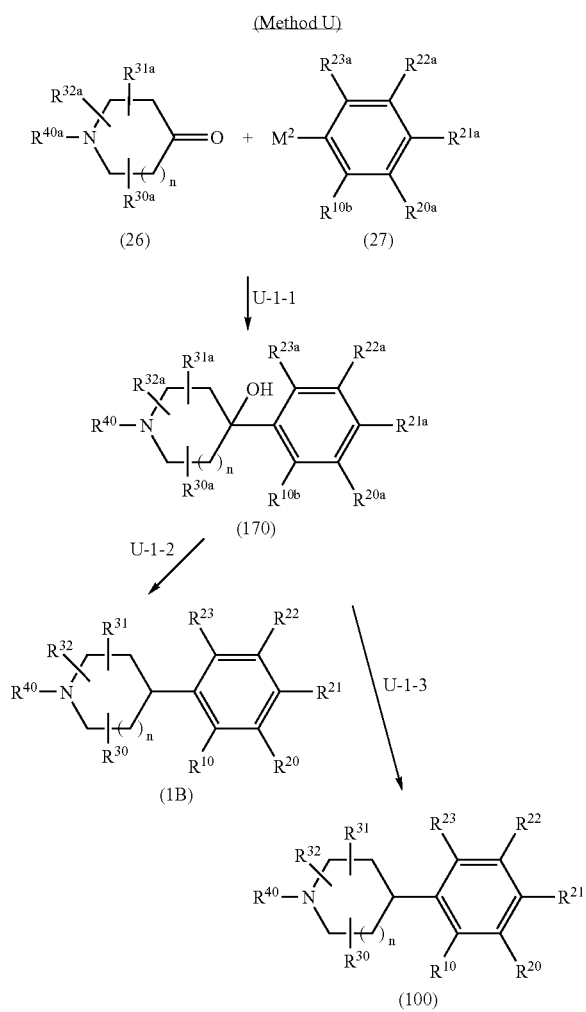

Method U is a method of producing compound (1B) of the invention (the compound according to the formula (1) wherein X1 CH) by reacting compound (26) with compound (27) (i.e. a lithium reagent or Grignard reagent) in an inert solvent to yield an adduct (170) (Step U-1-1), and then reducing the hydroxyl at the benzyl position of the resultant adduct (170) (Step U-1-2), and optionally removing protecting groups, or a method of producing compound (100) of the invention by the reaction in the same manner to yield an adduct (170) (Step U-1-1), then dehydrating the hydroxyl of the adduct (170) in the presence of or in the absence of acid (Step U-1-3), and further removing protecting groups if necessary.

In this scheme, R10, R20, R21, R22, R23, R30, R31, R32, R40, n, R10b, R20a, R21a, R22a, R23a, R30a, R31a, R32a and R40a have the same definitions as above. M2 is a lithium or magnesium halide.

(Step U-1-1)

There are no particular restrictions on the solvent used so long as it dissolves the starting compound to some extent and does not inhibit the reaction of this step, and specifically there may be mentioned ethers such as diethyl ether, diisopropyl ether, tetrahydrofuran, dioxane, dimethoxyethane and diethyleneglycol dimethyl ether, among which tetrahydrofuran is preferred.

The reaction temperature will differ depending on the starting materials, solvent and reagents, but will usually be between −80° C. and 30° C.

The reaction time will differ depending on the starting materials, solvent, reagents and reaction temperature, but will usually be 0.25 to 6 hours.

(Step U-1-2)

This step may be carried out by reduction in a manner similar to the hydrogenation described in Method A above, or by reduction using a trialkylsilyl hydride described hereunder, although there is no limitation to these methods.

There are no particular restrictions on the solvent used so long as it dissolves the starting compound to some extent and does not inhibit the reaction of this step, and specifically there may be mentioned, in the case of reduction reaction using a trialkylsilyl hydride, halogenated hydrocarbons such as chloroform, dichloromethane, 1,2-dichloroethane and carbon tetrachloride (particularly dichloromethane).

There are no particular restrictions on the reducing agents used so long as it can yield the target compound and does not produce any unseparable by-products, and specifically there may be mentioned trialkylsilyl hydrides such as triethylsilyl hydride and triisopropylsilyl hydride, among which triethylsilyl hydride is preferred.

There are no particular restrictions on the additive used so long as it can yield the target compound and does not produce any unseparable by-products, and specifically there may be mentioned halo-substituted acetic acids such as trifluoroacetic acid, and Lewis acids such as boron trifluoride.

The reaction temperature will differ depending on the starting materials, solvent and reagents, but will usually be between −70° C. and 50° C.

The reaction time will differ depending on the starting materials, solvent, reagents and reaction temperature, but will usually be 0.5 to 48 hours.

(Step U-1-3)

There are no particular restrictions on the solvent used so long as it dissolves the starting compound to some extent and does not inhibit the reaction of this step, and specifically there may be mentioned, ethers such as diethyl ether, tetrahydrofuran, dioxane, dimethoxyethane and diethyleneglycol dimethylether, aromatic hydrocarbons such as toluene, benzene and xylene, halogenated hydrocarbons such as chloroform, dichloromethane, 1,2-dichloroethane and carbon tetrachloride, water, and the mixed solvent thereof, or without solvent.

There are no particular restrictions on the reducing agents used so long as it can yield the target compound and does not produce any unseparable by-products, and specifically there may be mentioned trialkylsilyl hydrides such as triethylsilyl hydride and triisopropylsilyl hydride, among which triethylsilyl hydride is preferred, and tetrahydrofuran, toluene, dichloromethane, chloroform or water is preferred.

There are no particular restrictions on the acid additive used so long as it can yield the target compound and does not produce any unseparable by-products, and specifically there may be mentioned halo-substituted acetic acids such as trifluoroacetic acid, Lewis acids such as boron trifluoride, organic sulfonic acids such as toluenesulfonic acid and camphor sulfonic acid, and inorganic acids such as hydrochloric acid and hydrogen bromide.

The reaction temperature will differ depending on the starting materials, solvent and reagents, but will usually be between –80° C. and 180° C.

The reaction time will differ depending on the starting materials, solvent, reagents and reaction temperature, but will usually be 0.25 to 24 hours.

Compounds (1B) and (100) of the invention may be isolated or purified from the reaction mixture obtained above, by the method described below.

When R10 of the resultant compound (1B) is optionally substituted 5- to 10-membered cycloalkenyl, it may be subjected to the hydrogenation described above in Method A to yield compound (1B) of the invention wherein R10 is 5- to 10-membered cycloalkyl optionally substituted with the corresponding substituent.

When the resultant compound is to be converted to an acid salt, this may be carried out by a conventional method. The step of producing the salt and the step of hydrogenation may be carried out in a different order where appropriate.

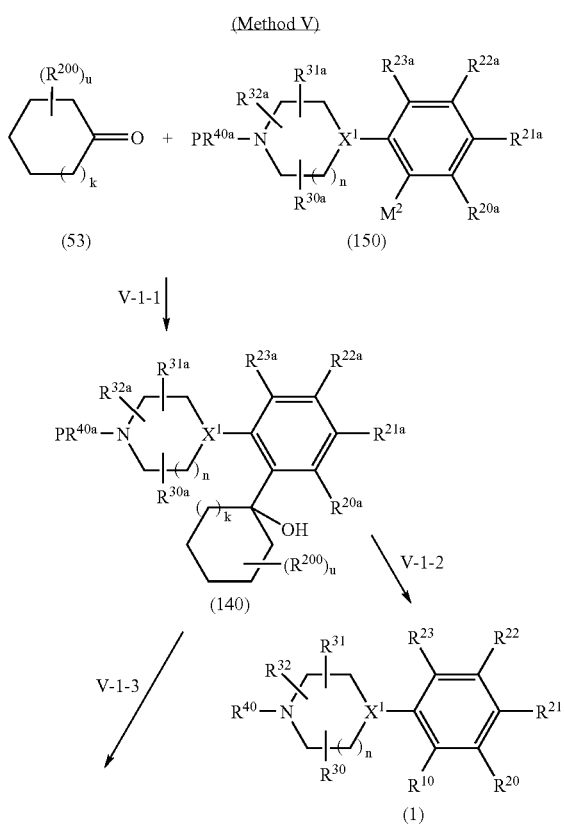

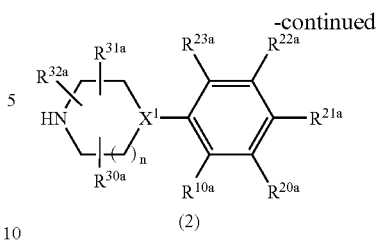

Method V is a method of producing compound (1) of the invention by reacting compound (53) with compound (150) (i.e. a lithium reagent or Grignard reagent) in an inert solvent to yield an adduct (140) (Step V-1-1), and then, if necessary, reducing or dehydrating the hydroxyl at the benzyl position of the resultant adduct (140) (Step V-1-2), and optionally removing protecting groups, or a method of producing compound (2) by the reaction in the same manner to yield an adduct (140) (Step V-1-1), then, if necessary, reducing or dehydrating the hydroxyl at the benzyl position of the adduct (140) (Step V-1-3), and further removing protecting groups.

In this scheme, R10, R20, R21, R22, R23, R30, R31, R32, R40, X1, n, R10a, R20a, R21a, R22a, R23a, R30a, R31a and R32a have the same definitions as above. M2 is a lithium or magnesium halide. R200 has the same definition as substituents included in Group A1 above, or represents the substituents, the substituents thereon being protected. u is an integer of 0, 1, 2, 3, 4 or 5. k is an integer of 0, 1, 2, 3, 4 or 5. PR40a has the same definition as R40a above or represents protecting group for amino (preferably, t-butoxycarbonyl or benzyl).

This method may be performed in a manner similar to Method U and subsequently hydrogenation described in Method A.

Compound (1) of the invention and compound (2) may be isolated or purified from the reaction mixture obtained above, by the method described below.

When R10 of the resultant compound (1) is optionally substituted 5- to 10-membered cycloalkenyl, it may be subjected to the hydrogenation described above in Method A to yield compound (1) of the invention wherein R10 is 5- to 10-membered cycloalkyl optionally substituted with the corresponding substituent.

When the resultant compound is to be converted to an acid salt, this may be carried out by a conventional method. The step of producing the salt and the step of hydrogenation may be carried out in a different order where appropriate.

Removal of the protecting group(s) will differ depending on their types, and it may be carried out in the following manner, according to protocols commonly known in the field of synthetic organic chemistry such as the protocol described in, for example, T. W. Greene, (Protective Groups in Organic Synthesis) or John Wiley & Sons: J. F. W. McOmis, (Protective Groups in Organic Chemistry), Plenum Press.

When the amino-protecting group is an optionally substituted silyl group such as trimethylsilyl, triethylsilyl, triisopropylsilyl, t-butyldimethylsilyl or t-butyldiphenylsilyl, it will usually be removed by treatment with a fluoride anion-generating compound such as tetrabutylammonium fluoride, hydrofluoric acid, hydrofluoric acid-pyridine or potassium fluoride.

The inert solvent used for the reaction is not particularly restricted so long as it does not inhibit the reaction, and for example, ethers such as diethyl ether, diisopropyl ether, tetrahydrofuran, dioxane, dimethoxyethane and diethyleneglycol dimethyl ether are preferred.

There are no particular restrictions on the reaction temperature and reaction time, but normally the reaction temperature will be between 0° C. and 50° C., and the reaction time will be between 10 to 18 hours.

When the amino-protecting group is an optionally substituted aliphatic acyl group, an optionally substituted aromatic acyl group, an optionally substituted alkoxycarbonyl group or a substituted methylene group which forms a Schiff base, it may be removed by treatment with an acid or base in the presence of an aqueous solvent.

The acid used for this reaction is not particularly restricted so long as it is an acid which is ordinarily used for removal of the amino-protecting group, and for example, it may be an inorganic acid such as hydrobromic acid, hydrochloric acid, sulfuric acid, perchloric acid, phosphoric acid or nitric acid, or an organic acid such as trifluoroacetic acid and trifluoromethanesulfonic acid, among which hydrochloric acid or trifluoroacetic acid is preferred.

The base used for this reaction is not particularly restricted so long as it is a base which is ordinarily used for removal of the amino-protecting group, but there are preferably used alkali metal carbonic acid salts such as lithium carbonate, sodium carbonate and potassium carbonate; alkali metal hydroxides such as lithium hydroxide, sodium hydroxide and potassium hydroxide; metal alkoxides such as lithium methoxide, sodium methoxide, sodium ethoxide and potassium-t-butoxide; and ammonia mixtures such as ammonia water and concentrated ammonia-methanol.

The solvent used for the reaction may be, for example, an alcohol such as methanol, ethanol, n-propanol, isopropanol, n-butanol, isobutanol, t-butanol, isoamyl alcohol, diethylene glycol, glycerin, octanol, cyclohexanol or methylcellosolve; an ether such as diethyl ether, diisopropyl ether, tetrahydrofuran, dioxane, dimethoxyethane or diethyleneglycol dimethyl ether; water; or a mixture of water and any of the aforementioned solvents, among which alcohols (most preferably ethanol) are preferred.

The reaction temperature and the reaction time will differ depending on the starting compounds, the solvent and the acid or base used and are not particularly restricted, but in order to inhibit by-products, the reaction temperature will usually be between 0° C. and 150° C. and the reaction time will usually be 1 to 10 hours.

When the amino-protecting group is an optionally substituted aralkyl group or an optionally substituted aralkyloxycarbonyl group, a method of contact with a reducing agent in an inert solvent (preferably catalytic reduction at ordinary temperature in the presence of a catalyst) or a method of removal by oxidation is generally preferred.

The inert solvent used for removal by catalytic reduction is not particularly restricted so long as it is inert to the reaction, and for example, it may be an aliphatic hydrocarbon such as hexane, heptane, ligroin or petroleum ether; an aromatic hydrocarbon such as toluene, benzene or xylene; an ester such as methyl acetate, ethyl acetate, propyl acetate, butyl acetate or diethyl carbonate; an ether such as diethyl ether, diisopropyl ether, tetrahydrofuran, dioxane, dimethoxyethane or diethyleneglycol dimethyl ether; an alcohol such as methanol, ethanol, n-propanol, isopropanol, n-butanol, isobutanol, t-butanol, isoamyl alcohol, diethylene glycol, glycerin, octanol, cyclohexanol or methylcellosolve; an organic acid such as acetic acid; water; or a mixture of any of these solvents with water, among which alcohols, ethers, organic acids and water (most preferably alcohols and organic acids) are preferred.

The catalyst used for removal by catalytic reduction is preferably palladium-carbon, Raney nickel, platinum oxide, platinum-black, rhodium-aluminum oxide, triphenylphosphine-rhodium chloride or palladium-barium sulfate.

There are no particular restrictions on the pressure, but it will ordinarily be from 1 to 10 atmospheres.

The reaction temperature and the reaction time will differ depending on the starting materials, catalyst and insert solvent, but usually the reaction temperature will be between 0° C. and 100° C., and the reaction time will be between 5 minutes and 72 hours.

The inert solvent used for removal by oxidation is not particularly restricted so long as it does not participate in the reaction, but water-containing organic solvents are preferred. Such organic solvents include, for example, halogenated hydrocarbons such as chloroform, dichloromethane, 1,2-dichloroethane and carbon tetrachloride; nitriles such as acetonitrile; ethers such as diethyl ether, diisopropyl ether, tetrahydrofuran, dioxane, dimethoxyethane and diethyleneglycol dimethyl ether; ketones such as acetone; amides such as formamide, dimethylformamide, dimethylacetamide and hexamethylphosphoric triamide; and sulfoxides such as dimethylsulfoxide and sulfolane, among which halogenated hydrocarbons, ethers or sulfoxides (most preferably halogenated hydrocarbons and sulfoxides) are preferred.

The oxidizing agent used for this reaction is not particularly restricted so long as it is an oxidizing agent used for removal of the amino-protecting group, but it is preferably potassium persulfate, sodium persulfate, ammonium cerium nitrate (CAN) or 2,3-dichloro-5,6-dicyano-p-benzoquinone (DDQ).

The reaction temperature and the reaction time will differ depending on the starting compounds, oxidizing agent and solvent, but usually the reaction temperature will be between 0° C. and 150° C., and the reaction time will be between 10 minutes and 24 hours.

When the amino-protecting group is an optionally substituted aralkyl group, the protecting group may be removed using an acid or base.

The acid used for this reaction is not particularly restricted so long as it is an acid used for removal of the optionally substituted aralkyl group as the amino-protecting group, and for example, it may be a Bronsted acid, e.g. an inorganic acid such as hydrochloric acid, hydrobromic acid, sulfuric acid, perchloric acid or phosphoric acid, or an organic acid such as acetic acid, formic acid, oxalic acid, methanesulfonic acid, p-toluenesulfonic acid, camphor sulfonic acid, trifluoroacetic acid or trifluoromethanesulfonic acid; a Lewis acid such as zinc chloride, tin tetrachloride, boron trichloride, boron trifluoride or boron tribromide; or an acidic ion-exchange resin, among which inorganic acids and organic acids (most preferably hydrochloric acid, acetic acid and trifluoroacetic acid) are preferred.

The base used for the reaction is not particularly restricted so long as it is a base ordinarily used for removal of the optionally substituted aralkyl group as the amino-protecting group, but it is preferably an alkali metal carbonate such as lithium carbonate, sodium carbonate or potassium carbonate; an alkali metal hydroxide such as lithium hydroxide, sodium hydroxide or potassium hydroxide; a metal alkoxide such as lithium methoxide, sodium methoxide, sodium ethoxide or potassium-t-butoxide; or an ammonia mixture such as aqueous ammonia or concentrated ammonia-methanol.

The inert solvent used for the first stage of the reaction is not particularly restricted so long as it is inert to the reaction, and as examples there may be mentioned aliphatic hydrocarbons such as hexane, heptane, ligroin and petroleum ether; aromatic hydrocarbons such as benzene, toluene and xylene; halogenated hydrocarbons such as chloroform, dichloromethane, 1,2-dichloroethane and carbon tetrachloride; esters such as methyl acetate, ethyl acetate, propyl acetate, butyl acetate and diethyl carbonate; ethers such as diethyl ether, diisopropyl ether, tetrahydrofuran, dioxane, dimethoxyethane and diethyleneglycol dimethyl ether; alcohols such as methanol, ethanol, n-propanol, isopropanol, n-butanol, isobutanol, t-butanol, isoamyl alcohol, diethylene glycol, glycerin, octanol, cyclohexanol and methylcellosolve; amides such as formamide, dimethylformamide, dimethylacetamide and hexamethylphosphoric triamide; water; and mixtures of the aforementioned solvents, among which ethers, alcohols and water (most preferably dioxane, tetrahydrofuran, ethanol or water) are preferred.

The reaction temperature will differ depending on the starting compounds and the acid and solvent used, but will ordinarily be between −20° C. and the boiling temperature (preferably between 0° C. and 100° C.).

The reaction time will differ depending on the starting compounds, the acid and inert solvent used and the reaction temperature, but will ordinarily be between 15 minutes and 48 hours (preferably between 30 minutes and 20 hours).

When the amino-protecting group is an optionally substituted alkenyloxycarbonyl group, usually the removal may be accomplished by treatment with an acid or base, under the same conditions as removal reaction when the amino-protecting group is an optionally substituted aliphatic acyl group, an optionally substituted aromatic acyl group, an optionally substituted alkoxycarbonyl group or a substituted methylene group which forms a Schiff base.

In the case of an allyloxycarbonyl group, it is particularly convenient to employ a method of removal using palladium and triphenylphosphine or nickel-tetracarbonyl, as the removal can be carried out with few by-products.

When the amino-protecting group is an optionally substituted alkyl group, optionally substituted alkenyl group or optionally substituted sulfonyl group, usually the removal may be accomplished by treatment with an acid or base, under the same conditions as removal reaction when the amino-protecting group is an aliphatic acyl group, an aromatic acyl group, an alkoxycarbonyl group or a substituted methylene group which forms a Schiff base.

When the hydroxyl-protecting group is, for example, an optionally substituted silyl group such as trimethylsilyl, triethylsilyl, triisopropylsilyl, t-butyldimethylsilyl or t-butyldiphenylsilyl, it will usually be removed by treatment with a fluoride anion-generating compound such as tetrabutylammonium fluoride, hydrofluoric acid, hydrofluoric acid-pyridine or potassium fluoride, or with an inorganic acid such as hydrochloric acid, hydrobromic acid, sulfuric acid, perchloric acid or phosphoric acid, or an organic acid such as acetic acid, formic acid, oxalic acid, methanesulfonic acid, p-toluenesulfonic acid, camphor sulfonic acid, trifluoroacetic acid or trifluoromethanesulfonic acid.

For removal with fluoride anion, an organic acid such as formic acid, acetic acid or propionic acid may be added to accelerate the reaction.

The inert solvent used for the reaction is not particularly restricted so long as it is inert to the reaction, but it is preferably an ether such as diethyl ether, diisopropyl ether, tetrahydrofuran, dioxane, dimethoxyethane or diethyleneglycol dimethyl ether; a nitrile such as acetonitrile or isobutyronitrile; an organic acid such as acetic acid; water; or a mixture of these solvents.

The reaction temperature and the reaction time will differ depending on the starting compounds, catalyst and inert solvent used, but ordinarily the reaction temperature will be between 0° C. and 100° C. (preferably between 10° C. and 50° C.), and the reaction time will be 1 to 24 hours.

When the hydroxyl-protecting group is an optionally substituted aralkyl group or an optionally substituted aralkyloxycarbonyl group, a method of contact with a reducing agent in an inert solvent (preferably catalytic reduction at ordinary temperature in the presence of a catalyst) or a method of removal using an oxidizing agent is generally preferred.

The inert solvent used for removal by catalytic reduction is not particularly restricted so long as it does not participate in the reaction, and as examples there may be mentioned aliphatic hydrocarbons such as hexane, heptane, ligroin and petroleum ether; aromatic hydrocarbons such as toluene, benzene and xylene; esters such as ethyl acetate and propyl acetate; ethers such as diethyl ether, diisopropyl ether, tetrahydrofuran, dioxane, dimethoxyethane and diethyleneglycol dimethyl ether; alcohols such as methanol, ethanol, n-propanol, isopropanol, n-butanol, isobutanol, t-butanol, isoamyl alcohol, diethylene glycol, glycerin, octanol, cyclohexanol and methylcellosolve; amides such as formamide, dimethylformamide, dimethylacetamide, N-methyl-2-pyrrolidone and hexamethylphosphoric triamide; aliphatic acids such as formic acid and acetic acid; water; and mixtures of these solvents, among which alcohols (most preferably methanol and ethanol) are preferred.

There are no particular restrictions on the catalyst used for removal by catalytic reduction so long as it is one commonly used for removal of the hydroxyl-protecting group by catalytic reduction, and as examples there may be mentioned palladium-carbon, palladium black, Raney nickel, platinum oxide, platinum black, rhodium-aluminum oxide, triphenylphosphine-rhodium chloride or palladium-barium sulfate, among which palladium-carbon is preferred.

There are no particular restrictions on the pressure, but it will ordinarily be from 1 to 10 atmospheres.

The reaction temperature and the reaction time will differ depending on the starting compounds, catalyst and insert solvent, but usually the reaction temperature will be between 0° C. and 100° C. (preferably between 20° C. and 70° C.), and the reaction time will be between 5 minutes and 48 hours (preferably between 1 hour and 24 hours).

The inert solvent used for removal by oxidation is not particularly restricted so long as it does not participate in the reaction, but it is preferably a water-containing solvent, and there may be mentioned as examples ketones such as acetone; halogenated hydrocarbons such as methylene chloride, chloroform and carbon tetrachloride; nitriles such as acetonitrile; ethers such as diethyl ether, tetrahydrofuran and dioxane; amides such as dimethylformamide, dimethylacetamide and hexamethylphosphoric triamide; and sulfoxides such as dimethylsulfoxide.

The oxidizing agent used for this reaction is not particularly restricted so long as it is an oxidizing agent used for removal of the hydroxyl-protecting group, but it is preferably potassium persulfate, sodium persulfate, ammonium cerium nitrate (CAN) or 2,3-dichloro-5,6-dicyano-p-benzoquinone (DDQ).

The reaction temperature and the reaction time will differ depending on the starting compounds, oxidizing agent and inert solvent, but usually the reaction temperature will be between 0° C. and 150° C., and the reaction time will be between 10 minutes and 24 hours.

The removal can also be accomplished by reaction with an alkali metal such as lithium metal or sodium metal in liquid ammonia or an alcohol such as methanol, ethanol, n-propanol, isopropanol, n-butanol, isobutanol, t-butanol, isoamyl alcohol, diethylene glycol, glycerin, octanol, cyclohexanol or methylcellosolve, at a temperature of between −78° C. and 0° C.

The removal can also be accomplished using aluminum chloride-sodium iodide or an alkylsilyl iodide such as trimethylsilyl iodide, in an inert solvent.

The inert solvent used in this reaction is not particularly restricted so long as it does not participate in the reaction, but it is preferably a halogenated hydrocarbon such as methylene chloride, chloroform or carbon tetrachloride; a nitrile such as acetonitrile; or a mixture of these solvents.

The reaction temperature and the reaction time will differ depending on the starting compounds and the inert solvent, but usually the reaction temperature will be between 0° C. and 50° C., and the reaction time will be between 5 minutes and 72 hours.

When the hydroxyl-protecting group is an aliphatic acyl group, an aromatic acyl group or an optionally substituted alkoxycarbonyl group, it may be removed by treatment with a base in an inert solvent.

There are no particular restrictions on the base used for this reaction so long as it is a base ordinarily used for removal of the hydroxyl-protecting group, and for example, it may be an alkali metal carbonic acid salt such as lithium carbonate, sodium carbonate or potassium carbonate; an alkali hydrogencarbonate such as lithium hydrogencarbonate, sodium hydrogencarbonate or potassium hydrogencarbonate; an alkali metal hydroxide such as lithium hydroxide, sodium hydroxide or potassium hydroxide; a metal alkoxide such as lithium methoxide, sodium methoxide, sodium ethoxide or potassium-t-butoxide; or an ammonia mixture such as aqueous ammonia or concentrated ammonia-methanol, among which alkali metal hydroxides, metal alkoxides and ammonia mixtures (most preferably alkali metal hydroxides and metal alkoxides) are preferred.

The inert solvent used for this reaction is not particularly restricted so long as it is ordinarily used for hydrolysis reaction, but it is preferably an ether such as diethyl ether, diisopropyl ether, tetrahydrofuran, dioxane, dimethoxyethane or diethyleneglycol dimethyl ether; an alcohol such as methanol, ethanol, n-propanol, isopropanol, n-butanol, isobutanol, t-butanol, isoamyl alcohol, diethylene glycol, glycerin, octanol, cyclohexanol or methylcellosolve; water; or a mixture of these solvents.

The reaction temperature and the reaction time will differ depending on the starting compounds and the base and inert solvent used, but in order to inhibit by-products, the reaction temperature will usually be between −20° C. and 150° C., and the reaction time will usually be 1-10 hours.

When the hydroxyl-protecting group is optionally substituted alkoxymethyl, optionally substituted alkylthiomethyl, tetrahydropyranyl, tetrahydrothiopyranyl, tetrahydrofuranyl, tetrahydrothiofuranyl or optionally substituted ethyl such as 1-ethoxyethyl, it will usually be removed by treatment with an acid in an inert solvent.

There are no particular restrictions on the acid used for this reaction so long as it is an acid used for removal of the hydroxyl-protecting group, but usually compounds ordinarily used as Bronsted acids or Lewis acids may be mentioned, and preferred are Bronsted acids including hydrogen chloride; inorganic acids such as hydrochloric acid, sulfuric acid and nitric acid; and organic acids such as acetic acid, trifluoroacetic acid, methanesulfonic acid and p-toluenesulfonic acid; or Lewis acids such as boron trifluoride, while strong acid cation exchange resins such as DOWEX 50W may also be used.

There are no particular restrictions on the inert solvent used for this reaction so long as it is inert to the reaction, and for example, there may be mentioned aliphatic hydrocarbons such as hexane, heptane, ligroin and petroleum ether; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethyleneglycol dimethyl ether; alcohols such as methanol, ethanol, n-propanol, isopropanol, n-butanol, isobutanol, t-butanol, isoamyl alcohol, diethylene glycol, glycerin, octanol, cyclohexanol and methylcellosolve; ketones such as acetone, methyl ethyl ketone, methyl isobutyl ketone, isophorone and cyclohexanone; water; and mixtures of these solvents, among which ethers and alcohols (most preferably tetrahydrofuran and methanol) are preferred.

The reaction temperature and the reaction time will differ depending on the starting compound and the acid and inert solvent used, but usually the reaction temperature will be between −10° C. and 200° C. (preferably between 0° C. and 150° C.), and the reaction time will be between 5 minutes and 48 hours (preferably between 30 minutes and 10 hours).

When the hydroxyl-protecting group is an optionally substituted alkenyloxycarbonyl group or optionally substituted sulfonyl group, usually the removal may be accomplished by treatment with a base, under the same conditions as removal reaction when the hydroxyl-protecting group is the aforementioned optionally substituted aliphatic acyl group, optionally substituted aromatic acyl group or optionally substituted alkoxycarbonyl group.

In the case of an allyloxycarbonyl group, it is particularly convenient to employ a method of removal using palladium and triphenylphosphine or bis(methyldiphenylphosphine)(1, 5-cyclooctadiene)iridium(I) hexafluorophosphate, as the removal can be carried out with few by-products.

When the carboxyl-protecting group is a lower alkyl group, a lower alkenyl group or a lower alkynyl group, or an optionally substituted silyl group, or when the compound has been converted to an ortho ester for the purpose of protection, a method of removal by treatment with an acid or base, or using an enzyme, is preferred.

There are no particular restrictions on the acid used for this reaction so long as it is used for removal of the carboxyl-protecting group, and for example, it may be hydrochloric acid, sulfuric acid, phosphoric acid or hydrobromic acid.

There are no particular restrictions on the base used for this reaction so long as it is used for removal of the carboxyl-protecting group, and for example, it may be an alkali metal carbonate such as sodium carbonate or potassium carbonate; an alkali metal hydroxide such as sodium hydroxide or potassium hydroxide; or concentrated ammonia-methanol solution, among which sodium hydroxide is preferred.

Isomerization may occur with hydrolysis using a base.

There are no particular restrictions on the enzyme used for the reaction so long as it is an enzyme used for removal of the carboxyl-protecting group, and for example, it may be a lipase or an esterase.

The solvent used for this reaction may be, for example, water, an alcohol such as methanol, ethanol or n-propanol; an ether such as tetrahydrofuran or dioxane; or a mixture of any of these solvents with water, among which an alcohol (most preferably methanol) is preferred.

The reaction temperature and the reaction time will differ depending on the starting compounds, the solvent and the reagents used and are not particularly restricted, but in order to inhibit by-products, the reaction temperature will usually be between 0° C. and 220° C., and the reaction time will usually be between 30 minutes and 10 hours.

When the carboxyl-protecting group is an optionally substituted aralkyl group or halogeno lower alkyl group, it will usually be removed by reduction in a solvent.

The reduction method is preferably a method by chemical reduction with zinc-acetic acid when the carboxyl-protecting group is a halogeno lower alkyl group, and when it is an optionally substituted aralkyl group, the method may be one of catalytic reduction using a catalyst such as palladium-carbon or platinum, or a method of chemical reduction using an alkali metal sulfide such as potassium sulfide or sodium sulfide.

The solvent used is not particularly restricted so long as it does not participate in the reaction, but there are preferred alcohols such as methanol and ethanol; ethers such as tetrahydrofuran and dioxane; aliphatic acids such as acetic acid; and mixtures of these solvents with water.

The reaction temperature and the reaction time will differ depending on the starting compounds, the solvent and the reduction method, but usually the reaction temperature will be between 0° C. and approximately room temperature and the reaction time will be between 5 minutes and 12 hours.

If the carbonyl group has been protected by conversion to a cyclic or acyclic ketal formed using, for example, an alcohol such as methanol, isopropanol or diethylene glycol or a thiol such as methanethiol, ethanethiol or propanedithiol, an acid may be used for reconversion to a carbonyl group.

The acid used for this reaction is not particularly restricted so long as it is an acid ordinarily used for reconversion to a carbonyl group from a cyclic or acyclic ketal formed for the purpose of protecting the carbonyl group, and for example, it may be a Bronsted acid, e.g. an inorganic acid such as hydrochloric acid, hydrobromic acid, sulfuric acid, perchloric acid or phosphoric acid, or an organic acid such as acetic acid, formic acid, oxalic acid, methanesulfonic acid, p-toluenesulfonic acid, camphor sulfonic acid, trifluoroacetic acid or trifluoromethanesulfonic acid; a Lewis acid such as zinc chloride, tin tetrachloride, boron trichloride, boron trifluoride or boron tribromide; or an acidic ion exchange resin, among which inorganic acids and organic acids (most preferably hydrochloric acid and p-toluenesulfonic acid) are preferred.

There are no particular restrictions on the inert solvent used for the first stage of the reaction so long as it is inert to the reaction, and as examples there may be mentioned aliphatic hydrocarbons such as hexane, heptane, ligroin and petroleum ether; aromatic hydrocarbons such as benzene, toluene and xylene; halogenated hydrocarbons such as chloroform, dichloromethane, 1,2-dichloroethane and carbon tetrachloride; esters such as methyl acetate, ethyl acetate, propyl acetate, butyl acetate and diethyl carbonate; ethers such as diethyl ether, diisopropyl ether, tetrahydrofuran, dioxane, dimethoxyethane and diethyleneglycol dimethyl ether; alcohols such as methanol, ethanol, n-propanol, isopropanol, n-butanol, isobutanol, t-butanol, isoamyl alcohol, diethylene glycol, glycerin, octanol, cyclohexanol and methylcellosolve; amides such as formamide, dimethylformamide, dimethylacetamide and hexamethylphosphoric triamide; water; and mixtures of these solvents, among which ethers, alcohols and water (most preferably acetone, tetrahydrofuran and water) are preferred.

The reaction temperature will differ depending on the starting compounds and the acid and solvent used, but usually it will be between −20° C. and the boiling point (preferably between 0° C. and 100° C.).

The reaction time will differ depending on the starting compounds, the acid and inert solvent used and the reaction temperature, but usually it will be between 5 minutes and 48 hours, (preferably between 10 minutes and 24 hours).

In the case of a cyclic or acyclic ketal formed using a thiol, it is particularly convenient to employ a method of removal using a substance such as Raney nickel or silver nitrate.

In the case of conversion to a cyclic ketal using, for example, formalin or acetone as protection of a diol, an acid may be used for reconversion to the diol.

The acid used for this reaction is not particularly restricted so long as it is an acid ordinarily used for reconversion to a diol from a cyclic or acyclic ketal formed for the purpose of protecting the diol, and for example, it may be a Bronsted acid, e.g. an inorganic acid such as hydrochloric acid, hydrobromic acid, sulfuric acid, perchloric acid or phosphoric acid, or an organic acid such as acetic acid, formic acid, oxalic acid, methanesulfonic acid, p-toluenesulfonic acid, camphor sulfonic acid, trifluoroacetic acid or trifluoromethanesulfonic acid; a Lewis acid such as zinc chloride, tin tetrachloride, boron trichloride, boron trifluoride or boron tribromide; or an acidic ion exchange resin, among which inorganic acids and organic acids (most preferably hydrochloric acid and p-toluenesulfonic acid) are preferred.

There are no particular restrictions on the inert solvent used for the first stage of the reaction so long as it is inert to the reaction, and as examples there may be mentioned aliphatic hydrocarbons such as hexane, heptane, ligroin and petroleum ether; aromatic hydrocarbons such as benzene, toluene and xylene; halogenated hydrocarbons such as chloroform, dichloromethane, 1,2-dichloroethane and carbon tetrachloride; esters such as methyl acetate, ethyl acetate, propyl acetate, butyl acetate and diethyl carbonate; ethers such as diethyl ether, diisopropyl ether, tetrahydrofuran, dioxane, dimethoxyethane and diethyleneglycol dimethyl ether; alcohols such as methanol, ethanol, n-propanol, isopropanol, n-butanol, isobutanol, t-butanol, isoamyl alcohol, diethylene glycol, glycerin, octanol, cyclohexanol and methylcellosolve; amides such as formamide, dimethylformamide, dimethylacetamide and hexamethylphosphoric triamide; water; and mixtures of these solvents, among which ethers, alcohols and water (most preferably acetone, tetrahydrofuran and water) are preferred.

The reaction temperature will differ depending on the starting compounds and the acid and solvent used, but usually it will be between −20° C. and the boiling point (preferably between 0° C. and 100° C.).

The reaction time will differ depending on the starting compounds, the acid and inert solvent used and the reaction temperature, but usually it will be between 5 minutes and 48 hours (preferably between 10 minutes and 24 hours).

Removal of the protecting groups for amino, hydroxyl, carbonyl and/or carboxyl groups, or a diol, may be carried out in an appropriate order, for the desired removal reaction.

After completion of the reactions of each of the methods and steps described above, the target compound of each step may be recovered from the reaction mixture according to conventional procedures.

For example, when the entire reaction mixture is a liquid, it may be returned to room temperature if necessary, or cooled on ice, then allowed to neutralization of an acid, an alkali, an oxidizing agent or a reducing agent if necessary, and then water and an organic solvent such as ethyl acetate which is immiscible with water and which does not react with the target compound may be added, and the layer containing the target compound is separated. Next, there may be added a solvent which is immiscible with the resultant layer and which does not react with the target compound, and the layer containing the target compound may be washed and separated. If the layer is an organic layer, it may be dried using a desiccant such as anhydrous magnesium sulfate or anhydrous sodium sulfate, the solvent may be distilled off to recover the target compound. If the layer is an aqueous layer, it may be electrically desalted and then lyophilized to recover the target compound.

When the entire reaction mixture is a liquid, if possible the substances other than the target compound (for example, solvents, reagents, etc.) may be simply distilled off at atmospheric pressure or under reduced pressure to recover the target compound.

When the target compound alone precipitates as a solid, or when the entire reaction mixture is a liquid and the target compound alone precipitates as a solid during the recovery procedure, the target compound may be first filtered by a filtration method and the filtered target compound washed with a suitable organic or inorganic solvent and dried to allow treatment of the mother liquor in the same manner as when the entire reaction mixture is a liquid, in order to recover the target compound.

When only the reagent or catalyst is present in solid form, or when the entire reaction mixture is a liquid and the reagent or catalyst alone precipitates as a solid during the recovery procedure, with the target compound dissolved in the solution, the reagent or catalyst may be first filtered by a filtration method and the filtered reagent or catalyst washed with a suitable organic or inorganic solvent, and then the obtained wash liquids combined as the mother liquor and the obtained mixture treated in the same manner as when the entire reaction mixture is a liquid, in order to recover the target compound.

Particularly when substances other than the target compound in the reaction mixture do not inhibit the reaction of the subsequent step, the reaction mixture may be used directly for the subsequent step without isolation of the target compound.

The purity of the target compound recovered by the method described above may be improved by appropriately employing a recrystallization method, chromatography method or distillation method.

When the recovered target compound is a solid, it will usually be possible to improve the purity of the target compound by recrystallization. For recrystallization, a single solvent or multiple solvents which do not react with the target compound may be used. Specifically, the target compound is first dissolved in the single or multiple solvents which do not react therewith, either at room temperature or with heating. The resulting solution is either cooled on ice or allowed to stand at room temperature to crystallization of the target compound from the mixture.

When the recovered target compound is a liquid or a solid, the purity of the target compound may be improved by any of various chromatography methods. A weak acid silica gel such as Silica Gel 60 (340-400 mesh) by Merck Co. or BW-300 (300 mesh) by Fuji Silysia Chemical Ltd. may be used in most cases. When the target compound is basic and adsorption is too strong on the aforementioned silica gels, Propylamine Coating Silica Gel (200-300 mesh) by Fuji Silysia Chemical Ltd. or the like may be used. When the target compound is dipolar or must be eluted with a polar solvent such as methanol, NAM-200H or NAM-300H by Nam Research Co. may be used. These silica gels may be used for elution of the target compound with a single solvent or multiple solvents which do not react with the target compound, followed by distilling off of the solvent, to yield the target compound with improved purity.

When the recovered target compound is a liquid, its purity may be improved by a distillation method. For distillation, the target compound is subjected to reduced pressure at room temperature or with heating to distill off the target compound.

Representative examples of production methods for compounds (1) and (100) according to the present invention have been described above, but the starting compounds and reagents used for production of the compounds of the invention may also form salts, hydrates or solvates, which will differ depending on the starting materials and solvents used, and are not particularly restricted so long as they do not inhibit the reaction. The solvents used will also differ depending on the starting materials and reagents, but of course they are not particularly restricted so long as they dissolve the starting materials to some extent and do not inhibit the reaction. When compounds (1) and (100) of the invention are obtained in the free form, a conventional procedure may be carried out to convert it to a salt or hydrate which compounds (1) and (100) may form.

When compounds (1) and (100) of the invention are obtained as a salt of compounds (1) and (100) or a hydrate of compounds (1) and (100), it may be converted to the free form of compounds (1) and (100) according to a conventional procedure.

Also, the various isomers obtained for compounds (1) and (100) according to the invention (for example, geometric isomers, optical isomers based on asymmetric carbons, rotational isomers, stereoisomers and tautomers, etc.) may be purified and isolated using ordinary separation means such as recrystallization, diastereomer salt methods, enzyme fractionation methods, and various chromatography (for example, thin-layer chromatography, column chromatography, gas chromatography and the like).

The starting compounds for Method A, Method B, Method C, Method D, Method E, Method F, Method G, Method H, Method K, Method M, Method N, Method P, Method Q, Method R, Method S, Method T, Method U and Method V described above may be commercially available compounds, or they may be easily produced from commercially available compounds by methods which are well known in the field. They may also be produced by the following methods.

Production Method for Compound (2A) (Method 1-1)

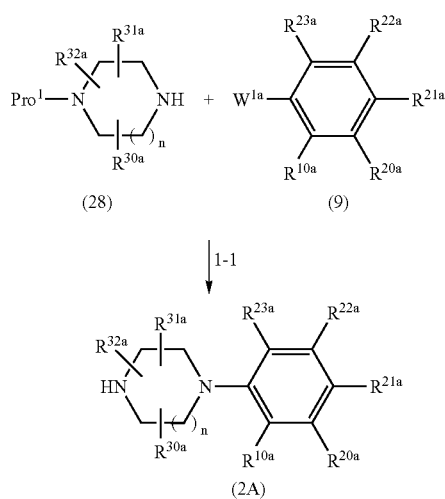

This method is a method of producing compound (2A) (the compound (2) above wherein X1 is nitrogen) by reacting compound (28) with compound (9) (amination or amidation) in an inert solvent, in the presence of a palladium(0) catalyst or copper catalyst, in the presence or in the absence of a base, in the presence or in the absence of an additive, under or not under an inert gas atmosphere, and then removing the protecting group Pro 1.

In this scheme, n, W1a, R10a, R20a, R21a, R22a, R23a, R30a, R31a and R32a have the same definitions as above. Also, Pro1 is an amino-protecting group, and for example, it may be an optionally substituted silyl group such as trimethylsilyl, triethylsilyl or t-butyldiphenylsilyl, an optionally substituted aliphatic acyl group such as formyl or acetyl, an optionally substituted aromatic acyl group such as benzoyl, an optionally substituted alkoxycarbonyl group such as ethoxycarbonyl or t-butoxycarbonyl, a substituted methylene group which forms a Schiff base, an optionally substituted aralkyl group such as benzyl, 4-methoxybenzyl or 4-nitrobenzyl, an optionally substituted aralkyloxycarbonyl group such as benzyloxycarbonyl, 4-methoxybenzyloxycarbonyl or 4-nitrobenzyloxycarbonyl, an optionally substituted alkenyloxycarbonyl group such as vinyloxycarbonyl or allyloxycarbonyl, an optionally substituted alkyl group, an optionally substituted alkenyl group or an optionally substituted sulfonyl group, preferably a lower alkoxycarbonyl group such as methoxycarbonyl, ethoxycarbonyl, t-butoxycarbonyl or isobutoxycarbonyl, a lower alkoxycarbonyl group substituted with a halogen or tri lower alkyl silyl, such as 2,2,2-trichloroethoxycarbonyl or 2-trimethylsilylethoxycarbonyl, an alkenyloxycarbonyl group such as vinyloxycarbonyl or allyloxycarbonyl, an optionally substituted aralkyloxycarbonyl group such as benzyloxycarbonyl, 4-methoxybenzyloxycarbonyl, 3,4-dimethoxybenzyloxycarbonyl, 2-nitrobenzyloxycarbonyl or 4-nitrobenzyloxycarbonyl, or an optionally substituted aralkyl group such as benzyl, 4-methoxybenzyl, 3,4-dimethoxybenzyl, 2-nitrobenzyl or 4-nitrobenzyl, and more preferably benzyl, 4-methoxybenzyl, 4-nitrobenzyl, ethoxycarbonyl, t-butoxycarbonyl or benzyloxycarbonyl.

The method may be carried out in a manner similar to Method F described above.

Production Method for Compound (2A) (Method 1-2)

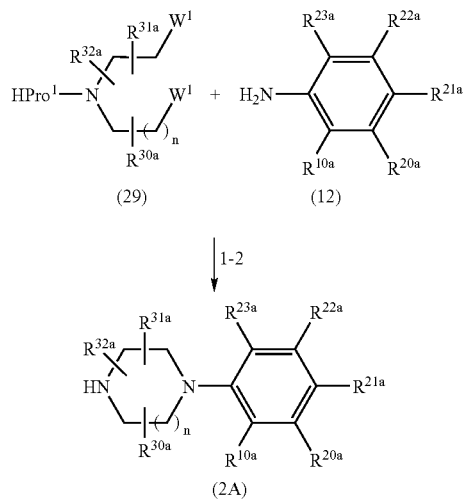

This method is a method of producing compound (2A) (the compound (2) above wherein X1 is nitrogen) by reacting compound (29) with compound (12) in an inert solvent or without a solvent, under or not under an inert gas atmosphere, in the presence or in the absence of a base, in the presence or in the absence of an additive to yield compound (2A), and afterwards removing the protecting group Pro1.

In this scheme, n, W1, R10a, R20a, R21a, R22a, R23a, R30a, R31a and R32a have the same definitions as above.

HPro1 is hydrogen or has the same definition as group Pro1 above.

This method may be carried out in a manner similar to Method H described above.

Production Method for Compound (2C) (Method 1-3)

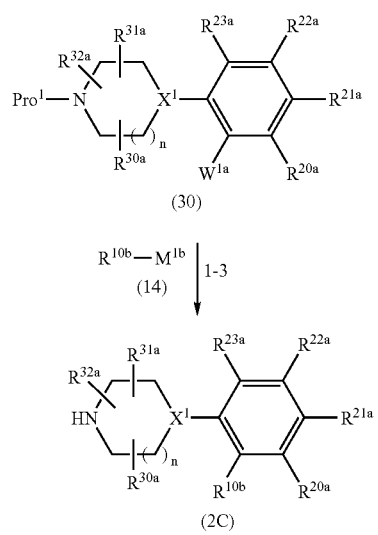

This method is a method of producing compound (2C) (the compound (2) above wherein R10 is R10b) by reacting compound (30) with compound (14) in an inert solvent, in the presence of a palladium(0) catalyst, under or not under an inert gas atmosphere, in the presence or in the absence of a base, in the presence or in the absence of an additive, and then removing the protecting group Pro 1.

In this scheme, X1, n, W1a, M1b, Pro1, R10b, R20a, R21a, R22a, R23a, R30a, R31a and R32a have the same definitions as above.

This method may be carried out in a manner similar to Method K described above.

Production Method for Compound (2C) (Method 1-4)

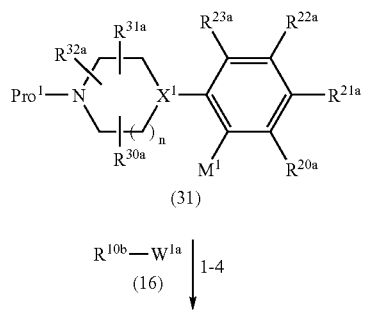

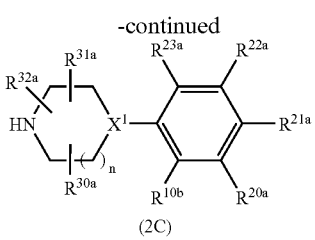

(2C)

This method is a method of producing compound (2c) (the compound (2) above wherein R10 is R10b) by reacting compound (31) with compound (16) in an inert solvent, in the presence of a palladium(0) catalyst, under or not under an inert gas atmosphere, in the presence or in the absence of a base, in the presence or in the absence of an additive, and then removing the protecting group Pro1.

In this scheme, X1, n, W1a, M1, Pro1, R10b, R20a, R21a, R22a, R23a, R30a, R31a and R32a have the same definitions as above.

This method may be carried out in a manner similar to Method K described above.

Production Method for Compound (2A) (Method 1-5)

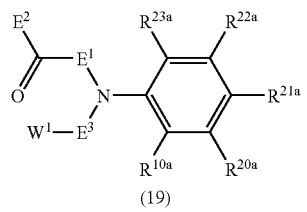

(19)

HPro$^{1a}$—NH$_2$ | 1-5
(33)

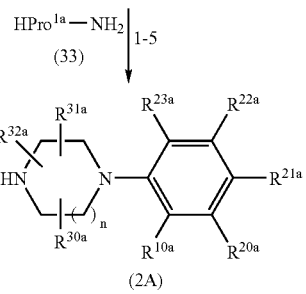

(2A)

This method is a method of producing compound (2A) (the compound (2) above wherein X1 is nitrogen) by reacting compound (19) and compound (33) in an inert solvent, in the presence of a reducing agent, in the presence or in the absence of an acid, in the presence or in the absence of an additive, to yield compound (2A), and afterward removing the protecting group Pro1a by the method described above.

In this scheme, n, W1, E1, E2, E3, R10a, R20a, R21a, R22a, R23a, R30a, R31a and R32a have the same definitions as above.

Also, HPro1a is hydrogen or a group represented by Pro1a below.

Group Pro1a is an optionally substituted aralkyl group such as benzyl, 4-methoxybenzyl, 3,4-dimethoxybenzyl, 2-nitrobenzyl or 4-nitrobenzyl, and is preferably benzyl.

This method may be carried out in a manner similar to Method C described above.

Production Method for Compound (2A) (Method 1-6)

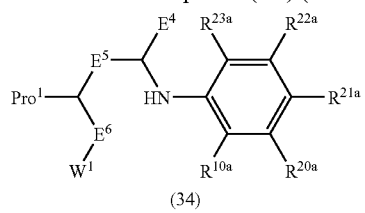

(34)

| 1-6

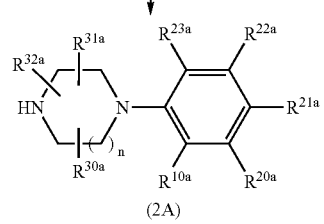

(2A)

This method is a method of producing compound (2A) (the compound (2) above wherein X1 is nitrogen) by reacting a base with compound (34) in an inert solvent, and then removing the protecting group Pro1 by the method described above.

In this scheme, n, W1, Pro1, E4, E5, E6, R10a, R20a, R21a, R22a, R23a, R30a, R31a and R32a have the same definitions as above.

This method may be carried out in a manner similar to Method A described above.

Production Method for Compounds (2B) and (200) (Method 1-7)

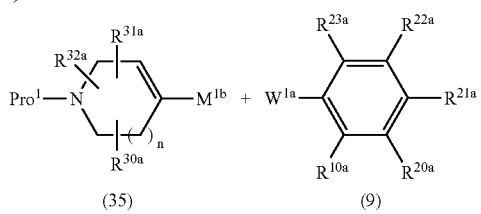 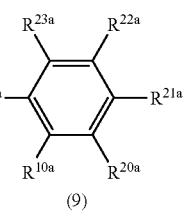

(35)            (9)

1-7-2

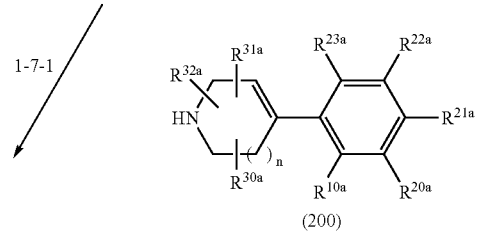

(200)

1-7-1

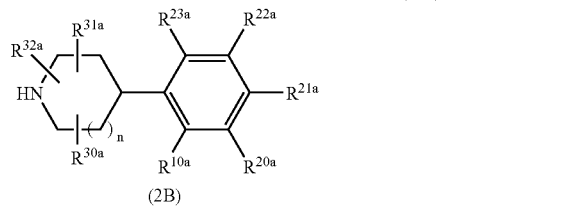

(2B)

This method is a method of producing compound (2B) (the compound (2) above wherein X1 is CH) by reacting compound (35) with compound (9) in an inert solvent, in the presence of a palladium(0) catalyst, subjecting it to hydrogenation reaction, and then removing the protecting group Pro1 (Method 1-7-1), or a method of producing compound (200)

by reacting compound (35) with compound (9) in the same manner, then removing the protecting group Pro1 (Method 1-7-2).

In this scheme, n, W1a, M1, Pro1, R10a, R20a, R21a, R22a, R23a, R30a, R31a and R32a have the same definitions as above.

This method may be carried out in a manner similar to Method K described above, followed by hydrogenation reaction in a manner similar to Method A above.

Production Method for Compounds (2B) and (200C) (Method 1-8)

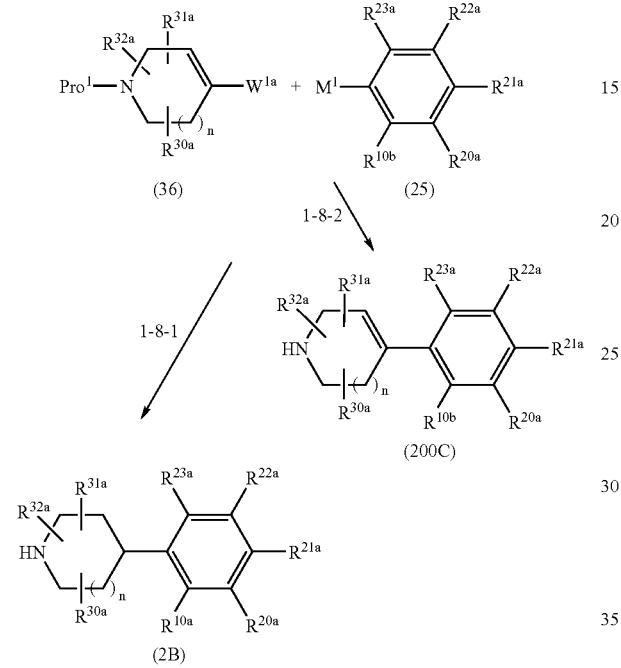

This method is a method of producing compound (2B) (the compound (2) above wherein X1 is CH) by reacting compound (36) with compound (25) in an inert solvent, in the presence of a palladium(0) catalyst, subjecting it to hydrogenation reaction, and then removing the protecting group Pro1 (Method 1-8-1), or a method of producing compound (200C) (the compound (200) above wherein R10 is R10b) by reacting compound (36) with compound (25) in the same manner, then removing the protecting group Pro1 (Method 1-8-2).

In this scheme, n, W1a, M1, Pro1, R10a, R10b, R20a, R21a, R22a, R23a, R30a, R31a and R32a have the same definitions as above.

This method may be carried out in a manner similar to Method K described above, followed by hydrogenation reaction in a manner similar to Method A above.

Production Method for Compounds (2B) and (200C) (Method 1-9)

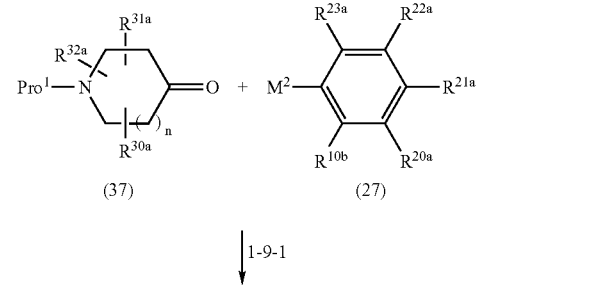

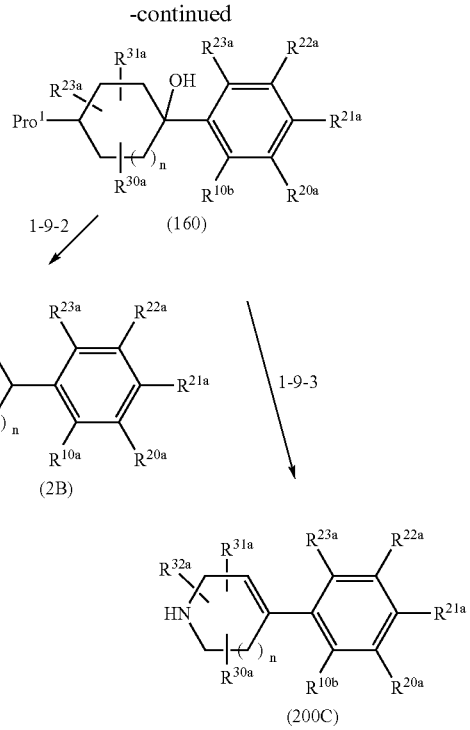

This method is a method of producing compound (2B) (the compound (2) above wherein X1 is CH) by reacting compound (37) with compound (27) (i.e., a lithium reagent or Grignard reagent) in an inert solvent, in the presence of an inert gas to yield an adduct (160) (Step 1-9-1), and then reducing hydroxyl at the benzyl position of the resultant adduct (160) (Step 1-9-2), and removing the protecting group Pro1, or a method of producing compound (200C) (the compound (200) above wherein R10 is R10b) by reacting in the same manner to yield an adduct (160) (Step 1-9-1), then dehydrating hydroxyl at the benzyl position of the resultant adduct (160) in the presence of or in the absence of acid (Step 1-9-3), and further removing the protecting group Pro 1.

In this scheme, n, M2, Pro1, R10a, R10b, R20a, R21a, R22a, R23a, R30a, R31a and R32a have the same definitions as above.

This method may be carried out in a manner similar to Method U described above.

Production Method for Compound (19) (Method 2)

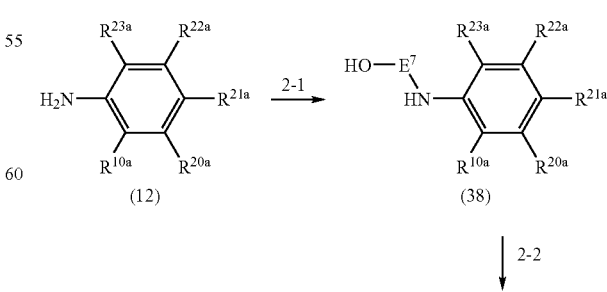

-continued

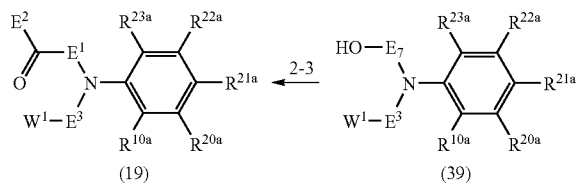

Production Method for Compound (21) and compound (34) (Method 3)

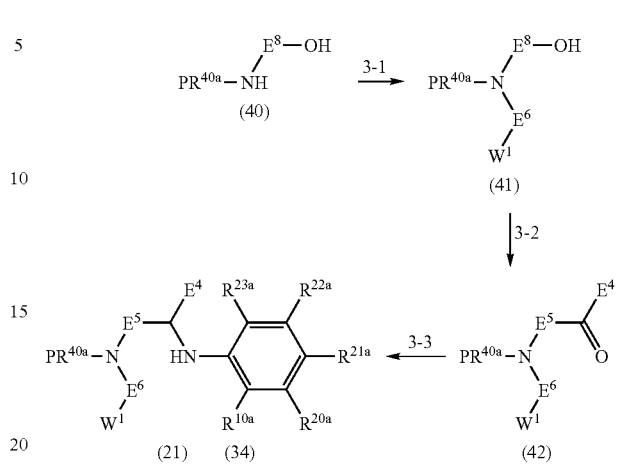

This method is a method of producing compound (19) by reacting an N-alkylating agent with compound (12) in an inert solvent to yield compound (38) (Step 2-1), and then reacting an N-alkylating agent or N-carbonylating agent with compound (38) to yield compound (39) (Step 2-2), and reacting an oxidizing agent with compound (39) in the presence or in the absence of an additive (Step 2-3).

In this scheme, W1, E1, E2, E3, R10a, R20a, R21a, R22a and R23a have the same definitions as above. Also, E7 is a group suitable for obtaining the desired group of the formula E2(CO)E1-.

Step 2-1 and Step 2-2 may be carried out in a manner similar to Method A described above.

(Step 2-3)

There are no particular restrictions on the solvent used so long as it dissolves the starting compound to some extent and does not inhibit the reaction of this step, and specifically there may be mentioned halogenated hydrocarbons such as chloroform, dichloromethane, 1,2-dichloroethane and carbon tetrachloride, and nitrites such as acetonitrile and isobutyronitrile, among which halogenated hydrocarbons (particularly dichloromethane) are preferred.

There are no particular restrictions on the oxidizing agent used so long as it can yield the target compound and does not produce any unseparable by-products, and specifically there may be mentioned chromic acids such as pyridinium chlorochromate (PCC) and pyridinium dichromate (PDC), Dess-Martin reagent (Dess D. B., Martin J. C., *J. Am. Chem. Soc.*, (1991), 113, 7277), or catalytic amounts of dimethylsulfoxide oxidizing agents such as tetrapropylammonium perruthenate (VII) (TPAP; Ley S. V. et al., *Synthesis*, (1994), 639) and dimethylsulfoxide-oxalyl chloride (Swern oxidizing agent; D. Swern et al., *Synthesis*, (1981), 165), in the presence of N-methylmorpholine-N-oxide (NMO) as an auxiliary oxidizing agent, among which dimethylsulfoxide-oxalyl chloride (Swern oxidizing agent) is preferred.

There are no particular restrictions on the additive used so long as it can yield the target compound and does not produce any unseparable by-products, and specifically there may be mentioned Celite and molecular sieve, among which molecular sieve is preferred.

The reaction temperature will differ depending on the starting materials, solvent and reagents, but will usually be between −80° C. and 60° C., and is preferably between −80° C. and 40° C.

The reaction time will differ depending on the starting materials, solvent, reagents and reaction temperature, but will usually be 0.1 to 100 hours, and is preferably 1 to 12 hours.

Compound (38), compound (39) or compound (19) may be isolated or purified from the reaction mixtures obtained above by the methods described above.

This method is a method of producing compound (21) or compound (34) by reacting an N-alkylating agent or N-carbonylating agent with compound (40) in an inert solvent to yield compound (41) (Step 3-1), and then oxidizing compound (41) to yield compound (42) (Step 3-2), and reacting compound (42) with compound (12) (Step 3-3).

In this scheme, W1, E4, E5, E6, R10a, R20a, R21a, R22a and R23a have the same definitions as above. Also, E8 is a group suitable for obtaining the desired group of the formula E4(CO)E5. PR40a has the same definition as R40a above, or is an amino-protecting group (preferably t-butoxycarbonyl or benzyl).

Step 3-1 in this method may be carried out in a manner similar to Method A above, Step 3-2 may be carried out in a manner similar to Method 2 above (Step 2-3), and Step 3-3 may be carried out in a manner similar to Method C above.

Production Method for Compound (24A), Compound (36A), Compound (22), Compound (35), Compound (24B) and Compound (36B) (Method 4)

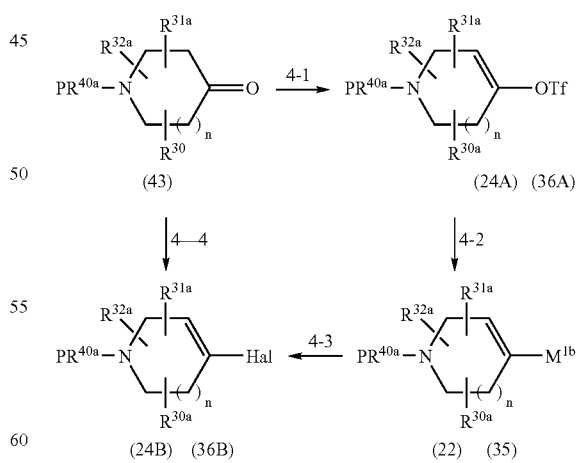

This method is a method of introducing a trifluoromethanesulfonyl group into compound (43) in an inert solvent under an inert gas atmosphere to yield compound (24A) or compound (36A) (Step 4-1), and then reacting compound (24A) or compound (36A) with boron metal reagent or tin metal reagent in the presence of a palladium(0) catalyst to yield compound (22) or compound (35) (Step 4-2), and reacting compound (22) or compound (35) with a halogenating reagent, in the presence or in the absence of a base, to yield compound (24B) or compound (36B) (Step 4-3). Compound (43) may also be directly reacted with a halogenating agent to produce compound (24B) or compound (36B) (Step 4-4).

In this scheme, n, R30a, R31a, R32a and PR40a have the same definitions as above.

Also, Hal represents chlorine, bromine or iodine.

M1b is a group of the formula $B(OE^{10c})_2$ or $Sn(E^{10b})_3$ (wherein $E^{10c}$ represents C1-6 alkyl or the two of $E^{10c}$ bond together to form C2-3 alkylene optionally substituted with methyl, and $E^{10b}$ represents C1-6 alkyl).

Tf is trifluoromethanesulfonyl.

(Step 4-1)

There are no particular restrictions on the solvent used so long as it dissolves the starting compound to some extent and does not inhibit the reaction of this step, and specifically there may be mentioned ethers such as diethyl ether, tetrahydrofuran and dioxane, among which tetrahydrofuran is preferred.

This step is preferably carried out under a dried inert gas atmosphere. The inert gas is preferably argon or nitrogen.

There are no particular restrictions on the base used so long as it can yield the target compound and does not produce any unseparable by-products, and specifically there may be mentioned alkali metal amides such as lithium bis(trimethylsilyl)amide, sodium bis(trimethylsilyl)amide and lithium diisopropylamide, among which lithium bis(trimethylsilyl)amide or lithium (diisopropylamide) is preferred.

There are no particular restrictions on the trifluoromethanesulfonylating reagent used so long as it can yield the target compound and does not produce any unseparable by-products, but it is preferably N-phenyl bis(trifluoromethanesulfonimide).

The reaction temperature for enolation will differ depending on the starting materials, solvent and reagents, but will usually be between −100 and 20° C., and is preferably between −80 and −30° C.

The reaction temperature for conversion to a leaving group will differ depending on the starting materials, solvent and reagents, but will usually be between −100° C. and 50° C., and is preferably between −80° C. and 30° C.

The reaction time for enolation will differ depending on the starting materials, solvent, reagents and reaction temperature, but will usually be 0.1 to 5 hours, and is preferably 0.1 to 3 hours.

The reaction time for conversion to a leaving group will differ depending on the starting materials, solvent, reagents and reaction temperature, but will usually be 0.1 to 24 hours, and is preferably 0.5 to 12 hours.

In addition to the method described above, compound (44) may be produced by reacting a ketone compound (43) with trifluoromethanesulfonic anhydride in an inert solvent such as dichloromethane, in the presence of an organic base such as 2,6-di-t-butyl-4-methylpyridine, as described in David Crich et al., Synthesis, (2001), 2, 323, for example.

(Step 4-2)

(Production Method for Compound (22) and Compound (35) as Boronate Derivatives)

There are no particular restrictions on the solvent used so long as it dissolves the starting compound to some extent and does not inhibit the reaction of this step, and specifically there may be mentioned amides such as formamide, dimethylformamide, dimethylacetamide and hexamethylphosphoric triamide; or sulfoxides such as dimethylsulfoxide and sulfolane, ethers such as diethyl ether, diisopropyl ether, tetrahydrofuran, dioxane, dimethoxyethane and diethyleneglycol dimethyl ether, and aromatic hydrocarbons such as benzene, toluene and xylene, among which dimethylsulfoxide and dioxane are preferred.

There are no particular restrictions on the metal catalyst used so long as it can yield the target compound and does not produce any unseparable by-products, and specifically there may be mentioned divalent palladium compounds such as [1,1'-bis(diphenylphosphino)triphenylphosphine]palladium (II) chloride and 0-valent palladium compounds such as tetrakis(triphenylphosphine)palladium, among which [1,1'-bis(diphenylphosphino)ferrocene]dichloropalladium(II) is preferred.

As bases to be used there may be mentioned potassium phenoxide, triethylamine, potassium phosphate, potassium carbonate and potassium acetates, among which potassium acetate is preferred.

The catalyst used may be triphenylarsine.

The reaction temperature will differ depending on the starting materials, solvent and reagents, but will usually be between 50° C. and 80° C.

The reaction time will differ depending on the starting materials, solvent, reagents and reaction temperature, but will usually be 1 to 6 hours, and is preferably 2 to 3 hours.

(Production Method for Compound (22) and compound (35) as tin derivatives)

There are no particular restrictions on the solvent used so long as it dissolves the starting compound to some extent and does not inhibit the reaction of this step, and specifically there may be mentioned amides such as formamide, dimethylformamide, dimethylacetamide and hexamethylphosphoric triamide, and ethers such as diethyl ether, diisopropyl ether, tetrahydrofuran, dioxane, dimethoxyethane and diethyleneglycol dimethyl ether, among which ethers (particularly tetrahydrofuran) are preferred.

There are no particular restrictions on the metal catalyst used so long as it can yield the target compound and does not produce any unseparable by-products, and specifically there may be mentioned 0-valent palladium compounds such as tetrakis(triphenylphosphine)palladium(0) and tris(dibenzylideneacetone)dipalladium(0).

As tin reagents to be used there may be mentioned hexamethylditin(IV), hexabutylditin(IV) and hexaphenylditin(IV), among which hexamethylditin(IV) is preferred.

The reaction temperature will differ depending on the starting materials, solvent and reagents, but will usually be between −70° C. and 80° C., and is preferably between 50° C. and 80° C.

The reaction time will differ depending on the starting materials, solvent, reagents and reaction temperature, but will usually be 1 to 8 hours, and is preferably 2 to 4 hours.

As supplementary literature to be used as reference for carrying out this method, there may be mentioned Kurt Ritter et al., Synthesis 1993; 735-762.

(Step 4-3)

There are no particular restrictions on the solvent used so long as it dissolves the starting compound to some extent and does not inhibit the reaction of this step, and specifically there may be mentioned halogenated hydrocarbons such as chloroform, dichloromethane, 1,2-dichloroethane and carbon tetrachloride, and ethers such as diethyl ether, diisopropyl ether, tetrahydrofuran, dioxane, dimethoxyethane and diethyleneglycol dimethyl ether, among which dichloromethane, carbon tetrachloride, diethyl ether and tetrahydrofuran are preferred.

There are no particular restrictions on the halogenating reagent used so long as it can yield the target compound and does not produce any unseparable by-products, and specifically there may be mentioned chlorine, bromine, iodine, N-chlorosuccinimide, N-bromosuccinimide, N-iodosuccinimide and copper chloride, among which chlorine, bromine and iodine are preferred.

When a base is used, there may be mentioned sodium hydroxide, pyridine and sodium methoxide.

The reaction temperature will differ depending on the starting materials, solvent and reagents, but will usually be between −78° C. and 25° C., and is preferably between 0° C. and 25° C.

The reaction time will differ depending on the starting materials, solvent, reagents and reaction temperature, but will usually be 1 to 24 hours, and is preferably 1 to 6 hours.

(Step 4-4)

There are no particular restrictions on the solvent used so long as it dissolves the starting compounds to some extent and does not inhibit the reaction of this step, and specifically there may be mentioned halogenated hydrocarbons such as chloroform, dichloromethane, 1,2-dichloroethane and carbon tetrachloride, and aromatic hydrocarbons such as benzene, toluene and xylene, among which chloroform, dichloromethane and carbon tetrachloride are preferred.

There are no particular restrictions on the halogenating agent used so long as it can yield the target compound and does not produce any unseparable by-products, and specifically there may be mentioned halogenating agents such as chlorine, oxalic chloride, thionyl chloride, phosphorus oxychloride, phosphorus trichloride, phosphorus pentachloride, bromine, oxalic bromide, thionyl bromide, phosphorus tribromide, 2,2,2-tribromo-1,3,2-benzodioxaphosphol, iodine and phosphorus triiodide, among which phosphorus trichloride, phosphorus tribromide, 2,2,2-tribromo-1,3,2-benzodioxaphosphol and phosphorus triiodide are preferred.

The reaction temperature will differ depending on the starting materials, solvent and reagents, but will usually be between 0° C. and 70° C.

The reaction time will differ depending on the starting materials, solvent, reagents and reaction temperature, but will usually be 1 to 24 hours.

Production Method for Compound (25), Compound (27) and Compound (9A) (Method 5)

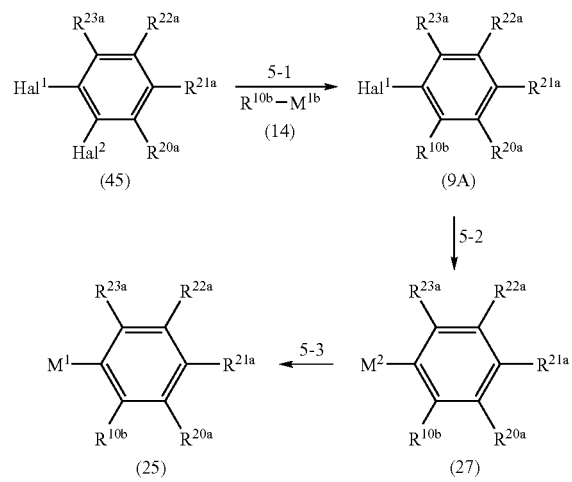

In this method, compound (45) is reacted with compound (14) in an inert solvent in the presence of a palladium(0) catalyst to yield compound (9A) (Step 5-1), and then compound (9A) is reacted with a lithiating agent or Grignard reagent-producing agent to yield compound (27) (Step 5-2) and compound (27) is reacted with a boron metal reagent or tin metal reagent to produce compound (25) (Step 5-3).

In this scheme, M1, M1b, M2, R10b, R20a, R21a, R22a and R23a have the same definitions as above.

Hal1 is chlorine or bromine, and Hal2 is iodine when Hal1 is bromine, and bromine or iodine when Hal1 is chlorine.

Step 5-1 of this method may be carried out in a manner similar to Method K above.

(Step 5-2)

This step will differ depending on the nature of M2.

(Grignard Reagent Production Step)

In this step, compound (9A) is directly reacted with magnesium metal in an inert solvent (direct method), or magnesium-halogen exchange reaction is carried out between compound (9A) and another Grignard reagent (indirect method) to produce compound (27) (i.e., a Grignard reagent).

(1) Direct Method

There are no particular restrictions on the solvent used so long as it dissolves the starting compound to some extent and does not inhibit the reaction of this step, and specifically there may be mentioned ethers such as diethyl ether, diisopropyl ether, tetrahydrofuran, dioxane, dimethoxyethane and diethyleneglycol dimethyl ether, and phosphoric amides such as hexamethylphosphoric triamide, among which ethers (particularly diethyl ether and tetrahydrofuran) are preferred.

The reaction method may be conducted according to a common procedure, and specifically magnesium metal is suspended in the solvent under an atmosphere of an inert gas such as nitrogen or argon, in the presence or in the absence of a catalytic amount of iodine or dibromoethane as an activating agent, and compound (9A) is slowly added to the reaction system. Upon completion of the reaction, compound (27) is produced in the supernatant, and it is usually used for the next step without isolation.

The reaction temperature will differ depending on the starting materials, solvent and reagents, but will usually be between −20° C. and 150° C., and is preferably between 0° C. and 100° C.

The reaction time will differ depending on the starting materials, solvent, reagents and reaction temperature, but will usually be 1 to 10 hours.

(2) Indirect Method

The solvent used, the reaction temperature and the reaction time are the same as for the direct method.

The reaction method may be carried out according to a common procedure, but compound (27) (i.e. an organic magnesium compound) may also be produced by reacting the halogen compound (9A) with isopropylmagnesium bromide or the like under an atmosphere of an inert gas such as nitrogen or argon. The resultant compound (27) is usually used for the next step without isolation.

(Lithiating Step)

In this step, lithium-halogen exchange reaction is carried out between the halogen compound (9A) and another alkyllithium reagent in an inert solvent, under an atmosphere of an inert gas such as nitrogen or argon, to produce an aryllithium reagent (27).

There are no particular restrictions on the solvent used so long as it dissolves the starting compound to some extent and does not inhibit the reaction of this step, and specifically there may be mentioned ethers such as diethyl ether, diisopropyl ether, tetrahydrofuran, dioxane, dimethoxyethane and diethyleneglycol dimethyl ether, and phosphoric amides such as hexamethylphosphoric triamide, among which ethers (particularly diethyl ether and tetrahydrofuran) are preferred.

There are no particular restrictions on the alkyllithium reagent used so long as it can yield the target compound and does not produce any unseparable by-products, and specifically there may be mentioned alkyllithium compounds such as n-butyllithium, sec-butyllithium and t-butyllithium, among which n-butyllithium is preferred.

The reaction temperature will differ depending on the starting materials, solvent and reagents, but will usually be between −100° C. and 0° C.

The reaction time will differ depending on the starting materials, solvent, reagents and reaction temperature, but will usually be between 10 minutes and 2 hours.

The resultant compound (27) is usually used for the next step without isolation.

(Step 5-3)

This step will differ depending on the nature of M1.

(Step for the Production of a Boronic Acid Reagent)

In this step, the lithium agent or Grignard reagent (27) produced in Step 5-2 is reacted with a borate reagent mentioned below to produce a boronic acid reagent compound (25).

There are no particular restrictions on the solvent used so long as it dissolves the starting compound to some extent and does not inhibit the reaction of this step, and specifically there may be mentioned ethers such as diethyl ether, diisopropyl ether, tetrahydrofuran, dioxane, dimethoxyethane and diethyleneglycol dimethyl ether, and phosphoric amides such as hexamethylphosphoric triamide, among which ethers (particularly diethyl ether and tetrahydrofuran) are preferred.

There are no particular restrictions on the borate reagent used so long as it can yield the target compound and does not produce any unseparable by-products, and specifically there may be mentioned trialkylborates such as triisopropylborate and trimethylborate, among which triisopropylborate are preferred.

The trialkylborate obtained may be easily hydrolyzed in water or aqueous ammonium chloride to produce a boronic acid reagent compound (25).

The reaction temperature will differ depending on the starting materials, solvent and reagents, but will usually be between −80° C. and 50° C., and is preferably between −80° C. and 30° C.

The reaction time will differ depending on the starting materials, solvent, reagents and reaction temperature, but will usually be 1 to 10 hours, and is preferably 2 to 6 hours.

(Step for the Production of a Tin Reagent)

In this step, the lithium agent or Grignard reagent (27) produced in Step 5-2 is reacted with the halogenated trialkyltin reagent mentioned below to produce a tin reagent compound (25).

There are no particular restrictions on the solvent used so long as it dissolves the starting compound to some extent and does not inhibit the reaction of this step, and specifically there may be mentioned ethers such as diethyl ether, diisopropyl ether, tetrahydrofuran, dioxane, dimethoxyethane and diethyleneglycol dimethyl ether, and phosphoric amides such as hexamethylphosphoric triamide, among which ethers (particularly diethyl ether and tetrahydrofuran) are preferred.

There are no particular restrictions on the halogenated trialkyltin reagent used so long as it can yield the target compound and does not produce any unseparable by-products, and specifically there may be mentioned halogenated trialkyltin compounds such as tributyltin chloride and trimethyltin chloride, among which tributyltin chloride is preferred.

The reaction temperature will differ depending on the starting materials, solvent and reagents, but will usually be between −80° C. and 50° C., and is preferably between −80° C. and 30° C.

The reaction time will differ depending on the starting materials, solvent, reagents and reaction temperature, but will usually be 1 to 10 hours, and is preferably 1 to 6 hours.

Production Method for Compound (9B) (Method 6)

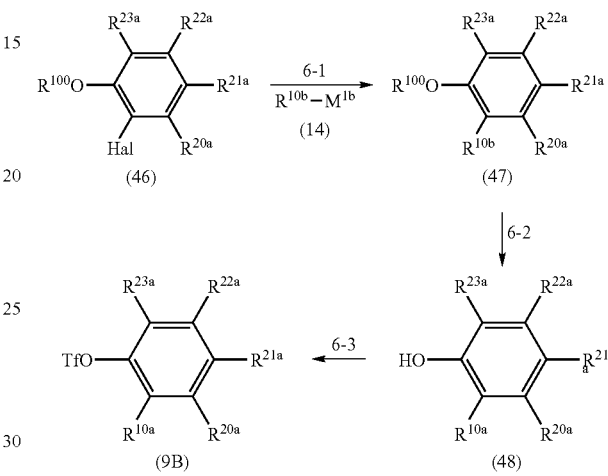

In this step, compound (46) is reacted with compound (14) in an inert solvent in the presence of a palladium(0) catalyst, to yield compound (47) (Step 6-1), and then compound (47) is reacted with a de-alkylating agent or de-aralkylating agent to yield compound (48) (Step 6-2), and a trifluoromethanesulfonyl group is introduced at the phenolic hydroxyl group of compound (48) to produce compound (9B) (Step 6-3).

In this scheme, Tf, M1b, Hal, R10a, R10b, R20a, R21a, R22a and R23a have the same definitions as above. Also, R100 represents C1-6 alkyl or optionally substituted aralkyl, and is preferably methyl or benzyl.

Step 6-1 of this method may be carried out in a manner similar to Method K described above.

(Step 6-2)

There are no particular restrictions on the solvent used so long as it dissolves the starting compounds to some extent and does not inhibit the reaction of this step, and specifically there may be mentioned alcohols such as methanol, ethanol and isopropanol, ethers such as diethyl ether, diisopropyl ether, tetrahydrofuran, dioxane, dimethoxyethane and diethyleneglycol dimethyl ether, aromatic hydrocarbons such as benzene, toluene and xylene, organic acids such as carbon disulfide, acetic acid and hydrogen bromide in acetic acid solution, organic bases such as quinoline and pyridine, and water. These may be selected as appropriate for the de-alkylating agent or de-aralkylating agent used.

There are no particular restrictions on the de-alkylating agent or de-aralkylating agent used so long as it can yield the target compound and does not produce any unseparable by-products, and specifically there may be mentioned Lewis acids such as boron tribromide, boron trichloride, boron triiodide and aluminum chloride, Bronsted acids such as hydrobromic acid, hydrochloric acid and hydrogen bromide in acetic acid solution, metal salts such as lithium iodide, and halogenated silanes such as trimethylsilane iodide.

The reaction temperature will differ depending on the starting materials, solvent and reagents, but will usually be between −80° C. and 250° C.

The reaction time will differ depending on the starting materials, solvent, reagents and reaction temperature, but will usually be 0.1 to 100 hours.

When R100 is an optionally substituted aralkyl group, the de-aralkylating step may be carried out according to the hydrogenation method described above for Method A.

The conditions may be selected as suitable for the starting materials, in order to allow selective deprotection.

As supplementary literature to be used as reference for carrying out this method, there may be mentioned M. Vivekananda Bhatt, Surendra U. Kulkarni et al., "Cleavage of Ethers" Synthesis (1983), 249 and T. W. Greene, (Protective Groups in Organic Synthesis), John Wiley & Sons: J. F. W. McOmis, (Protective Groups in Organic Chemistry), Plenum Press.

Step 6-3 may be carried out in a manner similar to Method A or Method B described above.

Production Method for Compound (25A) (Method 7)

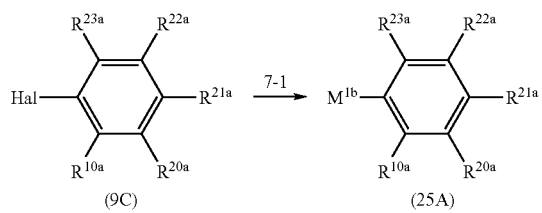

In this method, compound (9C) is reacted with a boron metal reagent or tin metal reagent in an inert solvent in the presence of a palladium(0) catalyst, to produce compound (25A).

In this scheme, M1b, Hal, R10a, R20a, R21a, R22a and R23a have the same definitions as above.

This method may be carried out in a manner similar to Step 4-2 of Method 4.

Production Method for Compound (13A) (Method 8)

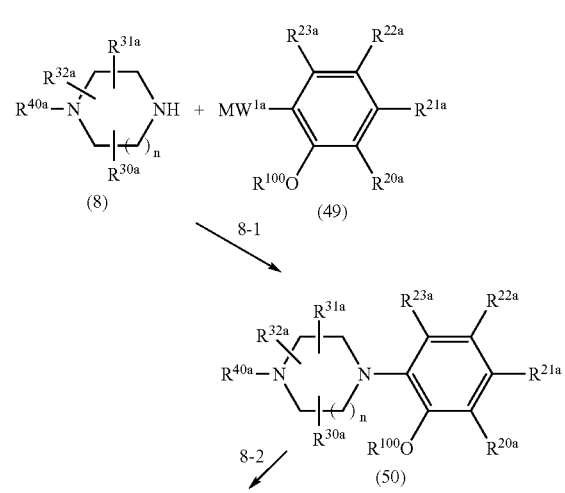

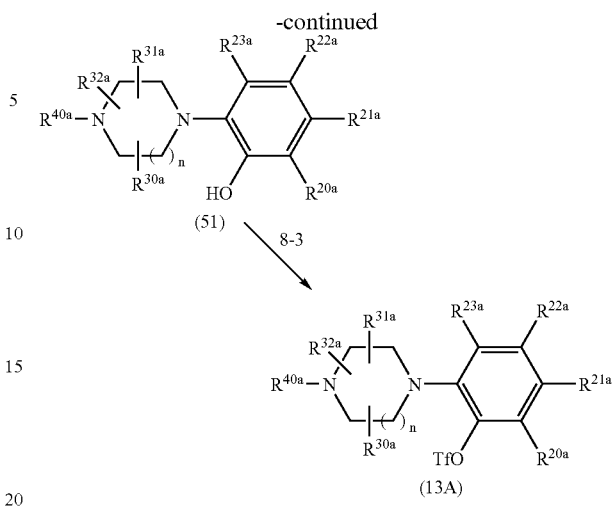

In this method, compound (49) is reacted with compound (8) (amination or amidation), in an inert solvent in the presence of a palladium(0) catalyst or copper catalyst, in the presence or in the absence of a base, in the presence or in the absence of an additive, under or not under an inert gas atmosphere, to yield compound (50) (Step 8-1), and then compound (50) is reacted with a de-alkylating agent or de-aralkylating agent to yield compound (51) (Step 8-2), and a trifluoromethanesulfonyl group is introduced at the phenolic hydroxyl of compound (51) to produce compound (13A) (Step 8-3).

In this scheme, Tf, n, R20a, R21a, R22a, R23a, R30a, R31a, R32a, R40a, R100 have the same definitions as above. Also, MW1a has the same definition as M1a or W1a above.

Step 8-1 of this method may be carried out in a manner similar to Method F or Method G described above, Step 8-2 may be carried out in a manner similar to Step 6-2 described above, and Step 8-3 may be carried out in a manner similar to Method A or Method B described above.

Production Method for Compound (15) and Compound (13B) (Method 9)

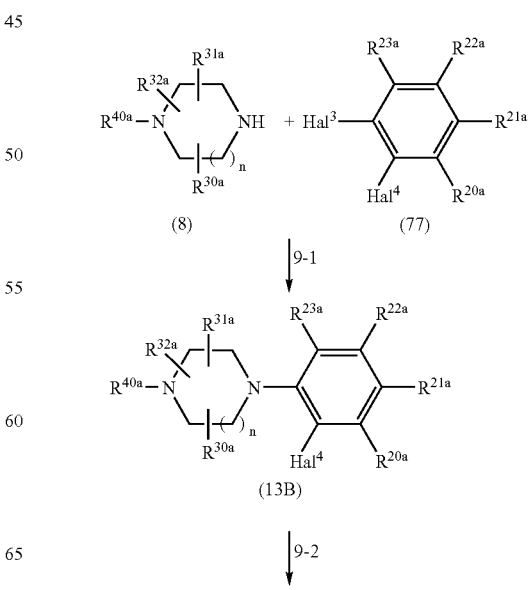

83

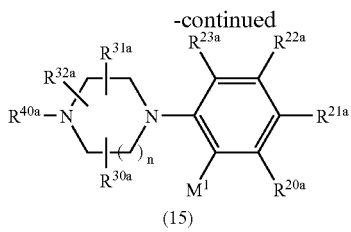

(15)

In this method, compound (77) is reacted with compound (8), in an inert solvent, in the presence of a palladium(0) catalyst or copper catalyst, in the presence or in the absence of a base, in the presence or in the absence of an additive, under or not under an inert gas atmosphere, to yield compound (13B) (Step 9-1), and then compound (13B) is reacted with a metal reagent to produce compound (15) (Step 9-2).

In this scheme, n, M1, R20a, R21a, R22a, R23a, R30a, R31a, R32a and R40a have the same definitions as above.

Hal4 is chlorine or bromine, and Hal3 is iodine when Hal4 is bromine, and bromine or iodine when Hal4 is chlorine.

Step 9-1 of this method may be carried out in a manner similar to Method F above, and Step 9-2 may be carried out in a manner similar to Step 5-2 and Step 5-3, or Method 7, above.

Production Method for Compound (16A), Compound (14) and Compound (16B) (Method 10)

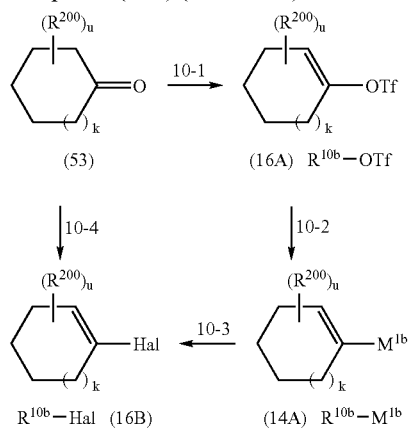

In this method, a leaving group is introduced into compound (53), in an inert solvent, under or not under inert gas atmosphere, to yield compound (16A) (Step 10-1), and then compound (16A) is reacted with a boron metal reagent or tin metal reagent in the presence of a palladium(0) catalyst to yield compound (14) (Step 10-2), and compound (14) is reacted with a halogenating reagent to produce compound (16B) (Step 10-3).

Alternatively, compound (53) is reacted directly with a halogenating agent to produce compound (16B) (Step 10-4).

In this scheme, Tf, R10b, M1b and Hal have the same definitions as above.

Also, R200 has the same definition as the substituents of Substituent Group A above, or represents the substituents, the substituents thereon being protected. u is an integer of 0, 1, 2, 3, 4 or 5. k is an integer of 0, 1, 2, 3, 4 or 5.

Step 10-1 of this method may be carried out in a manner similar to Method 4-1 above, Step 10-2 may be carried out in a manner similar to Step 4-2 above, and Step 10-3 may be carried out in a manner similar to Step 4-3 above. Step 10-4 may be carried out in a manner similar to Step 4-4 above.

84

Production Method for Compound (12) (Method 11)

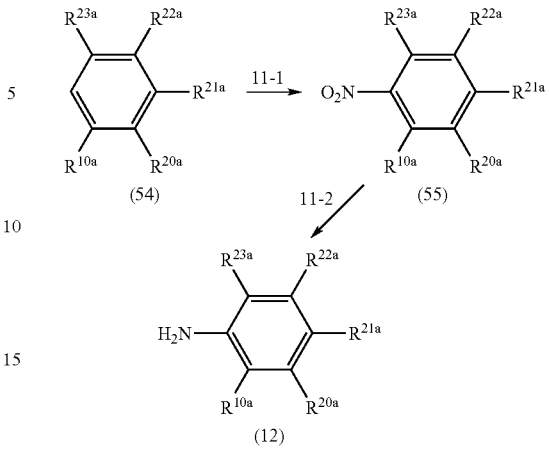

In this step, compound (54) is reacted with a nitrating reagent to yield compound (55) (Step 11-1), and then a metal or metal salt is used in the presence of an acid for reduction of compound (55) to produce compound (12) (Step 11-2).

In this scheme, R10a, R20a, R21a, R22a and R23a have the same definitions as above.

(Step 11-1)

There are no particular restrictions on the solvent used so long as it dissolves the starting compounds to some extent and does not inhibit the reaction of this step, and specifically there may be mentioned a sulfuric acid and nitric acid mixture or an acetic acid and nitric acid mixture, where the nitric acid solvent reacts as a nitrating agent.

The reaction temperature will differ depending on the starting materials, solvent and reagents, but will usually be between −20° C. and 150° C., and is preferably between 0° C. and 80° C.

The reaction time will differ depending on the starting materials, solvent, reagents and reaction temperature, but will usually be 0.5 to 48 hours, and is preferably 1 to 12 hours.

(Step 11-2)

There are no particular restrictions on the solvent used so long as it dissolves the starting compounds to some extent and does not inhibit the reaction of this step, and specifically there may be mentioned water, alcohols such as methanol and ethanol, amides such as formamide, dimethylformamide, dimethylacetamide and hexamethylphosphoric triamide, organic acids such as acetic acid, and mixtures of these solvents, among which a mixed solvent of ethanol and water, a mixed solvent of ethanol dimethylformamide and water, or acetic acid is preferred.

There are no particular restrictions on the metal or metal salt used so long as it can yield the target compound and does not produce any unseparable by-products, and specifically there may be mentioned metals such as iron powder, tin powder and zinc powder, and metal salts such as tin(II) chloride, among which a metal (particularly iron powder) is preferred.

There are no particular restrictions on the acid used so long as it can yield the target compound and does not produce any unseparable by-products, and specifically there may be mentioned organic acids such as acetic acid, and inorganic acids such as hydrochloric acid and ammonium chloride, among which ammonium chloride is preferred.

The equivalents of the metal or metal salt used will differ depending on the starting materials, solvent and reagents, but will usually be a proportion of 2-15 and preferably 3-6, in terms of the molar ratio with respect to the starting material.

The reaction temperature will differ depending on the starting materials, solvent and reagents, but will usually be between 0° C. and 150° C., and is preferably between 0° C. and 100° C.

The reaction time will differ depending on the starting materials, solvent, reagents and reaction temperature, but will usually be 0.5 to 48 hours, and is preferably 1 to 12 hours.

Compound (55) or compound (12) may be isolated or purified from the reaction mixture obtained above by the method described above.

Production Method for Compound (55A) (Method 12)

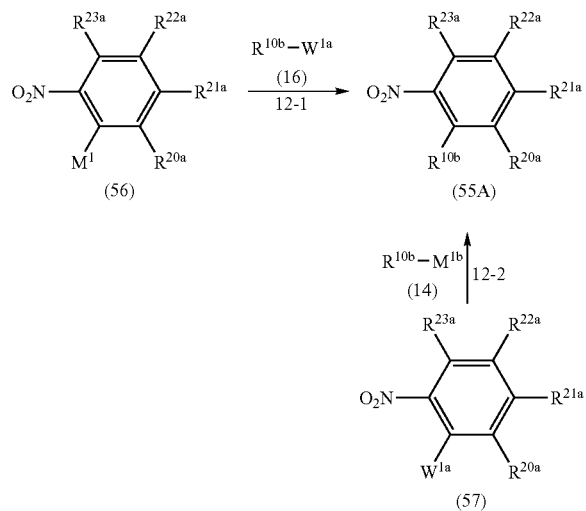

In this method, compound (56) is reacted with compound (16) described above to produce compound (55A) (Method 12-1), or compound (57) is reacted with compound (14) described above to produce compound (55A) (Method 12-2), in an inert solvent, in the presence of a palladium catalyst (0), under or not under an inert gas atmosphere, in the presence or in the absence of a base, in the presence or in the absence of an additive.

In this scheme, W1a, M1, M1b, R10b, R20a, R21a, R22a and R23a have the same definitions as above.

Method 12-1 of this method may be carried out in a manner similar to Method K described above, and Method 12-2 may be carried out in a manner similar to Method K described above.

When a compound of the present invention is to be used as a medicament, it will normally be mixed with appropriate additives for use as a formulation.

However, this does not preclude the use of the compounds of the invention by itself as medicament.

Such additives may include excipients, binders, lubricants, disintegrators, coloring agents, taste correctives, emulsifiers, surfactants, dissolving aids, suspending agents, isotonizing agents, buffering agents, antiseptics, antioxidants, stabilizers, absorption accelerators and the like which are commonly used in pharmaceuticals, and they may be added in appropriate combinations as desired.

As examples of such excipients there may be mentioned lactose, white soft sugar, glucose, corn starch, mannitol, sorbitol, starch, alpha starch, dextrin, crystalline cellulose, soft silicic anhydride, aluminum silicate, calcium silicate, magnesium aluminometasilicate, calcium hydrogenphosphate, and the like.

As examples of binders there may be mentioned polyvinyl alcohol, methylcellulose, ethylcellulose, gum Arabic, tragacanth, gelatin, shellac, hydroxypropylmethylcellulose, hydroxypropylcellulose, carboxymethylcellulose sodium, polyvinylpyrrolidone, macrogol, and the like.

As examples of lubricants there may be mentioned magnesium stearate, calcium stearate, sodium stearyl fumarate, talc, polyethylene glycol, colloidal silica, and the like.

As examples of disintegrators, there may be mentioned crystalline cellulose, agar, gelatin, calcium carbonate, sodium hydrogencarbonate, calcium citrate, dextrin, pectin, low-substituted hydroxypropylcellulose, carboxymethylcellulose, carboxymethylcellulose calcium, croscarmellose sodium, carboxymethyl starch, and carboxymethyl starch sodium, and the like.

As coloring agents there may be mentioned those approved for addition to pharmaceuticals, such as iron sesquioxide, yellow iron sesquioxide, carmine, caramel, β-carotene, titanium oxide, talc, riboflavin sodium phosphate, yellow aluminum lake and the like.

As taste correctives there may be mentioned cocoa powder, menthol, aromatic powders, mentha oil, borneol, powdered cinnamon bark, and the like.

As emulsifiers or surfactants there may be mentioned stearyl triethanolamine, sodium lauryl sulfate, lauryl aminopropionic acid, lecithin, glycerin monostearate, sucrose fatty acid esters, glycerin fatty acid esters, and the like.

As dissolving aids there may be mentioned polyethylene glycol, propylene glycol, benzyl benzoate, ethanol, cholesterol, triethanolamine, sodium carbonate, sodium citrate, polysorbate 80, nicotinamide, and the like.

As suspending agents there may be mentioned the surfactants referred to above, as well as hydrophilic polymers such as polyvinyl alcohol, polyvinylpyrrolidone, methylcellulose, hydroxymethylcellulose, hydroxyethylcellulose, hydroxypropylcellulose and the like.

As isotonizing agents there may be mentioned glucose, sodium chloride, mannitol, sorbitol and the like.

As buffering agents there may be mentioned buffering solutions of phosphate, acetate, carbonate, citrate and the like.

As antiseptics there may be mentioned methylparaben, propylparaben, chlorobutanol, benzyl alcohol, phenethyl alcohol, dehydroacetic acid, sorbic acid, and the like.

As antioxidants there may be mentioned sulfite, ascorbic acid, α-tocopherol, and the like.

As stabilizers there may be mentioned those commonly used in pharmaceuticals.

As absorption accelerators there may also be mentioned those commonly used in pharmaceuticals.

The formulation may be in an oral form such as tablets, powders, granules, capsules, syrups, lozenges or inhalants, an external application form such as suppository, ointment, eye salve, tape, eye drop, nasal drop, ear drop, pap or lotion, or an injection.

An oral formulation will be formulated using an appropriate combination of additives among those mentioned above. The surface thereof may also be coated if necessary.

An external application will be formulated using an appropriate combination of additives among those mentioned above, and particularly excipients, binders, taste correctives, emulsifiers, surfactants, dissolving aids, suspending agents, isotonizing agents, antiseptics, antioxidants, stabilizers and absorption accelerators.

An injection will be formulated using an appropriate combination of additives among those mentioned above, and particularly emulsifiers, surfactants, dissolving aids, suspending agents, isotonizing agents, buffering agents, antiseptics, antioxidants, stabilizers and absorption accelerators.

When a compound of the invention is to be used as a drug, the dosage thereof will differ depending on the symptoms and age of the patient, but it will ordinarily be 0.15 to 5000 mg (preferably 0.5 to 1500 mg) in the case of an oral formulation, 0.5 to 1500 mg (preferably 1.5 to 500 mg) in the case of an external application, and 0.3 to 5000 mg (preferably 1 to 500 mg) in the case of an injection, per day, administered at once or divided over 2 to 6 times. For an oral formulation or injection, this represents the actual administered dose, while for an external application this represents the actual absorbed dose.

Compounds (1) and (100) according to the invention may be produced by the specific processes described in the following examples. It is to be understood, however, that these examples merely serve as illustration and are not intended to restrict the compounds of the invention under any circumstances.

EXAMPLES

Silica gel used in the following Examples are silica gel 60 (Merck & Co., Inc) or BW300 (Fuji Silysia Chemical Ltd.) unless otherwise mentioned, and NH silica gel used are Chromatorex-NH silica gel (Fuji Silysia Chemical Ltd.), propylamine-coated one.

Example 1

1-[2-(4,4-Dimethylcyclohexyl)-5-methoxyphenyl]-4-pentylpiperazine hydrochloride

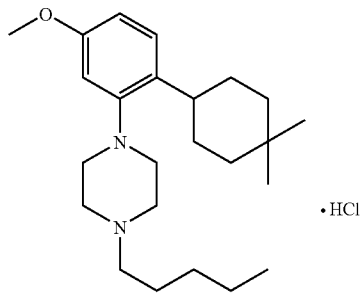

4,4-Dimethylcyclohexanone

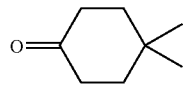

Reference: Bruce H. Lipshutz, John Keith, Patrick Papa, and Randall Vivian, Tetrahedron Lett., 1998, 39, 4627.

1a

Trifluoromethanesulfonic acid 4,4-dimethylcyclohex-1-enyl ester

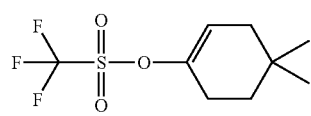

A mixture of lithium bis(trimethylsilyl)amide (1M solution in tetrahydrofuran, 172 mL, 172 mmol) and anhydrous tetrahydrofuran (400 mL) was stirred, and then cooled to below −70° C. in a dry ice-acetone bath under a nitrogen atmosphere. A solution of 4,4-dimethylcyclohexanone (18 g, 143 mmol) in anhydrous tetrahydrofuran (100 mL) was added dropwise to the solution over 30 minutes. After stirring for 2 hours and 10 minutes under the same conditions, N-phenyl bis(trifluoromethanesulfonimide) (54 g, 150 mmol) was added to the reaction mixture, and stirring was continued for 16 hours while slowly warmed to room temperature.

Saturated aqueous ammonium chloride was added to the reaction mixture to quench the reaction. Hexane and water were added to the mixture, and the organic layer and aqueous layer were separated. The organic layer was washed with brine and then dried over anhydrous magnesium sulfate. The aqueous layer was re-extracted with hexane and treated in the same manner as the organic layer. The two organic layers were combined, the desiccant was filtered off and the filtrate was concentrated under reduced pressure. The residue was purified by silica gel column chromatography (ethyl acetate/hexane) to give 26.8 g of the title compound as a light yellow oil.

$^1$H-NMR (400 MHz, CDCl$_3$) δ: 0.97 (s, 6H), 1.54 (t, J=6.4 Hz, 2H), 1.96-1.98 (m, 2H), 2.31-2.36 (m, 2H), 5.66-5.69 (m, 1H).

1b 2-(4,4-Dimethylcyclohex-1-enyl)-4,4,5,5-tetramethyl-[1,3,2]dioxaborolane

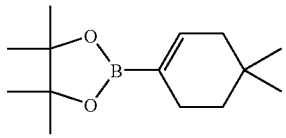

To a mixture of trifluoromethanesulfonic acid 4,4-dimethylcyclohex-1-enyl ester (19 g, 73.4 mmol) prepared in Example (1a), bis(pinacolato)diboron (21.5 g, 84.6 mmol), 1,1′-bis(diphenylphosphino)ferrocene dichloropalladium(II) dichloromethane complex (3 g, 3.68 mmol) and potassium acetate (21.7 g, 221 mmol) was added dioxane (200 mL), and the mixture was stirred under a nitrogen atmosphere at an external temperature of 80° C. for 17 hours.

After air-cooling the reaction mixture to room temperature, and insoluble matters were filtered off through Celite. The resultant filtrate was concentrated under reduced pressure, ethyl acetate and water were added to the residue, and the organic layer was separated off. The organic layer was washed with brine and then dried over anhydrous sodium sulfate. The desiccant was filtered off and the filtrate was concentrated under reduced pressure. The residue was purified by silica gel column chromatography (ethyl acetate/hexane) to give 12.5 g of the title compound as a light yellow oil.

$^1$H-NMR (400 MHz, CDCl$_3$) δ: 0.88 (s, 6H), 1.26 (s, 12H), 1.32 (t, J=6.4 Hz, 2H), 1.85-1.87 (m, 2H), 2.10-2.15 (m, 2H), 6.49-6.51 (m, 1H).

1c 1-(4,4-Dimethylcyclohex-1-enyl)-4-methoxy-2-nitrobenzene

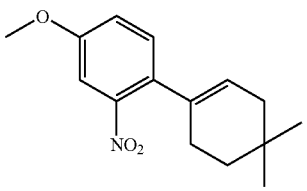

To a mixture of 4-bromo-3-nitroanisole (3.3 g, 14.1 mmol), 2-(4,4-dimethylcyclohex-1-enyl)-4,4,5,5-tetramethyl-[1,3,2]dioxaborolane (4.0 g, 16.9 mmol) prepared in Example (1b), tripotassium phosphate (4.5 g, 21.3 mmol) and 1,2-dimethoxyethane (30 mL) was added tetrakis(triphenylphosphine)palladium(0) (0.82 g, 0.71 mmol) with stirring at room temperature under a nitrogen atmosphere. The mixture was then stirred at an external temperature of 80° C. for 24 hours.

After cooling the reaction mixture to room temperature, brine was added and the mixture was extracted with ethyl acetate. The organic layer was dried over anhydrous magnesium sulfate, the desiccant was filtered off and then the filtrate was concentrated under reduced pressure. The residue was purified by silica gel column chromatography (ethyl acetate/hexane) to give 3.5 g of the title compound as a yellow oil.

$^1$H-NMR (400 MHz, CDCl$_3$) δ: 0.99 (s, 3H), 1.26 (s, 3H), 1.49 (t, J=6.4 Hz, 2H), 1.78-1.90 (m, 2H), 2.20-2.26 (m, 2H), 3.84 (s, 3H), 5.49-5.54 (m, 1H), 7.04 (dd, J=8.4, 2.8 Hz, 1H), 7.16 (d, J=8.4 Hz, 1H), 7.29 (d, J=2.8 Hz, 1H).

1d 2-(4,4-Dimethylcyclohex-1-enyl)-5-methoxyphenylamine

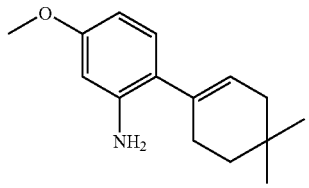

To a solution of 1-(4,4-dimethylcyclohex-1-enyl)-4-methoxy-2-nitrobenzene (3.5 g, 13.4 mmol) prepared in Example (1c) in ethanol (30 mL) were added a solution (5 mL) of aqueous ammonium chloride (2.9 g, 54 mmol) and iron powder (1.5 g, 26.8 mmol), and the mixture was stirred at an external temperature of 90° C. for 1 hour and 30 minutes. The reaction mixture was passed through Celite, brine was added to the filtrate and the mixture was extracted with ethyl acetate. The organic layer was dried over anhydrous magnesium sulfate, and the desiccant was filtered off. The filtrate was concentrated under reduced pressure to give 3.35 g of the title compound as a yellow oil.

$^1$H-NMR (400 MHz, CDCl$_3$) δ: 0.99 (s, 3H), 1.26 (s, 3H), 1.50 (t, J=6.4 Hz, 2H), 1.94-1.98 (m, 2H), 2.20-2.28 (m, 2H), 3.75 (s, 3H), 5.62-5.66 (m, 1H), 6.24 (d, J=2.8 Hz, 1H), 6.29 (dd, J=8.4, 2.8 Hz, 1H), 6.88 (d, J=8.4 Hz, 1H).

The 2H of NH$_2$ could not be identified.

1e

1-[2-(4,4-Dimethylcyclohex-1-enyl)-5-methoxyphenyl]piperazine

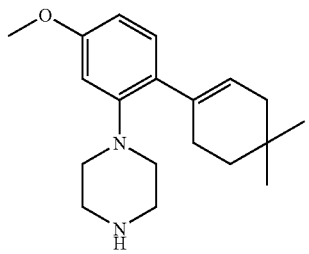

A solution of 2-(4,4-dimethylcyclohex-1-enyl)-5-methoxyphenylamine (3.35 g, 14.5 mmol) prepared in Example (1d) and bis(2-chloroethyl)amine hydrochloride (3.1 g, 17.4 mmol) in 1,2-dichlorobenzene (10 mL) was stirred at 210° C. for 30 minutes. Nitrogen gas was blown into the reactor several times during the reaction to remove the excess hydrogen chloride gas in the reactor. The reaction mixture was cooled to room temperature, saturated aqueous sodium hydrogencarbonate was added and the mixture was extracted with ethyl acetate. The organic layer was dried over anhydrous magnesium sulfate. The desiccant was filtered off and the filtrate was concentrated under reduced pressure. The resultant residue was purified by NH silica gel column chromatography (ethyl acetate/hexane) to give 2.1 g of the title compound as a yellow oil.

$^1$H-NMR (400 MHz, CDCl$_3$) δ: 0.97 (s, 6H), 1.44 (t, J=6.4 Hz, 2H), 1.90-1.98 (m, 2H), 2.34-2.48 (m, 2H), 2.94-3.32 (m, 8H), 3.78 (s, 3H), 5.58-5.66 (m, 1H), 6.48 (dd, J=8.4, 2.8 Hz, 1H), 6.50 (d, J=2.8 Hz, 1H), 6.99 (d, J=8.4 Hz, 1H).

The 1H of NH could not be identified.

MS m/e (ESI) 301 (MH$^+$).

1f

1-[2-(4,4-Dimethylcyclohex-1-enyl)-5-methoxyphenyl]-4-pentylpiperazine hydrochloride

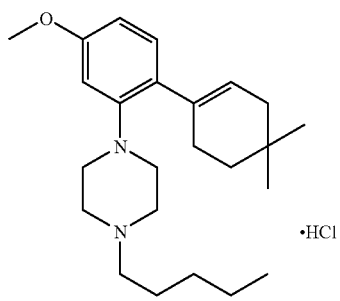

To a solution of 1-[2-(4,4-dimethylcyclohex-1-enyl)-5-methoxyphenyl]piperazine (90 mg, 0.29 mmol) prepared in Example (1e) in tetrahydrofuran (10 mL) were added valeraldehyde (31 mg, 0.36 mmol), sodium triacetoxyborohydride (95 mg, 0.59 mmol) and acetic acid (35 mg, 0.59 mmol) in that order, and the mixture was stirred for 3 hours. Saturated aqueous sodium hydrogencarbonate was added to the reaction mixture and the mixture was extracted with ethyl acetate. The organic layer was dried over anhydrous magnesium sulfate, the desiccant was filtered off and then the filtrate was concentrated under reduced pressure. The resultant residue was purified by NH silica gel column chromatography (ethyl acetate/hexane) to give 110 mg of 1-[2-(4,4-dimethylcyclohex-1-enyl)-5-methoxyphenyl]-4-pentylpiperazine as a light yellow oil.

MS m/e (ESI) 371 (MH$^+$).

The obtained compound was dissolved in ethyl acetate, a 4N solution of hydrogen chloride in ethyl acetate was added and the mixture was stirred at room temperature for 30 minutes. The solvent was distilled off under reduced pressure, and then diethyl ether was added to the residue and the mixture was filtered to give 50 mg of the title compound as a light yellow solid.

$^1$H-NMR (400 MHz, CD$_3$OD) δ: 0.97 (s, 3H), 0.97 (t, J=7.2 Hz, 3H), 1.00 (s, 3H), 1.34-1.50 (m, 8H), 1.72-1.85 (m, 4H), 2.94-3.40 (m, 6H), 3.45-3.88 (m, 4H), 3.76 (s, 3H), 5.62-5.68 (m, 1H), 6.48-6.64 (m, 3H). MS m/e (ESI) 371 (MH$^+$).

1g

1-[2-(4,4-Dimethylcyclohexyl)-5-methoxyphenyl]-4-pentylpiperazine hydrochloride

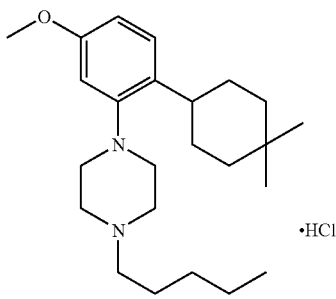

To a solution of 1-[2-(4,4-dimethylcyclohex-1-enyl)-5-methoxyphenyl]-4-pentylpiperazine hydrochloride (44 mg) prepared in Example (1f) in methanol (5 mL) was added 10% palladium on carbon (100 mg, wet), and the mixture was stirred for 17 hours under a hydrogen atmosphere at atmospheric pressure and room temperature. The reaction mixture was passed through Celite, and the filtrate was concentrated under reduced pressure. Diethyl ether was added to the residue and the mixture was filtered to give 17 mg of the title compound as a light yellow solid.

$^1$H-NMR (400 MHz, CD$_3$OD) δ: 0.97 (s, 3H), 0.96 (t, J=7.2 Hz, 3H), 1.04 (s, 3H), 1.36-1.86 (m, 14H), 2.8-2.95 (m, 1H), 3.06-3.40 (m, 10H), 3.77 (s, 3H), 6.70 (d, J=2.8 Hz, 1H), 6.74 (dd, J=8.4, 2.8 Hz, 1H), 7.22 (d, J=8.4 Hz, 1H). MS m/e (ESI) 373 (MH$^+$).

Example 2

4-Butyl-1-[2-(4-t-butylcyclohexyl)phenyl]piperazin-2-one hydrochloride

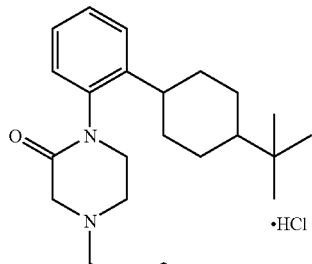

2a

Trifluoromethanesulfonic acid 4-t-butylcyclohex-1-enyl ester

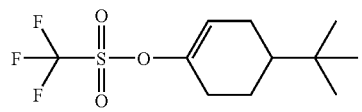

A solution of diisopropylamine (22 mL, 0.157 mol) in anhydrous tetrahydrofuran (500 mL) was cooled to below −70° C. in a dry ice-acetone bath under a nitrogen atmosphere. n-Butyllithium (1.56 M solution in hexane, 100 mL, 0.156 mol) was slowly added dropwise to the stirred solution over 15 minutes. The reaction mixture was then warmed to −10° C. and then cooled to below −70° C. again. After stirring for 10 minutes, a solution of 4-t-butylcyclohexanone (20.05 g, 0.13 mol) in anhydrous tetrahydrofuran (100 mL) was gradually added dropwise to the reaction mixture over 15 minutes. After stirring for 30 minutes, a solution of N-phenyl bis(trifluoromethanesulfonimide) (51.09 g, 0.143 mol) in anhydrous tetrahydrofuran (200 mL) was gradually added dropwise to the reaction mixture over 15 minutes and the mixture was stirred for 30 minutes. The dry ice bath was then exchanged with an ice bath, and stirring was continued for 30 minutes and then for another 30 minutes at room temperature.

Ethyl acetate and brine were added to the reaction mixture and the mixture was extracted with ethyl acetate. The collected organic layer was dried over anhydrous sodium sulfate. The desiccant was filtered off and the filtrate was concentrated under reduced pressure. The resultant residue was purified by silica gel column chromatography (ethyl acetate/hexane) to give 33.1 g of the title compound as a light yellow oil, in racemic form at the position of t-butyl.

$^1$H-NMR (400 MHz, CDCl$_3$) δ: 0.90 (s, 9H), 1.24-1.44 (m, 2H), 1.90-2.00 (m, 2H), 2.16-2.25 (m, 1H), 2.32-2.46 (m, 2H), 5.72-5.76 (m, 1H).

2b

1-(4-t-Butylcyclohex-1-enyl)-2-nitrobenzene

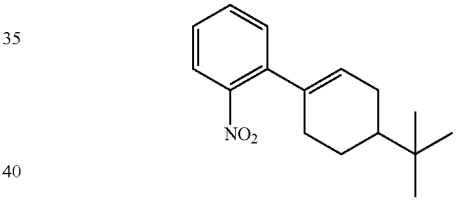

A mixture of trifluoromethanesulfonic acid 4-t-butylcyclohex-1-enyl ester (7.16 g, 25 mmol) prepared in Example (2a), 2-nitrophenylboronic acid (5 g, 30 mmol), 2N aqueous sodium carbonate (25 mL), toluene (70 mL) and ethanol (35 mL) was stirred at room temperature under a nitrogen atmosphere. To the mixture was added tetrakis(triphenylphosphine)palladium(0) (1.5 g, 1.3 mmol). The mixture was then stirred at an external temperature of 90° C. for 1 hour and 30 minutes.

Ethyl acetate, water and brine were added to the reaction mixture and the mixture was extracted with ethyl acetate. The collected organic layer was dried over anhydrous sodium sulfate. The desiccant was filtered off and the filtrate was concentrated under reduced pressure. The resultant residue was purified by silica gel column chromatography (ethyl acetate/hexane) to give 4.89 g of the title compound as a yellowish-brown oil, in racemic form at the position of t-butyl.

$^1$H-NMR (400 MHz, CDCl$_3$) δ: 0.90 (s, 9H), 1.32-1.44 (m, 2H), 1.86-1.97 (m, 2H), 2.14-2.28 (m, 2H), 2.28-2.40 (m, 1H), 5.62-5.66 (m, 1H), 7.26 (dd, J=7.6, 1.2 Hz, 1H), 7.34 (ddd, J=8.0, 7.6, 1.2 Hz, 1H), 7.49 (td, J=7.6, 1.2 Hz, 1H), 7.77 (dd, J=8.0, 1.2 Hz, 1H).

2c 2-(4-t-Butylcyclohexyl)phenylamine

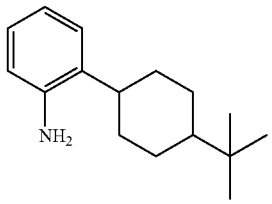

A mixture of 1-(4-t-butylcyclohex-1-enyl)-2-nitrobenzene (4.89 g, 18.86 mmol) prepared in Example (2b), 10% palladium on carbon (1.5 g, wet) and ethyl acetate (25 mL) was stirred for 4 hours under a hydrogen atmosphere at atmospheric pressure and room temperature.

The reaction mixture was filtered, and the filtrate was concentrated under reduced pressure. The resultant residue was purified by silica gel column chromatography (ethyl acetate/hexane) to give 3.34 g of the title compound as a light brown oil, as a mixture of diastereomers at the position of t-butylcyclohexyl.

$^1$H-NMR (400 MHz, CDCl$_3$) δ: 0.86 (s, 9H×0.6), 0.89 (s, 9H×0.4), 1.08-1.50 (m, 4H), 1.60-2.14 (m, 5H), 2.36-2.46 (m, 1H×0.4), 2.90-2.96 (m, 1H×0.6), 3.63 (brs, 2H), 6.64-6.69 (m, 1H), 6.73-6.79 (m, 1H), 6.98-7.04 (m, 1H), 7.10 (dd, J=7.6, 1.2 Hz, 1H×0.4), 7.34 (dd, J=7.6, 1.2 Hz, 1H×0.6).

2d

2-[2-(4-t-Butylcyclohexyl)phenylamino]ethanol

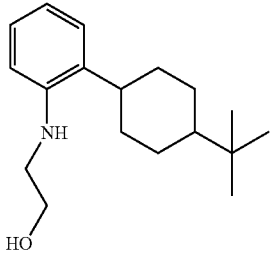

A mixture of 2-(4-t-butylcyclohexyl)phenylamine (1.2 g, 5.19 mmol) prepared in Example (2c), 2-bromoethanol (0.76 mL, 10.72 mmol), triethylamine (1.12 mL, 8.04 mmol) and toluene (20 mL) was heated at reflux for 16 hours and 20 minutes under a nitrogen atmosphere.

Ethyl acetate and water were added to the reaction mixture and the mixture was extracted with ethyl acetate. The collected organic layer was washed with brine and then dried over anhydrous sodium sulfate. The desiccant was filtered off and the filtrate was concentrated under reduced pressure. The resultant residue was purified by silica gel column chromatography (ethyl acetate/hexane) to give 538 mg of the title compound as a light red oil, as a mixture of diastereomers at the position of t-butylcyclohexyl.

$^1$H-NMR (400 MHz, CDCl$_3$) δ: 0.86 (s, 9H×0.6), 0.90 (s, 9H×0.4), 1.08-1.50 (m, 4H), 1.60-2.12 (m, 5H), 2.36-2.45 (m, 1H×0.4), 2.91-2.96 (m, 1H×0.6), 3.33-3.38 (m, 2H), 3.85-3.92 (m, 2H), 6.67 (dd, J=8.0, 1.2 Hz, 1H×0.6), 6.68 (dd, J=8.0, 1.2 Hz, 1H×0.4), 6.75 (td, J=8.0, 1.2 Hz, 1H×0.6), 6.76 (td, J=8.0, 1.2 Hz, 1H×0.4), 7.08-7.15 (m, 1H+1H×0.4), 7.37 (dd, J=8.0, 1.2 Hz, 1H×0.6).

Each 1H of NH and OH could not be identified.

2e

N-[2-(4-t-Butylcyclohexyl)phenyl]-2-chloro-N-(2-hydroxyethyl)acetamide

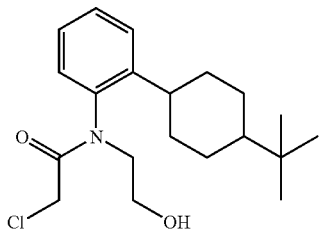

A solution of 2-[2-(4-t-butylcyclohexyl)phenylamino]ethanol (248 mg, 0.9 mmol) prepared in Example (2d) in anhydrous tetrahydrofuran (5 mL) was cooled in an ice water bath under a nitrogen atmosphere. Chloroacetyl chloride (0.08 mL, 1 mmol) was added thereto and the mixture was stirred for 40 minutes.

Ethyl acetate, saturated aqueous sodium hydrogencarbonate and water were added to the reaction mixture and the mixture was extracted with ethyl acetate. The collected organic layer was washed with brine and then dried over anhydrous sodium sulfate. The desiccant was filtered off and the filtrate was concentrated under reduced pressure. The resultant residue was purified by silica gel column chromatography (ethyl acetate/hexane) to give 258 mg of the title compound as a colorless oil, as a mixture of diastereomers at the position of t-butylcyclohexyl.

$^1$H-NMR (400 MHz, CDCl$_3$) δ: 0.88 (s, 9H×0.4), 0.92 (s, 9H×0.6), 1.08-1.20 (m, 1H), 1.21-1.32 (m, 2H), 1.42-1.94 (m, 6H), 2.54 (tt, J=12.0, 3.2 Hz, 1H×0.4), 2.74-2.85 (m, 1H), 2.90-2.98 (m, 1H×0.6), 3.22 (dd, J=4.8, 4.0 Hz, 1H×0.4), 3.25 (dd, J=4.8, 4.0 Hz, 1H×0.6), 3.69-3.90 (m, 4H), 4.38-4.47 (m, 1H), 7.21 (d, J=7.6 Hz, 1H×0.6), 7.21 (d, J=7.6 Hz, 1H×0.4), 7.23-7.29 (m, 1H), 7.37-7.43 (m, 1H+1H×0.4), 7.58 (dd, J=7.6, 1.2 Hz, 1H×0.6).

2f

N-[2-(4-t-Butylcyclohexyl)phenyl]-2-chloro-N-(2-oxoethyl)acetamide

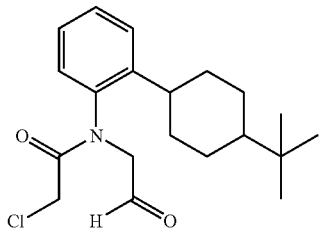

A solution of oxalyl chloride (0.24 mL, 2.75 mmol) in anhydrous dichloromethane (5 mL) was cooled to below −65° C. in a dry ice-acetone bath under a nitrogen atmosphere. A solution of anhydrous dimethylsulfoxide (0.38 mL, 5.35 mmol) in anhydrous dichloromethane (5 mL) was gradually added dropwise thereto over 8 minutes. The reaction mixture was then warmed to −20° C. and then cooled to below −65° C. again. A solution of N-[2-(4-t-butylcyclohexyl)phenyl]-2-chloro-N-(2-hydroxyethyl)acetamide (256 mg, 0.727 mmol) prepared in Example (2e) in anhydrous dichloromethane (5 mL) was gradually added dropwise to the reaction mixture over 11 minutes. After stirring for 30 minutes, triethylamine (0.96 mL, 6.89 mmol) was added and the reaction mixture was gradually warmed to room temperature.

Saturated aqueous ammonium chloride, ethyl acetate and water were added to the reaction mixture and the mixture was extracted with ethyl acetate. The collected organic layer was washed with a saturated aqueous citric acid, water, saturated aqueous sodium hydrogencarbonate and brine in that order and then dried over anhydrous sodium sulfate. The desiccant was filtered off and the filtrate was concentrated under reduced pressure to give 303 mg of a crude product of the title compound as a light yellow oil, as a mixture of diastereomers at the position of t-butylcyclohexyl. This was used without purification for the following reaction.

2g

4-Butyl-1-[2-(4-t-butylcyclohexyl)phenyl]piperazin-2-one hydrochloride

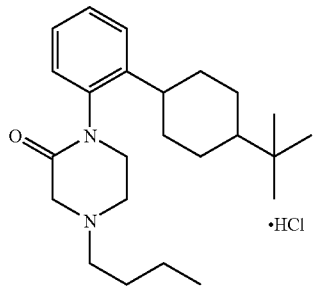

A solution of the crude product of N-[2-(4-t-butylcyclohexyl)phenyl]-2-chloro-N-(2-oxoethyl)acetamide (301 mg) prepared in Example (2f) in 1,2-dichloroethane (7 mL) was cooled in an ice water bath under a nitrogen atmosphere. Molecular Sieve 4 Å (150 mg), n-butylamine (0.091 mL, 0.921 mmol) and sodium triacetoxyborohydride (187 mg, 0.882 mmol) were added thereto in that order, and stirring was continued for 20 hours with slowly warmed to room temperature.

Insoluble matters were filtered off, and then saturated aqueous ammonium chloride, ethyl acetate and water were added to the filtrate and the filtrate was extracted with ethyl acetate. The collected organic layer was washed with saturated aqueous sodium hydrogencarbonate and brine in that order and then dried over anhydrous sodium sulfate. The desiccant was filtered off and the filtrate was concentrated under reduced pressure. The resultant residue was purified by silica gel column chromatography (ethyl acetate/hexane) to give 163 mg of 4-butyl-1-[2-(4-t-butylcyclohexyl)phenyl]piperazin-2-one as a light yellow oil, as a mixture of diastereomers at the position of t-butylcyclohexyl.

$^1$H-NMR (400 MHz, CDCl$_3$) δ: 0.88 (s, 9H×0.4), 0.89 (s, 9H×0.6), 0.95 (t, J=7.2 Hz, 3H), 1.03-2.00 (m, 13H), 2.40-2.51 (m, 2H+1H×0.4), 2.64-2.77 (m, 1H), 2.86-3.00 (m, 1H+1H×0.6), 3.16 (d, J=16.4 Hz, 1H×0.6), 3.24 (d, J=16.4 Hz, 1H×0.4), 3.37-3.45 (m, 2H), 3.62-3.73 (m, 1H), 7.12 (dd, J=7.6, 1.2 Hz, 1H), 7.21-7.36 (m, 2H+1H×0.4), 7.56 (dd, J=7.6, 1.2 Hz, 1H×0.6).

The obtained compound was dissolved in ethyl acetate, and a 4N solution of hydrogen chloride in ethyl acetate was added. The solution was concentrated under reduced pressure, and diethyl ether was added to the resultant residue to solidify. The solid was triturated by sonication, filtered and then dried under reduced pressure to give 102 mg of the title compound as a light brown solid, as a mixture of diastereomers at the position of t-butylcyclohexyl.

MS m/e (ESI) 371 (MH$^+$).

Example 3

4-[3-(4,4-Dimethylcyclohexyl)-4-(4-isobutylpiperazin-1-yl)phenyl]morpholine hydrochloride

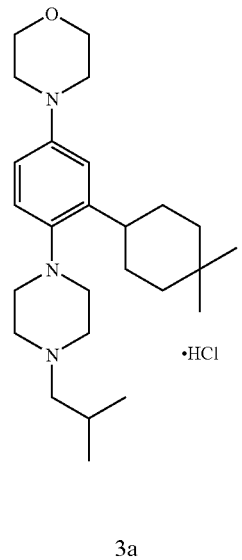

3a 1-(4,4-Dimethylcyclohex-1-enyl)-2-nitrobenzene

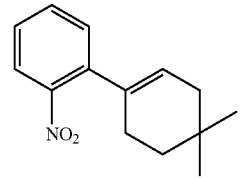

To a solution of 2-nitrophenylboronic acid (14.2 g, 85.19 mmol) in toluene (250 mL)-ethanol (125 mL) were added trifluoromethanesulfonic acid 4,4-dimethylcyclohex-1-enyl ester (20 g, 77.44 mmol) prepared in Example (1a), tetrakis(triphenylphosphine)palladium(0) (4.5 g, 3.87 mmol) and 2N aqueous sodium carbonate (128 mL, 256 mmol). The mixture was stirred at an external temperature of 100° C. for 1 hour and 45 minutes under a nitrogen atmosphere.

After air-cooling the reaction mixture to room temperature, it was passed through Celite and insoluble matters were filtered off. Ethyl acetate and water were added to the resultant filtrate and the filtrate was extracted with ethyl acetate.

The collected organic layer was washed with water and brine in that order and then dried over anhydrous magnesium sulfate. The desiccant was filtered off, and the filtrate was concentrated under reduced pressure. The resultant residue was purified by silica gel column chromatography (ethyl acetate/hexane) to give 16.3 g of the title compound as a brown oil.

$^1$H-NMR (400 MHz, CDCl$_3$) δ: 1.00 (s, 6H), 1.51 (t, J=6.4 Hz, 2H), 1.92-1.94 (m, 2H), 2.24-2.29 (m, 2H), 5.55-5.57 (m, 1H), 7.27 (dd, J=7.6, 1.6 Hz, 1H), 7.34 (ddd, J=7.6, 7.6, 1.6 Hz, 1H), 7.50 (ddd, J=7.6, 7.6, 1.6 Hz, 1H), 7.77 (dd, J=7.6, 1.6 Hz, 1H).

3b 2-(4,4-Dimethylcyclohexyl)phenylamine

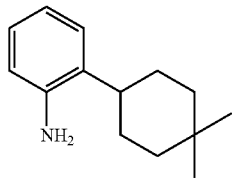

A mixture of 1-(4,4-dimethylcyclohex-1-enyl)-2-nitrobenzene (16.3 g, 70.5 mmol) prepared in Example (3a), 10% palladium on carbon (1 g, wet) and ethyl acetate (100 mL) was stirred for 14 hours and 30 minutes under a hydrogen atmosphere at atmospheric pressure and room temperature.

The reaction mixture was filtered and the filtrate was concentrated under reduced pressure. A mixture of the resultant residue, 10% palladium on carbon (3 g, wet) and ethyl alcohol (200 mL) was stirred for 30 hours and 30 minutes under a hydrogen atmosphere at atmospheric pressure and room temperature.

After the reaction completed, the reaction mixture was filtered, and the filtrate was concentrated under reduced pressure. The resultant residue was purified by silica gel column chromatography (ethyl acetate/hexane) to give 11.79 g of the title compound as a light yellow solid.

$^1$H-NMR (400 MHz, CDCl$_3$) δ: 0.97 (s, 3H), 0.99 (s, 3H), 1.36 (td, J=13.2, 4.0 Hz, 2H), 1.47-1.73 (m, 6H), 2.38 (tt, J=11.6, 3.6 Hz, 1H), 3.63 (brs, 2H), 6.68 (dd, J=7.6, 1.6 Hz, 1H), 6.77 (ddd, J=7.6, 7.6, 1.6 Hz, 1H), 7.01 (ddd, J=7.6, 7.6, 1.6 Hz, 1H), 7.14 (dd, J=7.6, 1.6 Hz, 1H).

3c

1-[2-(4,4-Dimethylcyclohexyl)phenyl]piperazine

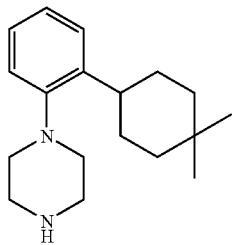

To a solution of 2-(4,4-dimethylcyclohexyl)phenylamine (11.79 g, 57.98 mmol) prepared in Example (3b) in 1,2-dichlorobenzene (30 mL) was added bis(2-chloroethyl) amine hydrochloride (12.42 g, 69.58 mmol), and the mixture was stirred at an external temperature of 200° C. for 2 hours and 30 minutes under a nitrogen atmosphere. During the reaction, nitrogen was passed through the reactor several times to remove the hydrogen chloride gas.

After air-cooling the reaction mixture to room temperature, ethyl acetate and saturated aqueous sodium hydrogencarbonate were added and the mixture was extracted with ethyl acetate. The collected organic layer was washed with water and brine in that order and then dried over anhydrous sodium sulfate. The desiccant was filtered off, and the filtrate was concentrated under reduced pressure. The resultant residue was purified by NH silica gel column chromatography (ethyl acetate/hexane) to give 12.15 g of the title compound as a brown oil.

$^1$H-NMR (400 MHz, CDCl$_3$) δ: 0.97 (s, 3H), 1.01 (s, 3H), 1.34 (td, J=12.8, 4.4 Hz, 2H), 1.48-1.68 (m, 6H), 2.82-2.84 (m, 4H), 2.95-3.03 (m, 5H), 7.05-7.27 (m, 4H).

The 1H of NH could not be identified.

3d

4-[2-(4,4-Dimethylcyclohexyl)phenyl]piperazine-1-carboxylic acid t-butyl ester

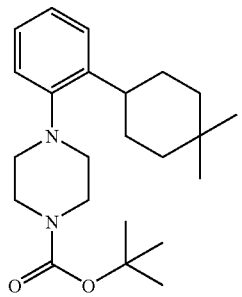

A mixture of 1-[2-(4,4-dimethylcyclohexyl)phenyl]piperazine (11 g, 40.4 mmol) prepared in Example (3c), triethylamine (6.2 mL, 44.4 mmol), 4-dimethylaminopyridine (247 mg, 2.02 mmol) and dichloromethane (180 mL) was stirred at an external temperature of 0° C. under a nitrogen atmosphere. A mixture of di-t-butyl dicarbonate (9.7 g, 44.4 mmol) and dichloromethane (20 mL) was added thereto.

After stirring for 2 hours and 50 minutes under the same conditions, saturated aqueous sodium hydrogencarbonate was added to the reaction mixture and the mixture was extracted with dichloromethane. The collected organic layer was washed with brine and then dried over anhydrous sodium sulfate. The desiccant was filtered off, and the filtrate was concentrated under reduced pressure. The resultant residue was purified by silica gel column chromatography (ethyl acetate/hexane) to give 14.89 g of the title compound as a light yellow oil.

$^1$H-NMR (400 MHz, CDCl$_3$) δ: 0.96 (s, 3H), 1.01 (s, 3H), 1.31 (td, J=12.8, 4.4 Hz, 2H), 1.49 (s, 9H), 1.49-1.69 (m, 6H), 2.81 (brs, 4H), 2.95-3.02 (m, 1H), 3.57 (brs, 4H), 7.06 (dd, J=7.6, 1.6 Hz, 1H), 7.10 (ddd, J=7.6, 7.6, 1.6 Hz, 1H), 7.16 (ddd, J=7.6, 7.6, 2.0 Hz, 1H), 7.28 (dd, J=7.6, 2.0 Hz, 1H).

3e

4-[4-Bromo-2-(4,4-dimethylcyclohexyl)phenyl]piperazine-1-carboxylic acid t-butyl ester

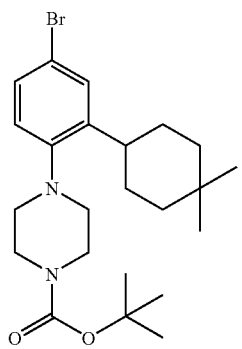

A mixture of 4-[2-(4,4-dimethylcyclohexyl)phenyl]piperazine-1-carboxylic acid t-butyl ester (8 g, 21.5 mmol) prepared in Example (3d), sodium acetate (17.6 g, 215 mmol) and methanol (300 mL) was stirred at an external temperature of room temperature under a nitrogen atmosphere. Bromine (1.1 mL, 21.5 mmol) was added dropwise thereto over 20 minutes, and the mixture was stirred for 17 hours under the same conditions. Sodium acetate (8.8 g, 107.5 mmol) was added thereto, and then bromine (0.4 mL, 7.8 mmol) was added dropwise and the mixture was stirred for 1 hour under the same conditions.

A saturated aqueous solution of sodium sulfite was added to the reaction mixture and the mixture was extracted with ethyl acetate. The collected organic layer was washed with brine and then dried over anhydrous magnesium sulfate. The desiccant was filtered off, and the filtrate was concentrated under reduced pressure. The resultant residue was purified by silica gel column chromatography (ethyl acetate/hexane) to give 7.97 g of the title compound as a light yellow solid.

$^1$H-NMR (400 MHz, CDCl$_3$) δ: 0.96 (s, 3H), 1.01 (s, 3H), 1.24-1.34 (m, 2H), 1.41-1.64 (m, 6H), 1.49 (s, 9H), 2.77 (brs, 4H), 2.89-2.97 (m, 1H), 3.55 (brs, 4H), 6.92 (d, J=8.4 Hz, 1H), 7.25 (dd, J=8.4, 2.4 Hz, 1H), 7.35 (d, J=2.4 Hz, 1H).

3f

4-[2-(4,4-Dimethylcyclohexyl)-4-morpholin-4-ylphenyl]piperazine-1-carboxylic acid t-butyl ester

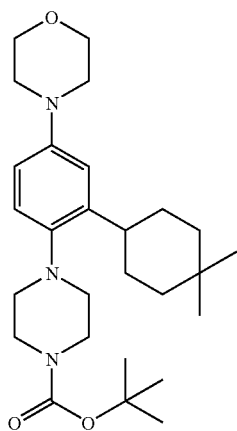

A mixture of 4-[4-bromo-2-(4,4-dimethylcyclohexyl)phenyl]piperazine-1-carboxylic acid t-butyl ester (1 g, 2.22 mmol) prepared in Example (3e), morpholine (290 mg, 3.32 mmol), sodium t-butoxide (533 mg, 5.55 mmol), palladium (II) acetate (50 mg, 0.222 mmol), tri-t-butylphosphonium tetrafluoroborate (193 mg, 0.666 mmol) and xylene (10 mL) was stirred at an external temperature of 100° C. for 1 hour and 15 minutes under a nitrogen atmosphere.

After air-cooling the reaction mixture to room temperature, the mixture was passed through Celite and insoluble matters were filtered off, and then the resultant filtrate was concentrated under reduced pressure. The resultant residue was purified by silica gel column chromatography (ethyl acetate/hexane) to give 864 mg of the title compound as a yellow solid.

$^1$H-NMR (400 MHz, CDCl$_3$) δ: 0.96 (s, 3H), 1.01 (s, 3H), 1.23-1.66 (m, 8H), 1.48 (s, 9H), 2.75 (s, 4H), 2.93-3.01 (m, 1H), 3.12 (m, 4H), 3.49 (brs, 4H), 3.86 (m, 4H), 6.70 (dd, J=8.8, 2.8 Hz, 1H), 6.83 (d, J=2.8 Hz, 1H), 7.01 (d, J=8.8 Hz, 1H).

3g

4-[3-(4,4-Dimethylcyclohexyl)-4-piperazin-1-ylphenyl]morpholine

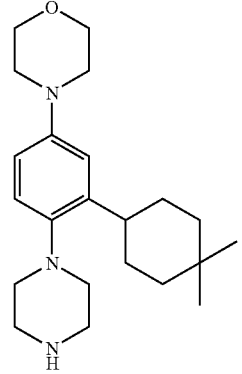

A solution of 4-[2-(4,4-dimethylcyclohexyl)-4-morpholin-4-ylphenyl]piperazine-1-carboxylic acid t-butyl ester (864 mg, 1.89 mmol) prepared in Example (3f) in ethyl acetate (15 mL)-dichloromethane (2 mL) was stirred at room temperature under a nitrogen atmosphere. A 4N solution of hydrogen chloride in ethyl acetate (15 mL, 60 mmol) was added dropwise thereto, and the mixture was stirred 12 hours under the same conditions.

After the reaction completed, saturated aqueous sodium carbonate was added to the reaction mixture to make the mixture basic. Chloroform and water were added thereto and the mixture was extracted with chloroform. The collected organic layer was washed with brine and then dried over anhydrous sodium sulfate. The desiccant was filtered off and the filtrate was concentrated under reduced pressure. The resultant residue was purified by NH silica gel column chromatography (ethyl acetate/hexane) to give 621 mg of the title compound as a colorless solid.

$^1$H-NMR (400 MHz, CDCl$_3$) δ: 0.97 (s, 3H), 1.01 (s, 3H), 1.31-1.64 (m, 8H), 2.77-2.93 (m, 4H), 2.96-3.01 (m, 5H), 3.11-3.14 (m, 4H), 3.85-3.87 (m, 4H), 6.72 (dd, J=8.8, 2.8 Hz, 1H), 6.84 (d, J=2.8 Hz, 1H), 7.07 (d, J=8.8 Hz, 1H).

The 1H of NH could not be identified.

3h

4-[3-(4,4-Dimethylcyclohexyl)-4-(4-isobutylpiperazine-1-yl)phenyl]morpholine hydrochloride

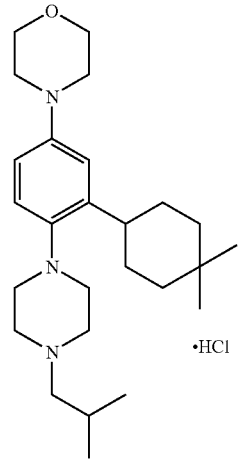

To a mixture of 4-[3-(4,4-dimethylcyclohexyl)-4-piperazin-1-ylphenyl]morpholine (100 mg, 0.28 mmol) prepared in Example (3g), isobutylaldehyde (40 mg, 0.559 mmol) and tetrahydrofuran (2 mL) was added sodium triacetoxyborohydride (119 mg, 0.559 mmol) at room temperature under a nitrogen atmosphere.

After stirring for 2 hours and 50 minutes, saturated aqueous sodium hydrogencarbonate and water were added to the reaction mixture and the mixture was extracted with ethyl acetate. The collected organic layer was washed with water and brine in that order and then dried over anhydrous sodium sulfate. The desiccant was filtered off, and the filtrate was concentrated under reduced pressure. The resultant residue was purified by NH silica gel column chromatography (ethyl acetate/hexane) to give 114 mg of 4-[3-(4,4-dimethylcyclohexyl)-4-(4-isobutylpiperazine-1-yl)phenyl]morpholine as a colorless solid.

$^1$H-NMR (400 MHz, CDCl$_3$) δ: 0.93 (d, J=6.4 Hz, 6H), 0.97 (s, 3H), 1.01 (s, 3H), 1.34 (td, J=12.8, 4.8 Hz, 2H), 1.43-1.62 (m, 6H), 1.83 (dq, J=7.2, 6.4 Hz, 1H), 2.16 (d, J=7.2 Hz, 2H), 2.53 (brs, 4H), 2.82-2.85 (m, 4H), 2.93-3.01 (m, 1H), 3.11-3.13 (m, 4H), 3.85-3.87 (m, 4H), 6.71 (dd, J=8.8, 2.8 Hz, 1H), 6.83 (d, J=2.8 Hz, 1H), 7.09 (d, J=8.8 Hz, 1H).

This product was dissolved in a mixed solvent of ethyl acetate and dichloromethane, and then a 4N solution of hydrogen chloride in ethyl acetate was added. The produced hydrochloride was filtered to give 127 mg of the title compound as a colorless solid.

MS m/e (ESI) 414 (MH$^+$).

Example 4

1-Butyl-4-[2-(3,3,5,5-tetramethylcyclohex-1-enyl)phenyl]piperazine hydrochloride

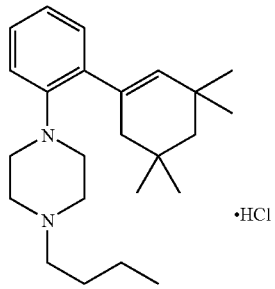

4a

Trifluoromethanesulfonic acid 3,3,5,5-tetramethylcyclohex-1-enyl ester

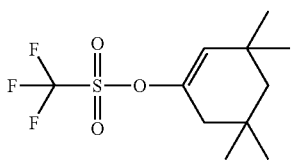

A solution of 3,3,5,5-tetramethylcyclohexanone (12.8 g, 82.98 mmol) in anhydrous tetrahydrofuran (300 mL) was cooled to below −70° C. in a dry ice-acetone bath under a nitrogen atmosphere. To the stirred solution was gradually added dropwise lithium bis(trimethylsilyl)amide (1M solution in tetrahydrofuran, 100 mL, 100 mmol) over 15 minutes. After stirring for 40 minutes under the same conditions, a solution of N-phenyl bis(trifluoromethanesulfonimide) (32.51 g, 91 mmol) in anhydrous tetrahydrofuran (150 mL) was added to the reaction mixture, and stirring was continued for 13 hours and 30 minutes with slowly warmed to room temperature.

Ethyl acetate and brine were added to the reaction mixture and the mixture was extracted with ethyl acetate. The collected organic layer was dried over anhydrous sodium sulfate. The desiccant was filtered off and the filtrate was concentrated under reduced pressure. The resultant residue was purified by silica gel column chromatography (ethyl acetate/hexane) to give 23.65 g of the title compound as a colorless oil.

$^1$H-NMR (400 MHz, CDCl$_3$) δ: 1.04 (s, 6H), 1.09 (s, 6H), 1.35 (s, 2H), 2.08 (s, 2H), 5.51 (s, 1H).

4b 4,4,5,5-Tetramethyl-2-(3,3,5,5-tetramethylcyclohex-1-enyl)-[1,3,2]dioxaborolane

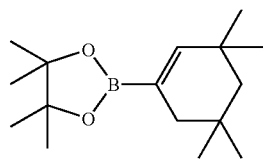

To a solution of trifluoromethanesulfonic acid 3,3,5,5-tetramethylcyclohex-1-enyl ester (45.94 g, 0.16 mol) prepared in Example (4a) in dioxane (500 mL) were added bis(pinacolato)diboron (44.9 g, 0.177 mol), 1,1'-bis(diphenylphosphino)ferrocene dichloropalladium(II) dichloromethane complex (4 g, 4.9 mmol) and potassium acetate (47.3 g, 0.482 mol), the mixture was stirred at an external temperature of 80° C. for 16 hours and 30 minutes.

Ethyl acetate, water and brine were added to the reaction mixture and the mixture was extracted with ethyl acetate. The collected organic layer was dried over anhydrous sodium sulfate. The desiccant was filtered off and the filtrate was concentrated under reduced pressure. The resultant residue was purified by silica gel column chromatography (ethyl acetate/hexane) to give 39.27 g of the title compound as a light yellow solid.

$^1$H-NMR (400 MHz, CDCl$_3$) δ: 0.92 (s, 6H), 1.01 (s, 6H), 1.27 (s, 12H), 1.31 (s, 2H), 1.84 (d, J=1.6 Hz, 2H), 6.26 (t, J=1.6 Hz, 1H).

4c 4-(2-Hydroxyphenyl)piperazine-1-carboxylic acid t-butyl ester

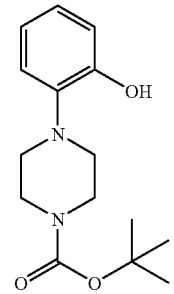

A suspension of 2-(1-piperazino)phenol (3.56 g, 20 mmol) in acetonitrile (15 mL) was stirred at room temperature. A solution of di-t-butyl dicarbonate (4.8 g, 22 mmol) in acetonitrile (15 mL) was added thereto.

After stirring for 1 hour, insoluble matters were filtered off and the filtrate was concentrated. Hexane was added to the residue prior to sonication. The resultant solid was filtered and dried under reduced pressure to give a crude product of the title compound (5.35 g) as a light brown solid.

¹H-NMR (400 MHz, CDCl₃) δ: 1.49 (s, 9H), 2.82 (t, J=4.8 Hz, 4H), 3.59 (t, J=4.8 Hz, 4H), 6.87 (td, J=7.6, 1.2 Hz, 1H), 6.96 (dd, J=8.0, 1.2 Hz, 1H), 7.07-7.14 (m, 2H).

The 1H of OH could not be identified.

4d 4-(2-Trifluoromethanesulfonyloxyphenyl)piperazine-1-carboxylic acid t-butyl ester

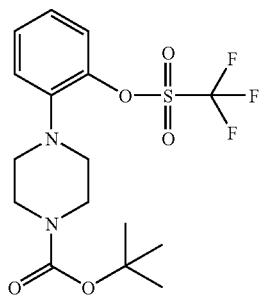

A mixture of 4-(2-hydroxyphenyl)piperazine-1-carboxylic acid t-butyl ester (4.61 g, 16.56 mmol) prepared in Example (4c), triethylamine (11.5 mL, 82.5 mmol) and dichloromethane (100 mL) was cooled in an ice bath under a nitrogen atmosphere. Trifluoromethanesulfonic anhydride (4 mL, 23.78 mmol) was gradually added dropwise over 40 minutes with stirring the mixture.

After stirring for 17 minutes under the same conditions, saturated aqueous ammonium chloride, ethyl acetate and water were added to the reaction mixture and the mixture was extracted with ethyl acetate. The collected organic layer was washed twice with saturated aqueous ammonium chloride, subsequently washed with brine, and then dried over anhydrous sodium sulfate. The desiccant was filtered off and the filtrate was concentrated under reduced pressure. The resultant residue was purified by silica gel column chromatography (ethyl acetate/hexane) to give 5.54 g of the title compound as a light yellow solid.

¹H-NMR (400 MHz, CDCl₃) δ: 1.48 (s, 9H), 2.95 (t, J=4.8 Hz, 4H), 3.62 (t, J=4.8 Hz, 4H), 7.10-7.16 (m, 2H), 7.18 (dd, J=8.0, 1.6 Hz, 1H), 7.33 (ddd, J=7.2, 7.2, 1.6 Hz, 1H).

4e

4-[2-(3,3,5,5-Tetramethylcyclohex-1-enyl)phenyl]piperazine-1-carboxylic acid t-butyl ester

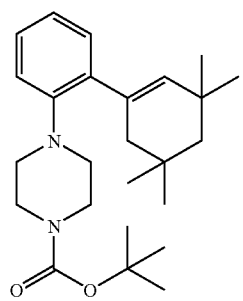

A mixture of 4-(2-trifluoromethanesulfonyloxyphenyl)piperazine-1-carboxylic acid t-butyl ester (6.16 g, 15 mmol) prepared in Example (4d), 4,4,5,5-tetramethyl-2-(3,3,5,5-tetramethylcyclohex-1-enyl)-[1,3,2]dioxaborolane (4.6 g, 17.41 mmol) prepared in Example (4b), tripotassium phosphate (3.2 g, 15 mmol), 1,2-dimethoxyethane (60 mL) and water (3 mL) was stirred at room temperature under a nitrogen atmosphere. Tetrakis(triphenylphosphine)palladium(0) (1.74 g, 1.5 mmol) was added to the mixture. The mixture was then stirred at an external temperature of 85° C. for 2 hours and 20 minutes.

Ethyl acetate and water were added to the reaction mixture and then this was passed through Celite and filtered. The organic extract from the filtrate was dried over anhydrous sodium sulfate. The desiccant was filtered off and the filtrate was concentrated under reduced pressure. The resultant residue was purified by silica gel column chromatography (ethyl acetate/hexane) to give 5.78 g of the title compound as a light yellow oil.

¹H-NMR (400 MHz, CDCl₃) δ: 1.02 (s, 6H), 1.07 (s, 6H), 1.40 (s, 2H), 1.48 (s, 9H), 2.16 (d, J=1.6 Hz, 2H), 2.91 (t, J=5.2 Hz, 4H), 3.51 (t, J=5.2 Hz, 4H), 5.50 (t, J=1.6 Hz, 1H), 6.97 (dd, J=8.0, 1.2 Hz, 1H), 7.01 (ddd, J=8.0, 8.0, 1.2 Hz, 1H), 7.09 (dd, J=8.0, 1.6 Hz, 1H), 7.20 (ddd, J=8.0, 8.0, 1.6 Hz, 1H).

4f

1-[2-(3,3,5,5-Tetramethylcyclohex-1-enyl)phenyl]piperazine

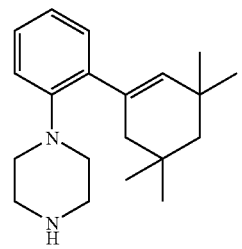

A mixture of 4-[2-(3,3,5,5-tetramethylcyclohex-1-enyl)phenyl]piperazine-1-carboxylic acid t-butyl ester (1.78 g, 4.47 mmol) prepared in Example (4e), trifluoroacetic acid (5 mL, 64.9 mmol) and dichloromethane (15 mL) was stirred at room temperature for 8 hours and 20 minutes.

The reaction mixture was made basic with a 5N aqueous sodium hydroxide, with cooled in an ice water bath. Ethyl acetate and water were then added and the mixture was extracted with ethyl acetate. The collected organic layer was washed with brine and then dried over anhydrous sodium sulfate. The desiccant was filtered off and the filtrate was concentrated under reduced pressure to give a crude product of the title compound (1.62 g) as a light brown solid.

¹H-NMR (400 MHz, CDCl₃) δ: 1.03 (s, 6H), 1.07 (s, 6H), 1.41 (s, 2H), 2.12 (d, J=1.6 Hz, 2H), 3.14 (t, J=6.0 Hz, 4H), 3.19 (t, J=6.0 Hz, 4H), 5.49 (t, J=1.6 Hz, 1H), 7.01-7.11 (m, 3H), 7.22 (ddd, J=8.0, 7.2, 2.0 Hz, 1H).

The 1H of NH could not be identified.

4g

1-Butyl-4-[2-(3,3,5,5-tetramethylcyclohex-1-enyl)phenyl]piperazine hydrochloride

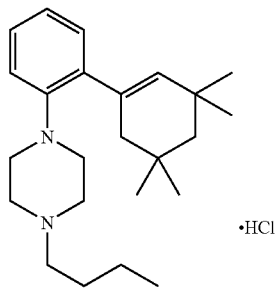

To a mixture of 1-[2-(3,3,5,5-tetramethylcyclohex-1-enyl)phenyl]piperazine (150 mg, 0.503 mmol) prepared in Example (4f), butyraldehyde (0.09 mL, 1.011 mmol) and tetrahydrofuran (7 mL) were added sodium triacetoxyborohydride (270 mg, 1.274 mmol) and acetic acid (0.03 mL, 0.524 mmol) in that order at room temperature.

After stirring for 30 minutes, ethyl acetate, saturated aqueous sodium hydrogencarbonate and water were added to the reaction mixture and the mixture was extracted with ethyl acetate. The collected organic layer was washed with brine and then dried over anhydrous sodium sulfate. The desiccant was filtered off and the filtrate was concentrated under reduced pressure. The resultant residue was purified by NH silica gel column chromatography (ethyl acetate/hexane) to give 120 mg of 1-butyl-4-[2-(3,3,5,5-tetramethylcyclohex-1-enyl)phenyl]piperazine as a colorless oil.

$^1$H-NMR (400 MHz, CDCl$_3$) δ: 0.93 (t, J=7.2 Hz, 3H), 1.02 (s, 6H), 1.07 (s, 6H), 1.34 (q, J=7.2 Hz, 2H), 1.40 (s, 2H), 1.48-1.55 (m, 2H), 2.17 (d, J=1.6 Hz, 2H), 2.35-2.39 (m, 2H), 2.55 (brs, 4H), 3.02 (brs, 4H), 5.51 (t, J=1.6 Hz, 1H), 6.96-7.02 (m, 2H), 7.07 (dd, J=7.2, 1.6 Hz, 1H), 7.19 (ddd, J=8.0, 7.2, 1.6 Hz, 1H).

The product was dissolved in ethyl acetate and a 4N solution of hydrogen chloride in ethyl acetate was added. The solution was concentrated, diethyl ether and hexane were added to the resultant residue, and the crystals were filtered. These were then dried with a vacuum pump to give 124 mg of the title compound as colorless crystals.

MS m/e (ESI) 355 (MH$^+$).

Example 5

1-Cyclopropylmethyl-4-[2-(3,3,5,5-tetramethylcyclohex-1-enyl)phenyl]piperazine hydrochloride

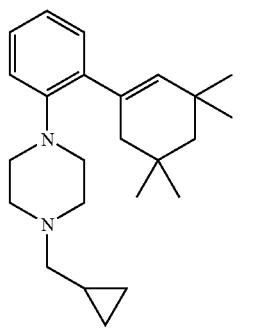

To a mixture of 1-[2-(3,3,5,5-tetramethylcyclohex-1-enyl)phenyl]piperazine (40 mg, 0.134 mmol) prepared in Example (4f), cyclopropanecarbaldehyde (0.014 mL, 0.187 mmol) and tetrahydrofuran (3 mL) were added sodium triacetoxyborohydride (34 mg, 0.16 mmol) and acetic acid (0.008 mL, 0.140 mmol) in that order at room temperature.

After stirring for 1 hour, ethyl acetate, saturated aqueous sodium hydrogencarbonate and water were added to the reaction mixture and the mixture was extracted with ethyl acetate. The collected organic layer was concentrated under reduced pressure, and the resultant residue was purified by NH silica gel column chromatography (ethyl acetate/hexane) to give 38 mg of 1-cyclopropylmethyl-4-[2-(3,3,5,5-tetramethylcyclohex-1-enyl)phenyl]piperazine. The target compound was confirmed by TLC and used for the following procedure.

The compound was dissolved in dichloromethane, and a 4N solution of hydrogen chloride in ethyl acetate was added. The solution was concentrated, and diethyl ether was added to the resultant residue to crystallize. Hexane was added thereto and supernatant diethyl ether-hexane solution was removed. The resultant residual solid was dried under reduced pressure to give 35 mg of the title compound as colorless crystals.

MS m/e (ESI) 353 (MH$^+$).

Example 6

1-[2-(4,4-Diethylcyclohexyl)-5-methoxyphenyl]-4-(tetrahydropyran-4-ylmethyl)piperazine hydrochloride

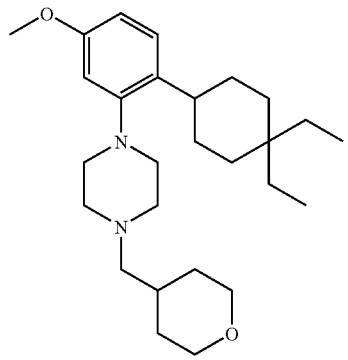

4,4-Diethyl-2-cyclohexenone

Reference: Michael E. Flaugh, Thomas A. Crowell, and Diane S. Farlow, J. Org. Chem., 1980, 45, 5399.

6a 4,4-Diethylcyclohexanone

A mixture of 4,4-diethyl-2-cyclohexenone (1 g, 6.57 mmol), 10% palladium on carbon (60 mg, wet) and ethyl acetate (15 mL) was stirred for 26 hours under a hydrogen atmosphere at atmospheric pressure and room temperature.

The reaction mixture was filtered, and then the filtrate was concentrated under reduced pressure to give a crude product of the title compound (720 mg) as a brown oil.

¹H-NMR (400 MHz, CDCl₃) δ: 0.85 (t, J=7.6 Hz, 6H), 1.43 (q, J=7.6 Hz, 4H), 1.65 (dd, J=7.2, 7.2 Hz, 4H), 2.31 (dd, J=7.2, 7.2 Hz, 4H).

6b

Trifluoromethanesulfonic acid 4,4-diethylcyclohex-1-enyl ester

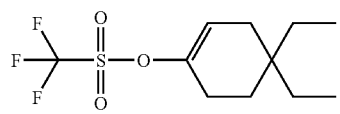

A solution of 4,4-diethylcyclohexanone (720 mg, 4.67 mmol) prepared in Example (6a) in anhydrous tetrahydrofuran (20 mL) was cooled to below −70° C. in a dry ice-acetone bath under a nitrogen atmosphere, and then stirred. Lithium bis(trimethylsilyl)amide (1M solution in tetrahydrofuran, 5.6 mL, 5.6 mmol) was gradually added dropwise to this solution. After stirring for 60 minutes under the same conditions, N-phenyl bis(trifluoromethanesulfonimide) (1.75 g, 4.9 mmol) was added to the reaction mixture, and stirring was continued for 27 hours with slowly warmed to room temperature.

Saturated aqueous ammonium chloride was added to the reaction mixture. Ethyl acetate and brine were then added to the reaction mixture and the organic layer was separated off. After washing the organic layer with diluted hydrochloric acid and saturated aqueous sodium hydrogencarbonate in that order, it was dried over anhydrous magnesium sulfate. The desiccant was filtered off and the filtrate was concentrated under reduced pressure. The resultant residue was purified by silica gel column chromatography (ethyl acetate/hexane) to give 710 mg of the title compound as a yellow oil.

¹H-NMR (400 MHz, CDCl₃) δ: 0.80 (t, J=7.6 Hz, 6H), 1.21-1.40 (m, 4H), 1.55 (t, J=6.6 Hz, 2H), 1.95 (dt, J=4.0, 2.8 Hz, 2H), 2.25-2.30 (m, 2H), 5.63-5.66 (m, 1H).

6c 2-(4,4-Diethylcyclohex-1-enyl)-4,4,5,5-tetramethyl-[1,3,2]dioxaborolane

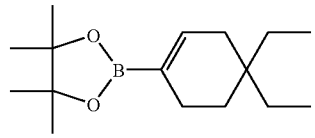

To a solution of trifluoromethanesulfonic acid 4,4-diethylcyclohex-1-enyl ester (5.11 g, 17.8 mmol) prepared in Example (6b) in dioxane (60 mL) were added bis(pinacolato)diboron (5.2 g, 20.5 mmol), 1,1'-bis(diphenylphosphino)ferrocene dichloropalladium(II) dichloromethane complex (580 mg, 0.71 mmol) and potassium acetate (5.3 g, 53.5 mmol), and the mixture was stirred at an external temperature of 90° C. for 4 hours.

The reaction mixture was air-cooled to room temperature, and insoluble matters were filtered off. Ethyl acetate and water were added to the resultant filtrate and the organic layer was separated off. The organic layer was washed with brine and then dried over anhydrous magnesium sulfate. The desiccant was filtered off and the filtrate was concentrated under reduced pressure. The resultant residue was purified by silica gel column chromatography (ethyl acetate/hexane) to give 4.16 g of the title compound as white crystals.

¹H-NMR (400 MHz, CDCl₃) δ: 0.76 (t, J=7.6 Hz, 6H), 1.13-1.37 (m, 18H), 1.84-1.86 (m, 2H), 2.05-2.10 (m, 2H), 6.48-6.50 (m, 1H).

6d 1-(4,4-Diethylcyclohex-1-enyl)-4-methoxy-2-nitrobenzene

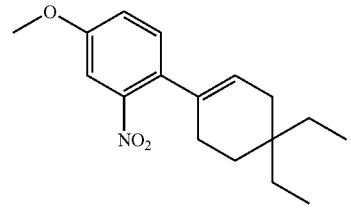

A mixture of 4-bromo-3-nitroanisole (2 g, 8.62 mmol), 2-(4,4-diethylcyclohex-1-enyl)-4,4,5,5-tetramethyl-[1,3,2]dioxaborolane (2.7 g, 10.3 mmol) prepared in Example (6c), tripotassium phosphate (2.7 g, 13.0 mmol) and 1,2-dimethoxyethane (20 mL) was stirred at room temperature under a nitrogen atmosphere, and then tetrakis(triphenylphosphine)palladium(0) (0.5 g, 0.43 mmol) was added. The mixture was then stirred at an external temperature of 80° C. for 26 hours.

After cooling the reaction mixture, brine was added and the mixture was extracted with ethyl acetate. The organic layer was dried over anhydrous magnesium sulfate. The desiccant was filtered off and the filtrate was concentrated under reduced pressure. The resultant residue was purified by silica gel column chromatography (ethyl acetate/hexane) to give 2.4 g of the title compound as a light yellow oil.

¹H-NMR (400 MHz, CDCl₃) δ: 0.82 (t, J=7.2 Hz, 6H), 1.22-1.54 (m, 6H), 1.87-1.94 (m, 2H), 2.14-2.20 (m, 2H), 3.84 (s, 3H), 5.48-5.54 (m, 1H), 7.04 (dd, J=8.4, 2.8 Hz, 1H), 7.16 (d, J=8.4 Hz, 1H), 7.29 (d, J=2.8 Hz, 1H).

6e 2-(4,4-Diethylcyclohex-1-enyl)-5-methoxyphenylamine

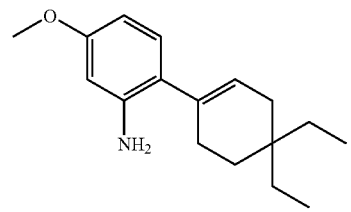

To a solution of 1-(4,4-diethylcyclohex-1-enyl)-4-methoxy-2-nitrobenzene (2.4 g, 8.3 mmol) prepared in Example (6d) in ethanol (20 mL) were added an aqueous solution (5 mL) of ammonium chloride (2.2 g, 41 mmol) and iron powder (1.2 g, 20.7 mmol), and the mixture was stirred at an external temperature of 90° C. for 1 hour. The reaction mixture was passed through Celite for filtration, and then brine was added to the filtrate and the mixture was extracted with ethyl acetate. The organic layer was dried over anhydrous magnesium sulfate, the desiccant was filtered off, and then the filtrate was concentrated under reduced pressure to give 2.6 g of the title compound as a yellow oil.

$^1$H-NMR (400 MHz, CDCl$_3$) δ: 0.82 (t, J=7.2 Hz, 6H), 1.21-1.56 (m, 6H), 1.92-1.96 (m, 2H), 2.16-2.22 (m, 2H), 3.75 (s, 3H), 5.61-5.65 (m, 1H), 6.24 (d, J=2.8 Hz, 1H), 6.29 (dd, J=8.4, 2.8 Hz, 1H), 6.87 (d, J=8.4 Hz, 1H).

The 2H of NH$_2$ could not be identified.

6f

1-[2-(4,4-Diethylcyclohex-1-enyl)-5-methoxyphenyl]piperazine

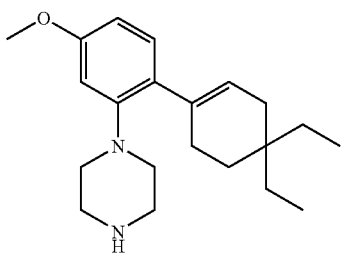

A solution of 2-(4,4-diethylcyclohex-1-enyl)-5-methoxyphenylamine (2.6 g, 10 mmol) prepared in Example (6e) and bis(2-chloroethyl)amine hydrochloride (2.2 g, 12 mmol) in 1,2-dichlorobenzene (10 mL) was stirred at an external temperature of 210° C. Nitrogen gas was blown into the reactor several times during the reaction to remove the excess hydrogen chloride gas in the reactor. After 1 hour, the reaction mixture was cooled to room temperature, and then saturated aqueous sodium hydrogencarbonate was added and the mixture was extracted with ethyl acetate. The organic layer was dried over anhydrous magnesium sulfate. The desiccant was filtered off and the filtrate was concentrated under reduced pressure. The resultant residue was purified by NH silica gel column chromatography (ethyl acetate/hexane) to give 1.4 g of the title compound as a yellow oil.

$^1$H-NMR (400 MHz, CDCl$_3$) δ: 0.82 (t, J=7.2 Hz, 6H), 1.22-1.52 (m, 6H), 1.90-1.96 (m, 2H), 2.38-2.46 (m, 2H), 2.78-3.04 (m, 8H), 3.79 (s, 3H), 5.61-5.66 (m, 1H), 6.50 (dd, J=8.4, 2.8 Hz, 1H), 6.52 (d, J=2.8 Hz, 1H), 6.99 (d, J=8.4 Hz, 1H).

The 1H of NH could not be identified.

MS m/e (ESI) 329 (MH$^+$).

6g

1-[2-(4,4-Diethylcyclohex-1-enyl)-5-methoxyphenyl]-4-(tetrahydropyran-4-ylmethyl)piperazine hydrochloride

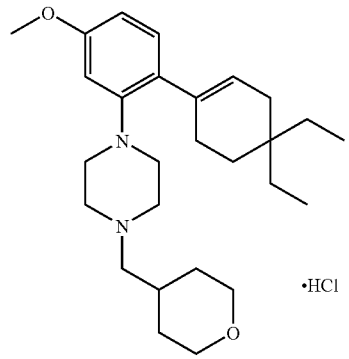

To a solution of 1-[2-(4,4-diethylcyclohex-1-enyl)-5-methoxyphenyl]piperazine (90 mg, 0.27 mmol) prepared in Example (6f) in tetrahydrofuran (10 mL) were added tetrahydropyran-4-carbaldehyde (37 mg, 0.32 mmol), sodium triacetoxyborohydride (87 mg, 0.41 mmol) and acetic acid (32 mg, 0.57 mmol) in that order, and the mixture was stirred at room temperature for 1 hour and 30 minutes. Saturated aqueous sodium hydrogencarbonate was added to the reaction mixture and the mixture was extracted with ethyl acetate. The organic layer was dried over anhydrous magnesium sulfate. The desiccant was filtered off and the filtrate was concentrated under reduced pressure. The resultant residue was purified by NH silica gel column chromatography (ethyl acetate/hexane) to give 50 mg of 1-[2-(4,4-diethylcyclohex-1-enyl)-5-methoxyphenyl]-4-(tetrahydropyran-4-ylmethyl)piperazine as a light yellow oil.

$^1$H-NMR (400 MHz, CDCl$_3$) δ: 0.82 (t, J=7.2 Hz, 6H), 1.40-1.94 (m, 13H), 2.22 (d, J=7.2 Hz, 2H), 2.35-2.58 (m, 6H), 2.94-3.18 (m, 4H), 3.38 (td, J=12, 2.0 Hz, 2H), 3.77 (s, 3H), 3.90-4.00 (m, 2H), 5.59-5.64 (m, 1H), 6.47 (dd, J=8.4, 2.8 Hz, 1H), 6.51 (d, J=2.8 Hz, 1H), 6.97 (d, J=8.4 Hz, 1H).

The obtained compound was dissolved in ethyl acetate, and then a 4N solution of hydrogen chloride in ethyl acetate was added and the mixture was stirred at room temperature for 15 minutes. The solvent was distilled off under reduced pressure and the residual solid was washed with diethyl ether. It was then filtered to give 50 mg of the title compound as a light yellow solid.

MS m/e (ESI) 427 (MH$^+$).

6h

1-[2-(4,4-Diethylcyclohexyl)-5-methoxyphenyl]-4-(tetrahydropyran-4-ylmethyl)piperazine hydrochloride

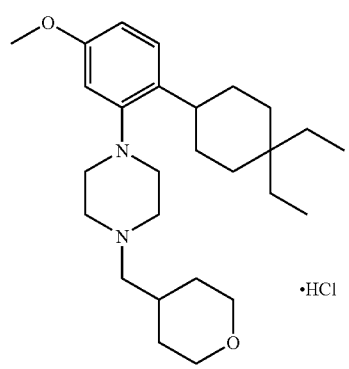

Ten percent of palladium on carbon (100 mg, wet) was added to a solution of 1-[2-(4,4-diethylcyclohex-1-enyl)-5- methoxyphenyl]-4-(tetrahydropyran-4-ylmethyl)piperazine hydrochloride (34 mg) prepared in Example (6g) in methanol (5 mL), and the mixture was stirred for 13 hours under a hydrogen atmosphere at atmospheric pressure and room temperature. The reaction mixture was passed through Celite for filtration, and the filtrate was concentrated under reduced pressure. The residual solid was washed with diethyl ether. It was then filtered to give 34 mg of the title compound as a light yellow solid.

$^1$H-NMR (400 MHz, CD$_3$OD) δ: 0.82 (t, J=7.2 Hz, 3H), 0.83 (t, J=7.2 Hz, 3H), 1.20-1.82 (m, 17H), 2.16-2.28 (m, 2H), 2.86-2.96 (m, 1H), 3.10-3.36 (m, 6H), 3.48 (td, J=12, 2.0 Hz, 2H), 3.68 (d, J=7.2 Hz, 2H), 3.77 (s, 3H), 3.98 (dd, J=7.2, 4.0 Hz, 2H), 6.72 (d, J=2.8 Hz, 1H), 6.74 (dd, J=8.4, 2.8 Hz, 1H), 7.20 (d, J=8.4 Hz, 1H). MS m/e (ESI) 429 (MH$^+$).

Example 7

1-Butyl-4-[2-(4-t-butylcyclohex-1-enyl)-4-(4-methoxypiperidin-1-yl)phenyl]piperazine hydrochloride

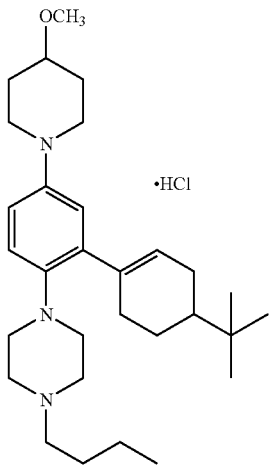

7a

4-Methoxypiperidine hydrochloride

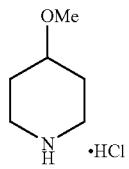

4-hydroxypiperidine-1-carboxylic acid t-butyl ester (25.5 g, 127 mmol) was added to a mixed solution of anhydrous tetrahydrofuran (100 mL) and dimethylformamide (40 mL). The solution was cooled to 0° C. in an ice bath with stirring. Sodium hydride (60% dispersion in oil, 7.6 g, 190 mmol) was gradually added over 3 minutes. The reaction mixture was warmed to room temperature, stirred for 70 minutes, and cooled to 0° C. again. A solution of methyl iodide (9.5 mL, 152 mmol) in anhydrous tetrahydrofuran (20 mL)-dimethylformamide (5 mL) was gradually added to the reaction mixture over 20 minutes. The ice bath was removed, and the reaction mixture was warmed to room temperature and stirred for 1 hour.

After the reaction, water and diethyl ether were added to the reaction mixture and the organic layer was separated off. The organic layer was washed 3 times with water, and then once with brine and dried over anhydrous sodium sulfate. The desiccant was filtered off and the filtrate was concentrated under reduced pressure.

Ethyl acetate (200 mL) was added to the residue, and the mixture was cooled to 0° C. and stirred. A 4N solution of hydrogen chloride in ethyl acetate (100 mL) was then gradually added over 10 minutes, and the temperature was slowly raised to room temperature.

After stirring for 13 hours, the reaction mixture was concentrated under reduced pressure. The residue was dissolved in a small amount of dichloromethane. An excess of ethyl acetate was then added and the precipitated solid was filtered out and dried under reduced pressure to give 17.0 g of the title compound as colorless crystals.

$^1$H-NMR (400 MHz, CDCl$_3$) δ: 1.95-2.02 (m, 2H), 2.05-2.15 (m, 2H), 3.14-3.30 (m, 4H), 3.32 (s, 3H), 3.52-3.57 (m, 1H).

The 1H of NH could not be identified.

7b 5-(4-Methoxypiperidin-1-yl)-2-nitrophenol

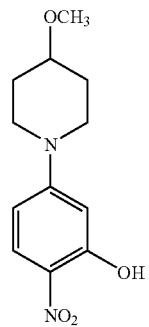

A mixture of 4-methoxypiperidine hydrochloride (9.10 g, 60.01 mmol) prepared in Example (7a), 5-fluoro-2-nitrophenol (6.91 g, 43.98 mmol) and dimethylformamide (12 mL) was stirred under a nitrogen atmosphere. Triethylamine (15.24 mL, 109.95 mmol) was added to the reaction mixture and the mixture was stirred at an external temperature of 80° C. for 3 hours and 30 minutes.

After the reaction, saturated aqueous ammonium chloride and a mixed solvent of ethyl acetate-diethyl ether was added to the reaction mixture. The organic layer was separated off, and the aqueous layer was extracted with diethyl ether. The obtained organic layers were combined and dried over anhydrous sodium sulfate. The desiccant was filtered off and the filtrate was concentrated under reduced pressure. The resultant residue was purified by silica gel column chromatography (ethyl acetate/hexane) to give 37.36 g of the title compound as orange crystals.

$^1$H-NMR (400 MHz, CDCl$_3$) δ: 1.60-1.68 (m, 2H), 1.83-1.90 (m, 2H), 3.26 (ddd, J=13.2, 8.0, 3.6 Hz, 2H), 3.32 (s, 3H), 3.42-3.47 (m, 1H), 3.62 (ddd, J=13.2, 7.6, 3.6 Hz, 2H), 6.24 (d, J=2.8 Hz, 1H), 6.36 (dd, J=10.0, 2.8 Hz, 1H), 7.87 (d, J=10.0 Hz, 1H).

The 1H of OH could not be identified.

7c

Trifluoromethanesulfonic acid 5-(4-methoxypiperidin-1-yl)-2-nitrophenyl ester

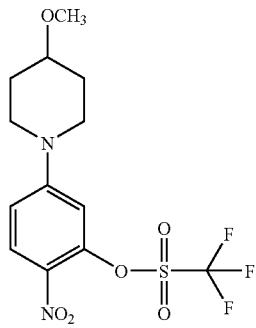

A mixture of 5-(4-methoxypiperidin-1-yl)-2-nitrophenol (2.35 g, 8.16 mmol) prepared in Example (7b), triethylamine (5.7 mL, 40.9 mmol) and dichloromethane (50 mL) was stirred in an ice water bath, and then trifluoromethanesulfonic anhydride (2 mL, 12.24 mmol) was gradually added dropwise for 15 minutes, and the mixture was stirred for 10 minutes under the same conditions.

Saturated aqueous ammonium chloride was added to the reaction mixture, and then ethyl acetate and water were added and the organic layer was separated off. The organic layer was dried over anhydrous sodium sulfate. The desiccant was filtered off and the filtrate was concentrated under reduced pressure. The resultant residue was purified by silica gel column chromatography (ethyl acetate/hexane) to give 3.276 g of the title compound as an orange solid.

$^1$H-NMR (400 MHz, CDCl$_3$) δ: 1.66-1.74 (m, 2H), 1.84-1.92 (m, 2H), 3.27 (ddd, J=13.2, 7.6, 3.6 Hz, 2H), 3.23 (s, 3H), 3.47 (m, 1H), 3.58 (ddd, J=12, 8.0, 3.6 Hz, 2H), 6.54 (d, J=2.8 Hz, 1H), 6.72 (dd, J=9.6, 2.8 Hz, 1H), 8.07 (d, J=9.6 Hz, 1H).

7d

2-(4-t-Butylcyclohex-1-enyl)-4,4,5,5-tetramethyl-[1,3,2]dioxaborolane

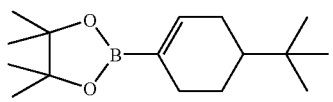

To trifluoromethanesulfonic acid 4-t-butylcyclohex-1-enyl ester (55.0 g, 192.1 mmol) prepared in Example (2a) were added bis(pinacolato)diboron (56.1 g, 220.9 mmol), 1,1'-bis(diphenylphosphino)ferrocene dichloropalladium(II) dichloromethane complex (4.88 g, 5.98 mmol), potassium acetate (56.6 g, 576.3 mmol) and dioxane (400 mL), and the mixture was stirred at an external temperature of 80° C. for 16 hours.

After the reaction, the reaction mixture was air-cooled to room temperature, ethyl acetate and water were added to the reaction mixture, and the organic layer was separated off. The obtained organic layer was again washed with water, and dried over anhydrous magnesium sulfate. The desiccant was filtered off and the filtrate was concentrated under reduced pressure. The resultant residue was purified by silica gel column chromatography (ethyl acetate/hexane) to give 38.97 g of the title compound as a light yellow solid, in racemic form at the position of t-butyl.

$^1$H-NMR (400 MHz, CDCl$_3$) δ: 0.85 (s, 9H), 1.00-1.43 (m, 14H), 1.78-1.90 (m, 2H), 1.98-2.17 (m, 2H), 2.24-2.32 (m, 1H), 6.59 (dd, J=2.0 Hz, 1H).

7e

1-[3-(4-t-Butylcyclohex-1-enyl)-4-nitrophenyl]-4-methoxypiperidine

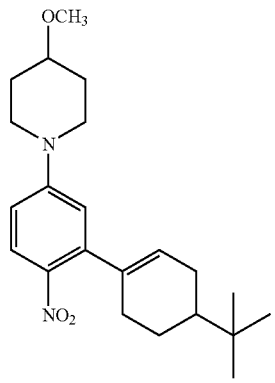

To a solution of trifluoromethanesulfonic acid 5-(4-methoxypiperidin-1-yl)-2-nitrophenyl ester (3.276 g, 8.52 mmol) prepared in Example (7c) in 1,2-dimethoxyethane (80 mL) were added 2-(4-t-butylcyclohex-1-enyl)-4,4,5,5-tetramethyl-[1,3,2]dioxaborolane (2.478 g, 9.38 mmol) prepared in Example (7d), tetrakis(triphenylphosphine)palladium(0) (492 mg, 0.426 mmol) and tripotassium phosphate (2.714 g, 12.79 mmol), and the mixture was stirred at an external temperature of 90° C. for 2 hours and 30 minutes under a nitrogen atmosphere.

After the reaction, brine and ethyl acetate were added to the reaction mixture. The organic layer was separated off and then dried over anhydrous sodium sulfate. The desiccant was filtered off and the filtrate was concentrated under reduced pressure. The resultant residue was purified by silica gel column chromatography (ethyl acetate/hexane) to give 1.87 g of the title compound as orange crystals, in racemic form at the position of t-butyl.

$^1$H-NMR (400 MHz, CDCl$_3$) δ: 0.90 (s, 9H), 1.38-1.43 (m, 2H), 1.64-1.74 (m, 2H), 1.86-2.00 (m, 3H), 2.13-2.33 (m, 4H), 3.21 (ddd, J=12.4, 8.4, 3.6 Hz, 2H), 3.38 (s, 3H), 3.46 (m, 1H), 3.67 (ddd, J=11.2, 7.2, 3.6 Hz, 2H), 5.57 (t, J=2.4 Hz, 1H), 6.54 (d, J=2.8 Hz, 1H), 6.72 (dd, J=9.6, 2.8 Hz, 1H), 8.07 (d, J=9.6 Hz, 1H).

7f

2-(4-t-Butylcyclohex-1-enyl)-4-(4-methoxypiperidin-1-yl)phenylamine

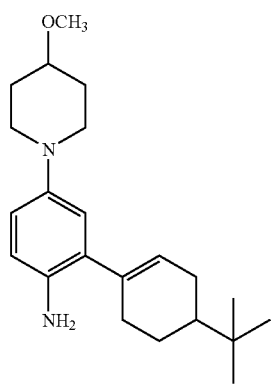

1-[3-(4-t-butylcyclohex-1-enyl)-4-nitrophenyl]-4-methoxypiperidine (1.87 g, 5.02 mmol) prepared in Example (7e), ammonium chloride (93.6 mg, 1.75 mmol), a mixed solution of ethanol (30 mL)-water (10 mL) and iron powder (981 mg, 17.57 mmol) were added in turn, and the mixture was stirred at an external temperature of 90° C. for 2 hours under a nitrogen atmosphere.

Ammonium chloride (30 mg, 0.56 mmol) and iron powder (300 mg, 5.37 mmol) were added to the reaction mixture, and the mixture was stirred for 3 hours and 15 minutes under the same conditions.

Insoluble matters of the reaction mixture were filtered, and then ethyl acetate and brine were added to the filtrate. The organic layer was separated off and then dried over anhydrous sodium sulfate. The desiccant was filtered off and the filtrate was concentrated under reduced pressure. The resultant residue was purified by NH silica gel column chromatography (ethyl acetate/hexane) to give 1.155 g of the title compound as a light yellow solid, in racemic form at the position of t-butyl.

$^1$H-NMR (400 MHz, CDCl$_3$) δ: 0.90 (s, 9H), 1.24-1.42 (m, 2H), 1.66-1.76 (m, 2H), 1.90-2.06 (m, 4H), 2.14-2.24 (m, 1H), 2.28-2.32 (m, 2H), 2.72-2.80 (m, 2H), 3.26-3.37 (m, 3H), 3.37 (s, 3H), 5.75 (brs, 1H), 6.63 (d, J=8.4 Hz, 1H), 6.67 (s, 1H), 6.71 (d, J=8.4 Hz, 1H).

The 2H of NH$_2$ could not be identified.

7g

1-[2-(4-t-Butylcyclohex-1-enyl)-4-(4-methoxypiperidin-1-yl)phenyl]piperazine

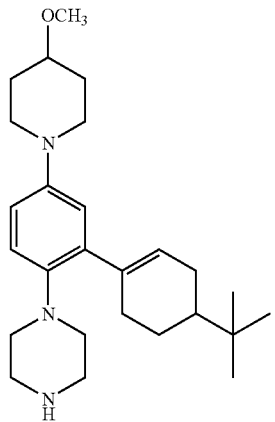

To a solution of 2-(4-t-butylcyclohex-1-enyl)-4-(4-methoxypiperidin-1-yl)phenylamine (1.155 g, 3.37 mmol) prepared in Example (7f) in 1,2-dichlorobenzene (15 mL) was added bis(2-chloroethyl)amine hydrochloride (722 mg, 4.04 mmol), and the mixture was stirred at an external temperature of 200° C. under a nitrogen atmosphere.

The excess hydrogen chloride gas in the reactor was removed using a stream of nitrogen several times during the reaction.

After 6 hours, the reaction mixture was cooled to room temperature. Aqueous potassium carbonate was added to the reaction mixture to make the aqueous layer basic, and then ethyl acetate and a small amount of methanol were added. The organic layer was separated off and then dried over anhydrous sodium sulfate. The desiccant was filtered off and the filtrate was concentrated under reduced pressure. The resultant residue was purified by NH silica gel column chromatography (ethyl acetate/hexane) to give 660 mg of the titled compound as a light yellow solid, in racemic form at the position of t-butyl.

$^1$H-NMR (400 MHz, CDCl$_3$) δ: 0.84 (s, 9H), 1.12-1.32 (m, 2H), 1.58-1.66 (m, 2H), 1.80-1.98 (m, 4H), 2.08-2.16 (m, 1H), 2.28-2.40 (m, 1H), 2.59-2.62 (m, 1H), 2.76 (td, J=12.0, 2.8 Hz, 4H), 2.83-2.91 (m, 6H), 3.22-3.28 (m, 1H), 3.31 (s, 3H), 3.36-3.42 (m, 2H), 5.63 (t, J=2.4 Hz, 1H), 6.67 (d, J=3.2 Hz, 1H), 6.70 (dd, J=8.4, 3.2 Hz, 1H), 6.81 (d, J=8.4 Hz, 1H).

The 1H of NH could not be identified.

7h

1-Butyl-4-[2-(4-t-butylcyclohex-1-enyl)-4-(4-methoxypiperidin-1-yl)phenyl]piperazine hydrochloride

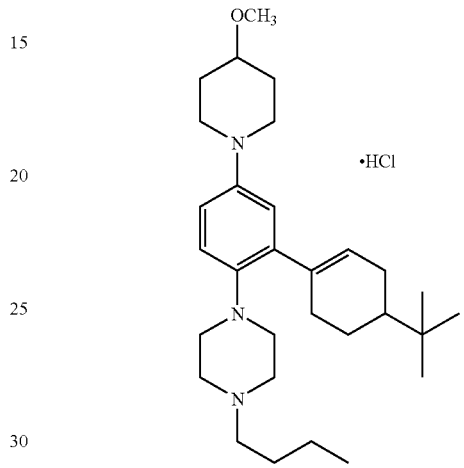

To a solution of 1-[2-(4-t-butylcyclohex-1-enyl)-4-(4-methoxypiperidin-1-yl)phenyl]piperazine (100 mg, 0.243 mmol) prepared in Example (7g) in tetrahydrofuran (3 mL) were added butyraldehyde (0.0281 mL, 0.316 mmol), sodium triacetoxyborohydride (87.1 mg, 0.316 mmol) and acetic acid (0.0267 mL, 0.466 mmol), and the mixture was stirred at room temperature for 4 hours and 30 minutes.

After the reaction completed, saturated aqueous sodium hydrogencarbonate was added to the reaction mixture and the mixture was extracted 3 times with ethyl acetate. The obtained organic layers were combined and dried over anhydrous sodium sulfate. The desiccant was filtered off and the filtrate was concentrated under reduced pressure. The resultant residue was purified by NH silica gel column chromatography (ethyl acetate/hexane) to give 103 mg of 1-butyl-4-[2-(4-t-butylcyclohex-1-enyl)-4-(4-methoxypiperidin-1-yl)phenyl]piperazine as a colorless solid, in racemic form at the position of t-butyl.

$^1$H-NMR (400 MHz, CDCl$_3$) δ: 0.89-0.96 (m, 12H), 1.18-1.39 (m, 4H), 1.48-1.60 (m, 2H), 1.64-1.74 (m, 2H), 1.86-2.06 (m, 4H), 2.14-2.23 (m, 1H), 2.30-2.42 (m, 3H), 2.47-2.60 (m, 4H), 2.66-2.74 (m, 1H), 2.78-2.86 (m, 2H), 2.89-3.06 (m, 4H), 3.28-3.35 (m, 1H), 3.37 (s, 3H), 3.41-3.48 (m, 2H), 5.69 (brs, 1H), 6.73 (s, 1H), 6.76 (d, J=8.4 Hz, 1H), 6.89 (d, J=8.4 Hz, 1H).

The product was dissolved in ethyl acetate (3 mL), and then a 4N solution of hydrogen chloride in ethyl acetate (0.11 mL, 0.44 mmol) was added.

The reaction solvent was removed under reduced pressure, diethyl ether was added and the resultant solid was filtered to give 83 mg of the title compound as a colorless solid, in racemic form at the position of t-butyl.

MS m/e (ESI) 468 (MH$^+$).

Example 8

1-Butyl-4-[2-(3,3,5,5-tetramethylcyclohexyl)phenyl]piperazine hydrochloride

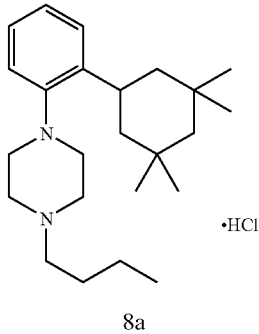

8a

4-[2-(3,3,5,5-Tetramethylcyclohexyl)phenyl]piperazine-1-carboxylic acid t-butyl ester

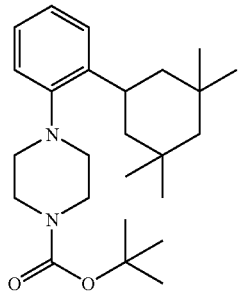

A mixture of 4-[2-(3,3,5,5-tetramethylcyclohex-1-enyl)phenyl]piperazine-1-carboxylic acid t-butyl ester (3.87 g, 9.71 mmol) prepared in Example (4e), 10% palladium on carbon (2.3 g, wet), methanol (25 mL) and tetrahydrofuran (25 mL) was stirred for 22 hours and 30 minutes under hydrogen atmosphere at atmospheric pressure and room temperature.

After filtering the reaction mixture, the filtrate was concentrated. Ethyl acetate was added to the residue, the mixture was filtered again, and the filtrate was concentrated under reduced pressure to give a crude product of the title compound (3.83 g) as a light yellow oil.

$^1$H-NMR (400 MHz, CDCl$_3$) δ: 0.92 (s, 6H), 1.12 (s, 6H), 1.12-1.47 (m, 6H), 1.49 (s, 9H), 2.83 (brs, 4H), 3.59 (tt, J=12.4, 2.8 Hz, 1H), 7.07 (td, J=7.6, 1.2 Hz, 1H), 7.10 (dd, J=7.6, 1.2 Hz, 1H), 7.16 (td, J=7.6, 2.0 Hz, 1H), 7.24 (dd, J=7.6, 2.0 Hz, 1H).

The 4H of the piperazine ring could not be identified.
MS m/e (ESI) 401 (MH$^+$).

8b

1-[2-(3,3,5,5-Tetramethylcyclohexyl)phenyl]piperazine

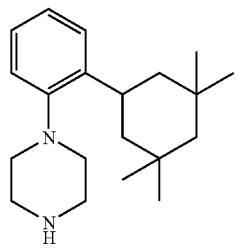

A mixture of 4-[2-(3,3,5,5-tetramethylcyclohexyl)phenyl]piperazine-1-carboxylic acid t-butyl ester (9.79 g, 24.44 mmol) prepared in Example (8a), trifluoroacetic acid (25 mL, 346 mmol) and dichloromethane (50 mL) was stirred at room temperature for 1 hour and 30 minutes.

After the reaction completed, the reaction mixture was cooled in an ice water bath and it was made basic with 5N aqueous sodium hydroxide. Ethyl acetate and water were then added thereto and the mixture was extracted with ethyl acetate. The collected organic layer was washed with brine and then dried over anhydrous sodium sulfate. The desiccant was filtered off and the filtrate was concentrated under reduced pressure. Hexane was added to the resultant residue to precipitate crystals, and the crystals were filtered and dried with a vacuum pump to give 4.94 g of the title compound as colorless crystals.

$^1$H-NMR (400 MHz, CDCl$_3$) for the lot of the above 4.94 g: δ: 0.94 (s, 6H), 1.11 (s, 6H), 1.13-1.44 (m, 6H), 3.17 (brs, 4H), 3.35 (brs, 4H), 3.47 (tt, J=12.4, 2.8 Hz, 1H), 7.10-7.30 (m, 4H).

The 1H of NH could not be identified.

After concentrating the mother liquor yielded at the filtration giving 4.94 g of the titled compound, the resultant residue was purified by NH silica gel column chromatography (ethyl acetate/hexane) to give 2.23 g of the title compound as colorless crystals.

$^1$H-NMR (400 MHz, CDCl$_3$) for the lot of the above 2.23 g: δ: 0.92 (s, 6H), 1.13 (s, 6H), 1.17-1.35 (m, 4H), 1.41-1.46 (m, 2H), 2.84-2.86 (m, 4H), 3.01-3.03 (m, 4H), 3.59 (tt, J=12.8, 2.8 Hz, 1H), 7.04-7.16 (m, 3H), 7.21 (dd, J=7.6, 1.6 Hz, 1H).

The 1H of NH could not be identified.

8c

1-Butyl-4-[2-(3,3,5,5-tetramethylcyclohexyl)phenyl]piperazine hydrochloride

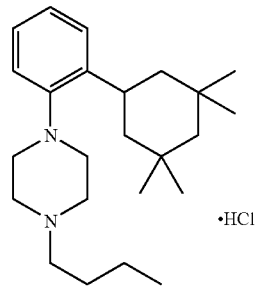

To a solution of 1-[2-(3,3,5,5-tetramethylcyclohexyl)phenyl]piperazine (300 mg, 1.00 mmol) prepared in Example (8b) in tetrahydrofuran (20 mL) were added butyraldehyde (107 mg, 1.49 mmol), sodium triacetoxyborohydride (420 mg, 1.99 mmol) and acetic acid (60 mg, 0.99 mmol) in that order, the mixture was stirred at room temperature for 13 hours and 30 minutes. After the reaction completed, saturated aqueous sodium hydrogencarbonate was added to the reaction mixture and the mixture was extracted with ethyl acetate. The organic layer was dried over anhydrous magnesium sulfate, and then the desiccant was filtered and the filtrate was concentrated under reduced pressure. The resultant residue was purified by NH silica gel column chromatography (ethyl acetate/heptane) to give 270 mg of 1-butyl-4-[2-(3,3,5,5-tetramethylcyclohexyl)phenyl]piperazine as a light yellow oil.

$^1$H-NMR (400 MHz, CDCl$_3$) δ: 0.92 (s, 6H), 0.94 (t, J=7.2 Hz, 3H), 1.12 (s, 6H), 1.20-1.60 (m, 10H), 2.37-2.41 (m, 2H), 2.40-2.62 (brs, 4H), 2.92 (t, J=4.8 Hz, 4H), 3.57 (tt, J=12.4, 2.8 Hz, 1H), 7.03-7.08 (m, 1H), 7.09-7.16 (m, 2H), 7.19-7.22 (m, 1H).

The product was dissolved in dichloromethane (5 mL), and then a 4N solution of hydrogen chloride in ethyl acetate (0.21 mL, 0.83 mmol) was added and the mixture was stirred at room temperature for 30 minutes. The solvent of the reaction mixture was distilled off under reduced pressure to give a crude product of the title compound (290 mg) as a light yellow solid. Ethyl acetate (30 mL) was added to the obtained crude product (290 mg) and the mixture was stirred at an external temperature of 100° C. for 2 hours to complete dissolution. It was then slowly air-cooled to room temperature and stirred for 21 hours. The precipitated hydrochloride was filtered to give 235 mg of the title compound as colorless crystals.

$^1$H-NMR (400 MHz, CD$_3$OD) δ: 0.96 (s, 6H), 1.03 (t, J=7.2 Hz, 3H), 1.18 (s, 6H), 1.18-1.52 (m, 10H), 1.72-1.81 (m, 2H), 3.10-3.75 (m, 8H), 3.56 (tt, J=12.4, 2.8 Hz, 1H), 7.13-7.20 (m, 3H), 7.26-7.29 (m, 1H). MS m/e (ESI) 357 (MH$^+$).

Example 9

1-Cyclopropylmethyl-4-[2-(3,3,5,5-tetramethylcyclohexyl)phenyl]piperazine hydrochloride

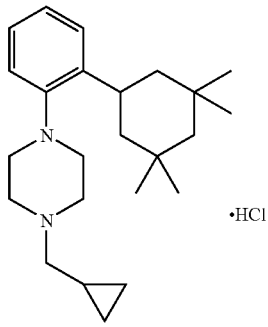

To a solution of 1-[2-(3,3,5,5-tetramethylcyclohexyl)phenyl]piperazine (200 mg, 0.666 mmol) prepared in Example (8b) in tetrahydrofuran (4 mL) was added cyclopropanecarbaldehyde (70 mg, 0.999 mmol), and the mixture was stirred at room temperature for 5 minutes. Sodium triacetoxyborohydride (282 mg, 1.33 mmol) was added to the reaction mixture, and after stirring for 5 minutes, acetic acid (0.038 mL, 0.666 mmol) was added and the mixture was stirred at room temperature for 2 hours.

After the reaction completed, saturated aqueous sodium hydrogencarbonate was added to the reaction mixture and the mixture was extracted with ethyl acetate. The organic layer was dried over anhydrous sodium sulfate. The desiccant was filtered off and the filtrate was concentrated under reduced pressure. The resultant residue was purified by NH silica gel column chromatography (ethyl acetate/heptane) to give 182 mg of 1-cyclopropylmethyl-4-[2-(3,3,5,5-tetramethylcyclohexyl)phenyl]piperazine as colorless crystals.

$^1$H-NMR (400 MHz, CDCl$_3$) δ: 0.12-0.16 (m, 2H), 0.52-0.56 (m, 2H), 0.88-0.96 (m, 1H), 0.92 (s, 6H), 1.12 (s, 6H), 1.13-1.45 (m, 6H), 2.32 (d, J=6.4 Hz, 2H), 2.70 (brs, 4H), 2.95 (t, J=4.4 Hz, 4H), 3.60 (tt, J=12.4, 2.8 Hz, 1H), 7.04-7.08 (m, 1H), 7.11-7.14 (m, 2H), 7.20-7.22 (m, 1H).

The obtained compound (147 mg, 0.415 mmol) was dissolved in dichloromethane (3 mL), and then a 4N solution of hydrogen chloride in ethyl acetate (0.11 mL, 0.456 mmol) was added to the mixture under a nitrogen atmosphere. After stirring for 15 minutes at room temperature, the solvent was distilled off under reduced pressure. Ethyl acetate (13 mL) was added to the resultant residue, and the mixture was stirred at an external temperature of 100° C. for 1 hour to complete dissolution. The solution was then air-cooled to room temperature and stirred for 19 hours and 45 minutes. The precipitated hydrochloride was filtered to give 134 mg of the title compound as colorless crystals.

MS m/e (ESI) 355 (MH$^+$).

Example 10

2-{4-[2-(4-t-Butylcyclohexyl)phenyl]piperazin-1-yl}-N-ethylacetamide hydrochloride

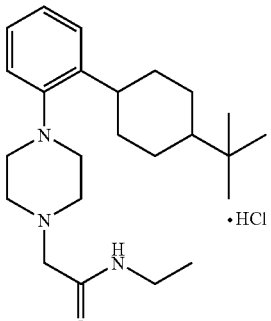

10a

1-[2-(4-t-Butylcyclohexyl)phenyl]piperazine

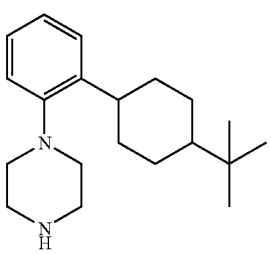

To a mixture of 2-(4-t-butylcyclohexyl)phenylamine (810 mg, 3.5 mmol) prepared in Example (2c) and 1,2-dichlorobenzene (5 mL) was added bis(2-chloroethyl)amine hydrochloride (750 mg, 4.2 mmol), and the mixture was heated at reflux for 1 hour and 30 minutes.

The reaction mixture was cooled to room temperature, saturated aqueous sodium hydrogencarbonate was added and the mixture was extracted with a mixed solvent of ethyl acetate and tetrahydrofuran. The collected organic layer was dried over anhydrous magnesium sulfate. The desiccant was filtered off and the filtrate was concentrated under reduced pressure. The resultant residue was purified by NH silica gel column chromatography (ethyl acetate/methanol) to give 420 mg of the title compound as a light yellow solid, as a mixture of diastereomers at the position of t-butylcyclohexyl.

MS m/e (ESI) 301 (MH$^+$).

10b

2-{4-[2-(4-t-Butylcyclohexyl)phenyl]piperazin-1-yl}-N-ethylacetamide hydrochloride

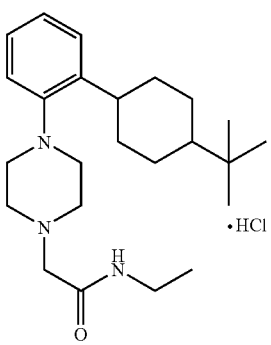

A mixture of 1-[2-(4-t-butylcyclohexyl)phenyl]piperazine (400 mg, 1.33 mmol) prepared in Example (10a), 2-chloro- N-ethylacetamide (200 mg, 1.65 mmol), potassium carbonate (400 mg, 2.89 mmol) and dimethylformamide (15 mL) was stirred at an external temperature of 115° C. for 2 hours.

After the reaction, ethyl acetate and water were added to the reaction mixture and the mixture was extracted with ethyl acetate. The collected organic layer was washed twice with water and then with brine, and then dried over anhydrous sodium sulfate. The desiccant was filtered off and the filtrate was concentrated under reduced pressure. The resultant residue was purified by NH silica gel column chromatography (ethyl acetate/hexane) to give 506 mg of 2-{4-[2-(4-t-butyl-cyclohexyl)phenyl]piperazin-1-yl}-N-ethylacetamide as a colorless oil, as a mixture of diastereomers at the position of t-butylcyclohexyl.

$^1$H-NMR (400 MHz, CDCl$_3$) δ: 0.88 (s, 9H×0.6), 0.90 (s, 9H×0.4), 1.10-1.21 (m, 6H), 1.35-1.48 (m, 2H), 1.68-1.98 (m, 4H), 2.67 (brs, 4H), 2.87-2.92 (m, 4H), 3.06 (s, 2H×0.6), 3.09 (s, 2H×0.4), 3.30-3.40 (m, 4H), 7.05-7.22 (m, 3H+1H×0.4), 7.44 (d, J=8.0 Hz, 1H×0.6).

The product was dissolved in ethyl acetate, and a 4N solution of hydrogen chloride in ethyl acetate was added. The solution was concentrated under reduced pressure, diethyl ether was added to the resultant residue and the precipitated crystals were filtered. The crystals were then dried under reduced pressure to give 476 mg of the title compound as colorless crystals, as a mixture of diastereomers at the position of t-butylcyclohexyl.

MS m/e (ESI) 386 (MH$^+$).

Example 11

2-{4-[2-(4-t-Butylcyclohexyl)phenyl]piperazin-1-yl}-1-(piperidin-1-yl)ethanone hydrochloride

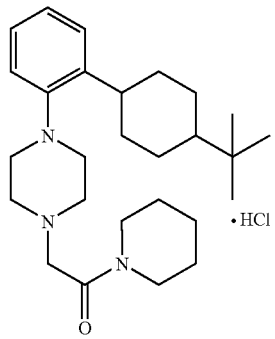

A mixture of 1-[2-(4-t-butylcyclohexyl)phenyl]piperazine (50 mg, 0.166 mmol) prepared in Example (10a), 1-(2-chloroacetyl)piperidine (33 mg, 0.204 mmol), potassium carbonate (60 mg, 0.434 mmol) and dimethylformamide (5 mL) was stirred at an external temperature of 115° C. for 2 hours.

Ethyl acetate, saturated aqueous ammonium chloride and water were added to the reaction mixture and the mixture was extracted with ethyl acetate. The collected organic layer was washed twice with brine and then with brine, and then dried over anhydrous sodium sulfate. The desiccant was filtered off and the filtrate was concentrated under reduced pressure. The resultant residue was purified by NH silica gel column chromatography (ethyl acetate/hexane) to give 51 mg of 2-{4-[2-(4-t-butylcyclohexyl)phenyl]piperazin-1-yl}-1-(piperidin-1-yl)ethanone as a colorless oil, as a mixture of diastereomers at the position of t-butylcyclohexyl.

$^1$H-NMR (400 MHz, CDCl$_3$) δ: 0.88 (s, 9H×0.6), 0.90 (s, 9H×0.4), 1.10-1.27 (m, 2H), 1.35-1.46 (m, 2H), 1.54-1.98 (m, 10H), 2.65 (brs, 4H), 2.85-2.92 (m, 4H), 2.94-3.04 (m, 1H×0.4), 3.24 (s, 2H×0.6), 3.26 (s, 2H×0.4), 3.35-3.47 (m, 1H+1H×0.6), 3.50-3.58 (m, 4H), 7.05-7.28 (m, 3H+1H×0.4), 7.40 (d, J=8.0 Hz, 1H×0.6).

The product was dissolved in ethyl acetate, and a 4N solution of hydrogen chloride in ethyl acetate was added. The solution was concentrated, ethyl acetate was added to the resultant residue, and the mixture was further concentrated.

Diethyl ether was added to the resultant residue, and the precipitated crystals were filtered and dried under reduced pressure to give 37 mg of the title compound as colorless crystals, as a mixture of diastereomers at the position of t-butylcyclohexyl.

MS m/e (ESI) 426 (MH$^+$).

Example 12 cis-4-(4-t-Butylcyclohexyl)-3-(4-butylpiperazine-1-yl)benzonitrile hydrochloride

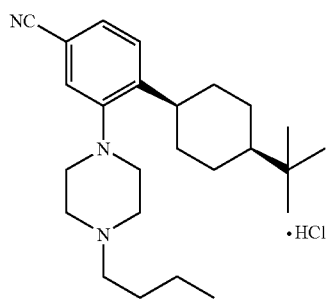

12a 1-(4-t-Butylcyclohex-1-enyl)-4-methoxy-2-nitrobenzene

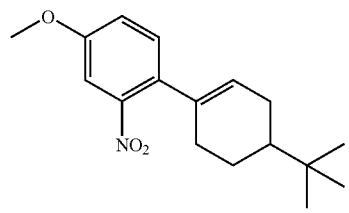

A mixture of 2-(4-t-butylcyclohex-1-enyl)-4,4,5,5-tetramethyl-[1,3,2]dioxaborolane (3.17 g, 12 mmol) prepared in Example (7d), 1-bromo-4-methoxy-2-nitrobenzene (2.32 g, 10 mmol), tripotassium phosphate (4.8 g, 15 mmol), 1,2-dimethoxyethane (30 mL) and water (5 mL) was stirred at room temperature under a nitrogen atmosphere. To this reaction mixture was added tetrakis(triphenylphosphine)palladium(0) (578 mg, 0.5 mmol). The mixture was stirred at an external temperature of 70° C. for 18 hours and 30 minutes.

Ethyl acetate and water were added to the reaction mixture, which was then passed through Celite for filtration. The filtrate was subjected to oil-water distribution and the obtained organic layer was dried over anhydrous sodium sulfate. The desiccant was filtered off and the filtrate was concentrated under reduced pressure. The resultant residue was purified by silica gel column chromatography (ethyl acetate/hexane) to give 2.89 g of the title compound as a yellow solid, in racemic form at the position of t-butyl.

$^1$H-NMR (400 MHz, CDCl$_3$) δ: 0.89 (s, 9H), 1.31-1.43 (m, 2H), 1.86-1.95 (m, 2H), 2.13-2.34 (m, 3H), 3.85 (s, 3H), 5.59-5.61 (m, 1H), 7.05 (dd, J=8.8, 2.4 Hz, 1H), 7.17 (d, J=8.8 Hz, 1H), 7.31 (d, J=2.4 Hz, 1H).

12b 2-(4-t-Butylcyclohexyl)-5-methoxyphenylamine

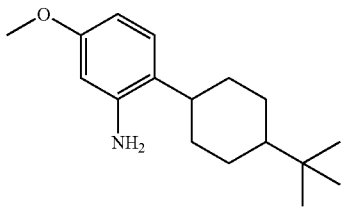

A mixture of 1-(4-t-butylcyclohex-1-enyl)-4-methoxy-2-nitrobenzene (2.89 g, 10.0 mmol) prepared in Example (12a), 10% palladium on carbon (1.0 g, wet), methanol (15 mL) and tetrahydrofuran (15 mL) was stirred for 12 hours under hydrogen atmosphere at atmospheric pressure and room temperature.

The reaction mixture was passed through Celite for filtration, and the filtrate was concentrated under reduced pressure. The resultant residue was purified by silica gel column chromatography (ethyl acetate) to give 2.56 g of the title compound as a yellow solid, as a mixture of diastereomers at the position of t-butylcyclohexyl.

$^1$H-NMR (400 MHz, CDCl$_3$) δ: 0.86 (s, 9H×0.65), 0.89 (s, 9H×0.35), 1.05-1.46 (m, 4H), 1.58-1.66 (m, 2H×0.65), 1.70-1.81 (m, 2H×0.65), 1.88-1.98 (m, 4H×0.35), 2.03-2.10 (m, 1H), 2.34 (tt, J=11.6, 3.2 Hz, 1H×0.35), 2.84-2.89 (m, 1H×0.65), 3.65 (brs, 2H), 3.74 (s, 3H×0.35), 3.75 (s, 3H×0.65), 6.25-6.26 (m, 1H), 6.32-6.36 (m, 1H), 7.00 (d, J=8.4 Hz, 1H×0.35), 7.24 (d, J=8.4 Hz, 1H×0.65).

12c

1-[2-(4-t-Butylcyclohexyl)-5-methoxyphenyl]piperazine

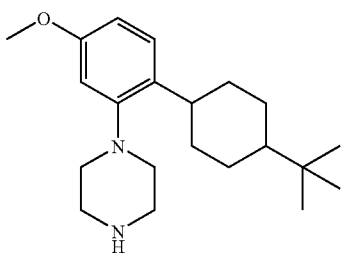

To a solution of 2-(4-t-butylcyclohexyl)-5-methoxyphenylamine (2.56 g, 9.79 mmol) prepared in Example (12b) in 1,2-dichlorobenzene (10 mL) was added bis(2-chloroethyl)amine hydrochloride (2.10 g, 11.75 mmol), the mixture was stirred at an external temperature of 200° C. under a nitrogen atmosphere.

During the reaction, a nitrogen stream was blown into the reactor to remove the hydrogen chloride gas in the reactor. This procedure was repeated several times.

After 1 hour and 30 minutes, the mixture was air cooled to room temperature. Saturated aqueous sodium hydrogencarbonate and ethyl acetate were added to the reaction mixture and the mixture was stirred, after which insoluble matters in the reaction mixture were filtered through Celite. The filtrate was extracted with ethyl acetate, the obtained organic layer was washed with brine and then dried over anhydrous sodium sulfate. The desiccant was filtered off and the filtrate was concentrated under reduced pressure. The resultant residue was purified by NH silica gel column chromatography (ethyl acetate/hexane) to give 1.77 g of the title compound as a brown oil, as a mixture of diastereomers at the position of t-butylcyclohexyl.

$^1$H-NMR (400 MHz, CDCl$_3$) δ: 0.88 (s, 9H×0.65), 0.89 (s, 9H×0.35), 1.09-1.21 (m, 4H), 1.36-1.45 (m, 1H), 1.56-1.63 (m, 1H), 1.68-1.97 (m, 4H), 2.77-2.83 (m, 4H), 2.91 (tt, J=12.4, 3.2 Hz, 1H×0.35), 2.98-3.03 (m, 4H), 3.32 (tt, J=5.2 Hz, 1H×0.65), 3.77 (s, 3H×0.35), 3.783 (s, 3H×0.65), 6.61-6.67 (m, 1H×0.65+2H×0.35), 6.73 (d, J=2.4 Hz, 1H×0.65), 7.13 (d, J=8.8 Hz, 1H×0.35), 7.34 (d, J=8.4 Hz, 1H×0.65).

12d 4-(4-t-Butylcyclohexyl)-3-piperazin-1-ylphenol

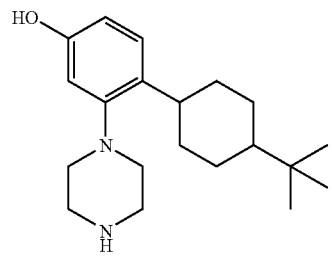

A mixture of 1-[2-(4-t-butylcyclohexyl)-5-methoxyphenyl]piperazine (1.77 g, 5.36 mmol) prepared in Example (12c), 48% hydrobromic acid (50 mL) and acetic acid (30 mL) was stirred at an external temperature of 130° C. for 8 hours and 30 minutes under a nitrogen atmosphere.

The reaction mixture was then cooled in an ice water bath and stirred. The reaction mixture was adjusted to pH 8-9 with 5N aqueous sodium hydroxide. The precipitated solid was filtered and washed with water, and then a mixed solvent of methanol and ethyl acetate (mixing ratio (v/v)=1/5) was added to the solid. Insoluble matters were filtered off and the filtrate was concentrated under reduced pressure. Diethyl ether was added to the resultant residue, and then the mixture was sonicated and the resulting solid was filtered. The solid was dried under reduced pressure to give 1.43 g of the title compound as a light brown solid, as a mixture of diastereomers at the position of t-butylcyclohexyl.

$^1$H-NMR (400 MHz, DMSO-d$_6$) δ: 0.85 (s, 9H×0.65), 0.86 (s, 9H×0.35), 1.00-1.90 (m, 9H), 2.17 (brs, 1H), 2.59-2.68 (m, 1H×0.35+4H), 2.75-2.83 (m, 4H), 3.20-3.25 (m, 1H×0.65), 6.40-6.46 (m, 1H×0.35+1H), 6.52 (d, J=2.8 Hz, 1H×0.65), 6.95 (d, J=8.4 Hz, 1H×0.35), 7.12 (d, J=8.4 Hz, 1H×0.65), 9.03 (brs, 1H×0.35), 9.05 (brs, 1H×0.65).

12e 4-(4-t-Butylcyclohexyl)-3-(4-butylpiperazine-1-yl)phenol

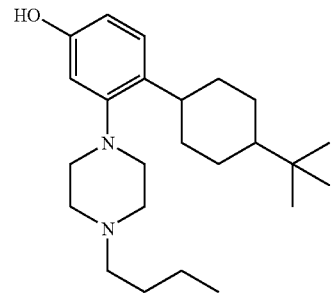

In anhydrous tetrahydrofuran (10 mL) was dissolved 4-(4-t-butylcyclohexyl)-3-piperazin-1-ylphenol (1 g, 3.16 mmol)

prepared in Example (12d), and the solution was cooled in an ice water bath under a nitrogen atmosphere. To the reaction mixture were added butyraldehyde (0.31 mL, 3.48 mmol), sodium triacetoxyborohydride (1 g, 4.74 mmol) and acetic acid (0.18 mL, 3.16 mmol) in that order, and the mixture was warmed to room temperature with stirring.

The mixture was then stirred for 4 hours and 30 minutes, and saturated aqueous sodium hydrogencarbonate was added to the reaction mixture to quench the reaction. Ethyl acetate and water were further added, and the resulting reaction mixture was transferred to a separatory funnel and vigorously shaken, and then allowed to stand. The separated aqueous layer was removed and the organic layer was washed with water and brine in that order and then dried over anhydrous sodium sulfate. The desiccant was filtered off and then the filtrate was concentrated under reduced pressure. The resultant residue was purified by NH silica gel column chromatography (ethyl acetate/hexane) to give 886 mg of the title compound as colorless crystals, as a mixture of diastereomers at the position of t-butylcyclohexyl.

$^1$H-NMR (400 MHz, CDCl$_3$) δ: 0.88 (s, 9H×0.7), 0.89 (s, 9H×0.3), 0.94 (t, J=7.6 Hz, 3H), 1.01-1.96 (m, 13H), 2.42-2.92 (m, 1H×0.3+10H), 3.28 (tt, J=5.2, 5.2 Hz, 1H×0.7), 6.53-6.59 (m, 1H), 6.65 (d, J=2.8 Hz, 1H×0.3), 6.71 (d, J=2.8 Hz, 1H×0.7), 7.06 (d, J=8.4 Hz, 1H×0.3), 7.27 (d, J=8.4 Hz, 1H×0.7).

The 1H of OH could not be identified.

12f

Trifluoromethanesulfonic acid cis-4-(4-t-butylcyclohexyl)-3-(4-butylpiperazin-1-yl)phenyl ester and Trifluoromethanesulfonic acid trans-4-(4-t-butylcyclohexyl)-3-(4-butylpiperazine-1-yl)phenyl ester

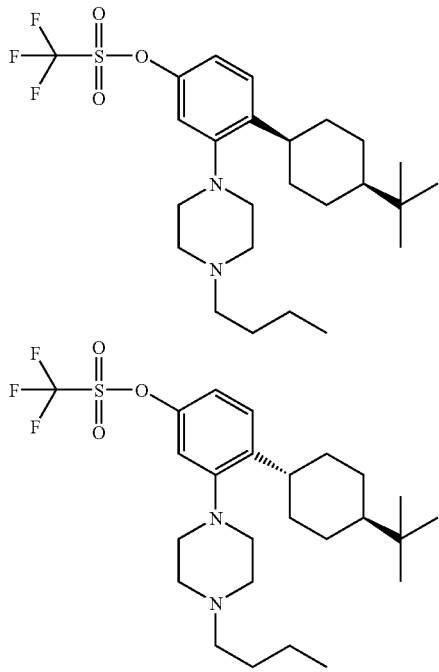

A solution of 4-(4-t-butylcyclohexyl)-3-(4-butylpiperazine-1-yl)phenol (1.6 g, 4.29 mmol) prepared in Example (12e) and triethylamine (3.1 mL, 22.24 mmol) in anhydrous dichloromethane (30 mL) was cooled in an ice-ethanol bath. Trifluoromethanesulfonic anhydride (1.1 mL, 6.54 mmol) was gradually added dropwise to the solution over 30 minutes with stirring.

After stirring for 30 minutes, ethyl acetate, saturated aqueous ammonium chloride and water were added to the reaction mixture and the mixture was extracted with ethyl acetate. The collected organic layer was washed with brine and then dried over anhydrous sodium sulfate. The desiccant was filtered off and the filtrate was concentrated under reduced pressure. The resultant residue was purified by silica gel column chromatography (ethyl acetate/hexane) to give 946 mg of trifluoromethanesulfonic acid cis-4-(4-t-butylcyclohexyl)-3-(4-butylpiperazine-1-yl)phenyl ester, 110 mg of trifluoromethanesulfonic acid trans-4-(4-t-butylcyclohexyl)-3-(4-butylpiperazine-1-yl)phenyl ester and 946 mg of a cis/trans mixture, each as a colorless oil. The cis/trans mixture was further purified by silica gel column chromatography (ethyl acetate/hexane) to give 214 mg of trifluoromethanesulfonic acid cis-4-(4-t-butylcyclohexyl)-3-(4-butylpiperazine-1-yl)phenyl ester, 82 mg of trifluoromethanesulfonic acid trans-4-(4-t-butylcyclohexyl)-3-(4-butylpiperazine-1-yl)phenyl ester and 434 mg of a cis/trans mixture, each as a colorless oil.

cis form: $^1$H-NMR (400 MHz, CDCl$_3$) δ: 0.89 (s, 9H), 0.94 (t, J=7.2 Hz, 3H), 1.15-1.45 (m, 6H), 1.47-1.67 (m, 3H), 1.67-1.80 (m, 2H), 1.86-1.95 (m, 2H), 2.37-2.44 (m, 2H), 2.59 (brs, 4H), 2.88 (t, J=4.8 Hz, 4H), 3.35 (tt, J=5.2, 5.2 Hz, 1H), 6.97 (dd, J=8.4, 2.8 Hz, 1H), 7.00 (d, J=2.8 Hz, 1H), 7.45 (d, J=8.4 Hz, 1H).

trans form: $^1$H-NMR (400 MHz, CDCl$_3$) δ: 0.90 (s, 9H), 0.95 (t, J=7.2 Hz, 3H), 1.08-1.20 (m, 2H), 1.32-1.46 (m, 4H), 1.48-1.62 (m, 3H), 1.78-1.94 (m, 4H), 2.40-2.46 (m, 2H), 2.62 (brs, 4H), 2.89 (t, J=4.8 Hz, 4H), 2.94 (tt, J=12.0, 3.6 Hz, 1H), 6.94 (d, J=2.4 Hz, 1H), 6.95 (dd, J=9.2, 2.4 Hz, 11H), 7.24 (d, J=9.2 Hz, 1H).

12g cis-4-(4-t-Butylcyclohexyl)-3-(4-butylpiperazine-1-yl)benzonitrile hydrochloride

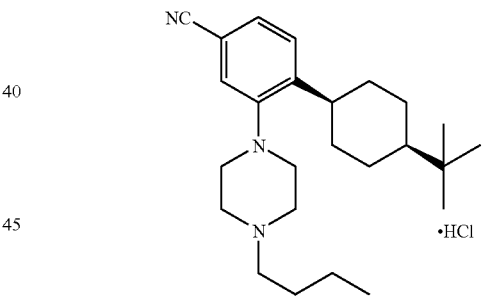

A mixture of trifluoromethanesulfonic acid cis-4-(4-t-butylcyclohexyl)-3-(4-butylpiperazine-1-yl)phenyl ester (1.16 g, 2.3 mmol) prepared in Example (12f), zinc cyanide (2.7 g, 23 mmol) and dimethylformamide (30 mL) was stirred at room temperature under a nitrogen atmosphere. Tetrakis(triphenylphosphine)palladium(0) (370 mg, 0.32 mmol) was added to this mixture. The mixture was then stirred at an external temperature of 100° C. for 19 hours and 10 minutes.

Ethyl acetate, dilute aqueous ammonia and water were added to the reaction mixture and the mixture was extracted with ethyl acetate. The collected organic layer was washed with dilute aqueous ammonia, water and brine in that order and then dried over anhydrous sodium sulfate. The desiccant was filtered off and the filtrate was concentrated under reduced pressure. The resultant residue was purified by NH silica gel column chromatography (ethyl acetate/hexane) to give 880 mg of cis-4-(4-t-butylcyclohexyl)-3-(4-butylpiperazine-1-yl)benzonitrile as a colorless oil.

$^1$H-NMR (400 MHz, CDCl$_3$) δ: 0.88 (s, 9H), 0.94 (t, J=7.2 Hz, 3H), 1.15-1.44 (m, 6H), 1.48-1.67 (m, 3H), 1.70-1.80 (m,

2H), 1.88-1.96 (m, 2H), 2.38-2.44 (m, 2H), 2.59 (brs, 4H), 2.88 (t, J=4.8 Hz, 4H), 3.38 (tt, J=5.6, 5.6 Hz, 1H), 7.34 (dd, J=7.6, 2.0 Hz, 1H), 7.35 (d, J=2.0 Hz, 1H), 7.47 (d, J=7.6 Hz, 1H).

The product was dissolved in ethyl acetate, and a 4N solution of hydrogen chloride in ethyl acetate was added. The solution was concentrated, diethyl ether and hexane were added to the resultant residue, and the precipitated crystals were filtered. The crystals were then dried under reduced pressure to give 892 mg of the title compound as colorless crystals.

MS m/e (ESI) 382 (MH+).

Example 13 trans-4-(4-t-Butylcyclohexyl)-3-(4-butylpiperazin-1-yl)benzonitrile hydrochloride

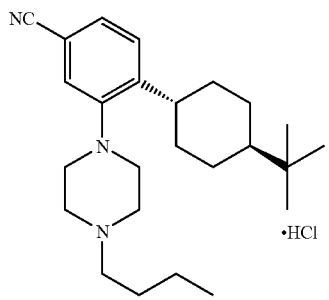

A mixture of trifluoromethanesulfonic acid trans-4-(4-t-butylcyclohexyl)-3-(4-butylpiperazine-1-yl)phenyl ester (30 mg, 0.0594 mmol) prepared in Example (12f), zinc cyanide (8 mg, 0.0681 mmol) and dimethylformamide (1 mL) was stirred at room temperature under a nitrogen atmosphere. Tetrakis(triphenylphosphine)palladium(0) (6 mg, 0.0052 mmol) was added to the mixture. The mixture was then stirred at an external temperature of 100° C. for 9 hours. Zinc cyanide (70 mg, 0.596 mmol) and tetrakis(triphenylphosphine) palladium(0) (20 mg, 0.0173 mmol) were further added to the reaction mixture, which was then stirred at an external temperature of 100° C. for 14 hours and 10 minutes.

After the reaction, ethyl acetate, dilute aqueous ammonia and water were added to the reaction mixture and the mixture was extracted with ethyl acetate. The collected organic layer was washed with dilute aqueous ammonia, water and brine in that order and then dried over anhydrous sodium sulfate. The desiccant was filtered off and the filtrate was concentrated under reduced pressure. The resultant residue was purified by NH silica gel column chromatography (ethyl acetate/hexane) to give 10 mg of trans-4-(4-t-butylcyclohexyl)-3-(4-butylpiperazine-1-yl)benzonitrile as a light yellow oil.

$^1$H-NMR (400 MHz, CDCl$_3$) δ: 0.90 (s, 9H), 0.95 (t, J=7.2 Hz, 3H), 1.09-1.20 (m, 2H), 1.31-1.46 (m, 4H), 1.49-1.58 (m, 3H), 1.77-1.96 (m, 4H), 2.40-2.46 (m, 2H), 2.62 (brs, 4H), 2.89 (t, J=5.2 Hz, 4H), 2.99 (tt, J=12.0, 3.2 Hz, 1H), 7.27 (d, J=7.6 Hz, 1H), 7.30 (d, J=1.6 Hz, 1H), 7.32 (dd, J=7.6, 1.6 Hz, 1H).

The product was dissolved in ethyl acetate, and a 4N solution of hydrogen chloride in ethyl acetate was added. The solution was concentrated, diethyl ether and hexane were added to the resultant residue to solidify, and it was then triturated by sonication. After removing the supernatant, the resultant residual solid was dried under reduced pressure to give 7 mg of the title compound as a white solid.

MS m/e (ESI) 382 (MH+).

Example 14

1-Butyl-4-(2-cyclohexylphenyl)piperazine hydrochloride

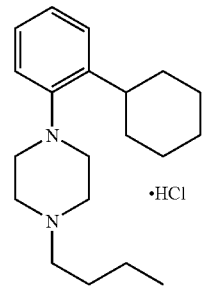

Trifluoromethanesulfonic acid cyclohex-1-enyl ester

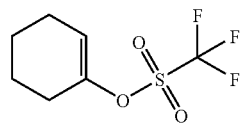

Reference: Crich, D.; Smith, M.; Yao, Q.; Picione, J.; Synthesis 2001, (2), 323-326.

14a 2-(Cyclohex-1-enyl)nitrobenzene

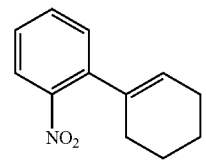

Trifluoromethanesulfonic acid cyclohex-1-enyl ester (1.0 g, 5.9 mmol) was used as the starting material instead of trifluoromethanesulfonic acid 4-t-butylcyclohex-1-enyl ester for reaction in a manner similar to Example (2b) and treated in a similar manner to give 0.56 g of the title compound as a red oil.

14b

2-Cyclohexylphenylamine

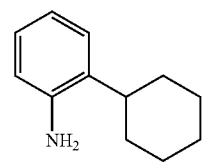

2-(Cyclohex-1-enyl)nitrobenzene (0.56 g, 2.75 mmol) prepared in Example (14a) was reacted and treated in a manner similar to Example (2c) to give 0.51 g of the title compound as a light yellow oil.

14c 1-(2-Cyclohexylphenyl)piperazine

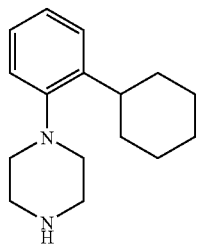

2-Cyclohexylphenylamine (0.48 g, 2.75 mmol) prepared in Example (14b) was reacted and treated in a manner similar to Example (3c) to give 0.25 g of the title compound as a light yellow oil.

14d

1-Butyl-4-(2-cyclohexylphenyl)piperazine hydrochloride

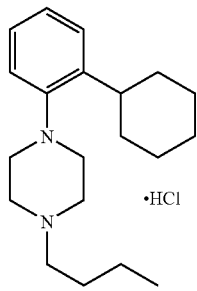

1-(2-Cyclohexylphenyl)piperazine (0.25 g, 1.02 mmol) prepared in Example (14c) was used as the starting material, and butyraldehyde was used instead of tetrahydropyran-4-carbaldehyde for the reaction and treatment in a manner similar to Example (6g) to give 195 mg of the title compound as a light yellow solid.

MS m/e (ESI) 301 (MH$^+$).

Example 15

1-Butyl-4-[2-(4-t-butylcyclohexyl)phenyl]piperazine hydrochloride

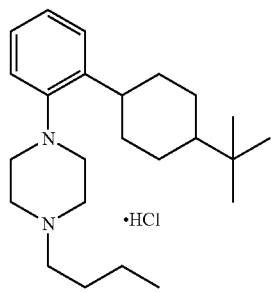

1-[2-(4-t-Butylcyclohexyl)phenyl]piperazine (160 mg, 0.53 mmol) prepared in Example (10a) was used as the starting material.

Reaction and treatment were carried out in a manner similar to Example (6g) using butyraldehyde instead of tetrahydropyran-4-carbaldehyde, to give 65 mg of the title compound as colorless crystals, as a mixture of diastereomers at the position of t-butylcyclohexyl.

MS m/e (ESI) 357 (MH$^+$).

Example 16

4-Butyl-1-[2-(4-t-butylcyclohexyl)phenyl]-3-methylpiperazin-2-one hydrochloride

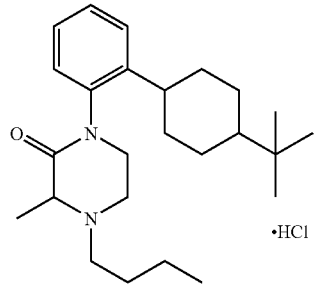

16a

N-[2-(4-t-Butylcyclohexyl)phenyl]-2-chloro-N-(2-hydroxyethyl)propionamide

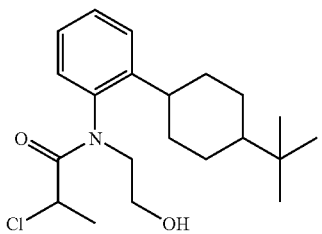

2-[2-(4-t-Butylcyclohexyl)phenylamino]ethanol (271 mg, 0.984 mmol) prepared in Example (2d) was used as the starting material.

2-Chloropropionylchloride was used instead of chloroacetyl chloride for reaction in a manner similar to Example (2e) and treated in a similar manner, to give 136 mg of the title compound as a colorless oil, as a mixture of diastereomers at the position of t-butylcyclohexyl and methyl.

16b

N-[2-(4-t-Butylcyclohexyl)phenyl]-2-chloro-N-(2-oxoethyl)propionamide

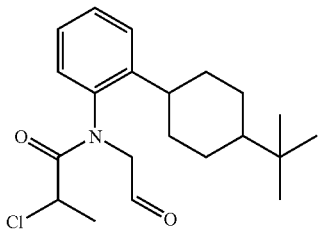

N-[2-(4-t-Butylcyclohexyl)phenyl]-2-chloro-N-(2-hydroxyethyl)propionamide (134 mg, 0.366 mmol) prepared in Example (16a) was used as the starting material.

This was reacted and treated in a manner similar to Example (2f) to give a crude product of the title compound (166 mg) as a light yellow oil, as a mixture of diastereomers at the position of t-butylcyclohexyl and methyl.

131

16c

4-Butyl-1-[2-(4-t-butylcyclohexyl)phenyl]-3-methylpiperazin-2-one hydrochloride

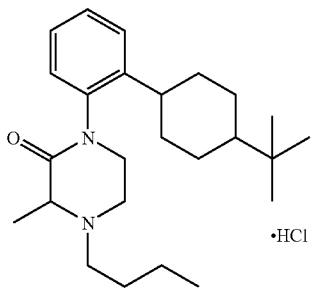

N-[2-(4-t-Butylcyclohexyl)phenyl]-2-chloro-N-(2-oxoethyl)propionamide (165 mg) prepared in Example (16b) was used as the starting material.

This was reacted and treated in a manner similar to Example (2g) to give 80 mg of 4-butyl-1-[2-(4-t-butylcyclohexyl)phenyl]-3-methylpiperazin-2-one as a light yellow oil, as a mixture of diastereomers at the position of t-butylcyclohexyl and methyl.

The product was converted to a hydrochloride by a method similar to Example (2g) to give 51 mg of the title compound as a light brown solid, as a mixture of diastereomers at the position of t-butylcyclohexyl and methyl.

MS m/e (ESI) 385 (MH$^+$).

Example 17

1-{4-[2-(4,4-Dimethylcyclohexyl)phenyl]piperazin-1-yl}butan-2-one hydrochloride

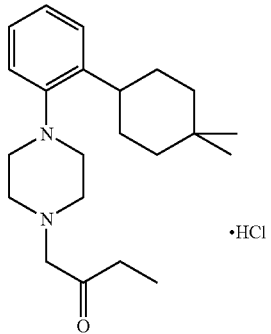

1-[2-(4,4-Dimethylcyclohexyl)phenyl]piperazine (420 mg, 1.54 mmol) prepared in Example (3c) was used as the starting material.

1-Bromo-2-butanone was used instead of 2-chloro-N-ethylacetamide and acetonitrile was used instead of dimethylformamide, for reaction in a manner similar to Example (10b) and treated in a similar manner to give 488 mg of 1-{4-[2-(4,4-dimethylcyclohexyl)phenyl]piperazin-1-yl}butan-2-one as a yellow oil.

$^1$H-NMR (400 MHz, CDCl$_3$) δ: 0.97 (s, 3H), 1.01 (s, 3H), 1.10 (t, J=7.2 Hz, 3H), 1.29-1.36 (m, 2H), 1.46-1.68 (m, 6H), 2.51 (q, J=7.2 Hz, 2H), 2.58-2.72 (br, 4H), 2.90-3.00 (m, 5H), 3.28 (s, 2H), 7.06-7.18 (m, 3H), 7.25-7.28 (m, 1H).

The oil was dissolved in dichloromethane, and a 4N solution of hydrogen chloride in ethyl acetate was added. The solution was diluted with hexane and concentrated under reduced pressure. To the resultant solid residue was added diethyl ether-hexane, it was triturated by sonication and then filtered to give 496 mg of the title compound as colorless crystals.

MS m/e (ESI) 343 (MH$^+$).

Example 18

4-[3-(4-t-Butylcyclohex-1-enyl)-4-(4-butylpiperazine-1-yl)phenyl]morpholine hydrochloride

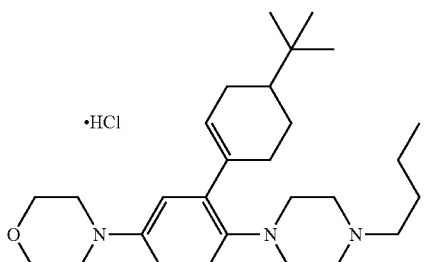

18a

Trifluoromethanesulfonic acid 5-morpholin-4-yl-2-nitrophenyl ester

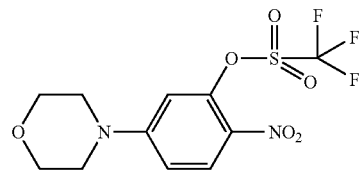

Reaction and treatment were carried out in a manner similar to Example (7c), using 5-morpholin-4-yl-2-nitrophenol (12 g, 53.5 mmol) as the starting material instead of 5-(4-methoxypiperidin-1-yl)-2-nitrophenol, and using pyridine instead of the dichloromethane-triethylamine solvent, to give 17.24 g of the title compound as yellow crystals.

18b

4-[3-(4-t-Butylcyclohex-1-enyl)-4-nitrophenyl]morpholine

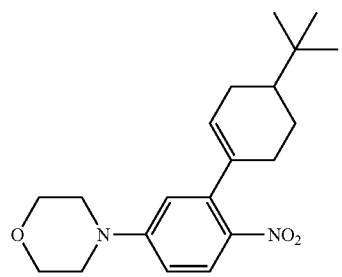

The trifluoromethanesulfonic acid 5-morpholin-4-yl-2-nitrophenyl ester (3.08 g, 8.64 mmol) prepared in Example (18a) was used as the starting material for reaction in a manner similar to Example (7e) and treated in a similar manner. Consequently, 2.68 g of the title compound was obtained as yellow crystals, in racemic form at the position of t-butyl.

18c

2-(4-t-Butylcyclohex-1-enyl)-4-morpholin-4-yl)phenylamine

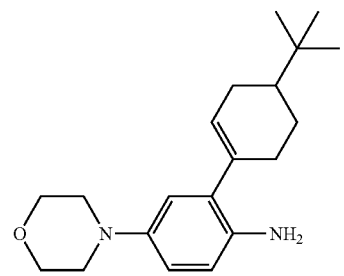

4-[3-(4-t-butylcyclohex-1-enyl)-4-nitrophenyl]morpholine (2.68 g, 7.77 mmol) prepared in Example (18b) was used as the starting material for reaction in a manner similar to Example (6e) and treated in a similar manner. Consequently, 2.19 g of the title compound was obtained as light brown crystals, in racemic form at the position of t-butyl.

18d

4-[3-(4-t-Butylcyclohex-1-enyl)-4-piperazin-1-ylphenyl]morpholine

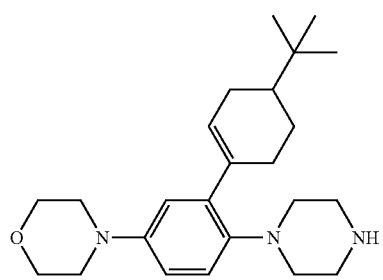

Reaction was conducted in a manner similar to Example (7g) at 200° C. for 18 hours, using the 2-(4-t-butylcyclohex-1-enyl)-4-morpholin-4-yl)phenylamine (2.19 g, 6.96 mmol) prepared in Example (18c) as the starting material, and then treatment was carried out in a similar manner. As a result there was obtained 1.84 g of the title compound as light brown crystals, in racemic form at the position of t-butyl.

18e

4-[3-(4-t-Butylcyclohex-1-enyl)-4-(4-butylpiperazin-1-yl)phenyl]morpholine hydrochloride

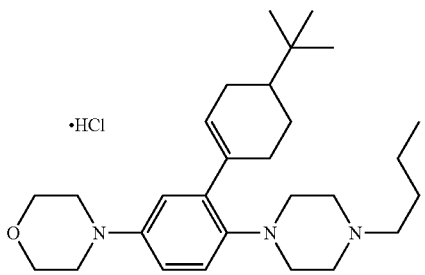

Reaction and treatment were carried out in a manner similar to Example (7h), using 4-[3-(4-t-butylcyclohex-1-enyl)-4-piperazin-1-ylphenyl]morpholine (0.32 g, 0.834 mmol) prepared in Example (18d) as the starting material. Consequently, 350 mg of the title compound was obtained as colorless crystals, in racemic form at the position of t-butyl.

MS m/e (ESI) 440 (MH$^+$).

Example 19

1-[2-(4-t-Butylcyclohexyl)phenyl]-4-(2-methoxyethyl)piperazine hydrochloride

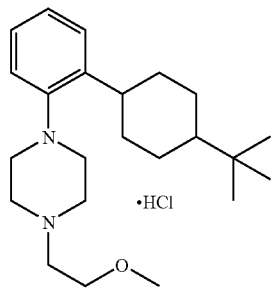

1-[2-(4-t-Butylcyclohexyl)phenyl]piperazine (100 mg, 0.333 mmol) prepared in Example (10a) was used as the starting material.

Reaction and treatment were carried out in a manner similar to Example (10b) using 2-bromoethylmethyl ether instead of 2-chloro-N-ethylacetamide, and acetonitrile instead of dimethylformamide, to give 115 mg of 1-[2-(4-t-butylcyclohexyl)phenyl]-4-(2-methoxyethyl)piperazine as a colorless oil, as a mixture of diastereomers at the position of t-butylcyclohexyl.

The oil was converted to a hydrochloride by a method similar to Example (10b) to give 124 mg of the title compound as colorless crystals, as a mixture of diastereomers at the position of t-butylcyclohexyl.

MS m/e (ESI) 359 (MH$^+$).

Example 20

1-[2-(4-t-Butylcyclohex-1-enyl)-4-(4-methoxypiperidin-1-yl)phenyl]-4-cyclopropylmethylpiperazine hydrochloride

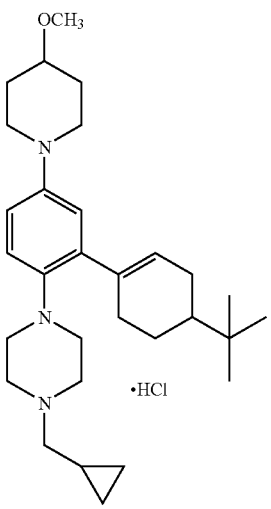

1-[2-(4-t-Butylcyclohex-1-enyl)-4-(4-methoxypiperidin-1-yl)phenyl]piperazine (100 mg, 0.243 mmol) prepared in Example (7g) was used as the starting material for reaction in a manner similar to Example (9) and treated in a similar manner, to give 104 mg of 1-[2-(4-t-butylcyclohex-1-enyl)-4-(4-methoxypiperidin-1-yl)phenyl]-4-cyclopropylmethylpiperazine as a colorless solid, in racemic form at the position of t-butylcyclohexyl. The product was converted to a hydrochloride by a method similar to Example (9) to give 79 mg of the title compound as a light yellow solid, in racemic form at the position of t-butyl.

MS m/e (ESI) 466 (MH⁺).

Example 21

1-Butyl-4-[2-(4,4-dimethylcyclohexyl)-4-(4-ethoxypiperidin-1-yl)phenyl]piperazine hydrochloride

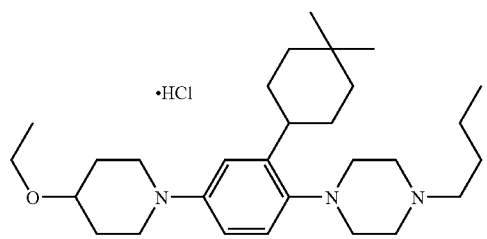

21a

4-Ethoxypiperidine hydrochloride

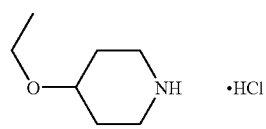

4-Hydroxypiperidine-1-carboxylic acid t-butyl ester (2.2 g, 10.9 mmol) was used as the starting material.

Ethyl iodide was used instead of methyl iodide for reaction in a manner similar to Example (7a) and treated in a similar manner, to give 1.3 g of the title compound as light yellow crystals.

21b

1-Butyl-4-[2-(4,4-dimethylcyclohexyl)phenyl]piperazine hydrochloride

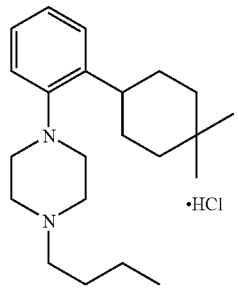

1-[2-(4,4-Dimethylcyclohexyl)phenyl]piperazine (65 mg, 0.239 mmol) prepared in Example (3c) was used as the starting material.

Reaction and treatment were carried out in a manner similar to Example (8c), to give 82 mg of the title compound as colorless crystals.

MS m/e (ESI) 329 (MH⁺).

21c

1-[4-Bromo-2-(4,4-dimethylcyclohexyl)phenyl]-4-butylpiperazine

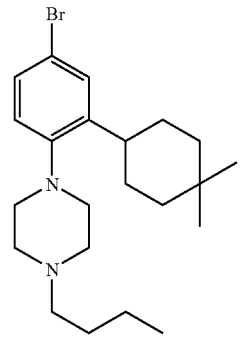

1-Butyl-4-[2-(4,4-dimethylcyclohexyl)phenyl]piperazine hydrochloride (64 mg, 0.175 mmol) prepared in Example (21b) was used as the starting material.

Reaction and treatment were carried out in a manner similar to Example (3e), excluding sodium acetate from the reagents used, to give 71 mg of the title compound as a light yellow oil.

21d

1-Butyl-4-[2-(4,4-dimethylcyclohexyl)-4-(4-ethoxypiperidin-1-yl)phenyl]piperazine hydrochloride

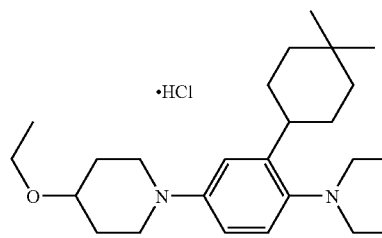

1-[4-Bromo-2-(4,4-dimethylcyclohexyl)phenyl]-4-butylpiperazine (20 mg, 0.0491 mmol) prepared in Example (21c) and 4-ethoxypiperidine hydrochloride (11 mg, 0.0638 mmol) prepared in Example (21a) were used as the starting materials.

Reaction and treatment were carried out in a manner similar to Example (3f), with further addition of sodium t-butoxide in an equivalent with respect to 4-ethoxypiperidine hydrochloride, to give 1-butyl-4-[2-(4,4-dimethylcyclohexyl)-4-(4-ethoxypiperidin-1-yl)phenyl]piperazine as a colorless oil.

The obtained oil was dissolved in ethyl acetate (3 mL), and then a 4N solution of hydrogen chloride in ethyl acetate (0.0082 mL) was added. The mixture was further diluted with hexane (5 mL) and concentrated under reduced pressure. The crude crystal product precipitated was washed with hexane and then dried to give 16 mg of the title compound as colorless crystals.

MS m/e (ESI) 456 (MH⁺).

Example 22

1-(Tetrahydropyran-4-ylmethyl)-4-[2-(3,3,5,5-tetramethylcyclohex-1-enyl)phenyl]piperazine hydrochloride

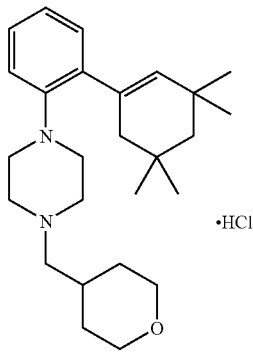

1-[2-(3,3,5,5-Tetramethylcyclohex-1-enyl)phenyl]piperazine (120 mg, 0.402 mmol) prepared in Example (4f) was used as the starting material.

Tetrahydropyran-4-carbaldehyde was used instead of butyraldehyde for reaction in a manner similar to Example (4g) and treated in a similar manner, to give 131 mg of 1-(tetrahydropyran-4-ylmethyl)-4-[2-(3,3,5,5-tetramethylcyclohex-1-enyl)phenyl]piperazine as a colorless oil.

$^1$H-NMR (400 MHz, CDCl$_3$) δ: 1.02 (s, 6H), 1.07 (s, 6H), 1.23-1.34 (m, 2H), 1.39 (s, 2H), 1.67-1.83 (m, 3H), 2.17 (d, J=1.6 Hz, 2H), 2.22 (d, J=6.8 Hz, 2H), 2.51 (brs, 4H), 2.99 (brs, 4H), 3.39 (td, J=12.0, 2.0 Hz, 2H), 3.95-3.99 (m, 2H), 5.50 (s, 1H), 6.96-7.00 (m, 2H), 7.07 (dd, J=7.6, 1.6 Hz, 1H), 7.18 (ddd, J=8.0, 8.0, 2.0 Hz, 1H).

This was converted to a hydrochloride by a method similar to Example (4g) to give 113 mg of the title compound as colorless crystals.

MS m/e (ESI) 397 (MH$^+$).

Example 23

1-{4-[2-(3,3,5,5-Tetramethylcyclohex-1-enyl)phenyl]piperazin-1-yl}butan-2-one hydrochloride

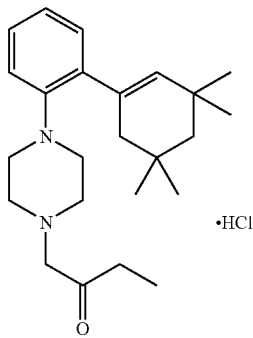

1-[2-(3,3,5,5-tetramethylcyclohex-1-enyl)phenyl]piperazine (40 mg, 0.134 mmol) prepared in Example (4f) was used as the starting material.

1-Bromo-2-butanone was used instead of 2-chloro-N-ethylacetamide and acetonitrile was used instead of dimethylformamide for reaction in a manner similar to Example (10b) and treated in a similar manner, to give 31 mg of 1-{4-[2-(3,3,5,5-tetramethylcyclohex-1-enyl)phenyl]piperazin-1-yl}butan-2-one as a colorless oil.

$^1$H-NMR (400 MHz, CDCl$_3$) δ: 1.02 (s, 6H), 1.06 (s, 6H), 1.08 (t, J=7.6 Hz, 3H), 1.39 (s, 2H), 2.16 (d, J=1.6 Hz, 2H), 2.49 (q, J=7.6 Hz, 2H), 2.59 (brs, 4H), 3.05 (t, J=4.8 Hz, 4H), 3.23 (s, 2H), 5.50 (t, J=1.6 Hz, 1H), 6.97-7.02 (m, 2H), 7.07 (dd, J=8.0, 1.6 Hz, 1H), 7.19 (ddd, J=8.0, 8.0, 1.6 Hz, 1H).

This was converted to a hydrochloride by a method similar to Example (4g) to give 38 mg of the title compound as a light brown solid.

MS m/e (ESI) 369 (MH$^+$).

Example 24

1-(2-Methoxyethyl)-4-[2-(3,3,5,5-tetramethylcyclohex-1-enyl)phenyl]piperazine hydrochloride

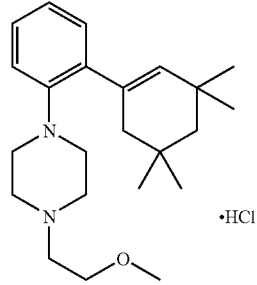

1-[2-(3,3,5,5-Tetramethylcyclohex-1-enyl)phenyl]piperazine (40 mg, 0.134 mmol) prepared in Example (4f) was used as the starting material.

2-Bromoethylmethyl ether was used instead of 2-chloro-N-ethylacetamide and acetonitrile was used instead of dimethylformamide for reaction in a manner similar to Example (10b) and treated in a similar manner, to give 31 mg of 1-(2-methoxyethyl)-4-[2-(3,3,5,5-tetramethylcyclohex-1-enyl)phenyl]piperazine.

$^1$H-NMR (400 MHz, CDCl$_3$) δ: 1.02 (s, 6H), 1.07 (s, 6H), 1.39 (s, 2H), 2.17 (d, J=1.2 Hz, 2H), 2.61 (brs, 4H), 2.62 (t, J=5.6 Hz, 2H), 3.03 (t, J=4.4 Hz, 4H), 3.37 (s, 3H), 3.55 (t, J=5.6 Hz, 2H), 5.50 (t, J=1.6 Hz, 1H), 6.96-7.02 (m, 2H), 7.07 (dd, J=7.6, 2.0 Hz, 1H), 7.18 (ddd, J=8.0, 8.0, 2.0 Hz, 1H).

This was converted to a hydrochloride by a method similar to Example (4g) to give 31 mg of the title compound as colorless crystals.

MS m/e (ESI) 357 (MH$^+$).

Example 25

1-{4-[2-(3,3,5,5-Tetramethylcyclohexyl)phenyl]piperazin-1-yl}butan-2-one hydrochloride

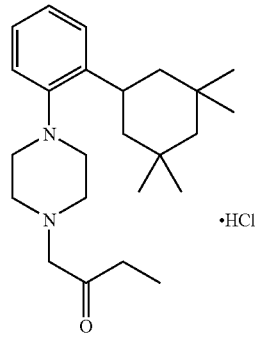

1-[2-(3,3,5,5-Tetramethylcyclohexyl)phenyl]piperazine (40 mg, 0.133 mmol) prepared in Example (8b) was used as the starting material.

1-Bromo-2-butanone was used instead of 2-chloro-N-ethylacetamide and acetonitrile was used instead of dimethylformamide for reaction in a manner similar to Example (10b) and treated in a similar manner, to give 33 mg of 1-{4-[2-(3,3,5,5-tetramethylcyclohexyl)phenyl]piperazin-1-yl}butan-2-one as a colorless oil.

$^1$H-NMR (400 MHz, CDCl$_3$) δ: 0.92 (s, 6H), 1.09 (t, J=7.2 Hz, 3H), 1.11 (s, 6H), 1.17-1.34 (m, 4H), 1.40-1.44 (m, 2H), 2.50 (q, J=7.2 Hz, 2H), 2.66 (brs, 4H), 2.96 (t, J=4.4 Hz, 4H), 3.27 (s, 2H), 3.55 (tt, J=12.8, 2.8 Hz, 1H), 7.06-7.11 (m, 1H), 7.13-7.17 (m, 2H), 7.22 (dd, J=8.0, 1.6 Hz, 1H).

This was converted to a hydrochloride by a method similar to Example (4g) to give 33 mg of the title compound as a light brown solid.

MS m/e (ESI) 371 (MH$^+$).

Example 26

1-(2-Methoxyethyl)-4-[2-(3,3,5,5-tetramethylcyclohexyl)phenyl]piperazine hydrochloride

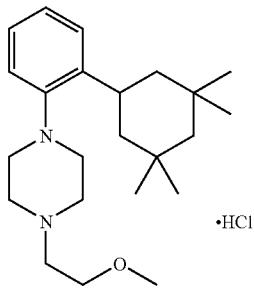

1-[2-(3,3,5,5-Tetramethylcyclohexyl)phenyl]piperazine (40 mg, 0.133 mmol) prepared in Example (8b) was used as the starting material.

2-Bromoethyl methyl ether was used instead of 2-chloro-N-ethylacetamide and acetonitrile was used instead of dimethylformamide for reaction in a manner similar to Example (10b) and treated in a similar manner, to give 37 mg of 1-(2-methoxyethyl)-4-[2-(3,3,5,5-tetramethylcyclohexyl)phenyl]piperazine.

$^1$H-NMR (400 MHz, CDCl$_3$) δ: 0.92 (s, 6H), 1.12 (s, 6H), 1.17-1.34 (m, 4H), 1.41-1.45 (m, 2H), 2.65 (t, J=5.6 Hz, 2H), 2.66 (brs, 4H), 2.95 (t, J=4.4 Hz, 4H), 3.37 (s, 3H), 3.51-3.62 (m, 3H), 7.05-7.11 (m, 1H), 7.12-7.17 (m, 2H), 7.22 (dd, J=7.6, 1.6 Hz, 1H).

This was converted to a hydrochloride by a method similar to Example (4g) to give 38 mg of the title compound as colorless crystals.

MS m/e (ESI) 359 (MH$^+$).

Example 27

1-Butyl-4-[5-methoxy-2-(3,3,5,5-tetramethylcyclohexyl)phenyl]piperazine hydrochloride

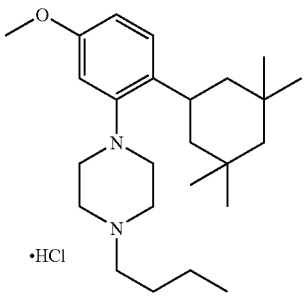

27a

4-Methoxy-2-nitro-1-(3,3,5,5-tetramethylcyclohex-1-enyl)benzene

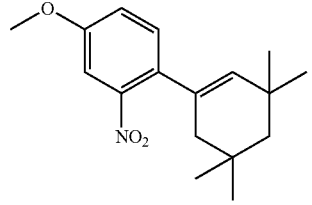

4,4,5,5-Tetramethyl-2-(3,3,5,5-tetramethylcyclohex-1-enyl)-[1,3,2]dioxaborolane (2.7 g, 10.3 mmol) prepared in Example (4b) was used instead of 2-(4,4-diethylcyclohex-1-enyl)-4,4,5,5-tetramethyl-[1,3,2]dioxaborolane for reaction in a manner similar to Example (6d) and treated in a similar manner, to give 2.5 g of the title compound as a yellow oil.

27b

5-Methoxy-2-(3,3,5,5-tetramethylcyclohex-1-enyl)phenylamine

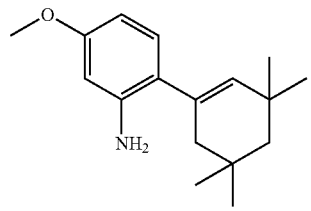

4-Methoxy-2-nitro-1-(3,3,5,5-tetramethylcyclohex-1-enyl)benzene (2.5 g, 8.6 mmol) prepared in Example (27a) was reacted and treated in a manner similar to Example (6e), to give 2.2 g of the title compound as a yellow oil.

27c

1-[5-Methoxy-2-(3,3,5,5-tetramethylcyclohex-1-enyl)phenyl]piperazine

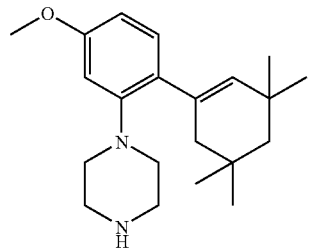

5-Methoxy-2-(3,3,5,5-tetramethylcyclohex-1-enyl)phenylamine (2.2 g, 8.6 mmol) prepared in Example (27b) was reacted and treated in a manner similar to Example (6f), to give 2.0 g of the title compound as a yellow solid.

27d

1-Butyl-4-[5-methoxy-2-(3,3,5,5-tetramethylcyclo-hex-1-enyl)phenyl]piperazine hydrochloride

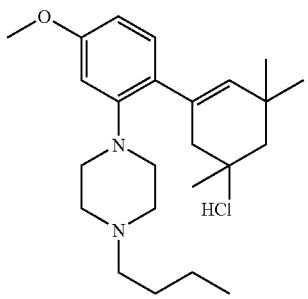

1-[5-Methoxy-2-(3,3,5,5-tetramethylcyclohex-1-enyl)phenyl]piperazine (115 mg, 0.35 mmol) prepared in Example (27c) was reacted and treated in a manner similar to Example (6g), using butyraldehyde instead of tetrahydropyran-4-carbaldehyde, to give 80 mg of the title compound as a light yellow oil.

27e

1-Butyl-4-[5-methoxy-2-(3,3,5,5-tetramethylcyclo-hexyl)phenyl]piperazine hydrochloride

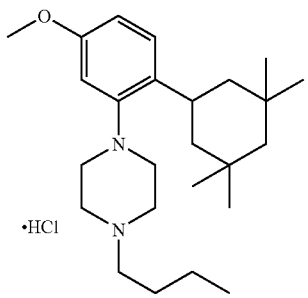

1-Butyl-4-[5-methoxy-2-(3,3,5,5-tetramethylcyclohex-1-enyl)phenyl]piperazine hydrochloride (70 mg, 0.16 mmol) prepared in Example (27d) was reacted and treated in a manner similar to Example (6h), to give 5 mg of the title compound as a light yellow solid.

MS m/e (ESI) 387 (MH$^+$).

Example 28

4-[4-(4-Propylpiperazin-1-yl)-3-(3,3,5,5-tetramethyl-cyclohex-1-enyl)phenyl]morpholine hydrochloride

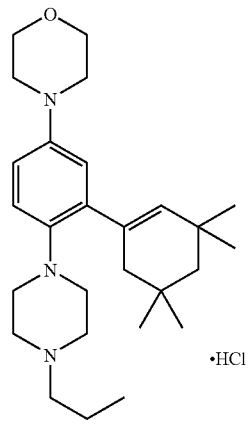

28a

5-Morpholin-4-yl-2-nitrophenol

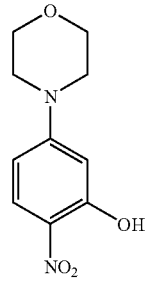

Commercially available 5-fluoro-2-nitrophenol (10 g, 63.65 mmol) was used as the starting material.

Morpholine was used instead of 4-methoxypiperidine hydrochloride, for reaction in a manner similar to Example (7b). Water was added to the reaction mixture, and then the precipitated crystals were filtered, washed with water and hexane and air-dried to give 14.04 g of the title compound as yellow crystals.

28b

Trifluoromethanesulfonic acid 5-morpholin-4-yl-2-nitrophenyl ester

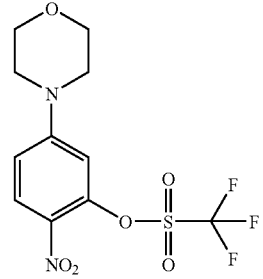

5-Morpholin-4-yl-2-nitrophenol (14.04 g, 62.63 mmol) prepared in Example (28a) was used as the starting material.

Reaction and treatment were carried out in a manner similar to Example (7c), to give 21.46 g of the title compound as yellow crystals.

28c

4-[4-Nitro-3-(3,3,5,5-tetramethylcyclohex-1-enyl)phenyl]morpholine

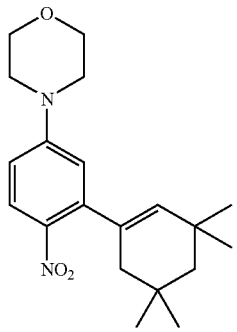

The trifluoromethanesulfonic acid 5-morpholin-4-yl-2-nitrophenyl ester (2 g, 5.6 mmol) prepared in Example (28b) was used as the starting material.

4,4,5,5-Tetramethyl-2-(3,3,5,5-tetramethylcyclohex-1-enyl)-[1,3,2]dioxaborolane prepared in Example (4b) was used instead of 2-(4-t-butylcyclohex-1-enyl)-(4,4,5,5-tetramethyl)-[1,3,2]dioxaborolane, and a mixed solvent of 1,2-dimethoxyethane-water was used as the solvent, for reaction in a manner similar to Example (7e) and treated in a similar manner, to give 1.7 g of the title compound as a yellow oil.

28d

4-Morpholin-4-yl-2-(3,3,5,5-tetramethylcyclohex-1-enyl)phenylamine

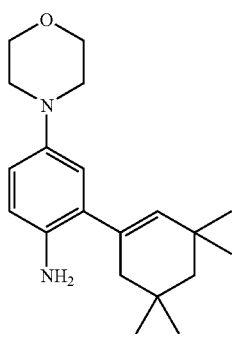

4-[4-Nitro-3-(3,3,5,5-tetramethylcyclohex-1-enyl)phenyl]morpholine (1 g, 2.9 mmol) prepared in Example (28c) was used as the starting material.

The reaction time was changed to 15 hours and 40 minutes, for reaction in a similar manner and treatment in a manner similar to Example (6e), to give 912 mg of the title compound as a yellow oil.

28e

4-[4-piperazin-1-yl-3-(3,3,5,5-tetramethylcyclohex-1-enyl)phenyl]morpholine

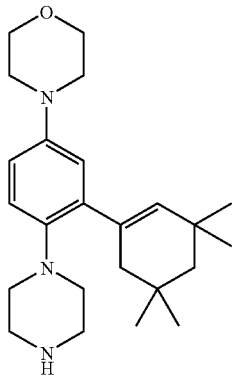

4-Morpholin-4-yl-2-(3,3,5,5-tetramethylcyclohex-1-enyl)phenylamine (910 mg, 2.89 mmol) prepared in Example (28d) was used as the starting material.

This was reacted and treated in a manner similar to Example (7g), to give 820 mg of the title compound as a light brown solid.

28f

4-[4-(4-Propylpiperazin-1-yl)-3-(3,3,5,5-tetramethylcyclohex-1-enyl)phenyl]morpholine hydrochloride

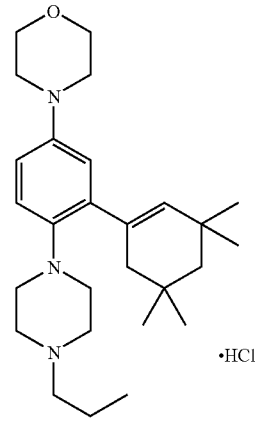

4-[4-piperazin-1-yl-3-(3,3,5,5-tetramethylcyclohex-1-enyl)phenyl]morpholine (120 mg, 0.313 mmol) prepared in Example (28e) was used as the starting material.

Propionaldehyde was used instead of butyraldehyde for reaction in a manner similar to Example (4g) and treated in a similar manner, to give 119 mg of 4-[4-(4-propylpiperazin-1-yl)-3-(3,3,5,5-tetramethylcyclohex-1-enyl)phenyl]morpholine as a white solid.

This was converted to a hydrochloride by a method similar to Example (4g) to give 135 mg of the title compound as a white solid.

MS m/e (ESI) 426 (MH⁺).

Example 29

4-[3-(4,4-Diethylcyclohex-1-enyl)-4-(4-pentylpiperazin-1-yl)phenyl]morpholine hydrochloride

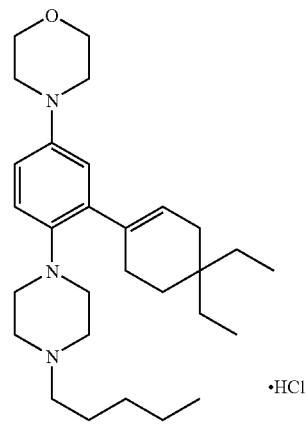

29a

4-[3-(4,4-Diethylcyclohex-1-enyl)-4-nitrophenyl]morpholine

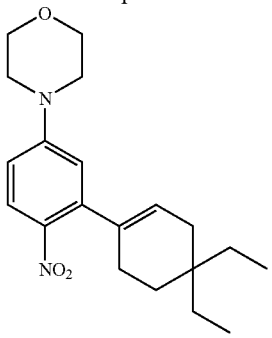

Trifluoromethanesulfonic acid 5-morpholin-4-yl-2-nitrophenyl ester (3 g, 8.42 mmol) prepared in Example (28b) was used as the starting material.

2-(4,4-Diethylcyclohex-1-enyl)-4,4,5,5-tetramethyl-[1,3,2]dioxaborolane prepared in Example (6c) was used instead of 2-(4-t-butyl-1-cyclohex-1-enyl)-(4,4,5,5-tetramethyl)[1,3,2]dioxaborolane, and a mixed solvent of 1,2-dimethoxyethane-water was used as the solvent, for reaction in a manner similar to Example (7e) and treated in a similar manner, to give 3.11 g of the title compound as a yellow oil.

29b 2-(4,4-Diethylcyclohex-1-enyl)-4-morpholin-4-ylphenylamine

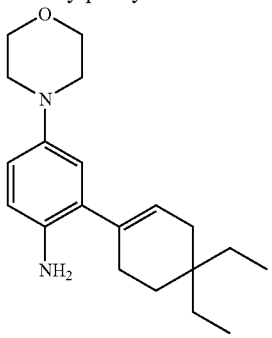

4-[3-(4,4-Diethylcyclohex-1-enyl)-4-nitrophenyl]morpholine (3.11 g, 9.03 mmol) prepared in Example (29a) was used as the starting material.

This was reacted and treated in a manner similar to Example (6e), to give 2.55 g of the title compound as a brown oil.

29c

4-[3-(4,4-Diethylcyclohex-1-enyl)-4-piperazin-1-ylphenyl]morpholine

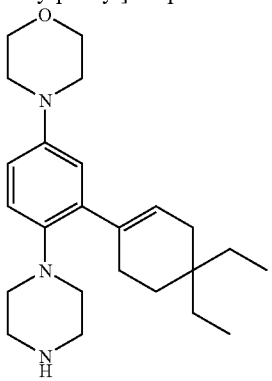

2-(4,4-Diethylcyclohex-1-enyl)-4-morpholin-4-ylphenylamine (2.55 g, 8.11 mmol) prepared in Example (29b) was used as the starting material.

This was reacted and treated in a manner similar to Example (7g), to give 2.01 g of the title compound as a light brown solid.

29d

4-[3-(4,4-Diethylcyclohex-1-enyl)-4-(4-pentylpiperazin-1-yl)phenyl]morpholine hydrochloride

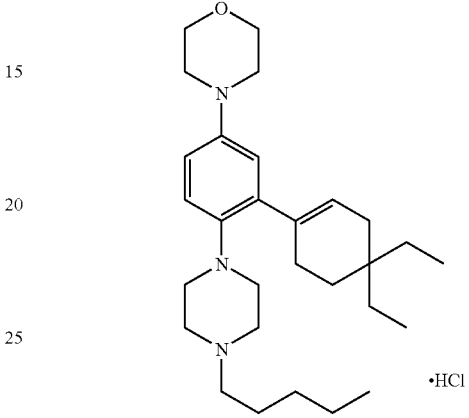

4-[3-(4,4-Diethylcyclohex-1-enyl)-4-piperazin-1-ylphenyl]morpholine (30 mg, 0.0782 mmol) prepared in Example (29c) was used as the starting material.

This was reacted and treated in a manner similar to Example (1f). The product was further converted to a hydrochloride by a method similar to Example (1f) to give 38.9 mg of the title compound as a white solid.

MS m/e (ESI) 454 (MH$^+$).

Example 30

1-{4-[2-(4,4-Diethylcyclohex-1-enyl)-4-morpholin-4-ylphenyl]piperazin-1-yl}butan-2-one hydrochloride

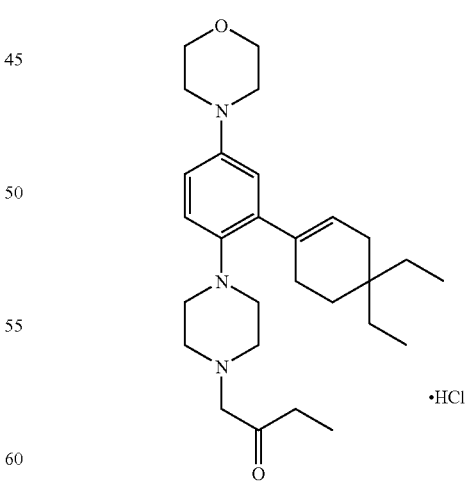

4-[3-(4,4-Diethylcyclohex-1-enyl)-4-piperazin-1-ylphenyl]morpholine (250 mg, 0.652 mmol) prepared in Example (29c) was used as the starting material.

1-Bromo-2-butanone was used instead of 2-chloro-N-ethylacetamide for reaction in a manner similar to Example (10b) and treated in a similar manner. The product was further

147 converted to a hydrochloride by a method similar to Example (4g) to give 320 mg of the title compound as a white solid.
MS m/e (ESI) 454 (MH⁺).

Example 31

1-Propyl-4-[2-(3,3,5,5-tetramethylcyclohexyl)phenyl]piperazine hydrochloride

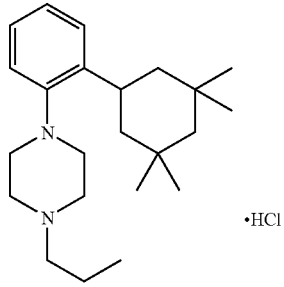

1-[2-(3,3,5,5-Tetramethylcyclohexyl)phenyl]piperazine (120 mg, 0.399 mmol) prepared in Example (8b) was used as the starting material.
Propionaldehyde was used instead of butyraldehyde for reaction in a manner similar to Example (4g) and treated in a similar manner, to give 104 mg of 1-propyl-4-[2-(3,3,5,5-tetramethylcyclohexyl)phenyl]piperazine as a colorless oil.
$^1$H-NMR (400 MHz, CDCl$_3$) δ: 0.92 (s, 6H), 0.93 (t, J=7.2 Hz, 3H), 1.13 (s, 6H), 1.16-1.35 (m, 4H), 1.40-1.46 (m, 2H), 1.51-1.60 (m, 2H), 2.35-2.39 (m, 2H), 2.61 (brs, 4H), 2.93 (t, J=4.8 Hz, 4H), 3.57 (tt, J=12.8, 2.8 Hz, 1H), 7.05-7.09 (m, 1H), 7.11-7.17 (m, 2H), 7.22 (dd, J=7.6, 1.2 Hz, 1H).
The product was converted to a hydrochloride by a method similar to Example (4g) to give 92 mg of the title compound as colorless crystals.
MS m/e (ESI) 343 (MH⁺).

Example 32

1-Butyl-4-[4-(4-methoxypiperidin-1-yl)-2-(3,3,5,5-tetramethylcyclohexyl)phenyl]piperazine hydrochloride

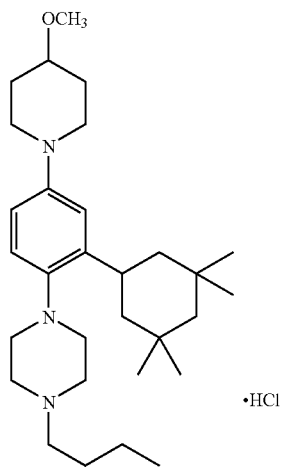

32a

4-Methoxy-1-[4-nitro-3-(3,3,5,5-tetramethylcyclohex-1-enyl)phenyl]piperidine

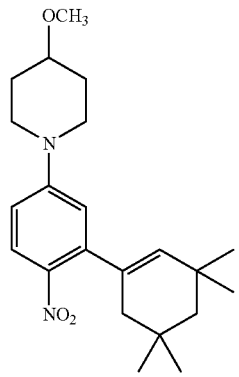

Trifluoromethanesulfonic acid 5-(4-methoxypiperidin-1-yl)-2-nitrophenyl ester (3 g, 7.81 mmol) prepared in Example (7c) was used as the starting material. 4,4,5,5-Tetramethyl-2-(3,3,5,5-tetramethylcyclohex-1-enyl)-[1,3,2]dioxaborolane prepared in Example (4b) was used instead of 4-t-butylcyclohex-1-enyl-(4,4,5,5-tetramethyl)-[1,3,2]dioxaborolane, and a mixed solvent of 1,2-dimethoxyethane-water was used as the solvent, for reaction in a manner similar to Example (7e) and treated in a similar manner, to give 2.89 g of the title compound as a yellow oil.

32b 4-(4-Methoxypiperidin-1-yl)-2-(3,3,5,5-tetramethylcyclohexyl)phenylamine

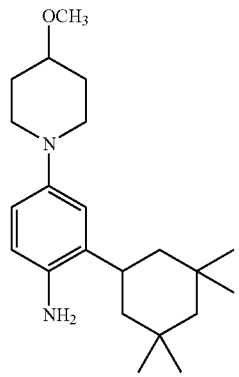

4-Methoxy-1-[4-nitro-3-(3,3,5,5-tetramethylcyclohex-1-enyl)phenyl]piperidine (1 g, 2.68 mmol) prepared in Example (32a) was used as the starting material.
Reaction and treatment were carried out in a manner similar to Example (2c), using a mixed solvent of methanol-tetrahydrofuran instead of ethyl acetate and changing the reaction time to 18 hours and 40 minutes, to give 845 mg of the title compound as a light brown oil.

32c

1-[4-(4-Methoxypiperidin-1-yl)-2-(3,3,5,5-tetramethylcyclohexyl)phenyl]piperazine

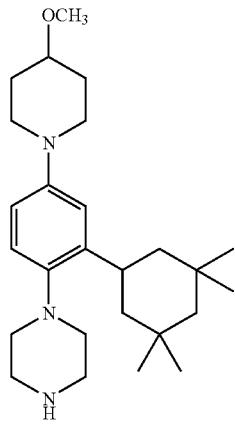

4-(4-Methoxypiperidin-1-yl)-2-(3,3,5,5-tetramethylcyclohexyl)phenylamine (843 mg, 2.45 mmol) prepared in Example (32b) was used as the starting material.

This was reacted and treated in a manner similar to Example (7g), to give 596 mg of the title compound as a light brown solid.

32d

1-Butyl-4-[4-(4-methoxypiperidin-1-yl)-2-(3,3,5,5-tetramethylcyclohexyl)phenyl]piperazine hydrochloride

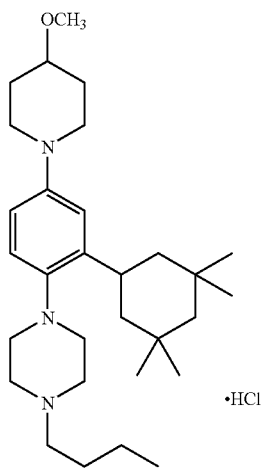

1-[4-(4-Methoxypiperidin-1-yl)-2-(3,3,5,5-tetramethylcyclohexyl)phenyl]piperazine (120 mg, 0.29 mmol) prepared in Example (32c) was used as the starting material.

This was reacted and treated in a manner similar to Example (4g), to give 130 mg of 1-butyl-4-[4-(4-methoxypiperidin-1-yl)-2-(3,3,5,5-tetramethylcyclohexyl)phenyl]piperazine as a light yellow solid.

The product was converted to a hydrochloride by a method similar to Example (4g) to give 143 mg of the title compound as a light brown solid.

MS m/e (ESI) 470 (MH$^+$).

Example 33

1-Butyl-4-(2-spiro[4.5]dec-8-ylphenyl)piperazine hydrochloride

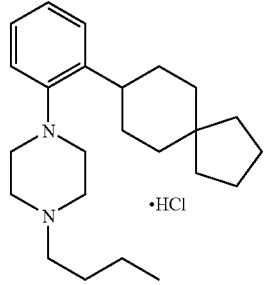

33a

Spiro[4.5]dec-6-en-8-one

To a solution of cyclopentanecarbaldehyde (10 g, 100 mmol) in toluene (100 mL) were added methyl vinyl ketone (7.8 g, 110 mmol) and p-toluenesulfonic acid (1.9 g, 10 mmol), and the mixture was stirred at 120° C. for 3 hours, using a Dean-Stark apparatus to remove water. The reaction mixture was air-cooled to room temperature, then saturated aqueous sodium hydrogencarbonate was added, and the mixture was extracted with ethyl acetate. The organic layer was dried over anhydrous magnesium sulfate. The desiccant was filtered off and the filtrate was concentrated under reduced pressure. The resultant residue was purified by silica gel column chromatography (ethyl acetate/hexane) to give 6.0 g of the title compound as a red oil.

33b

Spiro[4.5]decan-8-one

Spiro[4.5]dec-6-en-8-one (6.0 g, 40 mmol) prepared in Example (33a) was used for reaction in a manner similar to Example (6a) and treated in a similar manner, to give 6.0 g of the title compound as a red oil.

33c

Trifluoromethanesulfonic acid spiro[4.5]dec-7-en-8-yl ester

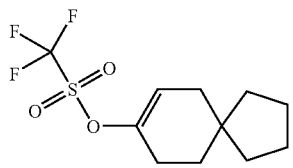

Spiro[4.5]decan-8-one (7.0 g, 46 mmol) prepared in Example (33b) was used for reaction in a manner similar to Example (6b) and treated in a similar manner, to give 3.7 g of the title compound as a yellow oil.

33d 4,4,5,5-Tetramethyl-2-spiro[4.5]dec-7-en-8-yl-[1,3,2]dioxaborolane

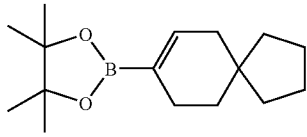

Trifluoromethanesulfonic acid spiro[4.5]dec-7-en-8-yl ester (3.7 g, 40 mmol) prepared in Example (33c) was used for reaction in a similar manner and treatment in a manner similar to Example (6c), to give 3.3 g of the title compound as a light yellow oil.

33e 4-(2-Spiro[4.5]dec-7-en-8-ylphenyl)piperazine-1-carboxylic acid t-butyl ester

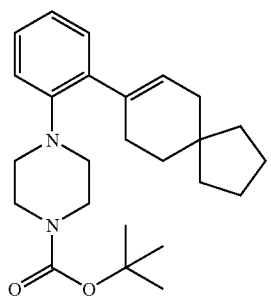

The 4,4,5,5-tetramethyl-2-spiro[4.5]dec-7-en-8-yl-[1,3,2]dioxaborolane (1.3 g, 4.95 mmol) prepared in Example (33d) was used for reaction in a manner similar to Example (4e) and treated in a similar manner, to give 1.0 g of the title compound as a light yellow oil.

33f 1-(2-Spiro[4.5]dec-7-en-8-ylphenyl)piperazine

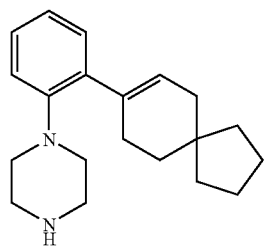

4-(2-Spiro[4.5]dec-7-en-8-ylphenyl)piperazine-1-carboxylic acid t-butyl ester (1.0 g, 2.5 mmol) prepared in Example (33e) was used for reaction in a manner similar to Example (4f) and treated in a similar manner, to give 0.6 g of the title compound as a yellow oil.

33g

1-Butyl-4-(2-spiro[4.5]dec-7-en-8-ylphenyl)piperazine hydrochloride

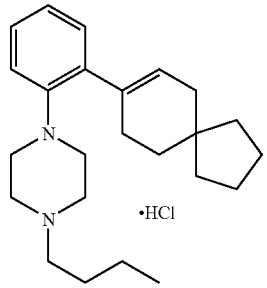

1-(2-Spiro[4.5]dec-7-en-8-ylphenyl)piperazine (140 mg, 0.47 mmol) prepared in Example (33f) was used for reaction in a manner similar to Example (4g) and treated in a similar manner, to give 125 mg of the title compound as a light yellow solid.

MS m/e (ESI) 353 (MH$^+$).

33h

1-Butyl-4-(2-spiro[4.5]dec-8-ylphenyl)piperazine hydrochloride

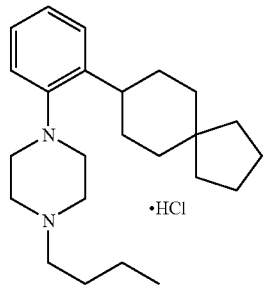

1-Butyl-4-(2-spiro[4.5]dec-7-en-8-ylphenyl)piperazine hydrochloride (40 mg, 0.10 mmol) prepared in Example (33g) was used for reaction in a manner similar to Example (6h) and treated in a similar manner, to give 33 mg of the title compound as a light yellow solid.

MS m/e (ESI) 355 (MH$^+$).

Example 34

1-Isobutyl-4-(2-spiro[2.5]oct-5-en-6-ylphenyl)piperazine hydrochloride

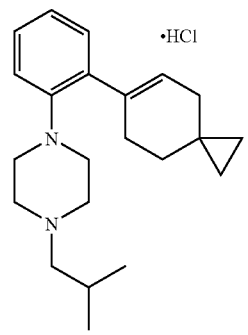

34a

Trifluoromethanesulfonic acid sipiro[2.5]oct-5-en-6-yl ester

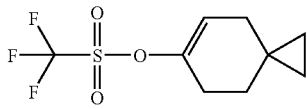

Spiro[2.5]octan-2-one (1.71 g, 13.77 mmol) was used as the starting material instead of 4,4-diethylcyclohexanone for reaction in a manner similar to Example (6b) and treated in a similar manner, to give 3.35 g of the title compound as a brown oil.

34b 4,4,5,5-Tetramethyl-2-spiro[2.5]oct-5-en-6-yl-[1,3,2]dioxaborolane

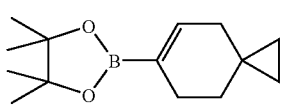

Trifluoromethanesulfonic acid spiro[2.5]oct-5-en-6-yl ester (3.34 g, 13.03 mmol) prepared in Example (34a) was used as the starting material instead of trifluoromethanesulfonic acid 4,4-diethylcyclohex-1-enyl ester for reaction in a manner similar to Example (6c) and treated in a similar manner, to give 2.35 g of the title compound as a yellow oil.

$^1$H-NMR (400 MHz, CDCl$_3$) δ: 0.25-0.30 (m, 4H), 1.27 (s, 12H), 1.34-1.37 (m, 2H), 1.97-1.99 (m, 2H), 2.19-2.23 (m, 2H), 6.55-6.60 (m, 1H).

34c 4-(2-Spiro[2.5]oct-5-en-6-ylphenyl)piperazine-1-carboxylic acid t-butyl ester

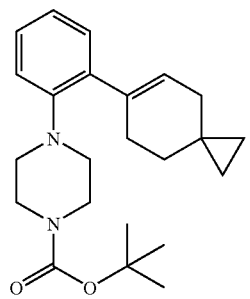

4-(2-Trifluoromethanesulfonyloxyphenyl)piperazine-1-carboxylic acid t-butyl ester (4.12 g, 10.03 mmol) prepared in Example (4d) was used as the starting material.

4,4,5,5-Tetramethyl-2-spiro[2.5]oct-5-en-6-yl-[1,3,2]dioxaborolane (2.35 g, 10.03 mmol) prepared in Example (34b) was used instead of 4,4,5,5-tetramethyl-2-(3,3,5,5-tetramethylcyclohex-1-enyl)[1,3,2]dioxaborolane for reaction in a manner similar to Example (4e) and treated in a similar manner, to give 3.09 g of the title compound as a light yellow solid.

34d 1-(2-Spiro[2.5]oct-5-en-6-ylphenyl)piperazine

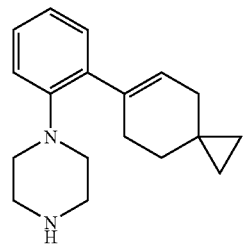

4-(2-Spiro[2.5]oct-5-en-6-ylphenyl)piperazine-1-carboxylic acid t-butyl ester (0.380 g, 1.03 mmol) prepared in Example (34c) was used as the starting material for reaction in a manner similar to Example (4f) and treated in a similar manner, to give 249 mg of the title compound as a light brown oil.

34e

1-Isobutyl-4-(2-spiro[2.5]oct-5-en-6-ylphenyl)piperazine hydrochloride

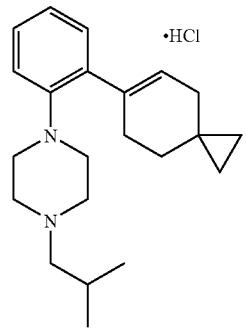

1-(2-Spiro[2.5]oct-5-en-6-ylphenyl)piperazine (66 mg, 0.246 mmol) prepared in Example (34d) was used as the starting material.

Isobutyraldehyde was used instead of tetrahydropyran-4-carbaldehyde for reaction in a manner similar to Example (6g) and treated in a similar manner, to give 76 mg of the title compound as colorless crystals.

MS m/e (ESI) 325 (MH$^+$).

Example 35

1-(2-Spiro[2.5]oct-5-en-6-ylphenyl)-4-(tetrahydropyran-4-ylmethyl)piperazine hydrochloride

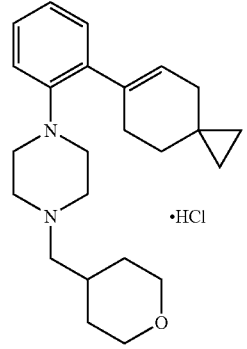

1-(2-Spiro[2.5]oct-5-en-6-ylphenyl)piperazine (20 mg, 0.0745 mmol) prepared in Example (34d) was used as the starting material.

Reaction and treatment were carried out in a manner similar to Example (6g), to give 24.3 mg of the title compound as a colorless solid.

MS m/e (ESI) 367 (MH$^+$).

Example 36

1-Isobutyl-4-(2-spiro[2.5]oct-6-ylphenyl)piperazine hydrochloride

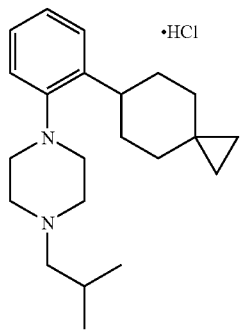

1-Isobutyl-4-(2-spiro[2.5]oct-5-en-6-ylphenyl)piperazine hydrochloride (20 mg, 0.0554 mmol) prepared in Example (34e) was used as the starting material.

Reaction were carried out in a manner similar to Example (6h) and stirring was continued for 6 hours, treatment was carried out in a similar manner to give 19 mg of the title compound as colorless crystals.

MS m/e (ESI) 327 (MH$^+$).

Example 37

1-[2-(4,4-Dimethylcyclohex-1-enyl)phenyl]-4-isobutylpiperazine hydrochloride

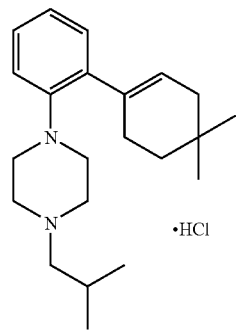

37a

4-[2-(4,4-Dimethylcyclohex-1-enyl)phenyl]piperazine-1-carboxylic acid t-butyl ester

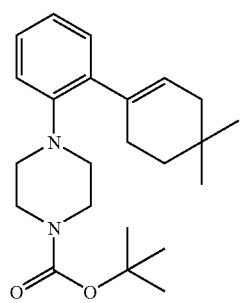

4-(2-Trifluoromethanesulfonyloxyphenyl)piperazine-1-carboxylic acid t-butyl ester (4.1 g, 10 mmol) prepared in Example (4d) was used as the starting material.

2-(4,4-Dimethylcyclohex-1-enyl)-4,4,5,5-tetramethyl[1,3,2]dioxaborolane (2.83 g, 12 mmol) prepared in Example (1b) was used instead of 4,4,5,5-tetramethyl-2-(3,3,5,5-tetramethylcyclohex-1-enyl)[1,3,2]dioxaborolane for reaction in a manner similar to Example (4e) and treated in a similar manner, to give 3.29 g of the title compound as a colorless solid.

37b

1-[2-(4,4-Dimethylcyclohex-1-enyl)phenyl]piperazine

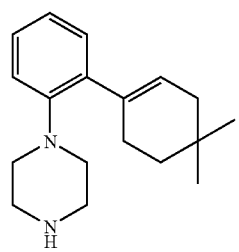

4-[2-(4,4-Dimethylcyclohex-1-enyl)phenyl]piperazine-1-carboxylic acid t-butyl ester (3.17 g, 8.56 mmol) prepared in Example (37a) was used as the starting material.

Dichloromethane was used instead of a mixed solvent of ethyl acetate-dichloromethane for reaction in a manner similar to Example (3g) and treated in a similar manner, to give 1.82 g of the title compound as a light green solid.

37c

1-[2-(4,4-Dimethylcyclohex-1-enyl)phenyl]-4-isobutylpiperazinee hydrochloride

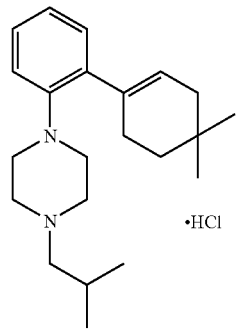

1-[2-(4,4-Dimethylcyclohex-1-enyl)phenyl]piperazine (200 mg, 0.740 mmol) prepared in Example (37b) was used as the starting material.

Reaction and treatment were carried out in a manner similar to Example (3h), to give 230 mg of 1-[2-(4,4-dimethylcyclohex-1-enyl)phenyl]-4-isobutylpiperazinee as a light yellow oil.

This was converted to a hydrochloride by a method similar to Example (3h) to give 255 mg of the title compound as a colorless solid.

MS m/e (ESI) 327 (MH$^+$).

Example 38

1-Cyclopropylmethyl-4-[2-(4,4-dimethylcyclohexyl)-4-(4-methoxypiperidin-1-yl)phenyl]piperazine hydrochloride

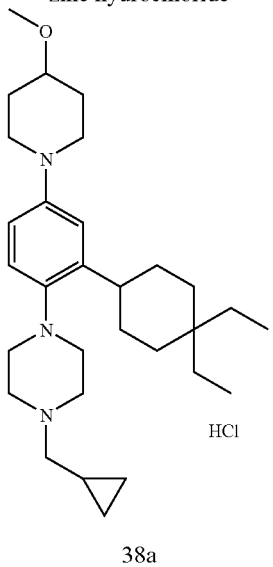

38a
4-[2-(4,4-Diethylcyclohex-1-enyl)phenyl]piperazine-1-carboxylic acid t-butyl ester

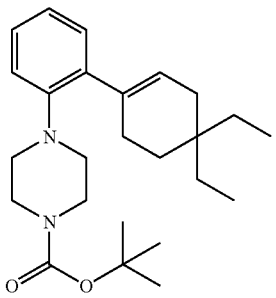

4-(2-Trifluoromethanesulfonyloxyphenyl)piperazine-1-carboxylic acid t-butyl ester (4.71 g, 11.5 mmol) prepared in Example (4d) was used as the starting material.
2-(4,4-Diethylcyclohex-1-enyl)-4,4,5,5-tetramethyl[1,3,2]dioxaborolane (3.7 g, 14.0 mmol) prepared in Example (6c) was used instead of 4,4,5,5-tetramethyl-2-(3,3,5,5-tetramethylcyclohex-1-enyl)[1,3,2]dioxaborolane for reaction in a manner similar to Example (4e) and treated in a similar manner, to give 3.94 g of the title compound as a brown oil.

38b
4-[2-(4,4-Diethylcyclohexyl)phenyl]piperazine-1-carboxylic acid t-butyl ester

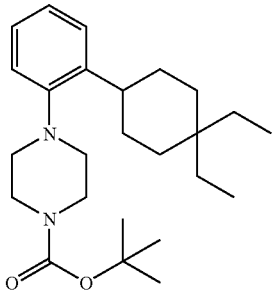

4-[2-(4,4-Diethylcyclohex-1-enyl)phenyl]piperazine-1-carboxylic acid t-butyl ester (3.96 g, 9.93 mmol) prepared in Example (38a) was used as the starting material.

Methanol alone was used as the solvent instead of a mixed solvent of tetrahydrofuran-methanol, for reaction in a manner similar to Example (8a) and treated in a similar manner. The resultant crude product was purified by silica gel column chromatography (ethyl acetate/hexane) to give 3.79 g of the title compound as a yellow oil.

38c
4-[4-Bromo-2-(4,4-dimethylcyclohexyl)phenyl]piperazine-1-carboxylic acid t-butyl ester

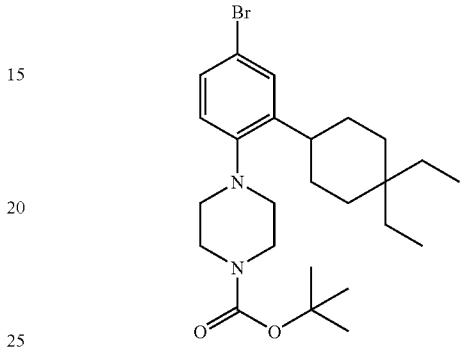

4-[2-(4,4-Diethylcyclohexyl)phenyl]piperazine-1-carboxylic acid t-butyl ester (3.79 g, 9.46 mmol) prepared in Example (38b) was used as the starting material.
This was reacted and treated in a manner similar to Example (3e), to give 2.75 g of the title compound as a white solid.

38d
4-[2-(4,4-Diethylcyclohexyl)-4-(4-methoxypiperidin-1-yl)phenyl]piperazine-1-carboxylic acid t-butyl ester

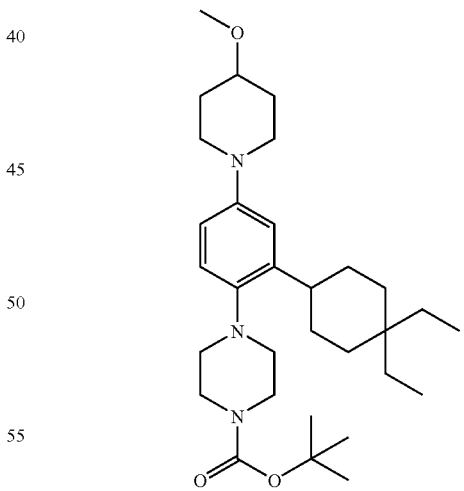

4-[4-Bromo-2-(4,4-dimethylcyclohexyl)phenyl]piperazine-1-carboxylic acid t-butyl ester (900 mg, 1.88 mmol) prepared in Example (38c) was dissolved in xylene (10 mL). 4-Methoxypiperidine hydrochloride (430 mg, 2.84 mmol) prepared in Example (7a), sodium t-butoxide (810 mg, 8.43 mmol), tri-t-butylphosphonium tetrafluoroborate (340 mg, 1.17 mmol) and palladium(II) acetate (105 mg, 0.47 mmol) were added to the mixed solution, and the mixture was stirred at an external temperature of 100° C. for 1 hour under nitrogen atmosphere.

Treatment was then carried out in a manner similar to Example (3f) to give 413 mg of the title compound as a light red solid.

38e

1-[2-(4,4-Diethylcyclohexyl)-4-(4-methoxypiperidin-1-yl)phenyl]piperazine

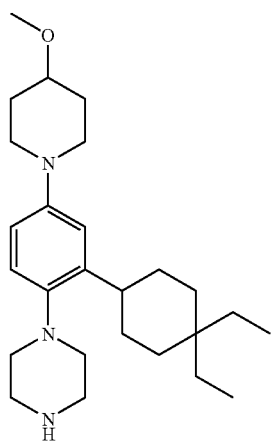

4-[2-(4,4-Diethylcyclohexyl)-4-(4-methoxypiperidin-1-yl)phenyl]piperazine-1-carboxylic acid t-butyl ester (413 mg, 0.80 mmol) prepared in Example (38d) was used as the starting material.

This was reacted in a manner similar to Example (8b), and treated in a similar manner using potassium carbonate instead of 5N aqueous sodium hydroxide, to give 283 mg of the title compound as a white solid.

38f

1-Cyclopropylmethyl-4-[2-(4,4-dimethylcyclohexyl)-4-(4-methoxypiperidin yl)phenyl]piperazine hydrochloride

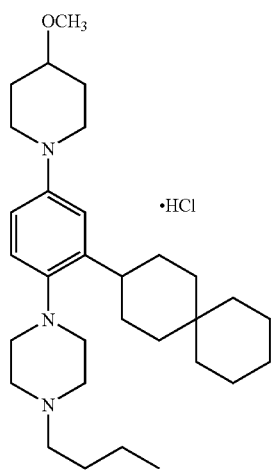

1-[2-(4,4-Diethylcyclohexyl)-4-(4-methoxypiperidin-1-yl)phenyl]piperazine (50 mg, 0.121 mmol) prepared in Example (38e) was used as the starting material.

This was reacted and treated in a manner similar to Example (9). The product was then converted to a hydrochloride by a method similar to Example (9) to give 60 mg of the title compound as a white solid.

MS m/e (ESI) 468 (MH$^+$).

Example 39

1-Butyl-4-[4-(4-methoxypiperidin-1-yl)-2-spiro[5.5]undec-3-yl-phenyl]piperazine

39a

Trifluoromethanesulfonic acid spiro[5.5]undec-2-en-3-yl ester

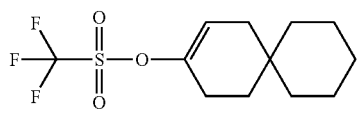

Spiro[5.5]undecan-3-one (15 g, 90.2 mmol) was used as the starting material instead of 4,4-diethylcyclohexanone for reaction in a manner similar to Example (6b) and treated in a similar manner, to give 20.9 g of the title compound as a brown oil.

39b 4,4,5,5-Tetramethyl-2-spiro[5.5]undec-2-en-3-yl-[1,3,2]dioxaborolane

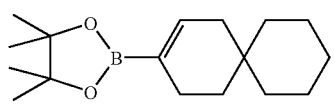

Trifluoromethanesulfonic acid spiro[5.5]undec-2-en-3-yl ester (10 g, 33.5 mmol) prepared in Example (39a) was used as the starting material instead of trifluoromethanesulfonic acid 4,4-diethylcyclohex-1-enyl ester for reaction in a manner similar to Example (6c) and treated in a similar manner, to give 7.64 g of the title compound as a yellow solid.

39c

4-Methoxy-1-(4-nitro-3-spiro[5.5]undec-2-en-3-yl-phenyl)piperidine

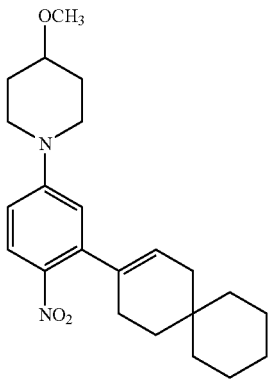

Trifluoromethanesulfonic acid 5-(4-methoxypiperidin-1-yl)-2-nitrophenyl ester (2.0 g, 5.43 mmol) prepared in Example (7c) was used as the starting material. 4,4,5,5-Tetramethyl-2-spiro[5.5]undec-2-en-3-yl-[1,3,2]dioxaborolane (1.65 g, 5.97 mmol) prepared in Example (39b) was used instead of 4-t-butylcyclohex-1-enyl-(4,4,5,5-tetramethyl)-[1,3,2]dioxaborolane for reaction in a manner similar to Example (7e) and treated in a similar manner, to give 2.331 g of the title compound as an orange oil.

39d

4-(4-Methoxypiperidin-1-yl)-2-spiro[5.5]undec-2-en-3-yl)phenylamine

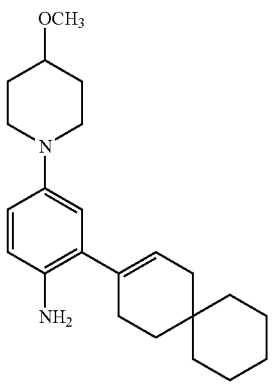

4-Methoxy-1-(4-nitro-3-spiro[5.5]undec-2-en-3-yl-phenyl)piperidine (2.331 g, 6.06 mmol) prepared in Example (39c) was used as the starting material for reaction in a manner similar to Example (6e) and treated in a similar manner, to give 1.79 g of the title compound as a yellow oil.

39e

1-[4-(4-Methoxypiperidin-1-yl)-2-spiro[5.5]undec-2-en-3-yl-phenyl]piperazine

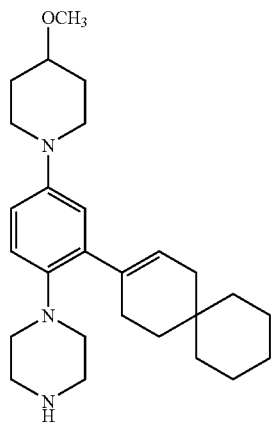

4-(4-Methoxypiperidin-1-yl)-2-spiro[5.5]undec-2-en-3-yl)phenylamine (1.79 g, 5.03 mmol) prepared in Example (39d) was used as the starting material for reaction in a manner similar to Example (7g) and treated in a similar manner, to give 1.071 g of the title compound as a light yellow solid.

39f

4-[4-(4-Methoxypiperidin-1-yl)-2-spiro[5.5]undec-2-en-3-ylphenyl]piperazine-1-carboxylic acid t-butyl ester

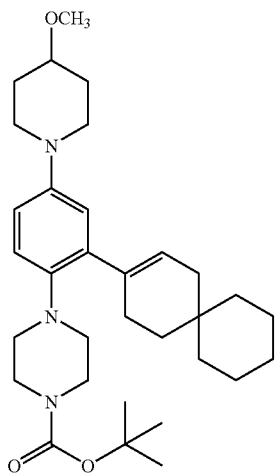

1-[4-(4-Methoxypiperidin-1-yl)-2-spiro[5.5]undec-2-en-3-yl-phenyl]piperazine (450 mg, 1.062 mmol) prepared in Example (39e) was used as the starting material for reaction in a manner similar to Example (3d) and treated in a similar manner, to give 524 mg of the title compound as a colorless solid.

39g

4-[4-(4-Methoxypiperidin-1-yl)-2-spiro[5.5]undec-3-ylphenyl]piperazine-1-carboxylic acid t-butyl ester

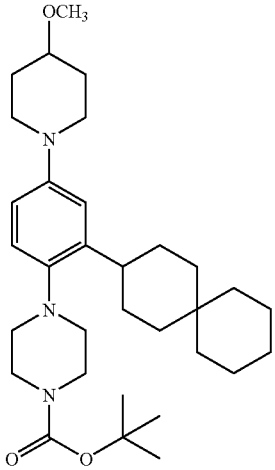

4-[4-(4-Methoxypiperidin-1-yl)-2-spiro[5.5]undec-2-en-3-ylphenyl]piperazine-1-carboxylic acid t-butyl ester (524 mg, 1.0 mmol) prepared in Example (39f) was used as the starting material. A mixed solution of methanol, tetrahydrofuran and ethyl acetate was used instead of a mixed solvent of methanol and tetrahydrofuran for reaction in a manner similar to Example (8a) and treated in a similar manner, to give 517 mg of the title compound as a colorless solid.

39h

1-[4-(4-Methoxypiperidin-1-yl)-2-spiro[5.5]undec-3-ylphenyl]piperazine

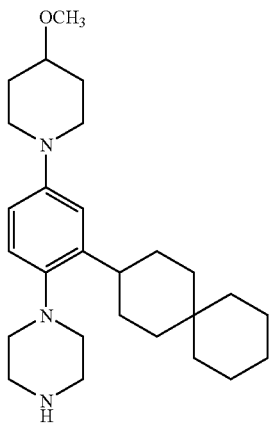

4-[4-(4-Methoxypiperidin-1-yl)-2-spiro[5.5]undec-3-ylphenyl]piperazine-1-carboxylic acid t-butyl ester (517 mg, 0.983 mmol) prepared in Example (39g) was used as the starting material for reaction in a manner similar to Example (8b) and treated in a similar manner, to give 367 mg of the title compound as a light yellow solid.

39i

1-Butyl-4-[4-(4-methoxypiperidin-1-yl)-2-spiro[5.5]undec-3-ylphenyl]piperazine hydrochloride

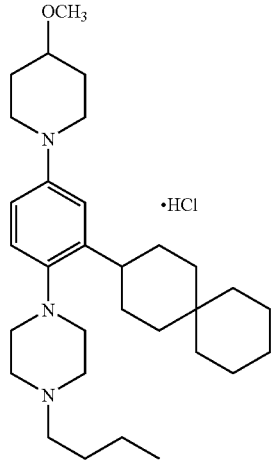

1-[4-(4-Methoxypiperidin-1-yl)-2-spiro[5.5]undec-3-ylphenyl]piperazine (50 mg, 0.117 mmol) prepared in Example (39h) was used as the starting material for reaction in a manner similar to Example (7h) and treated in a similar manner, to give 23 mg of 1-butyl-4-[4-(4-methoxypiperidin-1-yl)-2-spiro[5.5]undec-3-ylphenyl]piperazine as a colorless solid.

This was converted to a hydrochloride by a method similar to Example (7h) to give 28 mg of the title compound as a colorless solid.

MS m/e (ESI) 482 (MH$^+$).

Example 40

{4-[2-(3,3,5,5-Tetramethylcyclohexyl)phenyl]piperazin-1-yl}acetonitrile hydrochloride

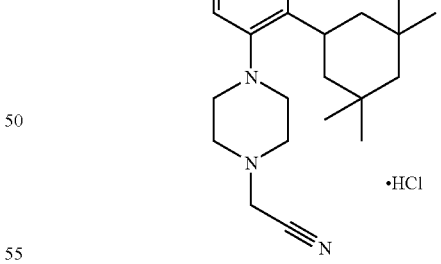

1-[2-(3,3,5,5-Tetramethylcyclohexyl)phenyl]piperazine (40 mg, 0.133 mmol) prepared in Example (8b) was used as the starting material.

Bromoacetonitrile was used instead of 2-chloro-N-ethylacetamide for reaction in a manner similar to Example (10b) and treated in a similar manner.

The obtained product was then converted to a hydrochloride by a method similar to Example (10b) to give 28 mg of the title compound as a colorless solid.

MS m/e (ESI) 340 (MH$^+$).

Example 41

1-(2-Ethoxyethyl)-4-[2-(3,3,5,5-tetramethylcyclohexyl)phenyl]piperazine hydrochloride

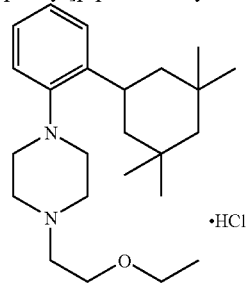

1-[2-(3,3,5,5-Tetramethylcyclohexyl)phenyl]piperazine (40 mg, 0.133 mmol) prepared in Example (8b) was used as the starting material.

2-Bromoethyl ethyl ether was used instead of 2-chloro-N-ethylacetamide for reaction in a manner similar to Example (10b) and treated in a similar manner.

The obtained product was then converted to a hydrochloride by a method similar to Example (10b) to give 34 mg of the title compound as a colorless solid.

MS m/e (ESI) 373 (MH$^+$).

Example 42

1-Cyclopropylmethyl-4-[2-(4,4-dimethylcyclohexyl)-4-piperidin-1-ylphenyl]piperazine hydrochloride

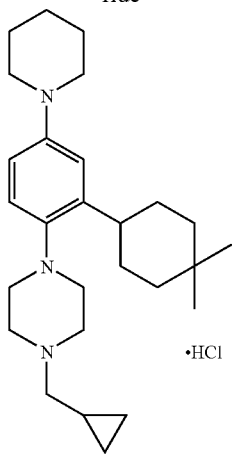

42a

4-[2-(4,4-Dimethylcyclohexyl)-4-piperidin-1-ylphenyl]piperazine-1-carboxylic acid t-butyl ester

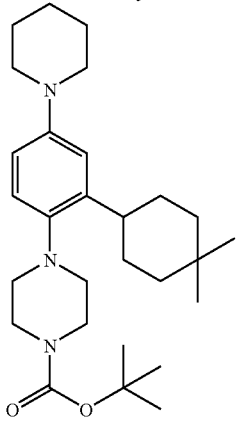

4-[4-Bromo-2-(4,4-dimethylcyclohexyl)phenyl]piperazine-1-carboxylic acid t-butyl ester (800 mg, 1.77 mmol) prepared in Example (3e) was used as the starting material.

Piperidine was used instead of morpholine for reaction in a manner similar to Example (3f) and treated in a similar manner, to give 597 mg of the title compound as a colorless solid.

42b

1-[2-(4,4-Dimethylcyclohexyl)-4-piperidin-1-ylphenyl]piperazine

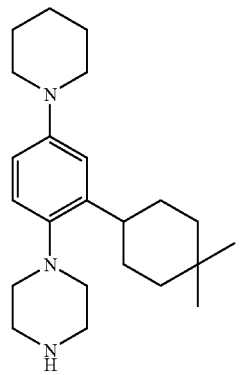

4-[2-(4,4-dimethylcyclohexyl)-4-piperidin-1-ylphenyl]piperazine-1-carboxylic acid t-butyl ester (597 mg, 1.31 mmol) prepared in Example (42a) was used as the starting material.

Reaction and treatment were carried out in a manner similar to Example (3g), to give 419 mg of the title compound as a colorless solid.

42c

1-Cyclopropylmethyl-4-[2-(4,4-dimethylcyclohexyl)-4-piperidin-1-ylphenyl]piperazine hydrochloride

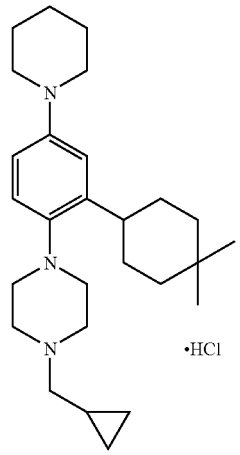

1-[2-(4,4-Dimethylcyclohexyl)-4-piperidin-1-ylphenyl]piperazine (50 mg, 0.141 mmol) prepared in Example (42b) was used as the starting material.

Cyclopropanecarbaldehyde was used instead of isobutyraldehyde for reaction in a manner similar to Example (3h) and treated in a similar manner.

The obtained product was then converted to a hydrochloride by a method similar to Example (3h) to give 65 mg of the title compound as a colorless solid.

MS m/e (ESI) 410 (MH$^+$).

Example 43

4-[4-(4-Butylpiperazin-1-yl)-5-(4,4-dimethylcyclohexyl)-2-methoxyphenyl]-morpholine hydrochloride

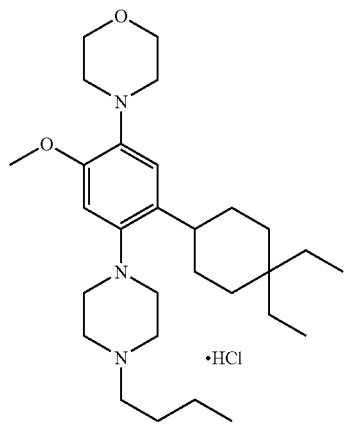

43a

4-[2-(4,4-Diethylcyclohex-1-enyl)-5-methoxyphenyl]piperazine-1-carboxylic acid t-butyl ester

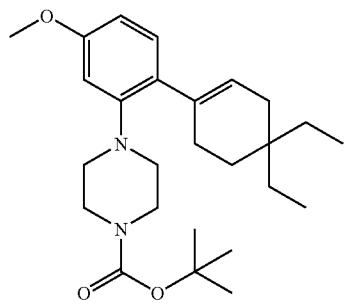

1-[2-(4,4-Diethylcyclohex-1-enyl)-5-methoxyphenyl]piperazine (0.9 g, 2.7 mmol) prepared in Example (6f) was used for reaction in a manner similar to Example (3d) and treated in a similar manner, using tetrahydrofuran instead of dichloromethane as the solvent according to Example (3d), to give 0.96 g of the title compound as a light yellow oil.

43b

1-[2-(4,4-Diethylcyclohexyl)-5-methoxyphenyl]piperazine-1-carboxylic acid t-butyl ester

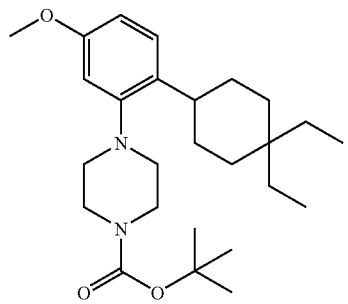

4-[2-(4,4-diethylcyclohex-1-enyl)-5-methoxyphenyl]piperazine-1-carboxylic acid t-butyl ester (0.96 g, 2.2 mmol) prepared in Example (43a) was used for reaction in a manner similar to Example (8a) and treated in a similar manner, using methanol instead of a mixed solvent of methanol and tetrahydrofuran, to give 0.95 g of the title compound as a light yellow oil.

43c

4-[4-Bromo-2-(4,4-dimethylcyclohexyl)-5-methoxyphenyl]piperazine-1-carboxylic acid t-butyl ester

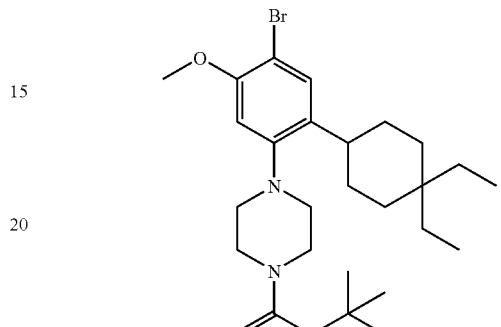

Reaction was carried out in a manner similar to Example (3e), using as the starting material the 1-[2-(4,4-dimethylcyclohexyl)-5-methoxyphenyl]piperazine-1-carboxylic acid t-butyl ester (0.9 g, 2.08 mmol) prepared in Example (43b) according to Example (3e), and using acetonitrile instead of methanol and N-bromosuccinimide instead of bromine. Saturated aqueous sodium hydrogencarbonate was added to the reaction mixture and the mixture was extracted with ethyl acetate, after which treatment was carried out in a similar manner to give 0.41 g of the title compound as a light yellow oil.

43d

4-[2-(4,4-Diethylcyclohexyl)-4-morpholino-5-methoxyphenyl]piperazine-1-carboxylic acid t-butyl ester

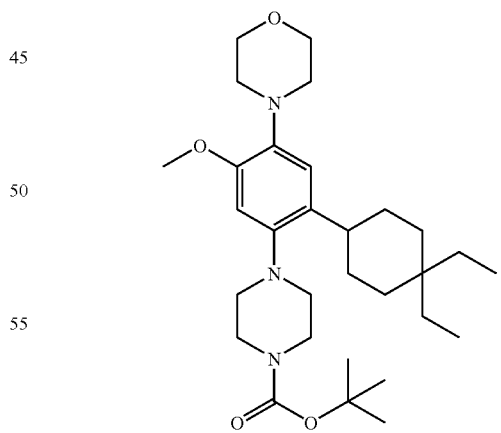

Reaction and treatment were carried out in a manner similar to Example (3f), using 4-[4-bromo-2-(4,4-dimethylcyclohexyl)-5-methoxyphenyl]piperazine-1-carboxylic acid t-butyl ester (200 mg, 0.39 mmol) prepared in Example (43c) as the starting material and using tri-t-butylphosphine instead of tri-t-butylphosphonium tetrafluoroborate, to give 80 mg of the title compound as a yellow oil.

43e

4-[5-(4,4-Diethylcyclohexyl)-2-methoxy-4-piperazin-1-ylphenyl]morpholine

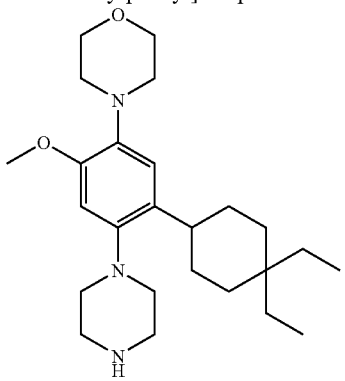

Reaction and treatment were carried out in a manner similar to Example (8b), using 4-[2-(4,4-dimethylcyclohexyl)-4-morpholino-5-methoxyphenyl]piperazine-1-carboxylic acid t-butyl ester (80 mg, 0.2 mmol) prepared in Example (43d) to give 40 mg of the title compound as a yellow solid.

43f

4-[4-(4-Butylpiperazin-1-yl)-5-(4,4-dimethylcyclohexyl)-2-methoxyphenyl]-morpholine hydrochloride

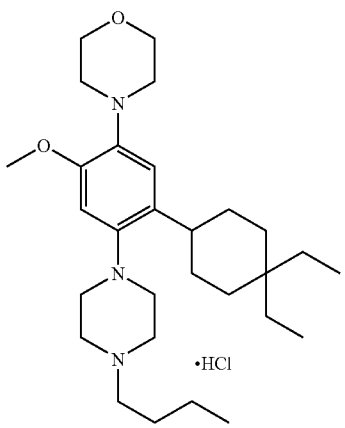

4-[5-(4,4-Diethylcyclohexyl)-2-methoxy-4-piperazin-1-ylphenyl]morpholine (20 mg, 0.048 mmol) prepared in Example (43e) was reacted and treated in a manner similar to Example (6g), using butyraldehyde instead of tetrahydropyran-4-carbaldehyde, to give 11 mg of the title compound as a light yellow solid.

MS m/e (ESI) 472 (MH+).

Example 44

1-Butyl-4-(2-cycloheptylphenyl)piperazine hydrochloride

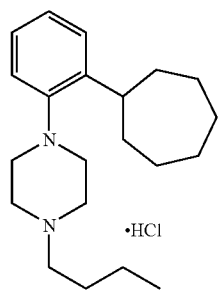

44a 1-(2-Nitrophenyl)cycloheptene

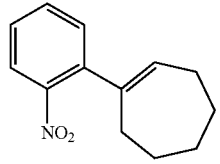

A mixture of trifluoromethanesulfonic acid cyclopent-1-enyl ester (2.50 g, 10.2 mmol), 2-nitrophenylboronic acid (2.04 g, 12.2 mmol), tetrakis(triphenylphosphine)palladium (0) (612 mg, 0.53 mmol), 2N aqueous solution of sodium carbonate (10.2 mL), toluene (32 mL) and ethanol (16 mL) was stirred for 2 hours and 30 minutes at an external temperature of 90° C. under a nitrogen atmosphere.

Ethyl acetate and brine were added to the reaction mixture and extraction was performed twice with ethyl acetate. The separated organic layer was dried over anhydrous sodium sulfate. The desiccant was filtered off and the filtrate was concentrated under reduced pressure. The obtained residue was purified by silica gel column chromatography (ethyl acetate/heptane) to give 1.937 g of the title compound as a light yellow oil.

$^1$H-NMR (400 MHz, CDCl$_3$) δ: 1.55-1.67 (m, 4H), 1.78-1.84 (m, 2H), 2.25-2.29 (m, 2H), 2.42-2.44 (m, 2H), 5.83 (t, J=6.4 Hz, 1H), 7.28 (dd, J=7.6, 1.2 Hz, 1H), 7.34 (ddd, J=8.0, 7.6, 1.2 Hz, 1H), 7.49 (ddd, J=7.6, 7.6, 1.2 Hz, 1H), 7.81 (dd, J=8.0, 1.2 Hz, 1H).

44b

2-Cycloheptylphenylamine

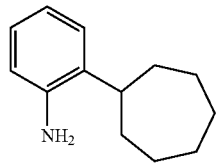

A mixture of the 1-(2-nitrophenyl)cycloheptene (1.00 g, 4.61 mmol) produced in Example (44a), 10% palladium on carbon (300 mg, wet) and methanol (130 mL) was stirred for 21 hours at atmospheric pressure and room temperature under a hydrogen atmosphere. The reaction mixture was filtered and the filtrate was concentrated under reduced pressure. The obtained residue was purified by silica gel column chromatography (ethyl acetate/heptane) to give 539 mg of the title compound as a light orange oil.

$^1$H-NMR (400 MHz, CDCl$_3$) δ: 1.49-1.78 (m, 8H), 1.80-1.87 (m, 2H), 1.91-1.96 (m, 2H), 2.60-2.70 (m, 1H), 3.61 (brs, 2H), 6.67 (dd, J=7.6, 1.2 Hz, 1H), 6.76 (dd, J=7.6, 7.6 Hz, 1H), 6.99 (ddd, J=7.6, 7.6, 1.2 Hz, 1H), 7.11 (d, J=7.6 Hz, 1H).

44c 1-(2-Cycloheptylphenyl)piperazine

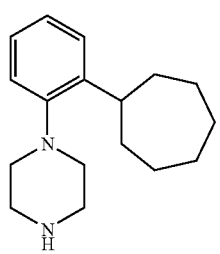

To a solution of the 2-cycloheptylphenylamine (539 mg, 2.85 mmol) produced in Example (44b) in 1,2-dichlorobenzene (7 mL) was added bis(2-chloroethyl)amine hydrochloride (610 mg, 3.42 mmol), and the mixture was stirred at an external temperature of 200° C. under a nitrogen atmosphere. During the reaction, a nitrogen stream was blown into the reactor to remove the hydrogen chloride gas in the reactor. This procedure was repeated several times. After 8 hours, the mixture was air-cooled to room temperature. To the reaction mixture were added aqueous solution of potassium carbonate, ethyl acetate and methanol, and extraction was performed three times with ethyl acetate. The obtained organic layers were dried over anhydrous sodium sulfate, and then the desiccant was filtered off and the filtrate was concentrated under reduced pressure. The obtained residue was purified by NH silica gel column chromatography (ethyl acetate/heptane) to give 540 mg of the title compound as a brown oil.

$^1$H-NMR (400 MHz, CDCl$_3$) δ: 1.50-1.84 (m, 12H), 2.82-2.84 (m, 4H), 3.01-3.03 (m, 4H), 3.28 (tt, J=10.0, 2.8 Hz, 1H), 7.03-7.07 (m, 2H), 7.12 (ddd, J=8.4, 6.8, 1.6 Hz, 1H), 7.20 (dd, J=7.6, 1.6 Hz, 1H).

The 1H of NH could not be identified.

44d

1-Butyl-4-(2-cycloheptylphenyl)piperazine hydrochloride

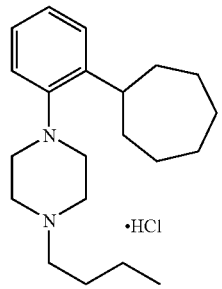

To a mixture of the 1-(2-cycloheptylphenyl)piperazine (25 mg, 0.0967 mmol) produced in Example (44c) and tetrahydrofuran (1 mL) were added butyraldehyde (0.011 mL, 0.126 mmol), sodium triacetoxyborohydride (26.6 mg, 0.126 mmol) and acetic acid (0.011 mL, 0.183 mmol), and the mixture was stirred for 19 hours and 30 minutes at room temperature. Saturated aqueous solution of sodium hydrogencarbonate was added to the reaction mixture and extraction was performed three times with ethyl acetate. The obtained organic layers were concentrated. The resultant residue was purified by NH silica gel column chromatography (ethyl acetate/heptane) to give 26.7 mg of 1-butyl-4-(2-cycloheptylphenyl)piperazine as a colorless oil.

$^1$H-NMR (400 MHz, CDCl$_3$) δ: 0.95 (t, J=7.2 Hz, 3H), 1.32-1.41 (m, 2H), 1.49-1.84 (m, 14H), 2.39-2.43 (m, 2H), 2.61 (brs, 4H), 2.89-2.92 (m, 4H), 3.27 (tt, J=10.0, 3.2 Hz, 1H), 7.03-7.15 (m, 3H), 7.21 (dd, J=7.6, 1.6 Hz, 1H).

This compound was dissolved in dichloromethane (1 mL) and a 4N solution of hydrogen chloride in ethyl acetate (0.0425 mL, 0.17 mmol) was added. This solution was concentrated under reduced pressure, and diethyl ether was added to the resultant residue to produce a solid, which was then triturated by sonication. This solid was filtered and then dried under reduced pressure to give 28.5 mg of the title compound as a colorless solid.

MS m/e (ESI) 315 (MH$^+$).

Example 45

1-Butyl-4-(2-cyclohept-1-enylphenyl)piperazine hydrochloride

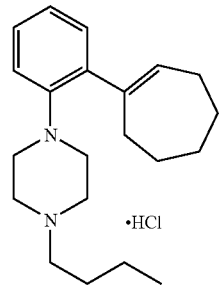

45a 1-(2-Cyclohept-1-enylphenyl)piperazine

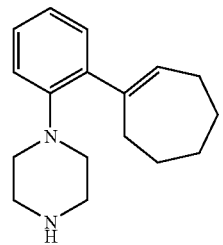

To a solution of 2-cyclohept-1-enylphenylamine (617 mg, 3.29 mmol) in 1,2-dichlorobenzene (8 mL) was added bis(2-chloroethyl)amine hydrochloride (705 mg, 3.95 mmol), and the mixture was stirred at an external temperature of 200° C. under a nitrogen atmosphere. During the reaction, a nitrogen stream was blown into the reactor to remove the hydrogen chloride gas in the reactor. This procedure was repeated several times. After 5 hours, the reaction mixture was air-cooled to room temperature, and then aqueous solution of potassium carbonate, ethyl acetate and methanol were added to the reaction mixture and extraction was performed three times with ethyl acetate. The obtained organic layers were dried over anhydrous sodium sulfate, and then the desiccant was filtered off and the filtrate was concentrated under reduced pressure. The resultant residue was purified by NH silica gel column chromatography (ethyl acetate/heptane) to give 387 mg of the title compound as a brown oil.

$^1$H-NMR (400 MHz, CDCl$_3$) δ: 1.54-1.63 (m, 4H), 1.78-1.84 (m, 2H), 2.23-2.27 (m, 2H), 2.55-2.58 (m, 2H), 2.92-3.01 (m, 8H), 5.85 (t, J=6.4 Hz, 1H), 6.94-6.98 (m, 2H), 7.09 (ddd, J=7.6, 1.6, 1.6 Hz, 1H), 7.20 (ddd, J=8.0, 7.6, 1.6 Hz, 1H).

The 1H of NH could not be identified.

45b

1-Butyl-4-(2-cyclohept-1-enylphenyl)piperazine hydrochloride

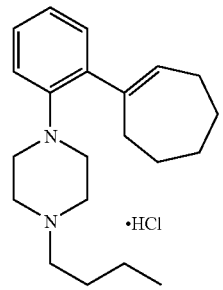

To a solution of the 1-(2-cyclohept-1-enylphenyl)piperazine (20 mg, 0.0780 mmol) produced in Example (45a) in tetrahydrofuran (1 mL) were added butyraldehyde (0.009 mL, 0.1014 mmol), sodium triacetoxyborohydride (21.5 mg, 0.1014 mmol) and acetic acid (0.009 mL, 0.1482 mmol), and the mixture was stirred for 23 hours and 10 minutes at room temperature.

Saturated aqueous solution of sodium hydrogencarbonate was added to the reaction mixture and extraction was performed three times with ethyl acetate. The organic layers was concentrated to produce a residue, which was purified by NH silica gel column chromatography (ethyl acetate/heptane) to give 19 mg of 1-butyl-4-(2-cyclohept-1-enylphenyl)piperazine as a colorless oil.

$^1$H-NMR (400 MHz, CDCl$_3$) δ: 0.94 (t, J=7.2 Hz, 3H), 1.35 (tq, J=7.2, 7.2 Hz, 2H), 1.48-1.61 (m, 8H), 1.78-1.84 (m, 2H), 2.23-2.27 (m, 2H), 2.37-2.40 (m, 2H), 2.54-2.57 (m, 4H), 3.03 (brs, 4H), 5.85 (t, J=6.4 Hz, 1H), 6.93-6.99 (m, 2H), 7.08 (dd, J=7.6, 1.6 Hz, 1H), 7.19 (ddd, J=8.8, 7.2, 1.6 Hz, 1H).

This compound was dissolved in dichloromethane (1 mL) and a 4N solution of hydrogen chloride in ethyl acetate (0.0304 mL, 0.1216 mmol) was added.

The resulting solution was concentrated by nitrogen stream, and then diethyl ether was added to the resultant residue to produce a solid. The solid was triturated by sonication and the supernatant diethyl ether solution was removed. It was then dried under reduced pressure to give 20.3 mg of the title compound as a colorless solid.

MS m/e (ESI) 313 (MH$^+$).

Example 46

1-(2-Cyclooctylphenyl)-4-isobutylpiperazinee hydrochloride

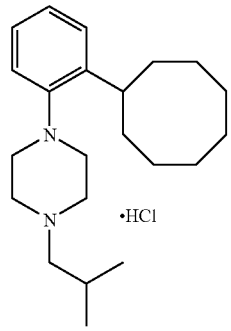

46a 1-(2-Cyclooct-1-enylphenyl)piperazine

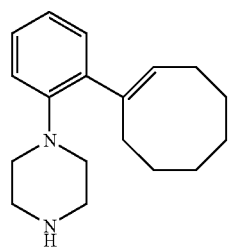

To a solution of 2-cyclooct-1-enylphenylamine (140 mg, 0.695 mmol) in 1,2-dichlorobenzene (2 mL) was added bis (2-chloroethyl)amine hydrochloride (149 mg, 0.835 mmol), and the mixture was stirred at an external temperature of 200° C. under a nitrogen atmosphere. During the reaction, a nitrogen stream was blown into the reactor to remove the hydrogen chloride gas in the reactor. This procedure was repeated several times. After 9 hours, the mixture was air-cooled to room temperature. Aqueous solution of potassium carbonate, ethyl acetate and methanol were added to the reaction mixture and extraction was performed three times with ethyl acetate. The obtained organic layers were dried over anhydrous sodium sulfate. The desiccant was filtered off and the filtrate was concentrated under reduced pressure. The resultant residue was purified by NH silica gel column chromatography (ethyl acetate/heptane) to give 100 mg of the title compound as a brown oil.

$^1$H-NMR (400 MHz, CDCl$_3$) δ: 1.35-1.77 (m, 8H), 2.23-2.28 (m, 2H), 2.74-2.77 (m, 2H), 2.94-3.02 (m, 8H), 5.63 (t, J=8.0 Hz, 1H), 6.93-6.97 (m, 2H), 7.08 (dd, J=7.6, 2.0 Hz, 1H), 7.21 (ddd, J=7.6, 7.6, 2.0 Hz, 1H).

The 1H of NH could not be identified.

46b 4-(2-Cyclooct-1-enylphenyl)piperazine-1-carboxylic acid t-butyl ester

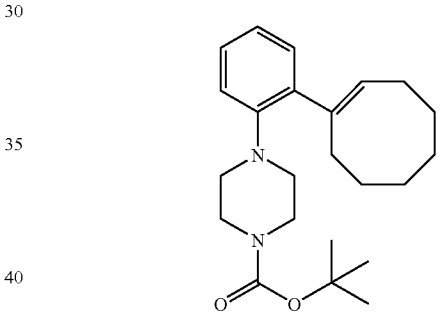

To 1-(2-cyclooct-1-enylphenyl)piperazine (100 mg, 0.37 mmol) produced in Example (46a) dissolved in dichloromethane (2.3 mL) were added di-t-butyl dicarbonate (96.9 mg, 0.444 mmol) and triethylamine (0.0645 mL, 0.463 mmol), and the mixture was stirred for 13 hours at room temperature. Then, di-t-butyl dicarbonate (15 mg, 0.0687 mmol) and 4-dimethylaminopyridine (10 mg, 0.0819 mmol) were further added thereto and followed by stirring for 30 minutes at room temperature.

Brine was added to the reaction mixture and extraction was performed twice with dichloromethane. The separated organic layer was dried over anhydrous sodium sulfate. The desiccant was filtered off and the filtrate was concentrated under reduced pressure. The resultant residue was purified by NH silica gel column chromatography (ethyl acetate/heptane) to give 128 mg of the title compound as a light yellow oil.

$^1$H-NMR (400 MHz, CDCl$_3$) δ: 1.35-1.70 (m, 17H), 2.23-2.28 (m, 2H), 2.71-2.74 (m, 2H), 2.95-2.98 (m, 4H), 3.47-3.50 (m, 4H), 5.62 (t, J=8.0 Hz, 1H), 6.91 (dd, J=7.6, 1.6 Hz, 1H), 6.96 (ddd, J=7.6, 7.6, 1.6 Hz, 1H), 7.08 (dd, J=7.6, 1.6 Hz, 1H), 7.21 (ddd, J=7.6, 7.6, 1.6 Hz, 1H).

46c

4-(2-Cyclooctylphenyl)piperazine-1-carboxylic acid t-butyl ester

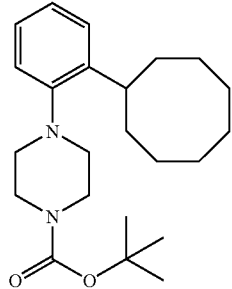

A mixture of the 4-(2-cyclooct-1-enylphenyl)piperazine-1-carboxylic acid t-butyl ester (128 mg, 0.345 mmol) produced in Example (46b), 10% palladium on carbon (50 mg, wet) and methanol (8 mL) was stirred for 3 hours at atmospheric pressure and room temperature under a hydrogen atmosphere.

The reaction mixture was filtered and the filtrate was concentrated under reduced pressure. To the resultant residue was added a mixture of 10% palladium on carbon (130 mg, wet) and methanol (5 mL)-tetrahydrofuran (3 mL), followed by stirring for 1 hour and 30 minutes at room temperature under hydrogen atmosphere at 4-5 atm.

The reaction mixture was filtered and the obtained filtrate was concentrated under reduced pressure to give a crude product of the title compound as a light yellow oil. This product was directly used without purification for the following reaction.

46d

1-(2-Cyclooctylphenyl)piperazine

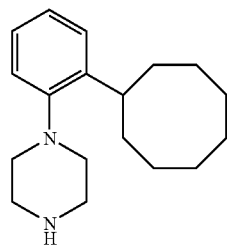

To a mixture of the crude product of 4-(2-cyclooctylphenyl)piperazine-1-carboxylic acid t-butyl ester produced in Example (46c), 1,2-dichloroethane (2 mL) and water (0.2 mL) was added trifluoroacetic acid (0.500 mL, 6.490 mmol), followed by stirring for 5 hours and 30 minutes at room temperature. Aqueous solution of potassium carbonate was added to the mixture to make the mixture basic. Ethyl acetate was then added thereto and extraction was performed three times with ethyl acetate. The organic layers were dried over anhydrous sodium sulfate. The desiccant was filtered off and the filtrate was concentrated under reduced pressure. The resultant residue was purified by NH silica gel column chromatography (ethyl acetate/heptane) to give 75 mg of the title compound as a light yellow oil.

$^1$H-NMR (400 MHz, CDCl$_3$) δ: 1.55-1.72 (m, 14H), 2.83-2.85 (m, 4H), 3.02-3.05 (m, 4H), 3.48-3.54 (m, 1H), 7.03-7.14 (m, 3H), 7.19 (dd, J=7.6, 4.4 Hz, 1H).

The 1H of NH could not be identified.

46e

1-(2-Cyclooctylphenyl)-4-isobutylpiperazinee hydrochloride

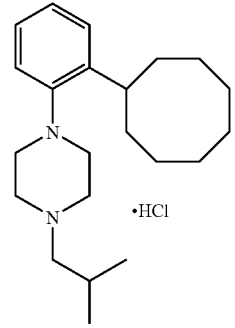

To a solution of the 1-(2-cyclooctylphenyl)piperazine (7 mg, 0.0257 mmol) produced in Example (46d) in tetrahydrofuran (1 mL) were added isobutyraldehyde (2.4 mg, 0.0334 mmol), sodium triacetoxyborohydride (7.1 mg, 0.0334 mmol) and acetic acid (0.0028 mL, 0.0448 mmol), followed by stirring for 17 hours and 10 minutes at room temperature. Saturated aqueous solution of sodium hydrogencarbonate was added to the reaction mixture and extraction was performed three times with ethyl acetate. The organic layers was concentrated to produce a residue, which was purified by NH silica gel column chromatography (ethyl acetate/heptane) to give 4.3 mg of 1-(2-cyclooctylphenyl)-4-isobutylpiperazinee as a colorless oil.

$^1$H-NMR (400 MHz, CDCl$_3$) δ: 0.93 (d, J=6.8 Hz, 6H), 1.46-1.88 (m, 15H), 2.16 (d, J=7.2 Hz, 2H), 2.55 (brs, 4H), 2.88-2.90 (m, 4H), 3.46-3.52 (m, 1H), 7.02-7.13 (m, 3H), 7.18 (dd, J=7.2, 1.6 Hz, 1H).

This compound was dissolved in dichloromethane (1 mL), and then a 4N solution of hydrogen chloride in ethyl acetate (0.0066 mL, 0.0262 mmol) was added. The mixture was concentrated under reduced pressure, and diethyl ether was added to the obtained residue to produce a solid, which was then triturated by sonication. The supernatant diethyl ether solution was removed and the resulting solid residue was dried under reduced pressure to give 4.4 mg of the title compound as a colorless solid.

MS m/e (ESI) 329 (MH$^+$).

Example 47

1-Butyl-4-(2-cyclooct-1-enylphenyl)piperazine hydrochloride

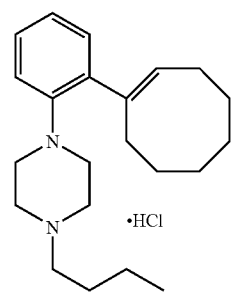

To a solution of 1-(2-cyclooct-1-enylphenyl)piperazine (11 mg, 0.0407 mmol) produced in Example (46a) in tetrahydrofuran (1 mL) were added butyraldehyde (0.0047 mL, 0.0529 mmol), sodium triacetoxyborohydride (11.2 mg, 0.0529 mmol) and acetic acid (0.0044 mL, 0.0773 mmol), followed by stirring for 14 hours and 20 minutes at room temperature. Saturated aqueous solution of sodium hydrogencarbonate was added to the reaction mixture and extraction was performed three times with ethyl acetate. The organic layer was concentrated to produce a residue, which was purified by NH silica gel column chromatography (ethyl acetate/heptane) to give 9.9 mg of 1-butyl-4-(2-cyclooct-1-enylphenyl)piperazine as a colorless oil.

¹H-NMR (400 MHz, CDCl₃) δ: 0.93 (t, J=7.6 Hz, 3H), 1.30-1.62 (m, 12H), 2.23-2.28 (m, 2H), 2.35-2.39 (m, 2H), 2.54 (brs, 4H), 2.73-2.76 (m, 2H), 3.07 (brs, 4H), 5.63 (t, J=8.4 Hz, 1H), 6.92-6.96 (m, 2H), 7.07 (dd, J=7.6, 2.0 Hz, 1H), 7.20 (ddd, J=8.8, 7.6, 2.0 Hz, 1H).

This compound was dissolved in dichloromethane (1 mL) and a 4N solution of hydrogen chloride in ethyl acetate (0.015 mL, 0.0606 mmol) was added.

The solution was concentrated under reduced pressure, and diethyl ether was added to the obtained residue to produce a solid, which was then triturated by sonication. The supernatant diethyl ether solution was removed and the resulting solid residue was dried under reduced pressure to give 10.9 mg of the title compound as a light brown solid.

MS m/e (ESI) 327 (MH⁺).

Example 48

1-(2-Methoxyethyl)-4-[4-(4-methoxypiperidin-1-yl)-2-spiro[5.5]undec-2-en-3-ylphenyl]piperazine hydrochloride

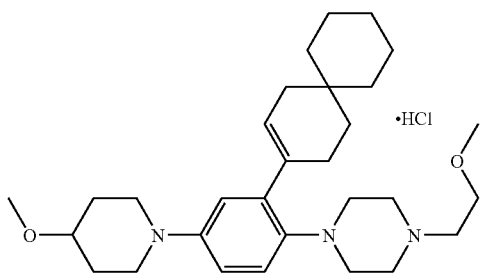

A mixture of 1-[4-(4-methoxypiperidin-1-yl)-2-spiro[5.5]undec-2-en-3-yl-phenyl]piperazine (20 mg, 0.0472 mmol) produced in Example (39e), 2-bromoethyl methyl ether (0.0049 mL, 0.0519 mmol), potassium carbonate (11.1 mg, 0.0803 mmol) and acetonitrile (1 mL) was stirred for 5 hours at an external temperature of 80° C. Ethyl acetate and brine were added to the reaction mixture and extraction was performed three times with ethyl acetate. The separated organic layers were concentrated. The resultant residue was purified by NH silica gel column chromatography (ethyl acetate/hexane) to give 1-(2-methoxyethyl)-4-[4-(4-methoxypiperidin-1-yl)-2-spiro[5.5]undec-2-en-3-ylphenyl]piperazine.

¹H-NMR (400 MHz, CDCl₃) δ: 1.33-1.56 (m, 10H), 1.61-1.75 (m, 4H), 1.94-2.05 (m, 4H), 2.42-2.48 (m, 2H), 2.56 (brs, 4H), 2.60 (t, J=5.6 Hz, 2H), 2.82 (ddd, J=12.8, 10.0, 2.8 Hz, 2H), 2.95 (brs, 4H), 3.27-3.35 (m, 1H), 3.36 (s, 3H), 3.37 (s, 3H), 3.40-3.47 (m, 2H), 3.53 (t, J=5.6 Hz, 2H), 5.58 (t, J=1.6 Hz, 1H), 6.70 (d, J=3.2 Hz, 1H), 6.75 (dd, J=8.8, 3.2 Hz, 1H), 6.89 (d, J=8.8 Hz, 1H).

This compound was dissolved in dichloromethane (1 mL) and a 4N solution of hydrogen chloride in ethyl acetate (0.0236 mL, 0.0944 mmol) was added. The solution was concentrated, and diethyl ether was added to the obtained residue to produce a solid, which was then triturated by sonication. The supernatant diethyl ether solution was removed and the resulting solid residue was dried under reduced pressure to give 16.8 mg of the title compound as a light yellow solid.

MS m/e (ESI) 482 (MH⁺).

Example 49

(R)-1-Butyl-4-[2-(4,4-dimethylcyclohexyl)-4-(3-methoxypiperidin-1-yl)phenyl]piperazine hydrochloride

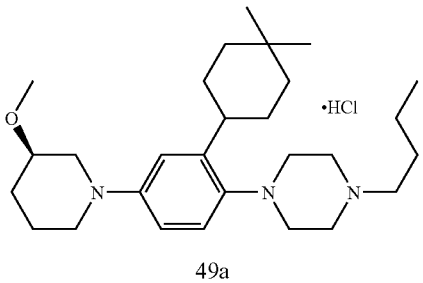

49a (R)-3-Methoxypiperidine hydrochloride

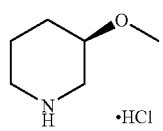

A mixture of (R)-3-hydroxypiperidine (2.709 g, 19.7 mmol), di-t-butyl dicarbonate (4.04 g, 31.5 mmol), dichloromethane (8 mL), triethylamine (5.76 mL, 41.34 mmol) and 4-dimethylaminopyridine (241 mg, 1.97 mmol) was stirred for 4 hours and 20 minutes at room temperature. To the reaction mixture were further added di-t-butyl dicarbonate (1.516 g, 11.82 mmol), triethylamine (1.91 mL, 11.82 mmol) and 4-dimethylaminopyridine (120 mg, 0.985 mmol), followed by stirring for 4 days at room temperature. Aqueous solution of ammonium chloride was added to the reaction mixture and extraction was performed twice with diethyl ether. The separated organic layer was washed with brine and then dried over anhydrous sodium sulfate. The desiccant was filtered off and the filtrate was concentrated under reduced pressure to give a crude product of (R)-3-hydroxypiperidine-1-carboxylic acid t-butyl ester.

Then, a portion of a mixed solvent of anhydrous tetrahydrofuran (82 mL)-dimethylformamide (33 mL) was added to a 60% suspension of sodium hydride in oil (1.18 g, 29.55 mmol), and the mixture was cooled to an external temperature of 0° C. and stirred under a nitrogen atmosphere. The crude product of (R)-3-methoxypiperidine-1-carboxylic acid t-butyl ester was dissolved in the remainder of the aforementioned mixed solvent of anhydrous tetrahydrofuran-dimethylformamide and then slowly added to the previous mixture. After stirring for 30 minutes under the same conditions, methyl iodide (1.84 mL, 27.55 mmol) was added to the reaction mixture. It was then slowly warmed to room temperature and further stirred for 13 hours. Ice and saturated aqueous solution of ammonium chloride were added to the reaction mixture and extraction was performed with diethyl ether. The organic layer was dried over anhydrous sodium sulfate. The desiccant was filtered off and the filtrate was concentrated under reduced pressure to give a crude product of (R)-3-methoxypiperidine-1-carboxylic acid t-butyl ester. Ethyl acetate (30 mL) was added to the crude product and the mixture was cooled to an external temperature of 0° C. and stirred. Then, a 4N solution of hydrogen chloride in ethyl acetate (147.8 mL, 591 mmol) was gradually added and the temperature was raised to room temperature. After stirring for 4 hours, the mixture was concentrated and dried under reduced pressure to give 4.311 g of a crude product of the title compound as a brown oil.

¹H-NMR (400 MHz, CDCl₃) δ: 1.63-1.75 (m, 1H), 1.79-1.98 (m, 2H), 2.00-2.11 (m, 1H), 2.99-3.22 (m, 3H), 3.28-3.36 (m, 1H), 3.41 (s, 3H), 3.62-3.65 (m, 1H).

The 1H of NH could not be identified.

49b (R)-1-Butyl-4-[2-(4,4-dimethylcyclohexyl)-4-(3-methoxypiperidin-1-yl)phenyl]piperazine hydrochloride

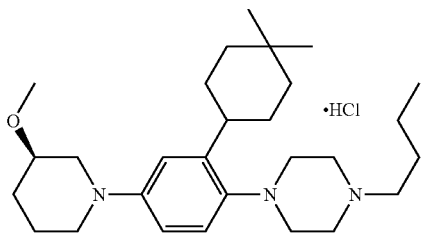

A mixture of 1-[4-bromo-2-(4,4-dimethylcyclohexyl)phenyl]-4-butylpiperazine (37.4 mg, 0.0918 mmol) produced in Example (21c), (R)-3-methoxypiperidine hydrochloride (16.7 mg, 0.110 mmol) produced in Example 49a, tripotassium phosphate (170 mg, 0.801 mmol), palladium(II) acetate (8.2 mg, 0.0365 mmol), tri-t-butylphosphonium tetrafluoroborate (32 mg, 0.110 mmol) and xylene (1.5 mL) was stirred for 4 hours and 30 minutes at an external temperature of 100° C. under a nitrogen atmosphere. The mixture was air-cooled to room temperature and then purified by NH silica gel column chromatography (ethyl acetate/hexane) to give 24 mg of (R)-1-butyl-4-[2-(4,4-dimethylcyclohexyl)-4-(3-methoxypiperidin-1-yl)phenyl]piperazine as a colorless oil.

$^1$H-NMR (400 MHz, CDCl$_3$) δ: 0.94 (t, J=7.6 Hz, 3H), 0.97 (s, 3H), 1.01 (s, 3H), 1.22-1.72 (m, 14H), 1.82-1.86 (m, 1H), 2.02-2.30 (m, 1H), 2.39-2.43 (m, 2H), 2.58 (brs, 4H), 2.66 (dd, J=11.6, 8.4 Hz, 1H), 2.74 (ddd, J=11.2, 11.2, 2.8 Hz, 1H), 2.82-2.88 (m, 4H), 2.90-3.00 (m, 1H), 3.31-3.38 (m, 1H), 3.39-3.46 (m, 4H), 3.60 (dd, J=11.6, 3.6 Hz, 1H), 6.74 (dd, J=8.8, 2.8 Hz, 1H), 6.86 (d, J=2.8 Hz, 1H), 7.06 (d, J=8.8 Hz, 1H).

This compound was dissolved in dichloromethane (1 mL), and then a 4N solution of hydrogen chloride in ethyl acetate (0.0273 mL, 0.109 mmol) was added.

This solution was concentrated to produce a residue, which was solidified by addition of diethyl ether, and then triturated by sonication. The supernatant diethyl ether solution was removed and the resulting solid was dried under reduced pressure to give 24.2 mg of the title compound as a colorless solid.

MS m/e 442 (ESI) (MH$^+$).

Example 50

(S)-1-Cyclopropylmethyl-4-[2-(4,4-dimethylcyclohexyl)-4-(3-methoxypiperidin-1-yl)phenyl]piperazine hydrochloride

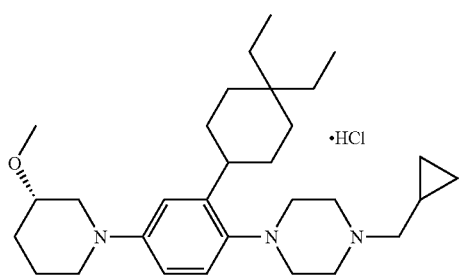

50a (S)-3-Methoxypiperidine hydrochloride

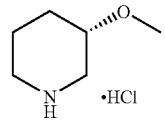

Reaction was carried out with conditions and procedures similar to those in Example (49a), using (S)-3-hydroxypiperidine (2 g, 14.5 mmol) as a starting material. The similar treatment was also carried out to give 3.237 g of a crude product of the title compound as an orange oil.

$^1$H-NMR (400 MHz, CDCl$_3$) δ: 1.63-1.77 (m, 1H), 1.78-1.96 (m, 2H), 1.98-2.09 (m, 1H), 2.99-3.22 (m, 3H), 3.26-3.34 (m, 1H), 3.41 (s, 3H), 3.62-3.65 (m, 1H).

The 1H of NH could not be identified.

50b (S)-4-[2-(4,4-Diethylcyclohexyl)-4-(3-methoxypiperidin-1-yl)phenyl]piperazine-1-carboxylic acid t-butyl ester

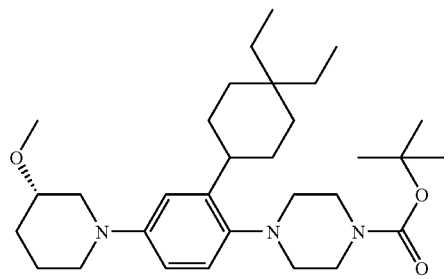

A mixture of 4-[4-bromo-2-(4,4-dimethylcyclohexyl)phenyl]piperazine-1-carboxylic acid t-butyl ester (153 mg, 0.32 mmol) produced in Example (38c), (S)-3-methoxypiperidine hydrochloride (72.8 mg, 0.48 mmol) produced in Example (50a), sodium t-butoxide (200 mg, 2.08 mmol), palladium(II) acetate (14.4 mg, 0.064 mmol), tri-t-butylphosphonium tetrafluoroborate (57.7 mg, 0.192 mmol) and xylene (4 mL) was stirred for 6 hours and 10 minutes at an external temperature of 100° C. under a nitrogen atmosphere. To the reaction mixture were further added sodium t-butoxide (100 mg, 1.04 mmol), palladium(II) acetate (7.2 mg, 0.032 mmol) and tri-t-butylphosphonium tetrafluoroborate (27.9 mg, 0.096 mmol), followed by stirring for 1 hour at an external temperature of 100° C. under a nitrogen atmosphere. The reaction mixture was air-cooled to room temperature and then purified by NH silica gel column chromatography (ethyl acetate/hexane) to give 59 mg of the title compound as a brown oil.

$^1$H-NMR (400 MHz, CDCl$_3$) δ: 0.79 (t, J=7.2 Hz, 3H), 0.81 (t, J=7.2 Hz, 3H), 1.14-1.71 (m, 23H), 1.83-1.92 (m, 1H), 2.03-2.10 (m, 1H), 2.65-2.82 (m, 10H), 2.92-3.01 (m, 1H), 3.33-3.47 (m, 5H), 3.57-3.62 (m, 1H), 6.74 (dd, J=8.8, 3.2 Hz, 1H), 6.85 (d, J=3.2 Hz, 1H), 6.99 (d, J=8.8 Hz, 1H).

50c

(S)-1-[2-(4,4-Diethylcyclohexyl)-4-(3-methoxypiperidin-1-yl)phenyl]piperazine

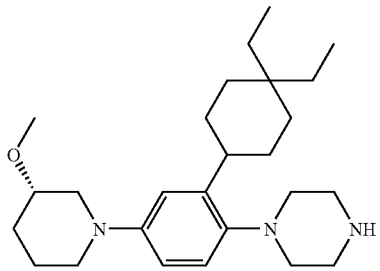

(S)-4-[2-(4,4-Diethylcyclohexyl)-4-(3-methoxypiperidin-1-yl)phenyl]piperazine-1-carboxylic acid t-butyl ester (59 mg, 0.1148 mmol) produced in Example (50b) was dissolved in a mixed solvent of dichloromethane (0.7 mL)-water (1 drop). Trifluoroacetic acid (0.177 mL, 2.296 mmol) was added thereto followed by stirring for 15 hours and 20 minutes under the same conditions. Aqueous solution of potassium carbonate was added to the reaction mixture to make the mixture basic. The mixture was then extracted with ethyl acetate. The separated organic layer was concentrated under reduced pressure to give a crude product of (S)-1-[2-(4,4-dimethylcyclohexyl)-4-(3-methoxypiperidin-1-yl)phenyl]piperazine as a brown oil. This was directly used without purification for the following reaction.

50d

(S)-1-Cyclopropylmethyl-4-[2-(4,4-dimethylcyclohexyl)-4-(3-methoxypiperidin-1-yl)phenyl]piperazine hydrochloride

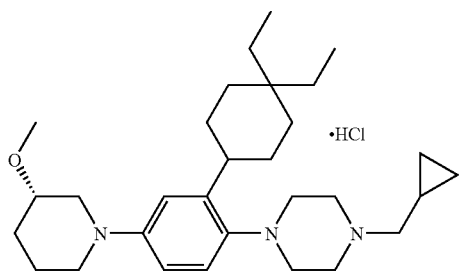

To a solution of the crude product of (S)-1-[2-(4,4-dimethylcyclohexyl)-4-(3-methoxypiperidin-1-yl)phenyl]piperazine produced in Example (50c) in tetrahydrofuran (1 mL) were added cyclopropanecarbaldehyde (0.0056 mL, 0.07462 mmol), sodium triacetoxyborohydride (16 mg, 0.07462 mmol) and acetic acid (0.0062 mL, 0.1091 mmol), followed by stirring for 5 hours at room temperature.

After the reaction, saturated aqueous solution of sodium hydrogencarbonate was added to the reaction mixture and extraction was performed three times with ethyl acetate. The separated organic layers were concentrated. The resultant residue was purified by NH silica gel column chromatography (ethyl acetate/heptane) to give (S)-1-cyclopropylmethyl-4-[2-(4,4-dimethylcyclohexyl)-4-(3-methoxypiperidin-1-yl)phenyl]piperazine.

$^1$H-NMR (400 MHz, CDCl$_3$) δ: 0.23-0.27 (m, 2H), 0.52-0.57 (m, 2H), 0.79 (t, J=7.6 Hz, 3H), 0.81 (t, J=7.6 Hz, 3H), 0.86-0.97 (m, 1H), 1.14-1.72 (m, 14H), 1.84-1.91 (m, 1H), 2.04-2.10 (m, 1H), 2.33 (d, J=6.8 Hz, 2H), 2.63-2.77 (m, 6H), 2.84-2.99 (m, 5H), 3.33-3.45 (m, 5H), 3.58-3.62 (m, 1H), 6.74 (dd, J=8.4, 2.8 Hz, 1H), 6.85 (d, J=2.8 Hz, 1H), 7.08 (d, J=8.4 Hz, 1H).

This compound was dissolved in dichloromethane (1 mL) and a 4N solution of hydrogen chloride in ethyl acetate (0.0287 mL, 0.1148 mmol) was added. This solution was concentrated to produce a residue, which was solidified by addition of diethyl ether, and was then triturated by sonication. The supernatant diethyl ether solution was removed and the resulting solid was dried under reduced pressure to give 17.5 mg of the title compound as a brown solid.

MS m/e 468 (ESI) (MH$^+$).

Example 51

1-Cyclopentyl-4-[2-(3,3,5,5-tetramethylcyclohexyl)phenyl]piperazine hydrochloride

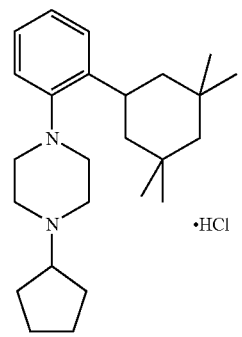

A mixture of 1-[2-(3,3,5,5-tetramethylcyclohexyl)phenyl]piperazine (25 mg, 0.0832 mmol) produced in Example (8b), cyclopentanone (9.1 mg, 0.108 mmol), sodium triacetoxyborohydride (33.5 mg, 0.158 mmol) and acetic acid (0.009 mL, 0.158 mmol) was stirred for 1 hour and 40 minutes at room temperature. Saturated aqueous solution of sodium hydrogencarbonate was added to the reaction mixture and extraction was performed three times with ethyl acetate. The organic layer was concentrated to produce a residue, which was purified by NH silica gel column chromatography (ethyl acetate/hexane) to give 1-cyclopentyl-4-[2-(3,3,5,5-tetramethylcyclohexyl)phenyl]piperazine as a colorless oil.

δ: 0.92 (s, 6H), 1.13 (s, 6H), 1.16-1.36 (m, 6H), 1.39-1.51 (m, 4H), 1.66-1.76 (m, 2H), 1.86-1.96 (m, 2H), 2.48-2.58 (m, 1H), 2.67 (brs, 4H), 2.89-2.98 (m, 4H), 3.52-3.61 (m, 1H), 7.04-7.14 (m, 3H), 7.21 (d, J=8.8 Hz, 1H).

This compound was dissolved in dichloromethane (1 mL), and then a 4N solution of hydrogen chloride in ethyl acetate (0.0416 mL, 0.166 mmol) was added. The solution was concentrated, and then diethyl ether was added to the obtained residue to produce a solid, which was then triturated by sonication. The supernatant diethyl ether solution was removed and the resulting solid was dried under reduced pressure to give 24.3 mg of the title compound as a colorless solid.

MS m/e 369 (ESI) (MH$^+$).

Example 52

1-(2-Methylsulfanylethyl)-4-[2-(3,3,5,5-tetramethylcyclohexyl)phenyl]piperazine hydrochloride

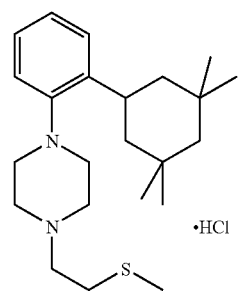

A mixture of the 1-[2-(3,3,5,5-tetramethylcyclohexyl)phenyl]piperazine (100 mg, 0.333 mmol) produced in Example (8b), 2-chloroethyl methyl sulfide (38.7 mg, 0.349 mmol), potassium carbonate (78.2 mg, 0.566 mmol) and acetonitrile (2 mL) was stirred for 8 hours and 30 minutes at an external temperature of 80° C. The reaction mixture was concentrated and the resultant residue was purified by NH silica gel column chromatography (ethyl acetate/heptane) to give 88 mg of 1-(2-methylsulfanylethyl)-4-[2-(3,3,5,5-tetramethylcyclohexyl)phenyl]piperazine as a colorless solid.

$^1$H-NMR (400 MHz, CDCl$_3$) δ: 0.93 (s, 6H), 1.12-1.46 (m, 12H), 2.14-2.18 (m, 2H), 2.55-2.75 (m, 9H), 2.93 (t, J=4.8 Hz, 4H), 3.48-3.60 (m, 1H), 7.05-7.17 (m, 3H), 7.23 (dd, J=7.6, 2.8 Hz, 1H).

After dissolving 1-(2-methylsulfanylethyl)-4-[2-(3,3,5,5-tetramethylcyclohexyl)phenyl]piperazine (22 mg, 0.0588 mmol) in dichloromethane (1.5 mL), a 4N solution of hydrogen chloride in ethyl acetate (0.0294 mL, 0.1175 mmol) was added. The solution was concentrated, diethyl ether was added to the obtained residue to produce a solid, and the supernatant diethyl ether solution was removed. The resultant solid was dried under reduced pressure to give 14 mg of the title compound as a colorless solid.

MS m/e (ESI) 375 (MH$^+$).

Example 53

1-(2-Cyclopropylethyl)-4-[2-(3,3,5,5-tetramethylcyclohexyl)phenyl]piperazine hydrochloride

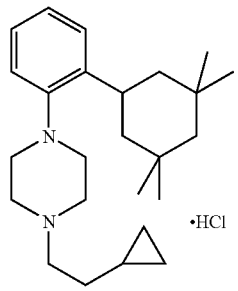

To a solution of cyclopropylacetaldehyde in 1,2-dichloroethane (0.29 M, 5 mL) were added 1-[2-(3,3,5,5-tetramethylcyclohexyl)phenyl]piperazine (25 mg, 0.0832 mmol) produced in Example (8b), sodium triacetoxyborohydride (22.9 mg, 0.108 mmol) and acetic acid (0.009 mL, 0.158 mmol), followed by stirring for 20 minutes at room temperature. Saturated aqueous solution of sodium hydrogencarbonate was added to the reaction mixture and extraction was performed twice with ethyl acetate. The organic layer was concentrated and the resultant residue was purified by NH silica gel column chromatography (ethyl acetate/heptane) to give 20.9 mg of 1-(2-cyclopropylethyl)-4-[2-(3,3,5,5-tetramethylcyclohexyl)phenyl]piperazine as a colorless oil.

$^1$H-NMR (400 MHz, CDCl$_3$) δ: 0.05-0.08 (m, 2H), 0.42-0.46 (m, 2H), 0.63-0.73 (m, 1H), 0.93 (s, 6H), 1.10-1.48 (m, 14H), 2.50-2.53 (m, 2H), 2.61 (brs, 4H), 2.92 (dd, J=4.4, 4.4 Hz, 4H), 3.52-3.63 (m, 1H), 7.05-7.17 (m, 3H), 7.22 (dd, J=7.2, 1.2 Hz, 1H).

This compound was dissolved in dichloromethane (1 mL) and a 4N solution of hydrogen chloride in ethyl acetate (0.0283 mL, 0.113 mmol) was added. The solution was concentrated, and diethyl ether was added to the obtained residue to produce a solid, which was then triturated by sonication. The supernatant diethyl ether solution was removed and the resulting solid was dried under reduced pressure to give 15.6 mg of the title compound as a colorless solid.

MS m/e 369 (ESI) (MH$^+$).

Example 54

1-Isobutyl-4-[2-(3,3,4,4-tetramethylcyclopent-1-enyl)phenyl]piperazine hydrochloride

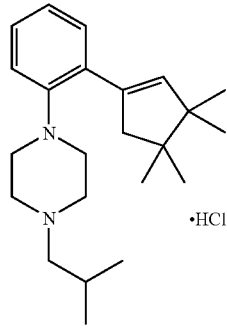

54a

Trifluoromethanesulfonic acid 3,3,4,4-tetramethylcyclopent-1-enyl ester

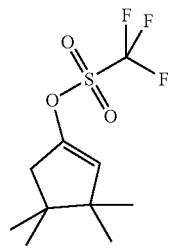

A solution of 3,3,4,4-tetramethylcyclopentanone (860 mg, 6.12 mmol) in anhydrous tetrahydrofuran (10 mL) was cooled to an internal temperature of −72° C. under a nitrogen atmosphere. To this stirred solution was slowly added dropwise bis(trimethylsilyl)amide lithium (1M solution in tetrahydrofuran, 7.34 mL, 7.34 mmol) over a period of 30 minutes. After stirring for 30 minutes under the same conditions, a solution of N-phenylbis(trifluoromethanesulfonimide) (2.41 g, 6.73 mmol) in anhydrous tetrahydrofuran (18 mL) was added to the reaction mixture, and stirring was continued for 16 hours and 30 minutes while gradually heating to room temperature. Ethyl acetate and 5N hydrochloric acid were added to the reaction mixture and extraction was performed three times with ethyl acetate. The separated organic layers were combined and washed 3 times with 5N hydrochloric acid. The obtained organic layer was dried over anhydrous sodium sulfate. The desiccant was filtered off and the filtrate was concentrated under reduced pressure. The resultant residue was purified by silica gel column chromatography (ethyl acetate/heptane) to give 992 mg of the title compound as a colorless oil.

$^1$H-NMR (400 MHz, CDCl$_3$) δ: 0.97 (s, 3H), 0.98 (s, 3H), 1.017 (s, 3H), 1.023 (s, 3H), 2.39 (d, J=1.6 Hz, 2H), 5.39 (t, J=1.6 Hz, 1H).

54b

1-Nitro-2-(3,3,4,4-tetramethylcyclopent-1-enyl)benzene

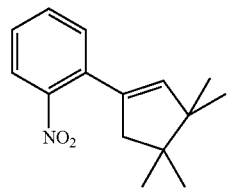

A mixture of the trifluoromethanesulfonic acid 3,3,4,4-tetramethylcyclopent-1-enyl ester (992 mg, 3.64 mmol) produced in Example (54a), 2-nitrophenylboronic acid (729 mg, 4.37 mmol), tetrakis(triphenylphosphine)palladium(0) (219 mg, 0.189 mmol), 2N aqueous solution of sodium carbonate (3.64 mL), toluene (12.5 mL) and ethanol (6.3 mL) was stirred for 6 hours at an external temperature of 90° C. under a nitrogen atmosphere. The reaction mixture was air-cooled to room temperature, and then ethyl acetate and brine were added and extraction was performed twice with ethyl acetate. The separated organic layer was dried over anhydrous sodium sulfate. The desiccant was filtered off and the filtrate was concentrated under reduced pressure. The resultant residue was purified by silica gel column chromatography (ethyl acetate/heptane) to give 891 mg of the title compound as a light brown oil.

$^1$H-NMR (400 MHz, CDCl$_3$) δ: 0.98 (s, 6H), 1.02 (s, 6H), 2.40 (d, J=1.6 Hz, 2H), 5.59 (t, J=1.6 Hz, 1H), 7.25-7.34 (m, 2H), 7.47 (ddd, J=8.0, 7.2, 1.2 Hz, 1H), 7.70 (dd, J=8.0, 1.2 Hz, 1H).

54c 2-(3,3,4,4-Tetramethylcyclopent-1-enyl)phenylamine

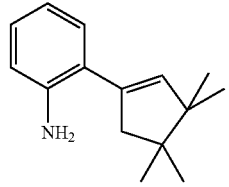

To a mixture of 1-nitro-2-(3,3,4,4-tetramethylcyclopent-1-enyl)benzene (441 mg, 1.8 mmol) produced in Example (54b), ethanol (10 mL) and water (3.3 mL) were added ammonium chloride (48.1 mg, 0.899 mmol) and iron powder (352 mg, 6.3 mmol), followed by stirring for 5 hours at an external temperature of 90° C. After further adding ammonium chloride (9.63 mg, 0.18 mmol) and iron powder (100 mg, 1.8 mmol) to the reaction mixture, stirring was continued for 12 hours at an external temperature of 75° C. The reaction mixture was cooled to room temperature and then filtered. The filtrate was concentrated under reduced pressure, and the resultant residue was purified by silica gel column chromatography (ethyl acetate/heptane) to give 331 mg of the title compound as a colorless oil.

$^1$H-NMR (400 MHz, CDCl$_3$) δ: 0.99 (s, 6H), 1.02 (s, 6H), 2.54 (d, J=1.2 Hz, 2H), 3.93 (brs, 2H), 5.74 (t, J=1.2 Hz, 1H), 6.68-6.74 (m, 2H), 6.99-7.06 (m, 2H).

54d

1-[2-(3,3,4,4-Tetramethylcyclopent-1-enyl)phenyl]piperazine

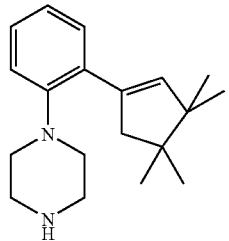

A mixture of 2-(3,3,4,4-tetramethylcyclopent-1-enyl)phenylamine (331 mg, 1.54 mmol) produced in Example (54c), 1,2-dichlorobenzene (4.7 mL) and bis(2-chloroethyl)amine hydrochloride (330 mg, 1.85 mmol) was stirred for 9 hours at an external temperature of 200° C. under a nitrogen atmosphere. During the reaction, a nitrogen stream was blown into the reactor several times to remove the hydrogen chloride gas in the reactor. The reaction mixture was air-cooled to room temperature, and then aqueous solution of potassium carbonate, ethyl acetate and methanol were added and extraction was performed three times with ethyl acetate. The obtained organic layers were dried over anhydrous sodium sulfate. The desiccant was filtered off and the filtrate was concentrated under reduced pressure. The obtained residue was purified by NH silica gel column chromatography (ethyl acetate/heptane) to give 223 mg of the title compound as a brown oil.

$^1$H-NMR (400 MHz, CDCl$_3$) δ: 0.97 (s, 6H), 1.00 (s, 6H), 2.60 (d, J=1.4 Hz, 2H), 2.90-2.96 (m, 4H), 2.98-3.02 (m, 4H), 6.00 (t, J=1.4 Hz, 1H), 6.94-6.99 (m, 2H), 7.15-7.19 (m, 2H).

The 1H of NH could not be identified.

54e

1-Isobutyl-4-[2-(3,3,4,4-tetramethylcyclopent-1-enyl)phenyl]piperazine hydrochloride

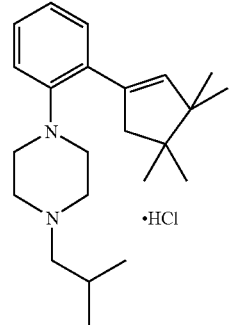

To a solution of the 1-[2-(3,3,4,4-tetramethylcyclopent-1-enyl)phenyl]piperazine (20 mg, 0.0703 mmol) produced in Example (54d) in tetrahydrofuran (1 mL) were added isobutyraldehyde (6.6 mg, 0.0914 mmol), sodium triacetoxyborohydride (19.4 mg, 0.0914 mmol) and acetic acid (0.0076 mL, 0.134 mmol), followed by stirring for 4 hours at room temperature. After further adding isobutyraldehyde (6.6 mg, 0.0914 mmol), sodium triacetoxyborohydride (19.4 mg, 0.0914 mmol) and acetic acid (0.0076 mL, 0.134 mmol) to the mixture, stirring was continued for 3 hours at room temperature. Saturated aqueous solution of sodium hydrogencarbonate was added to the reaction mixture and extraction was performed three times with ethyl acetate. The obtained organic layers were concentrated and the resultant residue was purified by NH silica gel column chromatography (ethyl acetate/heptane) to give 4.3 mg of 1-isobutyl-4-[2-(3,3,4,4-tetramethylcyclopent-1-enyl)phenyl]piperazine as a colorless oil.

$^1$H-NMR (400 MHz, CDCl$_3$) δ: 0.92 (d, J=6.4 Hz, 6H), 0.97 (s, 6H), 1.00 (s, 6H), 1.76-1.86 (m, 1H), 2.14 (d, J=7.6 Hz, 2H), 2.52 (brs, 4H), 2.59 (d, J=1.6 Hz, 2H), 2.98 (brs, 4H), 5.98 (t, J=1.6 Hz, 1H), 6.92-7.00 (m, 2H), 7.14-7.18 (m, 2H).

This compound was dissolved in dichloromethane (1 mL), and a 4N solution of hydrogen chloride in ethyl acetate (0.0063 mL, 0.0253 mmol) was added. The solution was concentrated under reduced pressure, and diethyl ether was added to the obtained residue to produce a solid, which was then triturated by sonication. The supernatant diethyl ether solution was removed and the resulting solid was dried under reduced pressure to give 4.8 mg of the title compound as a colorless solid.

MS m/e (ESI) 341 (MH$^+$).

Example 55

1-Propyl-4-[2-(3,3,4,4-tetramethylcyclopentyl)phenyl]piperazine hydrochloride

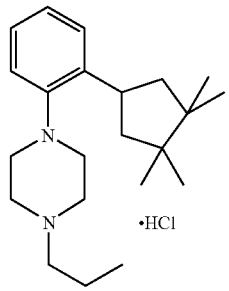

55a 2-(3,3,4,4-Tetramethylcyclopentyl)phenylamine

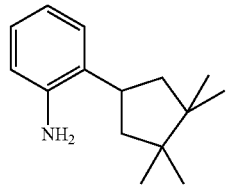

A mixture of 1-nitro-2-(3,3,4,4-tetramethylcyclopent-1-enyl)benzene (450 mg, 1.83 mmol) produced in Example (54b), 10% palladium on carbon (200 mg, wet) and methanol (40 mL) was stirred for 3 hours and 30 minutes at atmospheric pressure and room temperature under a hydrogen atmosphere. The reaction mixture was filtered, 10% palladium on carbon (200 mg, hydrous) and a 4N solution of hydrogen chloride in ethyl acetate (0.915 mL, 3.66 mmol) were added to the filtrate, and then stirring was continued for 13 hours and 30 minutes at room temperature and atmospheric pressure under a hydrogen atmosphere. The reaction mixture was filtered and the filtrate was concentrated under reduced pressure. The resultant residue was purified by silica gel column chromatography (ethyl acetate/heptane) to give 295 mg of the title compound as a brown oil.

$^1$H-NMR (400 MHz, CDCl$_3$) δ: 0.96 (s, 6H), 0.97 (s, 6H), 1.80 (dd, J=13.2, 8.8 Hz, 2H), 2.01 (dd, J=13.2, 9.2 Hz, 2H), 3.15-3.36 (m, 3H), 6.67 (dd, J=7.6, 1.2 Hz, 1H), 6.76 (ddd, J=7.6, 7.6, 1.2 Hz, 1H), 7.00 (ddd, J=7.6, 7.6, 1.2 Hz, 1H), 7.23 (d, J=7.6 Hz, 1H).

55b

1-[2-(3,3,4,4-Tetramethylcyclopentyl)phenyl]piperazine

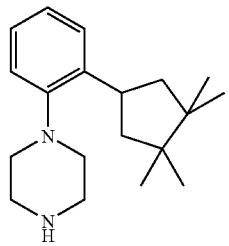

A mixture of 2-(3,3,4,4-tetramethylcyclopentylphenyl)amine (295 mg, 1.36 mmol) produced in Example (55a), 1,2-dichlorobenzene (3.84 mL) and bis(2-chloroethyl)amine hydrochloride (291 mg, 1.63 mmol) was stirred for 5 hours and 30 minutes at an external temperature of 200° C. under a nitrogen atmosphere. During the reaction, a nitrogen stream was blown into the reactor to remove the hydrogen chloride gas in the reactor. The reaction mixture was cooled to room temperature, and then aqueous solution of potassium carbonate, ethyl acetate and methanol were added and extraction was performed three times with ethyl acetate. The obtained organic layers were dried over anhydrous sodium sulfate. The desiccant was filtered off and the filtrate was concentrated under reduced pressure. The resultant residue was purified by NH silica gel column chromatography (ethyl acetate/heptane) to give 207 mg of the title compound as a brown oil.

$^1$H-NMR (400 MHz, CDCl$_3$) δ: 0.98 (s, 6H), 1.01 (s, 6H), 1.68 (dd, J=13.2, 9.2 Hz, 2H), 1.96 (dd, J=13.2, 9.2 Hz, 2H), 2.80-2.87 (m, 4H), 2.98-3.04 (m, 4H), 3.94 (tt, J=9.2, 9.2 Hz, 1H), 7.05-7.16 (m, 3H), 7.37 (dd, J=7.2, 1.6 Hz, 1H).

The 1H of NH could not be identified.

55c

1-Propyl-4-[2-(3,3,4,4-tetramethylcyclopentyl)phenyl]piperazine hydrochloride

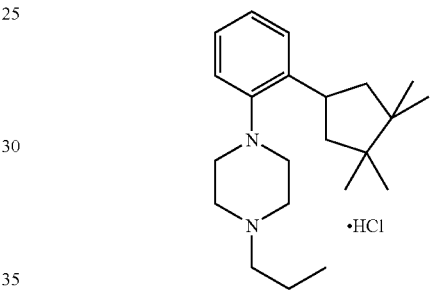

To a solution of the 1-[2-(3,3,4,4-tetramethylcyclopentyl)phenyl]piperazine (20 mg, 0.0698 mmol) produced in Example (55b) in tetrahydrofuran (1 mL) were added propionaldehyde (0.0065 mL, 0.0908 mmol), sodium triacetoxyborohydride (19.2 mg, 0.0908 mmol) and acetic acid (0.0076 mL, 0.133 mmol), followed by stirring for 3 hours at room temperature. After further adding propionaldehyde (0.0065 mL, 0.0908 mmol), sodium triacetoxyborohydride (19.2 mg, 0.0908 mmol) and 1,2-dichloroethane (1 mL) to the reaction mixture, stirring was continued for 18 hours and 30 minutes at room temperature. Saturated aqueous solution of sodium hydrogencarbonate was added to the reaction mixture and extraction was performed three times with ethyl acetate. The obtained organic layers were concentrated. The resultant residue was purified by NH silica gel column chromatography (ethyl acetate/heptane) to give 1.2 mg of 1-propyl-4-[2-(3,3,4,4-tetramethylcyclopentyl)phenyl]piperazine as a colorless oil.

$^1$H-NMR (400 MHz, CDCl$_3$) δ: 0.94 (t, J=7.2 Hz, 3H), 0.98 (s, 6H), 1.01 (s, 6H), 1.50-1.59 (m, 2H), 1.68 (dd, J=13.2, 9.6 Hz, 2H), 1.96 (dd, J=13.2, 9.6 Hz, 2H), 2.36-2.40 (m, 2H), 2.61 (brs, 4H), 2.91-2.93 (m, 4H), 3.92 (tt, J=9.6, 9.6 Hz, 1H), 7.06-7.15 (m, 3H), 7.36 (d, J=7.2 Hz, 1H).

This compound was dissolved in dichloromethane (1 mL), and a 4N solution of hydrogen chloride in ethyl acetate (0.0018 mL, 0.0730 mmol) was added. This solution was concentrated under reduced pressure, and diethyl ether was added to the obtained residue to produce a solid, which was then triturated by sonication. The solid was filtered and then dried under reduced pressure to give 1.7 mg of the title compound as a colorless solid.

MS m/e (ESI) 329 (MH$^+$).

Example 56

4-[4-(4-Pentylpiperazin-1-yl)-3-spiro[2.5]oct-5-en-6-ylphenyl]morpholine hydrochloride

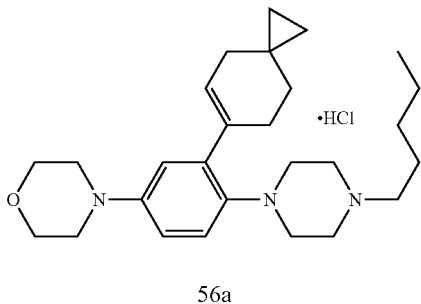

56a

4-(4-Morpholin-4-yl-2-spiro[2.5]oct-5-en-6-ylphenyl)piperazine-1-carboxylic acid t-butyl ester

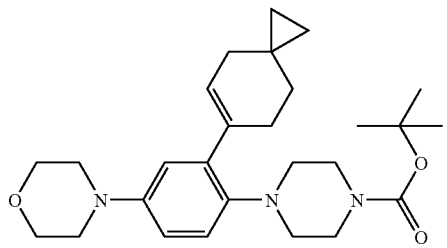

A mixture of 4-(4-morpholin-4-yl-2-trifluoromethanesulfonyloxyphenyl)piperazine-1-carboxylic acid t-butyl ester (1.49 g, 3.01 mmol), 1,2-dimethoxyethane (15 mL), water (1 mL), 4,4,5,5-tetramethyl-2-spiro[2.5]oct-5-en-6-yl-[1,3,2]dioxaborolane (1.13 g, 4.82 mmol) produced in Example (34b), tetrakis(triphenylphosphine)palladium(0) (278 mg, 0.241 mmol) and tripotassium phosphate (1.23 g, 5.78 mmol) was stirred for 13 hours and 20 minutes at an external temperature of 80-90° C. under a nitrogen atmosphere. Ethyl acetate and brine were added to the reaction mixture and extraction was performed three times with ethyl acetate. The organic layer was dried over anhydrous sodium sulfate, the desiccant was filtered off and the filtrate was concentrated under reduced pressure. The residue was purified by NH silica gel column chromatography (ethyl acetate/hexane) to give 1.23 g of the title compound as a colorless solid.

56b

4-(4-Piperazin-1-yl-3-spiro[2.5]oct-5-en-6-ylphenyl)morpholine

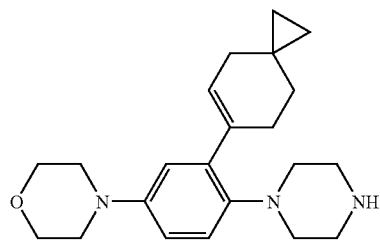

Reaction was conducted in a manner similar to Example (4f), using 4-(4-morpholin-4-yl-2-spiro[2.5]oct-5-en-6-ylphenyl)piperazine-1-carboxylic acid t-butyl ester (1.23 g, 2.71 mmol) produced in Example (56a) as a starting material, and then treatment was carried out in a similar manner to give 1.30 g of the title compound as a light brown solid.

$^1$H-NMR (400 MHz, CDCl$_3$) δ: 0.32-0.40 (m, 4H), 1.50 (t, J=6.4 Hz, 2H), 2.02-2.06 (m, 2H), 2.53 (d, J=1.6 Hz, 2H), 3.05-3.18 (m, 12H), 3.85 (t, J=4.8 Hz, 4H), 5.69-5.73 (m, 1H), 6.74 (d, J=2.4 Hz, 1H), 6.78 (dd, J=9.6, 2.4 Hz, 1H), 6.94 (d, J=9.6 Hz, 1H).

The 1H of NH could not be identified.

56c

4-[4-(4-Pentylpiperazin-1-yl)-3-spiro[2.5]oct-5-en-6-ylphenyl]morpholine hydrochloride

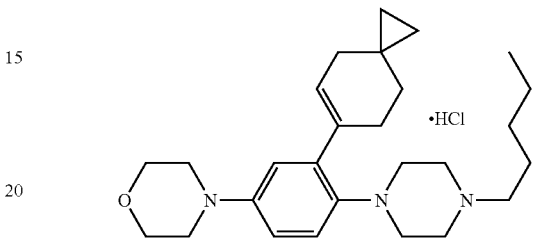

To a solution of 4-(4-piperazin-1-yl-3-spiro[2.5]oct-5-en-6-ylphenyl)morpholine (330 mg, 0.933 mmol) produced in Example (56b) in tetrahydrofuran (10 mL) were added valeraldehyde (104.5 mg, 1.214 mmol), sodium triacetoxyborohydride (257.2 mg, 1.214 mmol) and acetic acid (0.1015 mL, 1.774 mmol), followed by stirring for 1 hour and 30 minutes at room temperature. Saturated aqueous solution of sodium hydrogencarbonate was added to the reaction mixture and extraction was performed three times with ethyl acetate. The obtained organic layer was dried over anhydrous sodium sulfate. The desiccant was filtered off and the filtrate was concentrated under reduced pressure. The resultant residue was purified by NH silica gel column chromatography (ethyl acetate/hexane) to give 269 mg of the title compound as a colorless solid.

$^1$H-NMR (400 MHz, CDCl$_3$) δ: 0.33-0.38 (m, 4H), 0.91 (t, J=6.8 Hz, 3H), 1.24-1.38 (m, 4H), 1.48-1.55 (m, 4H), 2.02-2.05 (m, 2H), 2.34-2.38 (m, 2H), 2.47-2.62 (m, 6H), 2.99 (brs, 4H), 3.10-3.12 (m, 4H), 3.84-3.86 (m, 4H), 5.69-5.73 (m, 1H), 6.73-6.77 (m, 2H), 6.93 (d, J=8.4 Hz, 1H).

After dissolving 125 mg of this compound in dichloromethane (4 mL), a 4N solution of hydrogen chloride in ethyl acetate (0.147 mL, 0.590 mmol) was added. The solution was concentrated under reduced pressure, and diethyl ether was added to the obtained residue to produce a solid, which was then triturated by sonication. The solid was filtered and dried under reduced pressure to give 120 mg of the title compound as a colorless solid.

MS m/e (ESI) 424 (MH$^+$).

Example 57

1-[4-Bromo-2-(4,4-dimethylcyclohexyl)phenyl]-4-butylpiperazine

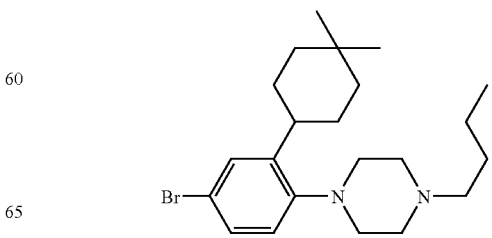

57a

1-[4-Bromo-2-(4,4-dimethylcyclohexyl)phenyl]piperazine

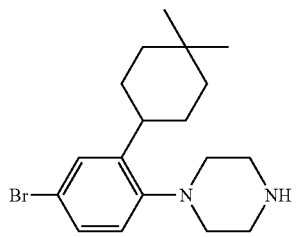

A mixture of 4-[4-bromo-2-(4,4-dimethylcyclohexyl)phenyl]piperazine-1-carboxylic acid t-butyl ester (1.5 g, 3.32 mmol) produced in Example (3e), trifluoroacetic acid (3 mL, 38.7 mmol) and dichloromethane (6 mL) was stirred for 2 hours and 30 minutes at room temperature. Saturated aqueous solution of sodium carbonate was added to the reaction mixture and extraction was performed with ethyl acetate. The separated organic layer was washed with water and brine in that order and then dried over anhydrous sodium sulfate. The desiccant was filtered off and the filtrate was concentrated under reduced pressure. The residue was dried under reduced pressure to give 1.21 g of a crude product of the title compound as a brown oil.

57b

1-[4-Bromo-2-(4,4-dimethylcyclohexyl)phenyl]-4-butylpiperazine

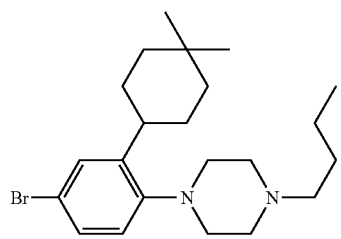

To a mixture of the crude product of 1-[4-bromo-2-(4,4-dimethylcyclohexyl)phenyl]piperazine produced in Example (57a) (1.21 g), butyraldehyde (0.35 mL, 3.98 mmol), acetic acid (0.1 mL, 3.32 mmol) and tetrahydrofuran (8 mL) was added sodium triacetoxyborohydride (1.1 g, 4.98 mmol), followed by stirring for 2 hours and 10 minutes at room temperature. Saturated aqueous solution of sodium hydrogencarbonate was added to the reaction mixture and extraction was performed with ethyl acetate. The separated organic layer was washed with water and brine in that order and then dried over anhydrous sodium sulfate. The desiccant was filtered off and the filtrate was concentrated under reduced pressure. The resultant residue was purified by NH silica gel column chromatography (ethyl acetate/hexane) to give 901 mg of the title compound as a yellow oil.

$^1$H-NMR (400 MHz, CDCl$_3$) δ: 0.94 (t, J=7.2 Hz, 3H), 0.97 (s, 3H), 1.01 (s, 3H), 1.24-1.60 (m, 12H), 2.38-2.44 (m, 2H), 2.59 (brs, 4H), 2.82-2.97 (m, 5H), 6.97 (d, J=8.8 Hz, 1H), 7.24 (dd, J=8.8, 2.4 Hz, 1H), 7.33 (d, J=2.4 Hz, 1H).

Example 58

1-[4-(4-Butylpiperazin-1-yl)-3-(4,4-dimethylcyclohexyl)phenyl]piperidine-4-carbonitrile hydrochloride A mixture of 1-[4-bromo-2-(4,4-dimethylcyclohexyl)phenyl]-4-butylpiperazine (50 mg, 0.123 mmol) produced in Example (57b), piperidine-4-carbonitrile hydrochloride (27 mg, 0.185 mmol), sodium t-butoxide (47 mg, 0.492 mmol), palladium(II) acetate (3 mg, 0.0123 mmol), tri-t-butylphosphonium tetrafluoroborate (11 mg, 0.0369 mmol) and xylene (1 mL) was stirred for 1 hour at an external temperature of 100° C.

The reaction mixture was purified by NH silica gel column chromatography (ethyl acetate/hexane) to give 32 mg of 1-[4-(4-butylpiperazine-1-yl)-3-(4,4-dimethylcyclohexyl)phenyl]piperidine-4-carbonitrile as a colorless solid.

$^1$H-NMR (400 MHz, CDCl$_3$) δ: 0.94 (t, J=7.6 Hz, 3H), 0.97 (s, 3H), 1.01 (s, 3H), 1.24-1.64 (m, 12H), 1.95-2.13 (m, 4H), 2.36-2.46 (m, 2H), 2.59 (brs, 4H), 2.72-2.79 (m, 1H), 2.86 (brs, 4H), 2.91-3.05 (m, 3H), 3.31-3.41 (m, 2H), 6.72 (dd, J=8.8, 2.8 Hz, 1H), 6.84 (d, J=2.8 Hz, 1H), 7.07 (d, J=8.8 Hz, 1H).

This compound was dissolved in ethyl acetate and a 4N solution of hydrogen chloride in ethyl acetate was added. The mixture was concentrated under reduced pressure. Hexane was added to the residue to produce a solid, which was then triturated by sonication. The supernatant hexane solution was removed and the solid was dried to give 25 mg of the title compound as a colorless solid.

MS m/e (ESI) 437 (MH$^+$).

Example 59

1-[4-Azetidin-1-yl-2-(4,4-dimethylcyclohexyl)phenyl]-4-butylpiperazine hydrochloride A mixture of 1-[4-bromo-2-(4,4-dimethylcyclohexyl)phenyl]-4-butylpiperazine (50 mg, 0.123 mmol) produced in Example (57b), azetidine hydrochloride (17 mg, 0.185 mmol), sodium t-butoxide (47 mg, 0.492 mmol), palladium (II) acetate (3 mg, 0.0123 mmol), tri-t-butylphosphonium tetrafluoroborate (11 mg, 0.0369 mmol) and xylene (1 mL) was stirred for 3 hours at an external temperature of 100° C. Water was added to the reaction mixture and extraction was performed with ethyl acetate. The separated organic layer was filtered through Celite. The solvent was distilled off by nitrogen stream to the filtrate. The resultant residue was purified by NH silica gel column chromatography (ethyl acetate/hexane) to give 1-[4-azetidin-1-yl-2-(4,4-dimethylcyclohexyl)phenyl]-4-butylpiperazine as a colorless solid.

$^1$H-NMR (400 MHz, CDCl$_3$) δ: 0.94 (t, J=7.6 Hz, 3H), 0.96 (s, 3H), 1.00 (s, 3H), 1.25-1.66 (m, 12H), 2.32 (quintet, J=7.2 Hz, 2H), 2.37-2.42 (m, 2H), 2.56 (brs, 4H), 2.84 (brs, 4H), 2.90-3.00 (m, 1H), 3.85 (t, J=7.2 Hz, 4H), 6.27 (dd, J=8.4, 2.8 Hz, 1H), 6.32 (d, J=2.8 Hz, 1H), 7.06 (d, J=8.4 Hz, 1H).

This compound was dissolved in ethyl acetate and a 4N solution of hydrogen chloride in ethyl acetate was added. The mixture was then concentrated under reduced pressure. Hexane was added to the residue to produce a solid, which was then triturated by sonication. The supernatant hexane solution was removed and the resulting solid was dried to give 20 mg of the title compound as a colorless solid.

MS m/e (ESI) 384 (MH⁺).

Example 60

1-[4-(4-Butylpiperazin-1-yl)-3-(4,4-dimethylcyclohexyl)phenyl]azepane hydrochloride

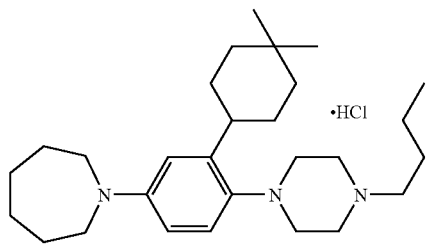

A mixture of 1-[4-bromo-2-(4,4-dimethylcyclohexyl)phenyl]-4-butylpiperazine (50 mg, 0.123 mmol) produced in Example (57b), hexamethyleneimine (18 mg, 0.185 mmol), sodium t-butoxide (30 mg, 0.308 mmol), palladium(II) acetate (3 mg, 0.0123 mmol), tri-t-butylphosphonium tetrafluoroborate (11 mg, 0.0369 mmol) and xylene (1 mL) was stirred for 3 hours at an external temperature of 100° C. Water was added to the reaction mixture and extraction was performed with ethyl acetate. The separated organic layer was filtered through Celite. The solvent was distilled off by nitrogen stream to the filtrate. The resultant residue was purified by NH silica gel column chromatography (ethyl acetate/hexane) to give 1-[4-(4-butylpiperazine-1-yl)-3-(4,4-dimethylcyclohexyl)phenyl]azepane as a yellow solid.

¹H-NMR (400 MHz, CDCl₃) δ: 0.94 (t, J=7.6 Hz, 3H), 0.97 (s, 3H), 1.01 (s, 3H), 1.28-1.85 (m, 20H), 2.36-2.44 (m, 2H), 2.58 (brs, 4H), 2.77-3.02 (m, 5H), 3.35-3.46 (m, 4H), 6.50 (dd, J=8.8, 3.2 Hz, 1H), 6.55 (d, J=3.2 Hz, 1H), 7.06 (d, J=8.8 Hz, 1H).

This compound was dissolved in ethyl acetate, and a 4N solution of hydrogen chloride in ethyl acetate was added. The mixture was concentrated under reduced pressure. Hexane was added to the residue to produce a solid, which was then triturated by sonication. The supernatant hexane solution was removed and the resulting solid was dried to give 36 mg of the title compound as a colorless solid.

MS m/e (ESI) 426 (MH⁺).

Example 61 cis-4-[4-(4-Cyclobutylmethylpiperazin-1-yl)-3-(4,4-dimethylcyclohexyl)phenyl]-2,6-dimethylmorpholine hydrochloride

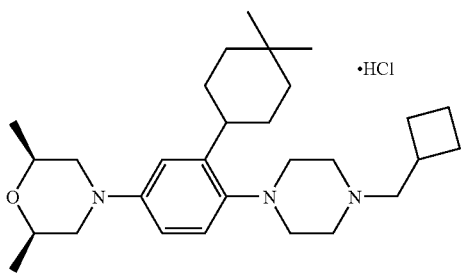

61a cis-4-[2-(4,4-Dimethylcyclohexyl)-4-(2,6-dimethylmorpholin-4-yl)phenyl]piperazine-1-carboxylic acid t-butyl ester

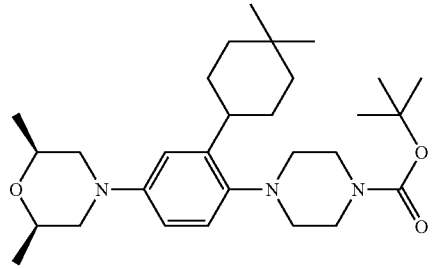

A mixture of the 4-[4-bromo-2-(4,4-dimethylcyclohexyl)phenyl]piperazine-1-carboxylic acid t-butyl ester (700 mg, 1.55 mmol) produced in Example (3e), cis-2,6-dimethylmorpholine (268 mg, 2.33 mmol), sodium t-butoxide (372 mg, 3.88 mmol), palladium(II) acetate (35 mg, 0.155 mmol), tri-t-butylphosphonium tetrafluoroborate (135 mg, 0.465 mmol) and xylene (7 mL) was stirred for 2 hours at an external temperature of 100° C. under a nitrogen atmosphere. The reaction mixture was air-cooled to room temperature, and then the insoluble matters were filtered off, water was added to the obtained filtrate and extraction was performed with ethyl acetate. The separated organic layer was washed with water and brine in that order and then dried over anhydrous sodium sulfate. The desiccant was filtered off and the filtrate was concentrated under reduced pressure. The resultant residue was purified by silica gel column chromatography (ethyl acetate/hexane) to give 648 mg of the title compound as yellow crystals.

¹H-NMR (400 MHz, CDCl₃) δ: 0.97 (s, 3H), 1.02 (s, 3H), 1.25 (s, 3H), 1.27 (s, 3H), 1.28-1.70 (m, 17H), 2.39 (dd, J=12.0, 10.4 Hz, 2H), 2.65-2.85 (m, 4H), 2.93-3.04 (m, 1H), 3.38 (d, J=10.4 Hz, 2H), 3.49 (brs, 4H), 3.75-3.88 (m, 2H), 6.70 (dd, J=8.8, 2.8 Hz, 1H), 6.82 (d, J=2.8 Hz, 1H), 7.01 (d, J=8.8 Hz, 1H).

61b cis-4-[3-(4,4-Dimethylcyclohexyl)-4-piperazin-1-ylphenyl]-2,6-dimethylmorpholine

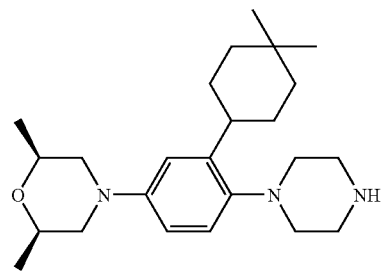

To cis-4-[2-(4,4-dimethylcyclohexyl)-4-(2,6-dimethylmorpholin-4-yl)phenyl]piperazine-1-carboxylic acid t-butyl ester (648 mg, 1.33 mmol) produced in Example (61a) was added a mixed solvent of ethyl acetate (5 mL)-dichloromethane (1 mL), followed by stirring at room temperature under a nitrogen atmosphere. A 4N solution of hydrogen chloride in ethyl acetate (5 mL, 20 mmol) was added dropwise thereto, followed by stirring for 17 hours under the same conditions. Saturated aqueous solution of sodium carbonate was added to the reaction mixture to make the mixture basic. Dichloromethane and water were added thereto and extraction was performed with dichloromethane. The separated organic layer was washed with brine and then dried over anhydrous sodium sulfate. The desiccant was filtered off and the filtrate was concentrated under reduced pressure. The resultant residue was purified by NH silica gel column chromatography (ethyl acetate/hexane) to give 451 mg of the title compound as light yellow crystals.

$^1$H-NMR (400 MHz, CDCl$_3$) δ: 0.97 (s, 3H), 1.03 (s, 3H), 1.25 (s, 3H), 1.27 (s, 3H), 1.40-1.70 (m, 8H), 2.39 (dd, J=11.6, 10.4 Hz, 2H), 2.72-2.83 (m, 4H), 2.91-3.04 (m, 5H), 3.38 (d, J=10.4, 2H), 3.75-3.88 (m, 2H), 6.71 (dd, J=8.4, 2.8 Hz, 1H), 6.82 (d, J=2.8 Hz, 1H), 7.06 (d, J=8.4 Hz, 1H).

The 1H of NH could not be identified.

61c cis-4-[4-(4-Cyclobutylmethylpiperazin-1-yl)-3-(4,4-dimethylcyclohexyl)phenyl]-2,6-dimethylmorpholine hydrochloride

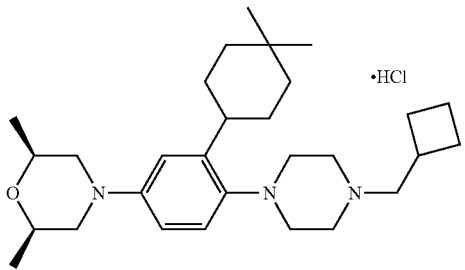

A mixture of the cis-4-[3-(4,4-dimethylcyclohexyl)-4-piperazin-1-ylphenyl]-2,6-dimethylmorpholine (30 mg, 0.0778 mmol) produced in Example (61b), bromomethylcyclobutane (23 mg, 0.156 mmol), potassium carbonate (22 mg, 0.156 mmol) and dimethylformamide (1 mL) was stirred for 1 hour at an external temperature of 80° C. Then, bromomethylcyclobutane (23 mg, 0.156 mmol) was further added and stirring was continued for 2 hours under the same conditions. Saturated aqueous solution of sodium hydrogencarbonate was added to the reaction mixture and extraction was performed with ethyl acetate. The separated organic layer was washed with water and brine in that order, and then the solvent was distilled off by nitrogen stream. The resultant residue was purified by NH silica gel column chromatography (ethyl acetate/hexane) to give cis-4-[4-(4-cyclobutylmethylpiperazin-1-yl)-3-(4,4-dimethylcyclohexyl)phenyl]-2,6-dimethylmorpholine as a colorless oil.

$^1$H-NMR (400 MHz, CDCl$_3$) δ: 0.98 (s, 3H), 1.02 (s, 3H), 1.15-2.15 (m, 20H), 2.39 (dd, J=11.6, 10.4 Hz, 2H), 2.43-3.03 (m, 12H), 3.37 (d, J=10.4, 2H), 3.75-3.88 (m, 2H), 6.70 (dd, J=8.8, 2.8 Hz, 1H), 6.81 (d, J=2.8 Hz, 1H), 7.07 (d, J=8.8 Hz, 1H).

This compound was dissolved in ethyl acetate, and a 4N solution of hydrogen chloride in ethyl acetate was added. The mixture was concentrated under reduced pressure. Hexane was added to the residue to produce a solid, which was then triturated by sonication. The supernatant hexane solution was removed and the resulting solid was dried to give 38 mg of the title compound as a colorless solid.

MS m/e (ESI) 454 (MH$^+$).

Example 62

4-[2-(4-t-Butylcyclohexyl)phenyl]piperazine-1-carboxylic acid ethyl ester

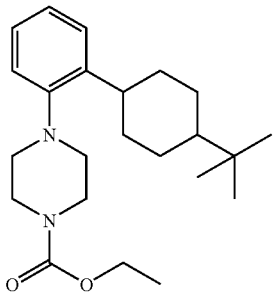

A mixture of the 1-[2-(4-t-butylcyclohexyl)phenyl]piperazine (92 mg, 0.306 mmol) produced in Example (10a), triethylamine (0.085 mL, 0.612 mmol) and dichloromethane (2 mL) was cooled in an ice bath and stirred. Ethyl chloroformate (0.032 mL, 0.337 mmol) was added to the mixture, followed by stirring for 2 hours under the same conditions. Saturated aqueous solution of sodium hydrogencarbonate was added to the reaction mixture and extraction was performed with ethyl acetate. The separated organic layer was washed with water and brine in that order and then dried over anhydrous sodium sulfate. The desiccant was filtered off and the filtrate was concentrated under reduced pressure. The resultant residue was purified by NH silica gel column chromatography (ethyl acetate/hexane) to give 100 mg of the title compound as a colorless oil, as a mixture of diastereomers at the position of t-butylcyclohexyl.

$^1$H-NMR (400 MHz, CDCl$_3$) δ: 0.88 (s, 9H×0.6), 0.90 (s, 9H×0.4), 1.10-2.00 (m, 12H), 2.72-2.93 (m, 4H), 2.97-3.08 (m, 1H×0.4), 3.39-3.75 (m, 4H+1H×0.6), 4.17 (q, J=7.2 Hz, 2H), 7.05-7.25 (m, 3H+1H×0.4), 7.45 (dd, J=8.0, 1.6 Hz, 1H×0.6). MS m/e (ESI) 373 (MH$^+$).

Example 63

4-[4-[2-(4-t-Butylcyclohexyl)phenyl]piperazin-1-yl] butan-2-one

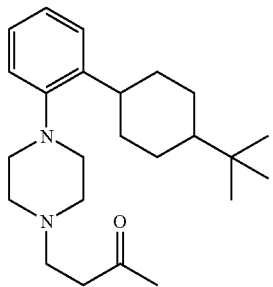

A mixture of the 1-[2-(4-t-butylcyclohexyl)phenyl]piperazine (30 mg, 0.0998 mmol) produced in Example (10a) and chloroform (0.5 mL) was cooled in an ice bath and stirred. Methyl vinyl ketone (0.017 mL, 0.200 mmol) was added to the mixture, followed by stirring for 2 hours under the same conditions. The reaction mixture was purified by NH silica gel column chromatography (ethyl acetate/hexane) to give 30 mg of the title compound as a colorless oil, as a mixture of diastereomers at the position of t-butylcyclohexyl.

$^1$H-NMR (400 MHz, CDCl$_3$) δ: 0.88 (s, 9H×0.6), 0.90 (s, 9H×0.4), 1.10-1.99 (m, 9H), 2.20 (s, 3H), 2.40-3.10 (m, 12H+1H×0.4), 3.34-3.43 (m, 1H×0.6), 7.03-7.23 (m, 3H+1H×0.4), 7.42 (d, J=7.6 Hz, 1H×0.6).

Example 64

4-[4-[2-(4-t-Butylcyclohexyl)phenyl]piperazin-1-yl]butan-2-ol hydrochloride

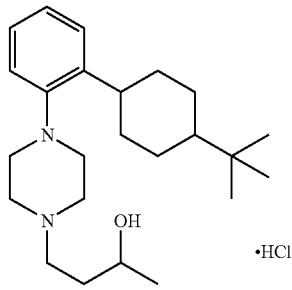

To a mixture of sodium borohydride (3 mg, 0.0675 mmol) and methanol (0.5 mL) was added a mixture of the 4-[4-[2-(4-t-butylcyclohexyl)phenyl]piperazin-1-yl]butan-2-one (25 mg, 0.0675 mmol) produced in (Example 63) in methanol (0.5 mL), followed by stirring for 4 hours at room temperature.

Saturated aqueous solution of sodium hydrogencarbonate was added to the reaction mixture and extraction was performed with ethyl acetate. The separated organic layer was washed with water and brine in that order and then dried over anhydrous sodium sulfate. The desiccant was filtered off and the filtrate was concentrated under reduced pressure. The resultant residue was purified by NH silica gel column chromatography (ethyl acetate/hexane) to give 23 mg of the title compound as a colorless oil, as a mixture of diastereomers at the positions of t-butylcyclohexyl and hydroxyl. This compound was dissolved in ethyl acetate, and a 4N solution of hydrogen chloride in ethyl acetate was added. The precipitated solid was filtered to give 22 mg of the title compound as colorless crystals, as a mixture of diastereomers at the positions of t-butylcyclohexyl and hydroxyl.

MS m/e (ESI) 373 (MH$^+$).

Example 65

3-[4-[2-(4-t-Butylcyclohexyl)phenyl]piperazin-1-yl]propionic acid methyl ester

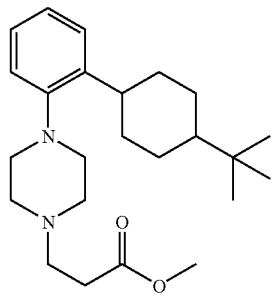

To a mixture of 1-[2-(4-t-butylcyclohexyl)phenyl]piperazine (530 mg, 1.76 mmol) produced in Example (10a) and tetrahydrofuran (2 mL) was added methyl acrylate (0.24 mL, 2.65 mmol), followed by stirring for 12 hours at an external temperature of 45° C. The reaction mixture was concentrated under reduced pressure and the resultant residue was purified by NH silica gel column chromatography (ethyl acetate/hexane) to give 643 mg of the title compound as colorless crystals, as a mixture of diastereomers at the position of t-butylcyclohexyl.

$^1$H-NMR (400 MHz, CDCl$_3$) δ: 0.88 (s, 9H×0.6), 0.90 (s, 9H×0.4), 1.08-1.99 (m, 9H), 2.25-3.05 (m, 12H+1H×0.4), 3.35-3.42 (m, 1H×0.6), 3.70 (s, 3H), 7.03-7.23 (m, 3H+1H×0.4), 7.42 (d, J=7.6 Hz, 1H×0.6). MS m/e (ESI) 387 (MH$^+$).

Example 66

3-[4-[2-(4-t-Butylcyclohexyl)phenyl]piperazin-1-yl]propionic acid

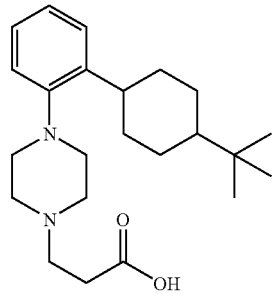

A mixture of 3-[4-[2-(4-t-butyl-cyclohexyl)phenyl]piperazin-1-yl]propionic acid methyl ester (600 mg, 1.55 mmol) produced in (Example 65), 2N aqueous solution of sodium hydroxide (5 mL, 10 mmol), methanol (2 mL), tetrahydrofuran (2 mL) and water (1 mL) was stirred for 12 hours and 40 minutes at room temperature. Then, 5N hydrochloric acid was added to the reaction mixture to adjust pH of the mixture to 6-7. The mixture was concentrated under reduced pressure. Methanol was then added thereto, the insoluble matters were filtered off, and the filtrate was concentrated under reduced pressure. The resultant residue was purified by NAM silica gel column chromatography (methanol/chloroform) to give a brown oil. Hexane was added thereto and the precipitated solid was filtered to give 414 mg of the title compound as colorless crystals, as a mixture of diastereomers at the position of t-butylcyclohexyl.

$^1$H-NMR (400 MHz, CDCl$_3$) δ: 0.89 (s, 9H×0.6), 0.90 (s, 9H×0.4), 1.06-1.99 (m, 9H), 2.50-3.30 (m, 12H+1H×0.4), 3.32-3.39 (m, 1H×0.6), 7.07-7.24 (m, 3H+1H×0.4), 7.44 (dd, J=8.0, 2.0 Hz, 1H×0.6).

The 1H of carboxylic acid could not be identified.

MS m/e (ESI) 373 (MH$^+$).

Example 67

3-[4-[2-(4-t-Butylcyclohexyl)phenyl]piperazin-1-yl]-N-ethylpropionamide hydrochloride

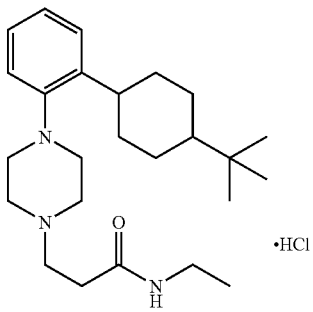

A mixture of 3-[4-[2-(4-t-butylcyclohexyl)phenyl]piperazin-1-yl]propionic acid (50 mg, 0.134 mmol) produced in (Example 66), 1-ethyl-3-(3-dimethylaminopropyl)carbodiimide hydrochloride (77 mg, 0.403 mmol), 1-hydroxybenzotriazole monohydrate (62 mg, 0.403 mmol), ethylamine hydrochloride (55 mg, 0.671 mmol), triethylamine (0.09 mL, 0.671 mmol) and dimethylformamide (1 mL) was stirred for 24 hours at room temperature. Saturated aqueous solution of sodium hydrogencarbonate was added to the reaction mixture and extraction was performed with ethyl acetate. The separated organic layer was washed with water and brine in that order and then dried over anhydrous sodium sulfate. The desiccant was filtered off and the filtrate was concentrated under reduced pressure. The resultant residue was purified by NH silica gel column chromatography (ethyl acetate/hexane) to give 53 mg of 3-[4-[2-(4-t-butylcyclohexyl)phenyl]piperazin-1-yl]-N-ethylpropionamide as a colorless oil, as a mixture of diastereomers at the position of t-butylcyclohexyl.

$^1$H-NMR (400 MHz, CDCl$_3$) δ: 0.89 (s, 9H×0.6), 0.90 (s, 9H×0.4), 1.08-1.99 (m, 12H), 2.35-3.04 (m, 12H+1H×0.4), 3.24-3.42 (m, 2H+1H×0.6), 7.07-7.25 (m, 3H+1H×0.4), 7.44 (dd, J=7.6, 1.6 Hz, 1H×0.6).

The 1H of NH could not be identified.

MS m/e (ESI) 400 (MH$^+$).

This compound was dissolved in ethyl acetate, and a 4N solution of hydrogen chloride in ethyl acetate was added. The precipitated solid was filtered to give 49 mg of the title compound as colorless crystals, as a mixture of diastereomers at the position of t-butylcyclohexyl.

Example 68

1-[2-(4,4-Dimethylcyclohexyl)phenyl]-4-furan-2-ylmethylpiperazine hydrochloride

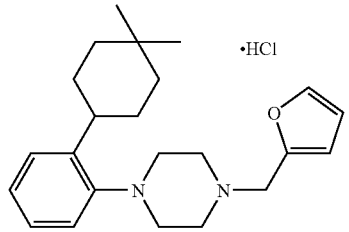

To a mixture of 1-[2-(4,4-dimethylcyclohexyl)phenyl]piperazine (30 mg, 0.11 mmol) produced in Example (3c), furan-2-carbaldehyde (21 mg, 0.22 mmol) and tetrahydrofuran (2 mL) was added sodium triacetoxyborohydride (119 mg, 0.559 mmol), followed by stirring for 1 hour and 50 minutes at room temperature. Saturated aqueous solution of sodium hydrogencarbonate was added to the reaction mixture and extraction was performed with ethyl acetate. The separated organic layer was filtered through Celite. The solvent was distilled off by nitrogen stream to the filtrate. The resultant residue was purified by NH silica gel column chromatography (ethyl acetate/heptane) to give 1-[2-(4,4-dimethylcyclohexyl)phenyl]-4-furan-2-ylmethylpiperazine. This compound was dissolved in dichloromethane, and a 4N solution of hydrogen chloride in ethyl acetate was added. The solvent was distilled off by nitrogen stream. Hexane was added to the obtained residue to produce a solid, which was then triturated by sonication. The supernatant hexane solution was removed and the resulting solid was dried to give 38 mg of the title compound as colorless crystals.

MS m/e (ESI) 353 (MH$^+$).

Example 69

1-[2-(4,4-Dimethylcyclohexyl)phenyl]-4-furan-3-ylmethylpiperazine hydrochloride

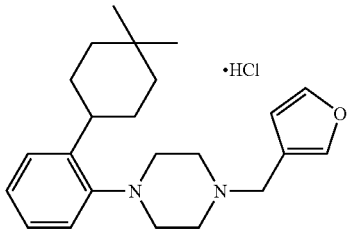

To a mixture of 1-[2-(4,4-dimethylcyclohexyl)phenyl]piperazine (30 mg, 0.11 mmol) produced in Example (3c), furan-3-carbaldehyde (21 mg, 0.22 mmol) and tetrahydrofuran (2 mL) was added sodium triacetoxyborohydride (119 mg, 0.559 mmol), followed by stirring for 1 hour and 50 minutes at room temperature. Saturated aqueous solution of sodium hydrogencarbonate was added to the reaction mixture and extraction was performed with ethyl acetate. The separated organic layer was filtered through Celite. The solvent was distilled off by nitrogen stream to the filtrate. The resultant residue was purified by NH silica gel column chromatography (ethyl acetate/heptane) to give 1-[2-(4,4-dimethylcyclohexyl)phenyl]-4-furan-3-ylmethylpiperazine. This compound was dissolved in dichloromethane, and a 4N solution of hydrogen chloride in ethyl acetate was added. The solvent was distilled off by nitrogen stream. Hexane was added to the obtained residue to produce a solid, which was then triturated by sonication. The supernatant hexane solution was removed and the resulting solid was dried to give 31 mg of the title compound as colorless crystals.

MS m/e (ESI) 353 (MH$^+$).

Example 70

1-[4-Methyl-2-(3,3,5,5-tetramethylcyclohexyl)phenyl]-4-propylpiperazine hydrochloride

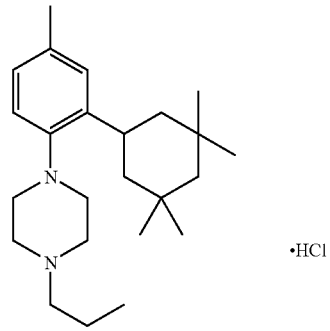

70a

4-[4-Methyl-2-(3,3,5,5-tetramethylcyclohexyl)phenyl]piperazine-1-carboxylic acid t-butyl ester

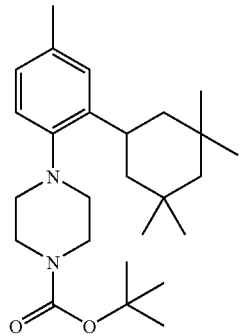

A mixture of 4-[4-bromo-2-(3,3,5,5-tetramethylcyclohexyl)phenyl]piperazine-1-carboxylic acid t-butyl ester (200 mg, 0.417 mmol) produced in Example (99a), cesium carbonate (408 mg, 1.25 mmol), tetrakis(triphenylphosphine)palladium(0) (50 mg, 0.0417 mmol) and dimethylformamide (4 mL) was stirred at room temperature under a nitrogen atmosphere. Trimethylboroxine (0.06 mL, 0.417 mmol) was added to the mixture, and stirring was continued for 9 hours at an external temperature of 100° C. Ethyl acetate and water were added to the reaction mixture and extraction was performed with ethyl acetate. The separated organic layer was washed with water and brine in that order and then dried over anhydrous magnesium sulfate. The desiccant was filtered off and the filtrate was concentrated under reduced pressure. The resultant residue was purified by silica gel column chromatography (ethyl acetate/hexane) to give 124 mg of the title compound as colorless crystals.

$^1$H-NMR (400 MHz, CDCl$_3$) δ: 0.93 (s, 6H), 1.11 (s, 6H), 1.13-1.44 (m, 6H), 1.48 (s, 9H), 2.30 (s, 3H), 2.79 (brs, 4H), 3.57 (tt, J=12.4, 2.8 Hz, 1H), 6.94-6.97 (m, 2H), 7.03 (brs, 1H).

The 4H of piperazine ring could not be identified.

70b

1-[4-Methyl-2-(3,3,5,5-tetramethylcyclohexyl)phenyl]piperazine

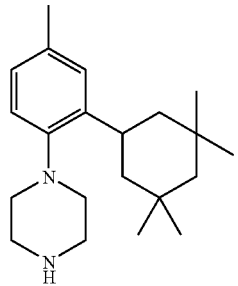

A mixture of 4-[4-methyl-2-(3,3,5,5-tetramethylcyclohexyl)phenyl]piperazine-1-carboxylic acid t-butyl ester (124 mg, 0.299 mmol) produced in Example (70a), trifluoroacetic acid (1 mL, 12.9 mmol) and dichloromethane (2 mL) was stirred for 2 hours and 30 minutes at room temperature. Saturated aqueous solution of sodium hydrogencarbonate was added to the reaction mixture and extraction was performed with ethyl acetate. The separated organic layer was concentrated under reduced pressure. The resultant residue was purified by NH silica gel column chromatography (ethyl acetate/hexane) to give 85 mg of the title compound as yellow crystals.

$^1$H-NMR (400 MHz, CDCl$_3$) δ: 0.93 (s, 6H), 1.12 (s, 6H), 1.13-1.48 (m, 6H), 2.30 (s, 3H), 2.82 (t, J=4.8 Hz, 4H), 3.02 (t, J=4.8 Hz, 4H), 3.59 (tt, J=12.4, 2.8 Hz, 1H), 6.97 (ddd, J=8.4, 2.0, 0.8 Hz, 1H), 6.99-7.05 (m, 2H).

The 1H of NH could not be identified.

70c

1-[4-Methyl-2-(3,3,5,5-tetramethylcyclohexyl)phenyl]-4-propylpiperazine hydrochloride

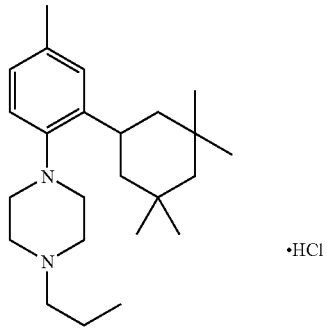

To a mixture of 1-[4-methyl-2-(3,3,5,5-tetramethylcyclohexyl)phenyl]piperazine (55 mg, 0.175 mmol) produced in Example (70b), propionaldehyde (20 mg, 0.350 mmol) and tetrahydrofuran (2 mL) was added sodium triacetoxyborohydride (75 mg, 0.350 mmol), followed by stirring for 1 hour and 15 minutes at room temperature. Saturated aqueous solution of sodium hydrogencarbonate was added to the reaction mixture and extraction was performed with ethyl acetate. The separated organic layer was dried over anhydrous sodium sulfate. The desiccant was filtered off and the filtrate was concentrated under reduced pressure. The resultant residue was purified by NH silica gel column chromatography (ethyl acetate/heptane) to give 56 mg of 1-[4-methyl-2-(3,3,5,5-tetramethylcyclohexyl)phenyl]-4-propylpiperazine as a colorless solid.

This compound was dissolved in dichloromethane, and then a 4N solution of hydrogen chloride in ethyl acetate was added and the mixture was concentrated under reduced pressure. Diethyl ether-hexane was added to the obtained residue to produce a solid, which was then triturated by sonication. The supernatant diethyl ether-hexane solution was removed and the resulting solid was dried to give 54 mg of the title compound as a colorless solid.

$^1$H-NMR (400 MHz, CDCl$_3$) δ: 0.91-0.95 (m, 9H), 1.12 (s, 6H), 1.13-1.60 (m, 8H), 2.29 (s, 3H), 2.34-2.38 (m, 2H), 2.59 (brs, 4H), 2.88-2.90 (m, 4H), 3.56 (tt, J=12.4, 2.8 Hz, 1H), 6.93-6.95 (m, 1H), 7.01-7.03 (m, 2H). MS m/e (ESI) 357 (MH$^+$).

Example 71

1-[3-Methyl-2-(3,3,5,5-tetramethylcyclohex-1-enyl)phenyl]-4-propylpiperazine hydrochloride

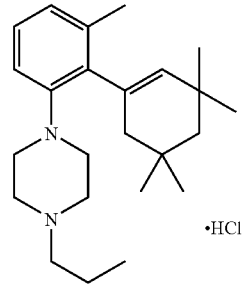

71a

1-Methyl-3-nitro-2-(3,3,5,5-tetramethylcyclohex-1-enyl)benzene

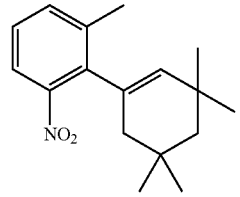

A mixture of 4,4,5,5-tetramethyl-2-(3,3,5,5-tetramethylcyclohex-1-enyl)[1,3,2]dioxaborolane (3.96 g, 15 mmol) produced in Example (4b), 2-bromo-3-nitrotoluene (2.48 g, 11.5 mmol), tetrakis(triphenylphosphine)palladium(0) (1.33 g, 1.15 mmol), tripotassium phosphate (3.66 g, 17.3 mmol), 1,2-dimethoxyethane (30 mL) and water (10 mL) was stirred for 10 hours and 20 minutes at an external temperature of 80° C. under a nitrogen atmosphere. Ethyl acetate and water were added to the reaction mixture, and it was filtered through Celite. The filtrate was then extracted with ethyl acetate. The separated organic layer was washed with water and brine in that order and then dried over anhydrous magnesium sulfate. The desiccant was filtered off and the filtrate was concentrated under reduced pressure. The resultant residue was purified by NH silica gel column chromatography (hexane) to give 3.14 g of the title compound as a yellow oil.

$^1$H-NMR (400 MHz, CDCl$_3$) δ: 1.01 (s, 3H), 1.06 (s, 3H), 1.07 (s, 3H), 1.10 (s, 3H), 1.37-1.46 (m, 2H), 1.90 (d, J=17.2 Hz, 1H), 2.14 (dd, J=17.2, 2.0 Hz, 1H), 2.33 (s, 3H), 5.23 (t, J=2.0 Hz, 1H), 7.24 (dd, J=8.0, 7.6 Hz, 1H), 7.36 (d, J=7.6 Hz, 1H), 7.53 (d, J=8.0 Hz, 1H).

71b

3-Methyl-2-(3,3,5,5-tetramethylcyclohex-1-enyl) phenylamine

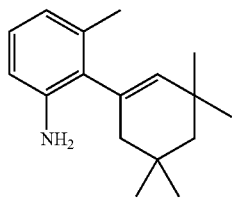

A mixture of the 1-methyl-3-nitro-2-(3,3,5,5-tetramethylcyclohex-1-enyl)benzene (1 g, 3.66 mmol) produced in Example (71a), iron powder (631 mg, 11.0 mmol), ammonium chloride (783 mg, 14.6 mmol), ethanol (15 mL), water (6 mL) and dimethylformamide (1 mL) was stirred for 3 hours and 30 minutes at an external temperature of 90° C. under a nitrogen atmosphere. Ethyl acetate and water were added to the reaction mixture, and it was filtered through Celite. The filtrate was then extracted with ethyl acetate. The separated organic layer was washed with water and brine in that order and then dried over anhydrous sodium sulfate. The desiccant was filtered off and the filtrate was concentrated under reduced pressure. The resultant residue was purified by NH silica gel column chromatography (ethyl acetate/hexane) to give 663 mg of the title compound as a light yellow oil.

$^1$H-NMR (400 MHz, CDCl$_3$) δ: 1.074 (s, 3H), 1.076 (s, 3H), 1.098 (s, 3H), 1.101 (s, 3H), 1.45 (s, 2H), 1.85 (dd, J=17.2, 1.2 Hz, 1H), 1.95 (dd, J=17.2, 1.2 Hz, 1H), 2.18 (s, 3H), 3.65 (brs, 2H), 5.38 (brs, 1H), 6.55 (d, J=7.6 Hz, 1H), 6.61 (d, J=7.2 Hz, 1H), 6.94 (dd, J=7.6, 7.2 Hz, 11H).

71c

1-[3-Methyl-2-(3,3,5,5-tetramethylcyclohex-1-enyl) phenyl]piperazine

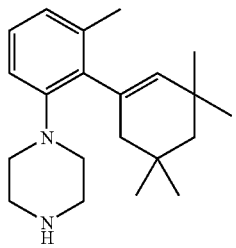

To a mixture of 3-methyl-2-(3,3,5,5-tetramethylcyclohex-1-enyl)phenylamine (663 mg, 2.72 mmol) produced in Example (71b) and 1,2-dichlorobenzene (3 mL) was added bis(2-chloroethyl)amine hydrochloride (632 mg, 3.54 mmol), followed by stirring for 5 hours and 50 minutes at an external temperature of 200° C. under a nitrogen atmosphere. During the reaction, a nitrogen stream was passed through the reactor several times. The reaction mixture was cooled to room temperature, chloroform and saturated solution of sodium hydrogencarbonate were added, and the filtrate obtained by filtration through Celite was extracted with chloroform. The separated organic layer was washed with brine and then dried over anhydrous sodium sulfate. The desiccant was filtered off and the filtrate was concentrated under reduced pressure. The resultant residue was purified by NH silica gel column chromatography (ethyl acetate/hexane) to give 625 mg of the title compound as a yellow solid.

$^1$H-NMR (400 MHz, CDCl$_3$) δ: 1.05 (s, 6H), 1.11 (s, 6H), 1.43 (s, 2H), 1.65 (d, J=16.8 Hz, 1H), 2.23 (s, 3H), 2.38 (d, J=16.8 Hz, 1H), 2.59-2.70 (m, 2H), 2.84-2.93 (m, 2H), 2.95-3.03 (m, 2H), 3.08-3.16 (m, 2H), 5.17 (s, 1H), 6.94 (d, J=7.2 Hz, 1H), 6.96 (d, J=8.0 Hz, 1H), 7.11 (dd, J=8.0, 7.2 Hz, 1H).

The 1H of NH could not be identified.

71d

1-[3-Methyl-2-(3,3,5,5-tetramethylcyclohex-1-enyl) phenyl]-4-propylpiperazine hydrochloride

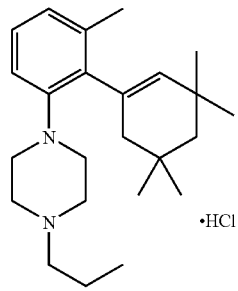

To a mixture of 1-[3-methyl-2-(3,3,5,5-tetramethylcyclohex-1-enyl)phenyl]piperazine (115 mg, 0.368 mmol) produced in Example (71c), propionaldehyde (0.079 mL, 1.1 mmol) and tetrahydrofuran (2 mL) was added sodium triacetoxyborohydride (246 mg, 1.1 mmol), followed by stirring for 1 hour and 30 minutes at room temperature. Saturated aqueous solution of sodium hydrogencarbonate was added to the reaction mixture and extraction was performed with ethyl acetate. The separated organic layer was washed with water and brine in that order and then dried over anhydrous sodium sulfate. The desiccant was filtered off and the filtrate was concentrated under reduced pressure. The resultant residue was purified by NH silica gel column chromatography (ethyl acetate/hexane) to give 124 mg of 1-[3-methyl-2-(3,3,5,5-tetramethylcyclohex-1-enyl)phenyl]-4-propylpiperazine as colorless crystals.

$^1$H-NMR (400 MHz, CDCl$_3$) δ: 0.92 (t, J=7.6 Hz, 3H), 1.05 (s, 6H), 1.10 (s, 3H), 1.11 (s, 3H), 1.43 (s, 2H), 1.48-1.57 (m, 2H), 1.64 (d, J=17.2 Hz, 1H), 2.23 (s, 3H), 2.31-2.35 (m, 2H), 2.38 (d, J=17.2 Hz, 1H), 2.42-2.66 (m, 4H), 2.67-2.78 (m, 2H), 3.18-3.28 (m, 2H), 5.18 (s, 1H), 6.94 (d, J=7.2 Hz, 1H), 6.99 (d, J=7.6 Hz, 1H), 7.11 (dd, J=7.6, 7.2 Hz, 1H).

This compound was dissolved in dichloromethane, and then a 4N solution of hydrogen chloride in ethyl acetate was added and the mixture was concentrated under reduced pressure. Diethyl ether-hexane was added to the obtained residue to produce a solid, which was triturated by sonication. It was then was filtered and dried to give 134 mg of the title compound as a colorless solid.

MS m/e (ESI) 355 (MH$^+$).

Example 72

1-[5-Methoxy-4-piperidin-1-yl-2-(3,3,5,5-tetramethylcyclohexyl)phenyl]-4-propylpiperazine hydrochloride

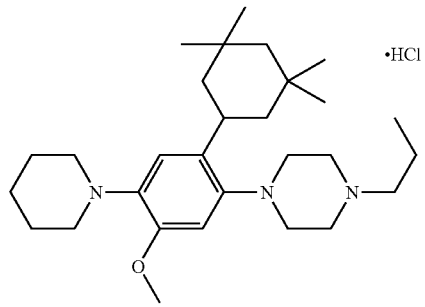

72a

4-[5-Methoxy-4-piperidin-1-yl-2-(3,3,5,5-tetramethylcyclohexyl)phenyl]piperazine-1-carboxylic acid t-butyl ester

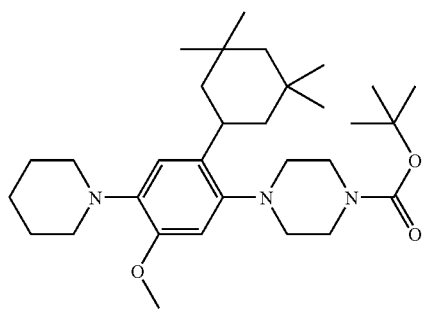

A mixture of 4-[4-bromo-5-methoxy-2-(3,3,5,5-tetramethylcyclohexyl)phenyl]piperazine-1-carboxylic acid t-butyl ester (509 mg, 1 mmol) produced by a synthetic procedure similar to Example (43c), piperidine (128 mg, 1.5 mmol), sodium t-butoxide (240 mg, 2.5 mmol), palladium(II) acetate (22 mg, 0.1 mmol), tri-t-butylphosphonium tetrafluoroborate (87 mg, 0.3 mmol) and xylene (3 mL) was stirred for 20 hours at an external temperature of 100° C. under a nitrogen atmosphere, and was then further stirred for 12 hours at an external temperature of 120° C. Ethyl acetate and water were added to the reaction mixture, which was then passed through Celite to remove insoluble materials. The resultant filtrate was extracted with ethyl acetate. The separated organic layer was washed with water and brine and then dried over anhydrous sodium sulfate. The desiccant was filtered off and the filtrate was concentrated under reduced pressure. The resultant residue was purified by silica gel column chromatography (ethyl acetate/hexane) to give 88 mg of the title compound as red crystals.

$^1$H-NMR (400 MHz, CDCl$_3$) δ: 0.92 (s, 6H), 1.10 (s, 6H), 1.14-1.65 (m, 17H), 1.74 (brs, 4H), 2.80 (brs, 4H), 2.95 (brs, 4H), 3.54 (t, J=12.4 Hz, 1H), 3.81 (s, 3H), 6.59 (s, 1H), 6.77 (s, 1H).

4H could not be identified.

72b

1-[5-Methoxy-4-piperidin-1-yl-2-(3,3,5,5-tetramethylcyclohexyl)phenyl]piperazine

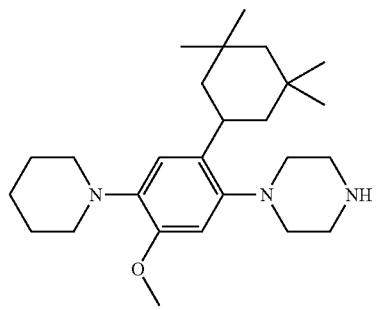

A mixture of the 4-[5-methoxy-4-piperidin-1-yl-2-(3,3,5,5-tetramethylcyclohexyl)phenyl]piperazine-1-carboxylic acid t-butyl ester (88 mg, 0.17 mmol) produced in Example (72a), trifluoroacetic acid (0.25 mL, 3.2 mmol) and dichloromethane (0.5 mL) was stirred for 1 hour and 10 minutes at room temperature. Saturated aqueous solution of sodium hydrogencarbonate was added to the reaction mixture and extraction was performed with ethyl acetate. The separated organic layer was dried over anhydrous sodium sulfate. The desiccant was filtered off and the filtrate was concentrated under reduced pressure. The resultant residue was purified by NH silica gel column chromatography (ethyl acetate/heptane) to give 56 mg of the title compound as a red solid.

$^1$H-NMR (400 MHz, CDCl$_3$) δ: 0.93 (s, 6H), 1.12 (s, 6H), 1.14-1.65 (m, 8H), 1.71-1.77 (m, 4H), 2.81-2.83 (m, 4H), 2.95 (t, J=5.2 Hz, 4H), 2.99-3.02 (m, 4H), 3.56 (tt, J=12.4, 2.8 Hz, 1H), 3.83 (s, 3H), 6.66 (s, 1H), 6.77 (s, 1H).

The 1H of NH could not be identified.

72c

1-[5-Methoxy-4-piperidin-1-yl-2-(3,3,5,5-tetramethylcyclohexyl)phenyl]-4-propylpiperazine hydrochloride

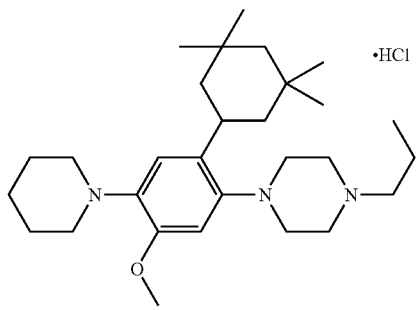

To a mixture of 1-[5-methoxy-4-piperidin-1-yl-2-(3,3,5,5-tetramethylcyclohexyl)phenyl]piperazine (5 mg, 0.0121 mmol) produced in Example (72b), propionaldehyde (1.4 mg, 0.0242 mmol) and tetrahydrofuran (0.3 mL) was added sodium triacetoxyborohydride (5 mg, 0.0242 mmol), followed by stirring for 1 hour and 10 minutes at room temperature. Saturated aqueous solution of sodium hydrogencarbonate was added to the reaction mixture and extraction was performed with ethyl acetate. The solvent was distilled off nitrogen stream to the separated organic layer. The resultant residue was purified by NH silica gel column chromatography (ethyl acetate/hexane) to give 1-[5-methoxy-4-piperidin-1-yl-2-(3,3,5,5-tetramethylcyclohexyl)phenyl]-4-propylpiperazine. This compound was dissolved in dichloromethane, and a 4N solution of hydrogen chloride in ethyl acetate was added. The solvent was distilled of by nitrogen stream. Heptane was added to the obtained residue to produce a solid, which was then triturated by sonication. The supernatant heptane solution was removed and the resulting solid was dried to give 6.1 mg of the title compound as a colorless solid.

$^1$H-NMR (400 MHz, CDCl$_3$) δ: 0.94 (s, 6H), 1.055 (t, J=7.6 Hz, 3H), 1.06 (s, 6H), 1.18-2.08 (m, 12H), 2.66-2.80 (m, 2H), 2.87-3.08 (m, 4H), 3.21-3.31 (m, 2H), 3.44-3.91 (m, 9H), 3.94 (s, 3H), 6.80 (s, 1H), 8.56 (s, 1H). MS m/e (ESI) 456 (MH$^+$).

Example 73

1-(2-Fluoroethyl)-4-[2-(3,3,5,5-tetramethylcyclohexyl)phenyl]piperazine hydrochloride

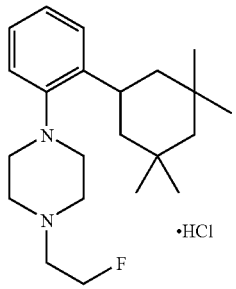

A mixture of 1-[2-(3,3,5,5-tetramethylcyclohexyl)phenyl]piperazine (30 mg, 0.1 mmol) produced in Example (8b), 1-bromo-2-fluoroethane (16.2 mg, 0.125 mmol), sodium iodide (1.5 mg, 0.01 mmol), potassium carbonate (20.8 mg, 0.15 mmol) and dimethylformamide (1 mL) was stirred for 2 hours at an external temperature of 80° C. Saturated aqueous solution of sodium hydrogencarbonate was added to the reaction mixture and extraction was performed with diethyl ether. The solvent was distilled off by nitrogen stream to the separated organic layer. The resultant residue was purified by NH silica gel column chromatography (ethyl acetate/heptane) to give 1-(2-fluoroethyl)-4-[2-(3,3,5,5-tetramethylcyclohexyl)phenyl]piperazine.

$^1$H-NMR (400 MHz, CDCl$_3$) δ: 0.93 (s, 6H), 1.13 (s, 6H), 1.15 (d, J=13.6 Hz, 1H), 1.23 (dd, J=12.4, 12.4 Hz, 2H), 1.33 (dt, J=13.6, 2.0 Hz, 1H), 1.40-1.48 (m, 2H), 2.71 (brs, 4H), 2.77 (dt, J=28.4, 4.8 Hz, 2H), 2.95 (t, J=4.8 Hz, 4H), 3.57 (tt, J=12.4, 2.8 Hz, 1H), 4.57 (dt, J=47.6, 4.8 Hz, 2H), 7.05-7.18 (m, 3H), 7.23 (dd, J=7.6, 1.6 Hz, 1H).

This compound was dissolved in dichloromethane, and a 4N solution of hydrogen chloride in ethyl acetate was added. The solvent was distilled off by nitrogen stream. Diethyl ether-heptane was added to the resultant residue to produce a solid, which was then triturated by sonication. The supernatant diethyl ether-heptane solution was removed and the resulting solid was dried to give 27.5 mg of the title compound as a colorless solid.

MS m/e (ESI) 347 (MH$^+$).

Example 74

1-(2,2-Difluoroethyl)-4-[2-(3,3,5,5-tetramethylcyclohexyl)phenyl]piperazine hydrochloride

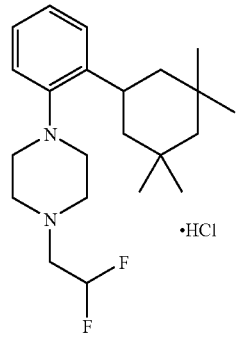

A mixture of 1-[2-(3,3,5,5-tetramethylcyclohexyl)phenyl]piperazine (30 mg, 0.1 mmol) produced in Example (8b), 2-bromo-1,1-difluoroethane (18.1 mg, 0.125 mmol), sodium iodide (1.5 mg, 0.01 mmol), potassium carbonate (20.8 mg, 0.15 mmol) and dimethylformamide (1 mL) was stirred for 2 hours at an external temperature of 80° C. After then further adding 2-bromo-1,1-difluoroethane (18.1 mg, 0.125 mmol) to the reaction mixture, it was further stirred for 6 hours and 30 minutes at an external temperature of 80° C. Saturated aqueous solution of sodium hydrogencarbonate was added to the reaction mixture and extraction was performed with diethyl ether. The solvent was distilled off by nitrogen stream to the separated organic layer. The resultant residue was purified by NH silica gel column chromatography (ethyl acetate/heptane) to give 1-(2,2-difluoroethyl)-4-[2-(3,3,5,5-tetramethylcyclohexyl)phenyl]piperazine.

$^1$H-NMR (400 MHz, CDCl$_3$) δ: 0.93 (s, 6H), 1.12 (s, 6H), 1.17 (d, J=14.0 Hz, 1H), 1.23 (dd, J=12.8, 12.8 Hz, 2H), 1.33 (dt, J=13.6, 2.0 Hz, 1H), 1.38-1.46 (m, 2H), 2.75 (brs, 4H), 2.81 (td, J=14.8, 4.4 Hz, 2H), 2.93 (t, J=4.8 Hz, 4H), 3.55 (tt, J=12.8, 2.8 Hz, 1H), 5.93 (tt, J=56.0, 4.4 Hz, 1H), 7.05-7.18 (m, 3H), 7.23 (dd, J=7.6, 1.6 Hz, 1H).

This compound was dissolved in dichloromethane, and a 4N solution of hydrogen chloride in ethyl acetate was added. The solvent was distilled off by nitrogen stream. Diethyl ether-heptane was added to the obtained residue to produce a solid, which was then triturated by sonication. The supernatant diethyl ether-heptane solution was removed and the resulting solid was dried to give 15.3 mg of the title compound as a colorless solid.

MS m/e (ESI) 365 (MH$^+$).

Example 75

1-(3-Fluoropropyl)-4-[2-(3,3,5,5-tetramethylcyclohexyl)phenyl]piperazine hydrochloride

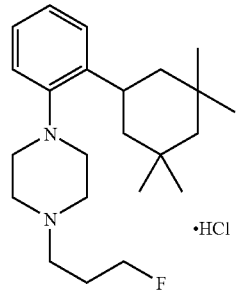

A mixture of 1-[2-(3,3,5,5-tetramethylcyclohexyl)phenyl]piperazine (30 mg, 0.1 mmol) produced in Example (8b), 1-bromo-3-fluoropropane (18.0 mg, 0.125 mmol), sodium iodide (1.5 mg, 0.01 mmol), potassium carbonate (20.8 mg, 0.15 mmol) and dimethylformamide (1 mL) was stirred for 2 hours at an external temperature of 80° C. Saturated aqueous solution of sodium hydrogencarbonate was added to the reaction mixture and extraction was performed with diethyl ether. The solvent was distilled off by nitrogen stream to the separated organic layer. The resultant residue was purified by NH silica gel column chromatography (ethyl acetate/beptane) to give 1-(3-fluoropropyl)-4-[2-(3,3,5,5-tetramethylcyclohexyl)phenyl]piperazine.

¹H-NMR (400 MHz, CDCl₃) δ: 0.93 (s, 6H), 1.12 (s, 6H), 1.15 (d, J=14.0 Hz, 1H), 1.23 (dd, J=12.8, 12.8 Hz, 2H), 1.33 (dt, J=13.6, 2.0 Hz, 1H), 1.38-1.47 (m, 2H), 1.86-2.01 (m, 2H), 2.53-2.57 (m, 2H), 2.61 (brs, 4H), 2.92 (t, J=4.8 Hz, 4H), 3.57 (tt, J=12.8, 2.8 Hz, 1H), 4.56 (dt, J=47.2, 6.0 Hz, 2H), 7.04-7.18 (m, 3H), 7.25 (dd, J=7.2, 2.0 Hz, 1H).

This compound was dissolved in dichloromethane, and a 4N solution of hydrogen chloride in ethyl acetate was added. The solvent was distilled off by nitrogen stream. Diethyl ether-heptane was added to the obtained residue to produce a solid, which was then triturated by sonication. The supernatant diethyl ether-heptane solution was removed and the resulting solid was dried to give 27.8 mg of the title compound as a colorless solid.

MS m/e (ESI) 361 (MH⁺).

Example 76

1-(4-Fluorobutyl)-4-[2-(3,3,5,5-tetramethylcyclohexyl)phenyl]piperazine hydrochloride

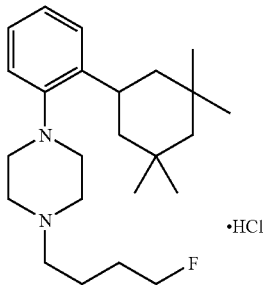

A mixture of 1-[2-(3,3,5,5-tetramethylcyclohexyl)phenyl]piperazine (30 mg, 0.1 mmol) produced in Example (8b), 1-bromo-4-fluorobutane (19.8 mg, 0.125 mmol), sodium iodide (1.5 mg, 0.01 mmol), potassium carbonate (20.8 mg, 0.15 mmol) and dimethylformamide (1 mL) was stirred for 2 hours at an external temperature of 80° C. Saturated aqueous solution of sodium hydrogencarbonate was added to the reaction mixture and extraction was performed with diethyl ether. The solvent was distilled off by nitrogen stream to the separated organic layer. The resultant residue was purified by NH silica gel column chromatography (ethyl acetate/heptane) to give 1-(4-fluorobutyl)-4-[2-(3,3,5,5-tetramethylcyclohexyl)phenyl]piperazine.

¹H-NMR (400 MHz, CDCl₃) δ: 0.93 (s, 6H), 1.12 (s, 6H), 1.15 (d, J=14.0 Hz, 1H), 1.23 (dd, J=12.4, 12.4 Hz, 2H), 1.32 (dt, J=13.6, 2.0 Hz, 1H), 1.39-1.48 (m, 2H), 1.60-1.84 (m, 4H), 2.43-2.46 (m, 2H), 2.61 (brs, 4H), 2.92 (t, J=4.8 Hz, 4H), 3.57 (tt, J=12.8, 2.8 Hz, 1H), 4.49 (dt, J=47.2, 6.0 Hz, 2H), 7.04-7.18 (m, 3H), 7.22 (dd, J=7.6, 1.6 Hz, 1H).

This compound was dissolved in dichloromethane, and a 4N solution of hydrogen chloride in ethyl acetate was added. The solvent was distilled off by nitrogen stream. Diethyl ether-heptane was added to the obtained residue to produce a solid, which was then triturated by sonication. The supernatant diethyl ether-heptane solution was removed and the resulting solid was dried to give 27.3 mg of the title compound as a colorless solid.

MS m/e (ESI) 375 (MH⁺).

Example 77

1-Allyl-4-[2-(3,3,5,5-tetramethylcyclohexyl)phenyl]piperazine hydrochloride

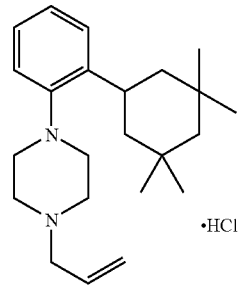

A mixture of 1-[2-(3,3,5,5-tetramethylcyclohexyl)phenyl]piperazine (30 mg, 0.1 mmol) produced in Example (8b), allyl bromide (14.8 mg, 0.12 mmol), potassium carbonate (20.8 mg, 0.15 mmol) and dimethylformamide (1 mL) was stirred for 4 hours and 20 minutes at an external temperature of 80° C. Saturated aqueous solution of sodium hydrogencarbonate was added to the reaction mixture and extraction was performed with ethyl acetate-dichloromethane. The separated organic layer was washed with water, and then the solvent was distilled off by nitrogen stream. The resultant residue was purified by NH silica gel column chromatography (ethyl acetate/heptane) to give 1-allyl-4-[2-(3,3,5,5-tetramethylcyclohexyl)phenyl]piperazine.

¹H-NMR (400 MHz, CDCl₃) δ: 0.93 (s, 6H), 1.13 (s, 6H), 1.15-1.28 (m, 3H), 1.33 (dt, J=13.6, 2.0 Hz, 1H), 1.38-1.48 (m, 2H), 2.60 (brs, 4H), 2.93 (t, J=4.8 Hz, 4H), 3.07 (ddd, J=6.8, 1.2, 1.2 Hz, 2H), 3.57 (tt, J=12.4, 2.8 Hz, 1H), 5.16-5.19 (m, 1H), 5.21-5.26 (m, 1H), 5.20 (ddt, J=17.2, 10.0, 6.8 Hz, 1H), 7.04-7.18 (m, 3H), 7.20-7.25 (m, 1H).

This compound was dissolved in dichloromethane, and a 4N solution of hydrogen chloride in ethyl acetate was added. The solvent was distilled off by nitrogen stream. Diethyl ether-heptane was added to the obtained residue to produce a solid, which was then triturated by sonication. The supernatant diethyl ether-heptane solution was removed and the resulting solid was dried to give 17.7 mg of the title compound as a colorless solid.

MS m/e (ESI) 341 (MH⁺).

Example 78

1-Prop-2-ynyl-4-[2-(3,3,5,5-tetramethylcyclohexyl)phenyl]piperazine hydrochloride

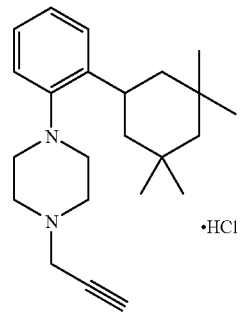

A mixture of 1-[2-(3,3,5,5-tetramethylcyclohexyl)phenyl]piperazine (30 mg, 0.1 mmol) produced in Example (8b), propargyl bromide (14.3 mg, 0.12 mmol), potassium carbonate (20.8 mg, 0.15 mmol) and dimethylformamide (1 mL) was stirred for 4 hours and 20 minutes at an external temperature of 80° C. Saturated aqueous solution of sodium hydrogencarbonate was added to the reaction mixture and extraction was performed with ethyl acetate-dichloromethane. The separated organic layer was washed with water, and then the solvent was distilled off by nitrogen stream. The resultant residue was purified by NH silica gel column chromatography (ethyl acetate/heptane) to give 1-prop-2-ynyl-4-[2-(3,3,5,5-tetramethylcyclohexyl)phenyl]piperazine.

$^1$H-NMR (400 MHz, CDCl$_3$) δ: 0.93 (s, 6H), 1.13 (s, 6H), 1.14-1.36 (m, 4H), 1.40-1.48 (m, 2H), 2.27 (t, J=2.4 Hz, 1H), 2.75 (brs, 4H), 2.96 (t, J=4.8 Hz, 4H), 3.37 (d, J=2.4 Hz, 2H), 3.56 (tt, J=12.4, 2.8 Hz, 1H), 7.05-7.18 (m, 3H), 7.23 (dd, J=8.0, 1.6 Hz, 1H).

This compound was dissolved in dichloromethane, and a 4N solution of hydrogen chloride in ethyl acetate was added. The solvent was distilled off by nitrogen stream. Diethyl ether-heptane was added to the obtained residue to produce a solid, which was then triturated by sonication. The supernatant diethyl ether-heptane solution was removed and the resulting solid was dried to give 6.6 mg of the title compound as a colorless solid.

MS m/e (ESI) 339 (MH$^+$).

Example 79

1-But-2-ynyl-4-[2-(3,3,5,5-tetramethylcyclohexyl)phenyl]piperazine hydrochloride

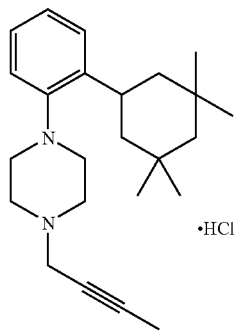

A mixture of the 1-[2-(3,3,5,5-tetramethylcyclohexyl)phenyl]piperazine (30 mg, 0.1 mmol) produced in Example (8b), 1-bromo-2-butyne (16.1 mg, 0.12 mmol), potassium carbonate (20.8 mg, 0.15 mmol) and dimethylformamide (1 mL) was stirred for 4 hours and 20 minutes at an external temperature of 80° C. Saturated aqueous solution of sodium hydrogencarbonate was added to the reaction mixture and extraction was performed with diethyl ether. The separated organic layer was washed with water, and then the solvent was distilled off by nitrogen stream. The resultant residue was purified by NH silica gel column chromatography (ethyl acetate/heptane) to give 1-but-2-ynyl-4-[2-(3,3,5,5-tetramethylcyclohexyl)phenyl]piperazine.

$^1$H-NMR (400 MHz, CDCl$_3$) δ: 0.93 (s, 6H), 1.14 (s, 6H), 1.14-1.36 (m, 4H), 1.40-1.48 (m, 2H), 1.84 (t, J=2.4 Hz, 3H), 2.73 (brs, 4H), 2.96 (t, J=4.8 Hz, 4H), 3.28 (q, J=2.4 Hz, 2H), 3.57 (tt, J=12.8, 2.8 Hz, 1H), 7.05-7.18 (m, 3H), 7.22 (dd, J=7.6, 1.6 Hz, 1H).

This compound was dissolved in dichloromethane, and a 4N solution of hydrogen chloride in ethyl acetate was added. The solvent was distilled off by nitrogen stream. Diethyl ether-heptane was added to the obtained residue to produce a solid, which was then triturated by sonication. The supernatant diethyl ether-heptane solution was removed and the resulting solid was dried to give 11.2 mg of the title compound as a colorless solid.

MS m/e (ESI) 353 (MH$^+$).

Example 80

1-[2-(3,3,5,5-Tetramethylcyclohexyl)phenyl]-4-(4,4,4-trifluorobutyl)piperazine hydrochloride

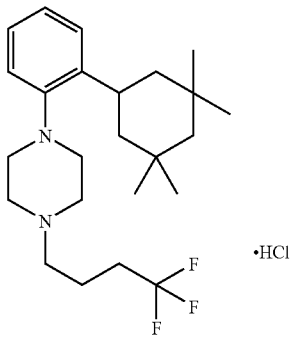

A mixture of the 1-[2-(3,3,5,5-tetramethylcyclohexyl)phenyl]piperazine (30 mg, 0.1 mmol) produced in Example (8b), 1-bromo-4,4,4-trifluorobutane (24.4 mg, 0.125 mmol), sodium iodide (1.5 mg, 0.01 mmol), potassium carbonate (20.8 mg, 0.15 mmol) and dimethylformamide (1 mL) was stirred for 2 hours and 30 minutes at an external temperature of 60° C. Aqueous solution of sodium hydrogencarbonate was added to the reaction mixture and extraction was performed with diethyl ether. The solvent was distilled off by nitrogen stream to the separated organic layer. The resultant residue was purified by NH silica gel column chromatography (ethyl acetate/heptane) to give 1-[2-(3,3,5,5-tetramethylcyclohexyl)phenyl]-4-(4,4,4-trifluorobutyl)piperazine.

This compound was dissolved in dichloromethane, and a 4N solution of hydrogen chloride in ethyl acetate was added. The solvent was distilled off by nitrogen stream. Diethyl ether-heptane was added to the obtained residue to produce a solid, which was then triturated by sonication. The supernatant diethyl ether-heptane solution was removed and the resulting solid was dried to give 27.5 mg of the title compound as a colorless solid.

$^1$H-NMR (400 MHz, CD$_3$OD) δ: 0.95 (s, 6H), 1.17 (s, 6H), 1.19-1.42 (m, 6H), 1.98-2.09 (m, 2H), 2.28-2.40 (m, 2H), 3.15 (s, 4H), 3.20-3.90 (m, 7H), 7.12-7.20 (m, 3H), 7.26-7.30 (m, 1H). MS m/e (ESI) 411 (MH$^+$).

Example 81

4-[3-(4-Butylpiperazin-1-yl)-4-(3,3,5,5-tetramethylcyclohexyl)phenyl]morpholine hydrochloride

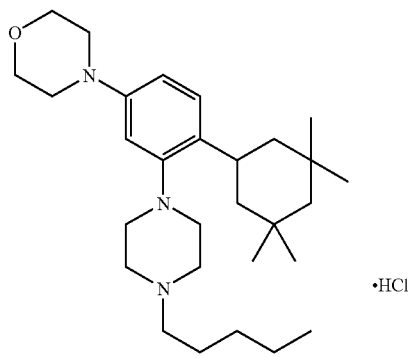

81a

3-Piperazin-1-yl-4-(3,3,5,5-tetramethylcyclohexyl)phenol

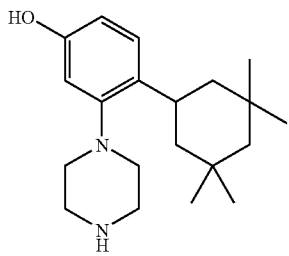

1-[5-Methoxy-2-(3,3,5,5-tetramethylcyclohex-1-enyl)phenyl]piperazine produced in Example (27c) was used as a starting material for N-butyloxycarbonylation and hydrogenation by conventional methods. A mixture of 4-[5-methoxy-2-(3,3,5,5-tetramethylcyclohexyl)phenyl]piperazine-1-carboxylic acid t-butyl ester (3.41 g, 7.92 mmol) obtained by the reaction, acetic acid (18 mL, 314 mmol) and 48% hydrobromic acid (36 mL, 318 mmol) was stirred for 8 hours and 20 minutes at an external temperature of 130° C. The reaction mixture was cooled in an ice water bath and stirred, and then 5N aqueous solution of sodium hydroxide was added dropwise thereto to adjust pH of the mixture to 8-9. The resultant solid was filtered to give 2.98 g of a crude product of the title compound as a light red solid.

¹H-NMR (400 MHz, CD₃OD) δ: 0.94 (s, 6H), 1.54 (s, 6H), 1.17-1.40 (m, 6H), 3.05 (t, J=4.8 Hz, 4H), 3.42 (tt, J=12.8, 2.8 Hz, 1H), 6.55-6.61 (m, 2H), 7.05 (d, J=8.0 Hz, 1H).

The 4H of piperazine ring and the 2H of NH and OH could not be identified.

81b

4-[5-Hydroxy-2-(3,3,5,5-tetramethylcyclohexyl)phenyl]piperazine-1-carboxylic acid t-butyl ester

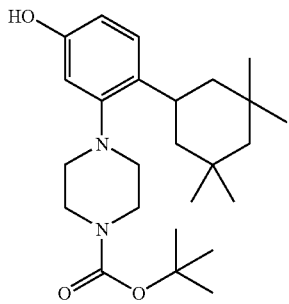

A mixture of the crude product of 3-piperazin-1-yl-4-(3,3,5,5-tetramethylcyclohexyl)phenol produced in Example (81a) (2.98 g) and a mixed solvent of chloroform-methanol (100 mL) was stirred at an external temperature of 0° C. A solution of di-t-butyl dicarbonate (1.81 g, 8.32 mmol) in chloroform was added dropwise thereto. After stirring for 2 hours and 30 minutes, the reaction mixture was concentrated under reduced pressure. Saturated aqueous solution of sodium carbonate and ethyl acetate were added to the obtained residue and extraction was performed with ethyl acetate. The separated organic layer was washed with water and brine in that order and then dried over anhydrous sodium sulfate. The desiccant was filtered off and the filtrate was concentrated under reduced pressure. The obtained residue was purified by NH silica gel column chromatography (ethyl acetate/heptane) to give 2.95 g of the title compound as a light red solid.

¹H-NMR (400 MHz, CDCl₃) δ: 0.91 (s, 6H), 1.10 (s, 6H), 1.11-1.43 (m, 6H), 1.49 (s, 9H), 2.80 (brs, 4H), 3.43 (tt, J=12.4, 2.8 Hz, 1H), 3.52 (brs, 4H), 6.55-6.57 (m, 2H), 7.06 (dd, J=7.2, 1.6 Hz, 1H).

The 1H of OH could not be identified.

81c

4-[5-(Nonafluorobutane-1-sulfonyloxy)-2-(3,3,5,5-tetramethylcyclohexyl)phenyl]piperazine-1-carboxylic acid t-butyl ester

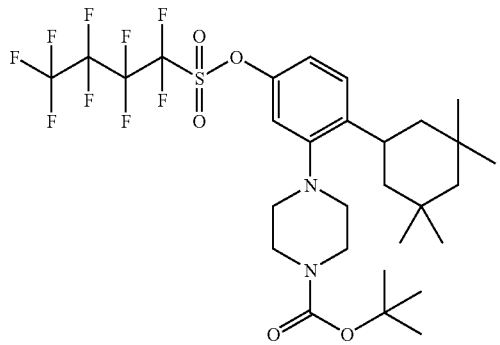

A mixture of 4-[5-hydroxy-2-(3,3,5,5-tetramethylcyclohexyl)phenyl]piperazine-1-carboxylic acid t-butyl ester (1.5 g, 3.60 mmol) produced in Example (81b), 4-dimethylaminopyridine (22.2 mg, 0.18 mmol), diisopropylethylamine (0.758 mL, 4.32 mmol) and dichloromethane (10 mL) was cooled in an ice water bath and stirred under a nitrogen atmosphere.

Perfluorobutanesulfonyl fluoride (0.773 mL, 3.96 mmol) was then added dropwise thereto. After stirring for 1 hour and 20 minutes under the same conditions, stirring was continued for 16 hours at room temperature. Water was added to the reaction mixture and extraction was performed with dichloromethane. The separated organic layer was washed with brine and then dried over anhydrous magnesium sulfate. The desiccant was filtered off and the filtrate was concentrated under reduced pressure. The resultant residue was purified by NH silica gel column chromatography (ethyl acetate/heptane) to give 2.41 g of the title compound as a light yellow oil.

¹H-NMR (400 MHz, CDCl₃) δ: 0.93 (s, 6H), 1.11 (s, 6H), 1.13-1.46 (m, 6H), 1.49 (s, 9H), 2.82 (brs, 4H), 3.51 (tt, J=12.4, 2.8 Hz, 1H), 3.57 (brs, 4H), 6.91 (d, J=2.4 Hz, 1H), 6.99 (dd, J=8.8, 2.4 Hz, 1H), 7.27 (d, J=8.4 Hz, 1H).

81d

4-[5-Morpholin-4-yl-2-(3,3,5,5-tetramethylcyclohexyl)phenyl]piperazine-1-carboxylic acid t-butyl ester

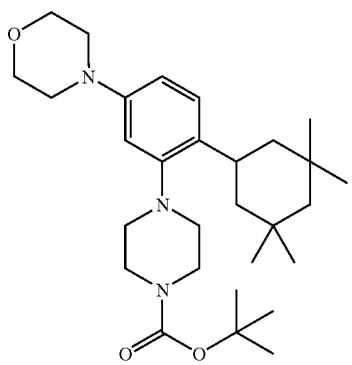

A mixture of 4-[5-(nonafluorobutane-1-sulfonyloxy)-2-(3,3,5,5-tetramethylcyclohexyl)phenyl]piperazine-1-carboxylic acid t-butyl ester (200 mg, 0.286 mmol) produced in Example (81c), morpholine (37.8 mg, 0.429 mmol), sodium t-butoxide (56.7 mg, 0.572 mmol), tris(dibenzylideneacetone)dipalladium(0) (13.1 mg, 0.0143 mmol), 2-dicyclohexylphosphino-2'-(N,N-dimethylamino)biphenyl (11.5 mg, 0.0286 mmol) and xylene (3 mL) was stirred for 13 hours and 30 minutes at an external temperature of 100° C. under a nitrogen atmosphere. The reaction mixture was filtered through Celite to remove insoluble materials, and the filtrate was concentrated under reduced pressure. The resultant residue was purified by NH silica gel column chromatography (ethyl acetate/heptane) to give 103 mg of the title compound as a light yellow oil.

$^1$H-NMR (400 MHz, CDCl$_3$) δ: 0.91 (s, 6H), 1.10 (s, 6H), 1.11-1.44 (m, 6H), 1.48 (s, 9H), 2.82 (brs, 4H), 3.10-3.12 (m, 4H), 3.45 (tt, J=12.8, 2.8 Hz, 1H), 3.83-3.85 (m, 4H), 6.62-6.68 (m, 2H), 7.12 (d, J=8.0 Hz, 1H).

The 4H of piperazine ring could not be identified.

81e

4-[3-piperazin-1-yl-4-(3,3,5,5-tetramethylcyclohexyl)phenyl]morpholine

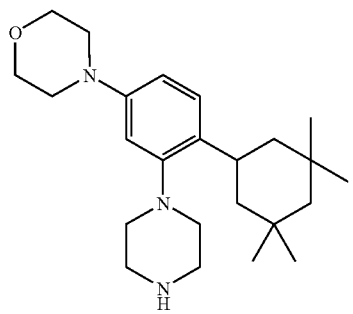

A mixture of 4-[5-morpholin-4-yl-2-(3,3,5,5-tetramethylcyclohexyl)phenyl]piperazine-1-carboxylic acid t-butyl ester (103 mg, 0.212 mmol) produced in Example (81d), trifluoroacetic acid (1 mL, 13.0 mmol) and dichloromethane (2 mL) was stirred for 1 hour at room temperature. Ethyl acetate and saturated aqueous solution of sodium hydrogencarbonate were added to the reaction mixture and extraction was performed with ethyl acetate. The separated organic layer was washed with water and brine in that order and then dried over anhydrous sodium sulfate. The desiccant was filtered off and the filtrate was concentrated under reduced pressure. The resultant residue was purified by silica gel column chromatography (ethyl acetate/heptane) to give 42 mg of the title compound as a colorless oil.

$^1$H-NMR (400 MHz, CDCl$_3$) δ: 0.91 (s, 6H), 1.11 (s, 6H), 1.12-1.45 (m, 6H), 2.80-2.90 (m, 4H), 3.00-3.03 (m, 4H), 3.11-3.13 (m, 4H), 3.45 (tt, J=12.8, 2.8 Hz, 1H), 3.80-3.90 (m, 4H), 6.63 (dd, J=8.4, 2.8 Hz, 1H), 6.68 (d, J=2.8 Hz, 1H), 7.11 (d, J=8.4 Hz, 1H).

The 1H of NH could not be identified.

81f

4-[3-(4-Butylpiperazin-1-yl)-4-(3,3,5,5-tetramethylcyclohexyl)phenyl]morpholine hydrochloride

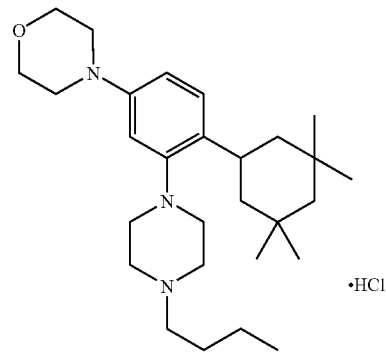

To a mixture of 4-[3-piperazin-1-yl-4-(3,3,5,5-tetramethylcyclohexyl)phenyl]morpholine (14 mg, 0.0363 mmol) produced in Example (81e), butyraldehyde (0.0097 mL, 0.109 mmol) and tetrahydrofuran (0.5 mL) was added sodium triacetoxyborohydride (23 mg, 0.109 mmol), followed by stirring for 1 hour and 30 minutes at room temperature. Saturated aqueous solution of sodium hydrogencarbonate was added to the reaction mixture and extraction was performed with ethyl acetate. The solvent was distilled of by nitrogen stream to the separated organic layer. The resultant residue was purified by NH silica gel column chromatography (ethyl acetate/heptane) to give 4-[3-(4-butylpiperazine-1-yl)-4-(3,3,5,5-tetramethylcyclohexyl)phenyl]morpholine.

$^1$H-NMR (400 MHz, CDCl$_3$) δ: 0.91 (s, 6H), 0.94 (t, J=7.2 Hz, 3H), 1.11 (s, 6H), 1.13-1.54 (m, 10H), 2.39 (t, J=7.6 Hz, 2H), 2.59 (brs, 4H), 2.92 (s, 4H), 3.10 (s, 4H), 3.43 (t, J=12.4 Hz, 1H), 3.84 (s, 4H), 6.63 (d, J=8.0 Hz, 1H), 6.70 (s, 1H), 7.10 (d, J=8.0 Hz, 1H).

This compound was dissolved in dichloromethane, and a 4N solution of hydrogen chloride in ethyl acetate was added. The solvent was distilled off by nitrogen stream. Diethyl ether-hexane was added to the obtained residue to produce a solid, which was then triturated by sonication. The supernatant diethyl ether-hexane solution was removed and the resulting solid was dried to give 17.2 mg of the title compound as a light red solid.

MS m/e (ESI) 442 (MH$^+$).

Example 82

1-[3-(4-Propylpiperazin-1-yl)-4-(3,3,5,5-tetramethylcyclohexyl)phenyl]ethanone hydrochloride

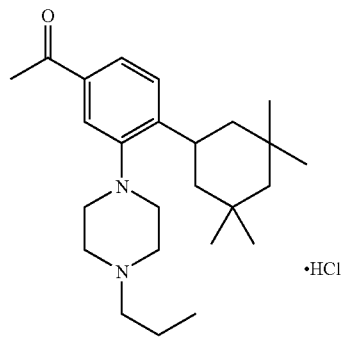

82a

4-[5-Acetyl-2-(3,3,5,5-tetramethylcyclohexyl)phenyl]piperazine-1-carboxylic acid t-butyl ester

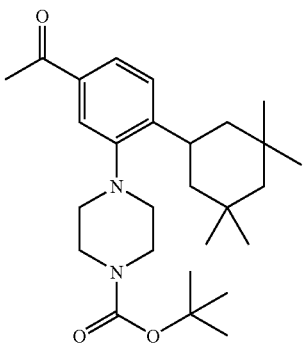

A mixture of 4-[5-(nonafluorobutane-1-sulfonyloxy)-2-(3,3,5,5-tetramethylcyclohexyl)phenyl]piperazine-1-carboxylic acid t-butyl ester (267 mg, 0.382 mmol) produced in Example (81c), tributyl(1-ethoxyvinyl)tin (0.16 mL, 0.458 mmol), dichlorobis(triphenylphosphine)palladium(II) (41 mg, 0.0573 mmol), lithium chloride (48.6 mg, 1.15 mmol) and dimethylformamide (3 mL) was stirred for 6 hours and 10 minutes at an external temperature of 90° C. under a nitrogen atmosphere. Saturated aqueous solution of sodium hydrogencarbonate and ethyl acetate were then added to the reaction mixture. The mixture was filtered through Celite, and the resultant filtrate was concentrated under reduced pressure. The residue was purified by NH silica gel column chromatography (ethyl acetate/heptane) to give 163 mg of the title compound as a colorless oil.

$^1$H-NMR (400 MHz, CDCl$_3$) δ: 0.94 (s, 6H), 1.12 (s, 6H), 1.14-1.46 (m, 6H), 1.49 (s, 9H), 2.56 (s, 3H), 2.76-2.92 (m, 4H), 3.61 (tt, J=12.4, 2.8 Hz, 1H), 7.31 (d, J=7.6 Hz, 1H), 7.64-7.68 (m, 2H).

The 4H of piperazine ring could not be identified.

82b

1-[3-piperazin-1-yl-4-(3,3,5,5-tetramethylcyclohexyl)phenyl]ethanone

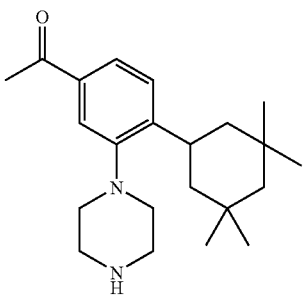

A mixture of 4-[5-acetyl-2-(3,3,5,5-tetramethylcyclohexyl)phenyl]piperazine-1-carboxylic acid t-butyl ester (163 mg, 0.368 mmol) produced in Example (82a), diethyl ether (2 mL) and heptane (2 mL) was stirred at room temperature. A 4N solution of hydrogen chloride in ethyl acetate (2 mL, 8 mmol) was added thereto, and the mixture was stirred for 18 hours and 30 minutes. Saturated aqueous solution of sodium hydrogencarbonate was added to the reaction mixture and extraction was performed with diethyl ether. The separated organic layer was washed with water and brine in that order. The mixture was then filtered through Celite, and the filtrate was concentrated under reduced pressure. The resultant residue was purified by NH silica gel column chromatography (ethyl acetate/heptane) to give 58 mg of the title compound as a light yellow oil.

$^1$H-NMR (400 MHz, CDCl$_3$) δ: 0.94 (s, 6H), 1.13 (s, 6H), 1.14-1.46 (m, 6H), 2.57 (s, 3H), 2.82-2.91 (m, 4H), 2.99-3.17 (m, 4H), 3.62 (tt, J=12.4, 2.8 Hz, 1H), 7.29 (d, J=8.0 Hz, 1H), 7.64 (dd, J=8.0, 2.0 Hz, 1H), 7.69 (d, J=2.0 Hz, 1H).

The 1H of NH could not be identified.

82c

1-[3-(4-Propylpiperazin-1-yl)-4-(3,3,5,5-tetramethylcyclohexyl)phenyl]ethanone hydrochloride

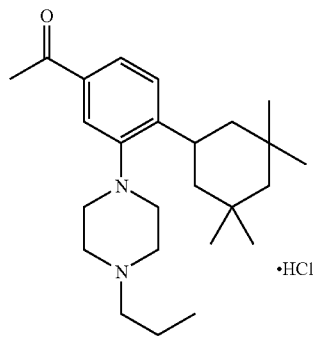

To a mixture of 1-[3-piperazin-1-yl-4-(3,3,5,5-tetramethylcyclohexyl)phenyl]ethanone (19 mg, 0.0555 mmol) produced in Example (82b), propionaldehyde (0.0119 mL, 0.166 mmol) and tetrahydrofuran (0.3 mL) was added sodium triacetoxyborohydride (35 mg, 0.166 mmol), followed by stirring for 1 hour at room temperature. Saturated aqueous solution of sodium hydrogencarbonate was added to the reaction mixture and extraction was performed with diethyl ether. The solvent was distilled off by nitrogen stream to the separated organic layer. The resultant residue was purified by NH silica gel column chromatography (ethyl acetate/heptane) to give 1-[3-(4-propylpiperazin-1-yl)-4-(3,3,5,5-tetramethylcyclohexyl)phenyl]ethanone.

$^1$H-NMR (400 MHz, CDCl$_3$) δ: 0.90-0.97 (m, 9H), 1.13 (s, 6H), 1.14-1.45 (m, 8H), 2.34-2.40 (m, 2H), 2.56 (s, 3H), 2.60 (brs, 4H), 2.90-3.00 (m, 4H), 3.59 (tt, J=12.4, 2.8 Hz, 1H), 7.29 (d, J=8.0 Hz, 1H), 7.64 (dd, J=8.0, 2.0 Hz, 1H), 7.70 (d, J=2.0 Hz, 1H).

This compound was dissolved in dichloromethane, and a 4N solution of hydrogen chloride in ethyl acetate was added. The solvent was distilled off by nitrogen stream. Diethyl ether-heptane was added to the obtained residue to produce a solid, which was then triturated by sonication. The supernatant diethyl ether-heptane solution was removed and the resulting solid was dried to give 15.5 mg of the title compound as a colorless solid.

MS m/e (ESI) 385 (MH$^+$).

Example 83

1-[4-[2-(4,4-Diethylcyclohexyl)phenyl]piperazin-1-yl]butan-1-one

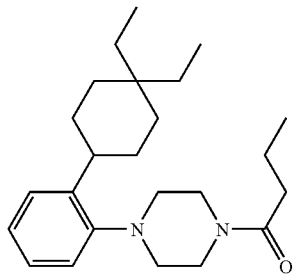

83a

1-[2-(4,4-Diethylcyclohexyl)phenyl]piperazine

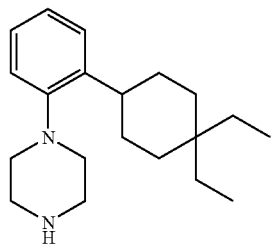

A mixture of 4-[2-(4,4-dimethylcyclohexyl)phenyl]piperazine-1-carboxylic acid t-butyl ester (1.12 g, 2.80 mmol) produced in Example (38b), trifluoroacetic acid (10 mL, 130 mmol) and dichloromethane (10 mL) was stirred for 10 minutes at an external temperature of 0° C., and the temperature was raised to room temperature followed by stirring for 30 minutes. Potassium carbonate was then gradually added to the reaction mixture to make the mixture basic. Then, ethyl acetate and water were added and extraction was performed with ethyl acetate.

The separated organic layer was washed with brine and dried over anhydrous magnesium sulfate. The desiccant was filtered off and then the filtrate was concentrated under reduced pressure. The resultant residue was purified by silica gel column chromatography (dichloromethane/methanol) to give 912 mg of the title compound as a white solid.

MS m/e (ESI) 301 (MH$^+$).

83b

1-[4-[2-(4,4-Diethylcyclohexyl)phenyl]piperazin-1-yl]butan-1-one

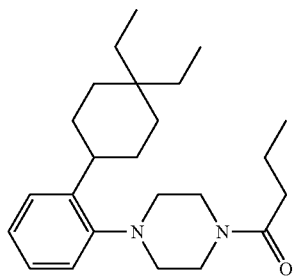

To a solution of 1-[2-(4,4-dimethylcyclohexyl)phenyl]piperazine (30 mg, 0.10 mmol) produced in Example (83a) in tetrahydrofuran (1 mL) was added triethylamine (15 mg, 0.15 mmol), followed by stirring at an external temperature of 0° C. Butyryl chloride (0.015 mL, 0.14 mmol) was added to the reaction mixture while stirring, and the stirring was continued for 9 hours and 30 minutes at an external temperature of 0° C. Saturated aqueous solution of sodium hydrogencarbonate was added to the reaction mixture and extraction was performed with ethyl acetate. The organic layer was washed with water and filtered through Celite, and the filtrate was concentrated. The resultant residue was purified by NH silica gel column chromatography (ethyl acetate/heptane) to give 27 mg of the title compound as a yellow solid.

MS m/e (ESI) 371 (MH$^+$).

Example 84

1-{4-[2-(4,4-Diethylcyclohexyl)-4-morpholin-4-ylphenyl]piperazin-1-yl}butan-2-one hydrochloride

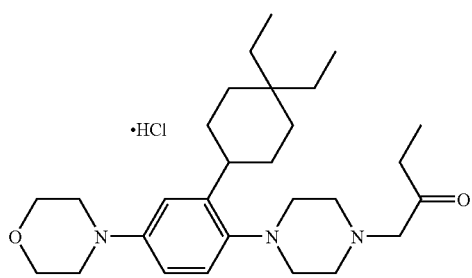

84a

4-[2-(4,4-Diethylcyclohexyl)-4-morpholin-4-yl)phenyl]piperazine-1-carboxylic acid t-butyl ester

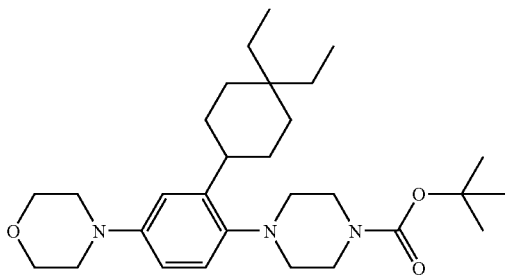

To a solution of 4-[4-bromo-2-(4,4-dimethylcyclohexyl)phenyl]piperazine-1-carboxylic acid t-butyl ester (500 mg, 1.0 mmol) produced in Example (38c) in xylene (10 mL) were added morpholine (245 mg, 2.82 mmol), sodium t-butoxide (450 mg, 4.68 mmol), tri-t-butylphosphonium tetrafluoroborate (340 mg, 1.17 mmol) and palladium(II) acetate (105 mg, 0.47 mmol), followed by stirring for 1 hour at an external temperature of 100° C. under a nitrogen atmosphere. The reaction mixture was air-cooled to room temperature and then filtered through Celite. The obtained filtrate was concentrated under reduced pressure, and the residue was partitioned between ethyl acetate and water. The obtained organic layer was washed with brine and dried over anhydrous magnesium sulfate. The desiccant was filtered off and the obtained filtrate was distilled off under reduced pressure. The resultant residue was purified by silica gel column chromatography (ethyl acetate/hexane) to give 573 mg of the title compound as a white solid.

84b

4-[3-(4,4-Diethylcyclohexyl)-4-piperazin-1-ylphenyl]morpholine

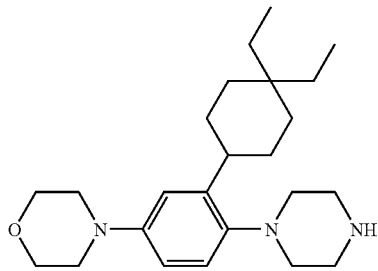

A mixture of 4-[2-(4,4-dimethylcyclohexyl)-4-morpholin-4-yl]phenyl]piperazine-1-carboxylic acid t-butyl ester (573 mg, 1.18 mmol) produced in Example (84a), trifluoroacetic acid (10 mL, 130 mmol) and dichloromethane (10 mL) was stirred for 10 minutes at an external temperature of 0° C., and then the stirring was continued for 30 minutes at room temperature. The reaction mixture was cooled in ice water, and potassium carbonate was added thereto to make the mixture basic. Then, ethyl acetate and water were added and extraction was performed with ethyl acetate. The separated organic layer was washed with brine and dried over anhydrous magnesium sulfate. The desiccant was filtered off and then the filtrate was concentrated under reduced pressure. The resultant residue was purified by NH silica gel column chromatography (ethyl acetate/hexane) to give 354 mg of the title compound as a white solid.

$^1$H-NMR (400 MHz, CDCl$_3$) δ: 0.75-0.85 (m, 6H), 1.16-1.68 (m, 13H), 2.76-2.79 (m, 4H), 2.98-3.00 (m, 4H), 3.11-3.13 (m, 4H), 3.85-3.87 (m, 4H), 6.70 (dd, J=8.8, 2.8 Hz, 1H), 6.81 (d, J=2.8 Hz, 1H), 7.05 (d, J=8.8 Hz, 1H).

The 1H of NH could not be identified.

84c

1-[4-[2-(4,4-Diethylcyclohexyl)-4-morpholin-4-ylphenyl]piperazin-1-yl]butan-2-one hydrochloride

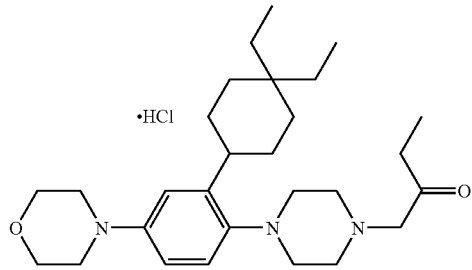

To a solution of 4-[3-(4,4-dimethylcyclohexyl)-4-piperazin-1-ylphenyl]morpholine (20 mg, 0.052 mmol) produced in Example (84b) in dimethylformamide (1 mL) were added potassium carbonate (11 mg, 0.078 mmol) and 1-bromo-2-butanone (9.4 mg, 0.063 mmol), followed by stirring for 2 hours and 5 minutes at an external temperature of 80° C. After air-cooling, water was added to the reaction mixture and extraction was performed with ethyl acetate. The organic layer was washed with water and then filtered through Celite, and the filtrate was concentrated. The resultant residue was purified by NH silica gel column chromatography (ethyl acetate/heptane) to give 1-[4-[2-(4,4-dimethylcyclohexyl)-4-morpholin-4-ylphenyl]piperazin-1-yl]butan-2-one. This compound was dissolved in ethyl acetate, and a 4N solution of hydrogen chloride in ethyl acetate (0.020 mL, 0.080 mmol) was added. The solution was concentrated under reduced pressure, and then hexane was added to the obtained residue to produce a solid. The solid was triturated by sonication and the supernatant hexane solution was removed. The obtained solid residue was dried under reduced pressure to give 25 mg of the title compound as a white solid.

MS m/e (ESI) 493 (MH$^+$).

Example 85

1-[4-Methoxy-2-(3,3,5,5-tetramethylcyclohexyl)phenyl]-4-(tetrahydropyran-4-ylmethyl)piperazine hydrochloride

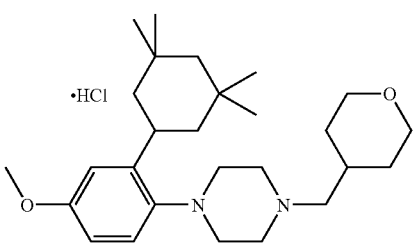

85a

4-Methoxy-1'-nitro-2-(3,3,5,5-tetramethylcyclohex-1'-enyl)benzene

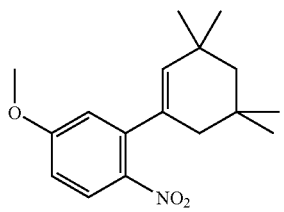

To a solution of 3-iodo-4-nitroanisole (4.21 g, 15.1 mmol) in 1,2-dimethoxyethane (50 mL) were added 4,4,5,5-tetramethyl-2-(3,3,5,5-tetramethylcyclohex-1-enyl)[1,3,2]dioxaborolane (4.78 g, 18.1 mmol) produced in Example (4b), tripotassium phosphate (4.81 g, 22.7 mmol) and water (3 mL). Then, tetrakis(triphenylphosphine)palladium(0) (870 mg, 0.755 mmol) was added to the mixture while stirring at room temperature under a nitrogen atmosphere. The mixture was then further stirred for 13 hours at an external temperature of 70° C. To the reaction mixture were added tetrakis(triphenylphosphine)palladium(0) (870 mg, 0.755 mmol) and water (3 mL), followed by stirring for 26 hours at an external temperature of 100° C. The reaction mixture was cooled, and then ethyl acetate was added and the mixture was filtered through Celite. The filtrate was concentrated to give a residue, which was subjected to extraction with ethyl acetate, and the organic layer was washed with brine. The organic layer was dried over anhydrous magnesium sulfate and then the desiccant was filtered off and the filtrate was concentrated under reduced pressure. The resultant residue was purified by silica gel column chromatography (ethyl acetate/heptane) to give 1.5 g of the title compound as a yellow solid.

$^1$H-NMR (400 MHz, CDCl$_3$) δ: 1.05 (s, 6H), 1.07 (s, 6H), 1.41 (s, 2H), 1.99 (d, J=1.6 Hz, 2H), 3.88 (s, 3H), 5.35 (m, 1H), 6.68 (d, J=2.4 Hz, 1H), 6.81 (dd, J=9.2, 2.4 Hz, 1H), 7.91 (d, J=9.2 Hz, 1H).

85b

4-Methoxy-2-(3,3,5,5-tetramethylcyclohexyl)phenylamine

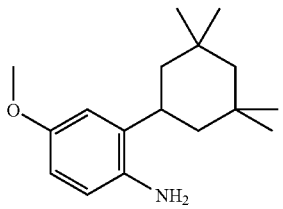

A mixture of 4-methoxy-1-nitro-2-(3,3,5,5-tetramethylcyclohex-1-enyl)benzene (1.0 g, 3.46 mmol) produced in Example (85a), 10% palladium on carbon (500 mg, wet), methanol (8 mL) and tetrahydrofuran (2 mL) was stirred overnight at room temperature and atmospheric pressure under a hydrogen atmosphere. The mixture was filtered through Celite to remove the catalyst, and the filtrate was concentrated. A crude product of the title compound was obtained as a brown oil. The crude product was used without purification for the following reaction.

85c

1-[4-Methoxy-2-(3,5,5-tetramethylcyclohexyl)phenyl]piperazine

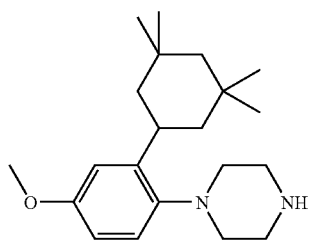

A mixture of the crude product of 4-methoxy-2-(3,3,5,5-tetramethylcyclohexyl)phenylamine produced in Example (85b), bis(2-chloroethyl)amine hydrochloride (770 mg, 4.33 mmol) and 1,2-dichlorobenzene (10 ml) was stirred for 2 hours at an external temperature of 220° C. During the reaction, the excess hydrogen chloride gas in the reactor was removed several times with nitrogen gas. Bis(2-chloroethyl)amine hydrochloride (180 mg, 1.01 mmol) was then added and the mixture was stirred for 1 hour under the same conditions. The reaction mixture was cooled to room temperature, saturated aqueous solution of sodium hydrogencarbonate was added and extraction was performed with chloroform. The aqueous layer was again extracted with chloroform, and the organic layers were combined, washed with brine and then dried over anhydrous magnesium sulfate. The desiccant was filtered off and the filtrate was concentrated under reduced pressure. The resultant residue was purified by NH silica gel column chromatography (ethyl acetate/heptane) to give 660 mg of the title compound as a brown solid.

$^1$H-NMR (400 MHz, CDCl$_3$) δ: 0.92 (s, 6H), 1.12 (s, 6H), 1.15-1.34 (m, 4H), 1.42-1.45 (m, 2H), 2.78-2.81 (m, 4H), 2.99-3.02 (m, 4H), 3.63 (tt, J=13, 2.8 Hz, 1H), 3.78 (s, 3H), 6.69 (dd, J=8.8, 2.8 Hz, 1H), 6.77 (d, J=2.8 Hz, 1H), 7.07 (d, J=8.8 Hz, 1H).

85d

1-[4-Methoxy-2-(3,355-tetramethylcyclohexyl)phenyl]-4-(tetrahydropyran-4-ylmethyl)piperazine hydrochloride

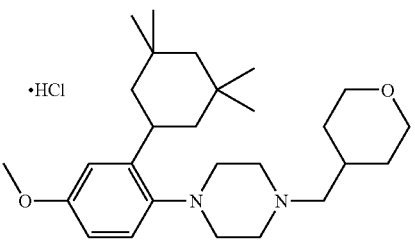

To a solution of 1-[4-methoxy-2-(3,3,5,5-tetramethylcyclohexyl)phenyl]piperazine (10 mg, 0.030 mmol) produced in Example (85c) in tetrahydrofuran (1 mL) were added tetrahydropyranyl-4-carbaldehyde (5.2 mg, 0.045 mmol), sodium triacetoxyborohydride (13 mg, 0.061 mmol) and acetic acid (1.8 mg, 0.030 mmol) in that order, followed by stirring for 60 minutes at room temperature. Saturated aqueous solution of sodium hydrogencarbonate was added to the reaction mixture, extraction was performed with ethyl acetate, and the organic layer was concentrated. The resultant residue was purified by NH silica gel column chromatography (ethyl acetate/heptane) to give 1-[4-methoxy-2-(3,3,5,5-tetramethylcyclohexyl)phenyl]-4-(tetrahydropyran-4-ylmethyl)piperazine.

$^1$H-NMR (400 MHz, CDCl$_3$) δ: 0.92 (s, 6H), 1.12 (s, 6H), 1.15-1.35 (m, 6H), 1.41-1.48 (m, 2H), 1.68-1.72 (m, 2H), 1.74-1.85 (m, 1H), 2.25 (d, J=7.2 Hz, 2H), 2.55 (brs, 4H), 2.84 (brs, 4H), 3.39 (ddd, J=12, 12, 2.0 Hz, 2H), 3.60 (tt, J=12, 2.8 Hz, 1H), 3.78 (s, 3H), 3.97 (ddd, J=12, 2.4, 2.0 Hz, 2H), 6.68 (dd, J=8.8, 2.8 Hz, 1H), 6.77 (d, J=2.8 Hz, 1H), 7.07 (d, J=8.8 Hz, 1H).

The obtained compound was dissolved in ethyl acetate, and a 4N solution of hydrogen chloride in ethyl acetate (0.010 mL, 0.040 mmol) was added. The solution was concentrated and hexane was added to the obtained residue to produce a solid, which was then triturated by sonication. The supernatant hexane solution was removed, and the solid residue was dried under reduced pressure to give 13.6 mg of the title compound as a white solid.

MS m/e (ESI) 429 (MH$^+$).

Example 86

1-Butyl-4-[4-methoxy-2-(3,3,5,5-tetramethylcyclohexyl)phenyl]piperazine hydrochloride

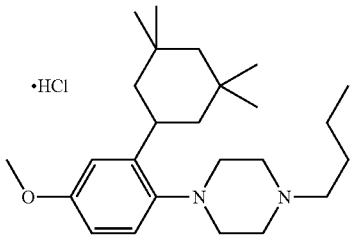

To a solution of 1-[4-methoxy-2-(3,3,5,5-tetramethylcyclohexyl)phenyl]piperazine (10 mg, 0.030 mmol) produced in Example (85c) in tetrahydrofuran (1 mL) were added butyraldehyde (3.3 mg, 0.045 mmol), sodium triacetoxyborohydride (13 mg, 0.061 mmol) and acetic acid (1.8 mg, 0.030 mmol) in that order, followed by stirring for 60 minutes at room temperature. Saturated aqueous solution of sodium hydrogencarbonate was added to the reaction mixture, extraction was performed with ethyl acetate, and the organic layer was concentrated. The resultant residue was purified by NH silica gel column chromatography (ethyl acetate/heptane) to give 1-butyl-4-[4-methoxy-2-(3,3,5,5-tetramethylcyclohexyl)phenyl]piperazine.

$^1$H-NMR (400 MHz, CDCl$_3$) δ: 0.92 (s, 6H), 0.94 (t, J=7.2 Hz, 3H), 1.12 (s, 6H), 1.15-1.54 (m, 10H), 2.34-2.40 (m, 2H), 2.57 (br, 4H), 2.87 (br, 4H), 3.59 (tt, J=12, 2.8 Hz, 1H), 3.77 (s, 3H), 6.67 (dd, J=8.8, 3.2 Hz, 1H), 6.75 (d, J=3.2 Hz, 1H), 7.08 (d, J=8.8 Hz, 1H).

The obtained compound was dissolved in ethyl acetate, and a 4N solution of hydrogen chloride in ethyl acetate (0.010 mL, 0.040 mmol) was added. The solution was concentrated and hexane was added to the obtained residue to produce a solid, which was then triturated by sonication. The supernatant hexane solution was removed, and the solid residue was dried under reduced pressure to give 8.6 mg of the title compound as a white solid.

MS m/e (ESI) 387 (MH$^+$).

Example 87

1-[4,5-Dimethoxy-2-(3,3,5,5-tetramethylcyclohexyl)phenyl]-4-isobutylpiperazinee hydrochloride

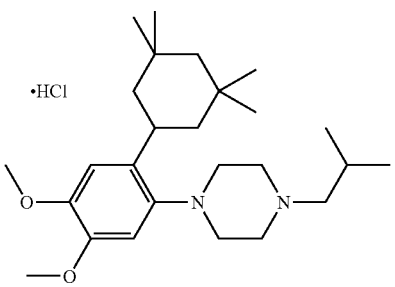

87a

1-Bromo-4,5-dimethoxy-2-nitrobenzene

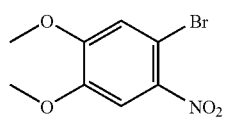

A mixture of concentrated nitric acid (14 mL) and acetic acid (42 mL) was cooled to 110° C. while stirring, and then 4-bromo-1,2-dimethoxybenzene (2 g, 9.21 mmol) was gradually added to the stirred mixture. The reaction mixture was warmed to 15° C., and stirring was continued for 60 minutes. The reaction mixture was cooled to 0° C. and stirred while adding ice water, and then extraction was performed with ether. The obtained organic layer was neutralized with saturated aqueous solution of sodium hydrogencarbonate and potassium carbonate, and then washed with water. After drying the organic layer over anhydrous magnesium sulfate, the desiccant was filtered off and the filtrate was concentrated under reduced pressure. The obtained crude product was recrystallized from ethanol to give 2.09 g of the title compound as light yellow crystals.

$^1$H-NMR (400 MHz, CDCl$_3$) δ: 3.94 (s, 3H), 3.97 (s, 3H), 7.12 (s, 1H), 7.57 (s, 1H).

87b 4,5-Dimethoxy-1-nitro-2-(3,3,5,5-tetramethylcyclohex-1-enyl)benzene

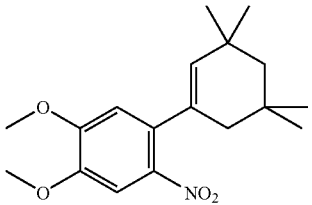

To a solution of 1-bromo-4,5-dimethoxy-2-nitrobenzene (1.06 g, 4.04 mmol) produced in Example (87a) in 1,2-dimethoxyethane (30 mL) were added 4,4,5,5-tetramethyl-2-(3,3,5,5-tetramethylcyclohex-1-enyl)[1,3,2]dioxaborolane (1.28 g, 4.85 mmol) produced in Example (4b), tripotassium phosphate (1.29 g, 6.06 mmol) and water (1.5 mL). Tetrakis (triphenylphosphine)palladium (230 mg, 0.20 mmol) was then added to the mixture while stirring at room temperature under a nitrogen atmosphere. The mixture was then stirred for 13 hours at an external temperature of 70° C., and stirring was continued for 3 hours at an external temperature of 100° C. Tetrakis(triphenylphosphine)palladium(0) (230 mg, 0.20 mmol) and water (2 mL) were added to the reaction mixture, and it was further stirred for 9 hours at an external temperature of 100° C. and then for 11 hours at an external temperature of 70° C. After cooling the reaction mixture, ethyl acetate was added and the mixture was filtered through Celite. The filtrate was concentrated and extracted with ethyl acetate, and the obtained organic layer was washed with brine. The organic layer was then dried over anhydrous magnesium sulfate, the desiccant was filtered off, and the filtrate was concentrated under reduced pressure. The resultant residue was purified by silica gel column chromatography (ethyl acetate/heptane) to give 1.1 g of the title compound as a brown oil.

$^1$H-NMR (400 MHz, CDCl$_3$) δ: 1.06 (s, 6H), 1.07 (s, 6H), 1.42 (s, 2H), 1.99 (d, J=1.6 Hz, 2H), 3.93 (s, 3H), 3.96 (s, 3H), 5.32 (m, 1H), 6.60 (s, 1H), 7.47 (s, 1H).

87c 4,5-Dimethoxy-2-(3,3,5,5-tetramethylcyclohexyl)phenylamine

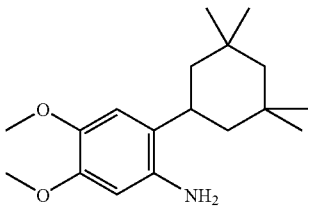

A mixture of 4,5-dimethoxy-1-nitro-2-(3,3,5,5-tetramethylcyclohex-1-enyl)benzene (1.0 g, 3.13 mmol) produced in Example (87b), 10% palladium on carbon (500 mg, wet), methanol (8 mL) and tetrahydrofuran (2 mL) was stirred for 13 hours at room temperature and atmospheric pressure under a hydrogen atmosphere. The mixture was filtered through Celite to remove the catalyst, and the filtrate was concentrated. A crude product of the title compound was obtained as a yellow oil. The crude product was used without purification for the following reaction.

87d

1-[4,5-Dimethoxy-2-(3,3,5,5-tetramethylcyclohexyl)phenyl]piperazine

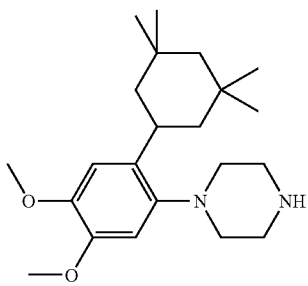

A mixture of the crude product of 4,5-dimethoxy-2-(3,3,5,5-tetramethylcyclohexyl)phenylamine produced in Example (87c), bis(2-chloroethyl)amine hydrochloride (700 mg, 3.91 mmol) and 1,2-dichlorobenzene (10 ml) was stirred for 2 hours at an external temperature of 220° C. During the reaction, nitrogen gas was blown in several times to remove the excess hydrogen chloride gas from the reactor. The reaction mixture was cooled to room temperature, saturated aqueous solution of sodium hydrogencarbonate was added and extraction was performed with chloroform. The aqueous layer was again extracted with chloroform, and the organic layers were combined, washed with brine and then dried over anhydrous magnesium sulfate. The desiccant was filtered off and the filtrate was concentrated under reduced pressure. The resultant residue was purified by NH silica gel column chromatography (ethyl acetate/heptane) to give 490 mg of the title compound as a brown oil.

$^1$H-NMR (400 MHz, CDCl$_3$) δ: 0.93 (s, 6H), 1.13 (s, 6H), 1.15-1.43 (m, 6H), 2.80-2.83 (m, 4H), 3.00-3.03 (m, 4H), 3.63 (tt, J=13, 2.8 Hz, 1H), 3.85 (s, 3H), 3.87 (s, 3H), 6.72 (s, 1H), 6.73 (s, 1H).

87e

1-[4,5-Dimethoxy-2-(3,3,5,5-tetramethylcyclohexyl)phenyl]-4-isobutylpiperazinee hydrochloride

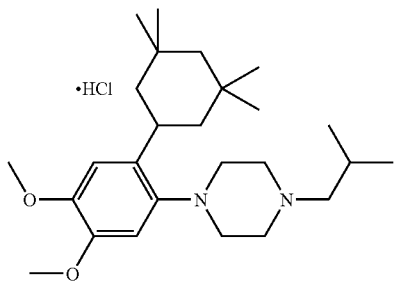

To a solution of the 1-[4,5-dimethoxy-2-(3,3,5,5-tetramethylcyclohexyl)phenyl]piperazine (10 mg, 0.028 mmol) produced in Example (87d) in tetrahydrofuran (1 mL) were added isobutyraldehyde (3.0 mg, 0.042 mmol), sodium triacetoxyborohydride (12 mg, 0.057 mmol) and acetic acid (1.7 mg, 0.028 mmol) in that order, followed by stirring for 60 minutes at room temperature. Saturated aqueous solution of sodium hydrogencarbonate was added to the reaction mixture, extraction was performed with ethyl acetate, and the organic layer was concentrated. The resultant residue was purified by NH silica gel column chromatography (ethyl acetate/heptane) to give 1-[4,5-dimethoxy-2-(3,3,5,5-tetramethylcyclohexyl)phenyl]-4-isobutylpiperazinee.

$^1$H-NMR (400 MHz, CDCl$_3$) δ: 0.86-1.44 (m, 6H), 0.93 (s, 6H), 0.93 (d, J=6.8 Hz, 6H), 1.12 (s, 6H), 1.82 (m, 1H), 2.15 (d, J=7.6 Hz, 2H), 2.55 (br, 4H), 2.87 (br, 4H), 3.61 (tt, J=13, 2.8 Hz, 1H), 3.84 (s, 3H), 3.87 (s, 3H), 6.71 (s, 1H), 6.76 (s, 1H).

The obtained compound was dissolved in ethyl acetate, and a 4N solution of hydrogen chloride in ethyl acetate (0.010 mL, 0.040 mmol) was added. The solution was concentrated, and hexane was added to the obtained residue to produce a solid, which was then triturated by sonication. The supernatant hexane solution was removed and the solid residue was dried under reduced pressure to give 10.3 mg of the title compound as a white solid.

MS m/e (ESI) 417 (MH$^+$).

Example 88

1-Butyl-4-[4-nitro-2-(3,3,5,5-tetramethylcyclohex-1-enyl)phenyl]piperazine hydrochloride

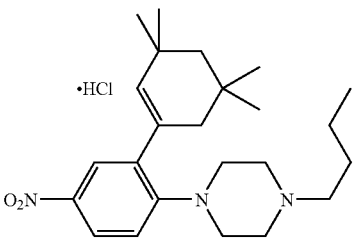

88a 4-(2-Chloro-4-nitrophenyl)piperazine-1-carboxylic acid t-butyl ester

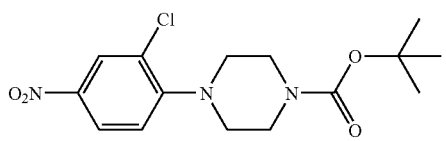

A mixture of 3-chloro-4-fluoronitrobenzene (5 g, 27.1 mmol), 1-piperazinecarboxylic acid t-butyl ester (5 g, 26.8 mmol) and dimethylformamide (10 mL) was stirred for 3 hours and 30 minutes at an external temperature of 130° C. After adding water to the air-cooled reaction mixture, extraction was performed 3 times with chloroform. The organic layers were washed with brine and dried over anhydrous magnesium sulfate. The desiccant was filtered off and the filtrate was concentrated under reduced pressure. The residue was purified by silica gel column chromatography (ethyl acetate/heptane) to give 5.93 g of the title compound as a yellow solid.

$^1$H-NMR (400 MHz, CDCl$_3$) δ: 1.49 (s, 9H), 3.15 (dd, J=5.2, 4.8 Hz, 4H), 3.63 (dd, J=5.2, 4.8 Hz, 4H), 7.04 (d, J=8.8 Hz, 1H), 8.11 (dd, J=8.8, 2.8 Hz, 1H), 8.27 (d, J=2.8 Hz, 1H).

88b

4-[4-Nitro-2-(3,3,5,5-tetramethylcyclohex-1-enyl)phenyl]piperazine-1-carboxylic acid t-butyl ester

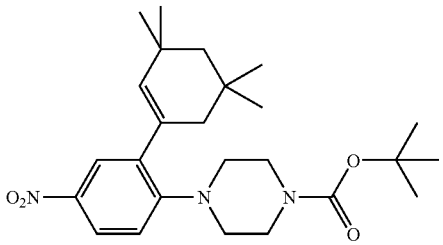

To a solution of 4-(2-chloro-4-nitrophenyl)piperazine-1-carboxylic acid t-butyl ester (5.93 g, 17.3 mmol) produced in Example (88a) in 1,2-dimethoxyethane (70 mL) were added 4,4,5,5-tetramethyl-2-(3,3,5,5-tetramethylcyclohex-1-enyl)[1,3,2]dioxaborolane (5.5 g, 20.8 mmol) produced in Example (4b), tripotassium phosphate (5.51 g, 26 mmol) and water (3 mL). Tetrakis(triphenylphosphine)palladium(0) (1.0 g, 0.865 mmol) was added to the mixture while stirring at room temperature under a nitrogen atmosphere. The mixture was then stirred for 3 hours at an external temperature of 80° C., and then for 7 hours at an external temperature of 100° C. Tetrakis(triphenylphosphine)palladium(0) (830 mg, 0.718 mmol) was added to the reaction mixture, and stirring was continued for 22 hours and 30 minutes. Ethyl acetate was added to the reaction mixture, which was then filtered through Celite. The filtrate was concentrated and the resultant residue was extracted with ethyl acetate, and the obtained organic layer was washed with water and brine. The organic layer was dried over anhydrous magnesium sulfate and then the desiccant was filtered off and the filtrate was concentrated under reduced pressure. The resultant residue was purified by silica gel column chromatography (ethyl acetate/heptane) to give 1.08 g of the title compound as an orange oil.

$^1$H-NMR (400 MHz, CDCl$_3$) δ: 1.03 (s, 6H), 1.10 (s, 6H), 1.42 (s, 2H), 1.49 (s, 9H), 2.11 (s, 2H), 3.07-3.10 (m, 4H), 3.53-3.56 (m, 4H), 5.67 (s, 1H), 6.94 (d, J=8.8 Hz, 1H), 7.93 (d, J=2.8 Hz, 1H), 8.06 (dd, J=8.8, 2.8 Hz, 1H).

88c

1-[4-Nitro-2-(3,3,5,5-tetramethylcylohex-1-enyl)phenyl]piperazine

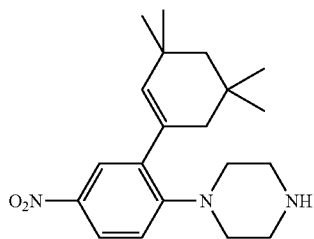

A solution of 4-[4-nitro-2-(3,3,5,5-tetramethylcyclohex-1-enyl)phenyl]piperazine-1-carboxylic acid t-butyl ester (300 mg, 0.676 mmol) produced in Example (88b) in dichloromethane (3 mL) was stirred at an external temperature of 0° C. Trifluoroacetic acid (1 mL) was gradually added dropwise thereto over a period of 15 minutes. The reaction mixture was allowed to warm to room temperature while stirring for 90 minutes. While cooled in an ice bath, saturated aqueous solution of sodium hydrogencarbonate to the mixture to make the mixture basic. Extraction was performed with ethyl acetate, and the separated organic layer was washed with water and then dried over anhydrous magnesium sulfate. The desiccant was filtered off and the filtrate was concentrated under reduced pressure. The resultant residue was purified by NH silica gel column chromatography (ethyl acetate/heptane) to give 180 mg of the title compound as a light yellow solid.

88d

1-Butyl-4-[4-nitro-2-(3,3,5,5-tetramethylcyclohex-1-enyl)phenyl]piperazine hydrochloride

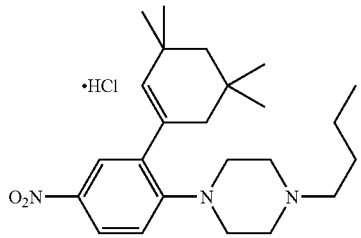

To a solution of 1-[4-nitro-2-(3,3,5,5-tetramethylcyclohex-1-enyl)phenyl]piperazine (10 mg, 0.029 mmol) produced in Example (88c) in tetrahydrofuran (1 mL) were added butyraldehyde (3.2 mg, 0.044 mmol), sodium triacetoxyborohydride (12 mg, 0.058 mmol) and acetic acid (2 mg, 0.029 mmol) in that order, followed by stirring for 3 hours at room temperature. Water was added to the reaction mixture, extraction was performed with ethyl acetate, and the organic layer was concentrated. The resultant residue was purified by NH silica gel column chromatography (ethyl acetate/heptane) to give 1-butyl-4-[4-nitro-2-(3,3,5,5-tetramethylcyclohex-1-enyl)phenyl]piperazine.

$^1$H-NMR (400 MHz, CDCl$_3$) δ: 0.94 (t, J=7.2 Hz, 3H), 1.03 (s, 6H), 1.10 (s, 6H), 1.25 (m, 1H), 1.32-1.38 (m, 2H), 1.43-1.53 (m, 2H), 1.65 (m, 1H), 2.11 (d, J=1.6 Hz, 2H), 2.36-2.40 (m, 2H), 2.56 (br, 4H), 3.19 (br, 4H), 5.67 (t, J=1.6 Hz, 1H), 6.94 (d, J=9.2 Hz, 1H), 7.92 (d, J=2.8 Hz, 1H), 8.04 (dd, J=9.2, 2.8 Hz, 1H).

The obtained compound was dissolved in ethyl acetate, and a 4N solution of hydrogen chloride in ethyl acetate (0.010 mL, 0.040 mmol) was added. The solution was concentrated, and hexane was added to the obtained residue to produce a solid, which was then triturated by sonication. The supernatant hexane solution was removed and the residue was concentrated to give 6.3 mg of the title compound as a white solid.

MS m/e (ESI) 400 (MH$^+$).

Example 89

1-Cyclobutyl-4-[2-(3,3,5,5-tetramethylcyclohexyl)phenyl]piperazine hydrochloride

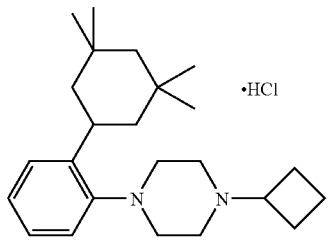

To a solution of 1-[2-(3,3,5,5-tetramethylcyclohexyl)phenyl]piperazine (20 mg, 0.067 mmol) produced in Example (8b) in tetrahydrofuran (1 mL) were added cyclobutanone (7.0 mg, 0.1 mmol), sodium triacetoxyborohydride (28 mg, 0.13 mmol) and acetic acid (4 mg, 0.067 mmol) in that order, followed by stirring for 30 minutes at room temperature. Saturated aqueous solution of sodium hydrogencarbonate was added to the reaction mixture, extraction was performed with ethyl acetate, and the organic layer was concentrated. The resultant residue was purified by NH silica gel column chromatography (ethyl acetate/heptane) to give 1-cyclobutyl-4-[2-(3,3,5,5-tetramethylcyclohexyl)phenyl]piperazine. The obtained compound was dissolved in ethyl acetate, and a 4N solution of hydrogen chloride in ethyl acetate (0.025 mL, 0.100 mmol) was added. The solution was concentrated, and hexane was added to the obtained residue to produce a solid. The solid was triturated by sonication and the supernatant hexane solution was removed. The solid residue was dried under reduced pressure to give 17.6 mg of the title compound as a white solid.

MS m/e (ESI) 355 (MH⁺).

Example 90

1-Cyclopropyl-4-[2-(3,3,5,5-tetramethylcyclohexyl)phenyl]piperazine hydrochloride

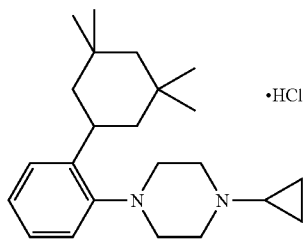

To a solution of 1-[2-(3,3,5,5-tetramethylcyclohexyl)phenyl]piperazine (30 mg, 0.1 mmol) produced in Example (8b) in methanol (3 mL) were added [(1-ethoxycyclopropyl)oxy]trimethylsilane (105 mg, 0.6 mmol), sodium cyanotrihydroborate (28.3 mg, 0.45 mmol), acetic acid (60.1 mg, 1 mmol) and molecular sieves 3A (50 mg) in that order, followed by stirring for 5 hours and 30 minutes at an external temperature of 80° C. Ethyl acetate was added to the reaction mixture, which was filtered through Celite, and the filtrate was concentrated. Water was then added to the residue, extraction was performed with ethyl acetate, and the organic layer was washed with 2N aqueous solution of sodium hydroxide and brine. The organic layer was dried over magnesium sulfate, the desiccant was filtered off, and then the filtrate was concentrated. The resultant residue was purified by NH silica gel column chromatography (ethyl acetate/heptane) to give 1-cyclopropyl-4-[2-(3,3,5,5-tetramethylcyclohexyl)phenyl]piperazine as a white solid. The obtained compound was dissolved in ethyl acetate, and a 4N solution of hydrogen chloride in ethyl acetate (0.040 mL, 0.160 mmol) was added. The solution was concentrated, and hexane was added to the obtained residue to produce a solid, which was then triturated by sonication. The supernatant hexane solution was removed and the resulting solid residue was dried under reduced pressure to give 37.7 mg of the title compound as a white solid.

MS m/e (ESI) 341 (MH⁺).

Example 91

2-{4-[2-(3,3,5,5-Tetramethylcyclohexyl)phenyl]piperazin-1-ylmethyl}cyclopropanecarboxylic acid ethyl ester hydrochloride

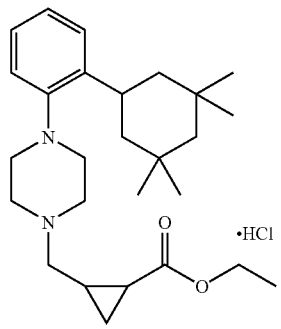

1-[2-(3,3,5,5-Tetramethylcyclohexyl)phenyl]piperazine (2.1 g, 7 mmol) produced in Example (8b) was used as a starting material. Reaction was conducted in a manner similar to Example (4g), using 2-formyl-1-cyclopropanecarboxylic acid ethyl ester (cis/trans mixture, predominantly trans) instead of butyraldehyde, and similar treatment was carried out to give 2.4 g of 2-{4-[2-(3,3,5,5-tetramethylcyclohexyl)phenyl]piperazin-1-ylmethyl}cyclopropanecarboxylic acid ethyl ester as a colorless oil.

¹H-NMR (400 MHz, CDCl₃) δ: 0.77-0.81 (m, 1H), 0.92 (s, 6H), 1.12 (s, 6H), 1.25-1.36 (m, 9H), 1.37-1.50 (m, 3H), 2.33-2.84 (m, 6H), 2.94 (t, J=4.8 Hz, 4H), 3.56 (tt, J=12.8, 2.8 Hz, 1H), 4.10-4.19 (m, 2H), 7.04-7.18 (m, 3H), 7.22 (d, J=7.6 Hz, 1H).

A 48 mg portion of this compound was converted to a hydrochloride by a method similar to in Example (4g) to give 52 mg of the title compound as a colorless solid.

MS m/e (ESI) 427 (MH⁺).

Example 92 trans-1-(2-Methoxymethylcyclopropylmethyl)-4-[2-(3,3,5,5-tetramethylcyclohexyl)phenyl]piperazine hydrochloride

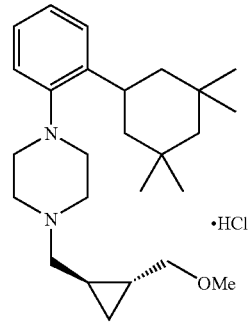

92a cis-(2-{4-[2-(3,3,5,5-Tetramethylcyclohexyl)phenyl]piperazin-1-ylmethyl}cyclopropyl)methanol and trans-(2-{4-[2-(3,3,5,5-Tetramethylcyclohexyl)phenyl]piperazin-1-ylmethyl}cyclopropyl)methanol

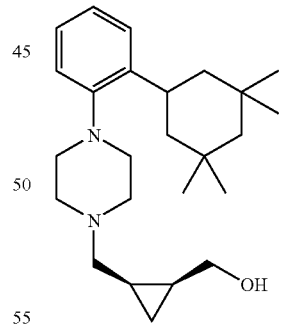

Lithium aluminum hydride (178 mg, 4.68 mmol) was suspended in anhydrous tetrahydrofuran (15 mL), and the suspension was stirred at room temperature under a nitrogen atmosphere. To the suspension was added a solution of 2-{4-[2-(3,3,5,5-tetramethylcyclohexyl)phenyl]piperazin-1-ylmethyl}cyclopropanecarboxylic acid ethyl ester (1 g, 2.34 mmol) produced in Example (91) in anhydrous tetrahydrofuran (15 mL), followed by stirring for 1 hour and 30 minutes at room temperature. Sodium fluoride (1 g) was added to the reaction mixture, and water (0.4 mL) was gradually added while blowing nitrogen. After stirring for 1 hour, the insoluble materials were filtered off and the filtrate was concentrated under reduced pressure. The resultant residue was purified by NH silica gel column chromatography (ethyl acetate/heptane). This procedure gave 173 mg of cis-(2-{4-[2-(3,3,5,5-tetramethylcyclohexyl)phenyl]piperazin-1-ylmethyl}cyclopropyl)methanol as colorless crystals, and 596 mg of trans-(2-{4-[2-(3,3,5,5-tetramethylcyclohexyl)phenyl]piperazin-1-ylmethyl}cyclopropyl)methanol as a colorless oil.

cis: $^1$H-NMR (400 MHz, CDCl$_3$) δ: 0.26 (q, J=4.8H, 1H), 0.83-0.88 (m, 1H), 0.92 (s, 6H), 1.12 (s, 6H), 1.15-1.46 (m, 8H), 2.24 (dd, J=13.2, 13.2 Hz, 1H), 2.60 (br, 4H), 2.75 (dd, J=13.2, 5.2 Hz, 1H), 2.87-3.00 (m, 4H), 3.12 (dd, J=13.2, 13.2 Hz, 1H), 3.55 (tt, J=12.8, 2.8 Hz, 1H), 4.02 (dd, J=13.2, 5.2 Hz, 1H), 7.04-7.16 (m, 3H), 7.21 (dd, J=7.6, 1.6 Hz, 1H).

The 1H of OH could not be identified.

trans: $^1$H-NMR (400 MHz, CDCl$_3$) δ: 0.41-0.47 (m, 1H), 0.49-0.55 (m, 1H), 0.90 (s, 6H), 1.12 (s, 6H), 1.15-1.47 (m, 8H), 2.30 (dd, J=12.8, 7.2 Hz, 1H), 2.44 (dd, J=12.8, 6.4 Hz, 1H), 2.70 (br, 4H), 2.94 (t, J=4.8 Hz, 4H), 3.45-3.60 (m, 3H), 7.04-7.17 (m, 3H), 7.21 (dd, J=7.2, 1.6 Hz, 1H).

The 1H of OH could not be identified.

92b trans-1-(2-Methoxymethylcyclopropylmethyl)-4-[2-(3,3,5,5-tetramethylcyclohexyl)phenyl]piperazine hydrochloride

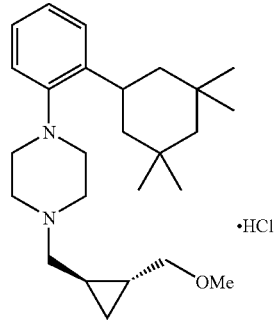

Sodium hydride (60%, oily) (31 mg, 0.78 mmol) was suspended in dimethylformamide (3 mL), and the suspension was stirred at room temperature under a nitrogen atmosphere. To the suspension was added a solution of trans-(2-{4-[2-(3,3,5,5-tetramethylcyclohexyl)phenyl]piperazin-1-ylmethyl}cyclopropyl)methanol (60 mg, 0.156 mmol) produced in Example (91a) in dimethylformamide (3 mL), and the mixture was stirred for 30 minutes under the same conditions. The reaction mixture was cooled in ice water, and then iodomethane (0.015 mL, 0.241 mmol) was added. The reaction mixture was then stirred for 3 hours and 30 minutes while increasing the temperature to room temperature. The reaction mixture was cooled at an external temperature of 0° C., and water was carefully added while blowing nitrogen. Then, ethyl acetate and water were added thereto and extraction was performed with ethyl acetate. The separated organic layer was washed twice with water and then once with brine, and dried over anhydrous sodium sulfate. The desiccant was filtered off and the filtrate was concentrated under reduced pressure. The resultant residue was purified by NH silica gel column chromatography (ethyl acetate/heptane) to give 28 mg of trans-1-(2-methoxymethylcyclopropylmethyl)-4-[2-(3,3,5,5-tetramethylcyclohexyl)phenyl]piperazine as a colorless oil.

$^1$H-NMR (400 MHz, CDCl$_3$) δ: 0.42-0.48 (m, 1H), 0.49-0.55 (m, 1H), 0.80-0.96 (m, 2H), 0.92 (s, 6H), 1.12 (s, 6H), 1.13-1.35 (m, 4H), 1.40-1.48 (m, 2H), 2.36 (dd, J=12.8, 6.8 Hz, 1H), 2.39 (dd, J=12.8, 6.8 Hz, 1H), 2.66 (br, 4H), 2.94 (t, J=5.2 Hz, 4H), 3.22 (dd, J=10.0, 7.2 Hz, 1H), 3.32 (dd, J=10.0, 6.4 Hz, 1H), 3.34 (s, 3H), 3.57 (tt, J=12.8, 2.8 Hz, 1H), 7.04-7.17 (m, 3H), 7.21 (dd, J=7.2, 1.2 Hz, 1H).

This compound was dissolved in dichloromethane, and a 4N solution of hydrogen chloride in ethyl acetate was added. Nitrogen was blown to the solution to remove the solvent. Diethyl ether was added to the obtained residue to produce a solid, which was then triturated by sonication. The supernatant diethyl ether solution was removed and the resulting solid residue was dried by blowing nitrogen, to give 13 mg of the title compound as a white solid.

MS m/e (ESI) 399 (MH$^+$).

Example 93 trans-1-(2-Fluoromethylcyclopropylmethyl)-4-[2-(3,3,5,5-tetramethylcyclohexyl)phenyl]piperazine hydrochloride

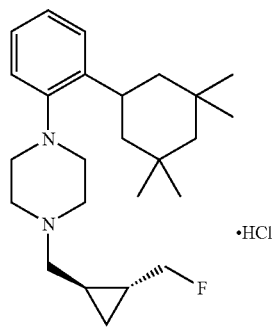

To a solution of trans-(2-{4-[2-(3,3,5,5-tetramethylcyclohexyl)phenyl]piperazin-1-ylmethyl}cyclopropyl)methanol (60 mg, 0.156 mmol) produced in Example (92a) in dichloromethane (5 mL) was added diethylaminosulfur trifluoride (DAST) (0.052 mL, 0.394 mmol), followed by stirring for 2 hours at room temperature under a nitrogen atmosphere. The reaction mixture was cooled at an external temperature of 0° C., saturated aqueous solution of sodium hydrogencarbonate was added, and the mixture was stirred. Then, ethyl acetate and water were added thereto and extraction was performed with ethyl acetate. The separated organic layer was washed with brine and then dried over anhydrous sodium sulfate. The desiccant was filtered off and the filtrate was concentrated under reduced pressure. The resultant residue was purified by NH silica gel column chromatography (ethyl acetate/heptane) to give 17 mg of trans-1-(2-fluoromethylcyclopropylmethyl)-4-[2-(3,3,5,5-tetramethylcyclohexyl)phenyl]piperazine as a colorless oil.

$^1$H-NMR (400 MHz, CDCl$_3$) δ: 0.50-0.64 (m, 2H), 0.92 (s, 6H), 0.93-1.03 (m, 1H), 1.05-1.47 (m, 13H), 2.32 (dd, J=12.8, 6.8 Hz, 1H), 2.45 (dd, J=12.8, 6.0 Hz, 1H), 2.69 (br, 4H), 2.94 (t, J=4.8 Hz, 4H), 3.56 (tt, J=12.8, 2.8 Hz, 1H), 4.21 (ddd, J=48.8, 9.6, 7.2 Hz, 1H), 4.34 (ddd, J=48.8, 9.6, 7.2 Hz, 1H), 7.04-7.17 (m, 3H), 7.21 (d, J=7.2, 1H).

This compound was dissolved in dichloromethane, and a 4N solution of hydrogen chloride in ethyl acetate was added. Nitrogen was then blown to the solution to remove the solvent. Diethyl ether was added to the obtained residue to produce a solid, which was then triturated by sonication. The supernatant diethyl ether solution was removed, and the obtained solid residue was dried by blowing nitrogen, to give 16 mg of the title compound as a white solid.

MS m/e (ESI), 387 (MH$^+$).

Example 94 trans-(2-{4-[2-(3,3,5,5-Tetramethylcyclohexyl)phenyl]piperazin-1-ylmethyl}cyclopropyl)acetonitrile hydrochloride

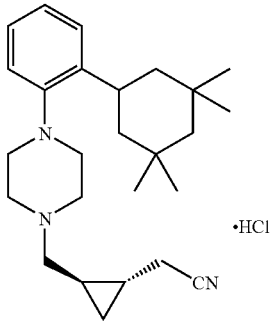

94a trans-(2-{4-[2-(3,3,5,5-Tetramethylcyclohexyl)phenyl]piperazin-1-ylmethyl}cyclopropyl)acetonitrile and trans-1-(2-Chloromethylcyclopropylmethyl)-4-[2-(3,3,5,5-tetramethylcyclohexyl)phenyl]piperazine

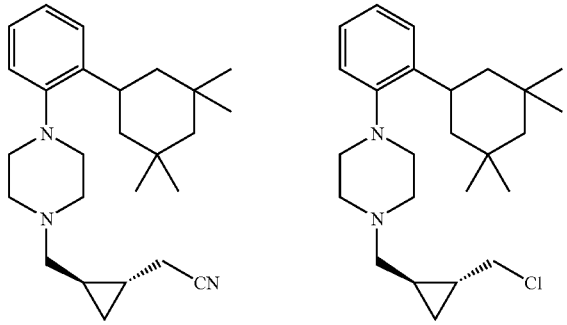

A solution of trans-(2-{4-[2-(3,3,5,5-tetramethylcyclohexyl)phenyl]piperazin-1-ylmethyl}cyclopropyl)methanol (60 mg, 0.156 mmol) produced in Example (92a) in dichloromethane (5 mL) was stirred at an external temperature of 0° C. under a nitrogen atmosphere. Triethylamine (0.065 mL, 0.468 mmol) and methanesulfonyl chloride (0.018 mL, 0.233 mmol) were added in that order to the mixture, followed by stirring for 30 minutes under the same conditions. Saturated aqueous solution of ammonium chloride was added to the reaction mixture, which was then washed with ethyl acetate and water and extracted with ethyl acetate. The separated organic layer was washed with brine and then dried over anhydrous sodium sulfate. The desiccant was filtered off and the filtrate was concentrated under reduced pressure. The resultant residue was dissolved again in dimethylsulfoxide (3 mL), and then tetrabutylammonium iodide (12 mg, 0.032 mmol) and potassium cyanide (34 mg, 0.522 mmol) were added thereto and the mixture was stirred for 2 hours at an external temperature of 70° C. Ethyl acetate and water were added to the reaction mixture and extraction was performed with ethyl acetate. The separated organic layer was washed twice with water and then once with brine, and dried over anhydrous sodium sulfate. The desiccant was filtered off and the filtrate was concentrated under reduced pressure. The resultant residue was purified by NH silica gel column chromatography (ethyl acetate/heptane) to give 8 mg of trans-(2-{4-[2-(3,3,5,5-tetramethylcyclohexyl)phenyl]piperazin-1-ylmethyl}cyclopropyl)acetonitrile as a colorless oil, and 19 mg of trans-1-(2-chloromethylcyclopropylmethyl)-4-[2-(3,3,5,5-tetramethylcyclohexyl)phenyl]piperazine as a colorless oil.

trans-(2-{4-[2-(3,3,5,5-Tetramethylcyclohexyl)phenyl]piperazin-1-ylmethyl}cyclopropyl)acetonitrile:
$^1$H-NMR (400 MHz, CDCl$_3$) δ: 0.53-0.65 (m, 2H), 0.87-1.00 (m, 8H), 1.12 (s, 6H), 1.22-1.47 (m, 6H), 2.30-2.50 (m, 4H), 2.67 (br, 4H), 2.94 (t, J=4.8 Hz, 4H), 3.56 (tt J=12.8, 2.8 Hz, 1H), 7.04-7.17 (m, 3H), 7.21 (dd, J=7.2, 1.6 Hz, 1H).

trans-1-(2-Chloromethylcyclopropylmethyl)-4-[2-(3,3,5,5-tetramethylcyclohexyl)phenyl]piperazine:
$^1$H-NMR (400 MHz, CDCl$_3$) δ: 0.55-0.66 (m, 2H), 0.92 (s, 6H), 0.94-1.11 (m, 2H), 1.12 (s, 6H), 1.13-1.46 (m, 6H), 2.33 (dd, J=12.8, 6.8 Hz, 1H), 2.45 (dd, J=12.4, 6.4 Hz, 1H), 2.68 (br, 4H), 2.94 (t, J=4.8 Hz, 4H), 3.47 (dd, J=11.2, 7.6 Hz, 1H), 3.50 (dd, J=11.2, 7.6 Hz, 1H), 3.56 (tt, J=12.8, 2.8 Hz, 1H), 7.04-7.17 (m, 3H), 7.21 (dd, J=7.6, 1.2 Hz, 1H).

94b trans-(2-[4-[2-(3,3,5,5-Tetramethylcyclohexyl)phenyl]piperazin-1-ylmethyl]cyclopropyl)acetonitrile hydrochloride

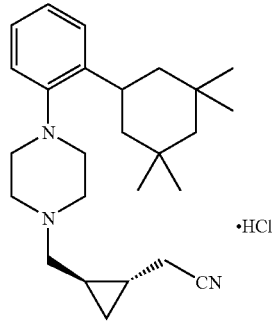

To trans-(2-{4-[2-(3,3,5,5-Tetramethylcyclohexyl)phenyl]piperazin-1-ylmethyl}cyclopropyl)acetonitrile (8 mg) produced in Example (94a) dissolved in dichloromethane was added a 4N solution of hydrogen chloride in ethyl acetate. Nitrogen was then blown to the solution to remove the solvent. Diethyl ether was added to the obtained residue to produce a solid, which was then triturated by sonication. The supernatant diethyl ether solution was removed and the resulting solid residue was dried by blowing nitrogen, to give 8 mg of the title compound as a light brown solid.

MS m/e (ESI) 394 (MH$^+$).

Example 95 trans-1-(2-Chloromethylcyclopropnlmethyl)-4-[2-(3,3,5,5-tetramethylcyclohexyl)phenyl]piperazine hydrochloride

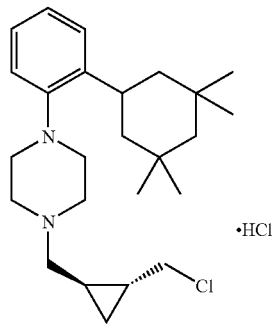

To trans-1-(2-chloromethylcyclopropylmethyl)-4-[2-(3,3,5,5-tetramethylcyclohexyl)phenyl]piperazine (19 mg) produced in Example (94a) dissolved in dichloromethane was added a 4N solution of hydrogen chloride in ethyl acetate.

Example 96

1-(2-Methylcyclopropylmethyl)-4-[2-(3,3,5,5-tetramethylcyclohexyl)phenyl]piperazine hydrochloride

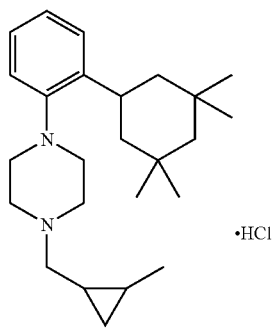

96a

2-Methyl-1-cyclopropanecarbaldehyde

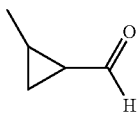

A solution of oxalyl chloride (0.916 ml, 10.5 mmol) in anhydrous dichloromethane (10 mL) was cooled to an internal temperature of below −65° C. under a nitrogen atmosphere. Anhydrous dimethylsulfoxide (1.49 mL, 21 mmol) was added dropwise thereto over a period of 15 minutes. After then heating the reaction mixture to −20° C., it was cooled again to below −65° C. A solution of 2-methylcyclopropanemethanol (258 mg, 3 mmol) in anhydrous dichloromethane (5 mL) was added dropwise to the reaction mixture over a period of 10 minutes. After stirring for 30 minutes under the same conditions, triethylamine (4.18 mL, 30 mmol) was added to the mixture, the temperature was gradually raised to room temperature. Saturated aqueous solution of ammonium chloride, diethyl ether and water were added to the reaction mixture and extraction was performed with diethyl ether. The separated organic layer was washed twice with saturated aqueous solution of citric acid, and then with saturated aqueous solution of sodium hydrogencarbonate and brine in that order, after which it was dried over anhydrous sodium sulfate. The desiccant was filtered off and the filtrate was concentrated under reduced pressure to give 730 mg of a crude product of the title compound as a light yellow oil, as a mixture of cis/trans at the position of cyclopropane ring. This product was directly used without purification for the following reaction.

Nitrogen was then blown to the solution to remove the solvent. Diethyl ether was added to the obtained residue to produce a solid, which was then triturated by sonication. The supernatant diethyl ether solution was removed and the obtained solid residue was dried by blowing nitrogen, to give 22 mg of the title compound as a light red solid.

MS m/e (ESI) 403 (MH+).

Example 96

96b 1-(2-Methylcyclopropylmethyl)-4-[2-(3,3,5,5-tetramethylcyclohexyl)phenyl]piperazine hydrochloride

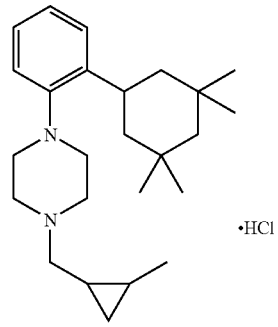

To a mixture of 1-[2-(3,3,5,5-tetramethylcyclohexyl)phenyl]piperazine (300 mg, 1 mmol) produced in Example (8b), the crude product of 2-methyl-1-cyclopropanecarbaldehyde produced in Example (96a) (365 mg) and tetrahydrofuran (10 mL) were added sodium triacetoxyborohydride (424 mg, 2 mmol) and acetic acid (0.057 mL, 1 mmol) in that order, followed by stirring for 15 hours and 30 minutes at room temperature. Ethyl acetate, saturated aqueous solution of sodium hydrogencarbonate and water were added to the reaction mixture and extraction was performed with ethyl acetate. The separated organic layer was washed with brine and then dried over anhydrous sodium sulfate. The desiccant was filtered off and the filtrate was concentrated under reduced pressure. The resultant residue was purified by NH silica gel column chromatography (ethyl acetate/heptane), to give 163 mg of 1-(2-methylcyclopropylmethyl)-4-[2-(3,3,5,5-tetramethylcyclohexyl)phenyl]piperazine as a colorless oil, as a mixture of cis/trans at the position of cyclopropane ring.

$^1$H-NMR (400 MHz, CDCl$_3$) δ: 0.24-0.32 (m, 2H), 0.50-0.55 (m, 2H), 0.92 (s, 6H), 1.06 (d, J=6.0 Hz, 3H), 1.12 (s, 6H), 1.16-1.48 (m, 6H), 2.18 (dd, J=12.4, 7.2 Hz, 1H×0.85), 2.33 (dd, J=12.0, 6.4 Hz, 1H×0.15), 2.50 (dd, J=12.4, 6.4 Hz, 1H×0.85), 2.56 (dd, J=12.4, 6.4 Hz, 1H×0.15), 2.67 (br, 4H), 2.95 (t, J=4.8 Hz, 4H), 3.58 (tt, J=12.8, 2.8 Hz, 1H), 7.05-7.18 (m, 3H), 7.22 (dd, J=7.2, 1.2 Hz, 1H).

This compound was dissolved in dichloromethane, and a 4N solution of hydrogen chloride in ethyl acetate was added. This solution was concentrated under reduced pressure, and diethyl ether was added to the obtained residue to produce a solid, which was filtered. It was then dried under reduced pressure to give 156 mg of the title compound as a white solid, as a mixture of cis/trans at the position of cyclopropane ring.

MS m/e (ESI) 369 (MH+).

Example 97

1-[3-Fluoro-2-(3,3,5,5-tetramethylcyclohex-1-enyl)phenyl]-4-(tetrahydropyran-4-ylmethyl)piperazine hydrochloride

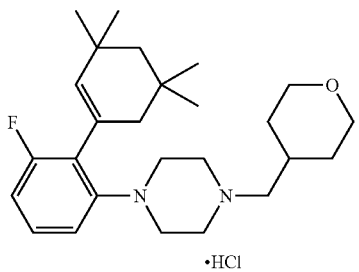

97a

Trifluoromethanesulfonic acid 2-fluoro-6-nitrophenyl ester

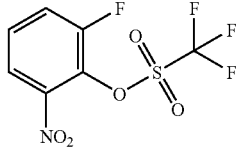

A mixture of 2-fluoro-6-nitrophenol (5 g, 31.83 mmol), triethylamine (22 mL, 157.84 mmol) and dichloromethane (100 mL) was cooled using an ice-methanol bath under a nitrogen atmosphere. To this mixture was added dropwise trifluoromethanesulfonic anhydride (8 mL, 47.55 mmol) over a period of 20 minutes, followed by stirring for 50 minutes under the same conditions. Saturated aqueous solution of ammonium chloride, ethyl acetate and water were added to the reaction mixture and extraction was performed with ethyl acetate. The separated organic layer was washed with saturated aqueous solution of ammonium chloride and brine, and then dried over anhydrous sodium sulfate. The desiccant was filtered off and the filtrate was concentrated under reduced pressure. The resultant residue was purified by silica gel column chromatography (ethyl acetate/hexane) to give 8.02 g of the title compound as an ochre oil.

$^1$H-NMR (400 MHz, CDCl$_3$) δ: 7.52-7.63 (m, 2H), 7.98 (dt, J=8.0, 2.0 Hz, 1H).

97b

1-Fluoro-3-nitro-2-(3,3,5,5-tetramethylcyclohex-1-enyl)benzene

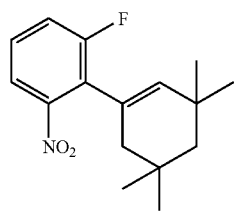

To a mixture of trifluoromethanesulfonic acid 2-fluoro-6-nitrophenyl ester (2.89 g, 10 mmol) produced in Example (97a), 4,4,5,5-tetramethyl-2-(3,3,5,5-tetramethylcyclohex-1-enyl)[1,3,2]dioxaborolane (3.17 g, 12 mmol) produced in Example (4b), toluene (30 mL) and ethanol (15 mL) were added sodium carbonate (1.6 g, 15.1 mmol), purified water (0.9 mL) and tetrakis(triphenylphosphine)palladium(0) (1.15 g, 1 mmol), followed by stirring for 2 hours at an external temperature of 100° C. under a nitrogen atmosphere. Ethyl acetate and water were added to the reaction mixture and extraction was performed with ethyl acetate. The separated organic layer was washed with brine and then dried over anhydrous sodium sulfate. The desiccant was filtered off and the filtrate was concentrated under reduced pressure. The resultant residue was purified by silica gel column chromatography (ethyl acetate/hexane) to give 2.25 g of the title compound as a light yellow oil.

$^1$H-NMR (400 MHz, CDCl$_3$) δ: 1.04 (s, 6H), 1.07 (s, 6H), 1.42 (s, 2H), 2.07 (s, 2H), 5.34 (t, J=2.0 Hz, 1H), 7.23-7.29 (m, 1H), 7.33 (ddd, J=8.0, 8.0, 5.2 Hz, 1H), 7.54 (ddd, J=8.0, 2.0, 1.2 Hz, 1H).

97c

3-Fluoro-2-(3,3,5,5-tetramethylcyclohex-1-enyl)phenyl amine

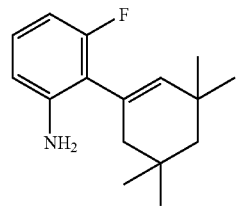

To a solution of 1-fluoro-3-nitro-2-(3,3,5,5-tetramethylcyclohex-1-enyl)benzene (2.25 g, 8.11 mmol) produced in Example (97b) in ethanol (45 mL) were added ammonium chloride (150 mg, 2.8 mmol), water (15 mL) and iron powder (1.6 g, 28.65 mmol), followed by stirring for 2 hours at an external temperature of 90° C. The reaction mixture was filtered and the filtrate was concentrated under reduced pressure. Ethyl acetate and water were added to the obtained residue and extraction was performed with ethyl acetate. The separated organic layer was washed with brine and then dried over anhydrous sodium sulfate. The desiccant was filtered off and the filtrate was concentrated under reduced pressure. The resultant residue was purified by NH silica gel column chromatography (ethyl acetate/heptane) to give 632 mg of the title compound as a light yellow oil.

$^1$H-NMR (400 MHz, CDCl$_3$) δ: 1.06 (s, 6H), 1.09 (s, 6H), 1.44 (s, 2H), 1.96 (s, 2H), 3.86 (brs, 2H), 5.51 (t, J=1.6 Hz, 1H), 6.43 (ddd, J=8.4, 8.0, 1.2 Hz, 1H), 6.46 (ddd, J=8.0, 1.2, 0.8 Hz, 1H), 6.96 (ddd, J=8.4, 8.0, 6.4 Hz, 1H).

97d

1-[3-Fluoro-2-(3,3,5,5-tetramethylcyclohex-1-enyl)phenyl]piperazine

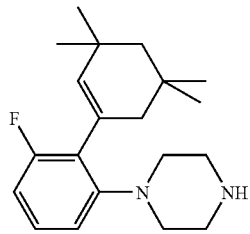

To a solution of 3-fluoro-2-(3,3,5,5-tetramethylcyclohex-1-enyl)phenylamine (623 mg, 2.52 mmol) produced in Example (97c) in 1,2-dichlorobenzene (7 mL) was added bis(2-chloroethyl)amine hydrochloride (560 mg, 3.14 mmol), followed by reflux for 5 hours at an external temperature of 200° C. under a nitrogen atmosphere. During the reaction, a nitrogen stream was circulated into the reactor several times to remove the hydrogen chloride gas. After cooling the reaction mixture to room temperature, ethyl acetate, tetrahydrofuran, methanol, saturated aqueous solution of sodium carbonate and water were added for partition between oil and water. The aqueous layer was further extracted with ethyl acetate, and the combined organic layer was dried over anhydrous sodium sulfate. The desiccant was filtered off and the filtrate was concentrated under reduced pressure. The resultant residue was purified by NH silica gel column chromatography (ethyl acetate/heptane) to give 214 mg of the title compound as a light brown oil.

$^1$H-NMR (400 MHz, CDCl$_3$) δ: 1.05 (s, 6H), 1.08 (s, 6H), 1.42 (s, 2H), 2.06 (s, 2H), 2.95 (brs, 8H), 5.43 (s, 1H), 6.74

(ddd, J=8.4, 8.0, 0.8 Hz, 1H), 6.79 (d, J=8.4 Hz, 1H), 7.12 (ddd, J=8.0, 8.0, 6.4 Hz, 1H).

The 1H of NH could not be identified.

97e

1-[3-Fluoro-2-(3,3,5,5-tetramethylcyclohex-1-enyl)phenyl]-4-(tetrahydropyran-4-ylmethyl)piperazine hydrochloride

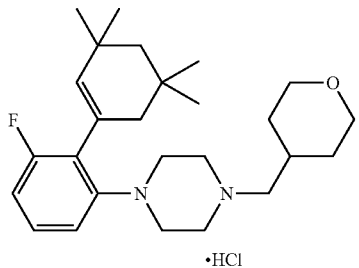

To a mixture of 1-[3-fluoro-2-(3,3,5,5-tetramethylcyclohex-1-enyl)phenyl]piperazine (115 mg, 0.363 mmol) produced in Example (97d), tetrahydropyran-4-carbaldehyde (62 mg, 0.543 mmol) and tetrahydrofuran (7 mL) were added sodium triacetoxyborohydride (154 mg, 0.726 mmol) and acetic acid (0.021 mL, 0.363 mmol) in that order, followed by stirring for 1 hour and 30 minutes at room temperature. Ethyl acetate, saturated aqueous solution of sodium hydrogencarbonate and water were added to the reaction mixture and extraction was performed with ethyl acetate. The separated organic layer was washed with brine and then dried over anhydrous sodium sulfate. The desiccant was filtered off and the filtrate was concentrated under reduced pressure. The resultant residue was purified by NH silica gel column chromatography (ethyl acetate/heptane) to give 108 mg of 1-[3-fluoro-2-(3,3,5,5-tetramethylcyclohex-1-enyl)phenyl]-4-(tetrahydropyran-4-ylmethyl)piperazine as a colorless oil.

$^1$H-NMR (400 MHz, CDCl$_3$) δ: 1.06 (s, 6H), 1.08 (s, 6H), 1.23-1.28 (m, 2H), 1.65-1.83 (m, 3H), 1.42 (s, 2H), 2.06 (s, 2H), 2.21 (d, J=7.2 Hz, 2H), 2.48 (brs, 4H), 2.99 (brs, 4H), 3.38 (td, J=12, 2.4 Hz, 2H), 3.94-4.00 (m, 2H), 5.42 (s, 1H), 6.72 (ddd, J=8.0, 8.0, 0.8 Hz, 1H), 6.77 (d, J=8.0 Hz, 1H), 7.10 (ddd, J=8.0, 8.0, 6.4 Hz, 1H).

This compound was dissolved in dichloromethane, and a 4N solution of hydrogen chloride in ethyl acetate was added. The solution was concentrated, and diethyl ether was added to the obtained residue to produce a solid which was then filtered. The solid was dried under reduced pressure to give 97 mg of the title compound as a white solid.

MS m/e (ESI) 415 (MH$^+$).

Example 98

(R)-1-Butyl-4-[2-(4,4-diethylcyclohexyl)-4-(3-methoxypyrrolidin-1-yl)phenyl]piperazine hydrochloride

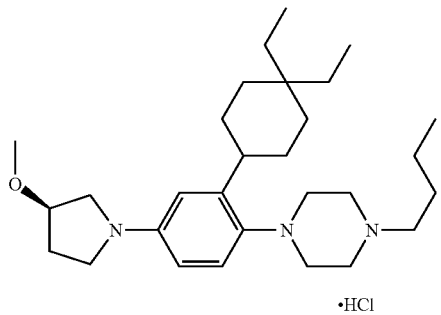

98a (R)-[2-(4,4-Diethylcyclohexyl)-4-(3-methoxypyrrolidin-1-yl)phenyl]piperazine-1'-carboxylic acid t-butyl ester

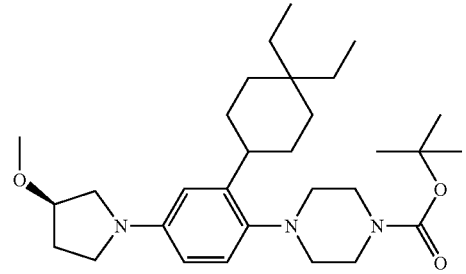

A mixture of 4-[4-bromo-2-(4,4-dimethylcyclohexyl)phenyl]piperazine-1-carboxylic acid t-butyl ester (454 mg, 0.947 mmol) produced in Example (38c), toluene (10 mL), (R)-3-methoxypyrrolidine hydrochloride (196 mg, 1.42 mmol), sodium t-butoxide (380 mg, 3.95 mmol), tri-t-butylphosphonium tetrafluoroborate (84 mg, 0.29 mmol) and palladium(II) acetate (32 mg, 0.14 mmol) was stirred for 5 hours at an external temperature of 90° C. under a nitrogen atmosphere. Insoluble materials of the reaction mixture were filtered off, and the filtrate was concentrated under reduced pressure. The resultant residue was purified by silica gel column chromatography (ethyl acetate/hexane) to obtain 193 mg of the title compound as a light brown solid.

$^1$H-NMR (400 MHz, CDCl$_3$) δ: 0.82 (t, J=7.6 Hz, 6H), 1.16-1.29 (m, 4H), 1.47 (s, 9H), 1.48-1.68 (m, 8H), 2.07-2.14 (m, 2H), 2.74 (brs, 4H), 2.93-3.03 (m, 1H), 3.13 (br, 4H), 3.28-3.51 (m, 7H), 4.05-4.11 (m, 1H), 6.38 (dd, J=8.8, 2.8 Hz, 1H), 6.43 (d, J=2.8 Hz, 1H), 7.01 (d, J=8.8 Hz, 1H).

98b (R)-1-[2-(4,4-Diethylcyclohexyl)-4-(3-methoxypyrrolidin-1-yl)phenyl]piperazine

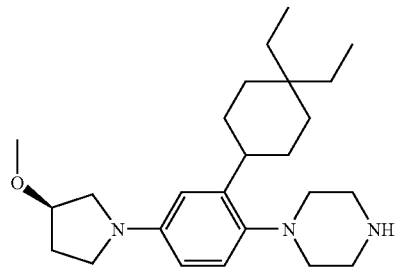

A mixture of (R)-[2-(4,4-dimethylcyclohexyl)-4-(3-methoxypyrrolidin-1-yl)phenyl]piperazine-1-carboxylic acid t-butyl ester (193 mg, 0.386 mmol) produced in Example (98a), trifluoroacetic acid (0.5 mL, 6.49 mmol) and dichloromethane (3 mL) was stirred for 14 hours and 30 minutes at room temperature. 5N aqueous solution of sodium hydroxide was added to the reaction mixture cooled in an ice water bath to make the mixture basic. Then, ethyl acetate and water were added and extraction was performed with ethyl acetate. The separated organic layer was washed with brine and then dried over anhydrous sodium sulfate. The desiccant was filtered off and the filtrate was concentrated under reduced pressure, to give 160 mg of a crude product of the title compound as a light brown oil.

$^1$H-NMR (400 MHz, CDCl$_3$) δ: 0.80 (t, J=7.6 Hz, 6H), 1.15-1.30 (m, 4H), 1.42-1.66 (m, 8H), 2.07-2.14 (m, 2H), 2.79 (t, J=4.8 Hz, 4H), 3.02 (t, J=4.8 Hz, 4H), 2.92-3.00 (m,

1H), 3.28-3.51 (m, 7H), 4.05-4.11 (m, 1H), 6.39 (dd, J=8.4, 2.8 Hz, 1H), 6.43 (d, J=2.8 Hz, 1H), 7.07 (d, J=8.4 Hz, 1H).
The 1H of NH could not be identified.

98c (R)-1-Butyl-4-[2-(4,4-dimethylcyclohexyl)-4-(3-methoxypyrrolidin-1-yl)phenyl]piperazine hydrochloride

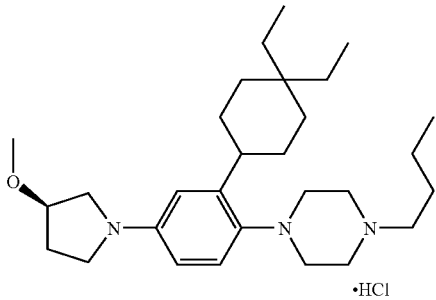

To a mixture of the crude product of (R)-1-[2-(4,4-dimethylcyclohexyl)-4-(3-methoxypyrrolidin-1-yl)phenyl]piperazine produced in Example (98b) (160 mg), butyraldehyde (0.052 mL, 0.584 mmol) and tetrahydrofuran (7 mL) were added sodium triacetoxyborohydride (164 mg, 0.774 mmol) and acetic acid (0.022 mL, 0.384 mmol) in that order, followed by stirring for 1 hour at room temperature. Ethyl acetate and saturated aqueous solution of sodium hydrogencarbonate were added to the reaction mixture and extraction was performed with ethyl acetate. The separated organic layer was washed with brine and then dried over anhydrous sodium sulfate. The desiccant was filtered off and the filtrate was concentrated under reduced pressure. The resultant residue was purified by NH silica gel column chromatography (ethyl acetate/hexane) to give 170 mg of (R)-1-butyl-4-[2-(4,4-dimethylcyclohexyl)-4-(3-methoxypyrrolidin-1-yl)phenyl]piperazine as a light brown oil.

$^1$H-NMR (400 MHz, CDCl$_3$) δ: 0.80 (t, J=7.6 Hz, 6H), 0.94 (t, J=7.2 Hz, 3H), 1.15-1.40 (m, 6H), 1.45-1.70 (m, 10H), 2.06-2.14 (m, 2H), 2.36-2.43 (m, 2H), 2.57 (br, 4H), 2.84 (brs, 4H), 2.90-3.00 (m, 1H), 3.27-3.50 (m, 7H), 4.05-4.10 (m, 1H), 6.37 (dd, J=8.8, 2.8 Hz, 1H), 6.42 (d, J=2.8 Hz, 1H), 7.08 (d, J=8.8 Hz, 1H).

This compound was dissolved in dichloromethane, and a 4N solution of hydrogen chloride in ethyl acetate was added. The solution was concentrated and diethyl ether was added to the obtained residue to produce a solid, which was then triturated by sonication. The supernatant diethyl ether solution was removed, and the solid residue was dried under reduced pressure to give 161 mg of the title compound as a light gray solid.

MS m/e (ESI) 456 (MH$^+$).

Example 99

1-Cyclopropylmethyl-4-[2-(3,3,5,5-tetramethylcyclohexyl)-4-thiazol-2-ylphenyl]piperazine dihydrochloride

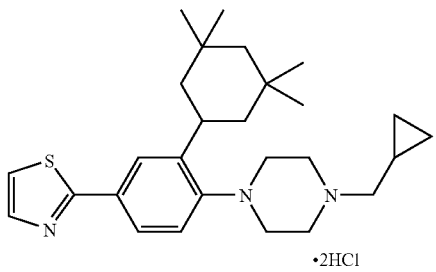

99a

4-[4-Bromo-2-(3,3,5,5-tetramethylcyclohexyl)phenyl]piperazine-1-carboxylic acid t-butyl ester

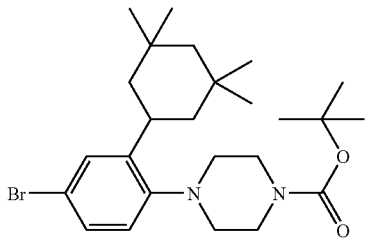

To a mixture of 4-[2-(3,3,5,5-tetramethylcyclohexyl)phenyl]piperazine-1-carboxylic acid t-butyl ester (2.93 g, 7.31 mmol) produced in Example (8a), sodium acetate (6 g, 73.14 mmol) and methanol (50 mL) was added bromine (0.37 mL, 7.22 mmol), followed by stirring for 20 minutes at room temperature under a nitrogen atmosphere. Saturated aqueous solution of sodium thiosulfate, ethyl acetate and water were added to the reaction mixture and extraction was performed with ethyl acetate. The separated organic layer was washed with brine and then dried over anhydrous sodium sulfate. The desiccant was filtered off and the filtrate was concentrated under reduced pressure. The resultant residue was purified by silica gel column chromatography (ethyl acetate/hexane) to give 2.67 g of the title compound as colorless crystals.

$^1$H-NMR (400 MHz, CDCl$_3$) δ: 0.93 (s, 6H), 1.10 (s, 6H), 1.12-1.45 (m, 6H), 1.49 (s, 9H), 2.79 (brs, 4H), 3.48 (br, 4H), 3.54 (tt, J=12.4, 2.8 Hz, 1H), 6.93 (d, J=8.4 Hz, 1H), 7.25 (dd, J=8.4, 2.4 Hz, 1H), 7.32 (d, J=2.4 Hz, 1H).

99b

4-[2-(3,3,5,5-Tetramethylcyclohexyl)-4-thiazol-2-ylphenyl]piperazine-1-carboxylic acid t-butyl ester

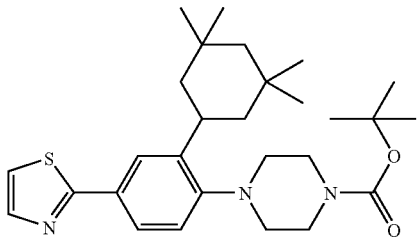

To a mixture of 4-[4-bromo-2-(3,3,5,5-tetramethylcyclohexyl)phenyl]piperazine-1-carboxylic acid t-butyl ester (150 mg, 0.313 mmol) produced in Example (99a), 2-(tributyltin)thiazole (0.16 mL), cesium fluoride (107 mg, 0.704 mmol) and dioxane (8 mL) was added tetrakis(triphenylphosphine)palladium(0) (40 mg, 0.035 mmol), followed by stirring for 3 hours at an external temperature of 100° C. under a nitrogen atmosphere. Ethyl acetate was added to the reaction mixture, insoluble materials were filtered off, and the filtrate was concentrated under reduced pressure. The resultant residue was purified by silica gel column chromatography (ethyl acetate/heptane) to give 115 mg of the title compound as light yellow crystals.

$^1$H-NMR (400 MHz, CDCl$_3$) δ: 0.94 (s, 6H), 1.12 (s, 6H), 1.15-1.46 (m, 6H), 1.50 (s, 9H), 2.87 (brs, 4H), 3.56 (tt, J=12.4, 3.2 Hz, 1H), 3.59 (br, 4H), 7.09 (d, J=8.4 Hz, 1H), 7.28 (d, J=3.2 Hz, 1H), 7.69 (dd, J=8.4, 2.4 Hz, 1H), 7.84 (d, J=3.2 Hz, 1H), 7.88 (d, J=2.4 Hz, 1H).

99c

1-[2-(3,3,5,5-Tetramethylcyclohexyl)-4-thiazol-2-ylphenyl]piperazine

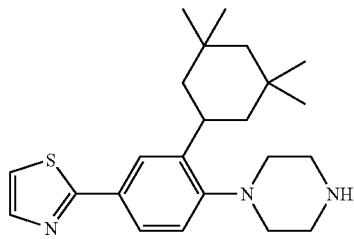

A mixture of 4-[2-(3,3,5,5-tetramethylcyclohexyl)-4-thiazol-2-ylphenyl]piperazine-1-carboxylic acid t-butyl ester (113 mg, 0.234 mmol) produced in Example (99b), trifluoroacetic acid (0.3 mL, 3.89 mmol) and dichloromethane (2 mL) was stirred for 1 hour and 50 minutes at room temperature. The reaction mixture was cooled in an ice water bath, and then 5N aqueous solution of sodium hydroxide was added thereto to make the mixture basic. Next, ethyl acetate and water were added and extraction was performed with ethyl acetate. The separated organic layer was washed with water and brine and then dried over anhydrous sodium sulfate. The desiccant was filtered off and the filtrate was concentrated under reduced pressure to give 91 mg of a crude product of the title compound as a light yellow solid.

$^1$H-NMR (400 MHz, CDCl$_3$) δ: 0.94 (s, 6H), 1.13 (s, 6H), 1.16-1.50 (m, 6H), 2.90 (t, J=4.8 Hz, 4H), 3.05 (t, J=4.8 Hz, 4H), 3.56 (tt, J=12.8, 2.8 Hz, 1H), 7.10 (d, J=8.4 Hz, 1H), 7.26 (d, J=3.2 Hz, 1H), 7.68 (dd, J=8.4, 2.4 Hz, 1H), 7.82 (d, J=3.2 Hz, 1H), 7.86 (d, J=2.4 Hz, 1H).

The 1H of NH could not be identified.

99d

1-Cyclopropylmethyl-4-[2-(3,3,5,5-tetramethylcyclohexyl)-4-thiazol-2-ylphenyl]piperazine dihydrochloride

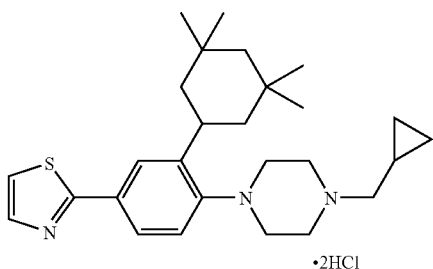

To a mixture of 1-[2-(3,3,5,5-tetramethylcyclohexyl)-4-thiazol-2-ylphenyl]piperazine (15 mg, 0.039 mmol) produced in Example (99c), cyclopropanecarbaldehyde (0.006 mL, 0.080 mmol) and tetrahydrofuran (2 mL) were added sodium triacetoxyborohydride (21 mg, 0.099 mmol) and acetic acid (0.003 mL, 0.052 mmol) in that order, followed by stirring for 1 hour and 40 minutes at room temperature. Ethyl acetate, saturated aqueous solution of sodium hydrogencarbonate and water were added to the reaction mixture and extraction was performed with ethyl acetate. The separated organic layer was concentrated by blowing nitrogen. The resultant residue was purified by NH silica gel column chromatography (ethyl acetate/hexane) to give 1-cyclopropylmethyl-4-[2-(3,3,5,5-tetramethylcyclohexyl)-4-thiazol-2-ylphenyl]piperazine. This compound was dissolved in dichloromethane, and a 4N solution of hydrogen chloride in ethyl acetate was added. The solution was concentrated by blowing nitrogen, and then diethyl ether was added to the obtained residue to produce a solid, which was then triturated by sonication. The supernatant diethyl ether solution was removed, and the obtained solid residue was dried by blowing nitrogen, to give 16 mg of the title compound as a light yellow solid.

MS m/e (ESI) 438 (MH$^+$).

Example 100

1-Cyclopropylmethyl-4-[4-pyridin-2-yl-2-(3,3,5,5-tetramethylcyclohexyl)phenyl]piperazine dihydrochloride

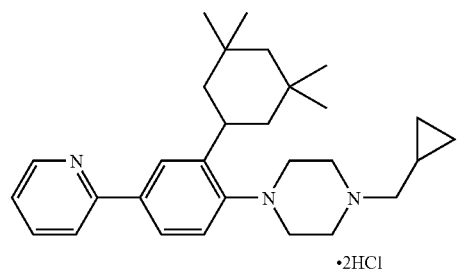

100a

4-[4-Pyridin-2-yl-2-(3,3,5,5-tetramethylcyclohexyl)phenyl]piperazine-1-carboxylic acid t-butyl ester

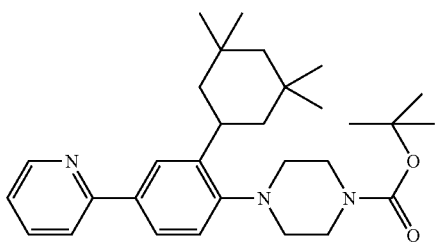

To a mixture of 4-[4-bromo-2-(3,3,5,5-tetramethylcyclohexyl)phenyl]piperazine-1-carboxylic acid t-butyl ester (100 mg, 0.209 mmol) produced in Example (99a), 2-(tributyltin)pyridine (0.08 mL, 0.25 mmol), cesium fluoride (68 mg, 0.448 mmol) and dioxane (15 mL) was added tetrakis(triphenylphosphine)palladium(0) (25 mg, 0.022 mmol), followed by stirring for 3 hours at an external temperature of 90° C. under a nitrogen atmosphere. Ethyl acetate was added to the reaction mixture, insoluble materials were filtered off, and the filtrate was concentrated under reduced pressure. The resultant residue was purified by silica gel column chromatography (ethyl acetate/hexane) to give 43 mg of the title compound as light yellow crystals.

$^1$H-NMR (400 MHz, CDCl$_3$) δ: 0.94 (s, 6H), 1.13 (s, 6H), 1.16-1.49 (m, 6H), 1.50 (s, 9H), 2.88 (brs, 4H), 3.59 (br, 4H), 3.61 (tt, J=12.8, 3.2 Hz, 1H), 7.15 (d, J=8.4 Hz, 1H), 7.19 (ddd, J=7.2, 4.8, 2.0 Hz, 1H), 7.68-7.76 (m, 3H), 7.89 (d, J=2.4 Hz, 1H), 8.68 (ddd, J=4.8, 1.6, 0.8 Hz, 1H).

100b

1-[4-Pyridin-2-yl-2-(3,3,5,5-tetramethylcyclohexyl)phenyl]piperazine

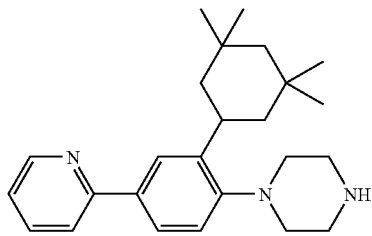

A mixture of 4-[4-pyridin-2-yl-2-(3,3,5,5-tetramethylcyclohexyl)phenyl]piperazine-1-carboxylic acid t-butyl ester (42 mg, 0.088 mmol) produced in Example (100a), trifluoroacetic acid (0.1 mL, 1.30 mmol) and dichloromethane (1 mL) was stirred for 17 hours and 50 minutes at room temperature. The reaction mixture was cooled in an ice water bath, and then 5N aqueous solution of sodium hydroxide was added to make the mixture basic. Then, ethyl acetate and water were added and extraction was performed with ethyl acetate. The separated organic layer was washed with brine and then dried over anhydrous sodium sulfate. The desiccant was filtered off and the filtrate was concentrated under reduced pressure to give 30 mg of a crude product of the title compound as a light yellow oil.

$^1$H-NMR (400 MHz, CDCl$_3$) δ: 0.94 (s, 6H), 1.14 (s, 6H), 1.17-1.52 (m, 6H), 2.90 (t, J=4.4 Hz, 4H), 3.05 (t, J=4.8 Hz, 4H), 3.61 (tt, J=12.8, 3.2 Hz, 1H), 7.14-7.18 (m, 2H), 7.66-7.75 (m, 3H), 7.87 (d, J=2.0 Hz, 1H), 8.66 (ddd, J=5.2, 1.6, 0.8 Hz, 1H).

The 1H of NH could not be identified.

100c

1-Cyclopropylmethyl-4-[4-pyridin-2-yl-2-(3,3,5,5-tetramethylcyclohexyl)phenyl]piperazine dihydrochloride

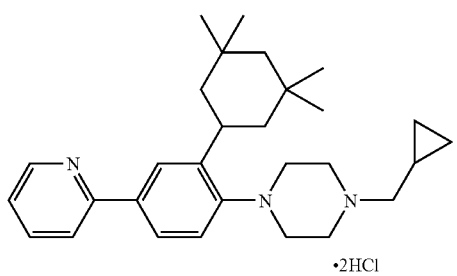

To a mixture of 1-[4-pyridin-2-yl-2-(3,3,5,5-tetramethylcyclohexyl)phenyl]piperazine (10 mg, 0.026 mmol) produced in Example (100b), cyclopropanecarbaldehyde (0.004 mL, 0.054 mmol) and tetrahydrofuran (2 mL) were added sodium triacetoxyborohydride (14 mg, 0.066 mmol) and acetic acid (0.002 mL, 0.035 mmol) in that order, followed by stirring for 40 minutes at room temperature. Ethyl acetate, saturated aqueous sodium hydrogencarbonate and water were added to the reaction mixture and extraction was performed with ethyl acetate. The separated organic layer was concentrated by blowing nitrogen. The resultant residue was purified by NH silica gel column chromatography (ethyl acetate/hexane) to give 1-cyclopropylmethyl-4-[4-pyridin-2-yl-2-(3,3,5,5-tetramethylcyclohexyl)phenyl]piperazine. This compound was dissolved in dichloromethane, and a 4N solution of hydrogen chloride in ethyl acetate was added. The solution was concentrated by blowing nitrogen gas, and diethyl ether was added to the obtained residue to produce a solid. After triturating the solid by sonication, the supernatant diethyl ether solution was removed. The solid residue was dried by blowing nitrogen, to give 3 mg of the title compound as a light yellow solid.

MS m/e (ESI) 432 (MH$^+$).

Example 101

1-Butyl-4-[2-(4-t-butylcyclohexyl)-5-(1H-tetrazol-5-yl)phenyl]piperazine hydrochloride

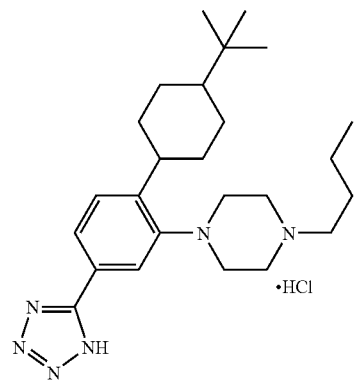

101a

[4-(4-t-Butylcyclohexyl)-3-(4-butylpiperazine-1-yl)phenyl]methanol

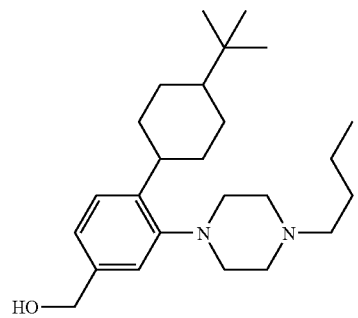

Lithium aluminum hydride (29 mg, 0.764 mmol) was suspended in anhydrous tetrahydrofuran (5 mL). To the suspension was added a solution of 4-(4-t-butylcyclohexyl)-3-(4-butylpiperazine-1-yl)benzoic acid methyl ester (308 mg, 0.743 mmol) in anhydrous tetrahydrofuran (5 mL) at room temperature under a nitrogen atmosphere, followed by stirring for 55 minutes. Sodium fluoride (262 mg) was added to the reaction mixture, and water (0.11 mL) was gradually added while blowing nitrogen. After stirring for 1 hour and 35 minutes, insoluble materials were filtered off and the filtrate was concentrated under reduced pressure. The obtained residue was dissolved in ethyl acetate, and anhydrous sodium sulfate was added for drying. The desiccant was filtered off and the filtrate was concentrated under reduced pressure to give 295 mg of a crude product of the title compound as a colorless oil.

$^1$H-NMR (400 MHz, CDCl$_3$) δ: 0.88 (s, 9H×0.6), 0.90 (s, 9H×0.4), 0.94 (t, J=7.2 Hz, 3H×0.6), 0.95 (t, J=7.2 Hz, 3H×0.4), 1.08-1.98 (m, 13H), 2.38-2.44 (m, 2H), 2.59 (brs, 4H), 2.89 (t, J=4.8 Hz, 4H×0.6), 2.90 (t, J=4.8 Hz, 4H×0.4), 2.97 (tt, J=12.4, 2.4 Hz, 1H×0.4), 3.37 (tt, J=5.2, 5.2 Hz, 1H×0.6), 4.63 (s, 2H), 7.04-7.08 (m, 1H), 7.11 (d, J=1.6 Hz, 1H×0.4), 7.17 (d, J=1.6 Hz, 1H×0.6), 7.20 (d, J=8.0 Hz, 1H×0.4), 7.40 (d, J=8.0 Hz, 1H×0.6).

The 1H of OH could not be identified.

101b 4-(4-t-Butylcyclohexyl)-3-(4-butylpiperazine-1-yl)benzaldehyde

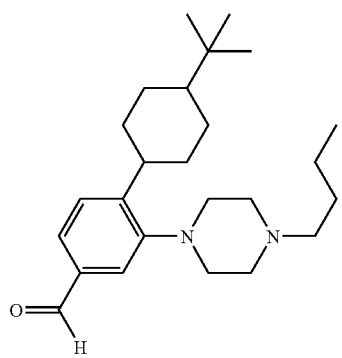

A mixture of the crude product of [4-(4-t-butylcyclohexyl)-3-(4-butylpiperazine-1-yl)phenyl]methanol produced in Example (101a) (294 mg), manganese(IV) oxide (1.3 g, 14.95 mmol) and chloroform (15 mL) was refluxed for 40 minutes. The reaction mixture was filtered and insoluble materials were filtered off. The filtrate was concentrated under reduced pressure to give 249 mg of a crude product of the title compound as an ochre oil. This product was directly used without purification for the following reaction.

101c 4-(4-t-Butylcyclohexyl)-3-(4-butylpiperazine-1-yl)benzaldehydeoxime

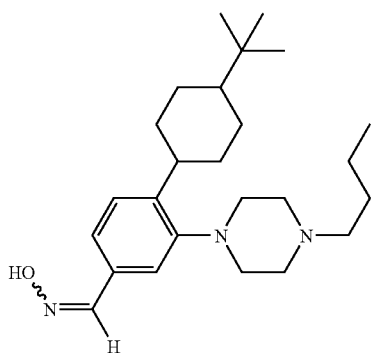

To a mixture of the crude product of 4-(4-t-butylcyclohexyl)-3-(4-butylpiperazine-1-yl)benzaldehyde produced in Example (101b) (247 mg), hydroxylammonium chloride (134 mg, 1.93 mmol) and ethanol (10 mL) were added sodium acetate (193 mg, 2.35 mmol) and water (1.5 mL), followed by stirring for 2 hours at room temperature. The reaction mixture was poured into ice water, and then ethyl acetate and saturated aqueous solution of ammonium chloride were added and extraction was performed with ethyl acetate. The separated organic layer was washed with brine and then dried over anhydrous sodium sulfate. The desiccant was filtered off, and the filtrate was concentrated under reduced pressure to give 271 mg of a crude product of the title compound as a light yellow solid. This product was directly used without purification for the following reaction.

101d 4-(4-t-Butylcyclohexyl)-3-(4-butylpiperazine-1-yl)benzonitrile

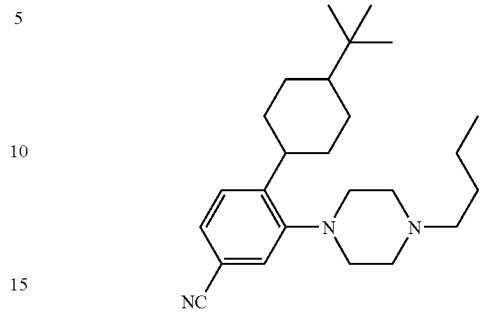

A mixture of the crude product of 4-(4-t-butylcyclohexyl)-3-(4-butylpiperazine-1-yl)benzaldehydeoxime produced in Example (101c) (269 mg), benzenesulfonyl chloride (0.11 mL, 0.862 mmol), pyridine (0.11 ml, 1.36 mmol) and tetrahydrofuran (15 mL) was refluxed for 4 hours and 30 minutes. After then distilling off tetrahydrofuran partially in the reaction mixture under reduced pressure, chloroform was added and the mixture was further refluxed for 1 hour. The reaction mixture was concentrated under reduced pressure, the obtained residue was poured into ice water, and then ethyl acetate and saturated aqueous solution of ammonium chloride were added and extraction was performed with ethyl acetate. The separated organic layer was washed twice with saturated aqueous ammonium chloride and once with brine, and then dried over anhydrous sodium sulfate. The desiccant was filtered off, and the filtrate was concentrated under reduced pressure to give a residue, which was purified by NH silica gel column chromatography (ethyl acetate/hexane, followed by ethyl acetate/methanol), to give 192 mg of the title compound as an ochre oil.

101e

1-Butyl-4-[2-(4-t-butylcyclohexyl)-5-(1H-tetrazol-5-yl)phenyl]piperazine hydrochloride

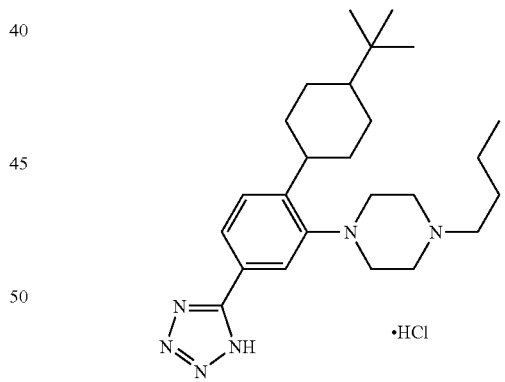

A mixture of 4-(4-t-butylcyclohexyl)-3-(4-butylpiperazine-1-yl)benzonitrile (146 mg, 0.383 mmol) produced in Example (101d), trimethyltin azide (160 mg, 0.777 mmol) and toluene (10 mL) was stirred for 14 hours and 20 minutes at an external temperature of about 130° C. The reaction mixture was concentrated under reduced pressure, and then methanol (6 mL) and 1N hydrochloric acid (6 mL) were added to the residue and the mixture was stirred for 2 hours and 10 minutes at room temperature. The reaction mixture was cooled in an ice water bath, and then 2N aqueous solution of sodium hydroxide was added to make the mixture basic, after which the mixture was neutralized again with saturated aqueous solution of ammonium chloride. Ethyl acetate, tetrahydrofuran and water were added thereto and extraction was performed with ethyl acetate. The separated organic layer was washed with brine and then dried over anhydrous sodium sulfate. The desiccant was filtered off and the filtrate was concentrated under reduced pressure. The resultant residue was dissolved in dichloromethane, and a 4N solution of hydrogen chloride in ethyl acetate was added. The mixture was then concentrated under reduced pressure, and diethyl ether was added to the obtained residue for crystallization. The crystals were filtered and dried under reduced pressure to give 133 mg of the title compound as colorless crystals.

MS m/e (ESI) 425 (MH$^+$).

Example 102

1-Butyl-4-[2-(3,3,5, 5-tetramethylcyclohexyl)phenyl]-1,2,3,6-tetrahydropyridine hydrochloride

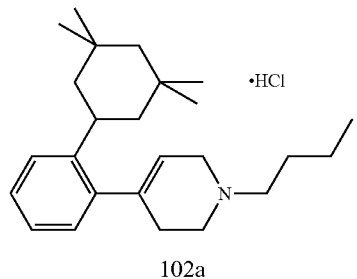

102a 2-(3,3,5,5-Tetramethylcyclohex-1-enyl)phenol

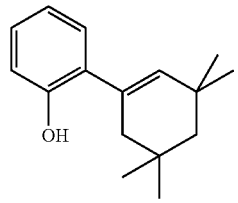

To a mixture of 2-(4,4,5,5-tetramethyl-[1,3,2]dioxaborolan-2-yl)phenol (3.5 g, 15.9 mmol), trifluoromethanesulfonic acid 3,3,5,5-tetramethylcyclohex-1-enyl ester (5 g, 17.4 mmol) produced in Example (4a) and 1,2-dimethoxyethane (20 mL) were added tetrakis(triphenylphosphine)palladium (0) (0.92 g, 0.79 mmol) and 2N aqueous solution of sodium carbonate (23.9 mL, 47.7 mmol), followed by stirring for 1 hour at an external temperature of 90° C. under a nitrogen atmosphere. Brine was added to the reaction mixture and extraction was performed with ethyl acetate. The organic layer was dried over anhydrous magnesium sulfate and then the solvent was distilled off under reduced pressure and the obtained residue was purified by silica gel column chromatography (ethyl acetate/heptane) to give 3.7 g of the title compound as a yellow oil.

$^1$H-NMR (400 MHz, CDCl$_3$) δ: 1.06 (s, 6H), 1.11 (s, 6H), 1.45 (s, 2H), 2.04 (d, J=1.6 Hz, 2H), 5.59 (s, 1H), 5.61 (t, J=1.6 Hz, 1H), 6.87 (td, J=7.6, 1.2 Hz, 1H), 6.90 (dd, J=7.6, 1.2 Hz, 1H), 7.03 (dd, J=7.6, 1.2 Hz, 1H), 7.12 (td, J=7.6, 1.2 Hz, 1H).

102b 2-(3.3, 5,5-Tetramethylcyclohexyl)phenol

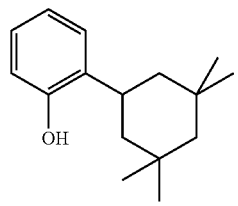

To a solution of 2-(3,3,5,5-tetramethylcyclohex-1-enyl) phenol (1.7 g, 7.4 mmol) produced in Example (102a) in methanol (30 mL) was added 10% palladium on carbon (0.5 g, wet), followed by stirring for 27 hours at room temperature and atmospheric pressure under a hydrogen atmosphere. The reaction mixture was filtered through Celite, and the filtrate was concentrated under reduced pressure to give 1.7 g of a crude product of the title compound as a light yellow oil.

$^1$H-NMR (400 MHz, CDCl$_3$) δ: 0.94 (s, 6H), 1.12 (s, 6H), 1.14-1.35 (m, 6H), 3.22 (tt, J=12.8, 2.8 Hz, 1H), 4.67 (s, 1H), 6.74 (dd, J=7.6, 1.2 Hz, 1H), 6.89 (td, J=7.6, 1.2 Hz, 1H), 7.05 (td, J=7.6, 1.2 Hz, 1H), 7.17 (dd, J=7.6, 1.2 Hz, 1H).

102c

Trifluoromethanesulfonic acid 2-(3,3,5,5-tetramethylcyclohexyl)phenyl ester

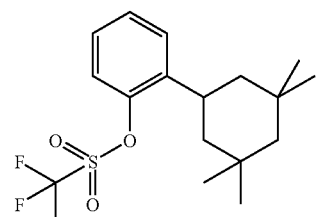

To a solution of 2-(3,3,5,5-tetramethylcyclohexyl)phenol (530 mg, 2.28 mmol) produced in Example (102b) in dichloromethane (20 mL) were added triethylamine (1.3 mL, 4.09 mmol) and trifluoromethanesulfonic anhydride (0.56 mL, 3.33 mmol) in that order while cooling in an ice bath, followed by stirring for 14 hours while heating to room temperature. Brine was added to the reaction mixture and extraction was performed with diethyl ether. The organic layer was dried over anhydrous magnesium sulfate and then filtered, and the filtrate was concentrated under reduced pressure. The resultant residue was purified by silica gel column chromatography (ethyl acetate/heptane) to give 0.83 g of the title compound as a light yellow oil.

$^1$H-NMR (400 MHz, CDCl$_3$) δ: 0.94 (s, 6H), 1.12 (s, 6H), 1.14-1.38 (m, 6H), 3.31 (tt, J=12.8, 2.8 Hz, 1H), 7.22-7.42 (m, 4H).

102d

4-[2-(3,3,5,5-Tetramethylcyclohexyl)phenyl]-3,6-dihydro-2H-pyridine-1-carboxylic acid t-butyl ester

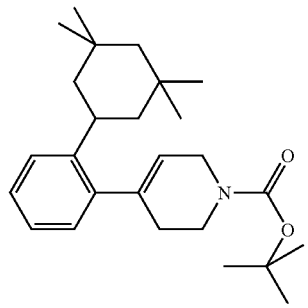

To a mixture of trifluoromethanesulfonic acid 2-(3,3,5,5-tetramethylcyclohexyl)phenyl ester (830 mg, 2.55 mmol) produced in Example (102c), 4-(4,4,5,5-tetramethyl-[1,3,2] dioxaborolan-2-yl)-3,6-dihydro-2H-pyridine-1-carboxylic acid t-butyl ester (631 mg, 2.04 mmol) (Paul R. Eastwood, Tetrahedron Lett., 2000, 41, 3705) and 1,2-dimethoxyethane (20 mL) were added tetrakis(triphenylphosphine)palladium (147 mg, 0.13 mmol) and 2N aqueous solution of sodium carbonate (3.8 mL, 7.6 mmol), followed by stirring for 8 hours at an external temperature of 90° C. under a nitrogen atmosphere. Brine was added to the reaction mixture and extraction was performed with ethyl acetate. The organic layer was dried over anhydrous magnesium sulfate and the filtrate was concentrated under reduced pressure. The resultant residue was purified by silica gel column chromatography (ethyl acetate/heptane) to give 570 mg of the title compound as a light yellow oil.

$^1$H-NMR (400 MHz, CDCl$_3$) δ: 1.03 (s, 6H), 1.12 (s, 6H), 1.16-1.48 (m, 6H), 1.49 (s, 9H), 2.32 (bs, 2H), 3.22 (tt, J=12.8, 2.8 Hz, 1H), 3.64 (bs, 2H), 4.02 (bs, 2H), 5.52 (bs, 1H), 6.74 (dd, J=7.6, 1.2 Hz, 1H), 6.89 (td, J=7.6, 1.2 Hz, 1H), 7.05 (td, J=7.6, 1.2 Hz, 1H), 7.17 (dd, J=7.6, 1.2 Hz, 1H).

102e

4-[2-(3,3,5,5-Tetramethylcyclohexyl)phenyl]-1,2,3,6-tetrahydropyridine

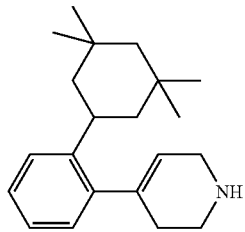

To a solution of 4-[2-(3,3,5,5-tetramethylcyclohexyl)phenyl]-3,6-dihydro-2H-pyridine-1-carboxylic acid t-butyl ester (570 mg, 1.43 mmol) produced in Example (102d) in dichloromethane (5 mL) was added trifluoroacetic acid (5 mL), followed by stirring for 30 minutes at room temperature. The reaction mixture was concentrated under reduced pressure, saturated aqueous solution of sodium hydrogencarbonate was added to the obtained residue, and extraction was performed with ethyl acetate. The organic layer was dried over anhydrous magnesium sulfate and then the filtrate was concentrated under reduced pressure. The resultant residue was purified by silica gel column chromatography (ethyl acetate/heptane) to give 430 mg of the title compound as a light yellow oil.

$^1$H-NMR (400 MHz, CDCl$_3$) δ: 0.92 (s, 6H), 1.05 (s, 6H), 1.10-1.52 (m, 6H), 2.35 (bs, 2H), 3.07 (tt, J=12.8, 2.8 Hz, 1H), 3.21 (t, J=5.6 Hz, 2H), 3.57-3.62 (m, 2H), 5.56-5.61 (m, 1H), 7.00 (dd, J=7.6, 1.2 Hz, 1H), 7.12 (td, 7.6, 1.2 Hz, 1H), 7.22-7.27 (m, 1H), 7.36 (td, J=7.6, 1.2 Hz, 1H).

The 1H of NH could not be identified.
MS m/e (ESI) 298 (MH$^+$).

102f

1-Butyl-4-[2-(3,3,5,5-tetramethylcyclohexyl)phenyl]-1,2,3,6-tetrahydropyridine hydrochloride

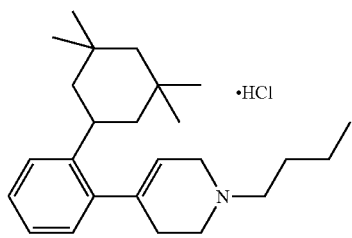

To a solution of 4-[2-(3,3,5,5-tetramethylcyclohexyl)phenyl]-1,2,3,6-tetrahydropyridine (130 mg, 0.44 mmol) produced in Example (102e) in tetrahydrofuran (2 mL) were added butyraldehyde (37.8 mg, 0.52 mmol), sodium triacetoxyborohydride (139 mg, 0.66 mmol) and acetic acid (52.5 mg, 0.87 mmol), followed by stirring for 13 hours at room temperature. Saturated aqueous solution of sodium hydrogencarbonate was added to the reaction mixture and extraction was performed with ethyl acetate. The organic layer was dried over anhydrous magnesium sulfate and then the filtrate was concentrated under reduced pressure. The resultant residue was purified by NH silica gel column chromatography (ethyl acetate/heptane) to give 70 mg of 1-butyl-4-[2-(3,3,5,5-tetramethylcyclohexyl)phenyl]-1,2,3,6-tetrahydropyridine as a light yellow oil.

$^1$H-NMR (400 MHz, CDCl$_3$) δ: 0.91 (s, 6H), 0.94 (t, J=7.2 Hz, 3H), 1.05 (s, 6H), 1.12-1.46 (m, 10H), 2.33-2.40 (m, 2H), 2.46 (t, J=7.2 Hz, 2H), 2.69 (t, J=5.6 Hz, 2H), 3.06-3.12 (m, 3H), 5.49-5.54 (m, 1H), 7.17-7.32 (m, 4H).

The obtained compound was dissolved in ethyl acetate, and then a 4N solution of hydrogen chloride in ethyl acetate was added and the mixture was stirred for 30 minutes at room temperature. The reaction mixture was concentrated under reduced pressure and hexane was added to the obtained residue to produce a solid, which was then triturated by sonication. The solid was filtered and dried under reduced pressure to give 68 mg of the title compound as a light yellow solid.

MS m/e (ESI) 354 (MH$^+$).

Example 103

1-Butyl-4-[2-(3,3,5,5-tetramethylcyclohexyl)phenyl]piperidine hydrochloride

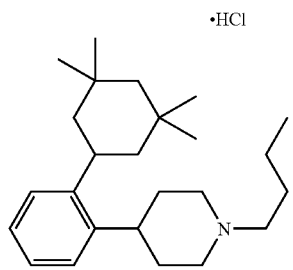

To a solution of 1-butyl-4-[2-(3,3,5,5-tetramethylcyclohexyl)phenyl]-1,2,3,6-tetrahydropyridine hydrochloride (48 mg, 0.12 mmol) produced in Example (102f) in methanol (3 mL) was added 10% palladium on carbon (100 mg, wet), followed by stirring for 4 hours at room temperature and atmospheric pressure under a hydrogen atmosphere. The reaction mixture was filtered through Celite, and the filtrate was concentrated under reduced pressure. Ether and hexane were added to the obtained residue to produce a solid, which was then triturated by sonication. The solid was filtered and dried under reduced pressure to give 9 mg of the title compound as a light yellow solid.

$^1$H-NMR (400 MHz, CD$_3$OD) δ: 0.97 (s, 6H), 1.03 (t, J=7.2 Hz, 3H), 1.19 (s, 6H), 1.30-1.52 (m, 8H), 1.74-1.84 (m, 2H), 1.96-2.17 (m, 4H), 3.02-3.30 (m, 6H), 3.68-3.77 (m, 2H), 7.14-7.30 (m, 4H). MS m/e (ESI) 356 (MH$^+$).

Example 104

4-[4-Methyl-2-(3,3,5,5-tetramethylcyclohexyl)phenyl]-1-propyl-1,2,3,6-tetrahydropyridine hydrochloride

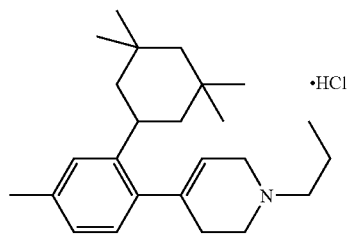

104a

1-Methoxy-4-methyl-2-(3,3,5,5-tetramethylcyclohex-1-enyl)benzene

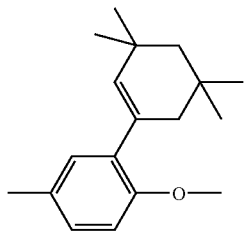

To a mixture of 2-methoxy-5-methylphenylboronic acid (1 g, 6.02 mmol), trifluoromethanesulfonic acid 3,3,5,5-tetramethylcyclohex-1-enyl ester (1.9 g, 6.62 mmol) produced in Example (4a) and 1,2-dimethoxyethane (30 mL) were added tetrakis(triphenylphosphine)palladium(0) (0.35 g, 0.30 mmol) and 2N aqueous solution of sodium carbonate (9.0 mL, 18.0 mmol), followed by stirring for 3 hours at an external temperature of 90° C. under a nitrogen atmosphere. Brine was added to the reaction mixture and extraction was performed with ethyl acetate. The organic layer was dried over anhydrous magnesium sulfate and filtrated, the resultant filtrate was concentrated under reduced pressure to give a residue, which was purified by silica gel column chromatography (ethyl acetate/heptane) to give 1.0 g of the title compound as a light yellow oil.

$^1$H-NMR (400 MHz, CDCl$_3$) δ: 1.01 (s, 6H), 1.07 (s, 6H), 1.39 (s, 2H), 2.07 (d, J=1.6 Hz, 2H), 2.28 (s, 3H), 3.75 (s, 3H), 5.42 (s, 1H), 6.73 (d, J=8.4 Hz, 1H), 6.91 (d, J=2.0 Hz, 1H), 6.97 (dd, J=8.4, 2.0 Hz, 1H).

104b

1-Methoxy-4-methyl-2-(3,3,5,5-tetramethylcyclohexyl)benzene

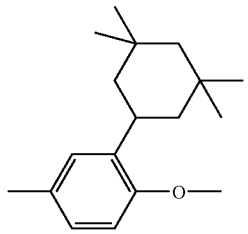

To a solution of 1-methoxy-4-methyl-2-(3,3,5,5-tetramethylcyclohex-1-enyl)benzene (1.0 g, 3.87 mmol) produced in Example (104a) in methanol (30 mL) was added 10% palladium on carbon (0.6 g, wet), followed by stirring for 12 hours at room temperature and atmospheric pressure under a hydrogen atmosphere. The reaction mixture was filtered through Celite, and the filtrate was concentrated under reduced pressure to give 1.0 g of a crude product of the title compound as a yellow oil.

$^1$H-NMR (400 MHz, CDCl$_3$) δ: 0.92 (s, 6H), 1.05 (s, 6H), 1.10-1.52 (m, 6H), 2.80 (s, 3H), 3.33 (tt, J=12.8, 2.8 Hz, 1H), 3.79 (s, 3H), 6.75 (d, J=8.4 Hz, 1H), 6.94 (d, J=2.0 Hz, 1H), 6.99 (dd, J=8.4, 2.0 Hz, 1H).

104c

4-Methyl-2-(3,3,5,5-tetramethylcyclohexyl)phenol

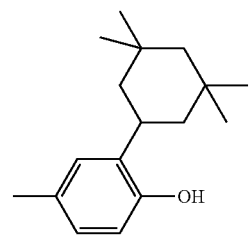

To a solution of 1-methoxy-4-methyl-2-(3,3,5,5-tetramethylcyclohexyl)benzene (1.0 g, 3.84 mmol) produced in Example (104b) in acetic acid (5 mL) was added 48% hydrobromic acid (10 mL, 59.3 mmol), followed by reflux for 12 hours. Saturated aqueous solution of sodium hydrogencarbonate was added to the cooled reaction mixture, and extraction was performed with ethyl acetate. The organic layer was dried over anhydrous magnesium sulfate and the filtrate was concentrated under reduced pressure to give a residue, which was purified by silica gel column chromatography (ethyl acetate/heptane) to give 450 mg of the title compound as a light yellow oil.

$^1$H-NMR (400 MHz, CDCl$_3$) δ: 0.94 (s, 6H), 1.12 (s, 6H), 1.16-1.60 (m, 6H), 2.26 (s, 3H), 3.18 (tt, J=12.8, 2.8 Hz, 1H), 4.47 (s, 1H), 6.64 (d, J=8.4 Hz, 1H), 6.84 (dd, J=8.4, 2.0 Hz, 1H), 6.96 (d, J=2.0 Hz, 1H).

104d

Trifluoromethanesulfonic acid 4-methyl-2-(3,3,5,5-tetramethylcyclohexyl)phenyl ester

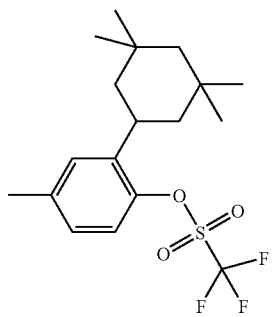

To a solution of 4-methyl-2-(3,3,5,5-tetramethylcyclohexyl)phenol (0.45 g, 1.83 mmol) produced in Example (104c) in dichloromethane (30 ml) cooled in an ice bath were added triethylamine (1.0 mL, 7.32 mmol) and trifluoromethanesulfonic anhydride (0.46 mL, 2.75 mmol) in that order, followed by stirring for 2 hours at an external temperature of 0° C. Brine was added to the reaction mixture and extraction was performed with ethyl acetate. The organic layer was dried over anhydrous magnesium sulfate, and the filtrate was concentrated under reduced pressure to give a residue, which was purified by silica gel column chromatography (ethyl acetate/heptane) to give 0.43 g of the title compound as a light yellow oil.

¹H-NMR (400 MHz, CDCl3) δ: 0.94 (s, 6H), 1.11 (s, 6H), 1.08-1.54 (m, 6H), 2.35 (s, 3H), 3.26 (tt, J=12.8, 2.8 Hz, 1H), 7.02 (dd, J=8.4, 2.0 Hz, 1H), 7.09 (d, J=8.4 Hz, 1H), 7.14 (d, J=2.0 Hz, 1H).

104e

4-[4-Methyl-2-(3,3,5,5-tetramethylcyclohexl)phenyl]-3,6-dihydro-2H-pyridine-1-carboxylic acid t-butyl ester

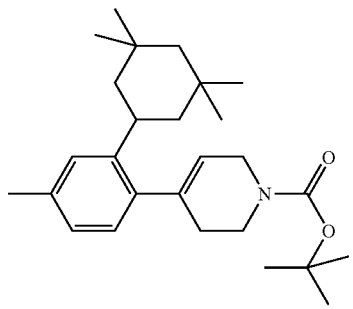

To a mixture of trifluoromethanesulfonic acid 4-methyl-2-(3,3,5,5-tetramethylcyclohexyl)phenyl ester (430 mg, 1.14 mmol) produced in Example (104d), 4-(4,4,5,5-tetramethyl[1,3,2]dioxaborolan-2-yl)-3,6-dihydro-2H-pyridine-1-carboxylic acid t-butyl ester (421 mg, 1.36 mmol) (Paul R. Eastwood, Tetrahedron Lett., 2000, 41, 3705) and 1,2-dimethoxyethane (20 mL) were added tetrakis(triphenylphosphine)palladium(0) (65 mg, 0.06 mmol) and 2N aqueous solution of sodium carbonate (1.72 mL, 3.41 mmol), followed by stirring for 8 hours at an external temperature of 90° C. under a nitrogen atmosphere. Brine was added to the reaction mixture and extraction was performed with ethyl acetate. The organic layer was dried over anhydrous magnesium sulfate and the filtrate was concentrated to give a residue, which was purified by silica gel column chromatography (ethyl acetate/heptane) to give 297 mg of the title compound as a light yellow oil.

¹H-NMR (400 MHz, CDCl₃) δ: 0.91 (s, 6H), 1.02 (s, 6H), 1.09-1.44 (m, 6H), 1.48 (s, 9H), 2.30 (bs, 2H), 2.33 (s, 3H), 3.04 (tt, J=12.8, 2.8 Hz, 1H), 3.63 (bs, 2H), 4.01 (bs, 2H), 5.49 (bs, 1H), 6.94 (s, 2H), 7.04 (s, 1H).

104f

4-[4-Methyl-2-(3,3,5,5-tetramethylcyclohexyl)phenyl]-1,2,3,6-tetrahydropyridine

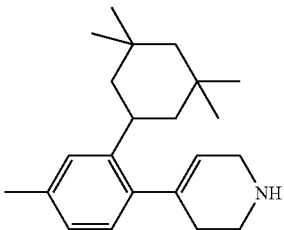

To a solution of 4-[4-methyl-2-(3,3,5,5-tetramethylcyclohexyl)phenyl]-3,6-dihydro-2H-pyridine-1-carboxylic acid t-butyl ester (297 mg, 0.72 mmol) produced in Example (104e) in dichloromethane (3 mL) was added trifluoroacetic acid (3 mL), followed by stirring for 30 minutes at room temperature. The reaction mixture was concentrated under reduced pressure, and then saturated aqueous solution of sodium hydrogencarbonate was added to the residue and extraction was performed with ethyl acetate. The organic layer was dried with a desiccant and then filtered. The filtrate was concentrated under reduced pressure to give 280 mg of a crude product of the title compound as a light yellow oil.

MS m/e (ESI) 312 (MH⁺).

104g

4-[4-Methyl-2-(3,3,5,5-tetramethylcyclohexyl)phenyl]-1-propyl-1,2,3,6-tetrahydropyridine hydrochloride

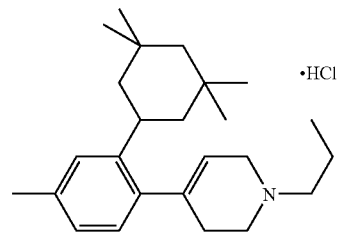

To a solution of 4-[4-methyl-2-(3,3,5,5-tetramethylcyclohexyl)phenyl]-1,2,3,6-tetrahydropyridine (70 mg, 0.23 mmol) produced in Example (104f) in tetrahydrofuran (2 mL) were added propionaldehyde (15.7 mg, 0.27 mmol), sodium triacetoxyborohydride (72 mg, 0.34 mmol) and acetic acid (27 mg, 0.45 mmol), followed by stirring for 12 hours at room temperature. Saturated aqueous solution of sodium hydrogencarbonate was added to the reaction mixture and extraction was performed with ethyl acetate. The organic layer was dried over anhydrous magnesium sulfate and the filtrate was concentrated to give a residue, which was purified by NH silica gel column chromatography (ethyl acetate/heptane) to give 63 mg of 4-[4-methyl-2-(3,3,5,5-tetramethylcyclohexyl)phenyl]-1-propyl-1,2,3,6-tetrahydropyridine as a light yellow oil.

MS m/e (ESI) 354 (MH⁺).

The obtained compound was dissolved in ethyl acetate, and a 4N solution of hydrogen chloride in ethyl acetate was added and the mixture was stirred for 30 minutes at room temperature. The solution was concentrated under reduced pressure, and then hexane was added to the residue to produce a solid which was triturated by sonication. The solid was filtered and dried under reduced pressure to give 60 mg of the title compound as a light yellow solid.

¹H-NMR (400 MHz, CD₃OD) δ: 0.95 (s, 6H), 1.06 (t, J=7.2 Hz, 3H), 1.11 (s, 6H), 1.16-1.46 (m, 8H), 1.77-1.89 (m, 2H), 2.31 (s, 3H), 2.56-2.68 (m, 2H), 3.01 (tt, J=12.8, 2.8 Hz, 1H), 3.12-3.24 (m, 2H), 3.76-3.92 (m, 2H), 5.58 (bs, 1H), 6.96 (s, 2H), 7.11 (s, 1H). MS m/e (ESI) 354 (MH⁺).

Example 105

4-[4-Methyl-2-(3,3,5,5-tetramethylcyclohexyl)phenyl]-1-propylpiperidine hydrochloride

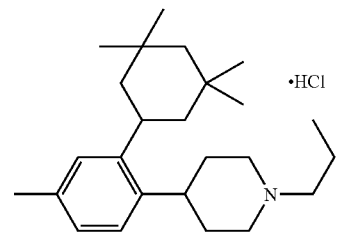

To a solution of 4-[4-methyl-2-(3,3,5,5-tetramethylcyclohexyl)phenyl]-1-propyl-1,2,3,6-tetrahydropyridine hydrochloride (50 mg, 0.13 mmol) produced in Example (104g) in methanol (10 mL) was added 10% palladium on carbon (50 mg, wet), followed by stirring for 2 hours at atmospheric pressure and room temperature under a hydrogen atmosphere. The reaction mixture was filtered through Celite, and the obtained filtrate was concentrated under reduced pressure. Hexane was added to the residue to produce a solid, which was then triturated by sonication. The solid was filtered and dried under reduced pressure to give 16 mg of the title compound as a light yellow solid.

$^1$H-NMR (400 MHz, CD$_3$OD) δ: 0.97 (s, 6H), 1.05 (t, 3H), 1.18 (s, 6H), 1.18-1.46 (m, 6H), 1.74-1.86 (m, 2H), 1.95-2.08 (m, 4H), 2.29 (s, 3H), 3.00-3.34 (m, 6H), 3.62-3.72 (m, 2H), 6.99 (dd, J=8.4, 2.0 Hz, 1H), 7.08 (d, J=2.0 Hz, 1H), 7.11 (d, J=8.4 Hz, 1H). MS m/e (ESI) 356 (MH$^+$).

Example 106

1-Butyl-4-[5-fluoro-2-(3,3,5,5-tetramethylcyclohex-1-enyl)phenyl]piperidine hydrochloride

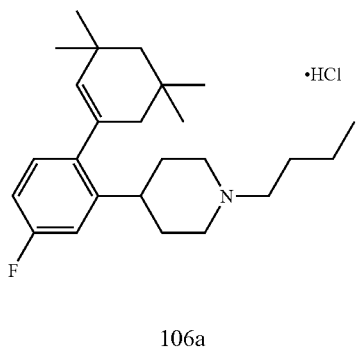

106a 4-(5-Fluoro-2-methoxyphenyl)-3,6-dihydro-2H-pyridine-1-carboxylic acid t-butyl ester

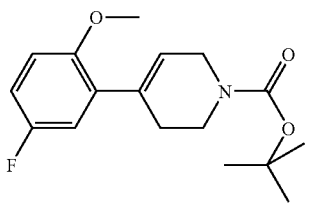

To a mixture of 5-fluoro-2-methoxyphenylboronic acid (1 g, 5.88 mmol), 4-trifluoromethanesulfonyloxy-3,6-dihydro-2H-pyridine-1-carboxylic acid t-butyl ester (4.22 g, 7.64 mmol) (David J. Wustrow, Lawrence D. Wise, Synthesis, 1991, 993) and 1,2-dimethoxyethane (30 mL) were added tetrakis(triphenylphosphine)palladium(0) (0.34 g, 0.29 mmol) and 2N aqueous solution of sodium carbonate (8.82 mL, 17.6 mmol), followed by stirring for 2 hours at an external temperature of 90° C. under a nitrogen atmosphere. Brine was added to the reaction mixture and extraction was performed with ethyl acetate. The organic layer was dried over anhydrous magnesium sulfate and the filtrate was concentrated to give a residue, which was purified by silica gel column chromatography (ethyl acetate/heptane) to give 2.3 g of the title compound as a yellow oil.

$^1$H-NMR (400 MHz, CDCl$_3$) δ: 1.49 (s, 9H), 2.47 (bs, 2H), 3.58 (t, J=5.6 Hz, 2H), 3.78 (s, 3H), 4.01-4.06 (m, 2H), 5.78 (bs, 1H), 6.77 (dd, J=8.4, 4.4 Hz, 1H), 6.88 (td, J=9.2, 3.2 Hz, 1H), 6.91 (dd, J=8.8, 3.2 Hz, 1H).

106b 4-(5-Fluoro-2-methoxyphenyl)piperidine-1-carboxylic acid t-butyl ester

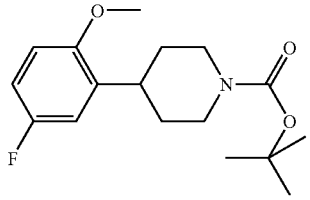

To a solution of 4-(5-fluoro-2-methoxyphenyl)-3,6-dihydro-2H-pyridine-1-carboxylic acid t-butyl ester (2.0 g, 6.5 mmol) produced in Example (106a) in methanol (30 mL) was added 10% palladium on carbon (0.99 g, wet), the mixture was stirred for 17 hours at atmospheric pressure and room temperature under a hydrogen atmosphere. The reaction mixture was filtered through Celite, and the obtained filtrate was concentrated under reduced pressure to give 2.0 g of the title compound as a light yellow oil.

$^1$H-NMR (400 MHz, CDCl$_3$) δ: 1.48 (s, 9H), 1.50-1.82 (m, 4H), 3.06 (tt, J=12.8, 2.8 Hz, 1H), 3.55-3.62 (m, 2H), 3.78 (s, 3H), 4.01-4.06 (m, 2H), 6.77 (dd, J=8.8, 4.8 Hz, 1H), 6.81-6.93 (m, 2H).

106c

4-Fluoro-2-piperidin-4-ylphenol

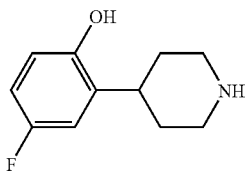

To a solution of 4-(5-fluoro-2-methoxyphenyl)piperidine-1-carboxylic acid t-butyl ester (2.0 g, 6.46 mmol) produced in Example (106b) in dichloromethane (50 mL) was added boron tribromide (1M solution in tetrahydrofuran, 19.4 mL, 19.4 mmol), followed by stirring for 4 hours at an external temperature of 60° C. Saturated aqueous solution of sodium hydrogencarbonate was added to the reaction mixture and extraction was performed with dichloromethane. The organic layer was dried over anhydrous magnesium sulfate, and the filtrate was concentrated under reduced pressure to give 840 mg of a crude product of the title compound as a yellow oil.

$^1$H-NMR (400 MHz, CDCl$_3$) δ: 1.80-2.00 (m, 4H), 2.80-3.16 (m, 4H), 3.44-3.54 (m, 2H), 6.59 (dd, J=9.2, 3.2 Hz, 1H), 6.64 (dd, J=8.8, 4.4 Hz, 1H), 6.75 (td, J=8.0, 3.2 Hz, 1H). 1H could not be identified.

MS m/e (ESI) 195 (MH$^+$).

106d 4-(5-Fluoro-2-hydroxyphenyl)piperidine-1-carboxylic acid t-butyl ester

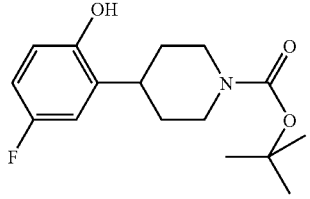

To a solution of 4-fluoro-2-piperidin-4-ylphenol (840 mg, 4.30 mmol) produced in Example (106c) in tetrahydrofuran (20 mL) were added triethylamine (0.78 mL, 5.59 mmol) and di-t-butyl dicarbonate (1.03 g, 4.73 mmol) in that order, followed by stirring for 1 hour and 30 minutes at room temperature. Brine was added to the reaction mixture and extraction was performed with ethyl acetate. The organic layer was dried over anhydrous magnesium sulfate and then the filtrate was concentrated under reduced pressure to give a residue, which was purified by silica gel column chromatography (ethyl acetate/heptane) to give 360 mg of the title compound as a yellow oil.

$^1$H-NMR (400 MHz, CDCl$_3$) δ: 1.48 (s, 9H), 1.50-1.62 (m, 2H), 1.77-1.85 (m, 2H), 2.70-2.90 (m, 2H), 3.00 (tt, J=12.8, 2.8 Hz, 11H), 4.16-4.32 (m, 2H), 5.21 (bs, 1H), 6.67 (dd, J=8.4, 4.4 Hz, 1H), 6.75 (td, J=8.4, 3.6 Hz, 1H), 6.81 (dd, J=8.4, 3.2 Hz, 1H).

106e 4-(5-Fluoro-2-trifluoromethanesulfonyloxyphenyl)piperidine-1-carboxylic acid t-butyl ester

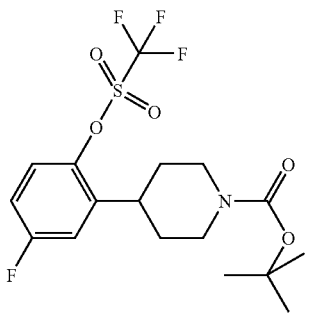

To a solution of 4-(5-fluoro-2-hydroxyphenyl)piperidine-1-carboxylic acid t-butyl ester (360 mg, 1.22 mmol) produced in Example (106d) in tetrahydrofuran (10 mL) was added sodium hydride (60% in oil, 58.6 mg, 1.46 mmol) while cooling in an ice bath, the mixture was stirred for 10 minutes. To the mixture was added N-phenylbis(trifluoromethanesulfonimide) (479 mg, 1.34 mmol), followed by stirring for 18 hours at room temperature. Brine was added to the reaction mixture and extraction was performed with ethyl acetate. The organic layer was dried over anhydrous magnesium sulfate and the filtrate was concentrated under reduced pressure to give a residue, which was purified by silica gel column chromatography (ethyl acetate/heptane) to give 523 mg of the title compound as a light yellow oil.

$^1$H-NMR (400 MHz, CDCl$_3$) δ: 1.25 (s, 9H), 1.40-1.90 (m, 4H), 2.70-2.92 (m, 2H), 3.00 (tt, J=12.8, 2.8 Hz, 1H), 4.16-4.34 (m, 2H), 6.88-6.96 (m, 2H), 7.01 (dd, J=8.8, 4.8 Hz, 1H).

106f

4-[5-Fluoro-2-(3,3,5,5-tetramethylcyclohex-1-enyl)phenyl]piperidine-1-carboxylic acid t-butyl ester

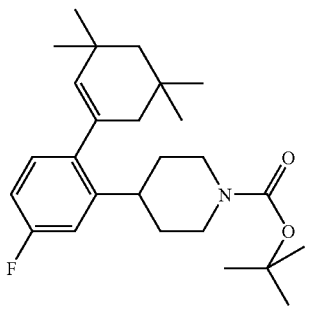

To a mixture of 4-(5-fluoro-2-trifluoromethanesulfonyloxyphenyl)piperidine-1-carboxylic acid t-butyl ester (523 mg, 1.22 mmol) produced in Example (106e), 4,4,5,5-tetramethyl-2-(3,3,5,5-tetramethylcyclohex-1-enyl)[1,3,2]dioxaborolane (387 mg, 1.46 mmol) produced in Example (4b) and 1,2-dimethoxyethane (10 mL) were added tetrakis(triphenylphosphine)palladium(0) (71 mg, 0.06 mmol) and 2N aqueous solution of sodium carbonate (1.83 ml, 3.66 mmol), followed by stirring for 1 hour and 30 minutes at an external temperature of 90° C. under a nitrogen atmosphere. Brine was added to the reaction mixture and extraction was performed with ethyl acetate. The organic layer was dried over anhydrous magnesium sulfate and the filtrate was concentrated under reduced pressure to give a residue, which was purified by silica gel column chromatography (ethyl acetate/heptane) to give 245 mg of the title compound as a light yellow oil.

$^1$H-NMR (400 MHz, CDCl$_3$) δ: 0.92 (s, 6H), 1.01 (s, 6H), 1.24 (s, 9H), 1.42 (s, 2H), 1.50-1.72 (m, 4H), 1.85 (s, 2H), 2.58-2.98 (m, 3H), 4.10-4.32 (m, 2H), 5.25 (s, 1H), 6.76-6.88 (m, 2H), 6.97 (dd, J=8.4, 2.4 Hz, 1H).

106g

4-[5-Fluoro-2-(3,3,5,5-tetramethylcyclohex-1-enyl)phenyl]piperidine

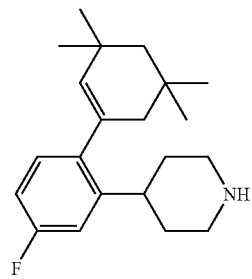

To a solution of 4-[5-fluoro-2-(3,3,5,5-tetramethylcyclohex-1-enyl)phenyl]piperidine-1-carboxylic acid t-butyl ester (245 mg, 0.59 mmol) produced in Example (106f) in dichloromethane (3 mL) was added trifluoroacetic acid (3 mL), followed by stirring for 30 minutes at room temperature. The reaction mixture was concentrated under reduced pressure, and then saturated aqueous solution of sodium hydrogencarbonate was added to the obtained residue and extraction was performed with ethyl acetate. The organic layer was dried over anhydrous magnesium sulfate, and the filtrate was concentrated under reduced pressure to give 220 mg of a crude product of the title compound as a light yellow solid.

$^1$H-NMR (400 MHz, CDCl$_3$) δ: 0.92 (s, 6H), 1.01 (s, 6H), 1.42 (s, 2H), 1.74-2.40 (m, 6H), 2.76-3.04 (m, 3H), 3.44-3.52 (m, 2H), 5.22 (s, 1H), 6.71 (dd, J=10.4, 2.4 Hz, 1H), 6.84 (td, J=8.4, 2.8 Hz, 1H), 6.97 (dd, J=8.4, 2.0 Hz, 1H).

The 1H of NH could not be identified.

MS m/e (ESI) 316 (MH$^+$).

106h

1-Butyl-4-[5-fluoro-2-(3,3,5,5-tetramethylcyclohex-1-enyl)phenyl]piperidine hydrochloride

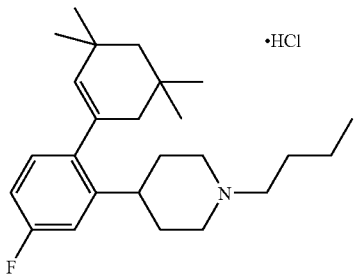

To a solution of 4-[5-fluoro-2-(3,3,5,5-tetramethylcyclohex-1-enyl)phenyl]piperidine (70 mg, 0.22 mmol) produced in Example (106g) in tetrahydrofuran (2 mL) were added butyraldehyde (19.2 mg, 0.27 mmol), sodium triacetoxyborohydride (71 mg, 0.33 mmol) and acetic acid (27 mg, 0.44 mmol), followed by stirring for 15 hours at room temperature. Saturated aqueous solution of sodium hydrogencarbonate was added to the reaction mixture and extraction was performed with ethyl acetate. The organic layer was dried over anhydrous magnesium sulfate and the filtrate was concentrated under reduced pressure to give a residue, which was purified by NH silica gel column chromatography (ethyl acetate/heptane) to give 55 mg of 1-butyl-4-[5-fluoro-2-(3,3,5,5-tetramethylcyclohex-1-enyl)phenyl]piperidine as a light yellow oil.

MS m/e (ESI) 372 (MH$^+$).

The obtained compound was dissolved in ethyl acetate, and then a 4N solution of hydrogen chloride in ethyl acetate was added and the mixture was stirred for 30 minutes at room temperature. The mixed solution was concentrated under reduced pressure, and then hexane was added to the residue to produce a solid which was then triturated by sonication. The solid was filtered and dried under reduced pressure to give 47 mg of the title compound as a light yellow solid.

$^1$H-NMR (400 MHz, CD$_3$OD) δ: 1.02 (t, J=7.2 Hz, 3H), 1.10 (s, 6H), 1.12 (s, 6H), 1.40-1.52 (m, 4H), 1.68-1.80 (m, 2H), 1.92-2.06 (m, 6H), 2.82-3.22 (m, 5H), 3.60-3.72 (m, 2H), 5.30 (t, J=1.6 Hz, 1H), 6.93 (td, J=8.4, 2.8 Hz, 1H), 6.99 (dd, J=8.0, 2.4 Hz, 1H), 7.05 (dd, J=8.4, 6.0 Hz, 1H). MS m/e (ESI) 372 (MH$^+$).

Example 107

1-Butyl-4-[5-fluoro-2-(3,3,5,5-tetramethylcyclohexyl)phenyl]piperidine hydrochloride

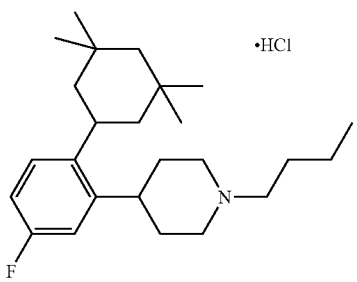

To a solution of 1-butyl-4-[5-fluoro-2-(3,3,5,5-tetramethylcyclohex-1-enyl)phenyl]piperidine hydrochloride (47 mg, 0.12 mmol) produced in Example (106h) in methanol (3 mL) was added 10% palladium on carbon (100 mg, wet), followed by stirring for 4 hours at atmospheric pressure and room temperature under a hydrogen atmosphere. The reaction mixture was filtered through Celite, and the filtrate was concentrated under reduced pressure. Hexane was added to the residue to produce a solid, which was then triturated by sonication. The solid was filtered and dried under reduced pressure to give 19 mg of the title compound as a light yellow solid.

$^1$H-NMR (400 MHz, CD$_3$OD) δ: 0.97 (s, 6H), 1.03 (t, J=7.2 Hz, 3H), 1.08-1.16 (m, 2H), 1.19 (s, 6H), 1.18-1.52 (m, 6H), 1.72-1.84 (m, 2H), 1.94-2.10 (m, 4H), 3.06-3.26 (m, 6H), 3.68-3.80 (m, 2H), 6.88-7.02 (m, 2H), 7.30 (dd, J=8.8, 6.0 Hz, 1H). MS m/e (ESI) 374 (MH$^+$).

Example 108

1-[2-(4-Cyclopropylmethylpiperazin-1-yl)phenyl]-3,3,5,5-tetramethylcyclohexanol

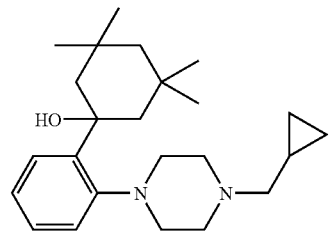

108a 1-(2-Bromophenyl)-4-cyclopropylmethylpiperazine

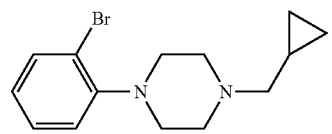

To a solution of 1-(2-bromophenyl)piperazine (3.0 g, 12.4 mmol) in tetrahydrofuran (30 mL) were added acetic acid (0.71 mL, 12.4 mmol), cyclopropanecarbaldehyde (1.39 mL, 18.66 mmol) and sodium triacetoxyborohydride (4.22 g, 19.9 mmol), followed by stirring for 88 hours at room temperature. Aqueous solution of potassium carbonate was added to the reaction mixture, extraction was performed with ethyl acetate, and the organic layer was concentrated. The resultant residue was purified by NH silica gel column chromatography (ethyl acetate/heptane) to give 3.773 g of the title compound as a colorless oil.

$^1$H-NMR (400 MHz, CDCl$_3$) δ: 0.13-0.16 (m, 2H), 0.52-0.57 (m, 2H), 0.87-0.95 (m, 1H), 2.34 (d, J=6.4 Hz, 2H), 2.60-2.85 (br, 4H), 3.03-3.17 (br, 4H), 6.88-7.55 (m, 4H).

108b

1-[2-(4-Cyclopropylmethylpiperazin-1-yl)phenyl]-3,3,5,5-tetramethylcyclohexanol

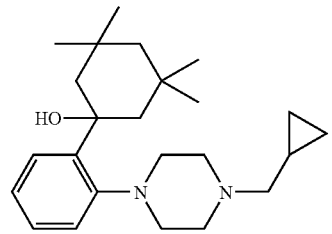

To a solution of 1-(2-bromophenyl)-4-cyclopropylmethylpiperazine (700 mg, 2.37 mmol) produced in Example (108a) in anhydrous tetrahydrofuran (7 mL) was added dropwise n-butyllithium (1.60 M solution in hexane, 1.63 mL, 2.61 mmol) over a period of 3 minutes at an external temperature of −70° C. After stirring for 45 minutes under the same conditions, 3,3,5,5-tetramethylcyclohexanone (0.49 mL, 2.85 mmol) was added dropwise to the reaction mixture over a period of 4 minutes at an external temperature of −70° C.

Stirring was continued for 15 minutes under the same conditions, and then for 18 hours and 30 minutes while warming until the external temperature reached room temperature. Water was added to the reaction mixture and extraction was performed with ethyl acetate. The separated organic layer was washed with brine and then dried over anhydrous sodium sulfate. The desiccant was filtered off and the filtrate was concentrated under reduced pressure. The resultant residue was purified by silica gel column chromatography (ethyl acetate/heptane) to give 765 mg of the title compound as a light yellow oil.

$^1$H-NMR (400 MHz, CDCl$_3$) δ: 0.12-0.17 (m, 2H), 0.53-0.57 (m, 2H), 0.85-0.95 (m, 1H), 0.93 (s, 6H), 1.13-1.79 (m, 6H), 1.38 (s, 6H), 2.26-2.33 (m, 2H), 2.34 (d, J=6.4 Hz, 2H), 3.00-3.04 (m, 2H), 3.09-3.14 (m, 4H), 7.15 (ddd, J=7.8, 7.8, 1.4 Hz, 1H), 7.22 (ddd, J=7.8, 7.8, 1.4 Hz, 1H), 7.31 (dd, J=7.8, 1.4 Hz, 1H), 7.36 (dd, J=7.8, 1.4 Hz, 1H), 8.11 (brs, 1H). MS m/e (ESI) 371 (MH$^+$).

Example 109

1-Cyclopropylmethyl-4-[2-(3,3,5,5-tetramethylcyclohex-1-enyl)phenyl]piperazine

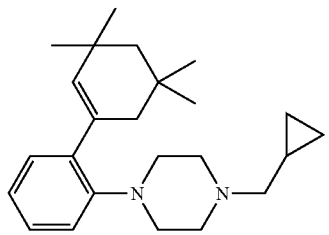

A mixture of 1-[2-(4-cyclopropylmethylpiperazin-1-yl)phenyl]-3,3,5,5-tetramethylcyclohexanol (250 mg, 0.675 mmol) produced in Example (108b), water (0.12 mL) and trifluoroacetic acid (1.04 mL, 13.5 mmol) was stirred for 21 hours at an external temperature of room temperature. Aqueous solution of potassium carbonate was added to the reaction mixture and then extraction was performed with ethyl acetate. Organic layer was concentrated under reduced pressure to give a residue, which was purified by NH silica gel column chromatography (ethyl acetate/heptane) to give 218 mg of the title compound as a colorless solid.

$^1$H-NMR (400 MHz, CDCl$_3$) δ: 0.11-0.15 (m, 2H), 0.51-0.56 (m, 2H), 0.85-0.95 (m, 1H), 1.02 (s, 6H), 1.07 (s, 6H), 1.39 (s, 2H), 2.17 (d, J=1.4 Hz, 2H), 2.29 (d, J=6.4 Hz, 2H), 2.50-2.75 (br, 4H), 2.95-3.10 (br, 4H), 5.50 (t, J=1.4 Hz, 1H), 6.95-7.08 (m, 3H), 7.16-7.20 (m, 1H).

Example 110

4-{4-[2-(3,3,5,5-Tetramethylcyclohexyl)phenyl]piperazin-1-yl}butan-2-one

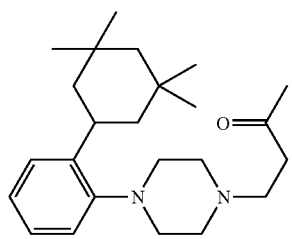

A mixture of 1-[2-(3,3,5,5-tetramethylcyclohexyl)phenyl]piperazine (160 mg, 0.532 mmol) produced in Example (8b), methyl vinyl ketone (0.058 mL, 0.692 mmol) and chloroform (0.7 mL) was stirred for 21 hours and 30 minutes at an external temperature of room temperature. The reaction mixture was diluted with ethyl acetate and then washed with aqueous solution of sodium hydrogencarbonate. The separated organic layer was concentrated under reduced pressure, and the obtained residue was purified by silica gel column chromatography (ethyl acetate/heptane) to give 155 mg of the title compound as a light brown oil.

MS m/e (ESI) 371 (MH$^+$).

Example 111

4-[4-[2-(3,3,5,5-Tetramethylcyclohexyl)phenyl]piperazin-1-yl]butan-2-ol hydrochloride

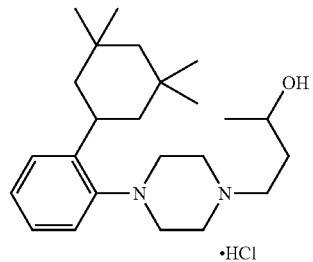

To a mixture of 4-[4-[2-(3,3,5,5-tetramethylcyclohexyl)phenyl]piperazin-1-yl]butan-2-one (138 mg, 0.372 mmol) produced in (Example 110) and methanol (1.5 mL) was gradually added sodium borohydride (14.1 mg, 0.372 mmol) at an external temperature of room temperature, followed by stirring for 2 hours under the same conditions. Aqueous solution of ammonium chloride was added to the reaction mixture, and stirring was continued for 20 minutes. After making the mixture basic with aqueous solution of potassium carbonate, extraction was performed with ethyl acetate. The separated organic layer was concentrated under reduced pressure to give a residue, which was purified by NH silica gel column chromatography (ethyl acetate/heptane) to give 136 mg of the free form of the title compound as a colorless oil. The free from of the title compound (19 mg, 0.051 mmol) was dissolved in a mixed solvent of ethyl alcohol and ethyl acetate, and then a 4N solution of hydrogen chloride in ethyl acetate (0.014 mL, 0.056 mmol) was added. The mixed solution was concentrated under reduced pressure and the resulting solid residue was washed with a diethyl ether-heptane mixed solvent and then dried under reduced pressure to give 21 mg of the title compound as a colorless solid.

MS m/e (ESI) 373 (MH$^+$).

Example 112

1-(3-Fluorobutyl)-4-[2-(3,3,5,5-tetramethylcyclohexyl)phenyl]piperazine hydrochloride

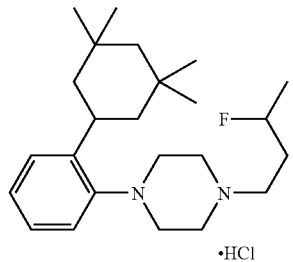

To a solution of 4-[4-[2-(3,3,5,5-tetramethylcyclohexyl)phenyl]piperazin-1-yl]butan-2-ol (40 mg, 0.107 mmol) produced as an intermediate in Example 111 in dichloromethane (1 mL) was added diethylaminosulfur trifluoride (DAST) (0.017 mL, 0.128 mmol) at an external temperature of −70° C. The mixture was then stirred for 15 hours while heating until the external temperature reached room temperature. The reaction mixture was then cooled to an external temperature of 0° C., aqueous solution of potassium carbonate was added and the mixture was stirred. The mixture was extracted with ethyl acetate to give an organic layer which was dried over anhydrous sodium sulfate. The desiccant was filtered off and the filtrate was concentrated under reduced pressure. The resultant residue was purified by NH silica gel column chromatography (ethyl acetate/heptane) to give 2.8 mg of 1-(3-fluorobutyl)-4-[2-(3,3,5,5-tetramethylcyclohexyl)phenyl]piperazine as a colorless oil. This compound was dissolved in ethyl acetate-ethanol and a 4N solution of hydrogen chloride in ethyl acetate (0.002 mL) was added. The reaction mixture was concentrated under reduced pressure, and the obtained solid residue was washed with a diethyl ether-heptane mixed solvent and then dried under reduced pressure to give 2.7 mg of the title compound as a colorless solid.

MS m/e (ESI) 375 (MH+).

Example 113

1-{4-[2-(3,3,5,5-Tetramethylcyclohexyl)phenyl]piperazin-1-yl}hexan-2-ol hydrochloride

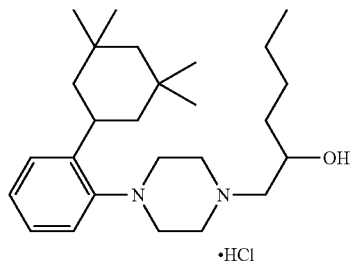

A mixture of 1-[2-(3,3,5,5-tetramethylcyclohexyl)phenyl]piperazine (120 mg, 0.399 mmol) produced in Example (8b), 1,2-epoxyhexane (240 mg, 2.39 mmol) and 2-propanol (0.8 mL) was stirred for 18 hours at an external temperature of 80° C. The reaction mixture was concentrated under reduced pressure to give a residue, which was purified by NH silica gel column chromatography (ethyl acetate/heptane) to give 116 mg of 1-{4-[2-(3,3,5,5-tetramethylcyclohexyl)phenyl]piperazin-1-yl}hexan-2-ol as a light yellow solid. This compound (12 mg, 0.030 mmol) was dissolved in diethyl ether and a 4N solution of hydrogen chloride in ethyl acetate (0.0083 mL, 0.033 mmol) was added. The mixed solution was concentrated under reduced pressure and the obtained solid residue was washed with a diethyl ether-heptane mixed solvent and then dried under reduced pressure to give 10 mg of the title compound as a colorless solid.

MS m/e (ESI) 401 (MH+).

Example 114

1-{4-[2-(3,3,5,5-Tetramethylcyclohexyl)phenyl]piperazin-1-yl}butan-2-ol hydrochloride

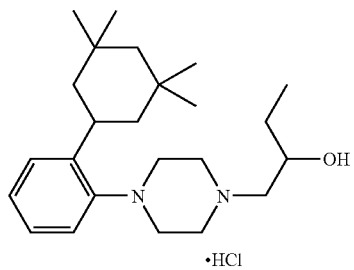

To a mixture of 1-{4-[2-(3,3,5,5-tetramethylcyclohexyl)phenyl]piperazin-1-yl}butan-2-one (298 mg, 0.802 mmol) produced as an intermediate in Example 25 and methanol (3 mL) was gradually added sodium borohydride (36.4 mg, 0.962 mmol) at an external temperature of room temperature, followed by stirring for 1 hour under the same conditions. Aqueous solution of ammonium chloride was added to the reaction mixture and the mixture was stirred overnight and the mixture was made basic with aqueous solution of potassium carbonate, and extraction was performed with ethyl acetate. The separated organic layer was concentrated under reduced pressure to give a residue, which was purified by NH silica gel column chromatography (ethyl acetate/heptane) to give 269 mg of the free form of the title compound as a colorless solid. The free form of the title compound (20 mg, 0.054 mmol) was dissolved in a mixed solvent of ethanol and ethyl acetate, and then a 4N solution of hydrogen chloride in ethyl acetate (0.015 mL, 0.059 mmol) was added. The mixed solution was concentrated under reduced pressure and the resulting solid residue was washed with a mixed solvent of diethyl ether and heptane and then dried under reduced pressure to give 20 mg of the title compound as a colorless solid.

MS m/e (ESI) 373 (MH+).

Example 115

2-{4-[2-(3,3,5,5-Tetramethylcyclohexyl)phenyl]piperazin-1-ylmethyl}butyronitrile hydrochloride

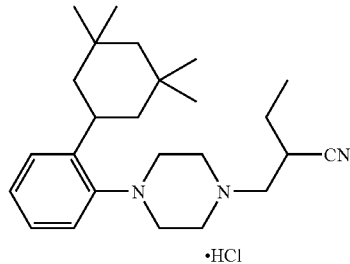

To a mixture of 1-{4-[2-(3,3,5,5-tetramethylcyclohexyl)phenyl]piperazin-1-yl}butan-2-one (80 mg, 0.216 mmol) produced as an intermediate in Example 25, 1,2-dimethoxyethane (2.5 mL) and t-butanol (0.1 mL) were added p-toluenesulfonylmethyl isocyanide (TosMIC) (46.4 mg, 0.238 mmol) and potassium t-butoxide (34 mg, 0.302 mmol) at an external temperature of 0° C., followed by stirring for 90 minutes under the same conditions. The external temperature was then raised to room temperature and stirring was continued for 30 minutes. Brine was added to the reaction mixture, extraction was performed with ethyl acetate, and the obtained organic layer was dried over anhydrous sodium sulfate. After removing the desiccant by filtration, the filtrate was concentrated under reduced pressure to give a residue, which was then purified by NH silica gel column chromatography (ethyl acetate/heptane) to give 66 mg of the free form of the title compound as a colorless oil. This compound (66 mg, 0.173 mmol) was dissolved in dichloromethane-ethyl acetate, and then a 4N solution of hydrogen chloride in ethyl acetate (0.046 mL, 0.18 mmol) was added. The mixed solution was concentrated under reduced pressure, and the resulting solid residue was washed with a diethyl ether-heptane mixed solvent and then dried under reduced pressure to give 65 mg of the title compound as a colorless solid.

MS m/e (ESI) 382 (MH+).

Example 116

1-Furan-3-ylmethyl-4-[2-(3,3,5,5-tetramethlcyclohexyl)phenyl]piperazine hydrochloride

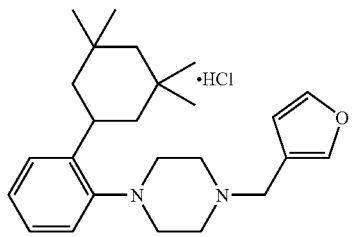

To a mixture of 1-[2-(3,3,5,5-tetramethylcyclohexyl)phenyl]piperazine (50 mg, 0.166 mmol) produced in Example (8b), furan-3-carbaldehyde (0.02 mL, 0.231 mmol) and tetrahydrofuran (3 mL) was added sodium triacetoxyborohydride (43 mg, 0.203 mmol), followed by stirring for 20 minutes at room temperature. Saturated aqueous solution of sodium hydrogencarbonate was added to the reaction mixture and extraction was performed with ethyl acetate. The solvent was distilled off by nitrogen stream. The resultant residue was purified by NH silica gel column chromatography (ethyl acetate/hexane) to give 1-furan-3-ylmethyl-4-[2-(3,3,5,5-tetramethylcyclohexyl)phenyl]piperazine. This compound was dissolved in dichloromethane, and a 4N solution of hydrogen chloride in ethyl acetate was added. The solvent was distilled off by nitrogen stream. Diethyl ether was added to the obtained residue to produce a solid, and after further adding hexane, the solid was triturated by sonication. The supernatant solution was removed and the obtained solid was dried to give 33 mg of the title compound as colorless crystals.

MS m/e (ESI) 381 (MH$^+$).

Example 117

1-Cyclopropylmethyl-4-[2-(3,3,5,5-tetramethylcyclohexyl)phenyl]piperazine methanesulfonate

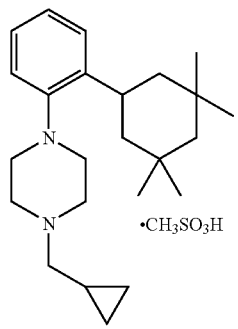

117a

Trifluoromethanesulfonic acid 3,3,5,5-tetramethylcyclohex-1-enyl ester

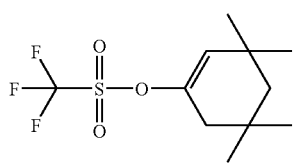

3,3,5,5-Tetramethylcyclohexanone (100.0 g, 648.3 mmol) was dissolved in anhydrous tetrahydrofuran (750 mL) under a nitrogen atmosphere, and the mixture was cooled and stirred at an external temperature of below –70° C. To the mixture was added dropwise bis(trimethylsilyl)amide lithium (1M solution in tetrahydrofuran, 778 mL, 778 mmol) over a period of 30 minutes under the same conditions, followed by stirring for 70 minutes under the same conditions. Then, a solution of N-phenylbis(trifluoromethanesulfonimide) (254.8 g, 713 mmol) in anhydrous tetrahydrofuran (1 L) was added dropwise to the reaction mixture over a period of 35 minutes. After stirring the mixture for 20 minutes under the same conditions, the mixture was stirred for 15 hours while gradually warmed to an external temperature of room temperature. Reaction was repeated twice more on the same scale as above, by the same procedure under the same reaction conditions. The three reaction mixtures were combined and subjected to the following treatment.

Ethyl acetate (1.5 L) was added to the combined reaction mixture, and then a solution of concentrated hydrochloric acid (450 mL) in ice water (5 L) was added while stirring. After stirring for a while, the separated organic layer was washed with brine (1.5 L), saturated aqueous solution of sodium hydrogencarbonate (1.5 L) and brine (1.5 L). The obtained organic layer was dried over anhydrous magnesium sulfate (1.5 kg) for 30 minutes while stirring. The desiccant was filtered off and the filtrate was concentrated under reduced pressure. The resultant residue was purified by silica gel column chromatography (hexane) and then dried under reduced pressure to give 520.94 g of the title compound as a light yellow oil.

$^1$H-NMR (400 MHz, CDCl$_3$) δ: 1.05 (s, 6H), 1.10 (s, 6H), 1.35 (s, 2H), 2.09 (d, J=1.2 Hz, 2H), 5.51 (t, J=1.2 Hz, 1H).

117b

1-Nitro-2-(3,3,5,5-tetramethylcyclohex-1-enyl)benzene

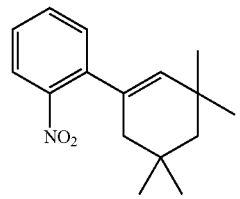

To a mixture of trifluoromethanesulfonic acid 3,3,5,5-tetramethylcyclohex-1-enyl ester (160.0 g, 558.8 mmol), 2-nitrophenylboronic acid (97.9 g, 586.8 mmol) and 1,2-dimethoxyethane (920 mL) were added sodium carbonate (118.5 g, 1.12 mol) and purified water (230 mL) while stirring at room temperature. Then, tetrakis(triphenylphosphine)palladium(0) (29.1 g, 25.1 mmol) was added to the mixture at room temperature (in an oil bath at room temperature), and the inside of the flask was replaced with nitrogen gas. The mixture was then stirred for 4 hours and 30 minutes at an external temperature of room temperature (in an oil bath at room temperature).

The same reaction was then repeated twice more by the same procedure under the same reaction conditions as above, but with an amount of 170.0 g (593.7 mmol) of trifluoromethanesulfonic acid 3,3,5,5-tetramethylcyclohex-1-enyl ester, a starting material, and the amounts of the other reagents changed to corresponding equivalents. The three reaction mixtures were combined and subjected to the following treatment.

Ethyl acetate (1.5 L) and water (4 L) were added to the combined reaction mixture, which was then stirred for 5 minutes. The mixture was filtered through Celite to remove insoluble materials. After stirring the obtained filtrate for a while, the organic layer was separated and the aqueous layer was extracted with ethyl acetate (1 L). The organic layers were combined and then dried over anhydrous magnesium sulfate (1 kg) for 20 minutes while stirring. The desiccant was filtered off and the filtrate was concentrated under reduced pressure. The resultant residue was purified by silica gel column chromatography (ethyl acetate/hexane) and then dried under reduced pressure to give 407.30 g of the title compound as a yellow solid.

$^1$H-NMR (400 MHz, CDCl$_3$) δ: 1.046 (s, 6H), 1.053 (s, 6H), 1.41 (s, 2H), 2.02 (d, J=1.6 Hz, 2H), 5.37 (t, J=1.6 Hz, 1H), 7.26 (dd, J=7.6, 1.6 Hz, 1H), 7.33 (ddd, J=8.0, 7.6, 1.6 Hz, 1H), 7.49 (ddd, J=7.6, 7.6, 1.2 Hz, 1H), 7.74 (dd, J=8.0, 1.2 Hz, 1H).

117c 2-(3,3,5,5-Tetramethylcyclohexyl)phenylamine

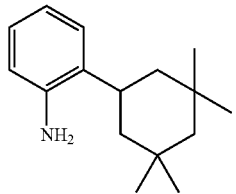

A mixture of 1-nitro-2-(3,3,5,5-tetramethylcyclohex-1-enyl)benzene (130.0 g, 501.3 mmol), 10% palladium on carbon (13.0 g, wet) and ethyl alcohol (1820 mL) was placed in a flask, then the inside of the flask was replaced with hydrogen, and the mixture was stirred for 78 hours at room temperature under a hydrogen atmosphere at atmospheric pressure. Reaction was repeated two more times on the same scale as above, by the same procedure under the same reaction conditions. The three reaction mixtures were combined and subjected to the following treatment.

The combined reaction mixture was filtered, and the filtrate was concentrated under reduced pressure. The obtained residue was diluted with ethyl acetate (700 mL) and hexane (200 mL), and then dried over anhydrous sodium sulfate (200 g) for 20 minutes while stirring. The desiccant was filtered off using a glass microfiber filter, and then the filtrate was concentrated and dried under reduced pressure to give 345.76 g of the title compound as a light brown oil.

$^1$H-NMR (400 MHz, CDCl$_3$) δ: 0.95 (s, 6H), 1.13 (s, 6H), 1.08-1.36 (m, 4H), 1.59-1.62 (m, 2H), 2.86 (tt, J=12.4, 2.8 Hz, 1H), 3.63 (brs, 2H), 6.70 (dd, J=7.6, 1.2 Hz, 1H), 6.78 (ddd, J=7.6, 7.6, 1.2 Hz, 1H), 7.02 (ddd, J=7.6, 7.6, 1.2 Hz, 1H), 7.12 (dd, J=7.6, 1.2 Hz, 1H).

117d

1-[2-(3,3,5,5-Tetramethylcyclohexyl)phenyl]piperazine

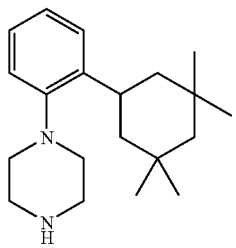

To a mixture of 2-(3,3,5,5-tetramethylcyclohexyl)phenylamine (168.0 g, 726.1 mmol) and 1,2-dichlorobenzene (1200 mL) was added bis(2-chloroethyl)amine hydrochloride (155.5 g, 871.3 mmol). The mixture was stirred for 7 hours at an external temperature of 190° C. under a nitrogen atmosphere. During the reaction, a nitrogen stream was passed through the reactor several times to remove the generated hydrogen chloride gas. Reaction was repeated once more on the same scale as above, by the same procedure under the same reaction conditions. The two reaction mixtures were combined and subjected to the following treatment.

After cooling to room temperature, the combined reaction mixture was diluted with ethyl acetate (6 L) and water (1 L). The mixture was then added to a mixture of potassium carbonate (1.3 kg) and water (5 L) while stirring. The mixture was stirred and allowed to stand, and the organic layer was separated. The aqueous layer was again extracted with ethyl acetate (2 L). The combined organic layers were washed with brine (3 L) and then dried over anhydrous sodium sulfate (3.5 kg). The desiccant was filtered off and the filtrate was concentrated under reduced pressure. The resultant residue was purified by NH silica gel column chromatography (ethyl acetate/hexane) and then dried under reduced pressure to give 241.67 g of the title compound as a light pink solid.

In addition to this, the above NH silica gel column chromatography purification also yielded 126.2 g of an oil as a mixture of the target compound and impurities. Hexane (150 mL) was added to the oil, and the mixture was stirred for 2 hours at 0° C. The produced precipitate was collected by suction filtration and then dried under reduced pressure to give 42.74 g of the title compound as a light pink solid. A total of 284.41 g of the title compound was obtained as a light pink solid.

$^1$H-NMR (400 MHz, CDCl$_3$) δ: 0.93 (s, 6H), 1.13 (s, 6H), 1.17-1.35 (m, 4H), 1.42-1.46 (m, 2H), 2.84-2.87 (m, 4H), 3.02-3.04 (m, 4H), 3.60 (tt, J=12.8, 2.8 Hz, 1H), 7.06-7.18 (m, 3H), 7.23 (dd, J=7.6, 1.6 Hz, 1H).

The 1H of NH could not be identified.

117f

1-Cyclopropylmethyl-4-[2-(3,3,5,5-tetramethylcyclohexyl)phenyl]piperazine

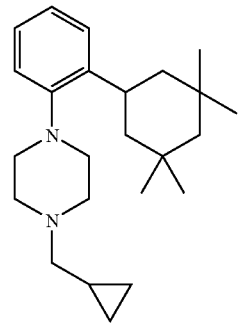

To a mixture of 1-[2-(3,3,5,5-tetramethylcyclohexyl)phenyl]piperazine (241.67 g, 804.3 mmol), acetic acid (46.0 mL, 804.3 mmol) and tetrahydrofuran (3300 mL) was added a mixed solution of cyclopropanecarbaldehyde (64.8 g, 924.9 mmol) and tetrahydrofuran (200 mL) while stirring at an external temperature of room temperature. After stirring for 10 minutes, sodium triacetoxyborohydride (238.6 g, 1126 mmol) was added portionwise to the reaction mixture over a period of 8 minutes. The mixture was then stirred for 3 hours at an external temperature of room temperature.

The reaction mixture was diluted with hexane (2 L) and water (1 L). This mixture was then added to a mixture of potassium carbonate (667 g) and water (3.5 L) while stirring. After stirring for a while and allowing the mixture to stand, the separated organic layer was washed sequentially with water (2 L) and brine (1.5 L). The organic layer was then dried over anhydrous sodium sulfate (1.5 kg), the desiccant was filtered off, and the obtained filtrate was concentrated under reduced pressure. The obtained residue was purified by NH silica gel column chromatography (ethyl acetate/hexane) and then concentrated under reduced pressure to give an oil. The oil was dissolved again in ethyl acetate (1 L), and the mixture was filtered through a glass microfibre filter to remove insoluble materials. The obtained filtrate was concentrated under reduced pressure, and then a vacuum pump was used for drying under reduced pressure for 2 hours at an external temperature of 50° C., to give 280.7 g of the title compound as crystals.

$^1$H-NMR (400 MHz, CDCl$_3$) δ: 0.12-0.16 (m, 2H), 0.52-0.56 (m, 2H), 0.88-0.96 (m, 1H), 0.92 (s, 6H), 1.12 (s, 6H), 1.13-1.34 (m, 4H), 1.41-1.47 (m, 2H), 2.32 (d, J=6.4 Hz, 2H), 2.40-2.98 (br, 4H), 2.94-2.96 (m, 4H), 3.58 (tt, J=12.6, 2.8 Hz, 1H), 7.05-7.18 (m, 3H), 7.22-7.24 (m, 1H).

117g

1-Cyclopropylmethyl-4-[2-(3,3,5,5-tetramethylcyclohexyl)phenyl]piperazine methanesulfonate

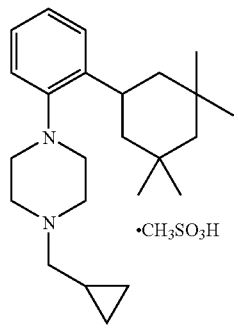

A mixture of 1-cyclopropylmethyl-4-[2-(3,3,5,5-tetramethylcyclohexyl)phenyl]piperazine (277.0 g, 781.2 mmol) and methyl ethyl ketone (2493 mL) was stirred while heating at an external temperature of 81° C. Methanesulfonic acid (76.58 g, 796.8 mmol) was then added dropwise thereto over a period of 3 minutes, to form a thoroughly dissolved state. After heating and stirring for 7 minutes at an external temperature of 81° C., the external temperature was gradually lowered and stirring was continued until the internal temperature reached 37° C. The reaction suspension containing the produced precipitate was transferred to another flask using methyl ethyl ketone (100 mL). The suspension was then concentrated under reduced pressure over a period of 1 hour and 20 minutes at an external temperature of 21° C. It was then dried under reduced pressure for 30 minutes at an external temperature of 40° C. for solidification of the flask contents, to give a crude solid product of the title compound. After adding a mixed solvent of ethyl acetate (1662 mL) and heptane (1108 mL) to this crude solid product, the resulting suspension was stirred for 1 hour at an external temperature of 65° C. The suspension was then further stirred while gradually lowering the external temperature, and after the external temperature reached 45° C., stirring was continued for 14 hours at an external temperature of room temperature. The obtained suspension was filtered and the precipitated solid was collected. The solid was washed with a mixed solvent of ethyl acetate (330 mL) and heptane (220 mL) and aircured by aspiration for 4 hours at room temperature. The obtained crystals were dried for 6 hours at 70° C. in a warm-air drier to give 335.9 g of the title compound as colorless (white) powdery crystals.

$^1$H-NMR (400 MHz, CDCl$_3$) δ: 0.47-0.51 (m, 2H), 0.81-0.85 (m, 2H), 0.94 (s, 6H), 1.10 (s, 6H), 1.15-1.43 (m, 7H), 2.85 (s, 3H), 2.95-3.11 (m, 6H), 3.43 (tt, J=12.6, 3.0 Hz, 1H), 3.52-3.61 (m, 2H), 3.80 (br d, J=11.2 Hz, 2H), 7.13-7.26 (m, 4H), 11.11 (br s, 1H).

Example 118

The following compounds were produced according to the common production methods described above, the methods described in the examples, or combinations thereof with well-known methods.

2-{4-[2-(4-t-Butylcyclohexyl)phenyl]piperazin-1-yl}-N-propylacetamide hydrochloride MS m/e (ESI) 400 (MH$^+$).

2-{4-[2-(4-t-Butylcyclohexyl)phenyl]piperazin-1-yl}-N,N-dimethylacetamide hydrochloride MS m/e (ESI) 386 (MH$^+$).

4-Benzyl-1-[2-(4-t-butylcyclohexyl)phenyl]piperazin-2-one hydrochloride

MS m/e (ESI) 405 (MH$^+$).

2-{4-[2-(4-t-Butylcyclohex-1-enyl)phenyl]piperazin-1-yl}-N-ethylacetamide hydrochloride MS m/e (ESI) 384 (MH$^+$).

1-[2-(4-t-Butylcyclohexyl)phenyl]-4-cyclopropylmethylpiperazine hydrochloride

MS m/e (ESI) 355 (MH$^+$).

1-[2-(4-t-Butylcyclohex-1-enyl)phenyl]-4-methylpiperazine hydrochloride

MS m/e (ESI) 313 (MH$^+$).

1-Furan-3-ylmethyl-4-[2-(3,3,5,5-tetramethylcyclohexyl)phenyl]piperazine hydrochloride MS m/e (ESI) 381 (MH$^+$).

1-[4-(4-Methoxypiperidin-1-yl)-2-(3,3,5,5-tetramethylcyclohex-1-enyl)phenyl]-4-propylpiperazine hydrochloride MS m/e (ESI) 454 (MH$^+$).

2-{4-[2-(4-t-Butylcyclohexyl)phenyl]piperazin-1-yl}-1-morpholin-4-ylethanone hydrochloride MS m/e (ESI) 428 (MH$^+$).

2-{4-[2-(4-t-Butylcyclohexyl)phenyl]piperazin-1-yl}-1-pyrrolidin-1-ylethanone hydrochloride MS m/e (ESI) 412 (MH$^+$).

1-Azepan-1-yl-2-{4-[2-(4-t-butylcyclohexyl)phenyl]piperazin-1-yl}ethanone hydrochloride MS m/e (ESI) 440 (MH$^+$).

3-(4-t-Butylcyclohexyl)-4-(4-butylpiperazine-1-yl) benzonitrile hydrochloride

MS m/e (ESI) 382 (MH$^+$).

1-Butyl-4-[2-(4-t-butylcyclohexyl)-4-pyridin-2-ylphenyl]piperazine hydrochloride MS m/e (ESI) 434 (MH$^+$).

4-(4-t-Butylcyclohex-1-enyl)-3-(4-butylpiperazine-1-yl)phenylamine hydrochloride MS m/e (ESI) 370 (MH$^+$).

[4-(4-t-Butylcyclohex-1-enyl)-3-(4-butylpiperazine-1-yl)phenyl]dimethylamine hydrochloride MS m/e (ESI) 398 (MH$^+$).

[4-(4-t-Butylcyclohexyl)-3-(4-butylpiperazine-1-yl)phenyl]dimethylamine hydrochloride MS m/e (ESI) 400 (MH$^+$).

1-[4-(4-Methoxypiperidin-1-yl-2-(3,3,5,5-tetramethylcyclohex-1-enyl)phenyl]-4-pentylpiperazine hydrochloride MS m/e (ESI) 482 (MH$^+$).

1-[2-(4-t-Butylcyclohex-1-enyl)-4-(4-methoxypiperidin-1-yl)phenyl]-4-propylpiperazine hydrochloride MS m/e (ESI) 454 (MH$^+$).

1-Butyl-4-[2-(4-t-butylcyclohexyl)-4-(4-methoxypiperidin-1-yl)phenyl]piperazine hydrochloride MS m/e (ESI) 470 (MH$^+$).

1-[4-(4-Methoxypiperidin-1-yl)-2-spiro[5.5]undec-2-en-3-ylphenyl]-4-pentylpiperazine hydrochloride MS m/e (ESI) 494 (MH$^+$).

1-[4-(2-Spiro[5.5]undec-3-ylphenyl)piperazin-1-yl]butan-2-one hydrochloride

MS m/e (ESI) 383 (MH$^+$).

1-Butyl-4-[2-(4-butylcyclohexyl)phenyl]piperazine hydrochloride

MS m/e (ESI) 357 (MH$^+$).

[4-(4-t-Butylcyclohexyl)-3-(4-butylpiperazine-1-yl)phenyl]acetic acid methyl ester hydrochloride MS m/e (ESI) 429 (MH$^+$).

[5-(4-t-Butylcyclohexyl)-4-(4-butylpiperazine-1-yl)-2-methoxyphenyl]dimethylamine hydrochloride MS m/e (ESI) 430 (MH$^+$).

1-Cyclopropylmethyl-4-[2-(4,4-diethylcyclohex-1-enyl)-5-methoxyphenyl]piperazine hydrochloride MS m/e (ESI) 383 (MH$^+$).

1-Cyclopropylmethyl-4-[2-(4,4-diethylcyclohexyl)-5-methoxy]phenyl]piperazine hydrochloride MS m/e (ESI) 385 (MH$^+$).

1-[2-(4,4-Diethylcyclohex-1-enyl)-5-methoxyphenyl]-4-propylpiperazine hydrochloride MS m/e (ESI) 371 (MH$^+$).

[4-(4-Butylpiperazin-1-yl)-5-(4,4-dimethylcyclohexyl)-2-methoxyphenyl]dimethylamine hydrochloride MS m/e (ESI) 430 (MH$^+$).

1-Propyl-4-(2-spiro[4.5]dec-7-en-8-ylphenyl)piperazine hydrochloride

MS m/e (ESI) 339 (MH$^+$).

1-Propyl-4-(2-spiro[4.5]dec-8-ylphenyl)piperazine hydrochloride

MS m/e (ESI) 341 (MH$^+$).

1-(2-Spiro[4.5]dec-8-ylphenyl)-4-(tetrahydropyran-4-ylmethyl)piperazine hydrochloride MS m/e (ESI) 397 (MH$^+$).

[4-(4-Butylpiperazin-1-yl)-2-methoxy-5-(3,3,5,5-tetramethylcyclohexyl)phenyl]dimethylamine hydrochloride MS m/e (ESI) 430 (MH$^+$).

4-[4-(4-Pentylpiperazin-1-yl)-3-spiro[4.5]dec-7-en-8-ylphenyl]morpholine hydrochloride MS m/e (ESI) 452 (MH$^+$).

1-Butyl-4-[2-(4-t-butylcyclohexyl)-5-methoxyphenyl]piperazine hydrochloride

MS m/e (ESI) 387 (MH$^+$).

1-Butyl-4-[2-(4-t-butylcyclohexyl)-4-methoxyphenyl]piperazine hydrochloride

MS m/e (ESI) 387 (MH$^+$).

2-{4-[2-(4-t-Butylcyclohexyl)-4-methoxyphenyl]piperazin-1-yl}-N,N-dimethylacetamide hydrochloride MS m/e (ESI) 416 (MH$^+$).

3-{4-[2-(4-t-Butylcyclohexyl)phenyl]piperazin-1-yl}propionic acid methyl ester

MS m/e (ESI) 387 (MH$^+$).

4-[4-(4-t-Butylcyclohexyl)-3-(4-butylpiperazin-1-yl)phenyl]morpholine hydrochloride MS m/e (ESI) 442 (MH$^+$).

1-[4-(4-t-Butylcyclohexyl)-3-(4-butylpiperazin-1-yl)
phenyl]ethanone hydrochloride MS m/e (ESI) 399 (MH$^+$).

4-[3-(4,4-Dimethylcyclohex-1-enyl)-4-(4-isobutylpiperazine-1-yl)-phenyl]morpholine hydrochloride MS m/e (ESI) 412 (MH$^+$).

cis-4-[4-(4-Butylpiperazin-1-yl)-3-(4,4-dimethylcyclohexyl)phenyl]-2,6-dimethylmorpholine hydrochloride MS m/e (ESI) 442 (MH$^+$).

4-[4-(4-Butylpiperazin-1-yl)-3-(4,4-dimethylcyclohex-1-enyl)phenyl]morpholine hydrochloride MS m/e (ESI) 412 (MH$^+$).

4-[3-(4,4-Dimethylcyclohex-1-enyl)-4-(4-propylpiperazin-1-yl)phenyl]morpholine hydrochloride MS m/e (ESI) 398 (MH$^+$).

1-Butyl-4-[2-(4,4-dimethylcyclohex-1-enyl)phenyl]
piperazine hydrochloride

MS m/e (ESI) 327 (MH$^+$).

4-[3-(4-t-Butylcyclohexyl)-4-(4-butylpiperazine-1-yl)phenyl]morpholine hydrochloride MS m/e (ESI) 442 (MH$^+$).

4-[2-(4,4-Dimethylcyclohexyl)phenyl]piperazine-1-carboxylic acid ethyl ester

MS m/e (ESI) 345 (MH$^+$).

1-[2-(4-t-Butylcyclohex-1-enyl)phenyl]-4-(2-methoxyethyl)piperazine hydrochloride MS m/e (ESI) 357 (MH$^+$).

4-[4-(4-Butylpiperazin-1-yl)-3-(4,4-dimethylcyclohexyl)phenyl]morpholine hydrochloride MS m/e (ESI) 414 (MH$^+$).

1-[2-(4-t-Butylcyclohexyl)phenyl]-4-(tetrahydropyran-4-ylmethyl)piperazine hydrochloride MS m/e (ESI) 399 (MH$^+$).

1-[2-(4-t-Butylcyclohexyl)phenyl]-4-furan-2-ylmethylpiperazine hydrochloride

MS m/e (ESI) 381 (MH$^+$).

1-[2-(4-t-Butylcyclohexyl)phenyl]-4-furan-3-ylmethylpiperazine hydrochloride

MS m/e (ESI) 381 (MH$^+$).

1-{4-[2-(4,4-Dimethylcyclohex-1-enyl)phenyl]piperazin-1-yl}butan-2-one hydrochloride MS m/e (ESI) 341 (MH$^+$).

4-[3-(4-t-Butylcyclohex-1-enyl)-4-(4-pentylpiperazin-1-yl)phenyl]morpholine hydrochloride MS m/e (ESI) 454 (MH$^+$).

1-Butyl-4-(2-spiro[2.5]oct-5-en-6-ylphenyl)piperazine hydrochloride

MS m/e (ESI) 325 (MH$^+$).

4-[4-(4-Butylpiperazin-1-yl)-3-(4,4-dimethylcyclohexyl)phenyl]morpholine hydrochloride MS m/e (ESI) 442 (MH$^+$).

4-[4-(4-Butylpiperazin-1-yl)-3-spiro[5.5]undec-3-ylphenyl]morpholine hydrochloride MS m/e (ESI) 454 (MH$^+$).

1-[2-(4,4-Diethylcyclohexyl)phenyl]-4-propylpiperazine hydrochloride

MS m/e (ESI) 343 (MH$^+$).

1-Cyclopropylmethyl-4-[2-(4,4-dimethylcyclohexyl)phenyl]piperazine hydrochloride MS m/e (ESI) 355 (MH$^+$).

1-[2-(4,4-Diethylcyclohex-1-enyl)-4-(4-methoxypiperidin-1-yl)pheny]-4-propylpiperazine hydrochloride MS m/e (ESI) 454 (MH$^+$).

1-[2-(4,4-Diethylcyclohexyl)-4-(4-methoxypiperidin-1-yl)phenyl]-4-pentylpiperazine hydrochloride MS m/e (ESI) 484 (MH$^+$).

1-{4-[2-(4,4-Diethylcyclohexyl)phenyl]piperazin-1-yl}butan-2-one hydrochloride

MS m/e (ESI) 371 (MH$^+$).

1-Butyl-4-[2-(4,4-dimethylcyclohexyl)phenyl]piperazine hydrochloride

MS m/e (ESI) 357 (MH$^+$).

4-[3-(4,4-Diethylcyclohex-1-enyl)-4-(4-propylpiperazin-1-yl)phenyl]morpholine hydrochloride MS m/e (ESI) 426 (MH$^+$).

4-{3-(4,4-Diethylcyclohex-1-enyl)-4-[4-(tetrahydropyran-4-ylmethyl)piperazin-1-yl]phenyl}morpholine hydrochloride MS m/e (ESI) 482 (MH$^+$).

1-{2-(4-t-Butylcyclohexyl)-4-(4-methoxypiperidin-1-yl)phenyl}-4-propylpiperazine hydrochloride MS m/e (ESI) 456 (MH$^+$).

1-{2-(4-t-Butylcyclohexyl)-4-(4-methoxypiperidin-1-yl)phenyl}-4-cyclopropylmethylpiperazine hydrochloride MS m/e (ESI) 468 (MH$^+$).

1-Propyl-4-(2-spiro[5.5]undec-2-en-3-ylphenyl)piperazine hydrochloride

MS m/e (ESI) 353 (MH$^+$).

1-Cyclopropylmethyl-4-(2-spiro[5.5]undec-2-en-3-ylphenyl)piperazine hydrochloride MS m/e (ESI) 365 (MH$^+$).

4-{4-(4-Butylpiperazin-1-yl)-3-spiro[5.5]undec-2-en-3-ylphenyl}morpholine hydrochloride MS m/e (ESI) 452 (MH$^+$).

4-{4-(4-Propylpiperazin-1-yl)-3-spiro[5.5]undec-2-en-3-ylphenyl}morpholine hydrochloride MS m/e (ESI) 438 (MH$^+$).

4-{4-(4-Cyclopropylmethylpiperazin-1-yl)-3-spiro[5.5]undec-2-en-3-ylphenyl}morpholine hydrochloride MS m/e (ESI) 450 (MH$^+$).

4-[4-{4-(3-Methylbutyl)piperazin-1-yl}-3-spiro[5.5]undec-2-en-3-ylphenyl]morpholine hydrochloride MS m/e (ESI) 466 (MH$^+$).

4-[3-Spiro[5.5]undec-2-en-3-yl-4-{4-(tetrahydropyran-4-ylmethyl)piperazin-1-yl}phenyl]morpholine hydrochloride MS m/e (ESI) 494 (MH$^+$).

4-{4-(4-Pentylpiperazin-1-yl)-3-spiro[0.5]undec-2-en-3-ylphenyl}morpholine hydrochloride MS m/e (ESI) 466 (MH$^+$).

1-(2-Methoxyethyl)-4-(2-spiro[0.5]undec-2-en-3-ylphenyl)piperazine hydrochloride MS m/e (ESI) 369 (MH$^+$).

1-{4-(2-Spiro[0.5]undec-2-en-3-ylphenyl)piperazin-1-yl}butan-2-one hydrochloride MS m/e (ESI) 381 (MH$^+$).

1-Propyl-4-(2-spiro[5.5]undec-3-ylphenyl)piperazine hydrochloride

MS m/e (ESI) 355 (MH$^+$).

1-Cyclopropylmethyl-4-(2-spiro[5.5]undec-3-ylphenyl)piperazine hydrochloride

MS m/e (ESI) 367 (MH$^+$).

1-(3-Methylbutyl)-4-(2-spiro[5.5]undec-3-ylphenyl)piperazine hydrochloride

MS m/e (ESI) 383 (MH$^+$).

1-Butyl-4-{4-(4-methoxypiperidin-1-yl)-2-spiro[5.5]undec-2-en-3-ylphenyl}piperazine hydrochloride MS m/e (ESI) 480 (MH$^+$).

4-[4-{4-(3-Methylbutyl)piperazin-1-yl}-3-spiro[5.5]undec-3-ylphenyl]morpholine hydrochloride MS m/e (ESI) 468 (MH$^+$).

4-[3-Spiro[5.5]undec-3-yl-4-{4-(tetrahydropyran-4-ylmethyl)piperazin-1-yl}phenyl]morpholine hydrochloride MS m/e (ESI) 496 (MH$^+$).

1-{4-(4-Morpholin-4-yl-2-spiro[5.5]undec-3-ylphenyl)piperazin-1-yl}butan-2-one hydrochloride MS m/e (ESI) 468 (MH$^+$).

1-(2-Methoxyethyl)-4-{4-(4-methoxypiperidin-1-yl)-2-spiro[5.5]undec-3-ylphenyl}piperazine hydrochloride MS m/e (ESI) 484 (MH$^+$).

1-Butyl-4-{4-(4-methoxypiperidin-1-yl)-2-spiro[2.5]oct-5-en-6-ylphenyl}piperazine hydrochloride MS m/e (ESI) 438 (MH$^+$).

1-{4-(4-Methoxypiperidin-1-yl)-2-spiro[2.5]oct-5-en-6-ylphenyl}-4-pentylpiperazine hydrochloride MS m/e (ESI) 452 (MH$^+$).

4-{4-(4-Isobutylpiperazine-1-yl)-3-spiro[2.5]oct-5-en-6-ylphenyl}morpholine hydrochloride MS m/e (ESI) 410 (MH$^+$).

4-{4-(4-Isobutylpiperazine-1-yl)-3-spiro[2.5]oct-6-ylphenyl}morpholine hydrochloride MS m/e (ESI) 412 (MH$^+$).

4-{4-(4-Pentylpiperazin-1-yl)-3-spiro[2.5]oct-6-ylphenyl}morpholine hydrochloride MS m/e (ESI) 426 (MH$^+$).

(S)-1-Butyl-4-{2-(4,4-dimethylcyclohexyl)-4-(3-methoxypiperidin-1-yl)phenyl}piperazine hydrochloride MS m/e (ESI) 442 (MH$^+$).

(R)-1-Cyclopropylmethyl-4-{2-(4,4-dimethylcyclo-
hexyl)-4-(3-methoxypiperidin-1-yl)
phenyl}piperazine hydrochloride MS m/e (ESI) 468 (MH⁺).

1-Isopropyl-4-{2-(3,3,5,5-tetramethylcyclohexyl)
phenyl}piperazine hydrochloride MS m/e (ESI) 343 (MH⁺).

1-Cyclopentyl-4-{2-(3,3,5,5-tetramethylcyclohexyl)
phenyl}piperazine hydrochloride MS m/e (ESI) 369 (MH⁺).

1-(2-Cycloheptylphenyl)-4-propylpiperazine
hydrochloride

MS m/e (ESI) 301 (MH⁺).

1-(2-Cycloheptylphenyl)-4-cyclopropylmethylpip-
erazine hydrochloride

MS m/e (ESI) 313 (MH⁺).

1-(2-Cycloheptylphenyl)-4-isobutylpiperazine
hydrochloride

MS m/e (ESI) 315 (MH⁺).

1-(2-Cycloheptylphenyl)-4-(tetrahydropyran-4-ylm-
ethyl)piperazine hydrochloride MS m/e (ESI) 357 (MH⁺).

1-(2-Cyclohept-1-enylphenyl)-4-propylpiperazine
hydrochloride

MS m/e (ESI) 299 (MH⁺).

1-(2-Cyclohept-1-enylphenyl)-4-cyclopropylmeth-
ylpiperazine hydrochloride

MS m/e (ESI) 311 (MH⁺).

1-(2-Cyclohept-1-enylphenyl)-4-isobutylpiperazinee
hydrochloride

MS m/e (ESI) 313 (MH⁺).

1-(2-Cyclohept-1-enylphenyl)-4-(tetrahydropyran-4-
ylmethyl)piperazine hydrochloride MS m/e (ESI) 355 (MH⁺).

1-(2-Cyclooct-1-enylphenyl)-4-cyclopropylmeth-
ylpiperazine hydrochloride

MS m/e (ESI) 325 (MH⁺).

1-(2-Cyclooctylphenyl)-4-cyclopropylmethylpipera-
zine hydrochloride

MS m/e (ESI) 327 (MH⁺).

1-Cyclopropylmethyl-4-[2-(3,3,4,4-tetramethylcy-
clopent-1-enyl)phenyl]piperazine hydrochloride MS m/e (ESI) 339 (MH⁺).

1-Butyl-4-{2-(3,3,4,4-tetramethylcyclopentyl)
phenyl}piperazine hydrochloride

MS m/e (ESI) 343 (MH⁺).

1-Cyclopropylmethyl-4-{2-(3,3,4,4-tetramethylcy-
clopentyl)phenyl}piperazine hydrochloride MS m/e (ESI) 341 (MH⁺).

1-Propyl-4-{2-(3,3,4,4-tetramethylcyclopent-1-enyl)
phenyl}piperazine hydrochloride MS m/e (ESI) 327 (MH⁺).

1-{2-(4-t-Butylcyclohexyl)phenyl}-4-(4,4,4-trifluo-
robutyl)piperazine hydrochloride MS m/e (ESI) 411 (MH⁺).

4-{3-(4-t-Butylcyclohexyl)-4-(4-butylpiperazine-1-
yl)phenyl}thiomorpholine hydrochloride MS m/e (ESI) 458 (MH⁺).

1-Butyl-4-{2-(4-t-butylcyclohexyl)-4-(4-ethoxypip-
eridin-1-yl)phenyl}piperazine hydrochloride MS m/e (ESI) 484 (MH⁺).

1-Furan-2-ylmethyl-4-(2-spiro[5.5]undec-2-en-3-
ylphenyl)piperazine hydrochloride MS m/e (ESI) 391 (MH⁺).

1-(2-Spiro[5.5]undec-2-en-3-ylphenyl)-4-(tetrahy-
dropyran-4-ylmethyl)piperazine hydrochloride MS m/e (ESI) 409 (MH⁺).

1-{4-(4-Methoxypiperidin-1-yl)-2-spiro[5.5]undec-
2-en-3-ylphenyl}-4-propylpiperazine hydrochloride MS m/e (ESI) 466 (MH⁺).

1-Cyclopropylmethyl-4-{4-(4-methoxypiperidin-1-
yl)-2-spiro[5.5]undec-2-en-3-ylphenyl}piperazine
hydrochloride MS m/e (ESI) 478 (MH⁺).

1-{4-(4-Methoxypiperidin-1-yl)-2-spiro[5.5]undec-
2-en-3-ylphenyl}-4-(3-methylbutyl)piperazine
hydrochloride MS m/e (ESI) 494 (MH⁺).

1-{4-(4-Methoxypiperidin-1-yl)-2-spiro[5.5]undec-
2-en-3-ylphenyl}-4-(tetrahydropyran-4-ylmethyl)
piperazine hydrochloride MS m/e (ESI) 522 (MH⁺).

1-Cyclopentyl-4-{4-(4-methoxypiperidin-1-yl)-2-
spiro[5.5]undec-2-en-3-ylphenyl}piperazine hydro-
chloride MS m/e (ESI) 492 (MH⁺).

4-{4-(4-Furan-2-ylmethylpiperazin-1-yl)-3-spiro[5.5]undec-2-en-3-ylphenyl}morpholine hydrochloride MS m/e (ESI) 476 (MH$^+$).

1-(2-Spiro[5.5]undec-3-ylphenyl)-4-(tetrahydropyran-4-ylmethyl)piperazine hydrochloride MS m/e (ESI) 411 (MH$^+$).

1-{4-(4-Methoxypiperidin-1-yl)-2-spiro[5.5]undec-3-ylphenyl}-4-(3-methylbutyl)piperazine hydrochloride MS m/e (ESI) 496 (MH$^+$).

1-{4-(4-Methoxypiperidin-1-yl)-2-spiro[5.5]undec-3-ylphenyl}-4-pentylpiperazine hydrochloride MS m/e (ESI) 496 (MH$^+$).

4-{4-(4-Isobutylpiperazine-1-yl)-3-spiro[5.5]undec-3-ylphenyl}morpholine hydrochloride MS m/e (ESI) 454 (MH$^+$).

4-{4-(4-Furan-3-ylmethylpiperazin-1-yl)-3-spiro[5.5]undec-3-ylphenyl}morpholine hydrochloride MS m/e (ESI) 478 (MH$^+$).

1-{4-(4-Methoxypiperidin-1-yl)-2-spiro[2.5]oct-5-en-6-ylphenyl}-4-propylpiperazine hydrochloride MS m/e (ESI) 424 (MH$^+$).

1-Cyclopropylmethyl-4-{4-(4-methoxypiperidin-1-yl)-2-spiro[2.5]oct-5-en-6-ylphenyl}piperazine hydrochloride MS m/e (ESI) 436 (MH$^+$).

1-Isobutyl-4-{4-(4-methoxypiperidin-1-yl)-2-spiro[2.5]oct-5-en-6-ylphenyl}piperazine hydrochloride MS m/e (ESI) 438 (MH$^+$).

4-{4-(4-Butylpiperazin-1-yl)-3-spiro[2.5]oct-5-en-6-ylphenyl}morpholine hydrochloride MS m/e (ESI) 410 (MH$^+$).

1-Butyl-4-{2-(4,4-dimethylcyclohexyl)-4-(4-isopropoxypiperidin-1-yl)phenyl}piperazine hydrochloride MS m/e (ESI) 470 (MH$^+$).

4-[3-Spiro[2.5]oct-6-yl-4-{4-(tetrahydropyran-4-ylmethyl)piperazin-1-yl}phenyl]morpholine hydrochloride MS m/e (ESI) 454 (MH$^+$).

(S)-1-{2-(4,4-Diethylcyclohexyl)-4-(3-methoxypiperidin-1-yl)phenyl}-4-pentylpiperazine hydrochloride MS m/e (ESI) 484 (MH$^+$).

1-Cyclohexyl-4-{2-(3,3,5,5-tetramethylcyclohexyl)phenyl}piperazine hydrochloride MS m/e (ESI) 383 (MH$^+$).

1-Isobutyl-4-{2-(3,3,4,4-tetramethylcyclopentyl)phenyl}piperazine hydrochloride

MS m/e (ESI) 343 (MH$^+$).

1-Butyl-4-[2-(4-t-butylcyclohexyl)-5-pyridin-3-ylphenyl]piperazine

MS m/e (ESI) 434 (MH$^+$).

4-[4-(4-t-Butylcyclohexyl)-3-(4-pentylpiperazin-1-yl)phenyl]morpholine hydrochloride MS m/e (ESI) 456 (MH$^+$).

4-{4-(4-t-Butylcyclohexyl)-3-[4-(3-methylbutyl)piperazin-1-yl]phenyl}morpholine hydrochloride MS m/e (ESI) 456 (MH$^+$).

[4-(4-t-Butylcyclohex-1-enyl)-3-(4-butylpiperazine-1-yl)phenyl]ethylamine hydrochloride MS m/e (ESI) 398 (MH$^+$).

4-[3-(4,4-Dimethylcyclohex-1-enyl)-4-(4-pentylpiperazin-1-yl)phenyl]morpholine hydrochloride MS m/e (ESI) 426 (MH$^+$).

4-{3-(4,4-Dimethylcyclohex-1-enyl)-4-[4-(tetrahydropyran-4-ylmethyl)piperazin-1-yl]phenyl}morpholine hydrochloride MS m/e (ESI) 454 (MH$^+$).

1-Butyl-4-[2-(4,4-dimethylcyclohex-1-enyl)-4-(4-methoxypiperidin-1-yl)phenyl]piperazine hydrochloride MS m/e (ESI) 440 (MH$^+$).

1-[2-(4,4-Dimethylcyclohex-1-enyl)-4-(4-methoxypiperidin-1-yl)phenyl]-4-propylpiperazine hydrochloride MS m/e (ESI) 426 (MH$^+$).

1-[2-(4,4-Dimethylcyclohex-1-enyl)-4-(4-methoxypiperidin-1-yl)phenyl]-4-pentylpiperazine hydrochloride MS m/e (ESI) 454 (MH$^+$).

1-[2-(4,4-Dimethylcyclohex-1-enyl)-4-(4-methoxypiperidin-1-yl)phenyl]-4-isobutylpiperazinee hydrochloride MS m/e (ESI) 440 (MH$^+$).

1-[2-(4,4-Dimethylcyclohex-1-enyl)-4-(4-methoxypiperidin-1-yl)phenyl]-4-(tetrahydropyran-4-ylmethyl)piperazine hydrochloride MS m/e (ESI) 482 (MH$^+$).

1-{4-[2-(4,4-Dimethylcyclohex-1-enyl)-4-(4-methoxypiperidin-1-yl)phenyl]piperazin-1-yl}butan-2-one hydrochloride MS m/e (ESI) 454 (MH$^+$).

4-[3-(4,4-Dimethylcyclohex-1-enyl)-4-(4-furan-3-ylmethylpiperazin-1-yl)phenyl]morpholine hydrochloride MS m/e (ESI) 436 (MH$^+$).

1-[2-(4,4-Dimethylcyclohex-1-enyl)-4-(4-methoxypiperidin-1-yl)phenyl]-4-furan-3-ylmethylpiperazine hydrochloride MS m/e (ESI) 464 (MH$^+$).

1-[2-(4,4-Dimethylcyclohex-1-enyl)phenyl]-4pentylpiperazine hydrochloride

MS m/e (ESI) 341 (MH$^+$).

1-Cyclopropylmethyl-4-[2-(4,4-dimethylcyclohex-1-enyl)phenyl]piperazine hydrochloride MS m/e (ESI) 325 (MH$^+$).

1-[2-(4,4-Dimethylcyclohex-1-enyl)phenyl]-4-(tetrahydropyran-4-ylmethyl)piperazine hydrochloride MS m/e (ESI) 369 (MH$^+$).

1-[2-(4,4-Dimethylcyclohex-1-enyl)phenyl]-4-furan-2-ylmethylpiperazine hydrochloride MS m/e (ESI) 351 (MH$^+$).

1-[2-(4,4-Dimethylcyclohex-1-enyl)phenyl]-4-furan-3-ylmethylpiperazine hydrochloride MS m/e (ESI) 351 (MH$^+$).

1-[2-(4,4-Dimethylcyclohex-1-enyl)phenyl]-4-(2-methoxyethyl)piperazine hydrochloride MS m/e (ESI) 329 (MH$^+$).

1-[2-(4,4-Dimethylcyclohexyl)phenyl]-4-pentylpiperazine hydrochloride

MS m/e (ESI) 343 (MH$^+$).

1-Cyclopropylmethyl-4-[2-(4,4-dimethylcyclohexyl)phenyl]piperazine hydrochloride MS m/e (ESI) 327 (MH$^+$).

4-[3-(4,4-Dimethylcyclohexyl)-4-(4-pentylpiperazin-1-yl)phenyl]morpholine hydrochloride MS m/e (ESI) 428 (MH$^+$).

4-[3-(4,4-Dimethylcyclohexyl)-4-(4-furan-2-ylmethylpiperazin-1-yl)phenyl]morpholine hydrochloride MS m/e (ESI) 438 (MH$^+$).

4-[3-(4,4-Dimethylcyclohexyl)-4-(4-furan-3-ylmethylpiperazin-1-yl)phenyl]morpholine hydrochloride MS m/e (ESI) 438 (MH$^+$).

1-[2-(4,4-Dimethylcyclohexyl)-4-(4-methoxypiperidin-1-yl)phenyl]-4-pentylpiperazine hydrochloride MS m/e (ESI) 456 (MH$^+$).

1-[2-(4,4-Dimethylcyclohexyl)-4-(4-methoxypiperidin-1-yl)phenyl]-4-isobutylpiperazine hydrochloride MS m/e (ESI) 442 (MH$^+$).

1-[2-(4,4-Dimethylcyclohexyl)-4-(4-methoxypiperidin-1-yl)phenyl]-4-(tetrahydropyran-4-ylmethyl)piperazine hydrochloride MS m/e (ESI) 484 (MH$^+$).

1-[2-(4,4-Dimethylcyclohexyl)-4-(4-methoxypiperidin-1-yl)phenyl]-4-furan-2-ylmethylpiperazine hydrochloride MS m/e (ESI) 466 (MH$^+$).

1-[2-(4,4-Dimethylcyclohexyl)-4-(4-methoxypiperidin-1-yl)phenyl]-4-furan-3-ylmethylpiperazine hydrochloride MS m/e (ESI) 466 (MH$^+$).

1-{4-[2-(4,4-Dimethylcyclohexyl)-4-(4-methoxypiperidin-1-yl)phenyl]piperazin-1-yl}butan-2-one hydrochloride MS m/e (ESI) 456 (MH$^+$).

1-[2-(4,4-Dimethylcyclohexyl)phenyl]-4-isobutylpiperazinee hydrochloride

MS m/e (ESI) 329 (MH$^+$).

1-Cyclobutylmethyl-4-[2-(3,3,5,5-tetramethylcyclohexyl)phenyl]piperazine hydrochloride MS m/e (ESI) 369 (MH$^+$).

{4-[2-(3,3,5,5-Tetramethylcyclohex-1-enyl)phenyl]piperazin-1-yl}acetonitrile hydrochloride MS m/e (ESI) 338 (MH$^+$).

1-(2-Ethoxyethyl)-4-[2-(3,3,5,5-tetramethylcyclohex-1-enyl)phenyl]piperazine hydrochloride MS m/e (ESI) 371 (MH$^+$).

1-Cyclobutylmethyl-4-[2-(3,3,5,5-tetramethylcyclohex-1-enyl)phenyl]piperazine hydrochloride MS m/e (ESI) 367 (MH$^+$).

cis-4-[3-(4,4-Dimethylcyclohexyl)-4-(4-propylpiperazin-1-yl)phenyl]-2,6-dimethylmorpholine hydrochloride MS m/e (ESI) 428 (MH$^+$).

cis-4-[3-(4,4-Dimethylcyclohexyl)-4-(4-pentylpiperazin-1-yl)phenyl]-2,6-dimethylmorpholine hydrochloride MS m/e (ESI) 456 (MH$^+$).

cis-4-{3-(4,4-Dimethylcyclohexyl)-4-[4-(tetrahydropyran-4-ylmethyl)piperazin-1-yl)phenyl]-2,6-dimethylmorpholine hydrochloride MS m/e (ESI) 484 (MH$^+$).

cis-4-[3-(4,4-Dimethylcyclohexyl)-4-(4-furan-3-ylmethylpiperazin-1-yl)phenyl]-2,6-dimethylmorpholine hydrochloride MS m/e (ESI) 466 (MH$^+$).

cis-1-{4-[2-(4,4-Dimethylcyclohexyl)-4-(2,6-dimethylmorpholin-4-yl)phenyl]piperazin-1-yl}butan-2-one hydrochloride MS m/e (ESI) 456 (MH$^+$).

cis-4-{3-(4,4-Dimethylcyclohexyl)-4-[4-(2-methoxyethyl)piperazin-1-yl]phenyl}-2,6-dimethylmorpholine hydrochloride MS m/e (ESI) 444 (MH$^+$).

cis-4-{3-(4,4-Dimethylcyclohexyl)-4-[4-(2-ethoxyethyl)piperazin-1-yl]phenyl}-2,6-dimethylmorpholine hydrochloride MS m/e (ESI) 458 (MH$^+$).

cis-4-[4-(4-Cyclobutylmethylpiperazin-1-yl)-3-(4,4-dimethylcyclohexyl)phenyl]-2,6-dimethylmorpholine hydrochloride MS m/e (ESI) 454 (MH$^+$).

1-Butyl-4-[2-(4,4-dimethylcyclohexyl)-4-pyrrolidin-1-ylphenyl]piperazine hydrochloride MS m/e (ESI) 398 (MH$^+$).

1-[3-(4,4-Dimethylcyclohexyl)-4-(4-pentylpiperazin-1-yl)phenyl]piperidine-4-carbonitrile hydrochloride MS m/e (ESI) 451 (MH$^+$).

1-[3-(4,4-Dimethylcyclohexyl)-4-(4-isobutylpiperazine-1-yl)phenyl]piperidine-4-carbonitrile hydrochloride MS m/e (ESI) 437 (MH$^+$).

4-[4-(Cyclobutylmethylpiperazin-1-yl)-3-(4,4-dimethylcyclohexyl)phenyl]morpholine hydrochloride MS m/e (ESI) 426 (MH$^+$).

1-Cyclobutylmethyl-4-[2-(4,4-dimethylcyclohexyl)-4-(4-methoxypiperidin-1-yl)phenyl]piperazine hydrochloride MS m/e (ESI) 454 (MH$^+$).

1-[2-(4,4-Dimethylcyclohexyl-4-piperidin-1-ylphenyl]-4-propylpiperazine hydrochloride MS m/e (ESI) 398 (MH$^+$).

1-[2-(4,4-Dimethylcyclohexyl)-4-piperidin-1-ylphenyl]-4-(tetrahydropyran-4-ylmethyl)piperazine hydrochloride MS m/e (ESI) 454 (MH$^+$).

1-{4-[2-(4,4-Dimethylcyclohexyl)-4-piperidin-1-ylphenyl]piperazin-1-yl}butan-2-one hydrochloride MS m/e (ESI) 426 (MH$^+$).

1-[2-(4,4-Dimethylcyclohexyl)-4-piperidin-1-ylphenyl]-4-(2-methoxyethyl)piperazine hydrochloride MS m/e (ESI) 414 (MH$^+$).

1-[2-(4,4-Dimethylcyclohexyl)-4-piperidin-1-ylphenyl]-4-(2-ethoxyethyl)piperazine hydrochloride MS m/e (ESI) 428 (MH$^+$).

1-[2-(4,4-Dimethylcyclohexyl)-4-pyrrolidin-1-ylphenyl]-4-propylpiperazine hydrochloride MS m/e (ESI) 384 (MH$^+$).

1-Cyclopropylmethyl-4-[2-(4,4-dimethylcyclohexyl)-4-pyrrolidin-1-ylphenyl]piperazine hydrochloride MS m/e (ESI) 396 (MH$^+$).

1-{4-[2-(4,4-Dimethylcyclohexyl)-4-pyrrolidin-1-ylphenyl]piperazin-1-yl}butan-2-one hydrochloride MS m/e (ESI) 412 (MH$^+$).

1-[2-(4,4-Dimethylcyclohexyl)-4-pyrrolidin-1-ylphenyl]-4-(2-methoxyethyl)piperazine hydrochloride MS m/e (ESI) 400 (MH$^+$).

1-[2-(4,4-Dimethylcyclohexyl)-4-pyrrolidin-1-ylphenyl]-4-(2-ethoxyethyl)piperazine hydrochloride MS m/e (ESI) 414 (MH$^+$).

1-[4-(4-Cyclobutylmethylpiperazin-1-yl)-3-(4,4-dimethylcyclohexyl)phenyl]piperidine-4-carbonitrile hydrochloride MS m/e (ESI) 449 (MH$^4$).

N-(2-{4-[2-(4-t-Butylcyclohexyl)phenyl]piperazin-1-yl}ethyl)acetamide hydrochloride MS m/e (ESI) 386 (MH$^+$).

1-Butyl-4-[2-(4-t-butylcyclohexyl)-5-(3,5-dimethyl-isoxazol-4-yl)phenyl]piperazine MS m/e (ESI) 452 (MH$^+$).

1-Butyl-4-[2-(4-t-butylcyclohexyl)-5-methylphenyl]piperazine hydrochloride

MS m/e (ESI) 371 (MH$^+$).

4-[4-(4-t-Butylcyclohexyl)-3-(4-propylpiperazin-1-yl)phenyl]morpholine hydrochloride MS m/e (ESI) 428 (MH$^+$).

4-[4-(4-t-Butylcyclohexyl)-3-(4-cyclopropylmethylpiperazin-1-yl)phenyl]morpholine hydrochloride MS m/e (ESI) 440 (MH$^+$).

4-[4-(4-t-Butylcyclohexyl)-3-[4-(2-methoxyethyl)piperazin-1-yl]phenyl]morpholine hydrochloride MS m/e (ESI) 444 (MH$^+$).

[4-(4-t-Butylcyclohexyl)-3-(4-butylpiperazine-1-yl)phenyl]ethylamine hydrochloride MS m/e (ESI) 400 (MH$^+$).

1-Butyl-4-[2-(4-t-butylcyclohexyl)-5-piperidin-1-ylphenyl]piperazine hydrochloride MS m/e (ESI) 440 (MH$^+$).

4-[4-(4-Cyclopropylmethylpiperazin-1-yl)-3-(4,4-dimethylcyclohex-1-enyl)phenyl]morpholine hydrochloride MS m/e (ESI) 410 (MH$^+$).

1-Cyclopropylmethyl-4-[2-(4,4-dimethylcyclohex-1-enyl)-4-(4-methoxypiperidin-1-yl)phenyl]piperazine hydrochloride MS m/e (ESI) 438 (MH$^+$).

1-[2-(4,4-Dimethylcyclohex-1-enyl)-4-(4-methoxypiperidin-1-yl)phenyl]-4-(2-methoxyethyl)piperazine hydrochloride MS m/e (ESI) 442 (MH$^+$).

4-[3-(4,4-Dimethylcyclohex-1-enyl)-4-(4-furan-2-ylmethylpiperazin-1-yl)phenyl]morpholine hydrochloride MS m/e (ESI) 436 (MH$^+$).

1-[2-(4,4-Dimethylcyclohex-1-enyl)-4-(4-methoxypiperidin-1-yl)phenyl]-4-furan-2-ylmethylpiperazine hydrochloride MS m/e (ESI) 464 (MH$^+$).

1-[2-(4,4-Dimethylcyclohex-1-enyl)phenyl]-4-(tetrahydropyran-4-yl)piperazine hydrochloride MS m/e (ESI) 355 (MH$^+$).

1-[2-(4,4-Dimethylcyclohexyl)phenyl]-4-(tetrahydropyran-4-yl)piperazine hydrochloride MS m/e (ESI) 357 (MH$^+$).

4-{3-(4,4-Dimethylcyclohexyl)-4-[4-(tetrahydropyran-4-ylmethyl)piperazin-1-yl]phenyl}morpholine hydrochloride MS m/e (ESI) 456 (MH$^+$).

1-{4-[2-(4,4-Dimethylcyclohexyl)-4-morpholin-4-ylphenyl]piperazin-1-yl}butan-2-one hydrochloride MS m/e (ESI) 428 (MH$^+$).

1-[2-(4,4-Dimethylcyclohexyl)-4-(4-methoxypiperidin-1-yl)phenyl]-4-propylpiperazine hydrochloride MS m/e (ESI) 428 (MH$^+$).

1-Cyclopropylmethyl-4-[2-(4,4-dimethylcyclohexyl)-4-(4-methoxypiperidin 1-yl)phenyl]piperazine hydrochloride MS m/e (ESI) 440 (MH$^+$).

cis-4-[3-(4,4-Dimethylcyclohexyl)-4-(4-isobutylpiperazine-1-yl)phenyl]-2,6-dimethylmorpholine hydrochloride MS m/e (ESI) 442 (MH$^+$).

cis-4-[4-(4-Cyclopropylmethylpiperazin-1-yl)-3-(4,4-dimethylcyclohexyl)phenyl]-2,6-dimethylmorpholine hydrochloride MS m/e (ESI) 440 (MH$^+$).

cis-4-[3-(4,4-Dimethylcyclohexyl)-4-(4-furan-2-ylmethylpiperazin-1-yl)phenyl]-2,6-dimethylmorpholine hydrochloride MS m/e (ESI) 466 (MH$^+$).

cis-{4-[2-(4,4-Dimethylcyclohexyl)-4-(2,6-dimethylmorpholin-4-yl)phenyl]piperazin-1-yl}acetonitrile hydrochloride MS m/e (ESI) 425 (MH$^+$).

1-[3-(4,4-Dimethylcyclohexyl)-4-(4-propylpiperazin-1-yl)phenyl]piperidine-4-carbonitrile hydrochloride MS m/e (ESI) 423 (MH$^+$).

1-[4-(4-Cyclopropylmethylpiperazin-1-yl)-3-(4,4-dimethylcyclohexyl)phenyl]piperidine-4-carbonitrile hydrochloride MS m/e (ESI) 435 (MH$^+$).

1-[3-(4,4-Dimethylcyclohexyl)-4-(4-furan-3-ylmethylpiperazin-1-yl)phenyl]piperidine-4-carbonitrile hydrochloride MS m/e (ESI) 461 (MH$^+$).

4-{3-(4,4-Dimethylcyclohexyl)-4-[4-(2-ethoxyethyl)piperazin-1-yl]phenyl}morpholine hydrochloride MS m/e (ESI) 430 (MH$^+$).

{4-[2-(4,4-Dimethylcyclohexyl)-4-(4-methoxypiperidin-1-yl)phenyl]piperazin-1-yl}acetonitrile hydrochloride MS m/e (ESI) 425 (MH$^+$).

1-[2-(4,4-Dimethylcyclohexyl)-4-piperidin-1-ylphenyl]-4-pentylpiperazine hydrochloride MS m/e (ESI) 426 (MH$^+$).

1-[2-(4,4-Dimethylcyclohexyl)-4-piperidin-1-ylphenyl]-4-isobutylpiperazinee hydrochloride MS m/e (ESI) 412 (MH$^+$).

1-[2-(4,4-Dimethylcyclohexyl)-4-piperidin-1-ylphenyl]-4-furan-2-ylmethylpiperazine hydrochloride MS m/e (ESI) 436 (MH$^+$).

1-[2-(4,4-Dimethylcyclohexyl)-4-piperidin-1-ylphenyl]-4-furan-3-ylmethylpiperazine hydrochloride MS m/e (ESI) 436 (MH$^+$).

{4-[2-(4,4-Dimethylcyclohexyl)-4-piperidin-1-ylphenyl]piperazin-1-yl}acetonitrile hydrochloride MS m/e (ESI) 395 (MH$^+$).

1-Cyclobutylmethyl-4-[2-(4,4-dimethylcyclohexyl)-4-piperidin-1-ylphenyl]piperazine hydrochloride MS m/e (ESI) 424 (MH$^+$).

1-[2-(4,4-Dimethylcyclohexyl)-4-pyrrolidin-1-ylphenyl]-4-pentylpiperazine hydrochloride MS m/e (ESI) 412 (MH$^+$).

1-[2-(4,4-Dimethylcyclohexyl)-4-pyrrolidin-1-ylphenyl]-4-isobutylpiperazinee hydrochloride MS m/e (ESI) 398 (MH$^+$).

1-[2-(4,4-Dimethylcyclohexyl)-4-pyrrolidin-1-ylphenyl]-4-furan-2-ylmethylpiperazine hydrochloride MS m/e (ESI) 422 (MH$^+$).

{4-[2-(4,4-Dimethylcyclohexyl)-4-pyrrolidin-1-ylphenyl]piperazin-1-yl}acetonitrile hydrochloride MS m/e (ESI) 381 (MH$^+$).

1-Cyclobutylmethyl-4-[2-(4,4-dimethylcyclohexyl)-4-pyrrolidin-1-ylphenyl]piperazine hydrochloride MS m/e (ESI) 410 (MH$^+$).

1-Butyl-4-[4-methyl-2-(3,3,5,5-tetramethylcyclohexyl)phenyl]piperazine hydrochloride MS m/e (ESI) 371 (MH$^+$).

1-Cyclopropylmethyl-4-[4-methyl-2-(3,3,5,5-tetramethylcyclohexyl)phenyl]piperazine hydrochloride MS m/e (ESI) 369 (MH$^+$).

1-[2-Methyl-6-(3,3,5,5-tetramethylcyclohexyl)phenyl]-4-propylpiperazine hydrochloride MS m/e (ESI) 357 (MH$^+$).

1-Butyl-4-[2-methyl-6-(3,3,5,5-tetramethylcyclohexyl)phenyl]piperazine hydrochloride MS m/e (ESI) 371 (MH$^+$).

1-Cyclopropylmethyl-4-[2-methyl-6-(3,3,5,5-tetramethylcyclohexyl)phenyl]piperazine hydrochloride MS m/e (ESI) 369 (MH$^+$).

1-[2-Methyl-6-(3,3,5,5-tetramethylcyclohex-1-enyl)phenyl]-4-propylpiperazine hydrochloride MS m/e (ESI) 355 (MH$^+$).

1-Butyl-4-[2-methyl-6-(3,3,5,5-tetramethylcyclohex-1-enyl)phenyl]piperazine hydrochloride MS m/e (ESI) 369 (MH$^+$).

1-Cyclopropylmethyl-4-[2-methyl-6-(3,3,5,5-tetramethylcyclohex-1-enyl)phenyl]piperazine hydrochloride MS m/e (ESI) 367 (MH$^+$).

1-Butyl-4-[5-methyl-2-(3,3,5,5-tetramethylcyclohexyl)phenyl]piperazine hydrochloride MS m/e (ESI) 371 (MH$^+$).

1-[5-Methyl-2-(3,3,5,5-tetramethylcyclohexyl)phenyl]-4-propylpiperazine hydrochloride MS m/e (ESI) 357 (MH$^+$).

1-Cyclopropylmethyl-4-[5-methyl-2-(3,3,5,5-tetramethylcyclohexyl)phenyl]piperazine hydrochloride MS m/e (ESI) 369 (MH$^+$).

1-Butyl-4-[3-methyl-2-(3,3,5,5-tetramethylcyclohex-1-enyl)phenyl]piperazine hydrochloride MS m/e (ESI) 369 (MH$^+$).

1-Cyclopropylmethyl-4-[3-methyl-2-(3,3,5,5-tetramethylcyclohex-1-enyl)phenyl]piperazine hydrochloride MS m/e (ESI) 367 (MH$^+$).

1-Cyclopropylmethyl-4-[5-methoxy-4-piperidin-1-yl-2-(3,3,5,5-tetramethylcyclohexyl)phenyl]piperazine hydrochloride MS m/e (ESI) 468 (MH$^+$).

1-[5-Methyl-2-(3,3,5,5-tetramethylcyclohex-1-enyl)phenyl]-4-propylpiperazine hydrochloride MS m/e (ESI) 355 (MH$^+$).

1-Butyl-4-[5-methyl-2-(3,3,5,5-tetramethylcyclohex-1-enyl)phenyl]piperazine hydrochloride MS m/e (ESI) 369 (MH$^+$).

1-Cyclopropylmethyl-4-[5-methyl-2-(3,3,5,5-tetramethylcyclohex-1-enyl)phenyl]piperazine hydrochloride MS m/e (ESI) 367 (MH$^+$).

1-[4-Methyl-2-(3,3,5,5-tetramethylcyclohex-1-enyl)phenyl]-4-propylpiperazine hydrochloride MS m/e (ESI) 355 (MH$^+$).

1-Butyl-4-[4-methyl-2-(3,3,5,5-tetramethylcyclohex-1-enyl)phenyl]piperazine hydrochloride MS m/e (ESI) 369 (MH$^+$).

1-Cyclopropylmethyl-4-[4-methyl-2-(3,3,5,5-tetramethylcyclohex-1-enyl)phenyl]piperazine hydrochloride MS m/e (ESI) 367 (MH$^+$).

1-[5-Furan-3-yl-2-(3,3,5,5-tetramethylcyclohexyl)phenyl]-4-propylpiperazine hydrochloride MS m/e (ESI) 409 (MH$^+$).

1-Cyclopropylmethyl-4-[5-furan-3-yl-2-(3,3,5,5-tetramethylcyclohexyl)phenyl]piperazine hydrochloride MS m/e (ESI) 421 (MH$^+$).

1-[5-Furan-2-yl-2-(3,3,5,5-tetramethylcyclohexyl)phenyl]-4-propylpiperazine hydrochloride MS m/e (ESI) 409 (MH$^+$).

4-[3-(4-Propylpiperazin-1-yl)-4-(3,3,5,5-tetramethylcyclohexyl)phenyl]morpholine hydrochloride MS m/e (ESI) 428 (MH$^+$).

4-[3-(4-Cyclopropylmethylpiperazin-1-yl)-4-(3,3,5,5-tetramethylcyclohexyl)phenyl]morpholine hydrochloride MS m/e (ESI) 440 (MH$^+$).

Dimethyl[3-(4-propylpiperazin-1-yl)-4-(3,3,5,5-tetramethylcyclohexyl)phenyl]amine hydrochloride MS m/e (ESI) 386 (MH$^+$).

[3-(4-Butylpiperazin-1-yl)-4-(3,3,5,5-tetramethylcyclohexyl)phenyl]dimethylamine hydrochloride MS m/e (ESI) 400 (MH$^+$).

[3-(4-Cyclopropylmethylpiperazin-1-yl)-4-(3,3,5,5-tetramethylcyclohexyl)phenyl]dimethylamine hydrochloride MS m/e (ESI) 398 (MH$^+$).

1-[3-(4-Butylpiperazin-1-yl)-4-(3,3,5,5-tetramethylcyclohexyl)phenyl]ethanone hydrochloride MS m/e (ESI) 399 (MH$^+$).

1-[3-(4-Cyclopropylmethylpiperazin-1-yl)-4-(3,3,5,5-tetramethylcyclohexyl)phenyl]ethanone hydrochloride MS m/e (ESI) 397 (MH$^+$).

1-[2-(4-t-Butylcyclohexyl)phenyl]-4-pentylpiperazine hydrochloride

MS m/e (ESI) 371 (MH$^+$).

1-Butyl-4-[2-(4,4-diethylcyclohex-1-enyl)phenyl]piperazine hydrochloride

MS m/e (ESI) 355 (MH$^+$).

1-Butyl-4-(2-spiro[5.5]undec-2-en-3-ylphenyl)piperazine hydrochloride

MS m/e (ESI) 367 (MH$^+$).

1-Butyl-4-(2-spiro[5.5]undec-3-ylphenyl)piperazine hydrochloride

MS m/e (ESI) 369 (MH$^+$).

1-[2-(4,4-Diethylcyclohex-1-enyl)phenyl]-4-propylpiperazine hydrochloride

MS m/e (ESI) 341 (MH$^+$).

1-[2-(4,4-Diethylcyclohex-1-enyl)phenyl]-4-isobutylpiperazinee hydrochloride

MS m/e (ESI) 355 (MH$^+$).

1-[2-(4,4-Diethylcyclohex-1-enyl)phenyl]-4-(3-methylbutyl)piperazine hydrochloride MS m/e (ESI) 369 (MH$^+$).

1-Cyclopropylmethyl-4-[2-(4,4-diethylcyclohex-1-enyl)phenyl]piperazine hydrochloride MS m/e (ESI) 353 (MH$^+$).

1-[2-(4,4-Diethylcyclohexyl)phenyl]-4-isobutylpiperazinee hydrochloride

MS m/e (ESI) 357 (MH$^+$).

1-{4-[2-(4,4-Diethylcyclohex-1-enyl)phenyl]piperazin-1-yl}butan-1-one

MS m/e (ESI) 369 (MH⁺).

1-{4-[2-(4,4-Diethylcyclohex-1-enyl)phenyl]piperazin-1-yl}butan-2-one hydrochloride MS m/e (ESI) 369 (MH⁺).

1-[2-(4,4-Diethylcyclohex-1-enyl)phenyl]-4-(2-methoxyethyl)piperazine hydrochloride MS m/e (ESI) 357 (MH⁺).

1-[2-(4,4-Diethylcyclohexyl)phenyl]-4-(2-methoxyethyl)piperazine hydrochloride

MS m/e (ESI) 359 (MH⁺).

1-[2-(4,4-Diethylcyclohex-1-enyl)phenyl]-4-(tetrahydropyran-4-ylmethyl)piperazine hydrochloride MS m/e (ESI) 397 (MH⁺).

1-[2-(4,4-Diethylcyclohexyl)phenyl]-4-(tetrahydropyran-4-ylmethyl)piperazine hydrochloride MS m/e (ESI) 399 (MH⁺).

4-[4-(4-Butylpiperazin-1-yl)-3-(4,4-diethylcyclohex-1-enyl)phenyl]morpholine hydrochloride MS m/e (ESI) 440 (MH⁺).

4-[4-(4-Cyclopropylmethylpiperazin-1-yl)-3-(4,4-diethylcyclohex-1-enyl)phenyl]morpholine hydrochloride MS m/e (ESI) 438 (MH⁺).

4-{3-(4,4-Diethylcyclohex-1-enyl)-4-[4-(tetrahydropyran-4-ylmethyl)piperazin-1-yl]phenyl}morpholine hydrochloride MS m/e (ESI) 482 (MH⁺).

4-{3-(4,4-Diethylcyclohex-1-enyl)-4-[4-(2-methoxyethyl)piperazin-1-yl]phenyl}morpholine hydrochloride MS m/e (ESI) 442 (MH⁺).

4-[3-(4,4-Diethylcyclohexyl)-4-(4-propylpiperazin-1-yl)phenyl]morpholine hydrochloride MS m/e (ESI) 428 (MH⁺).

4-[3-(4,4-Diethylcyclohexyl)-4-(4-isobutylpiperazine-1-yl]phenyl]morpholine hydrochloride MS m/e (ESI) 442 (MH⁺).

4-[3-(4,4-Diethylcyclohexyl)-4-(4-pentylpiperazin-1-yl)phenyl]morpholine hydrochloride MS m/e (ESI) 456 (MH⁺).

4-[4-(4-Cyclopropylmethylpiperazin-1-yl)-3-(4,4-dimethylcyclohexyl)phenyl]morpholine hydrochloride MS m/e (ESI) 440 (MH⁺).

4-{3-(4,4-Diethylcyclohexyl)-4-[4-(tetrahydropyran-4-ylmethyl)piperazin-1-yl]phenyl}morpholine hydrochloride MS m/e (ESI) 484 (MH⁺).

1-Butyl-4-[2-(4,4-diethylcyclohex-1-enyl)-4-(4-methoxypiperidin-1-yl)phenyl]piperazine hydrochloride MS m/e (ESI) 468 (MH⁺).

1-[2-(4,4-Diethylcyclohex-1-enyl)-4-(4-methoxypiperidin-1-yl)phenyl]-4-isobutylpiperazinee hydrochloride MS m/e (ESI) 468 (MH⁺).

1-[2-(4,4-Diethylcyclohex-1-enyl)-4-(4-methoxypiperidin-1-yl)phenyl]-4-pentylpiperazine hydrochloride MS m/e (ESI) 482 (MH⁺).

1-Cyclopropylmethyl-4-[2-(4,4-diethylcyclohex-1-enyl)-4-(4-methoxypiperidin-1-yl)phenyl]piperazine hydrochloride MS m/e (ESI) 466 (MH⁺).

1-[2-(4,4-Diethylcyclohex-1-enyl)-4-(4-methoxypiperidin-1-yl)phenyl]-4-(tetrahydropyran-4-ylmethyl)piperazine hydrochloride MS m/e (ESI) 510 (MH⁺).

1-Butyl-4-[2-(4,4-dimethylcyclohexyl)-4-(4-methoxypiperidin-1-yl)phenyl]piperazine hydrochloride MS m/e (ESI) 470 (MH⁺).

1-[2-(4,4-Diethylcyclohexyl)-4-(4-methoxypiperidin-1-yl)phenyl]-4-propylpiperazine hydrochloride MS m/e (ESI) 456 (MH⁺).

1-[2-(4,4-Diethylcyclohexyl)-4-(4-methoxypiperidin-1-yl)phenyl]-4-isobutylpiperazinee hydrochloride MS m/e (ESI) 470 (MH⁺).

1-[2-(4,4-Diethylcyclohexyl)-4-(4-methoxypiperidin-1-yl)phenyl]-4-(tetrahydropyran-4-ylmethylpiperazine hydrochloride MS m/e (ESI) 512 (MH⁺).

1-{4-[2-(4,4-Diethylcyclohex-1-enyl)-4-(4-methoxypiperidin-1-yl)phenyl]piperazin-1-yl}butan-2-one hydrochloride MS m/e (ESI) 482 (MH⁺).

1-[2-(4,4-Diethylcyclohex-1-enyl)-4-(4-methoxypiperidin-1-yl)phenyl]-4-(2-methoxyethyl)piperazine hydrochloride MS m/e (ESI) 470 (MH$^+$).

1-{4-[2-(4,4-Diethylcyclohexyl)-4-(4-methoxypiperidin-1-yl)phenyl]piperazin-1-yl}butan-2-one hydrochloride MS m/e (ESI) 484 (MH$^+$).

1-[2-(4,4-Diethylcyclohexyl)-4-(4-methoxypiperidin-1-yl)phenyl]-4-(2-methoxyethyl)piperazine hydrochloride MS m/e (ESI) 472 (MH$^+$).

4-[3-(4,4-Diethylcyclohex-1-enyl)-4-(4-furan-2-ylmethylpiperazin-1-yl)phenyl]morpholine hydrochloride MS m/e (ESI) 464 (MH$^+$).

4-[3-(4,4-Diethylcyclohex-1-enyl)-4-(4-furan-3-ylmethylpiperazin-1-yl)phenyl]morpholine hydrochloride MS m/e (ESI) 464 (MH$^+$).

4-[3-(4,4-Diethylcyclohexyl)-4-(4-furan-2-ylmethylpiperazin-1-yl)phenyl]morpholine hydrochloride MS m/e (ESI) 466 (MH$^+$).

4-[3-(4,4-Diethylcyclohexyl)-4-(4-furan-3-ylmethylpiperazin-1-yl)phenyl]morpholine hydrochloride MS m/e (ESI) 466 (MH$^+$).

1-[2-(4,4-Diethylcyclohex-1-enyl)-4-(4-methoxypiperidin-1-yl)phenyl]-4-furan-2-ylmethylpiperazine hydrochloride MS m/e (ESI) 492 (MH$^+$).

1-[2-(4,4-Diethylcyclohex-1-enyl)-4-(4-methoxypiperidin-1-yl)phenyl]-4-furan-3-ylmethylpiperazine hydrochloride MS m/e (ESI) 492 (MH$^+$).

1-[2-(4,4-Diethylcyclohexyl)-4-(4-methoxypiperidin-1-yl)phenyl]-4-furan-2-ylmethylpiperazine hydrochloride MS m/e (ESI) 494 (MH$^+$).

1-[2-(4,4-Diethylcyclohexyl)-4-(4-methoxypiperidin-1-yl)phenyl]-4-furan-3-ylmethylpiperazine hydrochloride MS m/e (ESI) 494 (MH$^+$).

1-[2-(4,4-Diethylcyclohex-1-enyl)phenyl]-4-furan-2-ylmethylpiperazine hydrochloride MS m/e (ESI) 379 (MH$^+$).

1-[2-(4,4-Diethylcyclohex-1-enyl)phenyl]-4-furan-3-ylmethylpiperazine hydrochloride MS m/e (ESI) 379 (MH$^+$).

{4-[2-(4,4-Diethylcyclohex-1-enyl)phenyl]piperazin-1-yl}morpholin-4-ylmethanone

MS m/e (ESI) 412 (MH$^+$).

1-[2-(4,4-Diethylcyclohexyl)phenyl]-4-furan-2-ylmethylpiperazine hydrochloride

MS m/e (ESI) 381 (MH$^+$).

1-[2-(4,4-Diethylcyclohexyl)phenyl]-4-furan-3-ylmethylpiperazine hydrochloride

MS m/e (ESI) 381 (MH$^+$).

{4-[2-(4,4-Diethylcyclohex-1-enyl)phenyl]piperazin-1-yl}piperidin-1-ylmethanone

MS m/e (ESI) 410 (MH$^+$).

{4-[2-(4,4-Diethylcyclohexyl)phenyl]piperazin-1-yl}piperidin-1-ylmethanone

MS m/e (ESI) 412 (MH$^+$).

1-[2-(4,4-Diethylcyclohexyl)phenyl]-4-pentylpiperazine hydrochloride

MS m/e (ESI) 371 (MH$^+$).

cis-4-[4-(4-Butylpiperazin-1-yl)-3-(4,4-dimethylcyclohexyl)phenyl]-2,6-dimethylmorpholine hydrochloride MS m/e (ESI) 470 (MH$^+$).

cis-4-[3-(4,4-Diethylcyclohexyl)-4-(4-pentylpiperazin-1-yl)phenyl]-2,6-dimethylmorpholine hydrochloride MS m/e (ESI) 484 (MH$^+$).

cis-4-[4-(4-Cyclopropylmethylpiperazin-1-yl)-3-(4,4-dimethylcyclohexyl)phenyl]-2,6-dimethylmorpholine hydrochloride MS m/e (ESI) 468 (MH$^+$).

1-[4-Methoxy-2-(3,3,5,5-tetramethylcyclohexyl)phenyl]-4-propylpiperazine hydrochloride MS m/e (ESI) 373 (MH$^+$).

1-[4-Methoxy-2-(3,3,5,5-tetramethylcyclohexyl)phenyl]-4-pentylpiperazine hydrochloride MS m/e (ESI) 401 (MH$^+$).

1-Isobutyl-4-[4-methoxy-2-(3,355-tetramethylcyclohexyl)phenyl]piperazine hydrochloride MS m/e (ESI) 387 (MH$^+$).

1-Cyclopropylmethyl-4-[4-methoxy-2-(3,3,5,5-tetramethylcyclohexyl)phenyl]piperazine hydrochloride MS m/e (ESI) 385 (MH$^+$).

1-[4,5-Dimethoxy-2-(3,3,5,5-tetramethylcyclohexyl)phenyl]-4-propylpiperazine hydrochloride MS m/e (ESI) 403 (MH$^+$).

1-Butyl-4-[4,5-dimethoxy-2-(3,3,5,5-tetramethylcyclohexyl)phenyl]piperazine hydrochloride MS m/e (ESI) 417 (MH$^+$).

1-[4,5-Dimethoxy-2-(3,3,5,5-tetramethylcyclohexyl)phenyl]-4-pentylpiperazine hydrochloride MS m/e (ESI) 431 (MH$^+$).

1-[4,5-Dimethoxy-2-(3,3,5,5-tetramethylcyclohexyl)phenyl]-4-(tetrahydropyran-4-ylmethyl)piperazine hydrochloride MS m/e (ESI) 459 (MH$^+$).

1-Cycloheptyl-4-[2-(3,3,5,5-tetramethylcyclohexyl)phenyl]piperazine hydrochloride MS m/e (ESI) 397 (MH$^+$).

1-(4-Methylcyclohexyl)-4-[2-(3,3,5,5-tetramethylcyclohexyl)phenyl]piperazine hydrochloride MS m/e (ESI) 397 (MH$^+$).

1-(1-Ethylpropyl)-4-[2-(3,3,5,5-tetramethylcyclohexyl)phenyl]piperazine hydrochloride MS m/e (ESI) 371 (MH$^+$).

1-(Tetrahydrothiopyran-4-yl)-4-[2-(3,3,5,5-tetramethylcyclohexyl)phenyl]piperazine hydrochloride MS m/e (ESI) 401 (MH$^+$).

cis-4-[3-(4,4-Diethylcyclohexyl)-4-(4-propylpiperazin-1-yl)phenyl]-2,6-dimethylmorpholine hydrochloride MS m/e (ESI) 456 (MH$^+$).

4-[5-(4,4-Diethylcyclohexyl)-2-methoxy-4-(4-pentylpiperazin-1-yl)phenyl]morpholine hydrochloride MS m/e (ESI) 486 (MH$^+$).

4-(4-Propylpiperazin-1-yl)-3-(3,3,5,5-tetramethylcyclohexyl)benzonitrile hydrochloride MS m/e (ESI) 368 (MH$^+$).

1-[3-Fluoro-2-(3,3,5,5-tetramethylcyclohex-1-enyl)phenyl]-4-propylpiperazine hydrochloride MS m/e (ESI) 359 (MH$^+$).

trans-2-{4-[2-(3,3,5,5-Ttramethylcyclohexyl)phenyl]piperazin-1-ylmethyl}cyclopropanecarboxylic acid dimethylamide hydrochloride MS m/e (ESI) 426 (MH$^+$).

1-{4-[2-(4-t-Butylcyclohexyl)phenyl]piperazin-1-yl}butan-2-one hydrochloride

MS m/e (ESI) 371 (MH$^+$).

1-{4-[2-(4-t-Butylcyclohexyl)phenyl]piperazin-1-yl}butan-2-ol hydrochloride

MS m/e (ESI) 373 (MH$^+$).

trans-4-Butyl-1-[2-(4-t-butylcyclohexyl)phenyl]piperazin-2-one hydrochloride

MS m/e (ESI) 371 (MH$^+$).

cis-4-Butyl-1-[2-(4-t-butylcyclohexyl)phenyl]piperazin-2-one hydrochloride

MS m/e (ESI) 371 (MH$^+$).

2-{4-[2-(4-t-Butylcyclohexyl)phenyl]piperazin-1-yl}acetamide hydrochloride

MS m/e (ESI) 358 (MH$^+$).

4-(4-t-Butylcyclohexyl)-3-(4-butylpiperazine-1-yl)benzonitrile hydrochloride

MS m/e (ESI) 382 (MH$^+$).

2-{4-[2-(4-t-Butylcyclohexyl)phenyl]piperazin-1-yl}-N-cyclopropylacetamide hydrochloride MS m/e (ESI) 398 (MH$^+$).

2-{4-[2-(4-t-Butylcyclohexyl)phenyl]piperazin-1-yl}-1-piperidin-1-ylpropan-1-one hydrochloride MS m/e (ESI) 440 (MH$^+$).

2-{4-[2-(4-t-Butylcyclohexyl)phenyl]piperazin-1-yl}-N-methylacetamide hydrochloride MS m/e (ESI) 372 (MH$^+$).

3-{4-[2-(4-t-Butylcyclohexyl)phenyl]piperazin-1-yl}pyrrolidin-2-one hydrochloride MS m/e (ESI) 384 (MH$^+$).

2-{4-[2-(4-t-Butylcyclohexyl)phenyl]piperazin-1-yl}-N-isopropylacetamide hydrochloride MS m/e (ESI) 400 (MH$^+$).

2-{4-[2-(4-t-Butylcyclohexyl)phenyl]piperazin-1-yl}-N-ethyl-N-methylacetamide hydrochloride MS m/e (ESI) 400 (MH$^+$).

2-{4-[2-(4-t-Butylcyclohexyl)phenyl]piperazin-1-yl}-N,N-diethylacetamide hydrochloride MS m/e (ESI) 414 (MH$^+$).

2-{4-[2-(4-t-Butylcyclohexyl)phenyl]piperazin-1-yl}-N-(2-methoxyethyl)acetamide hydrochloride MS m/e (ESI) 416 (MH$^+$).

1-[2-(4-t-Butylcyclohexyl)phenyl]-4-methylpiperazine hydrochloride

MS m/e (ESI) 315 (MH$^+$).

1-[2-(4-t-Butylcyclohexyl)phenyl]-4-ethylpiperazine hydrochloride

MS m/e (ESI) 329 (MH$^+$).

1-[2-(4-t-Butylcyclohex-1-enyl)phenyl]-4-ethylpiperazine hydrochloride

MS m/e (ESI) 327 (MH$^+$).

1-[2-(4-t-Butylcyclohex-1-enyl)phenyl]-4-cyclopropylmethylpiperazine hydrochloride MS m/e (ESI) 353 (MH$^+$).

N-Butyl-2-{4-[2-(4-t-butylcyclohexyl)phenyl]piperazin-1-yl}acetamide hydrochloride MS m/e (ESI) 414 (MH$^+$).

1-Azocan-1-yl-2-{4-[2-(4-t-butylcyclohexyl)phenyl]piperazin-1-yl}ethanone hydrochloride MS m/e (ESI) 454 (MH$^+$).

[3-(4-t-Butylcyclohexyl)-4-(4-butylpiperazine-1-yl)phenyl]methylamine hydrochloride MS m/e (ESI) 386 (MH$^+$).

[3-(4-t-Butylcyclohexyl)-4-(4-butylpiperazine-1-yl)phenyl]dimethylamine hydrochloride MS m/e (ESI) 400 (MH$^+$).

1-Butyl-4-[2-(4-t-butylcyclohexyl)-4-pyridin-3-ylphenyl]piperazine dihydrochloride MS m/e (ESI) 434 (MH$^+$).

[3-(4-t-Butylcyclohex-1-enyl)-4-(4-butylpiperazine-1-yl)phenyl]dimethylamine hydrochloride MS m/e (ESI) 398 (MH$^+$).

1-Propyl-4-[2-(3,3,5,5-tetramethylcyclohex-1-enyl)phenyl]piperazine hydrochloride MS m/e (ESI) 341 (MH$^+$).

1-(Tetrahydropyran-4-ylmethyl)-4-[2-(3,3,5,5-tetramethylcyclohexyl)phenyl]piperazine hydrochloride MS m/e (ESI) 399 (MH$^+$).

1-Butyl-4-[4-(4-methoxypiperidin-1-yl)-2-(3,3,5,5-tetramethylcyclohex-1-enyl)phenyl]piperazine hydrochloride MS m/e (ESI) 468 (MH$^+$).

1-Cyclopropylmethyl-4-[4-(4-methoxypiperidin-1-yl)-2-(3,3,5,5-tetramethylcyclohex-1-enyl)phenyl]piperazine hydrochloride MS m/e (ESI) 466 (MH$^+$).

1-[4-(4-Methoxypiperidin-1-yl)-2-(3,3,5,5-tetramethylcyclohex-1-enyl)phenyl]-4-(tetrahydropyran-4-ylmethyl)piperazine hydrochloride MS m/e (ESI) 510 (MH$^+$).

1-Furan-3-ylmethyl-4-[4-(4-methoxypiperidin-1-yl)-2-(3,355-tetramethylcyclohex-1-enyl)phenyl]piperazine hydrochloride MS m/e (ESI) 492 (MH$^+$).

1-{4-[4-(4-Methoxypiperidin-1-yl)-2-(3,3,5,5-tetramethylcyclohex-1-enyl)phenyl]piperazin-1-yl}butan-2-one hydrochloride MS m/e (ESI) 482 (MH$^+$).

1-(2-Methoxyethyl)-4-[4-(4-methoxypiperidin-1-yl)-2-(3,3,5,5-tetramethylcyclohex-1-enyl)phenyl]piperazine hydrochloride MS m/e (ESI) 470 (MH$^+$).

1-[4-(4-Methoxypiperidin-1-yl)-2-(3,3,5,5-tetramethylcyclohexyl)phenyl]-4-propylpiperazine hydrochloride MS m/e (ESI) 456 (MH$^+$).

1-Cyclopropylmethyl-4-[4-(4-methoxypiperidin-1-yl)-2-(3,3,5,5-tetramethylcyclohexyl)phenyl]piperazine hydrochloride MS m/e (ESI) 468 (MH$^+$).

1-[4-(4-Methoxypiperidin-1-yl)-2-(3,3,5,5-tetramethylcyclohexyl)phenyl]-4-(tetrahydropyran-4-ylmethyl)piperazine hydrochloride MS m/e (ESI) 512 (MH$^+$).

1-{4-[4-(4-Methoxypiperidin-1-yl)-2-(3,3,5,5-tetramethylcyclohexylphenyl]piperazin-1-yl}butan-2-one hydrochloride MS m/e (ESI) 484 (MH$^+$).

1-(2-Methoxyethyl)-4-[4-(4-methoxypiperidin-1-yl)-2-(3,3,5,5-tetramethylcyclohexyl)phenyl]piperazine hydrochloride MS m/e (ESI) 472 (MH$^+$).

4-[4-(4-Butylpiperazin-1-yl)-3-(3,3,5,5-tetramethyl-cyclohex-1-enyl)phenyl]morpholine hydrochloride MS m/e (ESI) 440 (MH$^+$).

4-[4-(4-Pentylpiperazin-1-yl)-3-(3,3,5,5-tetramethyl-cyclohex-1-enyl)phenyl]morpholine hydrochloride MS m/e (ESI) 454 (MH$^+$).

4-[4-(4-Cyclopropylmethylpiperazin-1-yl)-3-(3,3,5,5-tetramethylcyclohex-1-enyl)phenyl]morpholine hydrochloride MS m/e (ESI) 438 (MH$^+$).

4-{4-[4-(Tetrahydropyran-4-ylmethyl)piperazin-1-yl]-3-(3,3,5,5-tetramethylcyclohex-1-enyl)phenyl}morpholine hydrochloride MS m/e (ESI) 482 (MH$^+$).

4-[4-(4-Furan-3-ylmethylpiperazin-1-yl)-3-(3,3,5,5-tetramethylcyclohex-1-enyl)phenyl]morpholine hydrochloride MS m/e (ESI) 464 (MH$^+$).

1-{4-[4-Morpholin-4-yl-2-(3,3,5,5-tetramethylcyclohex-1-enyl)phenyl]piperazin-1-yl}butan-2-one hydrochloride MS m/e (ESI) 454 (MH$^+$).

4-[4-(4-Butylpiperazin-1-yl)-3-(3,3,5,5-tetramethylcyclohexyl)phenyl]morpholine hydrochloride MS m/e (ESI) 442 (MH$^+$).

4-[4-(4-Pentylpiperazin-1-yl)-3-(3,3,5,5-tetramethylcyclohexyl)phenyl]morpholine hydrochloride MS m/e (ESI) 456 (MH$^+$).

4-[4-(4-Cyclopropylmethylpiperazin-1-yl)-3-(3,3,5,5-tetramethylcyclohexyl)phenyl]morpholine hydrochloride MS m/e (ESI) 440 (MH$^+$).

4-{4-[4-(Tetrahydropyran-4-ylmethyl)piperazin-1-yl]-3-(3,3,5,5-tetramethylcyclohexyl)phenyl}morpholine hydrochloride MS m/e (ESI) 484 (MH$^+$).

4-[4-(4-Furan-3-ylmethylpiperazin-1-yl)-3-(3,3,5,5-tetramethylcyclohexyl)phenyl]morpholine hydrochloride MS m/e (ESI) 466 (MH$^+$).

1-{4-[4-Morpholin-4-yl-2-(3,3,5,5-tetramethylcyclohexyl)phenyl]piperazin-1-yl}butan-2-one hydrochloride MS m/e (ESI) 456 (MH$^+$).

4-{4-[4-(2-Methoxyethyl)piperazin-1-yl]-3-(3.3,5,5-tetramethylcyclohexyl)phenyl}morpholine hydrochloride MS m/e (ESI) 444 (MH$^+$).

1-[4-(4-Ethoxypiperidin-1-yl)-2-(3,3,5,5-tetramethylcyclohexyl)phenyl]-4-propylpiperazine hydrochloride MS m/e (ESI) 470 (MH$^+$).

1-{4-[4-(4-Ethoxypiperidin-1-yl)-2-(3,3,5,5-tetramethylcyclohexyl)phenyl]piperazin-1-yl}butan-2-one hydrochloride MS m/e (ESI) 498 (MH$^+$).

2-{4-[4-(4-Methoxypiperidin-1-yl)-2-(3,3,5,5-tetramethylcyclohexyl)phenyl]piperazin-1-yl}-N-methylacetamide hydrochloride MS m/e (ESI) 485 (MH$^+$).

(R)-1-[4-(3-Methoxypyrrolidin-1-yl)-2-(3,3,5,5-tetramethylcyclohexyl)phenyl]-4-propylpiperazine hydrochloride MS m/e (ESI) 442 (MH$^+$).

(R)-1-Butyl-4-[4-(3-methoxypyrrolidin-1-yl)-2-(3,3,5,5-tetramethylcyclohexyl)phenyl]piperazine hydrochloride MS m/e (ESI) 456 (MH$^+$).

(R)-1-Cyclopropylmethyl-4-[4-(3-methoxypyrrolidin-1-yl)-2-(3,3,5,5-tetramethylcyclohexyl)phenyl]piperazine hydrochloride MS m/e (ESI) 454 (MH$^+$).

cis-2,6-Dimethyl-4-[4-(4-propylpiperazin-1-yl)-3-(3,3,5,5-tetramethylcyclohexyl)phenyl]morpholine hydrochloride MS m/e (ESI) 456 (MH$^+$).

cis-4-[4-(4-Cyclopropylmethylpiperazin-1-yl)-3-(3,3,5,5-tetramethylcyclohexyl)phenyl]-2,6-dimethylmorpholine hydrochloride MS m/e (ESI) 468 (MH$^+$).

1-[4-(4-Butylpiperazin-1-yl)-3-(3,3,5,5-tetramethylcyclohexyl)phenyl]piperidine-4-carbonitrile hydrochloride MS m/e (ESI) 465 (MH$^+$).

(S)-1-[4-(3-Methoxypyrrolidin-1-yl)-2-(3,3,5,5-tetramethylcyclohexyl)phenyl]-4-propylpiperazine hydrochloride MS m/e (ESI) 442 (MH$^+$).

(S)-1-Butyl-4-[4-(3-methoxypyrrolidin-1-yl)-2-(3,3,5,5-tetramethylcyclohexyl)phenyl]piperazine hydrochloride MS m/e (ESI) 456 (MH$^+$).

(S)-1-Cyclopropylmethyl-4-[4-(3-methoxypyrrolidin-1-yl)-2-(3,3,5,5-tetramethylcyclohexylphenyl]piperazine hydrochloride MS m/e (ESI) 454 (MH$^+$).

1-[2-(4,4-Diethylcyclohexyl)-4-(4-ethoxypiperidin-1-yl)phenyl]-4-propylpiperazine hydrochloride MS m/e (ESI) 470 (MH$^+$).

1-Cyclopropylmethyl-4-[2-(4,4-dimethylcyclohexyl)-4-(4-ethoxypiperidin-1-yl)phenyl]piperazine hydrochloride MS m/e (ESI) 482 (MH$^+$).

1-Cyclopropylmethyl-4-[2-(4,4-dimethylcyclohexyl)-4-piperidin-1-ylphenyl]piperazine hydrochloride MS m/e (ESI) 438 (MH$^+$).

(R)-1-[2-(4,4-Diethylcyclohexyl)-4-(3-methoxypyrrolidin-1-yl)phenyl]-4-propylpiperazine hydrochloride MS m/e (ESI) 442 (MH$^+$).

(R)-1-Butyl-4-[2-(4,4-dimethylcyclohexyl)-4-(3-methoxypyrrolidin-1-yl)phenyl]piperazine hydrochloride MS m/e (ESI) 428 (MH$^+$).

(R)-1-[4-(3-Ethoxypyrrolidin-1-yl)-2-(3,3,5,5-tetramethylcyclohexyl)phenyl]-4-propylpiperazine hydrochloride MS m/e (ESI) 456 (MH$^+$).

(R)-1-Cyclopropylmethyl-4-[4-(3-ethoxypyrrolidin-1-yl)-2-(3,3,5,5-tetramethylcyclohexyl)phenyl]piperazine hydrochloride MS m/e (ESI) 468 (MH$^+$).

1-[4-Fluoro-2-(3,3,5,5-tetramethylcyclohex-1-enyl)phenyl]-4-propylpiperazine hydrochloride MS m/e (ESI) 359 (MH$^+$).

1-[4-Fluoro-2-(3,3,5,5-tetramethylcyclohexyl)phenyl]-4-propylpiperazine hydrochloride MS m/e (ESI) 361 (MH$^+$).

1-Cyclopropylmethyl-4-[4-fluoro-2-(3,3,5,5-tetramethylcyclohexyl)phenyl]piperazine hydrochloride MS m/e (ESI) 373 (MH$^+$).

1-Propyl-4-[4-pyridin-2-yl-2-(3,3,5,5-tetramethylcyclohexyl)phenyl]piperazine dihydrochloride MS m/e (ESI) 420 (MH$^+$).

1-Cyclopropylmethyl-4-[5-fluoro-2-(3,3,5,5-tetramethylcyclohexyl)phenyl]piperazine hydrochloride MS m/e (ESI) 373 (MH$^+$).

4-(4-Cyclopropylmethylpiperazin-1-yl)-3-(3,3,5,5-tetramethylcyclohexyl)benzonitrile hydrochloride MS m/e (ESI) 380 (MH$^+$).

1-Cyclopropylmethyl-4-[3-fluoro-2-(3,3,5,5-tetramethylcyclohex-1-enyl)phenyl]piperazine hydrochloride MS m/e (ESI) 371 (MH$^+$).

2-Butyl-5-[2-(3,3,5,5-tetramethylcyclohex-1-enyl)phenyl]-2,5-diazabicyclo[2.2.1]heptane hydrochloride MS m/e (ESI) 367 (MH$^+$).

1-[2-(4-t-Butylcyclohex-1-enyl)phenyl]-4-(1-methylbutyl)piperazine hydrochloride MS m/e (ESI) 369 (MH$^+$).

1-[2-(4-t-Butylcyclohexyl)phenyl]-4-(1-methylbutyl)piperazine hydrochloride

MS m/e (ESI) 371 (MH$^+$).

2-{4-[2-(4-t-Butylcyclohexyl)phenyl]piperazin-1-yl}-N-cyclohexylacetamide hydrochloride MS m/e (ESI) 440 (MH$^+$).

4-[2-(4-t-Butylcyclohexyl)phenyl]piperazine-1-carboxylic acid ethylamide

MS m/e (ESI) 372 (MH$^+$).

3-{4-[2-(4-t-Butylcyclohexyl)phenyl]piperazin-1-yl}-1-methylpyrrolidin-2-one hydrochloride MS m/e (ESI) 398 (MH$^+$).

1-[2-(4-t-Butylcyclohexyl)phenyl]-4-isobutylpiperazinee hydrochloride

MS m/e (ESI) 357 (MH$^+$).

1-[2-(4-t-Butylcyclohex-1-enyl)phenyl]-4-isobutylpiperazinee hydrochloride

MS m/e (ESI) 355 (MH$^+$).

2-{4-[2-(4-t-Butylcyclohexyl)phenyl]piperazin-1-yl}-1-(3,3-dimethylpiperidin-1-yl)ethanone hydrochloride MS m/e (ESI) 454 (MH$^+$).

1-Butyl-4-[2-(4-t-butylcyclohexyl)-4-thiophen-2-ylphenyl]piperazine hydrochloride MS m/e (ESI) 439 (MH$^+$).

1-Butyl-4-[2-(4-t-butylcyclohexyl)-4-methylphenyl]piperazine hydrochloride

MS m/e (ESI) 371 (MH$^+$).

1-Butyl-4-[2-(4-t-butylcyclohexyl)-4-thiazol-2-ylphenyl]piperazine dihydrochloride MS m/e (ESI) 440 (MH$^+$).

1-Butyl-4-[2-(4-t-butylcyclohex-1-enyl)-4-fluorophenyl]piperazine hydrochloride

MS m/e (ESI) 373 (MH$^+$).

1-Butyl-4-[2-(4-t-butylcyclohexyl)-4-fluorophenyl]piperazine hydrochloride

MS m/e (ESI) 375 (MH$^+$).

1-Pentyl-4-[2-(3,3,5,5-tetramethylcyclohex-1-enyl)phenyl]piperazine hydrochloride MS m/e (ESI) 369 (MH$^+$).

1-Isobutyl-4-[2-(3,3,5,5-tetramethylcyclohex-1-enyl)phenyl]piperazine hydrochloride MS m/e (ESI) 355 (MH$^+$).

1-Pentyl-4-[2-(3,3,5,5-tetramethylcyclohexyl)phenyl]piperazine hydrochloride

MS m/e (ESI) 371 (MH$^+$).

1-Isobutyl-4-[2-(3,3,5,5-tetramethylcyclohexyl)phenyl]piperazine hydrochloride

MS m/e (ESI) 357 (MH$^+$).

1-Furan-3-ylmethyl-4-[2-(3,3,5,5-tetramethylcyclohex-1-enyl)phenyl]piperazine hydrochloride MS m/e (ESI) 379 (MH$^+$).

1-Isobutyl-4-[4-(4-methoxypiperidin-1-yl)-2-(3,35,5-tetramethylcyclohex-1-enyl)phenyl]piperazine hydrochloride MS m/e (ESI) 468 (MH$^+$).

1-[4-(4-Methoxypiperidin-1-yl)-2-(3,3,5,5-tetramethylcyclohexyl)phenyl]-4-pentylpiperazine hydrochloride MS m/e (ESI) 484 (MH$^+$).

1-Isobutyl-4-[4-(4-methoxypiperidin-1-yl)-2-(3,3,5,5-tetramethylcyclohexyl)phenyl]piperazine hydrochloride MS m/e (ESI) 470 (MH$^+$).

1-Furan-3-ylmethyl-4-[4-(4-methoxypiperidin-1-yl)-2-(3,3,5,5-tetramethylcyclohexyl)phenyl]piperazine hydrochloride MS m/e (ESI) 494 (MH$^+$).

4-[4-(4-Isobutylpiperazine-1-yl)-3-(3,3,5,5-tetramethylcyclohex-1-enyl)phenyl]morpholine hydrochloride MS m/e (ESI) 440 (MH$^+$).

4-[4-(4-Propylpiperazin-1-yl)-3-(3,3,5,5-tetramethylcyclohexyl)phenyl]morpholine hydrochloride MS m/e (ESI) 428 (MH$^+$).

4-[4-(4-Isobutylpiperazine-1-yl)-3-(3,3,5,5-tetramethylcyclohexyl)phenyl]morpholine hydrochloride MS m/e (ESI) 442 (MH$^+$).

1-Butyl-4-[4-(4-ethoxypiperidin-1-yl)-2-(3,3,5,5-tetramethylcyclohexyl)phenyl]piperazine hydrochloride MS m/e (ESI) 484 (MH$^+$).

1-{4-[4-Piperidin-1-yl-2-(3,3,5,5-tetramethylcyclohexyl)phenyl]piperazin-1-yl}butan-2-one hydrochloride MS m/e (ESI) 454 (MH$^+$).

1-[4-Piperidin-1-yl-2-(3,3,5,5-tetramethylcyclohexyl)phenyl]-4-propylpiperazine hydrochloride MS m/e (ESI) 426 (MH$^+$).

1-Butyl-4-[4-piperidin-1-yl-2-(3,3,5,5-tetramethylcyclohexyl)phenyl]piperazine hydrochloride MS m/e (ESI) 440 (MH$^+$).

1-[4-(4-Cyclopropylmethylpiperazin-1-yl)-3-(3,3,5,5-tetramethylcyclohexyl)phenyl]azepane hydrochloride MS m/e (ESI) 452 (MH$^+$).

cis-4-[4-(4-Butylpiperazin-1-yl)-3-(3,3,5,5-tetramethylcyclohexyl)phenyl]-2,6-dimethylmorpholine hydrochloride MS m/e (ESI) 470 (MH$^+$).

1-[4-(4-Propylpiperazin-1-yl)-3-(3,3,5,5-tetramethylcyclohexyl)phenyl]piperidine-4-carbonitrile hydrochloride MS m/e (ESI) 451 (MH$^+$).

1-Butyl-4-[2-(4,4-dimethylcyclohexyl)-4-(4-ethoxypiperidin-1-yl)phenyl]piperazine hydrochloride MS m/e (ESI) 484 (MH$^+$).

1-[2-(4,4-Diethylcyclohexyl)-4-piperidin-1-ylphenyl]-4-propylpiperazine hydrochloride MS m/e (ESI) 426 (MH$^+$).

(R)-1-Butyl-4-[4-(3-ethoxypyrrolidin-1-yl)-2-(3,3,5,5-tetramethylcyclohexyl)phenyl]piperazine hydrochloride MS m/e (ESI) 470 (MH$^+$).

1-Butyl-4-[4-fluoro-2-(3,3,5,5-tetramethylcyclohex-1-enyl)phenyl]piperazine hydrochloride MS m/e (ESI) 373 (MH$^+$).

1-Cyclopropylmethyl-4-[4-fluoro-2-(3,3,5,5-tetramethylcyclohex-1-enyl)phenyl]piperazine hydrochloride MS m/e (ESI) 371 (MH$^+$).

1-[4-Fluoro-2-(3,3,5,5-tetramethylcyclohex-1-enyl)phenyl]-4-(tetrahydropyran-4-ylmethyl)piperazine hydrochloride MS m/e (ESI) 415 (MH$^+$).

1-Butyl-4-[4-fluoro-2-(3,3,5,5-tetramethylcyclohexyl)phenyl]piperazine hydrochloride MS m/e (ESI) 375 (MH$^+$).

1-[4-Fluoro-2-(3,3,5,5-tetramethylcyclohexyl)phenyl]-4-(tetrahydropyran-4-ylmethyl)piperazine hydrochloride MS m/e (ESI) 417 (MH$^+$).

1-[5-Fluoro-2-(3,3,5,5-tetramethylcyclohexyl)phenyl]-4-propylpiperazine hydrochloride MS m/e (ESI) 361 (MH$^+$).

1-Butyl-4-[5-fluoro-2-(3,3,5,5-tetramethylcyclohexyl)phenyl]piperazine hydrochloride MS m/e (ESI) 375 (MH$^+$).

1-[5-Fluoro-2-(3,3,5,5-tetramethylcyclohexyl)phenyl]-4-(tetrahydropyran-4-ylmethyl)piperazine hydrochloride MS m/e (ESI) 417 (MH$^+$).

4-(4-Butylpiperazin-1-yl)-3-(3,3,5,5-tetramethylcyclohexyl)benzonitrile hydrochloride MS m/e (ESI) 382 (MH$^+$).

4-[4-(Tetrahydropyran-4-ylmethyl)piperazin-1-yl]-3-(3,3,5,5-tetramethylcyclohexyl)benzonitrile hydrochloride MS m/e (ESI) 424 (MH$^+$).

1-(Tetrahydropyran-4-ylmethyl)-4-[2-(3,3,5,5-tetramethylcyclohexyl)-4-thiazol-2-ylphenyl]piperazine dihydrochloride MS m/e (ESI) 482 (MH$^+$).

1-Butyl-4-[3-fluoro-2-(3,3,5,5-tetramethylcyclohex-1-enyl)phenyl]piperazine hydrochloride MS m/e (ESI) 373 (MH$^+$).

2-{4-[2-(3,3,5,5-Tetramethylcyclohexyl)phenyl]piperazin-1-ylmethyl}cyclopropanecarboxylic acid methylamide hydrochloride MS m/e (ESI) 412 (MH$^+$).

cis-2-{4-[2-(3,3,5,5-Tetramethylcyclohexyl)phenyl]piperazin-1-ylmethyl}cyclopropanecarboxylic acid dimethylamide hydrochloride MS m/e (ESI) 426 (MH$^+$).

1-(1-Methylcyclopropylmethyl)-4-[2-(3,3,5,5-tetramethylcyclohexyl)phenyl]piperazine hydrochloride MS m/e (ESI) 369 (MH$^+$).

1-[2-(4-t-Butylcyclohexyl)phenyl]-4-propylpiperazine hydrochloride

MS m/e (ESI) 343 (MH$^+$).

1-Butyl-4-[2-(3,5-dimethylcyclohexyl)phenyl]piperazine hydrochloride

MS m/e (ESI) 329 (MH$^+$).

1-Butyl-4-[2-(4-trifluoromethylcyclohexyl)phenyl]piperazine hydrochloride

MS m/e (ESI) 369 (MH$^+$).

1-{4-[2-(4-t-Butylcyclohexyl)phenyl]piperazin-1-yl}butan-1-one

MS m/e (ESI) 393 (MNa$^+$).

1-Butyl-4-[2-(4-phenylcyclohexyl)phenyl]piperazine hydrochloride

MS m/e (ESI) 377 (MH$^+$).

3-[4-(4-t-Butylcyclohexyl)-3-(4-butylpiperazine-1-yl)phenyl]propionic acid methyl ester hydrochloride MS m/e (ESI) 443 (MH$^+$).

[4-(4-t-Butylcyclohexyl)-3-(4-butylpiperazine-1-yl)phenoxy]acetic acid ethyl ester hydrochloride MS m/e (ESI) 459 (MH$^+$).

1-[2-(4-t-Butylcyclohexyl)-4-piperidin-1-ylphenyl]-4-cyclopropylmethylpiperazine hydrochloride MS m/e (ESI) 438 (MH$^+$).

1-[2-(4-t-Butylcyclohexyl)-4-piperidin-1-ylphenyl]-4-propylpiperazine hydrochloride MS m/e (ESI) 426 (MH+).

4-[4-(4-t-Butylcyclohexyl)-5-(4-butylpiperazine-1-yl)-2-methoxyphenyl]morpholine hydrochloride MS m/e (ESI) 472 (MH+).

1-Butyl-4-[2-(4-t-butylcyclohexyl)-5-methoxy-4-(4-methoxypiperidin-1-yl)phenyl]piperazine hydrochloride MS m/e (ESI) 500 (MH+).

1-Butyl-4-[2-(4-t-butylcyclohexyl)-4-(4-ethoxypiperidin-1-yl)-5-methoxyphenyl]piperazine hydrochloride MS m/e (ESI) 514 (MH+).

1-[2-(4-t-Butylcyclohexyl)-5-methoxy-4-(4-methoxypiperidin-1-yl)phenyl]-4-cyclopropylmethylpiperazine hydrochloride MS m/e (ESI) 498 (MH+).

1-Butyl-4-[2-(4,4-diethylcyclohex-1-enyl)-5-methoxyphenyl]piperazine hydrochloride MS m/e (ESI) 385 (MH+).

1-Butyl-4-[2-(4,4-dimethylcyclohexyl)-5-methoxyphenyl]piperazine hydrochloride

MS m/e (ESI) 387 (MH+).

1-[2-(4,4-Diethylcyclohexyl)-5-methoxyphenyl]-4-propylpiperazine hydrochloride

MS m/e (ESI) 373 (MH+).

1-Butyl-4-[5-methoxy-2-(3,3,5,5-tetramethylcyclohex-1-enyl)phenyl]piperazine hydrochloride MS m/e (ESI) 385 (MH+).

1-[5-Methoxy-2-(3,3,5,5-tetramethylcyclohex-1-enyl)phenyl]-4-propylpiperazine hydrochloride MS m/e (ESI) 371 (MH+).

1-[5-Methoxy-2-(3,3,5,5-tetramethylcyclohexyl)phenyl]-4-propylpiperazine hydrochloride MS m/e (ESI) 373 (MH+).

4-[5-(4,4-Diethylcyclohexyl)-2-methoxy-4-(4-propylpiperazin-1-yl)phenyl]morpholine hydrochloride MS m/e (ESI) 458 (MH+).

1-Butyl-4-[2-(4,4-dimethylcyclohex-1-enyl)-5-methoxyphenyl]piperazine hydrochloride MS m/e (ESI) 357 (MH+).

1-Butyl-4-[2-(4,4-dimethylcyclohexyl)-5-methoxyphenyl]piperazine hydrochloride

MS m/e (ESI) 359 (MH+).

1-[2-(4,4-Dimethylcyclohex-1-enyl)-5-methoxyphenyl]-4-propylpiperazine hydrochloride MS m/e (ESI) 343 (MH+).

1-[2-(4,4-Dimethylcyclohexyl)-5-methoxyphenyl]-4-propylpiperazine hydrochloride

MS m/e (ESI) 345 (MH+).

1-Cyclopropylmethyl-4-[2-(4,4-dimethylcyclohex-1-enyl)-5-methoxyphenyl]piperazine hydrochloride MS m/e (ESI) 355 (MH+).

1-Cyclopropylmethyl-4-[2-(4,4-dimethylcyclohexyl)-5-methoxyphenyl]piperazine hydrochloride MS m/e (ESI) 357 (MH+).

1-[2-(4,4-Dimethylcyclohex-1-enyl)-5-methoxyphenyl]-4-(tetrahydropyran-4-ylmethyl)piperazine hydrochloride MS m/e (ESI) 399 (MH+).

1-[2-(4,4-Dimethylcyclohexyl)-5-methoxyphenyl]-4-(tetrahydropyran-4-ylmethyl)piperazine hydrochloride MS m/e (ESI) 401 (MH+).

1-[2-(4,4-Dimethylcyclohex-1-enyl)-5-methoxyphenyl]-4-pentylpiperazine hydrochloride MS m/e (ESI) 371 (MH+).

1-Cyclopropylmethyl-4-[5-methoxy-2-(3,3,5,5-tetramethylcyclohex-1-enyl)phenyl]piperazine hydrochloride MS m/e (ESI) 383 (MH+).

1-Cyclopropylmethyl-4-[5-methoxy-2-(3,355-tetramethylcyclohexyl)phenyl]piperazine hydrochloride MS m/e (ESI) 385 (MH+).

1-Butyl-4-(2-spiro[4.5]dec-7-en-8-ylphenyl)piperazine hydrochloride

MS m/e (ESI) 353 (MH+).

1-Cyclopropylmethyl-4-(2-spiro[4.5]dec-7-en-8-ylphenyl)piperazine hydrochloride

MS m/e (ESI) 351 (MH+).

1-Cyclopropylmethyl-4-(2-spiro[4.5]dec-8-ylphenyl)piperazine hydrochloride

MS m/e (ESI) 353 (MH+).

1-(2-Spiro[4.5]dec-7-en-8-ylphenyl)-4-(tetrahydropyran-4-ylmethyl)piperazine hydrochloride MS m/e (ESI) 395 (MH⁺).

1-[4-(2-Spiro[4.5]dec-7-en-8-ylphenyl)piperazin-1-yl]butan-2-one hydrochloride

MS m/e (ESI) 367 (MH⁺).

1-[4-(2-Spiro[4.5]dec-8-ylphenyl)piperazin-1-yl]butan-2-one hydrochloride

MS m/e (ESI) 369 (MH⁺).

1-{4-[2-(4,4-Dimethylcyclohex-1-enyl)-5-methoxyphenyl]piperazin-1-yl}butan-2-one hydrochloride MS m/e (ESI) 371 (MH⁺).

[2-Methoxy-4-(4-propylpiperazin-1-yl)-5-(3,3,5,5-tetramethylcyclohexyl)phenyl]dimethylamine hydrochloride MS m/e (ESI) 416 (MH⁺).

4-[4-(4-Propylpiperazin-1-yl)-3-spiro[4.5]dec-7-en-8-ylphenyl]morpholine hydrochloride MS m/e (ESI) 424 (MH⁺).

4-[4-(4-Butylpiperazin-1-yl)-3-spiro[4.5]dec-7-en-8-ylphenyl]morpholine hydrochloride MS m/e (ESI) 438 (MH⁺).

4-[4-(4-Cyclopropylmethylpiperazin-1-yl)-3-spiro[4.5]dec-7-en-8-ylphenyl]morpholine hydrochloride MS m/e (ESI) 436 (MH⁺).

4-{3-Spiro[4.5]dec-7-en-8-Yl-4-[4-(tetrahydropyran-4-Ylmethyl)piperazin-1-yl]phenyl}morpholine hydrochloride MS m/e (ESI) 480 (MH⁺).

4-[4-(4-Butylpiperazin-1-yl)-3-spiro[4.5]dec-8-ylphenyl]morpholine hydrochloride MS m/e (ESI) 440 (MH⁺).

4-[4-(4-Cyclopropylmethylpiperazin-1-yl)-3-spiro[4.5]dec-8-ylphenyl]morpholine hydrochloride MS m/e (ESI) 438 (MH⁺).

4-{3-Spiro[4.5]dec-8-yl-4-[4-(tetrahydropyran-4-ylmethyl)piperazin-1-yl]phenyl}morpholine hydrochloride MS m/e (ESI) 482 (MH⁺).

1-[4-(4-Morpholin-4-yl-2-spiro[4.5]dec-8-ylphenyl)piperazin-1-yl]butan-2-one hydrochloride MS m/e (ESI) 454 (MH⁺).

1-[4-(4-Methoxypiperidin-1-yl)-2-spiro[4.5]dec-7-en-8-ylphenyl]-4-propylpiperazine hydrochloride MS m/e (ESI) 452 (MH⁺).

1-Butyl-4-[4-(4-methoxypiperidin-1-yl)-2-spiro[4.5]dec-7-en-8-ylphenyl]piperazine hydrochloride MS m/me (ESI) 466 (MH⁺).

1-[4-(4-Methoxypiperidin-1-yl)-2-spiro[4.5]dec-7-en-8-ylphenyl]-4-pentylpiperazine hydrochloride MS m/e (ESI) 480 (MH⁺).

1-[4-(4-Methoxypiperidin-1-yl)-2-spiro[4.5]dec-7-en-8-ylphenyl]-4-(tetrahydropyran-4-ylmethyl)piperazine hydrochloride MS m/e (ESI) 508 (MH⁺).

1-Butyl-4-[4-(4-methoxypiperidin-1-yl)-2-spiro[4.5]dec-8-ylphenyl]piperazine hydrochloride MS m/e (ESI) 468 (MH⁺).

1-[4-(4-Methoxypiperidin-1-yl)-2-spiro[4.5]dec-8-ylphenyl]-4-(tetrahydropyran-4-ylmethyl)piperazine hydrochloride MS m/e (ESI) 510 (MH⁺).

1-{4-[4-(4-Methoxypiperidin-1-yl)-2-spiro[4.5]dec-8-ylphenyl]piperazin-1-yl}butan-2-one hydrochloride MS m/e (ESI) 482 (MH⁺).

[2-Methoxy-4-(4-pentylpiperazin-1-yl)-5-(3,3,5,5-tetramethylcyclohexyl)phenyl]dimethylamine hydrochloride MS m/e (ESI) 444 (MH⁺).

[4-(4-Cyclopropylmethylpiperazin-1-yl)-2-methoxy-5-(3,3,5,5-tetramethylcyclohexyl)phenyl]dimethylamine hydrochloride MS m/e (ESI) 428 (MH⁺).

[2-Methoxy-4-[4-(tetrahydropyran-4-ylmethyl)piperazin-1-yl]-5-(3,3,5,5-tetramethylcyclohexyl)phenyl]dimethylamine hydrochloride MS m/e (ESI) 472 (MH⁺).

1-Cyclopropylmethyl-4-(4-piperidin-1-yl-2-spiro[4.5]dec-8-ylphenyl)piperazine hydrochloride MS m/e (ESI) 436 (MH⁺).

1-Propyl-4-(4-pyrrolidin-1-yl-2-spiro[4.5]dec-8-ylphenyl)piperazine hydrochloride MS m/e (ESI) 410 (MH⁺).

1-Cyclopropylmethyl-4-(4-pyrrolidin-1-yl-2-spiro[4.5]dec-8-ylphenyl)piperazine hydrochloride MS m/e (ESI) 422 (MH+).

1-[5-Methoxy-4-pyrrolidin-1-yl-2-(3,3,5,5-tetramethylcyclohexyl)phenyl]-4-propylpiperazine hydrochloride MS m/e (ESI) 442 (MH+).

cis-2,6-Dimethyl-4-[4-(4-propylpiperazin-1-yl)-3-spiro[4.5]dec-8-ylphenyl]morpholine hydrochloride MS m/e (ESI) 454 (MH+).

cis-4-[4-(4-Butylpiperazin-1-yl)-3-spiro[4.5]dec-8-ylphenyl]-2,6-dimethylmorpholine hydrochloride MS m/e (ESI) 468 (MH+).

cis-4-[4-(4-Cyclopropylmethylpiperazin-1-yl)-3-spiro[4.5]dec-8-ylphenyl]-2,6-dimethylmorpholine hydrochloride MS m/e (ESI) 466 (MH+).

4-[2-Ethoxy-4-(4-pentylpiperazin-1-yl)-5-(3,3,5,5-tetramethylcyclohex-1-enyl)phenyl]morpholine hydrochloride MS m/e (ESI) 498 (MH+).

4-[2-Ethoxy-4-[4-(tetrahydropyran-4-ylmethyl)piperazin-1-yl]-5-(3,3,5,5-tetramethylcyclohex-1-enyl)phenyl]morpholine hydrochloride MS m/e (ESI) 526 (MH+).

4-[2-Ethoxy-4-(4-propylpiperazin-1-yl)-5-(3,3,5,5-tetramethylcyclohexyl)phenyl]morpholine hydrochloride MS m/e (ESI) 472 (MH+).

1-Cyclopropylmethyl-4-[2-(3,3,5,5-tetramethylcyclohexyl)phenyl]-1,2,3,6-tetrahydropyridine hydrochloride MS m/e (ESI) 352 (MH+).

1-Propyl-4-[2-(3,3,5,5-tetramethylcyclohexyl)phenyl]piperidine hydrochloride

MS m/e (ESI) 342 (MH+).

1-Propyl-4-[2-(3,3,5,5-tetramethylcyclohex-1-enyl)phenyl]piperidine hydrochloride MS m/e (ESI) 340 (MH+).

1-Butyl-4-[2-(3,3,5,5-tetramethylcyclohex-1-enyl)phenyl]piperidine hydrochloride MS m/e (ESI) 354 (MH+).

1-Cyclopropylmethyl-4-[2-(3,3,5,5-tetramethylcyclohex-1-enyl)phenyl]piperidine hydrochloride MS m/e (ESI) 352 (MH+).

1-(2-Fluoroethyl)-4-[2-(3,3,5,5-tetramethylcyclohexyl)phenyl]piperidine hydrochloride MS m/e (ESI) 346 (MH+).

1-(3-Fluoropropyl)-4-[2-(3,3,5,5-tetramethylcyclohexyl)phenyl]piperidine hydrochloride MS m/e (ESI) 360 (MH+).

1-(4-Fluorobutyl)-4-[2-(3,3,5,5-tetramethylcyclohexyl)phenyl]piperidine hydrochloride MS m/e (ESI) 374 (MH+).

1-Cyclopropylmethyl-4-[4-methyl-2-(3,3,5,5-tetramethylcyclohexyl)phenyl]-1,2,3,6-tetrahydropyridine hydrochloride MS m/e (ESI) 366 (MH+).

1-Butyl-4-[4-methyl-2-(3,3,5,5-tetramethylcyclohexyl)phenyl]piperidine hydrochloride MS m/e (ESI) 370 (MH+).

1-Cyclopropylmethyl-4-[4-methyl-2-(3,3,5,5-tetramethylcyclohexyl)phenyl]piperidine hydrochloride MS m/e (ESI) 368 (MH+).

4-[4-Fluoro-2-(3,3,5,5-tetramethylcyclohexyl)phenyl]-1-propyl-1,2,3,6-tetrahydropyridine hydrochloride MS m/e (ESI) 358 (MH+).

1-Butyl-4-[4-fluoro-2-(3,3,5,5-tetramethylcyclohexyl)phenyl]-1,2,3,6-tetrahydropyridine hydrochloride MS m/e (ESI) 372 (MH+).

1-Cyclopropylmethyl-4-[4-fluoro-2-(3,3,5,5-tetramethylcyclohexyl)phenyl]-1,2,3,6-tetrahydropyridine hydrochloride MS m/e (ESI) 370 (MH+).

4-[4-Fluoro-2-(3,3,5,5-tetramethylcyclohexyl)phenyl]-1-propylpiperidine hydrochloride MS m/e (ESI) 360 (MH+).

1-Butyl-4-[4-fluoro-2-(3,3,5,5-tetramethylcyclohexyl)phenyl]piperidine hydrochloride MS m/e (ESI) 374 (MH+).

1-Cyclopropylmethyl-4-[4-fluoro-2-(3,3,5,5-tetramethylcyclohexyl)phenyl]piperidine hydrochloride MS m/e (ESI) 372 (MH+).

1-Propyl-3-[2-(3,3,5,5-tetramethylcyclohex-1-enyl)
phenyl]pyrrolidine hydrochloride MS m/e (ESI) 326 (MH+).

1-Butyl-3-[2-(3,3,5,5-tetramethylcyclohex-1-enyl)
phenyl]pyrrolidine hydrochloride MS m/e (ESI) 340 (MH+).

1-Cyclopropylmethyl-3-[2-(3,3,5,5-tetramethylcy-
clohex-1-enyl)phenyl]pyrrolidine hydrochloride MS m/e (ESI) 338 (MH+).

1-Propyl-3-[2-(3,3,5,5-tetramethylcyclohexyl)phe-
nyl]pyrrolidine hydrochloride

MS m/e (ESI) 328 (MH+).

1-Butyl-3-[2-(3,3,5,5-tetramethylcyclohexyl)phenyl]
pyrrolidine hydrochloride

MS m/e (ESI) 342 (MH+).

1-Cyclopropylmethyl-3-[2-(3,3,5,5-tetramethylcy-
clohexyl)phenyl]pyrrolidine hydrochloride MS m/e (ESI) 340 (MH+).

1-Cyclopropylmethyl-4-[5-fluoro-2-(3,3,5,5-tetram-
ethylcyclohex-1-enyl)phenyl]piperidine hydrochlo-
ride MS m/e (ESI) 370 (MH+).

4-[5-Fluoro-2-(3,3,5,5-tetramethylcyclohexylphe-
nyl]-1-propylpiperidine hydrochloride MS m/e (ESI) 360 (MH+).

1-Cyclopropylmethyl-4-[5-fluoro-2-(3,3,5,5-tetram-
ethylcyclohexyl)phenyl]piperidine hydrochloride MS m/e (ESI) 372 (MH+).

1-Propyl-4-[2-(3,3,5,5-tetramethylcyclohex-1-enyl)
phenyl]azepane hydrochloride

MS m/e (ESI) 354 (MH+).

1-Butyl-4-[2-(3,3,5,5-tetramethylcyclohex-1-enyl)
phenyl]azepane hydrochloride

MS m/e (ESI) 368 (MH+).

1-Cyclopropylmethyl-4-[2-(3,3,5,5-tetramethylcy-
clohex-1-enyl)phenyl]azepane hydrochloride MS m/e (ESI) 366 (MH+).

1-Propyl-4-[2-(3,3,5,5-tetramethylcyclohexyl)phe-
nyl]azepane hydrochloride

MS m/e (ESI) 356 (MH+).

1-Butyl-4-[2-(3,3,5,5-tetramethylcyclohexyl)phenyl]
azepane hydrochloride

MS m/e (ESI) 370 (MH+).

1-Cyclopropylmethyl-4-[2-(3,3,5,5-tetramethylcy-
clohexyl)phenyl]azepane hydrochloride MS m/e (ESI) 368 (MH+).

4-[3-Fluoro-2-(3,3,5,5-tetramethylcyclohexyl)phe-
nyl]-1-propyl-1,2,3,6-tetrahydropyridine hydrochlo-
ride MS m/e (ESI) 358 (MH+).

1-Cyclopropylmethyl-4-[3-fluoro-2-(3,3,5,5-tetram-
ethylcyclohexyl)phenyl]1,2,3,6-tetrahydropyridine
hydrochloride MS m/e (ESI) 370 (MH+).

4-[3-Fluoro-2-(3,3,5,5-tetramethylcyclohexyl)phe-
nyl]-1-propylpiperidine hydrochloride MS m/e (ESI) 360 (MH+).

1-Butyl-4-[3-fluoro-2-(3,3,5,5-tetramethylcyclo-
hexyl)phenyl]piperidine hydrochloride MS m/e (ESI) 374 (MH+).

1-Cyclopropylmethyl-4-[3-fluoro-2-(3,3,5,5-tetram-
ethylcyclohexyl)phenyl]piperidine hydrochloride MS m/e (ESI) 372 (MH+).

1-Butyl-4-[2-fluoro-6-(3,3,5,5-tetramethylcyclo-
hexyl)phenyl)piperidine hydrochloride MS m/e (ESI) 374 (MH+).

1-Butyl-4-[2-(4-t-butylcyclohex-1-enyl)phenyl]pip-
erazine hydrochloride

MS m/e (ESI) 355 (MH+).

1-Butyl-4-[2-(4-t-butylcyclohex-1-enyl)-5-fluo-
rophenyl]piperazine hydrochloride MS m/e (ESI) 373 (MH+).

1-Butyl-4-[2-(4-t-butylcyclohexyl)-5-trifluorometh-
ylphenyl]piperazine hydrochloride MS m/e (ESI) 425 (MH+).

1-Butyl-4-[5-t-butyl-2-(4-t-butylcyclohexyl)phenyl]
piperazine hydrochloride

MS m/e (ESI) 413 (MH+).

[4-(4-t-Butylcyclohexyl)-3-(4-butylpiperazine-1-yl)
phenyl]acetic acid

MS m/e (ESI) 413 (M−).

1-{4-[2-(4-t-Butylcyclohex-1-enyl)phenyl]piperazin-1-yl}butan-1-one

MS m/e (ESI) 391 (MNa$^+$).

2-{4-[2-(4-t-Butylcyclohex-1-enyl)phenyl]piperazin-1-yl}-N,N-dimethylacetamide hydrochloride MS m/e (ESI) 384 (MH$^+$).

1-[2-(4-t-Butylcyclohexyl)phenyl]-4-(propane-1-sulfonyl)piperazine

MS m/e (ESI) 429 (MNa$^+$).

2-{4-[2-(4-t-Butylcyclohexyl)phenyl]piperazin-1-yl}-1-phenylethanone hydrochloride MS m/e (ESI) 419 (MH$^+$).

1-Butyl-4-[2-(4-t-butylcyclohex-1-enyl)-4-piperidin-1-ylphenyl]piperazine hydrochloride MS m/e (ESI) 438 (MH$^+$).

1-Butyl-4-[2-(4-t-butylcyclohexyl)-4-piperidin-1-ylphenyl]piperazine hydrochloride MS m/e (ESI) 440 (MH$^+$).

1-Butyl-4-[2-(4-t-butylcyclohexyl)-5-methoxy-4-piperidin-1-ylphenyl]piperazine hydrochloride MS m/e (ESI) 470 (MH$^+$).

4-[5-(4-t-Butylcyclohexyl)-4-(4-butylpiperazine-1-yl)-2-methoxyphenyl]-2,6-cis-dimethylmorpholine hydrochloride MS m/e (ESI) 500 (MH$^+$).

1-[2-(4-t-Butylcyclohexyl)-4-(piperidin-1-yl)phenyl]-4-(tetrahydropyran-4-ylmethyl)piperazine hydrochloride MS m/e (ESI) 482 (MH$^+$).

1-{4-[2-(4-t-Butylcyclohexyl)-5-methoxy-4-(4-methoxypiperidin-1-yl)phenyl]piperazin-1-yl}butan-1-one MS m/e (ESI) 514 (MH$^+$).

1-[2-(4-t-Butylcyclohexyl)-5-methoxy-4-(4-methoxypiperidin-1-yl)phenyl]-4-(tetrahydropyran-4-ylmethyl)piperazine hydrochloride MS m/e (ESI) 542 (MH$^+$).

1-[2-(4-t-Butylcyclohexyl)-5-methoxy-4-(4-methoxypiperidin-1-yl)phenyl]-4-propylpiperazine hydrochloride MS m/e (ESI) 486 (MH$^+$).

1-[2-(4,4-Diethylcyclohex-1-enyl)-5-methoxyphenyl]-4-(tetrahydropyran-4-ylmethyl)piperazine hydrochloride MS m/e (ESI) 427 (MH$^+$).

[5-(4,4-Diethylcyclohexyl)-2-methoxy-4-(4-propylpiperazin-1-yl)phenyl]dimethylamine hydrochloride MS m/e (ESI) 416 (MH$^+$).

1-[5-Methoxy-2-(3,3,5,5-tetramethylcyclohex-1-enyl)phenyl]-4-pentylpiperazine hydrochloride MS m/e (ESI) 399 (MH$^+$).

1-[5-Methoxy-2-(3,3,5,5-tetramethylcyclohexyl)phenyl]-4-pentylpiperazine hydrochloride MS m/e (ESI) 401 (MH$^+$).

1-Pentyl-4-(2-spiro[4.5]dec-7-en-8-ylphenyl)piperazine hydrochloride

MS m/e (ESI) 367 (MH$^+$).

1-Pentyl-4-(2-spiro[4.5]dec-8-ylphenyl)piperazine hydrochloride

MS m/e (ESI) 369 (MH$^+$).

1-{4-[2-(4,4-Dimethylcyclohexyl)-5-methoxyphenyl]piperazin-1-yl}butan-2-one hydrochloride MS m/e (ESI) 373 (MH$^+$).

1-[4-(4-Morpholin-4-yl-2-spiro[4.5]dec-7-en-8-ylphenyl)piperazin-1-yl]butan-2-one hydrochloride MS m/e (ESI) 452 (MH$^+$).

4-[4-(4-Propylpiperazin-1-yl)-3-spiro[4.5]dec-8-ylphenyl]morpholine hydrochloride MS m/e (ESI) 426 (MH$^+$).

4-[4-(4-Pentylpiperazin-1-yl)-3-spiro[4.5]dec-8-ylphenyl]morpholine hydrochloride MS m/e (ESI) 454 (MH$^+$).

1-Cyclopropylmethyl-4-[4-(4-methoxypiperidin-1-yl)-2-spiro[4.5]dec-7-en-8-ylphenyl]piperazine hydrochloride MS m/e (ESI) 464 (MH$^+$).

1-{4-[4-(4-Methoxypiperidin-1-yl)-2-spiro[4.5]dec-7-en-8-ylphenyl]piperazin-1-yl}butan-2-one hydrochloride MS m/e (ESI) 480 (MH$^+$).

1-[4-(4-Methoxypiperidin-1-yl)-2-spiro[4.5]dec-8-ylphenyl]-4-pentylpiperazine hydrochloride MS m/e (ESI) 482 (MH$^+$).

1-Cyclopropylmethyl-4-[4-(4-methoxypiperidin-1-yl)-2-spiro[4.5]dec-8-ylphenyl]piperazine hydrochloride MS m/e (ESI) 466 (MH$^+$).

1-Butyl-4-(4-piperidin-1-yl-2-spiro[4.5]dec-8-ylphenyl)piperazine hydrochloride

MS m/e (ESI) 438 (MH$^+$).

1-(4-Piperidin-1-yl-2-spiro[4.5]dec-8-ylphenyl)-4-(tetrahydropyran-4-ylmethyl)piperazine hydrochloride MS m/e (ESI) 480 (MH$^+$).

1-(4-Pyrrolidin-1-yl-2-spiro[4.5]dec-8-ylphenyl)-4-(tetrahydropyran-4-ylmethyl)piperazine hydrochloride MS m/e (ESI) 466 (MH$^+$).

1-Butyl-4-[5-methoxy-4-pyrrolidin-1-yl-2-(3,3,5,5-tetramethylcyclohexyl)phenyl]piperazine hydrochloride MS m/e (ESI) 456 (MH$^+$).

cis-2,6-Dimethyl-4-{3-spiro[4.5]dec-8-yl-4-[4-(tetrahydropyran-4-ylmethyl)piperazin-1-yl]phenyl}morpholine hydrochloride MS m/e (ESI) 510 (MH$^+$).

4-[2-Ethoxy-4-(4-pentylpiperazin-1-yl)-5-(3,3,5,5-tetramethylcyclohexyl)phenyl]morpholine hydrochloride MS m/e (ESI) 500 (MH$^+$).

4-[4-(4-Cyclopropylmethylpiperazin-1-yl)-2-ethoxy-5-(3,3,5,5-tetramethylcyclohexyl)phenyl]morpholine hydrochloride MS m/e (ESI) 484 (MH$^+$).

1-Propyl-4-[2-(3,3,5,5-tetramethylcyclohex-1-enyl)-5-trifluoromethylphenyl]piperazine hydrochloride MS m/e (ESI) 409 (MH$^+$).

1-Cyclopropylmethyl-4-[2-(3,3,5,5-tetramethylcyclohex-1-enyl)-5-trifluoromethylphenyl]piperazine hydrochloride MS m/e (ESI) 421 (MH$^+$).

1-Cyclopropylmethyl-4-[2-(3,3,5,5-tetramethylcyclohexyl)-5-trifluoromethylphenyl]piperazine hydrochloride MS m/e (ESI) 423 (MH$^+$).

1-Propyl-4-[2-(3,3,5,5-tetramethylcyclohexyl)phenyl]-1,2,3,6-tetrahydropyridine hydrochloride MS m/e (ESI) 340 (MH$^+$).

1-Cyclopropylmethyl-4-[2-(3,3,5,5-tetramethylcyclohexyl)phenyl]piperidine hydrochloride MS m/e (ESI) 354 (MH$^+$).

1-Butyl-4-[4-methyl-2-(3,3,5,5-tetramethylcyclohexyl)phenyl]-1,2,3,6-tetrahydropyridine hydrochloride MS m/e (ESI) 368 (MH$^+$).

4-[5-Fluoro-2-(3,3,5,5-tetramethylcyclohex-1-enyl)phenyl]-1-propylpiperidine hydrochloride MS m/e (ESI) 358 (MH$^+$).

1-Butyl-4-[3-fluoro-2-(3,3,5,5-tetramethylcyclohexyl)phenyl]-1,2,3,6-tetrahydropyridine hydrochloride MS m/e (ESI) 372 (MH$^+$).

1-Butyl-4-[2-fluoro-6-(3,3,5,5-tetramethylcyclohexyl)phenyl]-1,2,3,6-tetrahydropyridine hydrochloride MS m/e (ESI) 372 (MH$^+$).

1-Butyl-4-[2-(4-t-butylcyclohexyl)-4,5-dimethoxyphenyl]piperazine hydrochloride

MS m/e (ESI) 417 (MH$^+$).

1-Butyl-4-[2-(4-t-butylcyclohexyl)-6-methoxyphenyl]piperazine hydrochloride

MS m/e (ESI) 387 (MH$^+$).

1-Butyl-4-[2-(4-t-butylcyclohex-1-enyl)-5-methoxyphenyl]piperazine hydrochloride MS m/e (ESI) 385 (MH$^+$).

1-Butyl-4-[2-(4-t-butylcyclohexyl)-5-ethoxyphenyl]piperazine hydrochloride

MS m/e (ESI) 401 (MH$^+$).

1-[2-(4,4-Dimethylcyclohex-1-enyl)phenyl]-4-propylpiperazine hydrochloride

MS m/e (ESI) 313 (MH$^+$).

1-Butyl-4-[2-(4,4-dimethylcyclohexyl)phenyl]piperazine hydrochloride

MS m/e (ESI) 329 (MH$^+$).

1-[2-(4,4-Dimethylcyclohexyl)phenyl]-4-propylpiperazine hydrochloride

MS m/e (ESI) 315 (MH$^+$).

1-{4-[2-(4,4-Dimethylcyclohexyl)phenyl]piperazin-1-yl}butan-1-one

MS m/e (ESI) 343 (MH$^+$).

1-Butyl-4-(2-cyclohex-1-enylphenyl)piperazine hydrochloride

MS m/e (ESI) 299 (MH$^+$).

{4-[2-(4-t-Butylcyclohexyl)phenyl]piperazin-1-yl}acetonitrile hydrochloride

MS m/e (ESI) 340 (MH$^+$).

2-{4-[2-(4-t-Butylcyclohex-1-enyl)-4-morpholin-4-ylphenyl]piperazin-1-yl}-N-ethylacetamide hydrochloride MS m/e (ESI) 469 (MH$^+$).

4-[3-(4-t-Butylcyclohexyl)-4-(4-pentylpiperazin-1-yl)phenyl]morpholine hydrochloride MS m/e (ESI) 456 (MH$^+$).

4-[3-(4-t-Butylcyclohex-1-enyl)-4-(4-propylpiperazin-1-yl)phenyl]morpholine hydrochloride MS m/e (ESI) 426 (MH$^+$).

4-[3-(4-t-Butylcyclohexyl)-4-(4-propylpiperazin-1-yl)phenyl]morpholine hydrochloride MS m/e (ESI) 428 (MH$^+$).

4-{3-(4-t-Butylcyclohexyl)-4-[4-(3-methylbutyl)piperazin-1-yl]phenyl}morpholine hydrochloride MS m/e (ESI) 456 (MH$^+$).

4-{3-(4-t-Butylcyclohexyl)-4-[4-(tetrahydropyran-4-ylmethyl)piperazin-1-yl]phenyl}morpholine hydrochloride MS m/e (ESI) 484 (MH$^+$).

1-[2-(4-t-Butylcyclohexyl)phenyl]-4-(2-ethoxyethyl)piperazine hydrochloride

MS m/e (ESI) 373 (MH$^+$).

1-[2-(4-t-Butylcyclohex-1-enyl)phenyl]-4-(2-ethoxyethyl)piperazine hydrochloride MS m/e (ESI) 371 (MH$^+$).

4-{3-(4-t-Butylcyclohex-1-enyl)-4-[4-(3-methylbutyl)piperazin-1-yl]phenyl}morpholine hydrochloride MS m/e (ESI) 454 (MH$^+$).

4-{3-(4-t-Butylcyclohex-1-enyl)-4-[4-(tetrahydropyran-4-ylmethyl)piperazin-1-yl]phenyl}morpholine hydrochloride MS m/e (ESI) 482 (MH$^+$).

1-[2-(4-t-Butylcyclohexyl)phenyl]-4-(tetrahydrofuran-3-ylmethyl)piperazine hydrochloride MS m/e (ESI) 385 (MH$^+$).

1-Butyl-4-[2-(4,4-dimethylcyclohexyl)-4-(4-methoxypiperidin-1-yl)phenyl]piperazine hydrochloride MS m/e (ESI) 442 (MH$^+$).

1-[2-(4-t-Butylcyclohex-1-enyl)phenyl]-4-(tetrahydropyran-4-ylmethyl)piperazine hydrochloride MS m/e (ESI) 397 (MH$^+$).

1-Butyl-4-[2-(4,4-dimethylcyclohexyl)-4-piperidin-1-ylphenyl]piperazine hydrochloride MS m/e (ESI) 412 (MH$^+$).

[4-(4-Butylpiperazin-1-yl)-3-(4,4-dimethylcyclohexyl)phenyl]dimethylamine hydrochloride MS m/e (ESI) 372 (MH$^+$).

1-[2-(4,4-Dimethylcyclohexyl)phenyl]-4-(tetrahydropyran-4-ylmethyl)piperazine hydrochloride MS m/e (ESI) 371 (MH$^+$).

1-Propyl-4-(2-spiro[2.5]oct-5-en-6-ylphenyl)piperazine hydrochloride

MS m/e (ESI) 311 (MH$^+$).

1-Cyclopropylmethyl-4-(2-spiro[2.5]oct-5-en-6-ylphenyl)piperazine hydrochloride

MS m/e (ESI) 323 (MH$^+$).

1-Propyl-4-(2-spiro[2.5]oct-6-ylphenyl)piperazine hydrochloride

MS m/e (ESI) 313 (MH$^+$).

1-Cyclopropylmethyl-4-(2-spiro[2.5]oct-6-ylphenyl)piperazine hydrochloride

MS m/e (ESI) 325 (MH$^+$).

1-(2-Spiro[2.5]oct-6-ylphenyl)-4-(tetrahydropyran-4-ylmethyl)piperazine hydrochloride MS m/e (ESI) 369 (MH$^+$).

1-Butyl-4-(2-spiro[2.5]oct-6-ylphenyl)piperazine hydrochloride

MS m/e (ESI) 327 (MH$^+$).

1-[4-(2-Spiro[2.5]oct-6-ylphenyl)piperazin-1-yl]butan-2-one hydrochloride

MS m/e (ESI) 341 (MH$^+$).

1-Pentyl-4-(2-spiro[2.5]oct-5-en-6-ylphenyl)piperazine hydrochloride

MS m/e (ESI) 339 (MH$^+$).

1-Pentyl-4-(2-spiro[2.5]oct-6-ylphenyl)piperazine hydrochloride

MS m/e (ESI) 341 (MH$^+$).

1-Butyl-4-[4-(4-methoxypiperidin-1-yl)-2-spiro[2.5]oct-6-ylphenyl]piperazine hydrochloride MS m/e (ESI) 440 (MH$^+$).

1-Butyl-4-[4-(4-ethoxypiperidin-1-yl)-2-spiro[2.5]oct-6-ylphenyl]piperazine hydrochloride MS m/e (ESI) 454 (MH$^+$).

1-Butyl-4-(4-piperidin-1-yl-2-spiro[2.5]oct-6-ylphenyl)piperazine hydrochloride

MS m/e (ESI) 410 (MH$^+$).

1-[2-(4,4-Dimethylcyclohexyl)-4-(4-ethoxypiperidin-1-yl)phenyl]-4-pentylpiperazine hydrochloride MS m/e (ESI) 470 (MH$^+$).

1-[2-(4,4-Dimethylcyclohexyl)-4-(4-ethoxypiperidin-1-yl)phenyl]-4-propylpiperazine hydrochloride MS m/e (ESI) 442 (MH$^+$).

1-Cyclopropylmethyl-4-[2-(4,4-dimethylcyclohexyl)-4-(4-ethoxypiperidin-1-yl)phenyl]piperazine hydrochloride MS m/e (ESI) 454 (MH$^+$).

1-[2-(4,4-Dimethylcyclohexyl)-4-(4-ethoxypiperidin-1-yl)phenyl]-4-(tetrahydropyran-4-ylmethyl)piperazine hydrochloride MS m/e (ESI) 498 (MH$^+$).

1-Butyl-4-(4-pyrrolidin-1-yl-2-spiro[2.5]oct-6-ylphenyl)piperazine hydrochloride MS m/e (ESI) 396 (MH$^+$).

1-(4-Piperidin-1-yl-2-spiro[2.5]oct-6-ylphenyl)-4-propylpiperazine hydrochloride MS m/e (ESI) 396 (MH$^+$).

1-Cyclopropylmethyl-4-(4-piperidin-1-yl-2-spiro[2.5]oct-6-ylphenyl)piperazine hydrochloride MS m/e (ESI) 408 (MH$^+$).

1-(4-Piperidin-1-yl-2-spiro[2.5]oct-6-ylphenyl)-4-(tetrahydropyran-4-ylmethyl)piperazine hydrochloride MS m/e (ESI) 452 (MH$^+$).

1-(2-Ethoxyethyl)-4-(4-piperidin-1-yl-2-spiro[2.5]oct-6-ylphenyl)piperazine hydrochloride MS m/e (ESI) 426 (MH$^+$).

1-(2-Methoxyethyl)-4-(4-piperidin-1-yl-2-spiro[2.5]oct-6-ylphenyl)piperazine hydrochloride MS m/e (ESI) 412 (MH$^+$).

1-Cyclobutylmethyl-4-[2-(4,4-dimethylcyclohexyl)-4-(4-ethoxypiperidin-1-yl)phenyl]piperazine hydrochloride MS m/e (ESI) 468 (MH$^+$).

cis-2,6-Dimethyl-4-[4-(4-pentylpiperazin-1-yl)-3-spiro[2.5]oct-6-ylphenyl]morpholine hydrochloride MS m/e (ESI) 454 (MH$^+$).

cis-4-[4-(4-Butylpiperazin-1-yl-3-spiro[2.5]oct-6-ylphenyl]-2,6-dimethylmorpholine hydrochloride MS m/e (ESI) 440 (MH$^+$).

cis-4-[4-(4-Cyclopropylmethylpiperazin-1-yl)-3-spiro[2.5]oct-6-ylphenyl]-2,6-dimethylmorpholine hydrochloride MS m/e (ESI) 438 (MH$^+$).

cis-2,6-Dimethyl-4-{3-spiro[2.5]oct-6-yl-4-[4-(tetrahydropyran-4-ylmethyl)piperazin-1-yl]phenyl}morpholine hydrochloride MS m/e (ESI) 482 (MH$^+$).

1-[4-(4-Methoxypiperidin-1-yl)-2-spiro[2.5]oct-6-ylphenyl]-4-pentylpiperazine hydrochloride MS m/e (ESI) 454 (MH$^+$).

1-Butyl-4-(2-cyclopent-1-enylphenyl)piperazine hydrochloride

MS m/e (ESI) 285 (MH$^+$).

2-Methyl-1-{4-[2-(3,3,5,5-tetramethylcyclohexyl)phenyl]piperazin-1-yl}propan-2-ol hydrochloride MS m/e (ESI) 373 (MH$^+$).

4-[2-(4,4-Dimethylcyclohex-1-enyl)phenyl]piperazine-1-carboxylic acid ethyl ester MS m/e (ESI) 343 (MH$^+$).

1-{4-[2-(4,4-Dimethylcyclohex-1-enyl)phenyl]piperazin-1-yl}butan-1-one

MS m/e (ESI) 341 (MH$^+$).

4-[4-(4-Butylpiperazin-1-yl)-3-cyclohex-1-enylphenyl]morpholine hydrochloride

MS m/e (ESI) 384 (MH$^+$).

1-[2-(4,4-Dimethylcyclohexyl)phenyl]-4-(2-methoxyethyl)piperazine hydrochloride

MS m/e (ESI) 331 (MH$^+$).

4-{3-(4-t-Butylcyclohexyl)-4-[4-(4,4,4-trifluorobutyl)piperazin-1-yl]phenyl}morpholine hydrochloride MS m/e (ESI) 496 (MH$^+$).

4-{3-(4-t-Butylcyclohex-1-enyl)-4-[4-(4,4,4-trifluorobutyl)piperazin-1-yl]phenyl}morpholine hydrochloride MS m/e (ESI) 494 (MH$^+$).

4-[3-(4-t-Butylcyclohexyl)-4-(4-isobutylpiperazine-1-yl)phenyl]morpholine hydrochloride MS m/e (ESI) 442 (MH$^+$).

4-[3-(4-t-Butylcyclohexyl)-4-(4-cyclohexylmethylpiperazin-1-yl)phenyl]morpholine hydrochloride MS m/e (ESI) 482 (MH$^+$).

4-{3-(4-t-Butylcyclohexyl)-4-[4-(2-ethylbutyl)piperazin-1-yl]phenyl}morpholine hydrochloride MS m/e (ESI) 470 (MH$^+$).

1-[4-(2-Spiro[2.5]oct-5-en-6-ylphenyl)piperazin-1-yl]butan-2-one hydrochloride

MS m/e (ESI) 339 (MH$^+$).

4-[4-(4-Butylpiperazin-1-yl)-3-spiro[2.5]oct-6-ylphenyl]morpholine hydrochloride MS m/e (ESI) 412 (MH$^+$).

1-[2-(4,4-Dimethylcyclohexyl)-4-(4-ethoxypiperidin-1-yl)phenyl]-4-isobutylpiperazinee hydrochloride MS m/e (ESI) 456 (MH$^+$).

1-Pentyl-4-(4-piperidin-1-yl-2-spiro[2.5]oct-6-ylphenyl)piperazine hydrochloride MS m/e (ESI) 424 (MH$^+$).

1-Isobutyl-4-(4-piperidin-1-yl-2-spiro[2.5]oct-6-ylphenyl)piperazine hydrochloride MS m/e (ESI) 410 (MH$^+$).

1-Cyclobutylmethyl-4-(4-piperidin-1-yl-2-spiro[2.5]oct-6-ylphenyl)piperazine hydrochloride MS m/e (ESI) 422 (MH$^+$).

1-[2-(4,4-Dimethylcyclohexyl)-4-(4-ethoxypiperidin-1-yl)phenyl]-4-(2-ethoxyethyl)piperazine hydrochloride MS m/e (ESI) 472 (MH$^+$).

1-[2-(4,4-Dimethylcyclohexyl)-4-(4-ethoxypiperidin-1-yl)phenyl]-4-(2-methoxyethyl)piperazine hydrochloride MS m/e (ESI) 458 (MH$^+$).

cis-2,6-Dimethyl-4-[4-(4-propylpiperazin-1-yl)-3-spiro[2.5]oct-6-ylphenyl]morpholine hydrochloride MS m/e (ESI) 426 (MH$^+$).

cis-4-[4-(4-Isobutylpiperazine-1-yl)-3-spiro[2.5]oct-6-ylphenyl]-2,6-dimethylmorpholine hydrochloride MS m/e (ESI) 440 (MH$^+$).

1-Isobutyl-4-[4-(4-methoxypiperidin-1-yl)-2-spiro[2.5]oct-6-ylphenyl]piperazine hydrochloride MS m/e (ESI) 440 (MH$^+$).

1-Cyclopropylmethyl-4-[4-(4-methoxypiperidin-1-yl)-2-spiro[2.5]oct-6-ylphenyl]piperazine hydrochloride MS m/e (ESI) 438 (MH$^+$).

1-4-[4-(4-Methoxypiperidin-1-yl)-2-spiro[2.5]oct-6-ylphenyl]-4-(tetrahydropyran-4-ylmethyl)piperazine hydrochloride MS m/e (ESI) 482 (MH$^+$).

1-(4-Bromo-2-spiro[2.5]oct-6-ylphenyl)-4-butylpiperazine

MS m/e (ESI) 405 (MH$^+$).

1-Butyl-4-(2-cyclopentylphenyl)piperazine hydrochloride

MS m/e (ESI) 287 (MH$^+$).

1-(2-Cyclopentylphenyl)-4-propylpiperazine hydrochloride

MS m/e (ESI) 273 (MH$^+$).

1-(2-Cyclopentylphenyl)-4-cyclopropylmethylpiperazine hydrochloride

MS m/e (ESI) 285 (MH$^+$).

1-[4-{2-(4-t-Butylcyclohexyl)phenyl}piperazin-1-yl]-2-cyclohexylethanone

MS m/e (ESI) 425 (MH$^+$).

2-[4-{2-(4,4-Dimethylcyclohexyl)phenyl}piperazin-1-yl]cyclohexanone hydrochloride MS m/e (ESI) 369 (MH$^+$).

3-[4-{2-(4-t-Butylcyclohexyl)phenyl}piperazin-1-yl]piperidin-2-one hydrochloride MS m/e (ESI) 398 (MH$^+$).

2-{4-[2-(4-t-Butylcyclohexyl)phenyl}piperazin-1-yl]-N-(2-fluoroethyl)acetamide hydrochloride MS m/e (ESI) 404 (MH$^+$).

4-{3-(4-t-Butylcyclohexyl)-4-[4-(2-methoxyethyl)piperazin-1-yl]phenyl}morpholine hydrochloride MS m/e (ESI) 444 (MH$^+$).

2-{4-[2-(4-t-Butylcyclohexyl)phenyl]piperazin-1-yl}-1-phenylethanol hydrochloride MS m/e (ESI) 421 (MH+).

1-{4-[2-(4-t-Butylcyclohex-1-enyl)-4-morpholin-4-ylphenyl]piperazin-1-yl}butan-2-one hydrochloride MS m/e (ESI) 454 (MH+).

4-[3-(4-t-Butylcyclohex-1-enyl)-4-(4-cyclopropylmethylpiperazin-1-yl)phenyl]morpholine hydrochloride MS m/e (ESI) 438 (MH+).

1-Butyl-4-[2-(4-t-butylcyclohex-1-enyl)-4-(2,5-dimethylpyrrol-1-yl)phenyl]piperazine hydrochloride MS m/e (ESI) 448 (MH+).

4-[3-(4-t-Butylcyclohexyl)-4-[4-[2-(tetrahydropyran-4-yl)ethyl]piperazin-1-yl]phenyl]morpholine hydrochloride MS m/e (ESI) 498 (MH+).

1-[4-Bromo-2-(4-t-butylcyclohexyl)phenyl]-4-butylpiperazine hydrochloride

MS m/e (ESI) 435 (MH+).

4-[5-(4-t-Butylcyclohexyl)-4-(4-butylpiperazine-1-yl)-2-methoxyphenyl]morpholine hydrochloride MS m/e (ESI) 472 (MH+).

4-[3-(4-t-Butylcyclohexyl)-4-[4-(2-ethylbutyl)piperazin-1-yl]phenyl]morpholine hydrochloride MS m/e (ESI) 470 (MH+).

4-[3-(4-t-Butylcyclohex-1-enyl)-4-(4-isobutylpiperazine-1-yl)phenyl]morpholine hydrochloride MS m/e (ESI) 440 (MH+).

1-[2-(4-t-Butylcyclohexyl)phenyl]-4-(3-methylbutyl)piperazine hydrochloride

MS m/e (ESI) 371 (MH+).

1-[2-(4-t-Butylcyclohexyl)phenyl]-4-(tetrahydropyran-4-ylmethyl)piperazine hydrochloride MS m/e (ESI) 399 (MH+).

1-{2-(4-t-Butylcyclohexyl)phenyl}-4-(3-methylsulfonylpropyl)piperazine hydrochloride MS m/e (ESI) 389 (MH+).

1-[2-(4-t-Butylcyclohexyl)phenyl]-4-thiophen-3-ylmethylpiperazine hydrochloride

MS m/e (ESI) 397 (MH+).

4-[5-(4-t-Butylcyclohexyl)-2-methoxy-4-[4-(tetrahydropyran-4-ylmethyl)piperazin-1-yl]phenyl]morpholine hydrochloride MS m/e (ESI) 514 (MH+).

4-[3-(4-t-Butylcyclohexyl)-4-(4-butylpiperazin-1-yl)phenyl]-1-methylpiperazine dihydrochloride MS m/e (ESI) 455 (MH+).

4-[4-(4-t-Butylcyclohexyl)-3-[4-(tetrahydropyran-4-ylmethyl)piperazin-1-yl]phenyl]morpholine hydrochloride MS m/e (ESI) 484 (MH+).

4-[3-(4-t-Butylcyclohexyl)-4-(4-cyclopentylmethylpiperazin-1-yl)phenyl]morpholine hydrochloride MS m/e (ESI) 468 (MH+).

4-[3-(4-t-Butylcyclohex-1-enyl)-4-(4-cyclopentylmethylpiperazin-1-yl)phenyl]morpholine hydrochloride MS m/e (ESI) 466 (MH+).

1-[2-(4-t-Butylcyclohexyl)phenyl]-4-cyclopentylmethylpiperazine hydrochloride

MS m/e (ESI) 383 (MH+).

1-Butyl-4-[2-(4,4-dimethylcyclohexyl)-4-(4-methylpiperidin-1-yl)phenyl]piperazine hydrochloride MS m/e (ESI) 426 (MH+).

1-[2-(4-t-Butylcyclohex-1-enyl)phenyl]-4-pentylpiperazine hydrochloride

MS m/e (ESI) 369 (MH+).

1-Butyl-4-[2-(4-t-butylcyclohex-1-enyl)-5-pyrrolidin-1-ylphenyl]piperazine hydrochloride MS m/e (ESI) 424 (MH+).

1-Butyl-4-[2-(4-t-butylcyclohexyl)-5-pyrrolidin-1-ylphenyl]piperazine hydrochloride MS m/e (ESI) 426 (MH+).

1-Butyl-4-[2-(4,4-dimethylcyclohexyl)-4-(3,3-dimethylpiperidin-1-yl)phenyl]piperazine hydrochloride MS m/e (ESI) 440 (MH+).

1-(2-Spiro[5.5]undec-2-en-3-ylphenyl)-4-(tetrahydropyran-4-ylmethyl)piperazine hydrochloride MS m/e (ESI) 409 (MH+).

1-Cyclopropylmethyl-4-[2-(4,4-dimethylcyclohex-1-enyl)-4-(4-methoxypiperidin-1-yl)phenyl]piperazine hydrochloride MS m/e (ESI) 438 (MH+).

1-[2-(4,4-Dimethylcyclohex-1-enyl)-4-(4-methoxypiperidin-1-yl)phenyl]-4-furan-2-ylmethylpiperazine hydrochloride MS m/e (ESI) 464 (MH$^+$).

N-Ethyl-2-[4-[4-(4-methoxypiperidin-1-yl)-2-(3,3,5,5-tetramethylcyclohexyl)phenyl]piperazin-1-yl]acetamide hydrochloride MS m/e (ESI) 499 (MH$^+$).

[4-[2-(4,4-Diethylcyclohexyl)phenyl]piperazin-1-yl]morpholin-4-ylmethanone

MS m/e (ESI) 414 (MH$^+$).

1-[4-(4-Propylpiperazin-1-yl)-3-(3,3,1,5,5-tetramethylcyclohexyl)phenyl]azepane hydrochloride MS m/e (ESI) 440 (MH$^+$).

1-[4-(4-Butylpiperazin-1-yl)-3-(4,4-dimethylcyclohexyl)phenyl]azocane hydrochloride MS m/e (ESI) 440 (MH$^+$).

1-[2-(4,4-Dimethylcyclohexyl)-4-piperidin-1-ylphenyl]-4-furan-3-ylmethylpiperazine hydrochloride MS m/e (ESI) 436 (MH$^+$).

1-[4-{2-(4-Ethylcyclohex-3-enyl)-4-morpholin-4-ylphenyl}piperazin-1-yl]butan-2-one hydrochloride MS m/e (ESI) 426 (MH$^+$).

1-[4-(4-Bromopiperidin-1-yl)-2-(4,4-dimethylcyclohexyl)phenyl]-4-propylpiperazine hydrochloride MS m/e (ESI) 504 (MH$^+$).

1-Cyclopropylmethyl-4-[4-fluoro-2-(3,3,5,5-tetramethylcyclohexyl)phenyl]piperazine hydrochloride MS m/e (ESI) 373 (MH$^+$).

1-Cyclopropylmethyl-4-[4-[1,3,4]oxadiazol-2-yl-2-(3,3,5,5-tetramethylcyclohex-1-enyl)phenyl]piperazine hydrochloride MS m/e (ESI) 421 (MH$^+$).

1-Cyclohexylmethyl-4-[2-(3,3,5,5-tetramethylcyclohexyl)phenyl]piperazine hydrochloride MS m/e (ESI) 397 (MH$^+$).

1-(2-Ethylbutyl)-4-[2-(3,3,5,5-tetramethylcyclohexyl)phenyl]piperazine hydrochloride MS m/e (ESI) 385 (MH$^+$).

1-[5-[1,3,4]Oxadiazol-2-yl-2-(3,3,5,5-tetramethylcyclohex-1-enyl)phenyl]-4-propylpiperazine hydrochloride MS m/e (ESI) 409 (MH$^+$).

1-Methyl-4-[2-(3,3,5,5-tetramethylcyclohexyl)phenyl]piperazine hydrochloride

MS m/e (ESI) 315 (MH$^+$).

1-Ethyl-4-[2-(3,3,5,5-tetramethylcyclohexyl)phenyl]piperazine hydrochloride

MS m/e (ESI) 329 (MH$^+$).

1-Pyridin-4-ylmethyl-4-[2-(3,3,5,5-tetramethylcyclohexyl)phenyl]piperazine hydrochloride MS m/e (ESI) 392 (MH$^+$).

3-(4-Propylpiperazin-1-yl)-4-(3,3,5,5-tetramethylcyclohexyl)phenol hydrochloride MS m/e (ESI) 359 (MH$^+$).

3-(4-Butylpiperazin-1-yl)-4-(3,3,5,5-tetramethylcyclohexyl)phenol hydrochloride

MS m/e (ESI) 373 (MH$^+$).

3-(4-Cyclopropylmethylpiperazin-1-yl)-4-(3,3,5,5-tetramethylcyclohexyl)phenol hydrochloride MS m/e (ESI) 371 (MH$^+$).

1-Cyclopropylmethyl-4-[4-(6-methoxypyridin-2-yl)-2-(3,3,5,5-tetramethylcyclohexyl)phenyl]piperazine dihydrochloride MS m/e (ESI) 462 (MH$^+$).

2-[4-[2-(3,3,5,5-Tetramethylcyclohexyl)phenyl]piperazin-1-ylmethyl]cyclopropanecarboxylic acid hydrochloride MS m/e (ESI) 399 (MH$^+$).

1-(2-Methanesulfonylethyl)-4-{2-(3,3,5,5-tetramethylcyclohexyl)phenyl}piperazine hydrochloride MS m/e (ESI) 407 (MH$^+$).

1-Cyclopropylmethyl-4-[2-(3,3,5,5-tetramethylcyclohex-1-enyl)phenyl]-[4]diazepane hydrochloride MS m/e (ESI) 367 (MH$^+$).

1-[2-(3,3,5,5-Tetramethylcyclohexyl)phenyl]-4-(3,3,3-trifluoropropyl)piperazine hydrochloride MS m/e (ESI) 397 (MH$^+$).

Methyl-[2-[4-{2-(3,3,5,5-tetramethylcyclohexyl)phenyl}piperazin-1-yl]ethyl]amine dihydrochloride MS m/e (ESI) 358 (MH$^+$).

Dimethyl-{2-[4-{2-(3,3,5,5-tetramethylcyclohexyl)phenyl}piperazin-1-yl]ethyl}amine dihydrochloride MS m/e (ESI) 372 (MH$^+$).

2-Propyl-5-[2-(3,3,5,5-tetramethylcyclohex-1-enyl)
phenyl]-2,5-diazabicyclo[2.2.1]heptane hydrochloride MS m/e (ESI) 353 (MH$^+$).

2-Cyclopropylmethyl-5-[2-(3,3,5,5-tetramethylcyclohex-1-enyl)phenyl]-2,5-diazabicyclo[2.2.1]heptane hydrochloride MS m/e (ESI) 365 (MH$^+$).

1-{4-[2-(3,3,5,5-Tetramethylcyclohexyl)phenyl]piperazin-1-ylmethyl}cyclopropanol hydrochloride MS m/e (ESI) 371 (MH$^+$).

1-(Tetrahydropyran-4-yl)-4-[2-(3,3,5,5-tetramethylcyclohexyl)phenyl]piperazine hydrochloride MS m/e (ESI) 385 (MH$^+$).

1-[4-Fluoromethyl-2-(3,3,5,5-tetramethylcyclohexyl)phenyl]-4-propylpiperazine hydrochloride MS m/e (ESI) 375 (MH$^+$).

1-(Tetrahydropyran-4-ylmethyl)-4-[2-(3,3,4,4-tetramethylcyclopent-1-enyl)phenyl]piperazine hydrochloride MS m/e (ESI) 383 (MH$^+$).

2-[4-[2-(4-t-Butylcyclohexyl)phenyl]piperazin-1-yl]-N-pyridin-2-ylacetamide dihydrochloride MS m/e (ESI) 435 (MH$^+$).

Test Example 1

Evaluation of Compounds in Jurkat Cell Adhesion System

<Immobilization of Human Fibronectin in 96-Well Plate>

Human fibronectin (Becton Dickinson Biosciences) was diluted with phosphate-buffered saline (hereinafter abbreviated as PBS; Sigma) to 0.1-0.01 μg/ml, and the diluted solution was added to a 96-well plate (Becton Dickinson) at 50μl/well, and allowed to stand overnight at 4° C. On the following day, the supernatant was removed from the plate, and then PBS containing 1% bovine serum albumin (hereinafter abbreviated as BSA; Sigma) was added thereto at 100 μl/well and incubation was performed at 37° C. for 2 hours in a CO$_2$ incubator (Hirasawa).

<Adhesion Assay>

The supernatant was removed from each plate and Jurkat cells suspended in RPMI-1640 (Sigma) containing 1 mg/ml BSA were added at 80 μl/well for 2.5×10$^5$ cells/well. The compound diluted to different concentrations with RPMI-1640 containing 1 mg/ml BSA was immediately added at 10 μl/well, and then 100 nM phorbol myristate acetate (hereinafter abbreviated as PMA; Sigma) in RPMI-1640 containing 1 mg/ml BSA was added at 10 μl/well and the plate was incubated in a CO$_2$ incubator at 37° C. for 45-60 minutes. The supernatant was removed from the plate and each well was washed several times with 100 μl/well of RPMI-1640, after which 50 mM citrate buffer (pH 5.0) containing 3.75 mM p-nitrophenol-N-acetyl-β-D-glucosaminide (Sigma) and 0.25% Triton X-100 (Sigma) were added at 60 μl/well, and the mixture was placed in a CO$_2$ incubator and incubated at 37° C. for 45 minutes. After incubation, 50 mM glycine buffer (pH 10.4) containing 5 mM EDTA was added at 90 μl/well, and the absorbance at 405 nm was measured with an EL340 Automated Microplate Reader (BIO-TEK) to determine the adhered cell count. The concentration of each compound which inhibited the increase in the number of adhered cells by the PMA-stimulation by 50% was recorded as the IC50 (μM).

TABLE 1

| Example | IC50 (μM) |
|---|---|
| 1 | 4.5 |
| 7 | 2.5 |
| 8 | 2.2 |
| 9 | 3.1 |
| 10 | 4.7 |
| 12 | 3.1 |
| 13 | 3.9 |
| 14 | 4.9 |
| 15 | 2.3 |
| 17 | 6.1 |
| 18 | 2.6 |
| 19 | 6.2 |
| 20 | 7.7 |
| 22 | 2.2 |
| 28 | 3.1 |
| 30 | 5.5 |
| 31 | 4.5 |
| 32 | 3.6 |
| 47 | 5.0 |
| 48 | 7.9 |
| 69 | 3.6 |
| 85 | 6.4 |
| 103 | 4.5 |
| 117 | 4.7 |

Test Example 2

Evaluation of Compounds in Human Peripheral Blood Neutrophil Adhesion System

<Preparation of Human Peripheral Blood Neutrophils>

To a plastic centrifugation tube containing 100 units of heparin sodium (Shimizu Pharmaceutical) was added 25 ml of fresh blood sampled from a healthy human. After adding and mixing therewith 8 ml of physiological saline (Otsuka Pharmaceutical) containing 6% Dextran (Nacalai), the mixture was allowed to stand room temperature for 45 minutes for sedimentation of the erythrocytes. The resultant supernatant was transferred to another plastic centrifugation tube and combined with an equivalent volume of phosphate-buffered saline (hereinafter abbreviated as PBS; Sigma), and then centrifuged at 1600 rpm for 7 minutes at room temperature. The obtained hematocyte fraction was suspended in 4 ml of PBS, and the suspension was superposed on 4 ml of Ficoll-Paque™ PLUS (Amersham Biosciences). The resultant bilayer liquid was centrifuged at 2000 rpm for 30 minutes at room temperature, after which the supernatant was removed and the precipitate was suspended in 10 ml of PBS and centrifuged at 1200 rpm for 7 minutes, and the supernatant was removed. The resulting precipitate was suspended in 0.5 ml of PBS again, and then 10 ml of distilled water (Otsuka Pharmaceutical) was added, 0.5 ml of an aqueous solution containing 3 M NaCl was immediately added to restore isotonicity, the mixture was centrifuged at 1200 rpm for 7 minutes, and the obtained precipitate was suspended in PBS containing 1 mg/ml bovine serum albumin (hereinafter abbreviated as BSA; Sigma) again and stored in ice until being used for the experiment.

<Fluorescent Labeling of Human Peripheral Blood Neutrophils>

The obtained neutrophils were suspended in PBS containing 1 mg/ml BSA at $2\times10^7$ cells/ml. BCECF-AM (Dojin) was added to a final concentration of 5 µM, and the mixture was incubated at 37° C. for 45 minutes. It was then rinsed twice with PBS containing 1 mg/ml BSA by centrifugation, suspended again in PBS containing 1 mg/ml BSA at $5\times10^7$ cells/ml, and stored in ice until use.

<Preparation of HUVEC Immobilized Plate>

Human umbilical vein endothelial cells (hereinafter abbreviated as HUVEC) were suspended in MCDB131 medium (Chlorella Industries) containing 10% fetal calf serum and 30 µg/ml endothelial cell growth supplement (Becton Dickinson Bioscience). The suspension was added at $7.5\times10^3$ cells/well to a 96-well plate (Iwaki) immobilized with type I collagen, and cultured for 3 days in a $CO_2$ incubator (Hirasawa). Upon confirming confluency of the cells, the supernatant was discarded, the plate was rinsed twice with PBS, and then PBS containing 0.1% glutaraldehyde (Kanto Kagaku) was added at 100 µl/well and the HUVECs were immobilized for 5 minutes. The supernatant was discarded and the plate was washed twice with PBS, and then PBS was added at 100 µl/well and the mixture was stored at 4° C. until use.

<Adhesion Assay>

To 6.5 ml of RPMI-1640 medium (Sigma) containing 1 mg/ml of BSA were added 0.5 ml of a suspension of BCECF-AM labeled neutrophils at $5\times10^7$/ml stored in ice, which was mixed, and the mixture was added at 80 µl/well to a HUVEC immobilized plate. To this plate were immediately added 10 µl/well of a solution of the compound diluted at different concentrations with RPMI-1640 containing 1 mg/ml BSA, and 10 µl/well of 100 nM phorbol myristate acetate (hereinafter abbreviated as PMA; Sigma) in RPMI-1640 containing 1 mg/ml BSA, and the mixture was incubated in a $CO_2$ incubator at 37° C. for 45 minutes. The supernatant was removed from the plate, which was then washed several times with RPMI-1640 at 100 µl/well, and then PBS containing 0.1% NP-40 (Calbiochem) was added thereto at 100 µl/well and the fluorescent intensity was measured with an ARVO™SX 1420 multi label counter (Wallac) to determine the number of adhered cells. The concentration of each compound which inhibited the increase in the number of adhered cells by the PMA-stimulation by 50% was recorded as the IC50 (µM).

TABLE 2

| Example | IC50 (µM) |
| --- | --- |
| 1 | 9.1 |
| 7 | 9.8 |
| 8 | 22.5 |
| 9 | 6.7 |
| 10 | 15.6 |
| 12 | 18.3 |
| 13 | 53.9 |
| 14 | 19.7 |
| 15 | 21.0 |
| 17 | 17.9 |
| 18 | 12.1 |
| 19 | 11.6 |
| 20 | 6.1 |
| 22 | 18.1 |
| 28 | 8.5 |
| 30 | 16.9 |
| 31 | 9.5 |
| 32 | 7.0 |
| 47 | 11.8 |
| 48 | 4.9 |
| 69 | 9.4 |
| 85 | 16.4 |
| 103 | 19.3 |
| 117 | 7.1 |

Test Example 3

Evaluation of Compounds in Oxazolone-Induced Colon Neutrophil Infiltration Model <Sensitization with Oxazolone>

Five- to six-week-old male Balb/c mice (Charles River Japan) were shaven at the abdomen to an approximately 2 cm square area. A 100% ethanol solution containing 3% 4-ethoxymethylene-2-phenyl-2-oxazolin-5-one (hereinafter referred to as "oxazolone"; Sigma) was applied at 150 µl onto the abdomen of each mouse.

<Preparation of Emulsion Containing Oxazolone>

Distilled water (Otsuka Pharmaceutical) was added in an equivalent volume to 100% peanut oil (Kanto Kagaku) containing 1% oxazolone, and the components were vigorously mixed with a glass syringe (Top Co.), to prepare an emulsion containing 0.5% oxazolone.

<Induction with Oxazolone>

The mice were fasted on the 3rd day after oxazolone sensitization, and were injected with 100 µl of the emulsion containing 0.5% oxazolone prepared in the way described above intrarectally at a site approximately 3 cm from the anus under ether anesthesia on the 4th day.

<Colon-Infiltrating Neutrophil Assay>

Each compound was suspended or dissolved in an aqueous solution containing 0.5% methyl cellulose (Wako), and orally administered at 30 mg/kg 30 minutes prior to the intrarectal injection of oxazolone emulsion. Four hours after the intrarectal injection of oxazolone, mice were sacrificed by cervical dislocation, and colons were extirpated, dissected in the longitudinal direction, washed with physiological saline, and transferred to ice-cooled plastic centrifugation tubes. After adding 1 ml of 50 mM potassium phosphate buffer (hereinafter abbreviated as KPB) (pH 6.0) to the tube, and the tissue were homogenized with PHYSCOTRON (Microtec Nition Co., Ltd.), 2 ml of 50 mM KPB (pH 6.0) was added and the mixture was centrifuged at 3000 rpm, 4° C. for 10 minutes and the supernatant was removed. To the resultant precipitate was added 1 ml of 50 mM KPB (pH 6.0) containing 0.5% hexadecyltrimethyl-ammonium bromide (Sigma), and freeze-thawed 3 to 5 times using liquid nitrogen and hot water, centrifuged at 3000 rpm, 4° C. for 10 minutes to yield a supernatant. The myeloperoxidase enzyme activity in the supernatant was assayed in the following manner. Specifically, to 10 µl of the obtained supernatant was added 200 µl of 50 mM KPB (pH6.0) containing 0.017% o-dianisidine (Sigma) and 0.0005% hydrogen peroxide (Wako), incubated at 37° C., and the change in absorbance at 450 nm was continuously measured for 1 minute using an EL340 Automated Microplate Reader (BIO-TEK) in kinetic mode. The units were the rate of change in absorbance per minute (mO.D./min.). With regard to the effect of each compound, the inhibitory rate (%) with respect to the oxazolone control group, i.e. the oxazolone-injected/compound-free group, was shown in the table 3.

TABLE 3

| Example | Inhibitory rate (%) |
|---|---|
| 1 | 45 |
| 7 | 37 |
| 8 | 22 |
| 9 | 35 |
| 10 | 73 |
| 12 | 34 |
| 13 | 13 |
| 14 | 64 |
| 15 | 40 |
| 17 | 30 |
| 18 | 50 |
| 19 | 53 |
| 20 | 38 |
| 22 | 28 |
| 28 | 48 |
| 30 | 23 |
| 31 | 38 |
| 32 | 51 |

Test Example 4

Evaluation of Compounds in DSS-Induced Colitis Model

A 1-3% solution of dextran sulfate sodium (hereinafter abbreviated as DSS; ICN) in purified water (Otsuka Pharmaceutical) was fed freely to 6- to 7-week-old male Balb/c mice (Charles River Japan) for 5-7 days to induce colitis. Disease Activity Index (hereinafter abbreviated as DAI) scored based on fecal hardness, blood content in feces and body weight change, the number of neutrophils infiltrating the colon and the length of the colon were used as indexes to evaluate compounds. Each compound was suspended or dissolved in an aqueous solution containing 0.5% methyl cellulose (Wako), and orally administered at 30 mg/kg once a day, for 5-7 successive days. The compounds of Examples 1, 7, 8, 9, 10, 12, 13, 14, 15, 17, 18, 19, 20, 22, 28, 30, 31, 32 and 34 exhibited particularly good improvement in comparison with the DSS control group, i.e. the DSS water-loaded/compound-free group.

INDUSTRIAL APPLICABILITY

The compounds of the invention have excellent cell adhesion inhibitory action or cell infiltration inhibitory action, and can therefore serve as pharmaceuticals which are useful as therapeutic or prophylactic agents for various inflammatory diseases and autoimmune diseases associated with adhesion and infiltration of leukocytes, such as inflammatory bowel disease (particularly ulcerative colitis or Crohn's disease), irritable bowel syndrome, rheumatoid arthritis, psoriasis, multiple sclerosis, asthma and atopic dermatitis.

The invention claimed is:

1. A compound represented by the following general formula, a salt thereof or a hydrate of the foregoing:

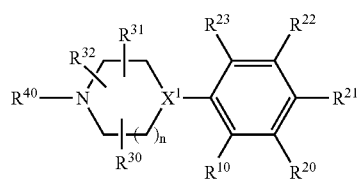

(1)

wherein R10 represents 5- to 10-membered cycloalkyl optionally substituted with a substituent selected from Group A1 or 5- to 10-membered cycloalkenyl optionally substituted with a substituent selected from Group A1, R20, R21, R22 and R23 may be the same or different and each represents hydrogen, hydroxyl, halogen, cyano, C2-7 alkylcarbonyl, nitro, amino, mono(C1-6 alkyl) amino, di(C1-6 alkyl)amino, C1-6 alkyl optionally substituted with a substituent selected from Group B1, C1-6 alkoxy optionally substituted with a substituent selected from Group B1, a 4- to 8-membered heterocyclic group optionally substituted with a substituent selected from Group C1 or a 5- to 10-membered heteroaryl ring group optionally substituted with a substituent selected from Group C1, R30, R31 and R32 may be the same or different and each represents hydrogen, hydroxyl, halogen, cyano, carboxyl, C1-6 alkyl, C1-6 alkoxy or C2-7 alkoxycarbonyl, or two of R30, R31 and R32 bond together to form oxo (═O) or methylene (—CH$_2$—) and the other represents hydrogen, hydroxyl, halogen, cyano, carboxyl, C1-6 alkyl, C1-6 alkoxy or C2-7 alkoxycarbonyl, R40 represents C1-10 alkyl optionally substituted with a substituent selected from Group D1,3- to 8-membered cycloalkyl optionally substituted with a substituent selected from Group E1, a 4- to 8-membered heterocyclic group optionally substituted with a substituent selected from Group E1, C2-7 alkenyl optionally substituted with a substituent selected from Group F1, C2-7 alkynyl optionally substituted with a substituent selected from Group F1, C2-7 alkylcarbonyl optionally substituted with a substituent selected from Group G1, mono(C1-6 alkyl)aminocarbonyl, 4- to 8-membered heterocyclic carbonyl, C2-7 alkoxycarbonyl or C1-6 alkylsulfonyl, n represents an integer of 0, 1 or 2, and X1 represents CH or nitrogen, wherein Group A1 consists of hydroxyl, halogen, cyano, C1-6 alkoxy, C1-6 alkyl, C1-6 haloalkyl, C2-7 alkylene, and phenyl optionally substituted with a substituent selected from Group C1, C1-6 alkyl, C1-6 haloalkyl and C2-7 alkylene, where C2-7 alkylene is permissible only in the case that a spiro union is formed together with the substituted 5- to 10-membered cycloalkyl or the substituted 5- to 10-membered cycloalkenyl, Group B1 consists of halogen, C2-7 alkoxycarbonyl and carboxyl, Group C1 consists of cyano, halogen, C1-6 alkyl and C1-6 alkoxy, Group D1 consists of hydroxyl, halogen, cyano, C1-6 alkoxy, C1-6 alkylthio, C1-6 alkylsulfonyl, C1-6 alkylsulfinyl, mono(C1-6 alkyl)amino, di(C1-6 alkyl)amino, C2-7 alkylcarbonylamino, 3- to 8-membered cycloalkyl optionally substituted with a substituent selected from Group H1, C2-7 alkoxycarbonyl, carboxyl, a 4- to 8-membered heterocyclic group, a 5- to 10-membered heteroaryl ring group, a 6- to 10-membered aryl ring group, C2-7 alkylcarbonyl, a 6- to 10-membered aryl ring carbonyl group, aminocarbonyl, mono(C 1-6 alkyl) aminocarbonyl optionally substituted with halogen, mono(3- to 8-membered cycloalkyl)aminocarbonyl, mono(C2-7 alkoxyalkyl)aminocarbonyl, di(C 1-6 alkyl) aminocarbonyl, mono(5- to 10-membered heteroaryl ring)aminocarbonyl, 4- to 8-membered heterocyclic carbonyl optionally substituted with C1-6 alkyl, and 5- to 10-membered heteroaryl ring carbonyl, Group E1 consists of halogen, C1-6 alkoxy, oxo (═O) and C1-6 alkyl, Group F1 consists of halogen and C1-6 alkoxy, Group G1 consists of 3- to 8-membered cycloalkyl, and Group H1 consists of hydroxyl, C1-6 haloalkyl, C1-6 alkyl, C2-7 alkoxyalkyl, mono(C1-6 alkyl)aminocarbonyl, di(C1-6 alkyl)aminocarbonyl, C2-7 alkoxycarbonyl, carboxyl and C2-7 cyanoalkyl, with the proviso that a compound represented by the formula

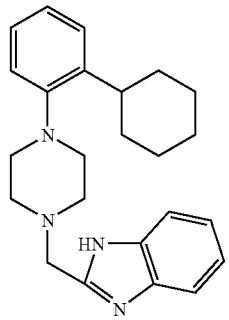

is excepted.

2. A compound represented by the following general formula, a salt thereof or a hydrate of the foregoing:

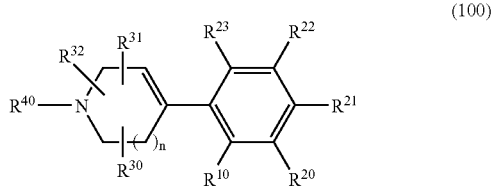

(100)

wherein R10 represents 5- to 10-membered cycloalkyl optionally substituted with a substituent selected from Group A1 or 5- to 10-membered cycloalkenyl optionally substituted with a substituent selected from Group A1, R20, R21, R22 and R23 may be the same or different and each represents hydrogen, hydroxyl, halogen, cyano, C2-7 alkylcarbonyl, nitro, amino, mono(C1-6 alkyl)amino, di(C1-6 alkyl)amino, C1-6 alkyl optionally substituted with a substituent selected from Group B1, C1-6 alkoxy optionally substituted with a substituent selected from Group B1, a 4- to 8-membered heterocyclic group optionally substituted with a substituent selected from Group C1 or a 5- to 10-membered heteroaryl ring group optionally substituted with a substituent selected from Group C1, R30, R31 and R32 may be the same or different and each represents hydrogen, hydroxyl, halogen, cyano, carboxyl, C1-6 alkyl, C1-6 alkoxy or C2-7 alkoxycarbonyl, or two of R30, R31 and R32 bond together to form oxo (═O) or methylene (—CH$_2$—) and the other represents hydrogen, hydroxyl, halogen, cyano, carboxyl, C1-6 alkyl, C1-6 alkoxy or C2-7 alkoxycarbonyl, R40 represents C1-10 alkyl optionally substituted with a substituent selected from Group D1,3- to 8-membered cycloalkyl optionally substituted with a substituent selected from Group E1, a 4- to 8-membered heterocyclic group optionally substituted with a substituent selected from Group E1, C2-7 alkenyl optionally substituted with a substituent selected from Group F1, C2-7 alkynyl optionally substituted with a substituent selected from Group F1, C2-7 alkylcarbonyl optionally substituted with a substituent selected from Group G1, mono(C1-6 alkyl)aminocarbonyl, 4- to 8-membered heterocyclic carbonyl, C2-7 alkoxycarbonyl or C1-6 alkylsulfonyl, n represents an integer of 0, 1 or 2, and wherein Group A1 consists of hydroxyl, halogen, cyano, C1-6 alkoxy, C1-6 alkyl, C1-6 haloalkyl, C2-7 alkylene, and phenyl optionally substituted with a substituent selected from Group C1, C1-6 alkyl, C1-6 haloalkyl and C2-7 alkylene, where C2-7 alkylene is permissible only in the case that a spiro union is formed together with the substituted 5- to 10-membered cycloalkyl or the substituted 5- to 10-membered cycloalkenyl, Group B1 consists of halogen, C2-7 alkoxycarbonyl and carboxyl, Group C1 consists of cyano, halogen, C1-6 alkyl and C1-6 alkoxy, Group D1 consists of hydroxyl, halogen, cyano, C1-6 alkoxy, C1-6 alkylthio, C1-6 alkylsulfonyl, C1-6 alkylsulfinyl, mono(C1-6 alkyl)amino, di(C1-6 alkyl)amino, C2-7 alkylcarbonylamino, 3- to 8-membered cycloalkyl optionally substituted with a substituent selected from Group H1, C2-7 alkoxycarbonyl, carboxyl, a 4- to 8-membered heterocyclic group, a 5- to 10-membered heteroaryl ring group, a 6- to 10-membered aryl ring group, C2-7 alkylcarbonyl, a 6- to 10-membered aryl ring carbonyl group, aminocarbonyl, mono(C1-6 alkyl)aminocarbonyl optionally substituted with halogen, mono(3- to 8-membered cycloalkyl)aminocarbonyl, mono(C2-7 alkoxyalkyl)aminocarbonyl, di(C1-6 alkyl)aminocarbonyl, mono(5- to 10-membered heteroaryl ring)aminocarbonyl, 4- to 8-membered heterocyclic carbonyl optionally substituted with C1-6 alkyl, and 5- to 10-membered heteroaryl ring carbonyl, Group E1 consists of halogen, C1-6 alkoxy, oxo (═O) and C1-6 alkyl, Group F1 consists of halogen and C1-6 alkoxy, Group G1 consists of 3- to 8-membered cycloalkyl, and Group H1 consists of hydroxyl, C1-6 haloalkyl, C1-6 alkyl, C2-7 alkoxyalkyl, mono(C1-6 alkyl)aminocarbonyl, di(C1-6 alkyl)aminocarbonyl, C2-7 alkoxycarbonyl, carboxyl and C2-7 cyanoalkyl.

3. The compound according to claim 1 or 2, the salt thereof or the hydrate of the foregoing, wherein R10 represents 5- to 10-membered cycloalkyl optionally substituted with a substituent selected from Group A2, or 5- to 10-membered cycloalkenyl optionally substituted with a substituent selected from Group A2, wherein Group A2 consists of hydroxyl, phenyl, C1-6 alkyl, C1-6 haloalkyl and C2-7 alkylene, where C2-7 alkylene is permissible only in the case that a spiro union is formed together with the substituted 5- to 10-membered cycloalkyl or the substituted 5- to 10-membered cycloalkenyl.

4. The compound according to claim 1 or 2, the salt thereof or the hydrate of the foregoing, wherein R10 represents 5- to 10-membered cycloalkyl optionally substituted with hydroxyl, phenyl, C1-6 alkyl, C1-6 haloalkyl, 1,2-ethylene, trimethylene, tetramethylene or pentamethylene, or 5- to 10-membered cycloalkenyl optionally substituted with hydroxyl, phenyl, C1-6 alkyl, C1-6 haloalkyl, 1,2-ethylene, trimethylene, tetramethylene or pentamethylene, where 1,2-ethylene, trimethylene, tetramethylene or pentamethylene is permissible only in the case that a spiro union is formed together with the substituted 5- to 10-membered cycloalkyl or the substituted 5- to 10-membered cycloalkenyl.

5. The compound according to claim 1 or 2, the salt thereof or the hydrate of the foregoing, wherein R10 represents cyclohexyl, 4-t-butylcyclohexyl, 4,4-dimethylcyclohexyl, 4,4-diethylcyclohexyl, 3,3,5,5-tetramethylcyclohexyl, 3,5-dimethylcyclohexyl, 4-phenylcyclohexyl, 4-trifluoromethylcyclohexyl, 4-n-butylcyclohexyl, cyclo pentyl, 3,3,4,4-tetramethylcyclopentyl, cycloheptyl, cyclooctyl or a group represented by the formula:

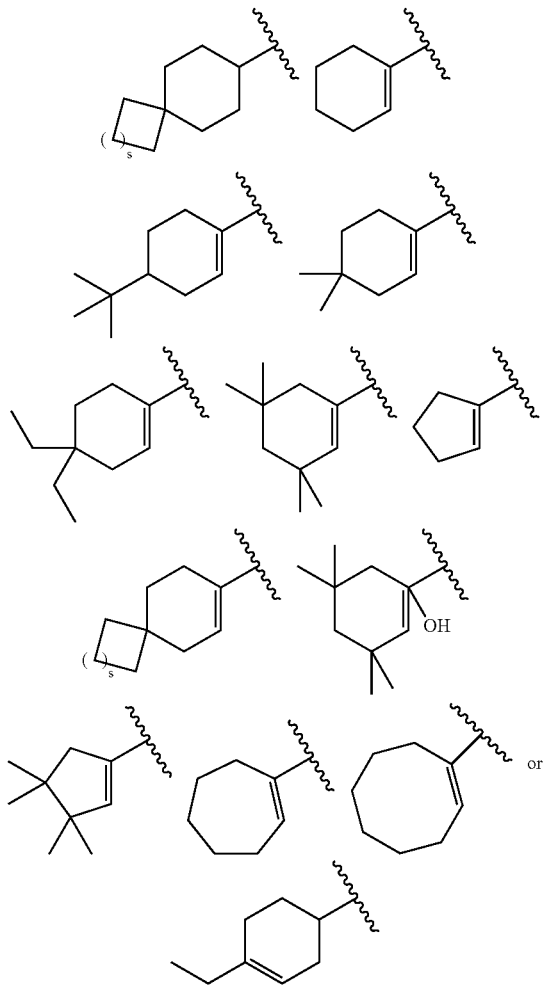

wherein s represents an integer of 0, 1, 2 or 3.

6. The compound according to claim 1 or 2, the salt thereof or the hydrate of the foregoing, wherein R20, R21, R22 and R23 may be the same or different and each represents hydrogen, hydroxyl, halogen, cyano, C2-7 alkylcarbonyl, nitro, amino, mono(C1-6 alkyl)amino, di(C1-6 alkyl)amino, C1-6 alkyl optionally substituted with a substituent selected from Group B1, C1-6 alkoxy optionally substituted with a substituent selected from Group B1, a 4- to 8-membered heterocyclic group optionally substituted with a substituent selected from Group C1 or a 5- to 6-membered heteroaryl ring group optionally substituted with a substituent selected from Group C1.

7. The compound according to claim 1 or 2, the salt thereof or the hydrate of the foregoing, wherein R20, R21, R22 and R23 may be the same or different and each represents hydrogen, hydroxyl, halogen, cyano, acetyl, nitro, amino, monomethylamino, monoethylamino, dimethylamino, C1-6 alkyl optionally substituted with a substituent selected from Group B1, C1-6 alkoxy optionally substituted with a substituent selected from Group B1, a 4- to 8-membered heterocyclic group optionally substituted with a substituent selected from Group C1, where the 4- to 8-membered heterocyclic group is derived by eliminating hydrogen linked to nitrogen of a 4- to 8-membered heterocycle, or a 5- to 6-membered heteroaryl ring group optionally substituted with a substituent selected from Group C2, wherein Group C2 consists of C1-6 alkoxy and C1-6 alkyl.

8. The compound according to claim 1 or 2, the salt thereof or the hydrate of the foregoing, wherein R20, R21, R22 and R23 may be the same or different and each represents hydrogen, halogen, cyano, acetyl, monomethylamino, monoethylamino, dimethylamino, methyl, methoxy, ethoxy, morpholin-4-yl optionally substituted with a substituent selected from Group C2, piperidin-1-yl optionally substituted with a substituent selected from Group C2, pyrrolidin-1-yl optionally substituted with a substituent selected from Group C2, azetidin-1-yl, pyridin-2-yl or pyridin-3-yl.

9. The compound according to claim 1 or 2, the salt thereof or the hydrate of the foregoing, wherein at least two of R20, R21, R22 and R23 are hydrogen, and the remaining groups, which may be the same or different, are hydrogen, halogen, cyano, acetyl, monomethylamino, monoethylamino, dimethylamino, methyl, methoxy, ethoxy, morpholin-4-yl optionally substituted with a substituent, selected from Group C2, piperidin-1-yl optionally substituted with a substituent selected from Group C2, pyrrolidin-1-yl optionally substituted with a substituent selected from Group C2, azetidin-1-yl, pyridin-2-yl or pyridin-3-yl.

10. The compound according to claim 1 or 2, the salt thereof or the hydrate of the foregoing, wherein three of R20, R21, R22 and R23 are hydrogen, and the remaining group is hydrogen, fluorine, cyano, dimethylamino, methyl, methoxy, morpholin-4-yl optionally substituted with a substituent selected from Group C3, piperidin-1-yl optionally substituted with a substituent selected from Group C3 or pyrrolidin-1-yl optionally substituted with a substituent selected from Group C3, wherein Group C3 consists of methoxy, ethoxy and methyl.

11. The compound according to claim 1 or 2, the salt thereof or the hydrate of the foregoing, wherein R30, R31 and R32 may be the same or different and each represents hydrogen or C1-6 alkyl, or R30 and R31 bond together to form oxo (=O) and R32 represents hydrogen or C1-6 alkyl.

12. The compound according to claim 1 or 2, the salt thereof or the hydrate of the foregoing, wherein R30, R31 and R32 may be the same or different and each represents hydrogen or methyl, or R30 and R31 bond together to form oxo (=O) and R32 represents hydrogen or methyl.

13. The compound according to claim 1 or 2, the salt thereof or the hydrate of the foregoing, wherein all of R30, R31 and R32 represent hydrogen.

14. The compound according to claim 1 or 2, the salt thereof or the hydrate of the foregoing, wherein R40 represents C1-6 alkyl optionally substituted with a substituent selected from Group D1, 3- to 8-membered cycloalkyl optionally substituted with a substituent selected from Group E1, C2-7 alkenyl, C2-7 alkynyl or C2-7 alkylcarbonyl.

15. The compound according to claim 1 or 2, the salt thereof or the hydrate of the foregoing, wherein R40 represents C1-6 alkyl optionally substituted with a substituent selected from Group D2, wherein Group D2 consists of hydroxyl, halogen, cyano, C1-6 alkoxy, 3- to 8-membered cycloalkyl, a 4- to 8-membered heterocyclic group, mono(C1-6 alkyl)aminocarbonyl, di(C1-6 alkyl)aminocarbonyl, C2-7 alkylcarbonyl, a 5-membered heteroaryl ring group, 4- to 8-membered heterocyclic carbonyl or phenyl.

16. The compound according to claim 1 or 2, the salt thereof or the hydrate of the foregoing, wherein R40 represents n-propyl, n-butyl, n-pentyl, isobutyl, ethylcarbonylmethyl, methoxyethyl, ethoxyethyl, cyclopropylmethyl or tetrahydropyran-4-ylmethyl.

17. The compound according to claim 1 or 2, the salt thereof or the hydrate of the foregoing, wherein n represents an integer of .

18. The compound according to claim 1, the salt thereof or the hydrate of the foregoing, wherein X1 represents nitrogen.

19. The compound according to claim 1 or 2, the salt thereof or the hydrate of the foregoing, selected from the compound group consisting of
- 1-[2-(4,4-dimethylcyclohexyl)-5-methoxyphenyl]-4-pentylpiperazine,
- 1-butyl-4-[2-(4-t-butylcyclohex-1-enyl)-4-(4-methoxypiperidin-1-yl)phenyl]piperazine,
- 1-butyl-4-[2-(3,3,5,5-tetramethylcyclohexyl)phenyl]piperazine,
- 2-{4-[2-(4-t-butylcyclohexyl)phenyl]piperazin-1-yl}-N-ethylacetamide,
- cis-4-(4-t-butylcyclohexyl)-3-(4-butylpiperazin-1-yl)benzonitrile,
- trans-4-(4-t-butylcyclohexyl)-3-(4-butylpiperazin-1-yl)benzonitrile,
- 1-butyl-4-(2-cyclohexylphenyl)piperazine,
- 1-butyl-4-[2-(4-t-butylcyclohexyl)phenyl]piperazine,
- 1-{4-[2-(4,4-dimethylcyclohexyl)phenyl]piperazin-1-yl}butan-2-one,
- 4-[3-(4-t-butylcyclohex-1-enyl)-4-(4-butylpiperazin-1-yl)phenyl]morpholine,
- 1-[2-(4-t-butylcyclohexyl)phenyl]-4-(2-methoxyethyl)piperazine,
- 1-[2-(4-t-butylcyclohex-1-enyl)-4-(4-methoxypiperidin-1-yl)phenyl]-4-cyclopropylmethylpiperazine,
- 1-(tetrahydropyran-4-ylmethyl)-4-[2-(3,3,5,5-tetramethylcyclohex-1-enyl)phenyl]piperazine,
- 4-[4-(4-propylpiperazin-1-yl)-3-(3,3,5,5-tetramethylcyclohex-1-enyl)phenyl]morpholine,
- 1-{4-[2-(4,4-diethylcyclohex-1-enyl)-4-morpholin-4-ylphenyl]piperazin-1-yl}butan-2-one,
- 1-propyl-4-[2-(3,3,5,5-tetramethylcyclohexyl)phenyl]piperazine,
- 1-butyl-4-[4-(4-methoxypiperidin-1-yl)-2-(3,3,5,5-tetramethylcyclohexyl)phenyl]piperazine,
- 1-butyl-4-[2-(3,5-dimethylcyclohexyl)phenyl]piperazine,
- 1-[2-(4,4-diethylcyclohexyl)phenyl]-4-(tetrahydropyran-4-ylmethyl)piperazine,
- 4-[4-(4-butylpiperazin-1-yl)-3-(3,3,5,5-tetramethylcyclohex-1-enyl)phenyl]morpholine,
- 4-[4-(4-butylpiperazin-1-yl)-3-(3,3,5,5-tetramethylcyclohexyl)phenyl]morpholine,
- 1-[4-(4-ethoxypiperidin-1-yl)-2-(3,3,5,5-tetramethylcyclohexyl)phenyl]-4-propylpiperazine,
- cis-4-[4-(4-butylpiperazin-1-yl)-3-(4,4-dimethylcyclohexyl)phenyl]-2,6-dimethylmorpholine,
- 4-{4-(4-pentylpiperazin-1-yl)-3-spiro[2.5]oct-6-ylphenyl}morpholine,
- 1-[3-fluoro-2-(3,3,5,5-tetramethylcyclohex-1-enyl)phenyl]-4-propylpiperazine,
- 1-cyclopropylmethyl-4-[2-(3,3,5,5-tetramethylcyclohexyl)phenyl]-1,2,3,6-tetrahydropyridine,
- 1-butyl-4-{2-(3,3,4,4-tetramethylcyclopentyl)phenyl}piperazine,
- 1-butyl-4-[2-(4,4-dimethylcyclohexyl)-4-(4-ethoxypiperidin-1-yl)phenyl]piperazine,
- 1-butyl-4-[2-(3,3,5,5-tetramethylcyclohex-1-enyl)phenyl]piperazine,
- 1-cyclopropylmethyl-4-[2-(3,3,5,5-tetramethylcyclohex-1-enyl)phenyl]piperazine,
- 1-{4-[2-(3,3,5,5-tetramethylcyclohex-1-enyl)phenyl]piperazin-1-yl}butan-2-one,
- 1-(2-methoxyethyl)-4-[2-(3,3,5,5-tetramethylcyclohex-1-enyl)phenyl]piperazine,
- 1-{4-[2-(3,3,5,5-tetramethylcyclohexyl)phenyl]piperazin-1-yl}butan-2-one,
- 1-(2-methoxyethyl)-4-[2-(3,3,5,5-tetramethylcyclohexyl)phenyl]piperazine,
- 4-[4-(4-butylpiperazin-1-yl)-5-(4,4-diethylcyclohexyl)-2-methoxyphenyl]-morpholine,
- 1-butyl-4-(2-spiro[4.5]dec-8-ylphenyl)piperazine,
- 1-[2-(4,4-dimethylcyclohex-1-enyl)phenyl]-4-isobutylpiperazine,
- 1-cyclopropylmethyl-4-[2-(4,4-diethylcyclohexyl)-4-(4-methoxypiperidin-1-yl)phenyl]piperazine,
- 4-[3-(4,4-dimethylcyclohexyl)-4-(4-isobutylpiperazin-1-yl)phenyl]morpholine,
- {4-[2-(3,3,5,5-tetramethylcyclohexyl)phenyl]piperazin-1-yl}acetonitrile,
- 1-(2-ethoxyethyl)-4-[2-(3,3,5,5-tetramethylcyclohexyl)phenyl]piperazine,
- (R)-1-butyl-4-[2-(4,4-diethylcyclohexyl)-4-(3-methoxypyrrolidin-1-yl)phenyl]piperazine,
- 1-[4-methyl-2-(3,3,5,5-tetramethylcyclohexyl)phenyl]-4-propylpiperazine,
- 1-[4-methoxy-2-(3,3,5,5-tetramethylcyclohexyl)phenyl]-4-(tetrahydropyran-4-ylmethyl)piperazine,
- 1-butyl-4-[2-(3,3,5,5-tetramethylcyclohexyl)phenyl]piperidine,
- 1-isobutyl-4-[2-(3,3,4,4-tetramethylcyclopent-1-enyl)phenyl]piperazine, and
- 1-[2-(4-cyclopropylmethylpiperazin-1-yl)phenyl]-3,3,5,5-tetramethylcyclohexanol.

20. A medicament composition comprising the compound according to claim 1 or 2, the salt thereof or the hydrate of the foregoing in association with a pharmaceutically acceptable additive.

21. A cell adhesion inhibitor or cell infiltration inhibitor composition comprising the compound according to claim 1 or 2, the salt thereof or the hydrate of the foregoing in association with a pharmaceutically acceptable additive.

22. A therapeutic composition for an inflammatory disease, comprising the compound according to claim 1 or 2, the salt thereof or the hydrate of the foregoing in association with a pharmaceutically acceptable additive.

23. A method of treating an inflammatory bowel disease, irritable bowel syndrome, rheumatoid arthritis, psoriasis, multiple sclerosis, asthma or atopic dermatitis in a patient, comprising administering to said patient a therapeutic composition containing the compound according to claim 1 or 2, the salt thereof or the hydrate of the foregoing in association with a pharmaceutically acceptable additive.

24. A method of treating an inflammatory bowel disease in a patient, comprising administering to said patient a therapeutic composition containing the compound according to claim 1 or 2, the salt thereof or the hydrate of the foregoing in association with a pharmaceutically acceptable additive.

25. A method of treating ulcerative colitis or Crohn's disease in a patient, comprising administering to said patient a therapeutic composition containing the compound according to claim 1 or 2, the salt thereof or the hydrate of the foregoing in association with a pharmaceutically acceptable additive.

* * * * *